United States Patent [19]
Stinchcomb et al.

[11] Patent Number: 5,877,021
[45] Date of Patent: Mar. 2, 1999

[54] B7-1 TARGETED RIBOZYMES

[75] Inventors: Dan T. Stinchcomb; Thale Jarvis; James McSwiggen, all of Boulder, Colo.

[73] Assignee: Ribozyme Pharmaceuticals, Inc., Boulder, Colo.

[21] Appl. No.: 585,684

[22] Filed: Jan. 12, 1996

Related U.S. Application Data

[60] Provisional application No. 60/000,951 Jul. 7, 1995.
[51] Int. Cl.[6] .............................. C12Q 1/68; C12N 5/08; C70H 21/02
[52] U.S. Cl. .......................... 435/366; 435/6; 435/91.31; 435/172.3; 435/320.1; 435/325; 536/23.1; 536/23.2; 536/24.5
[58] Field of Search ....................... 435/6, 91.31, 172.3, 435/172.1, 320.1, 325, 366; 536/23.1, 23.2, 24.5; 514/44

[56] References Cited

U.S. PATENT DOCUMENTS

| | | | |
|---|---|---|---|
| 4,987,071 | 1/1991 | Cech et al. | 435/91.31 |
| 5,359,051 | 10/1994 | Cook et al. | 536/26.7 |

FOREIGN PATENT DOCUMENTS

| | | |
|---|---|---|
| 0360257 | 3/1990 | European Pat. Off. |
| 0519463 | 12/1992 | European Pat. Off. |
| 9103162 | 3/1991 | WIPO |
| 9200092 | 1/1992 | WIPO |
| 9207065 | 4/1992 | WIPO |
| 9315187 | 8/1993 | WIPO |
| 9323569 | 11/1993 | WIPO |
| 9401547 | 1/1994 | WIPO |
| 9402595 | 2/1994 | WIPO |
| 9411011 | 5/1994 | WIPO |

OTHER PUBLICATIONS

Stull et al. Pharm. Res. 12: 465–483 (1995).
Gewirtz et al. PNAS 93:3161–3163 (1996).
Azuma et al., "B70 antigen is a second ligand for CTLA–4 and CD28," *Nature* 366:76–79 (1993).
Blazer et al., "In Vivo Blockade of CD28/CTLA4: B7/BB1 Interaction With CTLA4–Ig Reduces Lethal Murine Graft–Versus–Host Disease Across the Major Histocompatibility Complex Barrier in Mice," *Blood* 83:3815–3825 (1994).
Boussiotis et al., "Activated human B lymphocytes express three CTLA–4 counterreceptors that costimulate T–cell activation," *Proc. Natl. Acad. Sci. USA* 90:11059–11063 (1993).
Caine, "Immunosuppression for Organ Grafting," *Transplantation Proceedings* 24:1260–1262 (1992).
Carlson et al., "Immunomodulating Drugs," *Ann. N.Y. Acad. Sci.* 685:86–113 (1993).
Carter, "Adeno–Associated Virus Vectors," *Curr Opi, Biotech.* 3:533–539 (1992).
Chen et al., "Multitarget–Ribozyme Directed to Cleave at up to Nine Highly Conserved HIV–1 env RNA Regions Inhibits HIV–1 Replication–Potential Effectiveness Against Most Presently Sequenced HIV–1 Isolates," *Nucleic Acids Research* 20:4581–4589 (1992).
Chowrira et al., "In Vitro and in Vivo Comparison of Hammerhead, Hairpin, and Hepatitis Delta Virus Self–Processing Ribozyme Cassettes," *J. Biol. Chem.* 269:25856–25864 (1994).
Chowrira and Burke, "Extensive Phosphorothioate Substitution Yields Highly Active and Nuclease–Resistant Hairpin Ribozymes," *Nucleic Acids Res.* 20:2835–2840 (1992).
Clark and Ledbetter, "How B and T Cells Talk to Each Other," *Nature* 367:425–428 (1994).
Cohen, "New Protein Steals the Show As 'Costimulator' of T Cells," *Science* 262:844 (1993).
Collins and Olive, "Reaction Conditions and Kinetics of Self–Cleavage of a Ribozyme Derived From Neuropora VS RNA," *Biochemistry* 32:2795–2799 (1993).
Dropulic et al., "Functional Characterization of U5 Ribozyme: Intercellular Suppression of Human Immunodeficiency Virus Type 1 Expression," *Journal of Virology* 66:1432–1441 (1992).
Duval–Valentin, "Specific Inhibition of transcription by triple helix–forming oligonucleotides," *Proc. Natl. Acad. Sci. USA* 89:504 (1992).
Egholm et al., "PNA hybridizes to complementary oligonucleotides obeying the Watson–Crick hydrogen–bonding rules," *Nature* 365:566–568 (1993).
Elroy–Stein and Moss, "Cytoplasmic Expression System Based on Constitutive Synthesis of Bacteriophage T7 RNA Polymerase in Mammalian Cells," *Proc. Natl. Acad. Sci. USA* 87:6743–6747 (1990).
Finck et al., "Treatment of Murine Lupus with CTLA4Ig," *Science* 265:1225–1227 (1994).
Fodor et al., "Expression of a functional human complement inhibitor in a transgenic pig as a model for the prevention of xenogenic hyperacute organ rejection," *Proc. Natl. Acad. Sci. USA* 91:11153–11157 (1994).
Foy et al., "In Vivo CD40–gp39 Interactions Are Essential for Thymus–dependent Humoral Immunity. II. Prolonged Suppression of the Humoral Immune Response by an Antibody to the Ligand for CD40, gp39," *J. Exp. Med.* 178:1567–1575 (1993).
Freeman et al., "Uncovering of Functional Alternative CTLA–4 Counter–Receptor in B7–Deficient Mice," *Science* 262:907–909 (1993).
Fulehian et al., "Cyclosporin A Inhibits CD40 Ligand Expression in T Lymphocytes," *J. Clin. Invest.* 93:1315–1320 (1994).

(List continued on next page.)

*Primary Examiner*—John L. LeGuyader
*Attorney, Agent, or Firm*—Lyon & Lyon LLP

[57] ABSTRACT

Nucleic acid molecule which blocks synthesis and/or expression of an mRNA encoding B7-1.

11 Claims, 6 Drawing Sheets

OTHER PUBLICATIONS

Gao and Huang, "Cytoplasmic Expression of a Reporter Gene by Co–Delivery of T7 RNA Polymerase and T7 Promoter Sequence with Cationic Liposomes," *Nucleic Acids Res.* 21:2867–2872 (1993).

Guerrier–Takada et al., "The RNA Moiety of Ribonuclease P Is the Catalytic Subunit of the Enzyme," *Cell* 35:849–857 (1983).

Hampel et al., "'Hairpin' Catalytic RNA Model: Evidence for Helics and Sequence Requirement for Substrate RNA," *Nucleic Acids Research* 18:299–304 (1990).

Hampel and Tritz, "RNA Catalytic Properties of the Minimum (–)sTRSV Sequence," *Biochemistry* 28:4929–4933 (1989).

Harding et al., "CD28–mediated signalling co–stimulates murine T cells and prevents induction of anergy in T–cell clones," *Nature* 356:607–609 (1992).

Haseloff and Gerlach, "Simple RNA Enzymes with New and Highly Specific Endoribonuclease Activities," *Nature* 334:585–591 (1988).

Hathcock et al., "Identification of an Alternative CTLA–4 Ligand Costimulatory for T Cell Activation," *Science* 262:905–907 (1993).

Hathcock et al., "Comparative Analysis of B7–1 and B7–2 Costimulatory Ligands: Expression and Function," *J. Exp. Med.* 180:631–640 (1994).

Hertel et al., "Numbering System for the Hammerhead," *Nucleic Acids Res.* 20:3252 (1992).

Jaeger et al., "Improved Predictions of Secondary Structures for RNA," *Proc. Natl. Acad. Sci. USA* 86:7706–7710 (1989).

Janeway and Bottomly, "Signals and Signs for Lymphocyte Responses," *Cell* 76:275–285 (1994).

Jeffries and Symons, "A Catalytic 13–mer Ribozyme," *Nucleic Acids Research* 17:1371–1377 (1989).

Jenkins et al., "Molecular events in the induction of a nonresponsive state in interleukin 2–producig helper T–lymphocyte clones," *Proc. Natl. Acad. Sci. USA* 84:5409–5413 (1987).

Kashani–Sabet et al., "Reversal of the Malignant Phenotype by an Anti–ras Ribozyme," *Antisense Research & Development* 2:3–15 (1992).

Kemeny and Diaz–Sanchez, "Can persistent IgE responses be suppressed?" *Clin. Exp. Immunol.* 82:423–426 (1990).

Koulova et al., "The CD28 Ligand B7/BB1 Provides Costimulatory Signal for Alloactivation of $CD^+$ T Cells," *J. Exp. Med.* 173:759–762 (1991).

Kuchroo et al., "B7–1 and B7–2 Costimulatory Molecules Activate Differentially the Th1/Th2 Developmental Pathways: Application to Autoimmune Disease Therapy," *Cell* 80:707–718 (1995).

L'Huillier et al., "Cytoplasmic Delivery of Ribozymes Leads to Efficient Reduction in α–Lactalbumin mRNA Levels in C1271 Mouse," *Embo J.* 11:4411–4418 (1992).

Lenschow et al., "Expression and functional significance of an additional ligand for CTLA–4," *Proc. Natl. Acad. Sci. USA* 90:11054–11058 (1993).

Lenschow et al., "Long–Term Survival of Xenogenic Pancreatic Islet Grafts Induced by CTLA4Ig," *Science* 257:789–792 (1992).

Lieber et al., "Stable High–Level Gene Expression in Mammalian Cells by T7 Phage RNA Polymerase," *Methods Enzymol.* 217:47–66 (1993).

Linsley et al., "Immunosuppression in Vivo by a Soluble Form of the CTLA–4 T Cell Activation Molecule," *Science* 257:792–795 (1992).

Linsley et al., "Binding of the B Cell Activation Antigen B7 to CD28 Costimulates T Cell Proliferation and Interleukin 2 mRNA Accumulation," *J. Exp. Med.* 173:721–730 (1991).

Linsley et al., "Human B7–1 (CD80) and B7–2 (CD86) Bind with Similar Avidities but Distinct Kinetics to CD28 and CTLA–4 Receptors," *Immunity* 1:793–801 (1994).

Lisziewicz et al., "Inhibition of Human Immunodeficiency Virus Type 1 Replication by Regulated Expression of a Polymeric Tat Activation Response RNA Decoy as a Strategy for Gene Therapy in AIDS," *Proc. Natl. Acad. Sci. U.S.A.* 90:8000–8004 (1993).

Marshall et al., "The Molecular Basis for T Cell Help in Humoral Immunity: CD40 and Its Ligand, gp39," *J. Clin. Immun.* 13:165–174 (1993).

Milligan and Uhlenbeck, "Synthesis of Small RNAs Using T7 RNA Polymerase," *Methods Enzymol.* 180:51–62 (1989).

Nowak, "Xenotransplants Set to Resume," *Science* 266:1148–1151 (1994).

Ohkawa et al., "Activities of HIV–RNA Targeted Ribozymes Transcribed From a 'Shot–Gun' Type Ribozyme–trimming Plasmid," *Nucleic Acids Symp. Ser.* 27:15–16 (1992).

Ojwang et al., "Inhibition of Human Immunodeficiency Virus Type 1 Expression by a Hairpin Ribozyme," *Proc. Natl. Acad. Sci. USA* 89:10802–10806 (1992).

Perreault et al., "Mixed Deoxyribo–and Ribo–Oligonucleotides with Catalytic Acitvity," *Nature* 344:565–567 (1990).

Perrotta and Been, "Cleavage of Oligoribonucleotides by a Ribozyme Derived from the Hepatitis δ Virus RNA Sequence," *Biochemistry* 31:16–21 (1992).

Pieken et all, "Kinetic Characterization of Ribonuclease–Resistant 2'–Modified Hammerhead Ribozymes," *Science* 253:314–317 (1991).

Pretolani et al., "Cytokines–Eosinophil Interactions in Experimental Allergy," *Ann. N.Y. Acad. Sci.* 725:247–258 (1994).

Rossi et al, "Ribozymes as Anti–HIVI–1 Therapeutic Agents: Principles, Applications, and Problems," *Aids Research and Human Retroviruses* 8:183–189 (1992).

HAMMERHEAD RIBOZYME SUBSTRATE MOTIFS
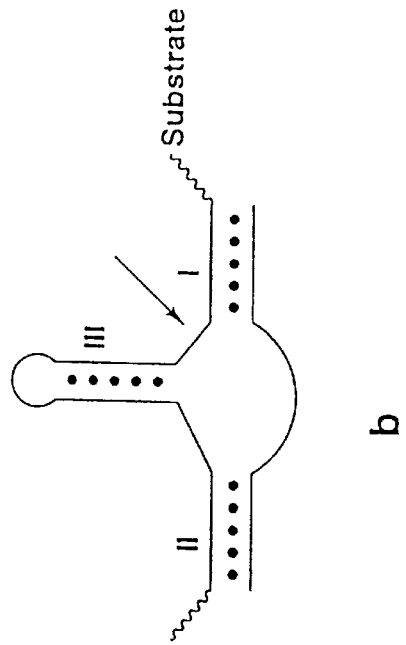
Fig. 2A
Fig. 2B
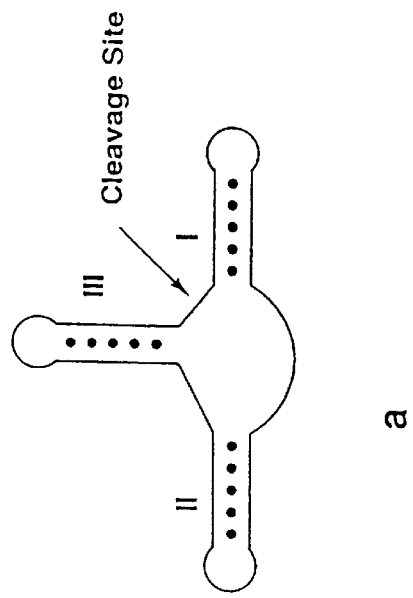
Fig. 2C
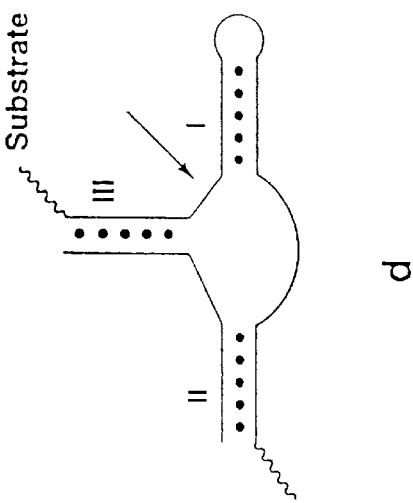
Fig. 2D
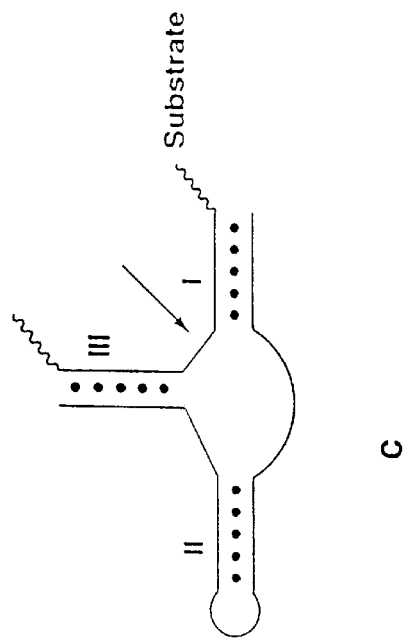

HEPATITIS DELTA VIRUS RIBOZYME

NEUROSPORA VS RNA ENZYME

RNase H Assay

- Body-labeled transcript (not purified)
- DNA oligo (10 nM, 100 nM and 1000 nM)
- RNAse H (0.08 - 1.0 u/μl)
- 37°C, 10 min

SEQUENCE LISTING ( 1 ) GENERAL INFORMATION:

( i i i ) NUMBER OF SEQUENCES: 2751

( 2 ) INFORMATION FOR SEQ ID NO:1:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

A A A C C C U C U G    U A A A G                                  1 5

( 2 ) INFORMATION FOR SEQ ID NO:2:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

CCUCUGUAAA GUAAC 15

( 2 ) INFORMATION FOR SEQ ID NO:3:

( i ) SEQUENCE CHARACTERISTICS:
       ( A ) LENGTH: 15 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:3:

GUAAAGUAAC AGAAG 15

( 2 ) INFORMATION FOR SEQ ID NO:4:

( i ) SEQUENCE CHARACTERISTICS:
       ( A ) LENGTH: 15 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:4:

CAGAAGUUAG AAGGG 15

( 2 ) INFORMATION FOR SEQ ID NO:5:

( i ) SEQUENCE CHARACTERISTICS:
       ( A ) LENGTH: 15 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:5:

AGAAGUUAGA AGGGG 15

( 2 ) INFORMATION FOR SEQ ID NO:6:

( i ) SEQUENCE CHARACTERISTICS:
       ( A ) LENGTH: 15 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:6:

GAAAUGUCGC CUCUC 15

( 2 ) INFORMATION FOR SEQ ID NO:7:

( i ) SEQUENCE CHARACTERISTICS:
       ( A ) LENGTH: 15 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:7:

GUCGCCUCUC UGAAG 15

( 2 ) INFORMATION FOR SEQ ID NO:8:

( i ) SEQUENCE CHARACTERISTICS:
       ( A ) LENGTH: 15 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:8:

CGCCUCUCUG AAGAU 15

( 2 ) INFORMATION FOR SEQ ID NO:9:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

UGAAGAUUAC CCAAA 15

( 2 ) INFORMATION FOR SEQ ID NO:10:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

GAAGAUUACC CAAAG 15

( 2 ) INFORMATION FOR SEQ ID NO:11:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

AAGUGAUUUG UCAUU 15

( 2 ) INFORMATION FOR SEQ ID NO:12:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

AGUGAUUUGU CAUUG 15

( 2 ) INFORMATION FOR SEQ ID NO:13:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

GAUUUGUCAU UGCUU 15

( 2 ) INFORMATION FOR SEQ ID NO:14:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

UUGUCAUUGC UUUAU 15

( 2 ) INFORMATION FOR SEQ ID NO:15:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

CAUUGCUUUA UAGAC         15

( 2 ) INFORMATION FOR SEQ ID NO:16:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

AUUGCUUUAU AGACU         15

( 2 ) INFORMATION FOR SEQ ID NO:17:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

UUGCUUUAUA GACUG         15

( 2 ) INFORMATION FOR SEQ ID NO:18:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

GCUUUAUAGA CUGUA         15

( 2 ) INFORMATION FOR SEQ ID NO:19:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

AGACUGUAAG AAGAG         15

( 2 ) INFORMATION FOR SEQ ID NO:20:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:20:

AGAACAUCUC AGAAG         15

( 2 ) INFORMATION FOR SEQ ID NO:21:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:21:

AACAUCUCAG AAGUG    15

( 2 ) INFORMATION FOR SEQ ID NO:22:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:22:

GUGGAGUCUU ACCCU    15

( 2 ) INFORMATION FOR SEQ ID NO:23:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:23:

GGAGUCUUAC CCUGA    15

( 2 ) INFORMATION FOR SEQ ID NO:24:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:24:

GAGUCUUACC CUGAA    15

( 2 ) INFORMATION FOR SEQ ID NO:25:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:25:

CUGAAAUCAA AGGAU    15

( 2 ) INFORMATION FOR SEQ ID NO:26:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:26:

AAAGGAUUUA AAGAA    15

( 2 ) INFORMATION FOR SEQ ID NO:27:

( i ) SEQUENCE CHARACTERISTICS:

(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:27:

AAGGAUUUAA AGAAA 15

(2) INFORMATION FOR SEQ ID NO:28:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:28:

AGGAUUUAAA GAAAA 15

(2) INFORMATION FOR SEQ ID NO:29:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:29:

GUGGAAUUUU UCUUC 15

(2) INFORMATION FOR SEQ ID NO:30:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:30:

UGGAAUUUUU CUUCA 15

(2) INFORMATION FOR SEQ ID NO:31:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:31:

GGAAUUUUUC UUCAG 15

(2) INFORMATION FOR SEQ ID NO:32:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:32:

GAAUUUUUCU UCAGC 15

(2) INFORMATION FOR SEQ ID NO:33:

(i) SEQUENCE CHARACTERISTICS:
(A) LENGTH: 15 base pairs
(B) TYPE: nucleic acid ( C ) STRANDEDNESS: single
( D ) TOPOLOGY: linear ( x i ) SEQUENCE DESCRIPTION: SEQ ID NO:33:

AAUUUUUCUU CAGCA 15

( 2 ) INFORMATION FOR SEQ ID NO:34:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:34:

UUUUUCUUCA GCAAG 15

( 2 ) INFORMATION FOR SEQ ID NO:35:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:35:

UUUUCUUCAG CAAGC 15

( 2 ) INFORMATION FOR SEQ ID NO:36:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:36:

UGAAACUAAA UCCAC 15

( 2 ) INFORMATION FOR SEQ ID NO:37:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:37:

ACUAAAUCCA CAACC 15

( 2 ) INFORMATION FOR SEQ ID NO:38:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:38:

ACAACCUUUG GAGAC 15

( 2 ) INFORMATION FOR SEQ ID NO:39:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:39:

CAACCUUUGG AGACC    15

( 2 ) INFORMATION FOR SEQ ID NO:40:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:40:

ACACCCUCCA AUCUC    15

( 2 ) INFORMATION FOR SEQ ID NO:41:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:41:

CUCCAAUCUC UGUGU    15

( 2 ) INFORMATION FOR SEQ ID NO:42:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:42:

CCAAUCUCUG UGUGU    15

( 2 ) INFORMATION FOR SEQ ID NO:43:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:43:

UGUGUGUUUU GUAAA    15

( 2 ) INFORMATION FOR SEQ ID NO:44:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:44:

GUGUGUUUUG UAAAC    15

( 2 ) INFORMATION FOR SEQ ID NO:45:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:45:

UGUGUUUUGU AAACA 15

( 2 ) INFORMATION FOR SEQ ID NO:46:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:46:

GUUUUGUAAA CAUCA 15

( 2 ) INFORMATION FOR SEQ ID NO:47:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:47:

UAAACAUCAC UGGAG 15

( 2 ) INFORMATION FOR SEQ ID NO:48:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:48:

GGAGGGUCUU CUACG 15

( 2 ) INFORMATION FOR SEQ ID NO:49:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:49:

AGGGUCUUCU ACGUG 15

( 2 ) INFORMATION FOR SEQ ID NO:50:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:50:

GGGUCUUCUA CGUGA 15

( 2 ) INFORMATION FOR SEQ ID NO:51:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:51:

GUCUUCUACG UGAGC 15

( 2 ) INFORMATION FOR SEQ ID NO:52:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:52:

GAGCAAUUGG AUUGU        15

( 2 ) INFORMATION FOR SEQ ID NO:53:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:53:

AUUGGAUUGU CAUCA        15

( 2 ) INFORMATION FOR SEQ ID NO:54:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:54:

GGAUUGUCAU CAGCC        15

( 2 ) INFORMATION FOR SEQ ID NO:55:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:55:

UUGUCAUCAG CCCUG        15

( 2 ) INFORMATION FOR SEQ ID NO:56:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:56:

UGCCUGUUUU GCACC        15

( 2 ) INFORMATION FOR SEQ ID NO:57:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:57:

GCCUGUUUUG CACCU        15

( 2 ) INFORMATION FOR SEQ ID NO:58:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:58:

CCUGUUUUGC ACCUG     15

( 2 ) INFORMATION FOR SEQ ID NO:59:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:59:

CCCUGGUCUU ACUUG     15

( 2 ) INFORMATION FOR SEQ ID NO:60:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:60:

CUGGUCUUAC UUGGG     15

( 2 ) INFORMATION FOR SEQ ID NO:61:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:61:

UGGUCUUACU UGGGU     15

( 2 ) INFORMATION FOR SEQ ID NO:62:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:62:

UCUUACUUGG GUCCA     15

( 2 ) INFORMATION FOR SEQ ID NO:63:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:63:

CUUGGGUCCA AAUUG     15

( 2 ) INFORMATION FOR SEQ ID NO:64:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:64:

UCCAAAUUGU UGGCU 15

( 2 ) INFORMATION FOR SEQ ID NO:65:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:65:

AAAUUGUUGG CUUUC 15

( 2 ) INFORMATION FOR SEQ ID NO:66:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:66:

GUUGGCUUUC ACUUU 15

( 2 ) INFORMATION FOR SEQ ID NO:67:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:67:

UUGGCUUUCA CUUUU 15

( 2 ) INFORMATION FOR SEQ ID NO:68:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:68:

UGGCUUUCAC UUUUG 15

( 2 ) INFORMATION FOR SEQ ID NO:69:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:69:

UUUCACUUUU GACCC 15

( 2 ) INFORMATION FOR SEQ ID NO:70:

( i ) SEQUENCE CHARACTERISTICS:
    ( A ) LENGTH: 15 base pairs (B) TYPE: nucleic acid
        (C) STRANDEDNESS: single
        (D) TOPOLOGY: linear (xi) SEQUENCE DESCRIPTION: SEQ ID NO:70:

UUCACUUUUG ACCCU                                                                                    15

(2) INFORMATION FOR SEQ ID NO:71:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:71:

UCACUUUUGA CCCUA                                                                                    15

(2) INFORMATION FOR SEQ ID NO:72:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:72:

UGACCCUAAG CAUCU                                                                                    15

(2) INFORMATION FOR SEQ ID NO:73:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:73:

UAAGCAUCUG AAGCC                                                                                    15

(2) INFORMATION FOR SEQ ID NO:74:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:74:

GGAACAUCAC CAUCC                                                                                    15

(2) INFORMATION FOR SEQ ID NO:75:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:75:

UCACCAUCCA AGUGU                                                                                    15

(2) INFORMATION FOR SEQ ID NO:76:

(i) SEQUENCE CHARACTERISTICS:
        (A) LENGTH: 15 base pairs
        (B) TYPE: nucleic acid
        (C) STRANDEDNESS: single ( D ) TOPOLOGY: linear ( x i ) SEQUENCE DESCRIPTION: SEQ ID NO:76:

CAAGUGUCCA UACCU                                                                                15

( 2 ) INFORMATION FOR SEQ ID NO:77:

( i ) SEQUENCE CHARACTERISTICS:
             ( A ) LENGTH: 15 base pairs
             ( B ) TYPE: nucleic acid
             ( C ) STRANDEDNESS: single
             ( D ) TOPOLOGY: linear ( x i ) SEQUENCE DESCRIPTION: SEQ ID NO:77:

UGUCCAUACC UCAAU                                                                                15

( 2 ) INFORMATION FOR SEQ ID NO:78:

( i ) SEQUENCE CHARACTERISTICS:
             ( A ) LENGTH: 15 base pairs
             ( B ) TYPE: nucleic acid
             ( C ) STRANDEDNESS: single
             ( D ) TOPOLOGY: linear ( x i ) SEQUENCE DESCRIPTION: SEQ ID NO:78:

CAUACCUCAA UUUCU                                                                                15

( 2 ) INFORMATION FOR SEQ ID NO:79:

( i ) SEQUENCE CHARACTERISTICS:
             ( A ) LENGTH: 15 base pairs
             ( B ) TYPE: nucleic acid
             ( C ) STRANDEDNESS: single
             ( D ) TOPOLOGY: linear ( x i ) SEQUENCE DESCRIPTION: SEQ ID NO:79:

CCUCAAUUUC UUUCA                                                                                15

( 2 ) INFORMATION FOR SEQ ID NO:80:

( i ) SEQUENCE CHARACTERISTICS:
             ( A ) LENGTH: 15 base pairs
             ( B ) TYPE: nucleic acid
             ( C ) STRANDEDNESS: single
             ( D ) TOPOLOGY: linear ( x i ) SEQUENCE DESCRIPTION: SEQ ID NO:80:

CUCAAUUUCU UUCAG                                                                                15

( 2 ) INFORMATION FOR SEQ ID NO:81:

( i ) SEQUENCE CHARACTERISTICS:
             ( A ) LENGTH: 15 base pairs
             ( B ) TYPE: nucleic acid
             ( C ) STRANDEDNESS: single
             ( D ) TOPOLOGY: linear ( x i ) SEQUENCE DESCRIPTION: SEQ ID NO:81:

UCAAUUUCUU UCAGC                                                                                15

( 2 ) INFORMATION FOR SEQ ID NO:82:

( i ) SEQUENCE CHARACTERISTICS:
             ( A ) LENGTH: 15 base pairs
             ( B ) TYPE: nucleic acid
             ( C ) STRANDEDNESS: single
             ( D ) TOPOLOGY: linear ( x i ) SEQUENCE DESCRIPTION: SEQ ID NO:82:

AAUUCUUUC AGCUC 15

( 2 ) INFORMATION FOR SEQ ID NO:83:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:83:

AUUUCUUUCA GCUCU 15

( 2 ) INFORMATION FOR SEQ ID NO:84:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:84:

UUUCUUUCAG CUCUU 15

( 2 ) INFORMATION FOR SEQ ID NO:85:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:85:

UUCAGCUCUU GGUGC 15

( 2 ) INFORMATION FOR SEQ ID NO:86:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:86:

CAGCUCUUGG UGCUG 15

( 2 ) INFORMATION FOR SEQ ID NO:87:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:87:

GGCUGGUCUU UCUCA 15

( 2 ) INFORMATION FOR SEQ ID NO:88:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:88:

CUGGUCUUUC UCACU 15

( 2 ) INFORMATION FOR SEQ ID NO:89:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:89:

UGGUCUUUCU CACUU 15

( 2 ) INFORMATION FOR SEQ ID NO:90:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:90:

GGUCUUUCUC ACUUC 15

( 2 ) INFORMATION FOR SEQ ID NO:91:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:91:

UCUUUCUCAC UUCUG 15

( 2 ) INFORMATION FOR SEQ ID NO:92:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:92:

UCUCACUUCU GUUCA 15

( 2 ) INFORMATION FOR SEQ ID NO:93:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:93:

CUCACUUCUG UUCAG 15

( 2 ) INFORMATION FOR SEQ ID NO:94:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:94:

CUUCUGUUCA GGUGU 15

( 2 ) INFORMATION FOR SEQ ID NO:95:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:95:

UUCUGUUCAG GUGUU         15

( 2 ) INFORMATION FOR SEQ ID NO:96:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:96:

CAGGUGUUAU CCACG         15

( 2 ) INFORMATION FOR SEQ ID NO:97:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:97:

AGGUGUUAUC CACGU         15

( 2 ) INFORMATION FOR SEQ ID NO:98:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:98:

GUGUUAUCCA CGUGA         15

( 2 ) INFORMATION FOR SEQ ID NO:99:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:99:

ACGCUGUCCU GUGGU         15

( 2 ) INFORMATION FOR SEQ ID NO:100:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:100:

CUGUGGUCAC AAUGU         15

( 2 ) INFORMATION FOR SEQ ID NO:101:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:101:

ACAAUGUUUC UGUUG 15

( 2 ) INFORMATION FOR SEQ ID NO:102:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:102:

CAAUGUUUCU GUUGA 15

( 2 ) INFORMATION FOR SEQ ID NO:103:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:103:

AAUGUUUCUG UUGAA 15

( 2 ) INFORMATION FOR SEQ ID NO:104:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:104:

UUUCUGUUGA AGAGC 15

( 2 ) INFORMATION FOR SEQ ID NO:105:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:105:

ACAAACUCGC AUCUA 15

( 2 ) INFORMATION FOR SEQ ID NO:106:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:106:

CUCGCAUCUA CUGGC 15

( 2 ) INFORMATION FOR SEQ ID NO:107:

( i ) SEQUENCE CHARACTERISTICS:

(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:107:

CGCAUCUACU GGCAA 15

(2) INFORMATION FOR SEQ ID NO:108:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:108:

GCUGACUAUG AUGUC 15

(2) INFORMATION FOR SEQ ID NO:109:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:109:

AUGAUGUCUG GGGAC 15

(2) INFORMATION FOR SEQ ID NO:110:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:110:

CAUGAAUAUA UGGCC 15

(2) INFORMATION FOR SEQ ID NO:111:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:111:

UGAAUAUAUG GCCCG 15

(2) INFORMATION FOR SEQ ID NO:112:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:112:

CCCGAGUACA AGAAC 15

(2) INFORMATION FOR SEQ ID NO:113:

(i) SEQUENCE CHARACTERISTICS:
(A) LENGTH: 15 base pairs
(B) TYPE: nucleic acid (C) STRANDEDNESS: single
            (D) TOPOLOGY: linear (xi) SEQUENCE DESCRIPTION: SEQ ID NO:113:

GGACCAUCUU UGAUA                                                    15

(2) INFORMATION FOR SEQ ID NO:114:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO:114:

ACCAUCUUUG AUAUC                                                    15

(2) INFORMATION FOR SEQ ID NO:115:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO:115:

CCAUCUUUGA UAUCA                                                    15

(2) INFORMATION FOR SEQ ID NO:116:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO:116:

CUUUGAUAUC ACUAA                                                    15

(2) INFORMATION FOR SEQ ID NO:117:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO:117:

UUGAUAUCAC UAAUA                                                    15

(2) INFORMATION FOR SEQ ID NO:118:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO:118:

UAUCACUAAU AACCU                                                    15

(2) INFORMATION FOR SEQ ID NO:119:

(i) SEQUENCE CHARACTERISTICS:
            (A) LENGTH: 15 base pairs
            (B) TYPE: nucleic acid
            (C) STRANDEDNESS: single
            (D) TOPOLOGY: linear ( x i ) SEQUENCE DESCRIPTION: SEQ ID NO:119:

CACUAAUAAC CUCUC 15

( 2 ) INFORMATION FOR SEQ ID NO:120:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:120:

AUAACCUCUC CAUUG 15

( 2 ) INFORMATION FOR SEQ ID NO:121:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:121:

AACCUCUCCA UUGUG 15

( 2 ) INFORMATION FOR SEQ ID NO:122:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:122:

UCUCCAUUGU GAUCC 15

( 2 ) INFORMATION FOR SEQ ID NO:123:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:123:

UUGUGAUCCU GGCUC 15

( 2 ) INFORMATION FOR SEQ ID NO:124:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:124:

CCUGGCUCUG CGCCC 15

( 2 ) INFORMATION FOR SEQ ID NO:125:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:125:

CGCCCAUCUG ACGAG                                                                15

( 2 ) INFORMATION FOR SEQ ID NO:126:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:126:

GGCACAUACG AGUGU                                                                15

( 2 ) INFORMATION FOR SEQ ID NO:127:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:127:

AGUGUGUUGU UCUGA                                                                15

( 2 ) INFORMATION FOR SEQ ID NO:128:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:128:

GUGUUGUUCU GAAGU                                                                15

( 2 ) INFORMATION FOR SEQ ID NO:129:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:129:

UGUUGUUCUG AAGUA                                                                15

( 2 ) INFORMATION FOR SEQ ID NO:130:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:130:

CUGAAGUAUG AAAAA                                                                15

( 2 ) INFORMATION FOR SEQ ID NO:131:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:131:

AGACGCUUUC AAGCG                                                                15

( 2 ) INFORMATION FOR SEQ ID NO:132:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:132:

GACGCUUUCA AGCGG            15

( 2 ) INFORMATION FOR SEQ ID NO:133:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:133:

ACGCUUUCAA GCGGG            15

( 2 ) INFORMATION FOR SEQ ID NO:134:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:134:

GUGACGUUAU CAGUC            15

( 2 ) INFORMATION FOR SEQ ID NO:135:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:135:

UGACGUUAUC AGUCA            15

( 2 ) INFORMATION FOR SEQ ID NO:136:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:136:

ACGUUAUCAG UCAAA            15

( 2 ) INFORMATION FOR SEQ ID NO:137:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:137:

UAUCAGUCAA AGCUG            15

( 2 ) INFORMATION FOR SEQ ID NO:138:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:138:

GCUGACUUCC CUACA          15

( 2 ) INFORMATION FOR SEQ ID NO:139:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:139:

CUGACUUCCC UACAC          15

( 2 ) INFORMATION FOR SEQ ID NO:140:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:140:

CUUCCCUACA CCUAG          15

( 2 ) INFORMATION FOR SEQ ID NO:141:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:141:

UACACCUAGU AUAUC          15

( 2 ) INFORMATION FOR SEQ ID NO:142:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:142:

ACCUAGUAUA UCUGA          15

( 2 ) INFORMATION FOR SEQ ID NO:143:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:143:

CUAGUAUAUC UGACU          15

( 2 ) INFORMATION FOR SEQ ID NO:144:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:144:

AGUAUAUCUG ACUUU 15

( 2 ) INFORMATION FOR SEQ ID NO:145:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:145:

UCUGACUUUG AAAUU 15

( 2 ) INFORMATION FOR SEQ ID NO:146:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:146:

CUGACUUUGA AAUUC 15

( 2 ) INFORMATION FOR SEQ ID NO:147:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:147:

UUGAAAUUCC AACUU 15

( 2 ) INFORMATION FOR SEQ ID NO:148:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:148:

UGAAAUUCCA ACUUC 15

( 2 ) INFORMATION FOR SEQ ID NO:149:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:149:

UCCAACUUCU AAUAU 15

( 2 ) INFORMATION FOR SEQ ID NO:150:

( i ) SEQUENCE CHARACTERISTICS:
    ( A ) LENGTH: 15 base pairs (B) TYPE: nucleic acid
        (C) STRANDEDNESS: single
        (D) TOPOLOGY: linear (xi) SEQUENCE DESCRIPTION: SEQ ID NO:150:

CCAACUUCUA AUAUU 15

(2) INFORMATION FOR SEQ ID NO:151:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:151:

AACUUCUAAU AUUAG 15

(2) INFORMATION FOR SEQ ID NO:152:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:152:

UUCUAAUAUU AGAAG 15

(2) INFORMATION FOR SEQ ID NO:153:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:153:

CUAAUAUUAG AAGGA 15

(2) INFORMATION FOR SEQ ID NO:154:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:154:

UAAUAUUAGA AGGAU 15

(2) INFORMATION FOR SEQ ID NO:155:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:155:

GAAGGAUAAU UUGCU 15

(2) INFORMATION FOR SEQ ID NO:156:

(i) SEQUENCE CHARACTERISTICS:
        (A) LENGTH: 15 base pairs
        (B) TYPE: nucleic acid
        (C) STRANDEDNESS: single ( D ) TOPOLOGY: linear ( x i ) SEQUENCE DESCRIPTION: SEQ ID NO:156:

GGAUAAUUUG CUCAA 15

( 2 ) INFORMATION FOR SEQ ID NO:157:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:157:

GAUAAUUUGC UCAAC 15

( 2 ) INFORMATION FOR SEQ ID NO:158:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:158:

AUUUGCUCAA CCUCU 15

( 2 ) INFORMATION FOR SEQ ID NO:159:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:159:

UCAACCUCUG GAGGU 15

( 2 ) INFORMATION FOR SEQ ID NO:160:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:160:

UGGAGGUUUU CCAGA 15

( 2 ) INFORMATION FOR SEQ ID NO:161:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:161:

GGAGGUUUUC CAGAG 15

( 2 ) INFORMATION FOR SEQ ID NO:162:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:162:

GAGGUUUUCC AGAGC 15

( 2 ) INFORMATION FOR SEQ ID NO:163:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:163:

AGGUUUUCCA GAGCC 15

( 2 ) INFORMATION FOR SEQ ID NO:164:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:164:

AGAGCCUCAC CUCUC 15

( 2 ) INFORMATION FOR SEQ ID NO:165:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:165:

CUCACCUCUC CUGGU 15

( 2 ) INFORMATION FOR SEQ ID NO:166:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:166:

CACCUCUCCU GGUUG 15

( 2 ) INFORMATION FOR SEQ ID NO:167:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:167:

UCCUGGUUGG AAAAU 15

( 2 ) INFORMATION FOR SEQ ID NO:168:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:168:

GAAGAAUUAA AUGCC 15

(2) INFORMATION FOR SEQ ID NO:169:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:169:

AAGAAUUAAA UGCCA 15

(2) INFORMATION FOR SEQ ID NO:170:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:170:

AUGCCAUCAA CACAA 15

(2) INFORMATION FOR SEQ ID NO:171:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:171:

CAACAGUUUC CCAAG 15

(2) INFORMATION FOR SEQ ID NO:172:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:172:

AACAGUUUCC CAAGA 15

(2) INFORMATION FOR SEQ ID NO:173:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:173:

ACAGUUUCCC AAGAU 15

(2) INFORMATION FOR SEQ ID NO:174:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:174:

CCAAGAUCCU GAAAC 15

( 2 ) INFORMATION FOR SEQ ID NO:175:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:175:

CUGAGCUCUA UGCUG 15

( 2 ) INFORMATION FOR SEQ ID NO:176:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:176:

GAGCUCUAUG CUGUU 15

( 2 ) INFORMATION FOR SEQ ID NO:177:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:177:

AUGCUGUUAG CAGCA 15

( 2 ) INFORMATION FOR SEQ ID NO:178:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:178:

UGCUGUUAGC AGCAA 15

( 2 ) INFORMATION FOR SEQ ID NO:179:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:179:

ACUGGAUUUC AAUAU 15

( 2 ) INFORMATION FOR SEQ ID NO:180:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:180:

CUGGAUUUCA AUAUG 15

( 2 ) INFORMATION FOR SEQ ID NO:181:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:181:

UGGAUUUCAA UAUGA 15

( 2 ) INFORMATION FOR SEQ ID NO:182:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:182:

UUUCAAUAUG ACAAC 15

( 2 ) INFORMATION FOR SEQ ID NO:183:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:183:

CACAGCUUCA UGUGU 15

( 2 ) INFORMATION FOR SEQ ID NO:184:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:184:

ACAGCUUCAU GUGUC 15

( 2 ) INFORMATION FOR SEQ ID NO:185:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:185:

CAUGUGUCUC AUCAA 15

( 2 ) INFORMATION FOR SEQ ID NO:186:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:186:

UGUGUCUCAU CAAGU 15

( 2 ) INFORMATION FOR SEQ ID NO:187:

( i ) SEQUENCE CHARACTERISTICS:

(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:187:

GUCUCAUCAA GUAUG 15

(2) INFORMATION FOR SEQ ID NO:188:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:188:

AUCAAGUAUG GACAU 15

(2) INFORMATION FOR SEQ ID NO:189:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:189:

UGGACAUUUA AGAGU 15

(2) INFORMATION FOR SEQ ID NO:190:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:190:

GGACAUUUAA GAGUG 15

(2) INFORMATION FOR SEQ ID NO:191:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:191:

GACAUUUAAG AGUGA 15

(2) INFORMATION FOR SEQ ID NO:192:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:192:

AGUGAAUCAG ACCUU 15

(2) INFORMATION FOR SEQ ID NO:193:

(i) SEQUENCE CHARACTERISTICS:
(A) LENGTH: 15 base pairs
(B) TYPE: nucleic acid (C) STRANDEDNESS: single
(D) TOPOLOGY: linear (xi) SEQUENCE DESCRIPTION: SEQ ID NO:193:

CAGACCUUCA ACUGG 15

(2) INFORMATION FOR SEQ ID NO:194:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:194:

AGACCUUCAA CUGGA 15

(2) INFORMATION FOR SEQ ID NO:195:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:195:

CUGGAAUACA ACCAA 15

(2) INFORMATION FOR SEQ ID NO:196:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:196:

AGAGCAUUUU CCUGA 15

(2) INFORMATION FOR SEQ ID NO:197:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:197:

GAGCAUUUUC CUGAU 15

(2) INFORMATION FOR SEQ ID NO:198:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:198:

AGCAUUUUCC UGAUA 15

(2) INFORMATION FOR SEQ ID NO:199:

(i) SEQUENCE CHARACTERISTICS:
(A) LENGTH: 15 base pairs
(B) TYPE: nucleic acid
(C) STRANDEDNESS: single
(D) TOPOLOGY: linear ( x i ) SEQUENCE DESCRIPTION: SEQ ID NO:199:

GCAUUUUCCU GAUAA                                                                                          15

( 2 ) INFORMATION FOR SEQ ID NO:200:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:200:

UCCUGAUAAC CUGCU                                                                                          15

( 2 ) INFORMATION FOR SEQ ID NO:201:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:201:

ACCUGCUCCC AUCCU                                                                                          15

( 2 ) INFORMATION FOR SEQ ID NO:202:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:202:

CUCCCAUCCU GGGCC                                                                                          15

( 2 ) INFORMATION FOR SEQ ID NO:203:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:203:

GGGCCAUUAC CUUAA                                                                                          15

( 2 ) INFORMATION FOR SEQ ID NO:204:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:204:

GGCCAUUACC UUAAU                                                                                          15

( 2 ) INFORMATION FOR SEQ ID NO:205:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:205:

```
AUUACCUUAA UCUCA                                                                                15
```

(2) INFORMATION FOR SEQ ID NO:206:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (xi) SEQUENCE DESCRIPTION: SEQ ID NO:206:

```
UUACCUUAAU CUCAG                                                                                15
```

(2) INFORMATION FOR SEQ ID NO:207:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (xi) SEQUENCE DESCRIPTION: SEQ ID NO:207:

```
CCUUAAUCUC AGUAA                                                                                15
```

(2) INFORMATION FOR SEQ ID NO:208:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (xi) SEQUENCE DESCRIPTION: SEQ ID NO:208:

```
UUAAUCUCAG UAAAU                                                                                15
```

(2) INFORMATION FOR SEQ ID NO:209:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (xi) SEQUENCE DESCRIPTION: SEQ ID NO:209:

```
UCUCAGUAAA UGGAA                                                                                15
```

(2) INFORMATION FOR SEQ ID NO:210:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (xi) SEQUENCE DESCRIPTION: SEQ ID NO:210:

```
AUGGAAUUUU UGUGA                                                                                15
```

(2) INFORMATION FOR SEQ ID NO:211:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (xi) SEQUENCE DESCRIPTION: SEQ ID NO:211:

```
UGGAAUUUUU GUGAU                                                                                15
```

( 2 ) INFORMATION FOR SEQ ID NO:212:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:212:

GGAAUUUUUG UGAUA 15

( 2 ) INFORMATION FOR SEQ ID NO:213:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:213:

GAAUUUUUGU GAUAU 15

( 2 ) INFORMATION FOR SEQ ID NO:214:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:214:

UUGUGAUAUG CUGCC 15

( 2 ) INFORMATION FOR SEQ ID NO:215:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:215:

CUGACCUACU GCUUU 15

( 2 ) INFORMATION FOR SEQ ID NO:216:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:216:

UACUGCUUUG CCCCA 15

( 2 ) INFORMATION FOR SEQ ID NO:217:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:217:

ACUGCUUUGC CCCAA 15

( 2 ) INFORMATION FOR SEQ ID NO:218:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:218:

GAGAGAUUGA GAAGG                                        15

( 2 ) INFORMATION FOR SEQ ID NO:219:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:219:

AAAGUGUACG CCCUG                                        15

( 2 ) INFORMATION FOR SEQ ID NO:220:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:220:

GCCCUGUAUA ACAGU                                        15

( 2 ) INFORMATION FOR SEQ ID NO:221:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:221:

CCUGUAUAAC AGUGU                                        15

( 2 ) INFORMATION FOR SEQ ID NO:222:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:222:

ACAGUGUCCG CAGAA                                        15

( 2 ) INFORMATION FOR SEQ ID NO:223:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:223:

AAAAGAUCUG AAGGU                                        15

( 2 ) INFORMATION FOR SEQ ID NO:224:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:224:

UGAAGGUAGC CUCCG 15

( 2 ) INFORMATION FOR SEQ ID NO:225:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:225:

GUAGCCUCCG UCAUC 15

( 2 ) INFORMATION FOR SEQ ID NO:226:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:226:

CCUCCGUCAU CUCUU 15

( 2 ) INFORMATION FOR SEQ ID NO:227:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:227:

CCGUCAUCUC UUCUG 15

( 2 ) INFORMATION FOR SEQ ID NO:228:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:228:

GUCAUCUCUU CUGGG 15

( 2 ) INFORMATION FOR SEQ ID NO:229:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:229:

CAUCUCUUCU GGGAU 15

( 2 ) INFORMATION FOR SEQ ID NO:230:

( i ) SEQUENCE CHARACTERISTICS:
    ( A ) LENGTH: 15 base pairs (B) TYPE: nucleic acid
(C) STRANDEDNESS: single
(D) TOPOLOGY: linear (xi) SEQUENCE DESCRIPTION: SEQ ID NO:230:

AUCUCUUCUG GGAUA                                                                                                15

(2) INFORMATION FOR SEQ ID NO:231:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:231:

CUGGGAUACA UGGAU                                                                                                15

(2) INFORMATION FOR SEQ ID NO:232:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:232:

CAUGGAUCGU GGGGA                                                                                                15

(2) INFORMATION FOR SEQ ID NO:233:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:233:

UGGGGAUCAU GAGGC                                                                                                15

(2) INFORMATION FOR SEQ ID NO:234:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:234:

GAGGCAUUCU UCCCU                                                                                                15

(2) INFORMATION FOR SEQ ID NO:235:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:235:

AGGCAUUCUU CCCUU                                                                                                15

(2) INFORMATION FOR SEQ ID NO:236:

(i) SEQUENCE CHARACTERISTICS:
(A) LENGTH: 15 base pairs
(B) TYPE: nucleic acid
(C) STRANDEDNESS: single (D) TOPOLOGY: linear (xi) SEQUENCE DESCRIPTION: SEQ ID NO:236:

GCAUUCUUCC CUUAA                                                                                        15

(2) INFORMATION FOR SEQ ID NO:237:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:237:

CAUUCUUCCC UUAAC                                                                                        15

(2) INFORMATION FOR SEQ ID NO:238:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:238:

CUUCCCUUAA CAAAU                                                                                        15

(2) INFORMATION FOR SEQ ID NO:239:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:239:

UUCCCUUAAC AAAUU                                                                                        15

(2) INFORMATION FOR SEQ ID NO:240:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:240:

AACAAAUUUA AGCUG                                                                                        15

(2) INFORMATION FOR SEQ ID NO:241:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:241:

ACAAAUUUAA GCUGU                                                                                        15

(2) INFORMATION FOR SEQ ID NO:242:

(i) SEQUENCE CHARACTERISTICS:
        (A) LENGTH: 15 base pairs
        (B) TYPE: nucleic acid
        (C) STRANDEDNESS: single
        (D) TOPOLOGY: linear ( x i ) SEQUENCE DESCRIPTION: SEQ ID NO:242:

CAAAUUUAAG CUGUU 15

( 2 ) INFORMATION FOR SEQ ID NO:243:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:243:

AAGCUGUUUU ACCCA 15

( 2 ) INFORMATION FOR SEQ ID NO:244:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:244:

AGCUGUUUUA CCCAC 15

( 2 ) INFORMATION FOR SEQ ID NO:245:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:245:

GCUGUUUUAC CCACU 15

( 2 ) INFORMATION FOR SEQ ID NO:246:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:246:

CUGUUUUACC CACUA 15

( 2 ) INFORMATION FOR SEQ ID NO:247:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:247:

ACCCACUACC UCACC 15

( 2 ) INFORMATION FOR SEQ ID NO:248:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:248:

ACUACCUCAC CUUCU                                                                                    15

( 2 ) INFORMATION FOR SEQ ID NO:249:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:249:

CUCACCUUCU UAAAA                                                                                    15

( 2 ) INFORMATION FOR SEQ ID NO:250:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:250:

UCACCUUCUU AAAAA                                                                                    15

( 2 ) INFORMATION FOR SEQ ID NO:251:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:251:

ACCUUCUUAA AAACC                                                                                    15

( 2 ) INFORMATION FOR SEQ ID NO:252:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:252:

CCUUCUUAAA AACCU                                                                                    15

( 2 ) INFORMATION FOR SEQ ID NO:253:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:253:

AAAACCUCUU UCAGA                                                                                    15

( 2 ) INFORMATION FOR SEQ ID NO:254:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:254:

AACCUCUUUC AGAUU                                                                                    15

( 2 ) INFORMATION FOR SEQ ID NO:255:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:255:

ACCUCUUUCA GAUUA　　　　　　　　　　　　　　　　　　　　　　　15

( 2 ) INFORMATION FOR SEQ ID NO:256:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:256:

CCUCUUUCAG AUUAA　　　　　　　　　　　　　　　　　　　　　　　15

( 2 ) INFORMATION FOR SEQ ID NO:257:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:257:

UUCAGAUUAA GCUGA　　　　　　　　　　　　　　　　　　　　　　　15

( 2 ) INFORMATION FOR SEQ ID NO:258:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:258:

UCAGAUUAAG CUGAA　　　　　　　　　　　　　　　　　　　　　　　15

( 2 ) INFORMATION FOR SEQ ID NO:259:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:259:

GAACAGUUAC AAGAU　　　　　　　　　　　　　　　　　　　　　　　15

( 2 ) INFORMATION FOR SEQ ID NO:260:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:260:

AACAGUUACA AGAUG　　　　　　　　　　　　　　　　　　　　　　　15

( 2 ) INFORMATION FOR SEQ ID NO:261:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:261:

CUGGCAUCCC UCUCC 15

( 2 ) INFORMATION FOR SEQ ID NO:262:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:262:

CAUCCCUCUC CUUUC 15

( 2 ) INFORMATION FOR SEQ ID NO:263:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:263:

UCCCUCUCCU UUCUC 15

( 2 ) INFORMATION FOR SEQ ID NO:264:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:264:

CUCUCCUUUC UCCCC 15

( 2 ) INFORMATION FOR SEQ ID NO:265:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:265:

UCUCCUUUCU CCCCA 15

( 2 ) INFORMATION FOR SEQ ID NO:266:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:266:

CUCCUUUCUC CCCAU 15

( 2 ) INFORMATION FOR SEQ ID NO:267:

( i ) SEQUENCE CHARACTERISTICS:

(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:267:

CCUUUCUCCC CAUAU 15

(2) INFORMATION FOR SEQ ID NO:268:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:268:

UCCCCAUAUG CAAUU 15

(2) INFORMATION FOR SEQ ID NO:269:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:269:

AUGCAAUUUG CUUAA 15

(2) INFORMATION FOR SEQ ID NO:270:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:270:

UGCAAUUUGC UUAAU 15

(2) INFORMATION FOR SEQ ID NO:271:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:271:

AUUUGCUUAA UGUAA 15

(2) INFORMATION FOR SEQ ID NO:272:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:272:

UUUGCUUAAU GUAAC 15

(2) INFORMATION FOR SEQ ID NO:273:

(i) SEQUENCE CHARACTERISTICS:
(A) LENGTH: 15 base pairs
(B) TYPE: nucleic acid (C) STRANDEDNESS: single
(D) TOPOLOGY: linear (xi) SEQUENCE DESCRIPTION: SEQ ID NO:273:

UUAAUGUAAC CUCUU  15

(2) INFORMATION FOR SEQ ID NO:274:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:274:

GUAACCUCUU CUUUU  15

(2) INFORMATION FOR SEQ ID NO:275:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:275:

AACCUCUUCU UUUGC  15

(2) INFORMATION FOR SEQ ID NO:276:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:276:

ACCUCUUCUU UUGCC  15

(2) INFORMATION FOR SEQ ID NO:277:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:277:

CUCUUCUUUU GCCAU  15

(2) INFORMATION FOR SEQ ID NO:278:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:278:

UCUUCUUUUG CCAUG  15

(2) INFORMATION FOR SEQ ID NO:279:

(i) SEQUENCE CHARACTERISTICS:
(A) LENGTH: 15 base pairs
(B) TYPE: nucleic acid
(C) STRANDEDNESS: single
(D) TOPOLOGY: linear ( x i ) SEQUENCE DESCRIPTION: SEQ ID NO:279:

CUUCUUUUGC CAUGU    15

( 2 ) INFORMATION FOR SEQ ID NO:280:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:280:

GCCAUGUUUC CAUUC    15

( 2 ) INFORMATION FOR SEQ ID NO:281:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:281:

CCAUGUUUCC AUUCU    15

( 2 ) INFORMATION FOR SEQ ID NO:282:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:282:

CAUGUUUCCA UUCUG    15

( 2 ) INFORMATION FOR SEQ ID NO:283:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:283:

UUUCCAUUCU GCCAU    15

( 2 ) INFORMATION FOR SEQ ID NO:284:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:284:

UUCCAUUCUG CCAUC    15

( 2 ) INFORMATION FOR SEQ ID NO:285:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:285:

CUGCCAUCUU GAAUU                                                                 15

( 2 ) INFORMATION FOR SEQ ID NO:286:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:286:

GCCAUCUUGA AUUGU                                                                 15

( 2 ) INFORMATION FOR SEQ ID NO:287:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:287:

CUUGAAUUGU CUUGU                                                                 15

( 2 ) INFORMATION FOR SEQ ID NO:288:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:288:

GAAUUGUCUU GUCAG                                                                 15

( 2 ) INFORMATION FOR SEQ ID NO:289:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:289:

AUUGUCUUGU CAGCC                                                                 15

( 2 ) INFORMATION FOR SEQ ID NO:290:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:290:

GUCUUGUCAG CCAAU                                                                 15

( 2 ) INFORMATION FOR SEQ ID NO:291:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:291:

AGCCAAUUCA UUAUC                                                                 15

( 2 ) INFORMATION FOR SEQ ID NO:292:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:292:

GCCAAUUCAU UAUCU     15

( 2 ) INFORMATION FOR SEQ ID NO:293:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:293:

AAUUCAUUAU CUAUU     15

( 2 ) INFORMATION FOR SEQ ID NO:294:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:294:

AUUCAUUAUC UAUUA     15

( 2 ) INFORMATION FOR SEQ ID NO:295:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:295:

UCAUUAUCUA UUAAA     15

( 2 ) INFORMATION FOR SEQ ID NO:296:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:296:

AUUAUCUAUU AAACA     15

( 2 ) INFORMATION FOR SEQ ID NO:297:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:297:

UAUCUAUUAA ACACU     15

(2) INFORMATION FOR SEQ ID NO:298:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:298:

AUCUAUUAAA CACUA     15

(2) INFORMATION FOR SEQ ID NO:299:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:299:

AAACACUAAU UUGAG     15

(2) INFORMATION FOR SEQ ID NO:300:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:300:

CUUUACACUG AUGAGGCCGA AAGGCCGAAA GGGUUU     36

(2) INFORMATION FOR SEQ ID NO:301:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:301:

GUUACUUCUG AUGAGGCCGA AAGGCCGAAA CAGAGG     36

(2) INFORMATION FOR SEQ ID NO:302:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:302:

CUUCUGUCUG AUGAGGCCGA AAGGCCGAAA CUUUAC     36

(2) INFORMATION FOR SEQ ID NO:303:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:303:

CCCUUCUCUG AUGAGGCCGA AAGGCCGAAA CUUCUG     36

(2) INFORMATION FOR SEQ ID NO:304:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:304:

CCCCUUCCUG AUGAGGCCGA AAGGCCGAAA ACUUCU  36

( 2 ) INFORMATION FOR SEQ ID NO:305:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:305:

GAGAGGCCUG AUGAGGCCGA AAGGCCGAAA CAUUUC  36

( 2 ) INFORMATION FOR SEQ ID NO:306:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:306:

CUUCAGACUG AUGAGGCCGA AAGGCCGAAA GGCGAC  36

( 2 ) INFORMATION FOR SEQ ID NO:307:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:307:

AUCUUCACUG AUGAGGCCGA AAGGCCGAAA GAGGCG  36

( 2 ) INFORMATION FOR SEQ ID NO:308:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:308:

UUUGGGUCUG AUGAGGCCGA AAGGCCGAAA UCUUCA  36

( 2 ) INFORMATION FOR SEQ ID NO:309:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:309:

CUUUGGGCUG AUGAGGCCGA AAGGCCGAAA AUCUUC  36

( 2 ) INFORMATION FOR SEQ ID NO:310:

( i ) SEQUENCE CHARACTERISTICS:
        ( A ) LENGTH: 36 base pairs (B) TYPE: nucleic acid
(C) STRANDEDNESS: single
(D) TOPOLOGY: linear (xi) SEQUENCE DESCRIPTION: SEQ ID NO:310:

AAUGACACUG AUGAGGCCGA AAGGCCGAAA UCACUU  36

(2) INFORMATION FOR SEQ ID NO:311:

(i) SEQUENCE CHARACTERISTICS:
  (A) LENGTH: 36 base pairs
  (B) TYPE: nucleic acid
  (C) STRANDEDNESS: single
  (D) TOPOLOGY: linear (xi) SEQUENCE DESCRIPTION: SEQ ID NO:311:

CAAUGACCUG AUGAGGCCGA AAGGCCGAAA AUCACU  36

(2) INFORMATION FOR SEQ ID NO:312:

(i) SEQUENCE CHARACTERISTICS:
  (A) LENGTH: 36 base pairs
  (B) TYPE: nucleic acid
  (C) STRANDEDNESS: single
  (D) TOPOLOGY: linear (xi) SEQUENCE DESCRIPTION: SEQ ID NO:312:

AAGCAAUCUG AUGAGGCCGA AAGGCCGAAA CAAAUC  36

(2) INFORMATION FOR SEQ ID NO:313:

(i) SEQUENCE CHARACTERISTICS:
  (A) LENGTH: 36 base pairs
  (B) TYPE: nucleic acid
  (C) STRANDEDNESS: single
  (D) TOPOLOGY: linear (xi) SEQUENCE DESCRIPTION: SEQ ID NO:313:

AUAAAGCCUG AUGAGGCCGA AAGGCCGAAA UGACAA  36

(2) INFORMATION FOR SEQ ID NO:314:

(i) SEQUENCE CHARACTERISTICS:
  (A) LENGTH: 36 base pairs
  (B) TYPE: nucleic acid
  (C) STRANDEDNESS: single
  (D) TOPOLOGY: linear (xi) SEQUENCE DESCRIPTION: SEQ ID NO:314:

GUCUAUACUG AUGAGGCCGA AAGGCCGAAA GCAAUG  36

(2) INFORMATION FOR SEQ ID NO:315:

(i) SEQUENCE CHARACTERISTICS:
  (A) LENGTH: 36 base pairs
  (B) TYPE: nucleic acid
  (C) STRANDEDNESS: single
  (D) TOPOLOGY: linear (xi) SEQUENCE DESCRIPTION: SEQ ID NO:315:

AGUCUAUCUG AUGAGGCCGA AAGGCCGAAA AGCAAU  36

(2) INFORMATION FOR SEQ ID NO:316:

(i) SEQUENCE CHARACTERISTICS:
  (A) LENGTH: 36 base pairs
  (B) TYPE: nucleic acid
  (C) STRANDEDNESS: single (D) TOPOLOGY: linear (xi) SEQUENCE DESCRIPTION: SEQ ID NO:316:

CAGUCUACUG AUGAGGCCGA AAGGCCGAAA AAGCAA 36

(2) INFORMATION FOR SEQ ID NO:317:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:317:

UACAGUCCUG AUGAGGCCGA AAGGCCGAAA UAAAGC 36

(2) INFORMATION FOR SEQ ID NO:318:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:318:

CUCUUCUCUG AUGAGGCCGA AAGGCCGAAA CAGUCU 36

(2) INFORMATION FOR SEQ ID NO:319:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:319:

CUUCUGACUG AUGAGGCCGA AAGGCCGAAA UGUUCU 36

(2) INFORMATION FOR SEQ ID NO:320:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:320:

CACUUCUCUG AUGAGGCCGA AAGGCCGAAA GAUGUU 36

(2) INFORMATION FOR SEQ ID NO:321:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:321:

AGGGUAACUG AUGAGGCCGA AAGGCCGAAA CUCCAC 36

(2) INFORMATION FOR SEQ ID NO:322:

(i) SEQUENCE CHARACTERISTICS:
        (A) LENGTH: 36 base pairs
        (B) TYPE: nucleic acid
        (C) STRANDEDNESS: single
        (D) TOPOLOGY: linear ( x i ) SEQUENCE DESCRIPTION: SEQ ID NO:322:

UCAGGGUCUG AUGAGGCCGA AAGGCCGAAA GACUCC    36

( 2 ) INFORMATION FOR SEQ ID NO:323:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:323:

UUCAGGGCUG AUGAGGCCGA AAGGCCGAAA AGACUC    36

( 2 ) INFORMATION FOR SEQ ID NO:324:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:324:

AUCCUUUCUG AUGAGGCCGA AAGGCCGAAA UUUCAG    36

( 2 ) INFORMATION FOR SEQ ID NO:325:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:325:

UUCUUUACUG AUGAGGCCGA AAGGCCGAAA UCCUUU    36

( 2 ) INFORMATION FOR SEQ ID NO:326:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:326:

UUUCUUUCUG AUGAGGCCGA AAGGCCGAAA AUCCUU    36

( 2 ) INFORMATION FOR SEQ ID NO:327:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:327:

UUUUCUUCUG AUGAGGCCGA AAGGCCGAAA AAUCCU    36

( 2 ) INFORMATION FOR SEQ ID NO:328:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:328:

```
GAAGAAACUG AUGAGGCCGA AAGGCCGAAA UUCCAC                                  36
```

(2) INFORMATION FOR SEQ ID NO:329:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:329:

```
UGAAGAACUG AUGAGGCCGA AAGGCCGAAA AUUCCA                                  36
```

(2) INFORMATION FOR SEQ ID NO:330:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:330:

```
CUGAAGACUG AUGAGGCCGA AAGGCCGAAA AAUUCC                                  36
```

(2) INFORMATION FOR SEQ ID NO:331:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:331:

```
GCUGAAGCUG AUGAGGCCGA AAGGCCGAAA AAAUUC                                  36
```

(2) INFORMATION FOR SEQ ID NO:332:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:332:

```
UGCUGAACUG AUGAGGCCGA AAGGCCGAAA AAAAUU                                  36
```

(2) INFORMATION FOR SEQ ID NO:333:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:333:

```
CUUGCUGCUG AUGAGGCCGA AAGGCCGAAA GAAAAA                                  36
```

(2) INFORMATION FOR SEQ ID NO:334:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:334:

```
GCUUGCUCUG AUGAGGCCGA AAGGCCGAAA AGAAAA                                  36
```

( 2 ) INFORMATION FOR SEQ ID NO:335:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:335:

GUGGAUUCUG AUGAGGCCGA AAGGCCGAAA GUUUCA 36

( 2 ) INFORMATION FOR SEQ ID NO:336:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:336:

GGUUGUGCUG AUGAGGCCGA AAGGCCGAAA UUUAGU 36

( 2 ) INFORMATION FOR SEQ ID NO:337:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:337:

GUCUCCACUG AUGAGGCCGA AAGGCCGAAA GGUUGU 36

( 2 ) INFORMATION FOR SEQ ID NO:338:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:338:

GGUCUCCCUG AUGAGGCCGA AAGGCCGAAA AGGUUG 36

( 2 ) INFORMATION FOR SEQ ID NO:339:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:339:

GAGAUUGCUG AUGAGGCCGA AAGGCCGAAA GGGUGU 36

( 2 ) INFORMATION FOR SEQ ID NO:340:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:340:

ACACAGACUG AUGAGGCCGA AAGGCCGAAA UUGGAG 36

( 2 ) INFORMATION FOR SEQ ID NO:341:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:341:

ACACACACUG AUGAGGCCGA AAGGCCGAAA GAUUGG     36

( 2 ) INFORMATION FOR SEQ ID NO:342:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:342:

UUUACAACUG AUGAGGCCGA AAGGCCGAAA CACACA     36

( 2 ) INFORMATION FOR SEQ ID NO:343:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:343:

GUUUACACUG AUGAGGCCGA AAGGCCGAAA ACACAC     36

( 2 ) INFORMATION FOR SEQ ID NO:344:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:344:

UGUUUACCUG AUGAGGCCGA AAGGCCGAAA AACACA     36

( 2 ) INFORMATION FOR SEQ ID NO:345:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:345:

UGAUGUUCUG AUGAGGCCGA AAGGCCGAAA CAAAAC     36

( 2 ) INFORMATION FOR SEQ ID NO:346:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:346:

CUCCAGUCUG AUGAGGCCGA AAGGCCGAAA UGUUUA     36

( 2 ) INFORMATION FOR SEQ ID NO:347:

( i ) SEQUENCE CHARACTERISTICS:

( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:347:

CGUAGAACUG AUGAGGCCGA AAGGCCGAAA CCCUCC 36

( 2 ) INFORMATION FOR SEQ ID NO:348:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:348:

CACGUAGCUG AUGAGGCCGA AAGGCCGAAA GACCCU 36

( 2 ) INFORMATION FOR SEQ ID NO:349:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:349:

UCACGUACUG AUGAGGCCGA AAGGCCGAAA AGACCC 36

( 2 ) INFORMATION FOR SEQ ID NO:350:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:350:

GCUCACGCUG AUGAGGCCGA AAGGCCGAAA GAAGAC 36

( 2 ) INFORMATION FOR SEQ ID NO:351:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:351:

ACAAUCCCUG AUGAGGCCGA AAGGCCGAAA UUGCUC 36

( 2 ) INFORMATION FOR SEQ ID NO:352:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:352:

UGAUGACCUG AUGAGGCCGA AAGGCCGAAA UCCAAU 36

( 2 ) INFORMATION FOR SEQ ID NO:353:

( i ) SEQUENCE CHARACTERISTICS:
( A ) LENGTH: 36 base pairs
( B ) TYPE: nucleic acid ( C ) STRANDEDNESS: single
( D ) TOPOLOGY: linear ( x i ) SEQUENCE DESCRIPTION: SEQ ID NO:353:

GGCUGAUCUG AUGAGGCCGA AAGGCCGAAA CAAUCC 36

( 2 ) INFORMATION FOR SEQ ID NO:354:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:354:

CAGGGCUCUG AUGAGGCCGA AAGGCCGAAA UGACAA 36

( 2 ) INFORMATION FOR SEQ ID NO:355:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:355:

GGUGCAACUG AUGAGGCCGA AAGGCCGAAA CAGGCA 36

( 2 ) INFORMATION FOR SEQ ID NO:356:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:356:

AGGUGCACUG AUGAGGCCGA AAGGCCGAAA ACAGGC 36

( 2 ) INFORMATION FOR SEQ ID NO:357:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:357:

CAGGUGCCUG AUGAGGCCGA AAGGCCGAAA AACAGG 36

( 2 ) INFORMATION FOR SEQ ID NO:358:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:358:

CAAGUAACUG AUGAGGCCGA AAGGCCGAAA CCAGGG 36

( 2 ) INFORMATION FOR SEQ ID NO:359:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:359:

CCCAAGUCUG AUGAGGCCGA AAGGCCGAAA GACCAG    36

( 2 ) INFORMATION FOR SEQ ID NO:360:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:360:

ACCCAAGCUG AUGAGGCCGA AAGGCCGAAA AGACCA    36

( 2 ) INFORMATION FOR SEQ ID NO:361:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:361:

UGGACCCUG AUGAGGCCGA AAGGCCGAAA GUAAGA    36

( 2 ) INFORMATION FOR SEQ ID NO:362:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:362:

CAAUUUGCUG AUGAGGCCGA AAGGCCGAAA CCCAAG    36

( 2 ) INFORMATION FOR SEQ ID NO:363:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:363:

AGCCAACCUG AUGAGGCCGA AAGGCCGAAA UUUGGA    36

( 2 ) INFORMATION FOR SEQ ID NO:364:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:364:

GAAAGCCCUG AUGAGGCCGA AAGGCCGAAA CAAUUU    36

( 2 ) INFORMATION FOR SEQ ID NO:365:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:365:

```
AAAGUGACUG  AUGAGGCCGA  AAGGCCGAAA  GCCAAC                                    36
```

( 2 ) INFORMATION FOR SEQ ID NO:366:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:366:

```
AAAAGUGCUG  AUGAGGCCGA  AAGGCCGAAA  AGCCAA                                    36
```

( 2 ) INFORMATION FOR SEQ ID NO:367:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:367:

```
CAAAAGUCUG  AUGAGGCCGA  AAGGCCGAAA  AAGCCA                                    36
```

( 2 ) INFORMATION FOR SEQ ID NO:368:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:368:

```
GGGUCAACUG  AUGAGGCCGA  AAGGCCGAAA  GUGAAA                                    36
```

( 2 ) INFORMATION FOR SEQ ID NO:369:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:369:

```
AGGGUCACUG  AUGAGGCCGA  AAGGCCGAAA  AGUGAA                                    36
```

( 2 ) INFORMATION FOR SEQ ID NO:370:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:370:

```
UAGGGUCCUG  AUGAGGCCGA  AAGGCCGAAA  AAGUGA                                    36
```

( 2 ) INFORMATION FOR SEQ ID NO:371:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:371:

```
AGAUGCUCUG  AUGAGGCCGA  AAGGCCGAAA  GGGUCA                                    36
```

( 2 ) INFORMATION FOR SEQ ID NO:372:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:372:

GGCUUCACUG AUGAGGCCGA AAGGCCGAAA UGCUUA     36

( 2 ) INFORMATION FOR SEQ ID NO:373:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:373:

GGAUGGUCUG AUGAGGCCGA AAGGCCGAAA UGUUCC     36

( 2 ) INFORMATION FOR SEQ ID NO:374:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:374:

ACACUUGCUG AUGAGGCCGA AAGGCCGAAA UGGUGA     36

( 2 ) INFORMATION FOR SEQ ID NO:375:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:375:

AGGUAUGCUG AUGAGGCCGA AAGGCCGAAA CACUUG     36

( 2 ) INFORMATION FOR SEQ ID NO:376:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:376:

AUUGAGGCUG AUGAGGCCGA AAGGCCGAAA UGGACA     36

( 2 ) INFORMATION FOR SEQ ID NO:377:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:377:

AGAAAUUCUG AUGAGGCCGA AAGGCCGAAA GGUAUG     36

( 2 ) INFORMATION FOR SEQ ID NO:378:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:378:

UGAAAGACUG AUGAGGCCGA AAGGCCGAAA UUGAGG      36

( 2 ) INFORMATION FOR SEQ ID NO:379:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:379:

CUGAAAGCUG AUGAGGCCGA AAGGCCGAAA AUUGAG      36

( 2 ) INFORMATION FOR SEQ ID NO:380:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:380:

GCUGAAACUG AUGAGGCCGA AAGGCCGAAA AAUUGA      36

( 2 ) INFORMATION FOR SEQ ID NO:381:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:381:

GAGCUGACUG AUGAGGCCGA AAGGCCGAAA GAAAUU      36

( 2 ) INFORMATION FOR SEQ ID NO:382:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:382:

AGAGCUGCUG AUGAGGCCGA AAGGCCGAAA AGAAAU      36

( 2 ) INFORMATION FOR SEQ ID NO:383:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:383:

AAGAGCUCUG AUGAGGCCGA AAGGCCGAAA AAGAAA      36

( 2 ) INFORMATION FOR SEQ ID NO:384:

( i ) SEQUENCE CHARACTERISTICS:
   ( A ) LENGTH: 36 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:384:

GCACCAACUG AUGAGGCCGA AAGGCCGAAA GCUGAA    36

( 2 ) INFORMATION FOR SEQ ID NO:385:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:385:

CAGCACCCUG AUGAGGCCGA AAGGCCGAAA GAGCUG    36

( 2 ) INFORMATION FOR SEQ ID NO:386:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:386:

UGAGAAACUG AUGAGGCCGA AAGGCCGAAA CCAGCC    36

( 2 ) INFORMATION FOR SEQ ID NO:387:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:387:

AGUGAGACUG AUGAGGCCGA AAGGCCGAAA GACCAG    36

( 2 ) INFORMATION FOR SEQ ID NO:388:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:388:

AAGUGAGCUG AUGAGGCCGA AAGGCCGAAA AGACCA    36

( 2 ) INFORMATION FOR SEQ ID NO:389:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:389:

GAAGUGACUG AUGAGGCCGA AAGGCCGAAA AAGACC    36

( 2 ) INFORMATION FOR SEQ ID NO:390:

( i ) SEQUENCE CHARACTERISTICS:
      ( A ) LENGTH: 36 base pairs ( B ) TYPE: nucleic acid
( C ) STRANDEDNESS: single
( D ) TOPOLOGY: linear ( x i ) SEQUENCE DESCRIPTION: SEQ ID NO:390:

CAGAAGUCUG AUGAGGCCGA AAGGCCGAAA GAAAGA 36

( 2 ) INFORMATION FOR SEQ ID NO:391:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:391:

UGAACAGCUG AUGAGGCCGA AAGGCCGAAA GUGAGA 36

( 2 ) INFORMATION FOR SEQ ID NO:392:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:392:

CUGAACACUG AUGAGGCCGA AAGGCCGAAA AGUGAG 36

( 2 ) INFORMATION FOR SEQ ID NO:393:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:393:

ACACCUGCUG AUGAGGCCGA AAGGCCGAAA CAGAAG 36

( 2 ) INFORMATION FOR SEQ ID NO:394:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:394:

AACACCUCUG AUGAGGCCGA AAGGCCGAAA ACAGAA 36

( 2 ) INFORMATION FOR SEQ ID NO:395:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:395:

CGUGGAUCUG AUGAGGCCGA AAGGCCGAAA CACCUG 36

( 2 ) INFORMATION FOR SEQ ID NO:396:

( i ) SEQUENCE CHARACTERISTICS:
( A ) LENGTH: 36 base pairs
( B ) TYPE: nucleic acid
( C ) STRANDEDNESS: single (D) TOPOLOGY: linear (x i) SEQUENCE DESCRIPTION: SEQ ID NO:396:

ACGUGGACUG AUGAGGCCGA AAGGCCGAAA ACACCU    36

(2) INFORMATION FOR SEQ ID NO:397:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:397:

UCACGUGCUG AUGAGGCCGA AAGGCCGAAA UAACAC    36

(2) INFORMATION FOR SEQ ID NO:398:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:398:

ACCACAGCUG AUGAGGCCGA AAGGCCGAAA CAGCGU    36

(2) INFORMATION FOR SEQ ID NO:399:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:399:

ACAUUGUCUG AUGAGGCCGA AAGGCCGAAA CCACAG    36

(2) INFORMATION FOR SEQ ID NO:400:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:400:

CAACAGACUG AUGAGGCCGA AAGGCCGAAA CAUUGU    36

(2) INFORMATION FOR SEQ ID NO:401:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:401:

UCAACAGCUG AUGAGGCCGA AAGGCCGAAA ACAUUG    36

(2) INFORMATION FOR SEQ ID NO:402:

(i) SEQUENCE CHARACTERISTICS:
        (A) LENGTH: 36 base pairs
        (B) TYPE: nucleic acid
        (C) STRANDEDNESS: single
        (D) TOPOLOGY: linear ( x i ) SEQUENCE DESCRIPTION: SEQ ID NO:402:

UUCAACACUG AUGAGGCCGA AAGGCCGAAA AACAUU    36

( 2 ) INFORMATION FOR SEQ ID NO:403:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:403:

GCUCUUCCUG AUGAGGCCGA AAGGCCGAAA CAGAAA    36

( 2 ) INFORMATION FOR SEQ ID NO:404:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:404:

UAGAUGCCUG AUGAGGCCGA AAGGCCGAAA GUUUGU    36

( 2 ) INFORMATION FOR SEQ ID NO:405:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:405:

GCCAGUACUG AUGAGGCCGA AAGGCCGAAA UGCGAG    36

( 2 ) INFORMATION FOR SEQ ID NO:406:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:406:

UUGCCAGCUG AUGAGGCCGA AAGGCCGAAA GAUGCG    36

( 2 ) INFORMATION FOR SEQ ID NO:407:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:407:

GACAUCACUG AUGAGGCCGA AAGGCCGAAA GUCAGC    36

( 2 ) INFORMATION FOR SEQ ID NO:408:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:408:

GUCCCCACUG AUGAGGCCGA AAGGCCGAAA CAUCAU 36

(2) INFORMATION FOR SEQ ID NO:409:

(i) SEQUENCE CHARACTERISTICS:
       (A) LENGTH: 36 base pairs
       (B) TYPE: nucleic acid
       (C) STRANDEDNESS: single
       (D) TOPOLOGY: linear (xi) SEQUENCE DESCRIPTION: SEQ ID NO:409:

GGCCAUACUG AUGAGGCCGA AAGGCCGAAA UUCAUG 36

(2) INFORMATION FOR SEQ ID NO:410:

(i) SEQUENCE CHARACTERISTICS:
       (A) LENGTH: 36 base pairs
       (B) TYPE: nucleic acid
       (C) STRANDEDNESS: single
       (D) TOPOLOGY: linear (xi) SEQUENCE DESCRIPTION: SEQ ID NO:410:

CGGGCCACUG AUGAGGCCGA AAGGCCGAAA UAUUCA 36

(2) INFORMATION FOR SEQ ID NO:411:

(i) SEQUENCE CHARACTERISTICS:
       (A) LENGTH: 36 base pairs
       (B) TYPE: nucleic acid
       (C) STRANDEDNESS: single
       (D) TOPOLOGY: linear (xi) SEQUENCE DESCRIPTION: SEQ ID NO:411:

GUUCUUGCUG AUGAGGCCGA AAGGCCGAAA CUCGGG 36

(2) INFORMATION FOR SEQ ID NO:412:

(i) SEQUENCE CHARACTERISTICS:
       (A) LENGTH: 36 base pairs
       (B) TYPE: nucleic acid
       (C) STRANDEDNESS: single
       (D) TOPOLOGY: linear (xi) SEQUENCE DESCRIPTION: SEQ ID NO:412:

UAUCAAACUG AUGAGGCCGA AAGGCCGAAA UGGUCC 36

(2) INFORMATION FOR SEQ ID NO:413:

(i) SEQUENCE CHARACTERISTICS:
       (A) LENGTH: 36 base pairs
       (B) TYPE: nucleic acid
       (C) STRANDEDNESS: single
       (D) TOPOLOGY: linear (xi) SEQUENCE DESCRIPTION: SEQ ID NO:413:

GAUAUCACUG AUGAGGCCGA AAGGCCGAAA GAUGGU 36

(2) INFORMATION FOR SEQ ID NO:414:

(i) SEQUENCE CHARACTERISTICS:
       (A) LENGTH: 36 base pairs
       (B) TYPE: nucleic acid
       (C) STRANDEDNESS: single
       (D) TOPOLOGY: linear (xi) SEQUENCE DESCRIPTION: SEQ ID NO:414:

UGAUAUCCUG AUGAGGCCGA AAGGCCGAAA AGAUGG 36

( 2 ) INFORMATION FOR SEQ ID NO:415:

( i ) SEQUENCE CHARACTERISTICS:
　　　　　　　　( A ) LENGTH: 36 base pairs
　　　　　　　　( B ) TYPE: nucleic acid
　　　　　　　　( C ) STRANDEDNESS: single
　　　　　　　　( D ) TOPOLOGY: linear ( x i ) SEQUENCE DESCRIPTION: SEQ ID NO:415:

UUAGUGACUG AUGAGGCCGA AAGGCCGAAA UCAAAG　　　　　　　　　　　　36

( 2 ) INFORMATION FOR SEQ ID NO:416:

( i ) SEQUENCE CHARACTERISTICS:
　　　　　　　　( A ) LENGTH: 36 base pairs
　　　　　　　　( B ) TYPE: nucleic acid
　　　　　　　　( C ) STRANDEDNESS: single
　　　　　　　　( D ) TOPOLOGY: linear ( x i ) SEQUENCE DESCRIPTION: SEQ ID NO:416:

UAUUAGUCUG AUGAGGCCGA AAGGCCGAAA UAUCAA　　　　　　　　　　　　36

( 2 ) INFORMATION FOR SEQ ID NO:417:

( i ) SEQUENCE CHARACTERISTICS:
　　　　　　　　( A ) LENGTH: 36 base pairs
　　　　　　　　( B ) TYPE: nucleic acid
　　　　　　　　( C ) STRANDEDNESS: single
　　　　　　　　( D ) TOPOLOGY: linear ( x i ) SEQUENCE DESCRIPTION: SEQ ID NO:417:

AGGUUAUCUG AUGAGGCCGA AAGGCCGAAA GUGAUA　　　　　　　　　　　　36

( 2 ) INFORMATION FOR SEQ ID NO:418:

( i ) SEQUENCE CHARACTERISTICS:
　　　　　　　　( A ) LENGTH: 36 base pairs
　　　　　　　　( B ) TYPE: nucleic acid
　　　　　　　　( C ) STRANDEDNESS: single
　　　　　　　　( D ) TOPOLOGY: linear ( x i ) SEQUENCE DESCRIPTION: SEQ ID NO:418:

GAGAGGUCUG AUGAGGCCGA AAGGCCGAAA UUAGUG　　　　　　　　　　　　36

( 2 ) INFORMATION FOR SEQ ID NO:419:

( i ) SEQUENCE CHARACTERISTICS:
　　　　　　　　( A ) LENGTH: 36 base pairs
　　　　　　　　( B ) TYPE: nucleic acid
　　　　　　　　( C ) STRANDEDNESS: single
　　　　　　　　( D ) TOPOLOGY: linear ( x i ) SEQUENCE DESCRIPTION: SEQ ID NO:419:

CAAUGGACUG AUGAGGCCGA AAGGCCGAAA GGUUAU　　　　　　　　　　　　36

( 2 ) INFORMATION FOR SEQ ID NO:420:

( i ) SEQUENCE CHARACTERISTICS:
　　　　　　　　( A ) LENGTH: 36 base pairs
　　　　　　　　( B ) TYPE: nucleic acid
　　　　　　　　( C ) STRANDEDNESS: single
　　　　　　　　( D ) TOPOLOGY: linear ( x i ) SEQUENCE DESCRIPTION: SEQ ID NO:420:

CACAAUGCUG AUGAGGCCGA AAGGCCGAAA GAGGUU　　　　　　　　　　　　36

( 2 ) INFORMATION FOR SEQ ID NO:421:

(i) SEQUENCE CHARACTERISTICS:
                (A) LENGTH: 36 base pairs
                (B) TYPE: nucleic acid
                (C) STRANDEDNESS: single
                (D) TOPOLOGY: linear (xi) SEQUENCE DESCRIPTION: SEQ ID NO:421:

GGAUCACCUG AUGAGGCCGA AAGGCCGAAA UGGAGA          36

(2) INFORMATION FOR SEQ ID NO:422:

(i) SEQUENCE CHARACTERISTICS:
                (A) LENGTH: 36 base pairs
                (B) TYPE: nucleic acid
                (C) STRANDEDNESS: single
                (D) TOPOLOGY: linear (xi) SEQUENCE DESCRIPTION: SEQ ID NO:422:

GAGCCAGCUG AUGAGGCCGA AAGGCCGAAA UCACAA          36

(2) INFORMATION FOR SEQ ID NO:423:

(i) SEQUENCE CHARACTERISTICS:
                (A) LENGTH: 36 base pairs
                (B) TYPE: nucleic acid
                (C) STRANDEDNESS: single
                (D) TOPOLOGY: linear (xi) SEQUENCE DESCRIPTION: SEQ ID NO:423:

GGGCGCACUG AUGAGGCCGA AAGGCCGAAA GCCAGG          36

(2) INFORMATION FOR SEQ ID NO:424:

(i) SEQUENCE CHARACTERISTICS:
                (A) LENGTH: 36 base pairs
                (B) TYPE: nucleic acid
                (C) STRANDEDNESS: single
                (D) TOPOLOGY: linear (xi) SEQUENCE DESCRIPTION: SEQ ID NO:424:

CUCGUCACUG AUGAGGCCGA AAGGCCGAAA UGGGCG          36

(2) INFORMATION FOR SEQ ID NO:425:

(i) SEQUENCE CHARACTERISTICS:
                (A) LENGTH: 36 base pairs
                (B) TYPE: nucleic acid
                (C) STRANDEDNESS: single
                (D) TOPOLOGY: linear (xi) SEQUENCE DESCRIPTION: SEQ ID NO:425:

ACACUCGCUG AUGAGGCCGA AAGGCCGAAA UGUGCC          36

(2) INFORMATION FOR SEQ ID NO:426:

(i) SEQUENCE CHARACTERISTICS:
                (A) LENGTH: 36 base pairs
                (B) TYPE: nucleic acid
                (C) STRANDEDNESS: single
                (D) TOPOLOGY: linear (xi) SEQUENCE DESCRIPTION: SEQ ID NO:426:

UCAGAACCUG AUGAGGCCGA AAGGCCGAAA CACACU          36

(2) INFORMATION FOR SEQ ID NO:427:

(i) SEQUENCE CHARACTERISTICS:

(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:427:

ACUUCAGCUG AUGAGGCCGA AAGGCCGAAA CAACAC 36

(2) INFORMATION FOR SEQ ID NO:428:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:428:

UACUUCACUG AUGAGGCCGA AAGGCCGAAA ACAACA 36

(2) INFORMATION FOR SEQ ID NO:429:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:429:

UUUUUCACUG AUGAGGCCGA AAGGCCGAAA CUUCAG 36

(2) INFORMATION FOR SEQ ID NO:430:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:430:

CGCUUGACUG AUGAGGCCGA AAGGCCGAAA GCGUCU 36

(2) INFORMATION FOR SEQ ID NO:431:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:431:

CCGCUUGCUG AUGAGGCCGA AAGGCCGAAA AGCGUC 36

(2) INFORMATION FOR SEQ ID NO:432:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:432:

CCCGCUUCUG AUGAGGCCGA AAGGCCGAAA AAGCGU 36

(2) INFORMATION FOR SEQ ID NO:433:

(i) SEQUENCE CHARACTERISTICS:
(A) LENGTH: 36 base pairs
(B) TYPE: nucleic acid ( C ) STRANDEDNESS: single
( D ) TOPOLOGY: linear ( x i ) SEQUENCE DESCRIPTION: SEQ ID NO:433:

GACUGAUCUG AUGAGGCCGA AAGGCCGAAA CGUCAC 36

( 2 ) INFORMATION FOR SEQ ID NO:434:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:434:

UGACUGACUG AUGAGGCCGA AAGGCCGAAA ACGUCA 36

( 2 ) INFORMATION FOR SEQ ID NO:435:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:435:

UUUGACUCUG AUGAGGCCGA AAGGCCGAAA UAACGU 36

( 2 ) INFORMATION FOR SEQ ID NO:436:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:436:

CAGCUUUCUG AUGAGGCCGA AAGGCCGAAA CUGAUA 36

( 2 ) INFORMATION FOR SEQ ID NO:437:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:437:

UGUAGGGCUG AUGAGGCCGA AAGGCCGAAA GUCAGC 36

( 2 ) INFORMATION FOR SEQ ID NO:438:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:438:

GUGUAGGCUG AUGAGGCCGA AAGGCCGAAA AGUCAG 36

( 2 ) INFORMATION FOR SEQ ID NO:439:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:439:

CUAGGUGCUG AUGAGGCCGA AAGGCCGAAA GGGAAG                                        36

( 2 ) INFORMATION FOR SEQ ID NO:440:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:440:

GAUAUACCUG AUGAGGCCGA AAGGCCGAAA GGUGUA                                        36

( 2 ) INFORMATION FOR SEQ ID NO:441:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:441:

UCAGAUACUG AUGAGGCCGA AAGGCCGAAA CUAGGU                                        36

( 2 ) INFORMATION FOR SEQ ID NO:442:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:442:

AGUCAGACUG AUGAGGCCGA AAGGCCGAAA UACUAG                                        36

( 2 ) INFORMATION FOR SEQ ID NO:443:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:443:

AAAGUCACUG AUGAGGCCGA AAGGCCGAAA UAUACU                                        36

( 2 ) INFORMATION FOR SEQ ID NO:444:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:444:

AAUUUCACUG AUGAGGCCGA AAGGCCGAAA GUCAGA                                        36

( 2 ) INFORMATION FOR SEQ ID NO:445:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:445:

GAAUUUCCUG AUGAGGCCGA AAGGCCGAAA AGUCAG    36

( 2 ) INFORMATION FOR SEQ ID NO:446:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:446:

AAGUUGGCUG AUGAGGCCGA AAGGCCGAAA UUUCAA    36

( 2 ) INFORMATION FOR SEQ ID NO:447:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:447:

GAAGUUGCUG AUGAGGCCGA AAGGCCGAAA AUUUCA    36

( 2 ) INFORMATION FOR SEQ ID NO:448:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:448:

AUAUUAGCUG AUGAGGCCGA AAGGCCGAAA GUUGGA    36

( 2 ) INFORMATION FOR SEQ ID NO:449:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:449:

AAUAUUACUG AUGAGGCCGA AAGGCCGAAA AGUUGG    36

( 2 ) INFORMATION FOR SEQ ID NO:450:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:450:

CUAAUAUCUG AUGAGGCCGA AAGGCCGAAA GAAGUU    36

( 2 ) INFORMATION FOR SEQ ID NO:451:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:451:

CUUCUAACUG AUGAGGCCGA AAGGCCGAAA UUAGAA    36

( 2 ) INFORMATION FOR SEQ ID NO:452:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:452:

UCCUUCUCUG AUGAGGCCGA AAGGCCGAAA UAUUAG    36

( 2 ) INFORMATION FOR SEQ ID NO:453:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:453:

AUCCUUCCUG AUGAGGCCGA AAGGCCGAAA AUAUUA    36

( 2 ) INFORMATION FOR SEQ ID NO:454:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:454:

AGCAAAUCUG AUGAGGCCGA AAGGCCGAAA UCCUUC    36

( 2 ) INFORMATION FOR SEQ ID NO:455:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:455:

UUGAGCACUG AUGAGGCCGA AAGGCCGAAA UUAUCC    36

( 2 ) INFORMATION FOR SEQ ID NO:456:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:456:

GUUGAGCCUG AUGAGGCCGA AAGGCCGAAA AUUAUC    36

( 2 ) INFORMATION FOR SEQ ID NO:457:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:457:

AGAGGUUCUG AUGAGGCCGA AAGGCCGAAA GCAAAU    36

( 2 ) INFORMATION FOR SEQ ID NO:458:

( i ) SEQUENCE CHARACTERISTICS:
　　　　　　　　( A ) LENGTH: 36 base pairs
　　　　　　　　( B ) TYPE: nucleic acid
　　　　　　　　( C ) STRANDEDNESS: single
　　　　　　　　( D ) TOPOLOGY: linear ( x i ) SEQUENCE DESCRIPTION: SEQ ID NO:458:

ACCUCCACUG AUGAGGCCGA AAGGCCGAAA GGUUGA　　　　　　　　36

( 2 ) INFORMATION FOR SEQ ID NO:459:

( i ) SEQUENCE CHARACTERISTICS:
　　　　　　　　( A ) LENGTH: 36 base pairs
　　　　　　　　( B ) TYPE: nucleic acid
　　　　　　　　( C ) STRANDEDNESS: single
　　　　　　　　( D ) TOPOLOGY: linear ( x i ) SEQUENCE DESCRIPTION: SEQ ID NO:459:

UCUGGAACUG AUGAGGCCGA AAGGCCGAAA CCUCCA　　　　　　　　36

( 2 ) INFORMATION FOR SEQ ID NO:460:

( i ) SEQUENCE CHARACTERISTICS:
　　　　　　　　( A ) LENGTH: 36 base pairs
　　　　　　　　( B ) TYPE: nucleic acid
　　　　　　　　( C ) STRANDEDNESS: single
　　　　　　　　( D ) TOPOLOGY: linear ( x i ) SEQUENCE DESCRIPTION: SEQ ID NO:460:

CUCUGGACUG AUGAGGCCGA AAGGCCGAAA ACCUCC　　　　　　　　36

( 2 ) INFORMATION FOR SEQ ID NO:461:

( i ) SEQUENCE CHARACTERISTICS:
　　　　　　　　( A ) LENGTH: 36 base pairs
　　　　　　　　( B ) TYPE: nucleic acid
　　　　　　　　( C ) STRANDEDNESS: single
　　　　　　　　( D ) TOPOLOGY: linear ( x i ) SEQUENCE DESCRIPTION: SEQ ID NO:461:

GCUCUGGCUG AUGAGGCCGA AAGGCCGAAA AACCUC　　　　　　　　36

( 2 ) INFORMATION FOR SEQ ID NO:462:

( i ) SEQUENCE CHARACTERISTICS:
　　　　　　　　( A ) LENGTH: 36 base pairs
　　　　　　　　( B ) TYPE: nucleic acid
　　　　　　　　( C ) STRANDEDNESS: single
　　　　　　　　( D ) TOPOLOGY: linear ( x i ) SEQUENCE DESCRIPTION: SEQ ID NO:462:

GGCUCUGCUG AUGAGGCCGA AAGGCCGAAA AAACCU　　　　　　　　36

( 2 ) INFORMATION FOR SEQ ID NO:463:

( i ) SEQUENCE CHARACTERISTICS:
　　　　　　　　( A ) LENGTH: 36 base pairs
　　　　　　　　( B ) TYPE: nucleic acid
　　　　　　　　( C ) STRANDEDNESS: single
　　　　　　　　( D ) TOPOLOGY: linear ( x i ) SEQUENCE DESCRIPTION: SEQ ID NO:463:

GAGAGGUCUG AUGAGGCCGA AAGGCCGAAA GGCUCU　　　　　　　　36

( 2 ) INFORMATION FOR SEQ ID NO:464:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:464:

ACCAGGACUG AUGAGGCCGA AAGGCCGAAA GGUGAG    36

( 2 ) INFORMATION FOR SEQ ID NO:465:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:465:

CAACCAGCUG AUGAGGCCGA AAGGCCGAAA GAGGUG    36

( 2 ) INFORMATION FOR SEQ ID NO:466:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:466:

AUUUCCCUG AUGAGGCCGA AAGGCCGAAA CCAGGA    36

( 2 ) INFORMATION FOR SEQ ID NO:467:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:467:

GGCAUUUCUG AUGAGGCCGA AAGGCCGAAA UUCUUC    36

( 2 ) INFORMATION FOR SEQ ID NO:468:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:468:

UGGCAUUCUG AUGAGGCCGA AAGGCCGAAA AUUCUU    36

( 2 ) INFORMATION FOR SEQ ID NO:469:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:469:

UUGUGUUCUG AUGAGGCCGA AAGGCCGAAA UGGCAU    36

( 2 ) INFORMATION FOR SEQ ID NO:470:

( i ) SEQUENCE CHARACTERISTICS:
  ( A ) LENGTH: 36 base pairs (B) TYPE: nucleic acid
(C) STRANDEDNESS: single
(D) TOPOLOGY: linear (xi) SEQUENCE DESCRIPTION: SEQ ID NO:470:

CUUGGGACUG AUGAGGCCGA AAGGCCGAAA CUGUUG 36

(2) INFORMATION FOR SEQ ID NO:471:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:471:

UCUUGGGCUG AUGAGGCCGA AAGGCCGAAA ACUGUU 36

(2) INFORMATION FOR SEQ ID NO:472:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:472:

AUCUUGGCUG AUGAGGCCGA AAGGCCGAAA AACUGU 36

(2) INFORMATION FOR SEQ ID NO:473:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:473:

GUUUCAGCUG AUGAGGCCGA AAGGCCGAAA UCUUGG 36

(2) INFORMATION FOR SEQ ID NO:474:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:474:

CAGCAUACUG AUGAGGCCGA AAGGCCGAAA GCUCAG 36

(2) INFORMATION FOR SEQ ID NO:475:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:475:

AACAGCACUG AUGAGGCCGA AAGGCCGAAA GAGCUC 36

(2) INFORMATION FOR SEQ ID NO:476:

(i) SEQUENCE CHARACTERISTICS:
(A) LENGTH: 36 base pairs
(B) TYPE: nucleic acid
(C) STRANDEDNESS: single (D) TOPOLOGY: linear (xi) SEQUENCE DESCRIPTION: SEQ ID NO:476:

UGCUGCUCUG AUGAGGCCGA AAGGCCGAAA CAGCAU                36

(2) INFORMATION FOR SEQ ID NO:477:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (xi) SEQUENCE DESCRIPTION: SEQ ID NO:477:

UUGCUGCCUG AUGAGGCCGA AAGGCCGAAA ACAGCA                36

(2) INFORMATION FOR SEQ ID NO:478:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (xi) SEQUENCE DESCRIPTION: SEQ ID NO:478:

AUAUUGACUG AUGAGGCCGA AAGGCCGAAA UCCAGU                36

(2) INFORMATION FOR SEQ ID NO:479:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (xi) SEQUENCE DESCRIPTION: SEQ ID NO:479:

CAUAUUGCUG AUGAGGCCGA AAGGCCGAAA AUCCAG                36

(2) INFORMATION FOR SEQ ID NO:480:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (xi) SEQUENCE DESCRIPTION: SEQ ID NO:480:

UCAUAUUCUG AUGAGGCCGA AAGGCCGAAA AAUCCA                36

(2) INFORMATION FOR SEQ ID NO:481:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (xi) SEQUENCE DESCRIPTION: SEQ ID NO:481:

GUUGUCACUG AUGAGGCCGA AAGGCCGAAA UUGAAA                36

(2) INFORMATION FOR SEQ ID NO:482:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (x i) SEQUENCE DESCRIPTION: SEQ ID NO:482:

ACACAUGCUG AUGAGGCCGA AAGGCCGAAA GCUGUG 36

(2) INFORMATION FOR SEQ ID NO:483:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:483:

GACACAUCUG AUGAGGCCGA AAGGCCGAAA AGCUGU 36

(2) INFORMATION FOR SEQ ID NO:484:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:484:

UUGAUGACUG AUGAGGCCGA AAGGCCGAAA CACAUG 36

(2) INFORMATION FOR SEQ ID NO:485:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:485:

ACUUGAUCUG AUGAGGCCGA AAGGCCGAAA GACACA 36

(2) INFORMATION FOR SEQ ID NO:486:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:486:

CAUACUUCUG AUGAGGCCGA AAGGCCGAAA UGAGAC 36

(2) INFORMATION FOR SEQ ID NO:487:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:487:

AUGUCCACUG AUGAGGCCGA AAGGCCGAAA CUUGAU 36

(2) INFORMATION FOR SEQ ID NO:488:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:488:

ACUCUUACUG AUGAGGCCGA AAGGCCGAAA UGUCCA 36

(2) INFORMATION FOR SEQ ID NO:489:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:489:

CACUCUUCUG AUGAGGCCGA AAGGCCGAAA AUGUCC 36

(2) INFORMATION FOR SEQ ID NO:490:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:490:

UCACUCUCUG AUGAGGCCGA AAGGCCGAAA AAUGUC 36

(2) INFORMATION FOR SEQ ID NO:491:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:491:

AAGGUCUCUG AUGAGGCCGA AAGGCCGAAA UUCACU 36

(2) INFORMATION FOR SEQ ID NO:492:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:492:

CCAGUUGCUG AUGAGGCCGA AAGGCCGAAA GGUCUG 36

(2) INFORMATION FOR SEQ ID NO:493:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:493:

UCCAGUUCUG AUGAGGCCGA AAGGCCGAAA AGGUCU 36

(2) INFORMATION FOR SEQ ID NO:494:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:494:

UUGGUUGCUG AUGAGGCCGA AAGGCCGAAA UUCCAG 36

( 2 ) INFORMATION FOR SEQ ID NO:495:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:495:

UCAGGAACUG AUGAGGCCGA AAGGCCGAAA UGCUCU     36

( 2 ) INFORMATION FOR SEQ ID NO:496:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:496:

AUCAGGACUG AUGAGGCCGA AAGGCCGAAA AUGCUC     36

( 2 ) INFORMATION FOR SEQ ID NO:497:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:497:

UAUCAGGCUG AUGAGGCCGA AAGGCCGAAA AAUGCU     36

( 2 ) INFORMATION FOR SEQ ID NO:498:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:498:

UUAUCAGCUG AUGAGGCCGA AAGGCCGAAA AAAUGC     36

( 2 ) INFORMATION FOR SEQ ID NO:499:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:499:

AGCAGGUCUG AUGAGGCCGA AAGGCCGAAA UCAGGA     36

( 2 ) INFORMATION FOR SEQ ID NO:500:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:500:

AGGAUGGCUG AUGAGGCCGA AAGGCCGAAA GCAGGU     36

( 2 ) INFORMATION FOR SEQ ID NO:501:

( i ) SEQUENCE CHARACTERISTICS:
   ( A ) LENGTH: 36 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:501:

GGCCCAGCUG AUGAGGCCGA AAGGCCGAAA UGGGAG 36

( 2 ) INFORMATION FOR SEQ ID NO:502:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:502:

UUAAGGUCUG AUGAGGCCGA AAGGCCGAAA UGGCCC 36

( 2 ) INFORMATION FOR SEQ ID NO:503:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:503:

AUUAAGGCUG AUGAGGCCGA AAGGCCGAAA AUGGCC 36

( 2 ) INFORMATION FOR SEQ ID NO:504:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:504:

UGAGAUUCUG AUGAGGCCGA AAGGCCGAAA GGUAAU 36

( 2 ) INFORMATION FOR SEQ ID NO:505:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:505:

CUGAGAUCUG AUGAGGCCGA AAGGCCGAAA AGGUAA 36

( 2 ) INFORMATION FOR SEQ ID NO:506:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:506:

UUACUGACUG AUGAGGCCGA AAGGCCGAAA UUAAGG 36

( 2 ) INFORMATION FOR SEQ ID NO:507:

( i ) SEQUENCE CHARACTERISTICS:

(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:507:

AUUUACUCUG AUGAGGCCGA AAGGCCGAAA GAUUAA 36

(2) INFORMATION FOR SEQ ID NO:508:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:508:

UUCCAUUCUG AUGAGGCCGA AAGGCCGAAA CUGAGA 36

(2) INFORMATION FOR SEQ ID NO:509:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:509:

UCACAAACUG AUGAGGCCGA AAGGCCGAAA UUCCAU 36

(2) INFORMATION FOR SEQ ID NO:510:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:510:

AUCACAACUG AUGAGGCCGA AAGGCCGAAA AUUCCA 36

(2) INFORMATION FOR SEQ ID NO:511:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:511:

UAUCACACUG AUGAGGCCGA AAGGCCGAAA AAUUCC 36

(2) INFORMATION FOR SEQ ID NO:512:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:512:

AUAUCACCUG AUGAGGCCGA AAGGCCGAAA AAAUUC 36

(2) INFORMATION FOR SEQ ID NO:513:

(i) SEQUENCE CHARACTERISTICS:
(A) LENGTH: 36 base pairs
(B) TYPE: nucleic acid ( C ) STRANDEDNESS: single
( D ) TOPOLOGY: linear ( x i ) SEQUENCE DESCRIPTION: SEQ ID NO:513:

GGCAGCACUG AUGAGGCCGA AAGGCCGAAA UCACAA 36

( 2 ) INFORMATION FOR SEQ ID NO:514:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:514:

AAAGCAGCUG AUGAGGCCGA AAGGCCGAAA GGUCAG 36

( 2 ) INFORMATION FOR SEQ ID NO:515:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:515:

UGGGGCACUG AUGAGGCCGA AAGGCCGAAA GCAGUA 36

( 2 ) INFORMATION FOR SEQ ID NO:516:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:516:

UUGGGGCCUG AUGAGGCCGA AAGGCCGAAA AGCAGU 36

( 2 ) INFORMATION FOR SEQ ID NO:517:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:517:

CCUUCUCCUG AUGAGGCCGA AAGGCCGAAA UCUCUC 36

( 2 ) INFORMATION FOR SEQ ID NO:518:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:518:

CAGGGCGCUG AUGAGGCCGA AAGGCCGAAA CACUUU 36

( 2 ) INFORMATION FOR SEQ ID NO:519:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:519:

ACUGUUACUG AUGAGGCCGA AAGGCCGAAA CAGGGC 36

( 2 ) INFORMATION FOR SEQ ID NO:520:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:520:

ACACUGUCUG AUGAGGCCGA AAGGCCGAAA UACAGG 36

( 2 ) INFORMATION FOR SEQ ID NO:521:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:521:

UUCUGCGCUG AUGAGGCCGA AAGGCCGAAA CACUGU 36

( 2 ) INFORMATION FOR SEQ ID NO:522:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:522:

ACCUUCACUG AUGAGGCCGA AAGGCCGAAA UCUUUU 36

( 2 ) INFORMATION FOR SEQ ID NO:523:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:523:

CGGAGGCCUG AUGAGGCCGA AAGGCCGAAA CCUUCA 36

( 2 ) INFORMATION FOR SEQ ID NO:524:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:524:

GAUGACGCUG AUGAGGCCGA AAGGCCGAAA GGCUAC 36

( 2 ) INFORMATION FOR SEQ ID NO:525:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:525:

AAGAGAUCUG AUGAGGCCGA AAGGCCGAAA CGGAGG                36

( 2 ) INFORMATION FOR SEQ ID NO:526:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:526:

CAGAAGACUG AUGAGGCCGA AAGGCCGAAA UGACGG                36

( 2 ) INFORMATION FOR SEQ ID NO:527:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:527:

CCCAGAACUG AUGAGGCCGA AAGGCCGAAA GAUGAC                36

( 2 ) INFORMATION FOR SEQ ID NO:528:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:528:

AUCCCAGCUG AUGAGGCCGA AAGGCCGAAA GAGAUG                36

( 2 ) INFORMATION FOR SEQ ID NO:529:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:529:

UAUCCCACUG AUGAGGCCGA AAGGCCGAAA AGAGAU                36

( 2 ) INFORMATION FOR SEQ ID NO:530:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:530:

AUCCAUGCUG AUGAGGCCGA AAGGCCGAAA UCCCAG                36

( 2 ) INFORMATION FOR SEQ ID NO:531:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:531:

UCCCCACCUG AUGAGGCCGA AAGGCCGAAA UCCAUG                36

( 2 ) INFORMATION FOR SEQ ID NO:532:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:532:

GCCUCAUCUG AUGAGGCCGA AAGGCCGAAA UCCCCA    36

( 2 ) INFORMATION FOR SEQ ID NO:533:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:533:

AGGGAAGCUG AUGAGGCCGA AAGGCCGAAA UGCCUC    36

( 2 ) INFORMATION FOR SEQ ID NO:534:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:534:

AAGGGAACUG AUGAGGCCGA AAGGCCGAAA AUGCCU    36

( 2 ) INFORMATION FOR SEQ ID NO:535:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:535:

UUAAGGGCUG AUGAGGCCGA AAGGCCGAAA GAAUGC    36

( 2 ) INFORMATION FOR SEQ ID NO:536:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:536:

GUUAAGGCUG AUGAGGCCGA AAGGCCGAAA AGAAUG    36

( 2 ) INFORMATION FOR SEQ ID NO:537:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:537:

AUUUGUUCUG AUGAGGCCGA AAGGCCGAAA GGGAAG    36

( 2 ) INFORMATION FOR SEQ ID NO:538:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:538:

AAUUUGUCUG AUGAGGCCGA AAGGCCGAAA AGGGAA      36

( 2 ) INFORMATION FOR SEQ ID NO:539:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:539:

CAGCUUACUG AUGAGGCCGA AAGGCCGAAA UUUGUU      36

( 2 ) INFORMATION FOR SEQ ID NO:540:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:540:

ACAGCUUCUG AUGAGGCCGA AAGGCCGAAA AUUUGU      36

( 2 ) INFORMATION FOR SEQ ID NO:541:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:541:

AACAGCUCUG AUGAGGCCGA AAGGCCGAAA AAUUUG      36

( 2 ) INFORMATION FOR SEQ ID NO:542:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:542:

UGGGUAACUG AUGAGGCCGA AAGGCCGAAA CAGCUU      36

( 2 ) INFORMATION FOR SEQ ID NO:543:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:543:

GUGGGUACUG AUGAGGCCGA AAGGCCGAAA ACAGCU      36

( 2 ) INFORMATION FOR SEQ ID NO:544:

( i ) SEQUENCE CHARACTERISTICS:
   ( A ) LENGTH: 36 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:544:

AGUGGGUCUG AUGAGGCCGA AAGGCCGAAA AACAGC 36

( 2 ) INFORMATION FOR SEQ ID NO:545:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:545:

UAGUGGGCUG AUGAGGCCGA AAGGCCGAAA AAACAG 36

( 2 ) INFORMATION FOR SEQ ID NO:546:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:546:

GGUGAGGCUG AUGAGGCCGA AAGGCCGAAA GUGGGU 36

( 2 ) INFORMATION FOR SEQ ID NO:547:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:547:

AGAAGGUCUG AUGAGGCCGA AAGGCCGAAA GGUAGU 36

( 2 ) INFORMATION FOR SEQ ID NO:548:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:548:

UUUUAAGCUG AUGAGGCCGA AAGGCCGAAA GGUGAG 36

( 2 ) INFORMATION FOR SEQ ID NO:549:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:549:

UUUUUAACUG AUGAGGCCGA AAGGCCGAAA AGGUGA 36

( 2 ) INFORMATION FOR SEQ ID NO:550:

( i ) SEQUENCE CHARACTERISTICS:
      ( A ) LENGTH: 36 base pairs ( B ) TYPE: nucleic acid
( C ) STRANDEDNESS: single
( D ) TOPOLOGY: linear ( x i ) SEQUENCE DESCRIPTION: SEQ ID NO:550:

GGUUUUUCUG AUGAGGCCGA AAGGCCGAAA GAAGGU 36

( 2 ) INFORMATION FOR SEQ ID NO:551:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:551:

AGGUUUUCUG AUGAGGCCGA AAGGCCGAAA AGAAGG 36

( 2 ) INFORMATION FOR SEQ ID NO:552:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:552:

UCUGAAACUG AUGAGGCCGA AAGGCCGAAA GGUUUU 36

( 2 ) INFORMATION FOR SEQ ID NO:553:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:553:

AAUCUGACUG AUGAGGCCGA AAGGCCGAAA GAGGUU 36

( 2 ) INFORMATION FOR SEQ ID NO:554:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:554:

UAAUCUGCUG AUGAGGCCGA AAGGCCGAAA AGAGGU 36

( 2 ) INFORMATION FOR SEQ ID NO:555:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:555:

UUAAUCUCUG AUGAGGCCGA AAGGCCGAAA AAGAGG 36

( 2 ) INFORMATION FOR SEQ ID NO:556:

( i ) SEQUENCE CHARACTERISTICS:
( A ) LENGTH: 36 base pairs
( B ) TYPE: nucleic acid
( C ) STRANDEDNESS: single (D) TOPOLOGY: linear (xi) SEQUENCE DESCRIPTION: SEQ ID NO:556:

UCAGCUUCUG AUGAGGCCGA AAGGCCGAAA UCUGAA 36

(2) INFORMATION FOR SEQ ID NO:557:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:557:

UUCAGCUCUG AUGAGGCCGA AAGGCCGAAA AUCUGA 36

(2) INFORMATION FOR SEQ ID NO:558:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:558:

AUCUUGUCUG AUGAGGCCGA AAGGCCGAAA CUGUUC 36

(2) INFORMATION FOR SEQ ID NO:559:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:559:

CAUCUUGCUG AUGAGGCCGA AAGGCCGAAA ACUGUU 36

(2) INFORMATION FOR SEQ ID NO:560:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:560:

GGAGAGGCUG AUGAGGCCGA AAGGCCGAAA UGCCAG 36

(2) INFORMATION FOR SEQ ID NO:561:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:561:

GAAAGGACUG AUGAGGCCGA AAGGCCGAAA GGGAUG 36

(2) INFORMATION FOR SEQ ID NO:562:

(i) SEQUENCE CHARACTERISTICS:
        (A) LENGTH: 36 base pairs
        (B) TYPE: nucleic acid
        (C) STRANDEDNESS: single
        (D) TOPOLOGY: linear -continued ( x i ) SEQUENCE DESCRIPTION: SEQ ID NO:562:

GAGAAAGCUG AUGAGGCCGA AAGGCCGAAA GAGGGA        36

( 2 ) INFORMATION FOR SEQ ID NO:563:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:563:

GGGGAGACUG AUGAGGCCGA AAGGCCGAAA GGAGAG        36

( 2 ) INFORMATION FOR SEQ ID NO:564:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:564:

UGGGGAGCUG AUGAGGCCGA AAGGCCGAAA AGGAGA        36

( 2 ) INFORMATION FOR SEQ ID NO:565:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:565:

AUGGGGACUG AUGAGGCCGA AAGGCCGAAA AAGGAG        36

( 2 ) INFORMATION FOR SEQ ID NO:566:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:566:

AUAUGGGCUG AUGAGGCCGA AAGGCCGAAA GAAAGG        36

( 2 ) INFORMATION FOR SEQ ID NO:567:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:567:

AAUUGCACUG AUGAGGCCGA AAGGCCGAAA UGGGGA        36

( 2 ) INFORMATION FOR SEQ ID NO:568:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:568:

```
UUAAGCACUG AUGAGGCCGA AAGGCCGAAA UUGCAU                              36
```

(2) INFORMATION FOR SEQ ID NO:569:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:569:

```
AUUAAGCCUG AUGAGGCCGA AAGGCCGAAA AUUGCA                              36
```

(2) INFORMATION FOR SEQ ID NO:570:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:570:

```
UUACAUUCUG AUGAGGCCGA AAGGCCGAAA GCAAAU                              36
```

(2) INFORMATION FOR SEQ ID NO:571:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:571:

```
GUUACAUCUG AUGAGGCCGA AAGGCCGAAA AGCAAA                              36
```

(2) INFORMATION FOR SEQ ID NO:572:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:572:

```
AAGAGGUCUG AUGAGGCCGA AAGGCCGAAA CAUUAA                              36
```

(2) INFORMATION FOR SEQ ID NO:573:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:573:

```
AAAAGAACUG AUGAGGCCGA AAGGCCGAAA GGUUAC                              36
```

(2) INFORMATION FOR SEQ ID NO:574:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:574:

```
GCAAAAGCUG AUGAGGCCGA AAGGCCGAAA GAGGUU                              36
```

( 2 ) INFORMATION FOR SEQ ID NO:575:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:575:

GGCAAAACUG AUGAGGCCGA AAGGCCGAAA AGAGGU     36

( 2 ) INFORMATION FOR SEQ ID NO:576:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:576:

AUGGCAACUG AUGAGGCCGA AAGGCCGAAA GAAGAG     36

( 2 ) INFORMATION FOR SEQ ID NO:577:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:577:

CAUGGCACUG AUGAGGCCGA AAGGCCGAAA AGAAGA     36

( 2 ) INFORMATION FOR SEQ ID NO:578:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:578:

ACAUGGCCUG AUGAGGCCGA AAGGCCGAAA AAGAAG     36

( 2 ) INFORMATION FOR SEQ ID NO:579:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:579:

GAAUGGACUG AUGAGGCCGA AAGGCCGAAA CAUGGC     36

( 2 ) INFORMATION FOR SEQ ID NO:580:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:580:

AGAAUGGCUG AUGAGGCCGA AAGGCCGAAA ACAUGG     36

( 2 ) INFORMATION FOR SEQ ID NO:581:

( i ) SEQUENCE CHARACTERISTICS:
 ( A ) LENGTH: 36 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:581:

CAGAAUGCUG AUGAGGCCGA AAGGCCGAAA AACAUG 36

( 2 ) INFORMATION FOR SEQ ID NO:582:

( i ) SEQUENCE CHARACTERISTICS:
 ( A ) LENGTH: 36 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:582:

AUGGCAGCUG AUGAGGCCGA AAGGCCGAAA UGGAAA 36

( 2 ) INFORMATION FOR SEQ ID NO:583:

( i ) SEQUENCE CHARACTERISTICS:
 ( A ) LENGTH: 36 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:583:

GAUGGCACUG AUGAGGCCGA AAGGCCGAAA AUGGAA 36

( 2 ) INFORMATION FOR SEQ ID NO:584:

( i ) SEQUENCE CHARACTERISTICS:
 ( A ) LENGTH: 36 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:584:

AAUUCAACUG AUGAGGCCGA AAGGCCGAAA UGGCAG 36

( 2 ) INFORMATION FOR SEQ ID NO:585:

( i ) SEQUENCE CHARACTERISTICS:
 ( A ) LENGTH: 36 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:585:

ACAAUUCCUG AUGAGGCCGA AAGGCCGAAA GAUGGC 36

( 2 ) INFORMATION FOR SEQ ID NO:586:

( i ) SEQUENCE CHARACTERISTICS:
 ( A ) LENGTH: 36 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:586:

ACAAGACCUG AUGAGGCCGA AAGGCCGAAA UUCAAG 36

( 2 ) INFORMATION FOR SEQ ID NO:587:

( i ) SEQUENCE CHARACTERISTICS:

(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:587:

CUGACAACUG AUGAGGCCGA AAGGCCGAAA CAAUUC 36

(2) INFORMATION FOR SEQ ID NO:588:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:588:

GGCUGACCUG AUGAGGCCGA AAGGCCGAAA GACAAU 36

(2) INFORMATION FOR SEQ ID NO:589:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:589:

AUUGGCUCUG AUGAGGCCGA AAGGCCGAAA CAAGAC 36

(2) INFORMATION FOR SEQ ID NO:590:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:590:

GAUAAUGCUG AUGAGGCCGA AAGGCCGAAA UUGGCU 36

(2) INFORMATION FOR SEQ ID NO:591:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:591:

AGAUAAUCUG AUGAGGCCGA AAGGCCGAAA AUUGGC 36

(2) INFORMATION FOR SEQ ID NO:592:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:592:

AAUAGAUCUG AUGAGGCCGA AAGGCCGAAA UGAAUU 36

(2) INFORMATION FOR SEQ ID NO:593:

(i) SEQUENCE CHARACTERISTICS:
(A) LENGTH: 36 base pairs
(B) TYPE: nucleic acid

-continued ( C ) STRANDEDNESS: single
      ( D ) TOPOLOGY: linear ( x i ) SEQUENCE DESCRIPTION: SEQ ID NO:593:

UAAUAGACUG AUGAGGCCGA AAGGCCGAAA AUGAAU    36

( 2 ) INFORMATION FOR SEQ ID NO:594:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:594:

UUUAAUACUG AUGAGGCCGA AAGGCCGAAA UAAUGA    36

( 2 ) INFORMATION FOR SEQ ID NO:595:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:595:

UGUUUAACUG AUGAGGCCGA AAGGCCGAAA GAUAAU    36

( 2 ) INFORMATION FOR SEQ ID NO:596:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:596:

AGUGUUUCUG AUGAGGCCGA AAGGCCGAAA UAGAUA    36

( 2 ) INFORMATION FOR SEQ ID NO:597:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:597:

UAGUGUUCUG AUGAGGCCGA AAGGCCGAAA AUAGAU    36

( 2 ) INFORMATION FOR SEQ ID NO:598:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:598:

CUCAAAUCUG AUGAGGCCGA AAGGCCGAAA GUGUUU    36

( 2 ) INFORMATION FOR SEQ ID NO:599:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:599:

GAGUUUUAUA CCUCA 15

( 2 ) INFORMATION FOR SEQ ID NO:600:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:600:

GUUUUAUACC UCAAU 15

( 2 ) INFORMATION FOR SEQ ID NO:601:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:601:

GUUUUAUACC UCAAU 15

( 2 ) INFORMATION FOR SEQ ID NO:602:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:602:

UAUACCUCAA UAGAC 15

( 2 ) INFORMATION FOR SEQ ID NO:603:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:603:

CCUCAAUAGA CUCUU 15

( 2 ) INFORMATION FOR SEQ ID NO:604:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:604:

CCUCAAUAGA CUCUU 15

( 2 ) INFORMATION FOR SEQ ID NO:605:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:605:

CCUCAAUAGA CUCUU 15

(2) INFORMATION FOR SEQ ID NO:606:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:606:

AUAGACUCUU ACUAG 15

(2) INFORMATION FOR SEQ ID NO:607:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:607:

AGACUCUUAC UAGUU 15

(2) INFORMATION FOR SEQ ID NO:608:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:608:

GACUCUUACU AGUUU 15

(2) INFORMATION FOR SEQ ID NO:609:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:609:

UCUUACUAGU UUCUC 15

(2) INFORMATION FOR SEQ ID NO:610:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:610:

UCUUACUAGU UUCUC 15

(2) INFORMATION FOR SEQ ID NO:611:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:611:

UCUUACUAGU UUCUC 15

( 2 ) INFORMATION FOR SEQ ID NO:612:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:612:

UCUUACUAGU UUCUC 15

( 2 ) INFORMATION FOR SEQ ID NO:613:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:613:

CUAGUUUCUC UUUUU 15

( 2 ) INFORMATION FOR SEQ ID NO:614:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:614:

CUAGUUUCUC UUUUU 15

( 2 ) INFORMATION FOR SEQ ID NO:615:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:615:

CUAGUUUCUC UUUUU 15

( 2 ) INFORMATION FOR SEQ ID NO:616:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:616:

UCUCUUUUUC AGGUU 15

( 2 ) INFORMATION FOR SEQ ID NO:617:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:617:

CUCUUUUUCA GGUUG 15

( 2 ) INFORMATION FOR SEQ ID NO:618:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:618:

CUCUUUUUCA GGUUG 15

( 2 ) INFORMATION FOR SEQ ID NO:619:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:619:

UCUUUUUCAG GUUGU 15

( 2 ) INFORMATION FOR SEQ ID NO:620:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:620:

UGAAACUCAA CCUUC 15

( 2 ) INFORMATION FOR SEQ ID NO:621:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:621:

UGAAACUCAA CCUUC 15

( 2 ) INFORMATION FOR SEQ ID NO:622:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:622:

UCAACCUUCA AAGAC 15

( 2 ) INFORMATION FOR SEQ ID NO:623:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:623:

UCAACCUUCA AAGAC 15

( 2 ) INFORMATION FOR SEQ ID NO:624:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:624:

UCAACCUUCA AAGAC 15

( 2 ) INFORMATION FOR SEQ ID NO:625:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:625:

CAACCUUCAA AGACA 15

( 2 ) INFORMATION FOR SEQ ID NO:626:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:626:

AGACACUCUG UUCCA 15

( 2 ) INFORMATION FOR SEQ ID NO:627:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:627:

ACUCUGUUCC AUUUC 15

( 2 ) INFORMATION FOR SEQ ID NO:628:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:628:

CUCUGUUCCA UUUCU 15

( 2 ) INFORMATION FOR SEQ ID NO:629:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:629:

UUCCAUUUCU GUGGA 15

( 2 ) INFORMATION FOR SEQ ID NO:630:

( i ) SEQUENCE CHARACTERISTICS:
    ( A ) LENGTH: 15 base pairs (B) TYPE: nucleic acid
                (C) STRANDEDNESS: single
                (D) TOPOLOGY: linear (xi) SEQUENCE DESCRIPTION: SEQ ID NO:630:

GUGGACUAAU AGGAU                                                                         15

(2) INFORMATION FOR SEQ ID NO:631:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (xi) SEQUENCE DESCRIPTION: SEQ ID NO:631:

GUGGACUAAU AGGAU                                                                         15

(2) INFORMATION FOR SEQ ID NO:632:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (xi) SEQUENCE DESCRIPTION: SEQ ID NO:632:

GUGGACUAAU AGGAU                                                                         15

(2) INFORMATION FOR SEQ ID NO:633:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (xi) SEQUENCE DESCRIPTION: SEQ ID NO:633:

GACUAAUAGG AUCAU                                                                         15

(2) INFORMATION FOR SEQ ID NO:634:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (xi) SEQUENCE DESCRIPTION: SEQ ID NO:634:

GACUAAUAGG AUCAU                                                                         15

(2) INFORMATION FOR SEQ ID NO:635:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (xi) SEQUENCE DESCRIPTION: SEQ ID NO:635:

AUAGGAUCAU CUUUA                                                                         15

(2) INFORMATION FOR SEQ ID NO:636:

(i) SEQUENCE CHARACTERISTICS:
                (A) LENGTH: 15 base pairs
                (B) TYPE: nucleic acid
                (C) STRANDEDNESS: single (D) TOPOLOGY: linear (xi) SEQUENCE DESCRIPTION: SEQ ID NO:636:

GGAUCAUCUU UAGCA 15

(2) INFORMATION FOR SEQ ID NO:637:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:637:

GGAUCAUCUU UAGCA 15

(2) INFORMATION FOR SEQ ID NO:638:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:638:

AUCAUCUUUA GCAUC 15

(2) INFORMATION FOR SEQ ID NO:639:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:639:

UCAUCUUUAG CAUCU 15

(2) INFORMATION FOR SEQ ID NO:640:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:640:

UCAUCUUUAG CAUCU 15

(2) INFORMATION FOR SEQ ID NO:641:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:641:

CAUCUUUAGC AUCUG 15

(2) INFORMATION FOR SEQ ID NO:642:

(i) SEQUENCE CHARACTERISTICS:
        (A) LENGTH: 15 base pairs
        (B) TYPE: nucleic acid
        (C) STRANDEDNESS: single
        (D) TOPOLOGY: linear ( x i ) SEQUENCE DESCRIPTION: SEQ ID NO:642:

CAUCUUUAGC AUCUG 15

( 2 ) INFORMATION FOR SEQ ID NO:643:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:643:

AUGCCAUCCA GGCUU 15

( 2 ) INFORMATION FOR SEQ ID NO:644:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:644:

GCUUCUUUUU CUACA 15

( 2 ) INFORMATION FOR SEQ ID NO:645:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:645:

GCUUCUUUUU CUACA 15

( 2 ) INFORMATION FOR SEQ ID NO:646:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:646:

CUUCUUUUUC UACAU 15

( 2 ) INFORMATION FOR SEQ ID NO:647:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:647:

CUUCUUUUUC UACAU 15

( 2 ) INFORMATION FOR SEQ ID NO:648:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:648:

CUUCUUUUUC UACAU    15

( 2 ) INFORMATION FOR SEQ ID NO:649:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:649:

CUUCUUUUUC UACAU    15

( 2 ) INFORMATION FOR SEQ ID NO:650:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:650:

UUCUUUUUCU ACAUC    15

( 2 ) INFORMATION FOR SEQ ID NO:651:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:651:

UUCUUUUUCU ACAUC    15

( 2 ) INFORMATION FOR SEQ ID NO:652:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:652:

UUCUUUUUCU ACAUC    15

( 2 ) INFORMATION FOR SEQ ID NO:653:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:653:

UUUUUCUACA UCUCU    15

( 2 ) INFORMATION FOR SEQ ID NO:654:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:654:

UACAUCUCUG UUUCU    15

( 2 ) INFORMATION FOR SEQ ID NO:655:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:655:

UCUCGAUUUU UGUGA     15

( 2 ) INFORMATION FOR SEQ ID NO:656:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:656:

UCUCGAUUUU UGUGA     15

( 2 ) INFORMATION FOR SEQ ID NO:657:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:657:

UCUCGAUUUU UGUGA     15

( 2 ) INFORMATION FOR SEQ ID NO:658:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:658:

CUCGAUUUUU GUGAG     15

( 2 ) INFORMATION FOR SEQ ID NO:659:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:659:

UCGAUUUUG UGAGC     15

( 2 ) INFORMATION FOR SEQ ID NO:660:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:660:

UCGAUUUUG UGAGC     15

( 2 ) INFORMATION FOR SEQ ID NO:661:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:661:

UCGAUUUUUG UGAGC    15

( 2 ) INFORMATION FOR SEQ ID NO:662:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:662:

CGAUUUUUGU GAGCC    15

( 2 ) INFORMATION FOR SEQ ID NO:663:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:663:

CGAUUUUUGU GAGCC    15

( 2 ) INFORMATION FOR SEQ ID NO:664:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:664:

GCUCCAUUGG CUCUA    15

( 2 ) INFORMATION FOR SEQ ID NO:665:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:665:

AUUGGCUCUA GAUUC    15

( 2 ) INFORMATION FOR SEQ ID NO:666:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:666:

UCUAGAUUCC UGGCU    15

( 2 ) INFORMATION FOR SEQ ID NO:667:

( i ) SEQUENCE CHARACTERISTICS:

(A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:667:

CCUGGCUUUC CCCAU                                                                                        15

(2) INFORMATION FOR SEQ ID NO:668:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:668:

CUGGCUUUCC CCAUC                                                                                        15

(2) INFORMATION FOR SEQ ID NO:669:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:669:

CUGGCUUUCC CCAUC                                                                                        15

(2) INFORMATION FOR SEQ ID NO:670:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:670:

CUGGCUUUCC CCAUC                                                                                        15

(2) INFORMATION FOR SEQ ID NO:671:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:671:

UGGCUUUCCC CAUCA                                                                                        15

(2) INFORMATION FOR SEQ ID NO:672:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:672:

UGGCUUUCCC CAUCA                                                                                        15

(2) INFORMATION FOR SEQ ID NO:673:

(i) SEQUENCE CHARACTERISTICS:
        (A) LENGTH: 15 base pairs
        (B) TYPE: nucleic acid (C) STRANDEDNESS: single
                (D) TOPOLOGY: linear (x i) SEQUENCE DESCRIPTION: SEQ ID NO:673:

UGGCUUUCCC CAUCA                                                                    15

(2) INFORMATION FOR SEQ ID NO:674:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (x i) SEQUENCE DESCRIPTION: SEQ ID NO:674:

UGGCUUUCCC CAUCA                                                                    15

(2) INFORMATION FOR SEQ ID NO:675:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (x i) SEQUENCE DESCRIPTION: SEQ ID NO:675:

UCCCCAUCAU GUUCU                                                                    15

(2) INFORMATION FOR SEQ ID NO:676:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (x i) SEQUENCE DESCRIPTION: SEQ ID NO:676:

UCCCCAUCAU GUUCU                                                                    15

(2) INFORMATION FOR SEQ ID NO:677:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (x i) SEQUENCE DESCRIPTION: SEQ ID NO:677:

UCAUGUUCUC CAAAG                                                                    15

(2) INFORMATION FOR SEQ ID NO:678:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (x i) SEQUENCE DESCRIPTION: SEQ ID NO:678:

AUGUUCUCCA AAGCA                                                                    15

(2) INFORMATION FOR SEQ ID NO:679:

(i) SEQUENCE CHARACTERISTICS:
                (A) LENGTH: 15 base pairs
                (B) TYPE: nucleic acid
                (C) STRANDEDNESS: single
                (D) TOPOLOGY: linear ( x i ) SEQUENCE DESCRIPTION: SEQ ID NO:679:

AUGUUCUCCA AAGCA 15

( 2 ) INFORMATION FOR SEQ ID NO:680:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:680:

AUGUUCUCCA AAGCA 15

( 2 ) INFORMATION FOR SEQ ID NO:681:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:681:

AAAGCAUCUG AAGCU 15

( 2 ) INFORMATION FOR SEQ ID NO:682:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:682:

AAAGCAUCUG AAGCU 15

( 2 ) INFORMATION FOR SEQ ID NO:683:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:683:

AAAGCAUCUG AAGCU 15

( 2 ) INFORMATION FOR SEQ ID NO:684:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:684:

UGAAGCUAUG GCUUG 15

( 2 ) INFORMATION FOR SEQ ID NO:685:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:685:

CAAUUGUCAG UUGAU 15

( 2 ) INFORMATION FOR SEQ ID NO:686:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:686:

CACCACUCCU CAAGU 15

( 2 ) INFORMATION FOR SEQ ID NO:687:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:687:

CUCAAGUUUC CAUGU 15

( 2 ) INFORMATION FOR SEQ ID NO:688:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:688:

CUCAAGUUUC CAUGU 15

( 2 ) INFORMATION FOR SEQ ID NO:689:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:689:

UCAAGUUUCC AUGUC 15

( 2 ) INFORMATION FOR SEQ ID NO:690:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:690:

CAAGUUUCCA UGUCC 15

( 2 ) INFORMATION FOR SEQ ID NO:691:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:691:

CAAGUUUCCA UGUCC 15

( 2 ) INFORMATION FOR SEQ ID NO:692:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:692:

GGCUCAUUCU UCUCU 15

( 2 ) INFORMATION FOR SEQ ID NO:693:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:693:

GGCUCAUUCU UCUCU 15

( 2 ) INFORMATION FOR SEQ ID NO:694:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:694:

GCUCAUUCUU CUCUU 15

( 2 ) INFORMATION FOR SEQ ID NO:695:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:695:

GCUCAUUCUU CUCUU 15

( 2 ) INFORMATION FOR SEQ ID NO:696:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:696:

UCAUUCUUCU CUUUG 15

( 2 ) INFORMATION FOR SEQ ID NO:697:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:697:

CAUUCUUCUC UUUGU 15

( 2 ) INFORMATION FOR SEQ ID NO:698:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:698:

CAUUCUUCUC UUUGU     15

( 2 ) INFORMATION FOR SEQ ID NO:699:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:699:

UUCUUCUCUU UGUGC     15

( 2 ) INFORMATION FOR SEQ ID NO:700:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:700:

UUCUUCUCUU UGUGC     15

( 2 ) INFORMATION FOR SEQ ID NO:701:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:701:

CUUCUCUUUG UGCUG     15

( 2 ) INFORMATION FOR SEQ ID NO:702:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:702:

CUUCUCUUUG UGCUG     15

( 2 ) INFORMATION FOR SEQ ID NO:703:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:703:

UUCUCUUUGU GCUGC     15

( 2 ) INFORMATION FOR SEQ ID NO:704:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:704:

GCUGAUUCGU CUUUC 15

( 2 ) INFORMATION FOR SEQ ID NO:705:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:705:

UUCGUCUUUC ACAAG 15

( 2 ) INFORMATION FOR SEQ ID NO:706:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:706:

UUCGUCUUUC ACAAG 15

( 2 ) INFORMATION FOR SEQ ID NO:707:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:707:

UCGUCUUUCA CAAGU 15

( 2 ) INFORMATION FOR SEQ ID NO:708:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:708:

CGUCUUUCAC AAGUG 15

( 2 ) INFORMATION FOR SEQ ID NO:709:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:709:

CGUCUUUCAC AAGUG 15

( 2 ) INFORMATION FOR SEQ ID NO:710:

( i ) SEQUENCE CHARACTERISTICS:
    ( A ) LENGTH: 15 base pairs (B) TYPE: nucleic acid
(C) STRANDEDNESS: single
(D) TOPOLOGY: linear (xi) SEQUENCE DESCRIPTION: SEQ ID NO:710:

CAAGUGUCUU CAGAU 15

(2) INFORMATION FOR SEQ ID NO:711:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:711:

GUGUCUUCAG AUGUU 15

(2) INFORMATION FOR SEQ ID NO:712:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:712:

UCCAAGUCAG UGAAA 15

(2) INFORMATION FOR SEQ ID NO:713:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:713:

GCUGCCUUGC CGUUA 15

(2) INFORMATION FOR SEQ ID NO:714:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:714:

UUGCCGUUAC AACUC 15

(2) INFORMATION FOR SEQ ID NO:715:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:715:

UUGCCGUUAC AACUC 15

(2) INFORMATION FOR SEQ ID NO:716:

(i) SEQUENCE CHARACTERISTICS:
(A) LENGTH: 15 base pairs
(B) TYPE: nucleic acid
(C) STRANDEDNESS: single -continued (D) TOPOLOGY: linear (xi) SEQUENCE DESCRIPTION: SEQ ID NO:716:

UACAACUCUC CUCAU                                                                 15

(2) INFORMATION FOR SEQ ID NO:717:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:717:

CUCUCCUCAU GAAGA                                                                 15

(2) INFORMATION FOR SEQ ID NO:718:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:718:

GAUGAGUCUG AAGAC                                                                 15

(2) INFORMATION FOR SEQ ID NO:719:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:719:

ACCGAAUCUA CUGGC                                                                 15

(2) INFORMATION FOR SEQ ID NO:720:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:720:

CGAAUCUACU GGCAA                                                                 15

(2) INFORMATION FOR SEQ ID NO:721:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:721:

GUGCUGUCUG UCAUU                                                                 15

(2) INFORMATION FOR SEQ ID NO:722:

(i) SEQUENCE CHARACTERISTICS:
        (A) LENGTH: 15 base pairs
        (B) TYPE: nucleic acid
        (C) STRANDEDNESS: single
        (D) TOPOLOGY: linear ( x i ) SEQUENCE DESCRIPTION: SEQ ID NO:722:

GUGCUGUCUG UCAUU  15

( 2 ) INFORMATION FOR SEQ ID NO:723:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:723:

UGUCUGUCAU UGCUG  15

( 2 ) INFORMATION FOR SEQ ID NO:724:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:724:

GGAAACUAAA AGUGU  15

( 2 ) INFORMATION FOR SEQ ID NO:725:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:725:

GGAAACUAAA AGUGU  15

( 2 ) INFORMATION FOR SEQ ID NO:726:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:726:

CCCGAGUAUA AGAAC  15

( 2 ) INFORMATION FOR SEQ ID NO:727:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:727:

CGGACUUUAU AUGAC  15

( 2 ) INFORMATION FOR SEQ ID NO:728:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:728:

```
        GGACUUUAUA  UGACA                                                               15
```

(2) INFORMATION FOR SEQ ID NO:729:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:729:

```
        ACUUUAUAUG  ACAAC                                                               15
```

(2) INFORMATION FOR SEQ ID NO:730:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:730:

```
        ACUACCUACU  CUCUU                                                               15
```

(2) INFORMATION FOR SEQ ID NO:731:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:731:

```
        ACUACCUACU  CUCUU                                                               15
```

(2) INFORMATION FOR SEQ ID NO:732:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:732:

```
        ACCUACUCUC  UUAUC                                                               15
```

(2) INFORMATION FOR SEQ ID NO:733:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:733:

```
        ACCUACUCUC  UUAUC                                                               15
```

(2) INFORMATION FOR SEQ ID NO:734:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:734:

```
        ACUCUCUUAU  CAUCC                                                               15
```

( 2 ) INFORMATION FOR SEQ ID NO:735:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:735:

CUCUCUUAUC AUCCU　　　　　　　　　　　　　　　　　　　　　　　　　　　15

( 2 ) INFORMATION FOR SEQ ID NO:736:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:736:

CUCUCUUAUC AUCCU　　　　　　　　　　　　　　　　　　　　　　　　　　　15

( 2 ) INFORMATION FOR SEQ ID NO:737:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:737:

CUCUCUUAUC AUCCU　　　　　　　　　　　　　　　　　　　　　　　　　　　15

( 2 ) INFORMATION FOR SEQ ID NO:738:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:738:

UUAUCAUCCU GGGCC　　　　　　　　　　　　　　　　　　　　　　　　　　　15

( 2 ) INFORMATION FOR SEQ ID NO:739:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:739:

UUAUCAUCCU GGGCC　　　　　　　　　　　　　　　　　　　　　　　　　　　15

( 2 ) INFORMATION FOR SEQ ID NO:740:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:740:

UGGUCCUUUC AGACC　　　　　　　　　　　　　　　　　　　　　　　　　　　15

( 2 ) INFORMATION FOR SEQ ID NO:741:

( i ) SEQUENCE CHARACTERISTICS:
   ( A ) LENGTH: 15 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:741:

GUCCUUUCAG ACCGG 15

( 2 ) INFORMATION FOR SEQ ID NO:742:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:742:

GUCCUUUCAG ACCGG 15

( 2 ) INFORMATION FOR SEQ ID NO:743:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:743:

GGCACAUACA GCUGU 15

( 2 ) INFORMATION FOR SEQ ID NO:744:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:744:

GCUGUGUCGU UCAAA 15

( 2 ) INFORMATION FOR SEQ ID NO:745:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:745:

GUGUCGUUCA AAAGA 15

( 2 ) INFORMATION FOR SEQ ID NO:746:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:746:

GUGUCGUUCA AAAGA 15

( 2 ) INFORMATION FOR SEQ ID NO:747:

( i ) SEQUENCE CHARACTERISTICS:

(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:747:

UGUCGUUCAA AAGAA 15

(2) INFORMATION FOR SEQ ID NO:748:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:748:

AUGAAGUUAA ACACU 15

(2) INFORMATION FOR SEQ ID NO:749:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:749:

AAACACUUGG CUUUA 15

(2) INFORMATION FOR SEQ ID NO:750:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:750:

AAACACUUGG CUUUA 15

(2) INFORMATION FOR SEQ ID NO:751:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:751:

UUGGCUUUAG UAAAG 15

(2) INFORMATION FOR SEQ ID NO:752:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:752:

UGGCUUUAGU AAAGU 15

(2) INFORMATION FOR SEQ ID NO:753:

(i) SEQUENCE CHARACTERISTICS:
(A) LENGTH: 15 base pairs
(B) TYPE: nucleic acid ( C ) STRANDEDNESS: single
( D ) TOPOLOGY: linear ( x i ) SEQUENCE DESCRIPTION: SEQ ID NO:753:

CUUUAGUAAA GUUGU                                                                                  15

( 2 ) INFORMATION FOR SEQ ID NO:754:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:754:

GUAAAGUUGU CCAUC                                                                                  15

( 2 ) INFORMATION FOR SEQ ID NO:755:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:755:

AAGUUGUCCA UCAAA                                                                                  15

( 2 ) INFORMATION FOR SEQ ID NO:756:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:756:

UGUCCAUCAA AGCUG                                                                                  15

( 2 ) INFORMATION FOR SEQ ID NO:757:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:757:

GCUGACUUCU CUACC                                                                                  15

( 2 ) INFORMATION FOR SEQ ID NO:758:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:758:

GCUGACUUCU CUACC                                                                                  15

( 2 ) INFORMATION FOR SEQ ID NO:759:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:759:

GCUGACUUCU CUACC                                                                                    15

( 2 ) INFORMATION FOR SEQ ID NO:760:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:760:

CUGACUUCUC UACCC                                                                                    15

( 2 ) INFORMATION FOR SEQ ID NO:761:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:761:

CUGACUUCUC UACCC                                                                                    15

( 2 ) INFORMATION FOR SEQ ID NO:762:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:762:

GACUUCUCUA CCCCC                                                                                    15

( 2 ) INFORMATION FOR SEQ ID NO:763:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:763:

GACUUCUCUA CCCCC                                                                                    15

( 2 ) INFORMATION FOR SEQ ID NO:764:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:764:

CUUCUCUACC CCCAA                                                                                    15

( 2 ) INFORMATION FOR SEQ ID NO:765:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:765:

CCAACAUAAC UGAGU 15

(2) INFORMATION FOR SEQ ID NO:766:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:766:

CCAACAUAAC UGAGU 15

(2) INFORMATION FOR SEQ ID NO:767:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:767:

AACCCAUCUG CAGAC 15

(2) INFORMATION FOR SEQ ID NO:768:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:768:

AACCCAUCUG CAGAC 15

(2) INFORMATION FOR SEQ ID NO:769:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:769:

AGACACUAAA AGGAU 15

(2) INFORMATION FOR SEQ ID NO:770:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:770:

AGACACUAAA AGGAU 15

(2) INFORMATION FOR SEQ ID NO:771:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:771:

AGACACUAAA AGGAU 15

( 2 ) INFORMATION FOR SEQ ID NO:772:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:772:

AAAGGAUUAC CUGCU 15

( 2 ) INFORMATION FOR SEQ ID NO:773:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:773:

AAAGGAUUAC CUGCU 15

( 2 ) INFORMATION FOR SEQ ID NO:774:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:774:

AAAGGAUUAC CUGCU 15

( 2 ) INFORMATION FOR SEQ ID NO:775:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:775:

ACCUGCUUUG CUUCC 15

( 2 ) INFORMATION FOR SEQ ID NO:776:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:776:

ACCUGCUUUG CUUCC 15

( 2 ) INFORMATION FOR SEQ ID NO:777:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:777:

CGGGGGUUUC CCAAA 15

( 2 ) INFORMATION FOR SEQ ID NO:778:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:778:

CGGGGGUUUC CCAAA                                          15

( 2 ) INFORMATION FOR SEQ ID NO:779:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:779:

CGGGGGUUUC CCAAA                                          15

( 2 ) INFORMATION FOR SEQ ID NO:780:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:780:

GGGGGUUUCC CAAAG                                          15

( 2 ) INFORMATION FOR SEQ ID NO:781:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:781:

GGGGGUUUCC CAAAG                                          15

( 2 ) INFORMATION FOR SEQ ID NO:782:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:782:

GGGGGUUUCC CAAAG                                          15

( 2 ) INFORMATION FOR SEQ ID NO:783:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:783:

GGGGUUUCCC AAAGC                                          15

( 2 ) INFORMATION FOR SEQ ID NO:784:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:784:

AAAGCCUCGC UUCUC 15

( 2 ) INFORMATION FOR SEQ ID NO:785:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:785:

AAAGCCUCGC UUCUC 15

( 2 ) INFORMATION FOR SEQ ID NO:786:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:786:

CUCGCUUCUC UUGGU 15

( 2 ) INFORMATION FOR SEQ ID NO:787:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:787:

CUCGCUUCUC UUGGU 15

( 2 ) INFORMATION FOR SEQ ID NO:788:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:788:

CGCUUCUCUU GGUUG 15

( 2 ) INFORMATION FOR SEQ ID NO:789:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:789:

UCUUGGUUGG AAAAU 15

( 2 ) INFORMATION FOR SEQ ID NO:790:

( i ) SEQUENCE CHARACTERISTICS:
    ( A ) LENGTH: 15 base pairs (B) TYPE: nucleic acid
        (C) STRANDEDNESS: single
        (D) TOPOLOGY: linear (xi) SEQUENCE DESCRIPTION: SEQ ID NO:790:

GAGAAUUACC UGGCA                                                                                    15

(2) INFORMATION FOR SEQ ID NO:791:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:791:

GAGAAUUACC UGGCA                                                                                    15

(2) INFORMATION FOR SEQ ID NO:792:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:792:

GAGAAUUACC UGGCA                                                                                    15

(2) INFORMATION FOR SEQ ID NO:793:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:793:

CUGGCAUCAA UACGA                                                                                    15

(2) INFORMATION FOR SEQ ID NO:794:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:794:

CUGGCAUCAA UACGA                                                                                    15

(2) INFORMATION FOR SEQ ID NO:795:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:795:

CAUCAAUACG ACAAU                                                                                    15

(2) INFORMATION FOR SEQ ID NO:796:

(i) SEQUENCE CHARACTERISTICS:
        (A) LENGTH: 15 base pairs
        (B) TYPE: nucleic acid
        (C) STRANDEDNESS: single (D) TOPOLOGY: linear (xi) SEQUENCE DESCRIPTION: SEQ ID NO:796:

CAUCAAUACG ACAAU 15

(2) INFORMATION FOR SEQ ID NO:797:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:797:

CGACAAUUUC CCAGG 15

(2) INFORMATION FOR SEQ ID NO:798:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:798:

GACAAUUUCC CAGGA 15

(2) INFORMATION FOR SEQ ID NO:799:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:799:

ACAAUUUCCC AGGAU 15

(2) INFORMATION FOR SEQ ID NO:800:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:800:

CCAGGAUCCU GAAUC 15

(2) INFORMATION FOR SEQ ID NO:801:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:801:

CCUGAAUCUG AAUUG 15

(2) INFORMATION FOR SEQ ID NO:802:

(i) SEQUENCE CHARACTERISTICS:
        (A) LENGTH: 15 base pairs
        (B) TYPE: nucleic acid
        (C) STRANDEDNESS: single
        (D) TOPOLOGY: linear ( x i ) SEQUENCE DESCRIPTION: SEQ ID NO:802:

CCUGAAUCUG AAUUG                    15

( 2 ) INFORMATION FOR SEQ ID NO:803:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:803:

GAAUUGUACA CCAUU                    15

( 2 ) INFORMATION FOR SEQ ID NO:804:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:804:

GCCAACUAGA UUUCA                    15

( 2 ) INFORMATION FOR SEQ ID NO:805:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:805:

GCCAACUAGA UUUCA                    15

( 2 ) INFORMATION FOR SEQ ID NO:806:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:806:

GCCAACUAGA UUUCA                    15

( 2 ) INFORMATION FOR SEQ ID NO:807:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:807:

ACUAGAUUUC AAUAC                    15

( 2 ) INFORMATION FOR SEQ ID NO:808:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:808:

ACUAGAUUUC AAUAC                                                    15

(2) INFORMATION FOR SEQ ID NO:809:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:809:

CUAGAUUUCA AUACG                                                    15

(2) INFORMATION FOR SEQ ID NO:810:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:810:

UAGAUUUCAA UACGA                                                    15

(2) INFORMATION FOR SEQ ID NO:811:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:811:

UACGACUCGC AACCA                                                    15

(2) INFORMATION FOR SEQ ID NO:812:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:812:

ACACCAUUAA GUGUC                                                    15

(2) INFORMATION FOR SEQ ID NO:813:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:813:

ACACCAUUAA GUGUC                                                    15

(2) INFORMATION FOR SEQ ID NO:814:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:814:

UAAGUGUCUC AUUAA                                                    15

(2) INFORMATION FOR SEQ ID NO:815:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:815:

UAAGUGUCUC AUUAA        15

(2) INFORMATION FOR SEQ ID NO:816:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:816:

AGUGUCUCAU UAAAU        15

(2) INFORMATION FOR SEQ ID NO:817:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:817:

GUCUCAUUAA AUAUG        15

(2) INFORMATION FOR SEQ ID NO:818:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:818:

AUUAAAUAUG GAGAU        15

(2) INFORMATION FOR SEQ ID NO:819:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:819:

AUUAAAUAUG GAGAU        15

(2) INFORMATION FOR SEQ ID NO:820:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:820:

GAGGACUUCA CCUGG        15

(2) INFORMATION FOR SEQ ID NO:821:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:821:

AGGACUUCAC CUGGG                    15

( 2 ) INFORMATION FOR SEQ ID NO:822:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:822:

UGCUCUUUGG GGCAG                    15

( 2 ) INFORMATION FOR SEQ ID NO:823:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:823:

CAGUCGUCGU CAUCG                    15

( 2 ) INFORMATION FOR SEQ ID NO:824:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:824:

UCGUCGUCAU CGUUG                    15

( 2 ) INFORMATION FOR SEQ ID NO:825:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:825:

UCAUCGUUGU CAUCA                    15

( 2 ) INFORMATION FOR SEQ ID NO:826:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:826:

UCGUUGUCAU CAUCA                    15

( 2 ) INFORMATION FOR SEQ ID NO:827:

( i ) SEQUENCE CHARACTERISTICS:

(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:827:

UUGUCAUCAU CAAAU 15

(2) INFORMATION FOR SEQ ID NO:828:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:828:

AAAUGCUUCU GUAAG 15

(2) INFORMATION FOR SEQ ID NO:829:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:829:

AAAUGCUUCU GUAAG 15

(2) INFORMATION FOR SEQ ID NO:830:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:830:

AAAUGCUUCU GUAAG 15

(2) INFORMATION FOR SEQ ID NO:831:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:831:

AAAUGCUUCU GUAAG 15

(2) INFORMATION FOR SEQ ID NO:832:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:832:

AAUGCUUCUG UAAGC 15

(2) INFORMATION FOR SEQ ID NO:833:

(i) SEQUENCE CHARACTERISTICS:
(A) LENGTH: 15 base pairs
(B) TYPE: nucleic acid ( C ) STRANDEDNESS: single
            ( D ) TOPOLOGY: linear ( x i ) SEQUENCE DESCRIPTION: SEQ ID NO:833:

A A G C U G U U U C   A G A A G                                                                                        1 5

( 2 ) INFORMATION FOR SEQ ID NO:834:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:834:

A A G C U G U U U C   A G A A G                                                                                        1 5

( 2 ) INFORMATION FOR SEQ ID NO:835:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:835:

A G C U G U U U C A   G A A G A                                                                                        1 5

( 2 ) INFORMATION FOR SEQ ID NO:836:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:836:

A C A G C C U U A C   C U U C G                                                                                        1 5

( 2 ) INFORMATION FOR SEQ ID NO:837:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:837:

A C A G C C U U A C   C U U C G                                                                                        1 5

( 2 ) INFORMATION FOR SEQ ID NO:838:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:838:

A C A G C C U U A C   C U U C G                                                                                        1 5

( 2 ) INFORMATION FOR SEQ ID NO:839:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:839:

CAGCCUUACC UUCGG         15

( 2 ) INFORMATION FOR SEQ ID NO:840:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:840:

CUUACCUUCG GGCCU         15

( 2 ) INFORMATION FOR SEQ ID NO:841:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:841:

UUACCUUCGG GCCUG         15

( 2 ) INFORMATION FOR SEQ ID NO:842:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:842:

UUACCUUCGG GCCUG         15

( 2 ) INFORMATION FOR SEQ ID NO:843:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:843:

GAAGCAUUAG CUGAA         15

( 2 ) INFORMATION FOR SEQ ID NO:844:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:844:

GAAGCAUUAG CUGAA         15

( 2 ) INFORMATION FOR SEQ ID NO:845:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:845:

AAGCAUUAGC UGAAC                                                                                        15

( 2 ) INFORMATION FOR SEQ ID NO:846:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:846:

AGACCGUCUU CCUUU                                                                                        15

( 2 ) INFORMATION FOR SEQ ID NO:847:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:847:

ACCGUCUUCC UUUAG                                                                                        15

( 2 ) INFORMATION FOR SEQ ID NO:848:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:848:

CCGUCUUCCU UUAGU                                                                                        15

( 2 ) INFORMATION FOR SEQ ID NO:849:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:849:

CUUCCUUUAG UUCUU                                                                                        15

( 2 ) INFORMATION FOR SEQ ID NO:850:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:850:

UUCUUCUCUG UCCAU                                                                                        15

( 2 ) INFORMATION FOR SEQ ID NO:851:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:851:

UCUCUGUCCA UGUGG                                                                                        15

( 2 ) INFORMATION FOR SEQ ID NO:852:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:852:

UCUCUGUCCA UGUGG    15

( 2 ) INFORMATION FOR SEQ ID NO:853:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:853:

GUGGGAUACA UGGUA    15

( 2 ) INFORMATION FOR SEQ ID NO:854:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:854:

ACAUGGUAUU AUGUG    15

( 2 ) INFORMATION FOR SEQ ID NO:855:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:855:

AUGGUAUUAU GUGGC    15

( 2 ) INFORMATION FOR SEQ ID NO:856:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:856:

UGUGGCUCAU GAGGU    15

( 2 ) INFORMATION FOR SEQ ID NO:857:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:857:

UGUGGCUCAU GAGGU    15

( 2 ) INFORMATION FOR SEQ ID NO:858:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:858:

GUACAAUCUU UCUUU                15

( 2 ) INFORMATION FOR SEQ ID NO:859:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:859:

ACAAUCUUUC UUUCA                15

( 2 ) INFORMATION FOR SEQ ID NO:860:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:860:

ACAAUCUUUC UUUCA                15

( 2 ) INFORMATION FOR SEQ ID NO:861:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:861:

CAAUCUUUCU UUCAG                15

( 2 ) INFORMATION FOR SEQ ID NO:862:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:862:

AAUCUUUCUU UCAGC                15

( 2 ) INFORMATION FOR SEQ ID NO:863:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:863:

AAUCUUUCUU UCAGC                15

( 2 ) INFORMATION FOR SEQ ID NO:864:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:864:

AAUCUUUCUU UCAGC      15

( 2 ) INFORMATION FOR SEQ ID NO:865:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:865:

UCUUUCUUUC AGCAC      15

( 2 ) INFORMATION FOR SEQ ID NO:866:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:866:

CUUUCUUUCA GCACC      15

( 2 ) INFORMATION FOR SEQ ID NO:867:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:867:

CUGAUCUUUC GGACA      15

( 2 ) INFORMATION FOR SEQ ID NO:868:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:868:

ACAAGAUAGA GUUAA      15

( 2 ) INFORMATION FOR SEQ ID NO:869:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:869:

UGAGGAUUUC UUUCC      15

( 2 ) INFORMATION FOR SEQ ID NO:870:

( i ) SEQUENCE CHARACTERISTICS:
    ( A ) LENGTH: 15 base pairs (B) TYPE: nucleic acid
(C) STRANDEDNESS: single
(D) TOPOLOGY: linear (xi) SEQUENCE DESCRIPTION: SEQ ID NO:870:

AGGAUUUCUU UCCAU                                                                                      15

(2) INFORMATION FOR SEQ ID NO:871:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:871:

GAUUUCUUUC CAUCA                                                                                      15

(2) INFORMATION FOR SEQ ID NO:872:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:872:

UUUCUUUCCA UCAGG                                                                                      15

(2) INFORMATION FOR SEQ ID NO:873:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:873:

UUUCCAUCAG GAAGC                                                                                      15

(2) INFORMATION FOR SEQ ID NO:874:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:874:

UUUCCAUCAG GAAGC                                                                                      15

(2) INFORMATION FOR SEQ ID NO:875:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:875:

GGCAAGUUUG CUGGG                                                                                      15

(2) INFORMATION FOR SEQ ID NO:876:

(i) SEQUENCE CHARACTERISTICS:
(A) LENGTH: 15 base pairs
(B) TYPE: nucleic acid
(C) STRANDEDNESS: single -continued (D) TOPOLOGY: linear (xi) SEQUENCE DESCRIPTION: SEQ ID NO:876:

CUUUGAUUGC UUGAU                                                    15

(2) INFORMATION FOR SEQ ID NO:877:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (xi) SEQUENCE DESCRIPTION: SEQ ID NO:877:

GUGGUAUAAG AAAAA                                                    15

(2) INFORMATION FOR SEQ ID NO:878:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (xi) SEQUENCE DESCRIPTION: SEQ ID NO:878:

GUGGUAUAAG AAAAA                                                    15

(2) INFORMATION FOR SEQ ID NO:879:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (xi) SEQUENCE DESCRIPTION: SEQ ID NO:879:

GCCUAGUCUU ACUGC                                                    15

(2) INFORMATION FOR SEQ ID NO:880:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (xi) SEQUENCE DESCRIPTION: SEQ ID NO:880:

CUAGUCUUAC UGCAA                                                    15

(2) INFORMATION FOR SEQ ID NO:881:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (xi) SEQUENCE DESCRIPTION: SEQ ID NO:881:

UGCAACUUGA UAUGU                                                    15

(2) INFORMATION FOR SEQ ID NO:882:

(i) SEQUENCE CHARACTERISTICS:
      (A) LENGTH: 15 base pairs
      (B) TYPE: nucleic acid
      (C) STRANDEDNESS: single
      (D) TOPOLOGY: linear ( x i ) SEQUENCE DESCRIPTION: SEQ ID NO:882:

ACUUGAUAUG UCAUG 15

( 2 ) INFORMATION FOR SEQ ID NO:883:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:883:

ACUUGAUAUG UCAUG 15

( 2 ) INFORMATION FOR SEQ ID NO:884:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:884:

GUUUGGUUGG UGUCU 15

( 2 ) INFORMATION FOR SEQ ID NO:885:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:885:

UGCCCUUUUC UGAAG 15

( 2 ) INFORMATION FOR SEQ ID NO:886:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:886:

GCCCUUUUCU GAAGA 15

( 2 ) INFORMATION FOR SEQ ID NO:887:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:887:

CCCUUUUCUG AAGAG 15

( 2 ) INFORMATION FOR SEQ ID NO:888:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:888:

CCCUUUUCUG AAGAG 15

(2) INFORMATION FOR SEQ ID NO:889:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:889:

CUAUGGUUGG GAUGU 15

(2) INFORMATION FOR SEQ ID NO:890:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:890:

GGGAUGUAAA AACGG 15

(2) INFORMATION FOR SEQ ID NO:891:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:891:

GGGAUGUAAA AACGG 15

(2) INFORMATION FOR SEQ ID NO:892:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:892:

AUAAUAUAAA UAUUA 15

(2) INFORMATION FOR SEQ ID NO:893:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:893:

UAUAAAUAUU AAAUA 15

(2) INFORMATION FOR SEQ ID NO:894:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:894:

UAAAUAUUAA AUAAA 15

( 2 ) INFORMATION FOR SEQ ID NO:895:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:895:

AAAUAUUAAA UAAAA     15

( 2 ) INFORMATION FOR SEQ ID NO:896:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:896:

AAAUAUUAAA UAAAA     15

( 2 ) INFORMATION FOR SEQ ID NO:897:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:897:

AGAGUAUUGA GCAAA     15

( 2 ) INFORMATION FOR SEQ ID NO:898:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:898:

UGAGGUACUG AUGAGGCCGA AAGGCCGAAA AAACUC     36

( 2 ) INFORMATION FOR SEQ ID NO:899:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:899:

AUUGAGGCUG AUGAGGCCGA AAGGCCGAAA UAAAAC     36

( 2 ) INFORMATION FOR SEQ ID NO:900:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:900:

AUUGAGGCUG AUGAGGCCGA AAGGCCGAAA UAAAAC     36

( 2 ) INFORMATION FOR SEQ ID NO:901:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:901:

GUCUAUUCUG AUGAGGCCGA AAGGCCGAAA GGUAUA 36

( 2 ) INFORMATION FOR SEQ ID NO:902:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:902:

AAGAGUCCUG AUGAGGCCGA AAGGCCGAAA UUGAGG 36

( 2 ) INFORMATION FOR SEQ ID NO:903:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:903:

AAGAGUCCUG AUGAGGCCGA AAGGCCGAAA UUGAGG 36

( 2 ) INFORMATION FOR SEQ ID NO:904:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:904:

AAGAGUCCUG AUGAGGCCGA AAGGCCGAAA UUGAGG 36

( 2 ) INFORMATION FOR SEQ ID NO:905:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:905:

CUAGUAACUG AUGAGGCCGA AAGGCCGAAA GUCUAU 36

( 2 ) INFORMATION FOR SEQ ID NO:906:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:906:

AACUAGUCUG AUGAGGCCGA AAGGCCGAAA GAGUCU 36

( 2 ) INFORMATION FOR SEQ ID NO:907:

( i ) SEQUENCE CHARACTERISTICS:

(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:907:

AAACUAGCUG AUGAGGCCGA AAGGCCGAAA AGAGUC 36

(2) INFORMATION FOR SEQ ID NO:908:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:908:

GAGAAACCUG AUGAGGCCGA AAGGCCGAAA GUAAGA 36

(2) INFORMATION FOR SEQ ID NO:909:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:909:

GAGAAACCUG AUGAGGCCGA AAGGCCGAAA GUAAGA 36

(2) INFORMATION FOR SEQ ID NO:910:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:910:

GAGAAACCUG AUGAGGCCGA AAGGCCGAAA GUAAGA 36

(2) INFORMATION FOR SEQ ID NO:911:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:911:

GAGAAACCUG AUGAGGCCGA AAGGCCGAAA GUAAGA 36

(2) INFORMATION FOR SEQ ID NO:912:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:912:

AAAAAGACUG AUGAGGCCGA AAGGCCGAAA AACUAG 36

(2) INFORMATION FOR SEQ ID NO:913:

(i) SEQUENCE CHARACTERISTICS:
(A) LENGTH: 36 base pairs
(B) TYPE: nucleic acid ( C ) STRANDEDNESS: single
            ( D ) TOPOLOGY: linear ( x i ) SEQUENCE DESCRIPTION: SEQ ID NO:913:

AAAAGACUG AUGAGGCCGA AAGGCCGAAA AACUAG        36

( 2 ) INFORMATION FOR SEQ ID NO:914:

( i ) SEQUENCE CHARACTERISTICS:
            ( A ) LENGTH: 36 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:914:

AAAAGACUG AUGAGGCCGA AAGGCCGAAA AACUAG        36

( 2 ) INFORMATION FOR SEQ ID NO:915:

( i ) SEQUENCE CHARACTERISTICS:
            ( A ) LENGTH: 36 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:915:

AACCUGACUG AUGAGGCCGA AAGGCCGAAA AAGAGA        36

( 2 ) INFORMATION FOR SEQ ID NO:916:

( i ) SEQUENCE CHARACTERISTICS:
            ( A ) LENGTH: 36 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:916:

CAACCUGCUG AUGAGGCCGA AAGGCCGAAA AAAGAG        36

( 2 ) INFORMATION FOR SEQ ID NO:917:

( i ) SEQUENCE CHARACTERISTICS:
            ( A ) LENGTH: 36 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:917:

CAACCUGCUG AUGAGGCCGA AAGGCCGAAA AAAGAG        36

( 2 ) INFORMATION FOR SEQ ID NO:918:

( i ) SEQUENCE CHARACTERISTICS:
            ( A ) LENGTH: 36 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:918:

ACAACCUCUG AUGAGGCCGA AAGGCCGAAA AAAAGA        36

( 2 ) INFORMATION FOR SEQ ID NO:919:

( i ) SEQUENCE CHARACTERISTICS:
            ( A ) LENGTH: 36 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:919:

GAAGGUUCUG AUGAGGCCGA AAGGCCGAAA GUUUCA　　　　　　　　　　　　36

( 2 ) INFORMATION FOR SEQ ID NO:920:

( i ) SEQUENCE CHARACTERISTICS:
　　　　( A ) LENGTH: 36 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:920:

GAAGGUUCUG AUGAGGCCGA AAGGCCGAAA GUUUCA　　　　　　　　　　　　36

( 2 ) INFORMATION FOR SEQ ID NO:921:

( i ) SEQUENCE CHARACTERISTICS:
　　　　( A ) LENGTH: 36 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:921:

GUCUUUGCUG AUGAGGCCGA AAGGCCGAAA GGUUGA　　　　　　　　　　　　36

( 2 ) INFORMATION FOR SEQ ID NO:922:

( i ) SEQUENCE CHARACTERISTICS:
　　　　( A ) LENGTH: 36 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:922:

GUCUUUGCUG AUGAGGCCGA AAGGCCGAAA GGUUGA　　　　　　　　　　　　36

( 2 ) INFORMATION FOR SEQ ID NO:923:

( i ) SEQUENCE CHARACTERISTICS:
　　　　( A ) LENGTH: 36 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:923:

GUCUUUGCUG AUGAGGCCGA AAGGCCGAAA GGUUGA　　　　　　　　　　　　36

( 2 ) INFORMATION FOR SEQ ID NO:924:

( i ) SEQUENCE CHARACTERISTICS:
　　　　( A ) LENGTH: 36 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:924:

UGUCUUUCUG AUGAGGCCGA AAGGCCGAAA AGGUUG　　　　　　　　　　　　36

( 2 ) INFORMATION FOR SEQ ID NO:925:

( i ) SEQUENCE CHARACTERISTICS:
　　　　( A ) LENGTH: 36 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:925:

UGGAACACUG AUGAGGCCGA AAGGCCGAAA GUGUCU 36

( 2 ) INFORMATION FOR SEQ ID NO:926:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:926:

GAAAUGGCUG AUGAGGCCGA AAGGCCGAAA CAGAGU 36

( 2 ) INFORMATION FOR SEQ ID NO:927:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:927:

AGAAAUGCUG AUGAGGCCGA AAGGCCGAAA ACAGAG 36

( 2 ) INFORMATION FOR SEQ ID NO:928:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:928:

UCCACAGCUG AUGAGGCCGA AAGGCCGAAA AUGGAA 36

( 2 ) INFORMATION FOR SEQ ID NO:929:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:929:

AUCCUAUCUG AUGAGGCCGA AAGGCCGAAA GUCCAC 36

( 2 ) INFORMATION FOR SEQ ID NO:930:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:930:

AUCCUAUCUG AUGAGGCCGA AAGGCCGAAA GUCCAC 36

( 2 ) INFORMATION FOR SEQ ID NO:931:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:931:

AUCCUAUCUG AUGAGGCCGA AAGGCCGAAA GUCCAC 36

( 2 ) INFORMATION FOR SEQ ID NO:932:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:932:

AUGAUCCCUG AUGAGGCCGA AAGGCCGAAA UUAGUC    36

( 2 ) INFORMATION FOR SEQ ID NO:933:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:933:

AUGAUCCCUG AUGAGGCCGA AAGGCCGAAA UUAGUC    36

( 2 ) INFORMATION FOR SEQ ID NO:934:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:934:

UAAAGAUCUG AUGAGGCCGA AAGGCCGAAA UCCUAU    36

( 2 ) INFORMATION FOR SEQ ID NO:935:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:935:

UGCUAAACUG AUGAGGCCGA AAGGCCGAAA UGAUCC    36

( 2 ) INFORMATION FOR SEQ ID NO:936:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:936:

UGCUAAACUG AUGAGGCCGA AAGGCCGAAA UGAUCC    36

( 2 ) INFORMATION FOR SEQ ID NO:937:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:937:

GAUGCUACUG AUGAGGCCGA AAGGCCGAAA GAUGAU    36

( 2 ) INFORMATION FOR SEQ ID NO:938:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:938:

AGAUGCUCUG AUGAGGCCGA AAGGCCGAAA AGAUGA  36

( 2 ) INFORMATION FOR SEQ ID NO:939:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:939:

AGAUGCUCUG AUGAGGCCGA AAGGCCGAAA AGAUGA  36

( 2 ) INFORMATION FOR SEQ ID NO:940:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:940:

CAGAUGCCUG AUGAGGCCGA AAGGCCGAAA AAGAUG  36

( 2 ) INFORMATION FOR SEQ ID NO:941:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:941:

CAGAUGCCUG AUGAGGCCGA AAGGCCGAAA AAGAUG  36

( 2 ) INFORMATION FOR SEQ ID NO:942:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:942:

AAGCCUGCUG AUGAGGCCGA AAGGCCGAAA UGGCAU  36

( 2 ) INFORMATION FOR SEQ ID NO:943:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:943:

UGUAGAACUG AUGAGGCCGA AAGGCCGAAA AGAAGC  36

( 2 ) INFORMATION FOR SEQ ID NO:944:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:944:

UGUAGAACUG AUGAGGCCGA AAGGCCGAAA AGAAGC 36

( 2 ) INFORMATION FOR SEQ ID NO:945:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:945:

AUGUAGACUG AUGAGGCCGA AAGGCCGAAA AAGAAG 36

( 2 ) INFORMATION FOR SEQ ID NO:946:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:946:

AUGUAGACUG AUGAGGCCGA AAGGCCGAAA AAGAAG 36

( 2 ) INFORMATION FOR SEQ ID NO:947:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:947:

AUGUAGACUG AUGAGGCCGA AAGGCCGAAA AAGAAG 36

( 2 ) INFORMATION FOR SEQ ID NO:948:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:948:

AUGUAGACUG AUGAGGCCGA AAGGCCGAAA AAGAAG 36

( 2 ) INFORMATION FOR SEQ ID NO:949:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:949:

GAUGUAGCUG AUGAGGCCGA AAGGCCGAAA AAAGAA 36

( 2 ) INFORMATION FOR SEQ ID NO:950:

( i ) SEQUENCE CHARACTERISTICS:
        ( A ) LENGTH: 36 base pairs (B) TYPE: nucleic acid
        (C) STRANDEDNESS: single
        (D) TOPOLOGY: linear (xi) SEQUENCE DESCRIPTION: SEQ ID NO:950:

GAUGUAGCUG AUGAGGCCGA AAGGCCGAAA AAAGAA                                                      36

(2) INFORMATION FOR SEQ ID NO:951:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:951:

GAUGUAGCUG AUGAGGCCGA AAGGCCGAAA AAAGAA                                                      36

(2) INFORMATION FOR SEQ ID NO:952:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:952:

AGAGAUGCUG AUGAGGCCGA AAGGCCGAAA GAAAAA                                                      36

(2) INFORMATION FOR SEQ ID NO:953:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:953:

AGAAACACUG AUGAGGCCGA AAGGCCGAAA GAUGUA                                                      36

(2) INFORMATION FOR SEQ ID NO:954:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:954:

UCACAAACUG AUGAGGCCGA AAGGCCGAAA UCGAGA                                                      36

(2) INFORMATION FOR SEQ ID NO:955:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:955:

UCACAAACUG AUGAGGCCGA AAGGCCGAAA UCGAGA                                                      36

(2) INFORMATION FOR SEQ ID NO:956:

(i) SEQUENCE CHARACTERISTICS:
        (A) LENGTH: 36 base pairs
        (B) TYPE: nucleic acid
        (C) STRANDEDNESS: single (D) TOPOLOGY: linear (xi) SEQUENCE DESCRIPTION: SEQ ID NO:956:

UCACAAACUG AUGAGGCCGA AAGGCCGAAA UCGAGA 36

(2) INFORMATION FOR SEQ ID NO:957:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:957:

CUCACAACUG AUGAGGCCGA AAGGCCGAAA AUCGAG 36

(2) INFORMATION FOR SEQ ID NO:958:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:958:

GCUCACACUG AUGAGGCCGA AAGGCCGAAA AAUCGA 36

(2) INFORMATION FOR SEQ ID NO:959:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:959:

GCUCACACUG AUGAGGCCGA AAGGCCGAAA AAUCGA 36

(2) INFORMATION FOR SEQ ID NO:960:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:960:

GCUCACACUG AUGAGGCCGA AAGGCCGAAA AAUCGA 36

(2) INFORMATION FOR SEQ ID NO:961:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:961:

GGCUCACCUG AUGAGGCCGA AAGGCCGAAA AAAUCG 36

(2) INFORMATION FOR SEQ ID NO:962:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:962:

GGCUCACCUG AUGAGGCCGA AAGGCCGAAA AAAUCG  36

(2) INFORMATION FOR SEQ ID NO:963:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:963:

UAGAGCCCUG AUGAGGCCGA AAGGCCGAAA UGGAGC  36

(2) INFORMATION FOR SEQ ID NO:964:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:964:

GAAUCUACUG AUGAGGCCGA AAGGCCGAAA GCCAAU  36

(2) INFORMATION FOR SEQ ID NO:965:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:965:

AGCCAGGCUG AUGAGGCCGA AAGGCCGAAA UCUAGA  36

(2) INFORMATION FOR SEQ ID NO:966:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:966:

AUGGGACUG AUGAGGCCGA AAGGCCGAAA GCCAGG  36

(2) INFORMATION FOR SEQ ID NO:967:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:967:

GAUGGGGCUG AUGAGGCCGA AAGGCCGAAA AGCCAG  36

(2) INFORMATION FOR SEQ ID NO:968:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:968:

```
GAUGGGGCUG  AUGAGGCCGA  AAGGCCGAAA  AGCCAG                                    36
```

( 2 ) INFORMATION FOR SEQ ID NO:969:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:969:

```
GAUGGGGCUG  AUGAGGCCGA  AAGGCCGAAA  AGCCAG                                    36
```

( 2 ) INFORMATION FOR SEQ ID NO:970:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:970:

```
UGAUGGGCUG  AUGAGGCCGA  AAGGCCGAAA  AAGCCA                                    36
```

( 2 ) INFORMATION FOR SEQ ID NO:971:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:971:

```
UGAUGGGCUG  AUGAGGCCGA  AAGGCCGAAA  AAGCCA                                    36
```

( 2 ) INFORMATION FOR SEQ ID NO:972:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:972:

```
UGAUGGGCUG  AUGAGGCCGA  AAGGCCGAAA  AAGCCA                                    36
```

( 2 ) INFORMATION FOR SEQ ID NO:973:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:973:

```
UGAUGGGCUG  AUGAGGCCGA  AAGGCCGAAA  AAGCCA                                    36
```

( 2 ) INFORMATION FOR SEQ ID NO:974:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:974:

```
AGAACAUCUG  AUGAGGCCGA  AAGGCCGAAA  UGGGGA                                    36
```

( 2 ) INFORMATION FOR SEQ ID NO:975:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:975:

AGAACAUCUG AUGAGGCCGA AAGGCCGAAA UGGGGA    36

( 2 ) INFORMATION FOR SEQ ID NO:976:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:976:

CUUUGGACUG AUGAGGCCGA AAGGCCGAAA ACAUGA    36

( 2 ) INFORMATION FOR SEQ ID NO:977:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:977:

UGCUUUGCUG AUGAGGCCGA AAGGCCGAAA GAACAU    36

( 2 ) INFORMATION FOR SEQ ID NO:978:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:978:

UGCUUUGCUG AUGAGGCCGA AAGGCCGAAA GAACAU    36

( 2 ) INFORMATION FOR SEQ ID NO:979:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:979:

UGCUUUGCUG AUGAGGCCGA AAGGCCGAAA GAACAU    36

( 2 ) INFORMATION FOR SEQ ID NO:980:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:980:

AGCUUCACUG AUGAGGCCGA AAGGCCGAAA UGCUUU    36

( 2 ) INFORMATION FOR SEQ ID NO:981:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:981:

AGCUUCACUG AUGAGGCCGA AAGGCCGAAA UGCUUU 36

( 2 ) INFORMATION FOR SEQ ID NO:982:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:982:

AGCUUCACUG AUGAGGCCGA AAGGCCGAAA UGCUUU 36

( 2 ) INFORMATION FOR SEQ ID NO:983:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:983:

CAAGCCACUG AUGAGGCCGA AAGGCCGAAA GCUUCA 36

( 2 ) INFORMATION FOR SEQ ID NO:984:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:984:

AUCAACUCUG AUGAGGCCGA AAGGCCGAAA CAAUUG 36

( 2 ) INFORMATION FOR SEQ ID NO:985:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:985:

ACUUGAGCUG AUGAGGCCGA AAGGCCGAAA GUGGUG 36

( 2 ) INFORMATION FOR SEQ ID NO:986:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:986:

ACAUGGACUG AUGAGGCCGA AAGGCCGAAA CUUGAG 36

( 2 ) INFORMATION FOR SEQ ID NO:987:

( i ) SEQUENCE CHARACTERISTICS:

(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:987:

ACAUGGACUG AUGAGGCCGA AAGGCCGAAA CUUGAG 36

(2) INFORMATION FOR SEQ ID NO:988:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:988:

GACAUGGCUG AUGAGGCCGA AAGGCCGAAA ACUUGA 36

(2) INFORMATION FOR SEQ ID NO:989:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:989:

GGACAUGCUG AUGAGGCCGA AAGGCCGAAA AACUUG 36

(2) INFORMATION FOR SEQ ID NO:990:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:990:

GGACAUGCUG AUGAGGCCGA AAGGCCGAAA AACUUG 36

(2) INFORMATION FOR SEQ ID NO:991:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:991:

AGAGAAGCUG AUGAGGCCGA AAGGCCGAAA UGAGCC 36

(2) INFORMATION FOR SEQ ID NO:992:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:992:

AGAGAAGCUG AUGAGGCCGA AAGGCCGAAA UGAGCC 36

(2) INFORMATION FOR SEQ ID NO:993:

(i) SEQUENCE CHARACTERISTICS:
(A) LENGTH: 36 base pairs
(B) TYPE: nucleic acid ( C ) STRANDEDNESS: single
( D ) TOPOLOGY: linear ( x i ) SEQUENCE DESCRIPTION: SEQ ID NO:993:

AAGAGAACUG AUGAGGCCGA AAGGCCGAAA AUGAGC　　　　　　　　　　　　36

( 2 ) INFORMATION FOR SEQ ID NO:994:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:994:

AAGAGAACUG AUGAGGCCGA AAGGCCGAAA AUGAGC　　　　　　　　　　　　36

( 2 ) INFORMATION FOR SEQ ID NO:995:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:995:

CAAAGAGCUG AUGAGGCCGA AAGGCCGAAA GAAUGA　　　　　　　　　　　　36

( 2 ) INFORMATION FOR SEQ ID NO:996:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:996:

ACAAAGACUG AUGAGGCCGA AAGGCCGAAA AGAAUG　　　　　　　　　　　　36

( 2 ) INFORMATION FOR SEQ ID NO:997:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:997:

ACAAAGACUG AUGAGGCCGA AAGGCCGAAA AGAAUG　　　　　　　　　　　　36

( 2 ) INFORMATION FOR SEQ ID NO:998:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:998:

GCACAAACUG AUGAGGCCGA AAGGCCGAAA GAAGAA　　　　　　　　　　　　36

( 2 ) INFORMATION FOR SEQ ID NO:999:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear (x i) SEQUENCE DESCRIPTION: SEQ ID NO:999:

GCACAAACUG AUGAGGCCGA AAGGCCGAAA GAAGAA　　　　　　　　36

(2) INFORMATION FOR SEQ ID NO:1000:

(i) SEQUENCE CHARACTERISTICS:
  (A) LENGTH: 36 base pairs
  (B) TYPE: nucleic acid
  (C) STRANDEDNESS: single
  (D) TOPOLOGY: linear (x i) SEQUENCE DESCRIPTION: SEQ ID NO:1000:

CAGCACACUG AUGAGGCCGA AAGGCCGAAA GAGAAG　　　　　　　　36

(2) INFORMATION FOR SEQ ID NO:1001:

(i) SEQUENCE CHARACTERISTICS:
  (A) LENGTH: 36 base pairs
  (B) TYPE: nucleic acid
  (C) STRANDEDNESS: single
  (D) TOPOLOGY: linear (x i) SEQUENCE DESCRIPTION: SEQ ID NO:1001:

CAGCACACUG AUGAGGCCGA AAGGCCGAAA GAGAAG　　　　　　　　36

(2) INFORMATION FOR SEQ ID NO:1002:

(i) SEQUENCE CHARACTERISTICS:
  (A) LENGTH: 36 base pairs
  (B) TYPE: nucleic acid
  (C) STRANDEDNESS: single
  (D) TOPOLOGY: linear (x i) SEQUENCE DESCRIPTION: SEQ ID NO:1002:

GCAGCACCUG AUGAGGCCGA AAGGCCGAAA AGAGAA　　　　　　　　36

(2) INFORMATION FOR SEQ ID NO:1003:

(i) SEQUENCE CHARACTERISTICS:
  (A) LENGTH: 36 base pairs
  (B) TYPE: nucleic acid
  (C) STRANDEDNESS: single
  (D) TOPOLOGY: linear (x i) SEQUENCE DESCRIPTION: SEQ ID NO:1003:

GAAAGACCUG AUGAGGCCGA AAGGCCGAAA AUCAGC　　　　　　　　36

(2) INFORMATION FOR SEQ ID NO:1004:

(i) SEQUENCE CHARACTERISTICS:
  (A) LENGTH: 36 base pairs
  (B) TYPE: nucleic acid
  (C) STRANDEDNESS: single
  (D) TOPOLOGY: linear (x i) SEQUENCE DESCRIPTION: SEQ ID NO:1004:

CUUGUGACUG AUGAGGCCGA AAGGCCGAAA GACGAA　　　　　　　　36

(2) INFORMATION FOR SEQ ID NO:1005:

(i) SEQUENCE CHARACTERISTICS:
  (A) LENGTH: 36 base pairs
  (B) TYPE: nucleic acid
  (C) STRANDEDNESS: single
  (D) TOPOLOGY: linear (x i) SEQUENCE DESCRIPTION: SEQ ID NO:1005:

CUUGUGACUG AUGAGGCCGA AAGGCCGAAA GACGAA 36

( 2 ) INFORMATION FOR SEQ ID NO:1006:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1006:

ACUUGUGCUG AUGAGGCCGA AAGGCCGAAA AGACGA 36

( 2 ) INFORMATION FOR SEQ ID NO:1007:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1007:

CACUUGUCUG AUGAGGCCGA AAGGCCGAAA AAGACG 36

( 2 ) INFORMATION FOR SEQ ID NO:1008:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1008:

CACUUGUCUG AUGAGGCCGA AAGGCCGAAA AAGACG 36

( 2 ) INFORMATION FOR SEQ ID NO:1009:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1009:

AUCUGAACUG AUGAGGCCGA AAGGCCGAAA CACUUG 36

( 2 ) INFORMATION FOR SEQ ID NO:1010:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1010:

AACAUCUCUG AUGAGGCCGA AAGGCCGAAA AGACAC 36

( 2 ) INFORMATION FOR SEQ ID NO:1011:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1011:

UUUCACUCUG AUGAGGCCGA AAGGCCGAAA CUUGGA 36

( 2 ) INFORMATION FOR SEQ ID NO:1012:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1012:

UAACGGCCUG AUGAGGCCGA AAGGCCGAAA GGCAGC      36

( 2 ) INFORMATION FOR SEQ ID NO:1013:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1013:

GAGUUGUCUG AUGAGGCCGA AAGGCCGAAA CGGCAA      36

( 2 ) INFORMATION FOR SEQ ID NO:1014:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1014:

GAGUUGUCUG AUGAGGCCGA AAGGCCGAAA CGGCAA      36

( 2 ) INFORMATION FOR SEQ ID NO:1015:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1015:

AUGAGGACUG AUGAGGCCGA AAGGCCGAAA GUUGUA      36

( 2 ) INFORMATION FOR SEQ ID NO:1016:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1016:

UCUUCAUCUG AUGAGGCCGA AAGGCCGAAA GGAGAG      36

( 2 ) INFORMATION FOR SEQ ID NO:1017:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1017:

GUCUUCACUG AUGAGGCCGA AAGGCCGAAA CUCAUC      36

( 2 ) INFORMATION FOR SEQ ID NO:1018:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1018:

GCCAGUACUG AUGAGGCCGA AAGGCCGAAA UUCGGU    36

( 2 ) INFORMATION FOR SEQ ID NO:1019:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1019:

UUGCCAGCUG AUGAGGCCGA AAGGCCGAAA GAUUCG    36

( 2 ) INFORMATION FOR SEQ ID NO:1020:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1020:

AAUGACACUG AUGAGGCCGA AAGGCCGAAA CAGCAC    36

( 2 ) INFORMATION FOR SEQ ID NO:1021:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1021:

AAUGACACUG AUGAGGCCGA AAGGCCGAAA CAGCAC    36

( 2 ) INFORMATION FOR SEQ ID NO:1022:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1022:

CAGCAAUCUG AUGAGGCCGA AAGGCCGAAA CAGACA    36

( 2 ) INFORMATION FOR SEQ ID NO:1023:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1023:

ACACUUUCUG AUGAGGCCGA AAGGCCGAAA GUUUCC    36

( 2 ) INFORMATION FOR SEQ ID NO:1024:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1024:

ACACUUUCUG AUGAGGCCGA AAGGCCGAAA GUUUCC 36

( 2 ) INFORMATION FOR SEQ ID NO:1025:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1025:

GUUCUUACUG AUGAGGCCGA AAGGCCGAAA CUCGGG 36

( 2 ) INFORMATION FOR SEQ ID NO:1026:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1026:

GUCAUAUCUG AUGAGGCCGA AAGGCCGAAA AGUCCG 36

( 2 ) INFORMATION FOR SEQ ID NO:1027:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1027:

UGUCAUACUG AUGAGGCCGA AAGGCCGAAA AAGUCC 36

( 2 ) INFORMATION FOR SEQ ID NO:1028:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1028:

GUUGUCACUG AUGAGGCCGA AAGGCCGAAA UAAAGU 36

( 2 ) INFORMATION FOR SEQ ID NO:1029:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1029:

AAGAGAGCUG AUGAGGCCGA AAGGCCGAAA GGUAGU 36

( 2 ) INFORMATION FOR SEQ ID NO:1030:

( i ) SEQUENCE CHARACTERISTICS:
    ( A ) LENGTH: 36 base pairs ( B ) TYPE: nucleic acid
( C ) STRANDEDNESS: single
( D ) TOPOLOGY: linear ( x i ) SEQUENCE DESCRIPTION: SEQ ID NO:1030:

AAGAGAGCUG AUGAGGCCGA AAGGCCGAAA GGUAGU 36

( 2 ) INFORMATION FOR SEQ ID NO:1031:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:1031:

GAUAAGACUG AUGAGGCCGA AAGGCCGAAA GUAGGU 36

( 2 ) INFORMATION FOR SEQ ID NO:1032:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:1032:

GAUAAGACUG AUGAGGCCGA AAGGCCGAAA GUAGGU 36

( 2 ) INFORMATION FOR SEQ ID NO:1033:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:1033:

GGAUGAUCUG AUGAGGCCGA AAGGCCGAAA GAGAGU 36

( 2 ) INFORMATION FOR SEQ ID NO:1034:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:1034:

AGGAUGACUG AUGAGGCCGA AAGGCCGAAA AGAGAG 36

( 2 ) INFORMATION FOR SEQ ID NO:1035:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:1035:

AGGAUGACUG AUGAGGCCGA AAGGCCGAAA AGAGAG 36

( 2 ) INFORMATION FOR SEQ ID NO:1036:

( i ) SEQUENCE CHARACTERISTICS:
( A ) LENGTH: 36 base pairs
( B ) TYPE: nucleic acid
( C ) STRANDEDNESS: single -continued (D) TOPOLOGY: linear (xi) SEQUENCE DESCRIPTION: SEQ ID NO:1036:

AGGAUGACUG AUGAGGCCGA AAGGCCGAAA AGAGAG 36

(2) INFORMATION FOR SEQ ID NO:1037:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1037:

GGCCCAGCUG AUGAGGCCGA AAGGCCGAAA UGAUAA 36

(2) INFORMATION FOR SEQ ID NO:1038:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1038:

GGCCCAGCUG AUGAGGCCGA AAGGCCGAAA UGAUAA 36

(2) INFORMATION FOR SEQ ID NO:1039:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1039:

GGUCUGACUG AUGAGGCCGA AAGGCCGAAA GGACCA 36

(2) INFORMATION FOR SEQ ID NO:1040:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1040:

CCGGUCUCUG AUGAGGCCGA AAGGCCGAAA AAGGAC 36

(2) INFORMATION FOR SEQ ID NO:1041:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1041:

CCGGUCUCUG AUGAGGCCGA AAGGCCGAAA AAGGAC 36

(2) INFORMATION FOR SEQ ID NO:1042:

(i) SEQUENCE CHARACTERISTICS:
        (A) LENGTH: 36 base pairs
        (B) TYPE: nucleic acid
        (C) STRANDEDNESS: single
        (D) TOPOLOGY: linear ( x i ) SEQUENCE DESCRIPTION: SEQ ID NO:1042:

ACAGCUGCUG AUGAGGCCGA AAGGCCGAAA UGUGCC　　　　　　　　　　　　　　36

( 2 ) INFORMATION FOR SEQ ID NO:1043:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1043:

UUUGAACCUG AUGAGGCCGA AAGGCCGAAA CACAGC　　　　　　　　　　　　　　36

( 2 ) INFORMATION FOR SEQ ID NO:1044:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1044:

UCUUUUGCUG AUGAGGCCGA AAGGCCGAAA CGACAC　　　　　　　　　　　　　　36

( 2 ) INFORMATION FOR SEQ ID NO:1045:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1045:

UCUUUUGCUG AUGAGGCCGA AAGGCCGAAA CGACAC　　　　　　　　　　　　　　36

( 2 ) INFORMATION FOR SEQ ID NO:1046:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1046:

UUCUUUUCUG AUGAGGCCGA AAGGCCGAAA ACGACA　　　　　　　　　　　　　　36

( 2 ) INFORMATION FOR SEQ ID NO:1047:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1047:

AGUGUUUCUG AUGAGGCCGA AAGGCCGAAA CUUCAU　　　　　　　　　　　　　　36

( 2 ) INFORMATION FOR SEQ ID NO:1048:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1048:

UAAAGCCCUG AUGAGGCCGA AAGGCCGAAA GUGUUU 36

( 2 ) INFORMATION FOR SEQ ID NO:1049:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1049:

UAAAGCCCUG AUGAGGCCGA AAGGCCGAAA GUGUUU 36

( 2 ) INFORMATION FOR SEQ ID NO:1050:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1050:

CUUUACUCUG AUGAGGCCGA AAGGCCGAAA AGCCAA 36

( 2 ) INFORMATION FOR SEQ ID NO:1051:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1051:

ACUUUACCUG AUGAGGCCGA AAGGCCGAAA AAGCCA 36

( 2 ) INFORMATION FOR SEQ ID NO:1052:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1052:

ACAACUUCUG AUGAGGCCGA AAGGCCGAAA CUAAAG 36

( 2 ) INFORMATION FOR SEQ ID NO:1053:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1053:

GAUGGACCUG AUGAGGCCGA AAGGCCGAAA CUUUAC 36

( 2 ) INFORMATION FOR SEQ ID NO:1054:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1054:

UUUGAUGCUG AUGAGGCCGA AAGGCCGAAA CAACUU 36

( 2 ) INFORMATION FOR SEQ ID NO:1055:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1055:

CAGCUUUCUG AUGAGGCCGA AAGGCCGAAA UGGACA      36

( 2 ) INFORMATION FOR SEQ ID NO:1056:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1056:

GGUAGAGCUG AUGAGGCCGA AAGGCCGAAA GUCAGC      36

( 2 ) INFORMATION FOR SEQ ID NO:1057:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1057:

GGUAGAGCUG AUGAGGCCGA AAGGCCGAAA GUCAGC      36

( 2 ) INFORMATION FOR SEQ ID NO:1058:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1058:

GGUAGAGCUG AUGAGGCCGA AAGGCCGAAA GUCAGC      36

( 2 ) INFORMATION FOR SEQ ID NO:1059:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1059:

GGGUAGACUG AUGAGGCCGA AAGGCCGAAA AGUCAG      36

( 2 ) INFORMATION FOR SEQ ID NO:1060:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1060:

GGGUAGACUG AUGAGGCCGA AAGGCCGAAA AGUCAG      36

( 2 ) INFORMATION FOR SEQ ID NO:1061:

( i ) SEQUENCE CHARACTERISTICS:
 ( A ) LENGTH: 36 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:1061:

GGGGGUACUG AUGAGGCCGA AAGGCCGAAA GAAGUC 36

( 2 ) INFORMATION FOR SEQ ID NO:1062:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1062:

GGGGGUACUG AUGAGGCCGA AAGGCCGAAA GAAGUC 36

( 2 ) INFORMATION FOR SEQ ID NO:1063:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1063:

UUGGGGGCUG AUGAGGCCGA AAGGCCGAAA GAGAAG 36

( 2 ) INFORMATION FOR SEQ ID NO:1064:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1064:

ACUCAGUCUG AUGAGGCCGA AAGGCCGAAA UGUUGG 36

( 2 ) INFORMATION FOR SEQ ID NO:1065:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1065:

ACUCAGUCUG AUGAGGCCGA AAGGCCGAAA UGUUGG 36

( 2 ) INFORMATION FOR SEQ ID NO:1066:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1066:

GUCUGCACUG AUGAGGCCGA AAGGCCGAAA UGGGUU 36

( 2 ) INFORMATION FOR SEQ ID NO:1067:

( i ) SEQUENCE CHARACTERISTICS:

(A) LENGTH: 36 base pairs
                (B) TYPE: nucleic acid
                (C) STRANDEDNESS: single
                (D) TOPOLOGY: linear (xi) SEQUENCE DESCRIPTION: SEQ ID NO:1067:

GUCUGCACUG AUGAGGCCGA AAGGCCGAAA UGGGUU          36

(2) INFORMATION FOR SEQ ID NO:1068:

(i) SEQUENCE CHARACTERISTICS:
                (A) LENGTH: 36 base pairs
                (B) TYPE: nucleic acid
                (C) STRANDEDNESS: single
                (D) TOPOLOGY: linear (xi) SEQUENCE DESCRIPTION: SEQ ID NO:1068:

AUCCUUUCUG AUGAGGCCGA AAGGCCGAAA GUGUCU          36

(2) INFORMATION FOR SEQ ID NO:1069:

(i) SEQUENCE CHARACTERISTICS:
                (A) LENGTH: 36 base pairs
                (B) TYPE: nucleic acid
                (C) STRANDEDNESS: single
                (D) TOPOLOGY: linear (xi) SEQUENCE DESCRIPTION: SEQ ID NO:1069:

AUCCUUUCUG AUGAGGCCGA AAGGCCGAAA GUGUCU          36

(2) INFORMATION FOR SEQ ID NO:1070:

(i) SEQUENCE CHARACTERISTICS:
                (A) LENGTH: 36 base pairs
                (B) TYPE: nucleic acid
                (C) STRANDEDNESS: single
                (D) TOPOLOGY: linear (xi) SEQUENCE DESCRIPTION: SEQ ID NO:1070:

AUCCUUUCUG AUGAGGCCGA AAGGCCGAAA GUGUCU          36

(2) INFORMATION FOR SEQ ID NO:1071:

(i) SEQUENCE CHARACTERISTICS:
                (A) LENGTH: 36 base pairs
                (B) TYPE: nucleic acid
                (C) STRANDEDNESS: single
                (D) TOPOLOGY: linear (xi) SEQUENCE DESCRIPTION: SEQ ID NO:1071:

AGCAGGUCUG AUGAGGCCGA AAGGCCGAAA UCCUUU          36

(2) INFORMATION FOR SEQ ID NO:1072:

(i) SEQUENCE CHARACTERISTICS:
                (A) LENGTH: 36 base pairs
                (B) TYPE: nucleic acid
                (C) STRANDEDNESS: single
                (D) TOPOLOGY: linear (xi) SEQUENCE DESCRIPTION: SEQ ID NO:1072:

AGCAGGUCUG AUGAGGCCGA AAGGCCGAAA UCCUUU          36

(2) INFORMATION FOR SEQ ID NO:1073:

(i) SEQUENCE CHARACTERISTICS:
                (A) LENGTH: 36 base pairs
                (B) TYPE: nucleic acid ( C ) STRANDEDNESS: single
( D ) TOPOLOGY: linear ( x i ) SEQUENCE DESCRIPTION: SEQ ID NO:1073:

AGCAGGUCUG AUGAGGCCGA AAGGCCGAAA UCCUUU    36

( 2 ) INFORMATION FOR SEQ ID NO:1074:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:1074:

GGAAGCACUG AUGAGGCCGA AAGGCCGAAA GCAGGU    36

( 2 ) INFORMATION FOR SEQ ID NO:1075:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:1075:

GGAAGCACUG AUGAGGCCGA AAGGCCGAAA GCAGGU    36

( 2 ) INFORMATION FOR SEQ ID NO:1076:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:1076:

UUUGGGACUG AUGAGGCCGA AAGGCCGAAA CCCCCG    36

( 2 ) INFORMATION FOR SEQ ID NO:1077:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:1077:

UUUGGGACUG AUGAGGCCGA AAGGCCGAAA CCCCCG    36

( 2 ) INFORMATION FOR SEQ ID NO:1078:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:1078:

UUUGGGACUG AUGAGGCCGA AAGGCCGAAA CCCCCG    36

( 2 ) INFORMATION FOR SEQ ID NO:1079:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:1079:

CUUUGGGCUG AUGAGGCCGA AAGGCCGAAA ACCCCC 36

( 2 ) INFORMATION FOR SEQ ID NO:1080:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1080:

CUUUGGGCUG AUGAGGCCGA AAGGCCGAAA ACCCCC 36

( 2 ) INFORMATION FOR SEQ ID NO:1081:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1081:

CUUUGGGCUG AUGAGGCCGA AAGGCCGAAA ACCCCC 36

( 2 ) INFORMATION FOR SEQ ID NO:1082:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1082:

GCUUUGGCUG AUGAGGCCGA AAGGCCGAAA AACCCC 36

( 2 ) INFORMATION FOR SEQ ID NO:1083:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1083:

GAGAAGCCUG AUGAGGCCGA AAGGCCGAAA GGCUUU 36

( 2 ) INFORMATION FOR SEQ ID NO:1084:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1084:

GAGAAGCCUG AUGAGGCCGA AAGGCCGAAA GGCUUU 36

( 2 ) INFORMATION FOR SEQ ID NO:1085:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1085:

ACCAAGACUG AUGAGGCCGA AAGGCCGAAA AGCGAG 36

( 2 ) INFORMATION FOR SEQ ID NO:1086:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1086:

ACCAAGACUG AUGAGGCCGA AAGGCCGAAA AGCGAG 36

( 2 ) INFORMATION FOR SEQ ID NO:1087:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1087:

CAACCAACUG AUGAGGCCGA AAGGCCGAAA GAAGCG 36

( 2 ) INFORMATION FOR SEQ ID NO:1088:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1088:

AUUUCCCUG AUGAGGCCGA AAGGCCGAAA CCAAGA 36

( 2 ) INFORMATION FOR SEQ ID NO:1089:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1089:

UGCCAGGCUG AUGAGGCCGA AAGGCCGAAA AUUCUC 36

( 2 ) INFORMATION FOR SEQ ID NO:1090:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1090:

UGCCAGGCUG AUGAGGCCGA AAGGCCGAAA AUUCUC 36

( 2 ) INFORMATION FOR SEQ ID NO:1091:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1091:

UGCCAGGCUG AUGAGGCCGA AAGGCCGAAA AUUCUC 36

( 2 ) INFORMATION FOR SEQ ID NO:1092:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1092:

UCGUAUUCUG AUGAGGCCGA AAGGCCGAAA UGCCAG    36

( 2 ) INFORMATION FOR SEQ ID NO:1093:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1093:

UCGUAUUCUG AUGAGGCCGA AAGGCCGAAA UGCCAG    36

( 2 ) INFORMATION FOR SEQ ID NO:1094:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1094:

AUUGUCGCUG AUGAGGCCGA AAGGCCGAAA UUGAUG    36

( 2 ) INFORMATION FOR SEQ ID NO:1095:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1095:

AUUGUCGCUG AUGAGGCCGA AAGGCCGAAA UUGAUG    36

( 2 ) INFORMATION FOR SEQ ID NO:1096:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1096:

CCUGGGACUG AUGAGGCCGA AAGGCCGAAA UUGUCG    36

( 2 ) INFORMATION FOR SEQ ID NO:1097:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1097:

UCCUGGGCUG AUGAGGCCGA AAGGCCGAAA AUUGUC    36

( 2 ) INFORMATION FOR SEQ ID NO:1098:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1098:

AUCCUGGCUG AUGAGGCCGA AAGGCCGAAA AAUUGU      36

( 2 ) INFORMATION FOR SEQ ID NO:1099:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1099:

GAUUCAGCUG AUGAGGCCGA AAGGCCGAAA UCCUGG      36

( 2 ) INFORMATION FOR SEQ ID NO:1100:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1100:

CAAUUCACUG AUGAGGCCGA AAGGCCGAAA UUCAGG      36

( 2 ) INFORMATION FOR SEQ ID NO:1101:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1101:

CAAUUCACUG AUGAGGCCGA AAGGCCGAAA UUCAGG      36

( 2 ) INFORMATION FOR SEQ ID NO:1102:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1102:

AAUGGUGCUG AUGAGGCCGA AAGGCCGAAA CAAUUC      36

( 2 ) INFORMATION FOR SEQ ID NO:1103:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1103:

UGAAAUCCUG AUGAGGCCGA AAGGCCGAAA GUUGGC      36

( 2 ) INFORMATION FOR SEQ ID NO:1104:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1104:

UGAAAUCCUG AUGAGGCCGA AAGGCCGAAA GUUGGC      36

( 2 ) INFORMATION FOR SEQ ID NO:1105:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1105:

UGAAAUCCUG AUGAGGCCGA AAGGCCGAAA GUUGGC      36

( 2 ) INFORMATION FOR SEQ ID NO:1106:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1106:

GUAUUGACUG AUGAGGCCGA AAGGCCGAAA UCUAGU      36

( 2 ) INFORMATION FOR SEQ ID NO:1107:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1107:

GUAUUGACUG AUGAGGCCGA AAGGCCGAAA UCUAGU      36

( 2 ) INFORMATION FOR SEQ ID NO:1108:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1108:

CGUAUUGCUG AUGAGGCCGA AAGGCCGAAA AUCUAG      36

( 2 ) INFORMATION FOR SEQ ID NO:1109:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1109:

UCGUAUUCUG AUGAGGCCGA AAGGCCGAAA AAUCUA      36

( 2 ) INFORMATION FOR SEQ ID NO:1110:

( i ) SEQUENCE CHARACTERISTICS:
        ( A ) LENGTH: 36 base pairs (B) TYPE: nucleic acid
(C) STRANDEDNESS: single
(D) TOPOLOGY: linear (xi) SEQUENCE DESCRIPTION: SEQ ID NO:1110:

UGGUUGCCUG AUGAGGCCGA AAGGCCGAAA GUCGUA 36

(2) INFORMATION FOR SEQ ID NO:1111:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:1111:

GACACUUCUG AUGAGGCCGA AAGGCCGAAA UGGUGU 36

(2) INFORMATION FOR SEQ ID NO:1112:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:1112:

GACACUUCUG AUGAGGCCGA AAGGCCGAAA UGGUGU 36

(2) INFORMATION FOR SEQ ID NO:1113:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:1113:

UUAAUGACUG AUGAGGCCGA AAGGCCGAAA CACUUA 36

(2) INFORMATION FOR SEQ ID NO:1114:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:1114:

UUAAUGACUG AUGAGGCCGA AAGGCCGAAA CACUUA 36

(2) INFORMATION FOR SEQ ID NO:1115:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:1115:

AUUUAAUCUG AUGAGGCCGA AAGGCCGAAA GACACU 36

(2) INFORMATION FOR SEQ ID NO:1116:

(i) SEQUENCE CHARACTERISTICS:
(A) LENGTH: 36 base pairs
(B) TYPE: nucleic acid
(C) STRANDEDNESS: single -continued (D) TOPOLOGY: linear (xi) SEQUENCE DESCRIPTION: SEQ ID NO:1116:

CAUAUUUCUG AUGAGGCCGA AAGGCCGAAA UGAGAC 36

(2) INFORMATION FOR SEQ ID NO:1117:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1117:

AUCUCCACUG AUGAGGCCGA AAGGCCGAAA UUUAAU 36

(2) INFORMATION FOR SEQ ID NO:1118:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1118:

AUCUCCACUG AUGAGGCCGA AAGGCCGAAA UUUAAU 36

(2) INFORMATION FOR SEQ ID NO:1119:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1119:

CCAGGUGCUG AUGAGGCCGA AAGGCCGAAA GUCCUC 36

(2) INFORMATION FOR SEQ ID NO:1120:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1120:

CCCAGGUCUG AUGAGGCCGA AAGGCCGAAA AGUCCU 36

(2) INFORMATION FOR SEQ ID NO:1121:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1121:

CUGCCCCUG AUGAGGCCGA AAGGCCGAAA AGAGCA 36

(2) INFORMATION FOR SEQ ID NO:1122:

(i) SEQUENCE CHARACTERISTICS:
        (A) LENGTH: 36 base pairs
        (B) TYPE: nucleic acid
        (C) STRANDEDNESS: single
        (D) TOPOLOGY: linear ( x i ) SEQUENCE DESCRIPTION: SEQ ID NO:1122:

CGAUGACCUG AUGAGGCCGA AAGGCCGAAA CGACUG　　　　　　　　　　　　36

( 2 ) INFORMATION FOR SEQ ID NO:1123:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1123:

CAACGAUCUG AUGAGGCCGA AAGGCCGAAA CGACGA　　　　　　　　　　　　36

( 2 ) INFORMATION FOR SEQ ID NO:1124:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1124:

UGAUGACCUG AUGAGGCCGA AAGGCCGAAA CGAUGA　　　　　　　　　　　　36

( 2 ) INFORMATION FOR SEQ ID NO:1125:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1125:

UGAUGAUCUG AUGAGGCCGA AAGGCCGAAA CAACGA　　　　　　　　　　　　36

( 2 ) INFORMATION FOR SEQ ID NO:1126:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1126:

AUUUGAUCUG AUGAGGCCGA AAGGCCGAAA UGACAA　　　　　　　　　　　　36

( 2 ) INFORMATION FOR SEQ ID NO:1127:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1127:

CUUACAGCUG AUGAGGCCGA AAGGCCGAAA GCAUUU　　　　　　　　　　　　36

( 2 ) INFORMATION FOR SEQ ID NO:1128:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1128:

CUUACAGCUG AUGAGGCCGA AAGGCCGAAA GCAUUU 36

( 2 ) INFORMATION FOR SEQ ID NO:1129:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1129:

CUUACAGCUG AUGAGGCCGA AAGGCCGAAA GCAUUU 36

( 2 ) INFORMATION FOR SEQ ID NO:1130:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1130:

CUUACAGCUG AUGAGGCCGA AAGGCCGAAA GCAUUU 36

( 2 ) INFORMATION FOR SEQ ID NO:1131:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1131:

GCUUACACUG AUGAGGCCGA AAGGCCGAAA AGCAUU 36

( 2 ) INFORMATION FOR SEQ ID NO:1132:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1132:

CUUCUGACUG AUGAGGCCGA AAGGCCGAAA CAGCUU 36

( 2 ) INFORMATION FOR SEQ ID NO:1133:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1133:

CUUCUGACUG AUGAGGCCGA AAGGCCGAAA CAGCUU 36

( 2 ) INFORMATION FOR SEQ ID NO:1134:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1134:

UCUUCUGCUG AUGAGGCCGA AAGGCCGAAA ACAGCU 36

( 2 ) INFORMATION FOR SEQ ID NO:1135:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1135:

CGAAGGUCUG AUGAGGCCGA AAGGCCGAAA GGCUGU 36

( 2 ) INFORMATION FOR SEQ ID NO:1136:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1136:

CGAAGGUCUG AUGAGGCCGA AAGGCCGAAA GGCUGU 36

( 2 ) INFORMATION FOR SEQ ID NO:1137:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1137:

CGAAGGUCUG AUGAGGCCGA AAGGCCGAAA GGCUGU 36

( 2 ) INFORMATION FOR SEQ ID NO:1138:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1138:

CCGAAGGCUG AUGAGGCCGA AAGGCCGAAA AGGCUG 36

( 2 ) INFORMATION FOR SEQ ID NO:1139:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1139:

AGGCCCGCUG AUGAGGCCGA AAGGCCGAAA GGUAAG 36

( 2 ) INFORMATION FOR SEQ ID NO:1140:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1140:

CAGGCCCCUG AUGAGGCCGA AAGGCCGAAA AGGUAA 36

( 2 ) INFORMATION FOR SEQ ID NO:1141:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1141:

CAGGCCCUG AUGAGGCCGA AAGGCCGAAA AGGUAA    36

( 2 ) INFORMATION FOR SEQ ID NO:1142:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1142:

UUCAGCUCUG AUGAGGCCGA AAGGCCGAAA UGCUUC    36

( 2 ) INFORMATION FOR SEQ ID NO:1143:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1143:

UUCAGCUCUG AUGAGGCCGA AAGGCCGAAA UGCUUC    36

( 2 ) INFORMATION FOR SEQ ID NO:1144:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1144:

GUUCAGCCUG AUGAGGCCGA AAGGCCGAAA AUGCUU    36

( 2 ) INFORMATION FOR SEQ ID NO:1145:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1145:

AAAGGAACUG AUGAGGCCGA AAGGCCGAAA CGGUCU    36

( 2 ) INFORMATION FOR SEQ ID NO:1146:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1146:

CUAAAGGCUG AUGAGGCCGA AAGGCCGAAA GACGGU    36

( 2 ) INFORMATION FOR SEQ ID NO:1147:

( i ) SEQUENCE CHARACTERISTICS:

(A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1147:

ACUAAAGCUG AUGAGGCCGA AAGGCCGAAA AGACGG         36

(2) INFORMATION FOR SEQ ID NO:1148:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1148:

AAGAACUCUG AUGAGGCCGA AAGGCCGAAA AGGAAG         36

(2) INFORMATION FOR SEQ ID NO:1149:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1149:

AUGGACACUG AUGAGGCCGA AAGGCCGAAA GAAGAA         36

(2) INFORMATION FOR SEQ ID NO:1150:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1150:

CCACAUGCUG AUGAGGCCGA AAGGCCGAAA CAGAGA         36

(2) INFORMATION FOR SEQ ID NO:1151:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1151:

CCACAUGCUG AUGAGGCCGA AAGGCCGAAA CAGAGA         36

(2) INFORMATION FOR SEQ ID NO:1152:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1152:

UACCAUGCUG AUGAGGCCGA AAGGCCGAAA UCCCAC         36

(2) INFORMATION FOR SEQ ID NO:1153:

(i) SEQUENCE CHARACTERISTICS:
        (A) LENGTH: 36 base pairs
        (B) TYPE: nucleic acid ( C ) STRANDEDNESS: single
        ( D ) TOPOLOGY: linear ( x i ) SEQUENCE DESCRIPTION: SEQ ID NO:1153:

CACAUAACUG AUGAGGCCGA AAGGCCGAAA CCAUGU 36

( 2 ) INFORMATION FOR SEQ ID NO:1154:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1154:

GCCACAUCUG AUGAGGCCGA AAGGCCGAAA UACCAU 36

( 2 ) INFORMATION FOR SEQ ID NO:1155:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1155:

ACCUCAUCUG AUGAGGCCGA AAGGCCGAAA GCCACA 36

( 2 ) INFORMATION FOR SEQ ID NO:1156:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1156:

ACCUCAUCUG AUGAGGCCGA AAGGCCGAAA GCCACA 36

( 2 ) INFORMATION FOR SEQ ID NO:1157:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1157:

AAAGAAACUG AUGAGGCCGA AAGGCCGAAA UUGUAC 36

( 2 ) INFORMATION FOR SEQ ID NO:1158:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1158:

UGAAAGACUG AUGAGGCCGA AAGGCCGAAA GAUUGU 36

( 2 ) INFORMATION FOR SEQ ID NO:1159:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1159:

UGAAAGACUG AUGAGGCCGA AAGGCCGAAA GAUUGU 36

( 2 ) INFORMATION FOR SEQ ID NO:1160:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1160:

CUGAAAGCUG AUGAGGCCGA AAGGCCGAAA AGAUUG 36

( 2 ) INFORMATION FOR SEQ ID NO:1161:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1161:

GCUGAAACUG AUGAGGCCGA AAGGCCGAAA AAGAUU 36

( 2 ) INFORMATION FOR SEQ ID NO:1162:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1162:

GCUGAAACUG AUGAGGCCGA AAGGCCGAAA AAGAUU 36

( 2 ) INFORMATION FOR SEQ ID NO:1163:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1163:

GCUGAAACUG AUGAGGCCGA AAGGCCGAAA AAGAUU 36

( 2 ) INFORMATION FOR SEQ ID NO:1164:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1164:

GUGCUGACUG AUGAGGCCGA AAGGCCGAAA GAAAGA 36

( 2 ) INFORMATION FOR SEQ ID NO:1165:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1165:

```
GGUGCUGCUG  AUGAGGCCGA  AAGGCCGAAA  AGAAAG                                          36
```

( 2 ) INFORMATION FOR SEQ ID NO:1166:

( i ) SEQUENCE CHARACTERISTICS:
            ( A ) LENGTH: 36 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1166:

```
UGUCCGACUG  AUGAGGCCGA  AAGGCCGAAA  GAUCAG                                          36
```

( 2 ) INFORMATION FOR SEQ ID NO:1167:

( i ) SEQUENCE CHARACTERISTICS:
            ( A ) LENGTH: 36 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1167:

```
UUAACUCCUG  AUGAGGCCGA  AAGGCCGAAA  UCUUGU                                          36
```

( 2 ) INFORMATION FOR SEQ ID NO:1168:

( i ) SEQUENCE CHARACTERISTICS:
            ( A ) LENGTH: 36 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1168:

```
GGAAAGACUG  AUGAGGCCGA  AAGGCCGAAA  UCCUCA                                          36
```

( 2 ) INFORMATION FOR SEQ ID NO:1169:

( i ) SEQUENCE CHARACTERISTICS:
            ( A ) LENGTH: 36 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1169:

```
AUGGAAACUG  AUGAGGCCGA  AAGGCCGAAA  AAUCCU                                          36
```

( 2 ) INFORMATION FOR SEQ ID NO:1170:

( i ) SEQUENCE CHARACTERISTICS:
            ( A ) LENGTH: 36 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1170:

```
UGAUGGACUG  AUGAGGCCGA  AAGGCCGAAA  GAAAUC                                          36
```

( 2 ) INFORMATION FOR SEQ ID NO:1171:

( i ) SEQUENCE CHARACTERISTICS:
            ( A ) LENGTH: 36 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1171:

```
CCUGAUGCUG  AUGAGGCCGA  AAGGCCGAAA  AAGAAA                                          36
```

( 2 ) INFORMATION FOR SEQ ID NO:1172:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1172:

GCUUCCUCUG AUGAGGCCGA AAGGCCGAAA UGGAAA       36

( 2 ) INFORMATION FOR SEQ ID NO:1173:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1173:

GCUUCCUCUG AUGAGGCCGA AAGGCCGAAA UGGAAA       36

( 2 ) INFORMATION FOR SEQ ID NO:1174:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1174:

CCCAGCACUG AUGAGGCCGA AAGGCCGAAA CUUGCC       36

( 2 ) INFORMATION FOR SEQ ID NO:1175:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1175:

AUCAAGCCUG AUGAGGCCGA AAGGCCGAAA UCAAAG       36

( 2 ) INFORMATION FOR SEQ ID NO:1176:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1176:

UUUUUCUCUG AUGAGGCCGA AAGGCCGAAA UACCAC       36

( 2 ) INFORMATION FOR SEQ ID NO:1177:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1177:

UUUUUCUCUG AUGAGGCCGA AAGGCCGAAA UACCAC       36

( 2 ) INFORMATION FOR SEQ ID NO:1178:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1178:

GCAGUAACUG AUGAGGCCGA AAGGCCGAAA CUAGGC    36

( 2 ) INFORMATION FOR SEQ ID NO:1179:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1179:

UUGCAGUCUG AUGAGGCCGA AAGGCCGAAA GACUAG    36

( 2 ) INFORMATION FOR SEQ ID NO:1180:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1180:

ACAUACCUG AUGAGGCCGA AAGGCCGAAA GUUGCA    36

( 2 ) INFORMATION FOR SEQ ID NO:1181:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1181:

CAUGACACUG AUGAGGCCGA AAGGCCGAAA UCAAGU    36

( 2 ) INFORMATION FOR SEQ ID NO:1182:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1182:

CAUGACACUG AUGAGGCCGA AAGGCCGAAA UCAAGU    36

( 2 ) INFORMATION FOR SEQ ID NO:1183:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1183:

AGACACCCUG AUGAGGCCGA AAGGCCGAAA CCAAAC    36

( 2 ) INFORMATION FOR SEQ ID NO:1184:

( i ) SEQUENCE CHARACTERISTICS:
   ( A ) LENGTH: 36 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:1184:

CUUCAGACUG AUGAGGCCGA AAGGCCGAAA AGGGCA 36

( 2 ) INFORMATION FOR SEQ ID NO:1185:

( i ) SEQUENCE CHARACTERISTICS:
   ( A ) LENGTH: 36 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:1185:

UCUUCAGCUG AUGAGGCCGA AAGGCCGAAA AAGGGC 36

( 2 ) INFORMATION FOR SEQ ID NO:1186:

( i ) SEQUENCE CHARACTERISTICS:
   ( A ) LENGTH: 36 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:1186:

CUCUUCACUG AUGAGGCCGA AAGGCCGAAA AAAGGG 36

( 2 ) INFORMATION FOR SEQ ID NO:1187:

( i ) SEQUENCE CHARACTERISTICS:
   ( A ) LENGTH: 36 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:1187:

CUCUUCACUG AUGAGGCCGA AAGGCCGAAA AAAGGG 36

( 2 ) INFORMATION FOR SEQ ID NO:1188:

( i ) SEQUENCE CHARACTERISTICS:
   ( A ) LENGTH: 36 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:1188:

ACAUCCCUG AUGAGGCCGA AAGGCCGAAA CCAUAG 36

( 2 ) INFORMATION FOR SEQ ID NO:1189:

( i ) SEQUENCE CHARACTERISTICS:
   ( A ) LENGTH: 36 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:1189:

CCGUUUUCUG AUGAGGCCGA AAGGCCGAAA CAUCCC 36

( 2 ) INFORMATION FOR SEQ ID NO:1190:

( i ) SEQUENCE CHARACTERISTICS:
   ( A ) LENGTH: 36 base pairs ( B ) TYPE: nucleic acid
( C ) STRANDEDNESS: single
( D ) TOPOLOGY: linear ( x i ) SEQUENCE DESCRIPTION: SEQ ID NO:1190:

CCGUUUUCUG AUGAGGCCGA AAGGCCGAAA CAUCCC 36

( 2 ) INFORMATION FOR SEQ ID NO:1191:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:1191:

UAAUAUUCUG AUGAGGCCGA AAGGCCGAAA UAUUAU 36

( 2 ) INFORMATION FOR SEQ ID NO:1192:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:1192:

UAUUUAACUG AUGAGGCCGA AAGGCCGAAA UUUAUA 36

( 2 ) INFORMATION FOR SEQ ID NO:1193:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:1193:

UUUAUUUCUG AUGAGGCCGA AAGGCCGAAA UAUUUA 36

( 2 ) INFORMATION FOR SEQ ID NO:1194:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:1194:

UUUUAUUCUG AUGAGGCCGA AAGGCCGAAA AUAUUU 36

( 2 ) INFORMATION FOR SEQ ID NO:1195:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:1195:

UUUUAUUCUG AUGAGGCCGA AAGGCCGAAA AUAUUU 36

( 2 ) INFORMATION FOR SEQ ID NO:1196:

( i ) SEQUENCE CHARACTERISTICS:
( A ) LENGTH: 36 base pairs
( B ) TYPE: nucleic acid
( C ) STRANDEDNESS: single (D) TOPOLOGY: linear (xi) SEQUENCE DESCRIPTION: SEQ ID NO:1196:

UUUGCUCCUG AUGAGGCCGA AAGGCCGAAA UACUCU 36

(2) INFORMATION FOR SEQ ID NO:1197:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:1197:

GAAAGCUUUG CUUCU 15

(2) INFORMATION FOR SEQ ID NO:1198:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:1198:

AAAGCUUUGC UUCUC 15

(2) INFORMATION FOR SEQ ID NO:1199:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:1199:

CUUUGCUUCU CUGCU 15

(2) INFORMATION FOR SEQ ID NO:1200:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:1200:

UUUGCUUCUC UGCUG 15

(2) INFORMATION FOR SEQ ID NO:1201:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:1201:

UGCUUCUCUG CUGCU 15

(2) INFORMATION FOR SEQ ID NO:1202:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO:1202:

CUGCUGUAAC AGGGA 15

(2) INFORMATION FOR SEQ ID NO:1203:

(i) SEQUENCE CHARACTERISTICS:
  (A) LENGTH: 15 base pairs
  (B) TYPE: nucleic acid
  (C) STRANDEDNESS: single
  (D) TOPOLOGY: linear (x i) SEQUENCE DESCRIPTION: SEQ ID NO:1203:

AGGGACUAGC ACAGA 15

(2) INFORMATION FOR SEQ ID NO:1204:

(i) SEQUENCE CHARACTERISTICS:
  (A) LENGTH: 15 base pairs
  (B) TYPE: nucleic acid
  (C) STRANDEDNESS: single
  (D) TOPOLOGY: linear (x i) SEQUENCE DESCRIPTION: SEQ ID NO:1204:

GUGGGGUCAU UUCCA 15

(2) INFORMATION FOR SEQ ID NO:1205:

(i) SEQUENCE CHARACTERISTICS:
  (A) LENGTH: 15 base pairs
  (B) TYPE: nucleic acid
  (C) STRANDEDNESS: single
  (D) TOPOLOGY: linear (x i) SEQUENCE DESCRIPTION: SEQ ID NO:1205:

GGGUCAUUUC CAGAU 15

(2) INFORMATION FOR SEQ ID NO:1206:

(i) SEQUENCE CHARACTERISTICS:
  (A) LENGTH: 15 base pairs
  (B) TYPE: nucleic acid
  (C) STRANDEDNESS: single
  (D) TOPOLOGY: linear (x i) SEQUENCE DESCRIPTION: SEQ ID NO:1206:

GGUCAUUUCC AGAUA 15

(2) INFORMATION FOR SEQ ID NO:1207:

(i) SEQUENCE CHARACTERISTICS:
  (A) LENGTH: 15 base pairs
  (B) TYPE: nucleic acid
  (C) STRANDEDNESS: single
  (D) TOPOLOGY: linear (x i) SEQUENCE DESCRIPTION: SEQ ID NO:1207:

GUCAUUUCCA GAUAU 15

(2) INFORMATION FOR SEQ ID NO:1208:

(i) SEQUENCE CHARACTERISTICS:
  (A) LENGTH: 15 base pairs
  (B) TYPE: nucleic acid
  (C) STRANDEDNESS: single
  (D) TOPOLOGY: linear (x i) SEQUENCE DESCRIPTION: SEQ ID NO:1208:

UCCAGAUAUU AGGUC        15

( 2 ) INFORMATION FOR SEQ ID NO:1209:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1209:

CAGAUAUUAG GUCAC        15

( 2 ) INFORMATION FOR SEQ ID NO:1210:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1210:

AGAUAUUAGG UCACA        15

( 2 ) INFORMATION FOR SEQ ID NO:1211:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1211:

AUUAGGUCAC AGCAG        15

( 2 ) INFORMATION FOR SEQ ID NO:1212:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1212:

AAUGGAUCCC CAGUG        15

( 2 ) INFORMATION FOR SEQ ID NO:1213:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1213:

GUGCACUAUG GGACU        15

( 2 ) INFORMATION FOR SEQ ID NO:1214:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1214:

ACUGAGUAAC AUUCU        15

( 2 ) INFORMATION FOR SEQ ID NO:1215:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1215:

GUAACAUUCU CUUUG                                                                            1 5

( 2 ) INFORMATION FOR SEQ ID NO:1216:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1216:

UAACAUUCUC UUUGU                                                                            1 5

( 2 ) INFORMATION FOR SEQ ID NO:1217:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1217:

ACAUUCUCUU UGUGA                                                                            1 5

( 2 ) INFORMATION FOR SEQ ID NO:1218:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1218:

AUUCUCUUUG UGAUG                                                                            1 5

( 2 ) INFORMATION FOR SEQ ID NO:1219:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1219:

UUCUCUUUGU GAUGG                                                                            1 5

( 2 ) INFORMATION FOR SEQ ID NO:1220:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1220:

AUGGCCUUCC UGCUC                                                                            1 5

( 2 ) INFORMATION FOR SEQ ID NO:1221:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1221:

UGGCCUUCCU GCUCU 15

( 2 ) INFORMATION FOR SEQ ID NO:1222:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1222:

UCCUGCUCUC UGGUG 15

( 2 ) INFORMATION FOR SEQ ID NO:1223:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1223:

CUGCUCUCUG GUGCU 15

( 2 ) INFORMATION FOR SEQ ID NO:1224:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1224:

UGCUGCUCCU CUGAA 15

( 2 ) INFORMATION FOR SEQ ID NO:1225:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1225:

UGCUCCUCUG AAGAU 15

( 2 ) INFORMATION FOR SEQ ID NO:1226:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1226:

UGAAGAUUCA AGCUU 15

( 2 ) INFORMATION FOR SEQ ID NO:1227:

( i ) SEQUENCE CHARACTERISTICS:

( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:1227:

GAAGAUUCAA GCUUA 15

( 2 ) INFORMATION FOR SEQ ID NO:1228:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:1228:

UCAAGCUUAU UUCAA 15

( 2 ) INFORMATION FOR SEQ ID NO:1229:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:1229:

CAAGCUUAUU UCAAU 15

( 2 ) INFORMATION FOR SEQ ID NO:1230:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:1230:

AGCUUAUUUC AAUGA 15

( 2 ) INFORMATION FOR SEQ ID NO:1231:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:1231:

GCUUAUUUCA AUGAG 15

( 2 ) INFORMATION FOR SEQ ID NO:1232:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:1232:

CUUAUUUCAA UGAGA 15

( 2 ) INFORMATION FOR SEQ ID NO:1233:

( i ) SEQUENCE CHARACTERISTICS:
( A ) LENGTH: 15 base pairs
( B ) TYPE: nucleic acid ( C ) STRANDEDNESS: single
( D ) TOPOLOGY: linear ( x i ) SEQUENCE DESCRIPTION: SEQ ID NO:1233:

UGCCAAUUUG CAAAC 15

( 2 ) INFORMATION FOR SEQ ID NO:1234:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:1234:

GCCAAUUUGC AAACU 15

( 2 ) INFORMATION FOR SEQ ID NO:1235:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:1235:

GCAAACUCUC AAAAC 15

( 2 ) INFORMATION FOR SEQ ID NO:1236:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:1236:

AAACUCUCAA AACCA 15

( 2 ) INFORMATION FOR SEQ ID NO:1237:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:1237:

GUGAGCUAGU AGUAU 15

( 2 ) INFORMATION FOR SEQ ID NO:1238:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:1238:

AGCUAGUAGU AUUUU 15

( 2 ) INFORMATION FOR SEQ ID NO:1239:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:1239:

UAGUAGUAUU UUGGC 15

( 2 ) INFORMATION FOR SEQ ID NO:1240:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1240:

GUAGUAUUUU GGCAG 15

( 2 ) INFORMATION FOR SEQ ID NO:1241:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1241:

UAGUAUUUUG GCAGG 15

( 2 ) INFORMATION FOR SEQ ID NO:1242:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1242:

AGUAUUUGG CAGGA 15

( 2 ) INFORMATION FOR SEQ ID NO:1243:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1243:

GAAAACUUGG UUCUG 15

( 2 ) INFORMATION FOR SEQ ID NO:1244:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1244:

ACUUGGUUCU GAAUG 15

( 2 ) INFORMATION FOR SEQ ID NO:1245:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1245:

CUUGGUUCUG AAUGA 15

(2) INFORMATION FOR SEQ ID NO:1246:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:1246:

AUGAGGUAUA CUUAG 15

(2) INFORMATION FOR SEQ ID NO:1247:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:1247:

GAGGUAUACU UAGGC 15

(2) INFORMATION FOR SEQ ID NO:1248:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:1248:

GUAUACUUAG GCAAA 15

(2) INFORMATION FOR SEQ ID NO:1249:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:1249:

UAUACUUAGG CAAAG 15

(2) INFORMATION FOR SEQ ID NO:1250:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:1250:

GAGAAAUUUG ACAGU 15

(2) INFORMATION FOR SEQ ID NO:1251:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:1251:

AGAAAUUUGA CAGUG 15

( 2 ) INFORMATION FOR SEQ ID NO:1252:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1252:

ACAGUGUUCA UUCCA 15

( 2 ) INFORMATION FOR SEQ ID NO:1253:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1253:

CAGUGUUCAU UCCAA 15

( 2 ) INFORMATION FOR SEQ ID NO:1254:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1254:

UGUUCAUUCC AAGUA 15

( 2 ) INFORMATION FOR SEQ ID NO:1255:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1255:

GUUCAUUCCA AGUAU 15

( 2 ) INFORMATION FOR SEQ ID NO:1256:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1256:

UCCAAGUAUA UGGGC 15

( 2 ) INFORMATION FOR SEQ ID NO:1257:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1257:

CAAGUAUAUG GGCCG 15

( 2 ) INFORMATION FOR SEQ ID NO:1258:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1258:

CACAAGUUUU GAUUC                                                                15

( 2 ) INFORMATION FOR SEQ ID NO:1259:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1259:

ACAAGUUUUG AUUCG                                                                15

( 2 ) INFORMATION FOR SEQ ID NO:1260:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1260:

CAAGUUUUGA UUCGG                                                                15

( 2 ) INFORMATION FOR SEQ ID NO:1261:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1261:

UUUUGAUUCG GACAG                                                                15

( 2 ) INFORMATION FOR SEQ ID NO:1262:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1262:

UUUGAUUCGG ACAGU                                                                15

( 2 ) INFORMATION FOR SEQ ID NO:1263:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1263:

GGACAGUUGG ACCCU                                                                15

( 2 ) INFORMATION FOR SEQ ID NO:1264:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1264:

UGAGACUUCA CAAUC 15

( 2 ) INFORMATION FOR SEQ ID NO:1265:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1265:

GAGACUUCAC AAUCU 15

( 2 ) INFORMATION FOR SEQ ID NO:1266:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1266:

UCACAAUCUU CAGAU 15

( 2 ) INFORMATION FOR SEQ ID NO:1267:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1267:

ACAAUCUUCA GAUCA 15

( 2 ) INFORMATION FOR SEQ ID NO:1268:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1268:

CAAUCUUCAG AUCAA 15

( 2 ) INFORMATION FOR SEQ ID NO:1269:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1269:

UUCAGAUCAA GGACA 15

( 2 ) INFORMATION FOR SEQ ID NO:1270:

( i ) SEQUENCE CHARACTERISTICS:
        ( A ) LENGTH: 15 base pairs (B) TYPE: nucleic acid
        (C) STRANDEDNESS: single
        (D) TOPOLOGY: linear (xi) SEQUENCE DESCRIPTION: SEQ ID NO:1270:

AAGGGCUUGU AUCAA  15

(2) INFORMATION FOR SEQ ID NO:1271:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:1271:

GGCUUGUAUC AAUGU  15

(2) INFORMATION FOR SEQ ID NO:1272:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:1272:

CUUGUAUCAA UGUAU  15

(2) INFORMATION FOR SEQ ID NO:1273:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:1273:

UCAAUGUAUC AUCCA  15

(2) INFORMATION FOR SEQ ID NO:1274:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:1274:

AAUGUAUCAU CCAUC  15

(2) INFORMATION FOR SEQ ID NO:1275:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:1275:

GUAUCAUCCA UCACA  15

(2) INFORMATION FOR SEQ ID NO:1276:

(i) SEQUENCE CHARACTERISTICS:
        (A) LENGTH: 15 base pairs
        (B) TYPE: nucleic acid
        (C) STRANDEDNESS: single (D) TOPOLOGY: linear (xi) SEQUENCE DESCRIPTION: SEQ ID NO:1276:

CAUCCAUCAC AAAAA 15

(2) INFORMATION FOR SEQ ID NO:1277:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (xi) SEQUENCE DESCRIPTION: SEQ ID NO:1277:

GAAUGAUUCG CAUCC 15

(2) INFORMATION FOR SEQ ID NO:1278:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (xi) SEQUENCE DESCRIPTION: SEQ ID NO:1278:

AAUGAUUCGC AUCCA 15

(2) INFORMATION FOR SEQ ID NO:1279:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (xi) SEQUENCE DESCRIPTION: SEQ ID NO:1279:

UUCGCAUCCA CCAGA 15

(2) INFORMATION FOR SEQ ID NO:1280:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (xi) SEQUENCE DESCRIPTION: SEQ ID NO:1280:

GAUGAAUUCU GAACU 15

(2) INFORMATION FOR SEQ ID NO:1281:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (xi) SEQUENCE DESCRIPTION: SEQ ID NO:1281:

AUGAAUUCUG AACUG 15

(2) INFORMATION FOR SEQ ID NO:1282:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (x i) SEQUENCE DESCRIPTION: SEQ ID NO:1282:

GAACUGUCAG UGCUU 15

(2) INFORMATION FOR SEQ ID NO:1283:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO:1283:

CAGUGCUUGC UAACU 15

(2) INFORMATION FOR SEQ ID NO:1284:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO:1284:

GCUUGCUAAC UUCAG 15

(2) INFORMATION FOR SEQ ID NO:1285:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO:1285:

GCUAACUUCA GUCAA 15

(2) INFORMATION FOR SEQ ID NO:1286:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO:1286:

CUAACUUCAG UCAAC 15

(2) INFORMATION FOR SEQ ID NO:1287:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO:1287:

CUUCAGUCAA CCUGA 15

(2) INFORMATION FOR SEQ ID NO:1288:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO:1288:

CUGAAAUAGU ACCAA 15

( 2 ) INFORMATION FOR SEQ ID NO:1289:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1289:

AAAUAGUACC AAUUU 15

( 2 ) INFORMATION FOR SEQ ID NO:1290:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1290:

UACCAAUUUC UAAUA 15

( 2 ) INFORMATION FOR SEQ ID NO:1291:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1291:

ACCAAUUUCU AAUAU 15

( 2 ) INFORMATION FOR SEQ ID NO:1292:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1292:

CCAAUUUCUA AUAUA 15

( 2 ) INFORMATION FOR SEQ ID NO:1293:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1293:

AAUUUCUAAU AUAAC 15

( 2 ) INFORMATION FOR SEQ ID NO:1294:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1294:

UUCUAAUAUA ACAGA 15

( 2 ) INFORMATION FOR SEQ ID NO:1295:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1295:

CUAAUAUAAC AGAAA                          15

( 2 ) INFORMATION FOR SEQ ID NO:1296:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1296:

AAUGUGUACA UAAAU                          15

( 2 ) INFORMATION FOR SEQ ID NO:1297:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1297:

UGUACAUAAA UUUGA                          15

( 2 ) INFORMATION FOR SEQ ID NO:1298:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1298:

CAUAAAUUUG ACCUG                          15

( 2 ) INFORMATION FOR SEQ ID NO:1299:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1299:

AUAAAUUUGA CCUGC                          15

( 2 ) INFORMATION FOR SEQ ID NO:1300:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1300:

ACCUGCUCAU CUAUA                          15

( 2 ) INFORMATION FOR SEQ ID NO:1301:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1301:

UGCUCAUCUA UACAC 15

( 2 ) INFORMATION FOR SEQ ID NO:1302:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1302:

CUCAUCUAUA CACGG 15

( 2 ) INFORMATION FOR SEQ ID NO:1303:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1303:

CAUCUAUACA CGGUU 15

( 2 ) INFORMATION FOR SEQ ID NO:1304:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1304:

ACACGGUUAC CCAGA 15

( 2 ) INFORMATION FOR SEQ ID NO:1305:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1305:

CACGGUUACC CAGAA 15

( 2 ) INFORMATION FOR SEQ ID NO:1306:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1306:

AGAACCUAAG AAGAU 15

( 2 ) INFORMATION FOR SEQ ID NO:1307:

( i ) SEQUENCE CHARACTERISTICS:

( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1307:

UGAGUGUUUU GCUAA                                                                                        15

( 2 ) INFORMATION FOR SEQ ID NO:1308:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1308:

GAGUGUUUUG CUAAG                                                                                        15

( 2 ) INFORMATION FOR SEQ ID NO:1309:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1309:

AGUGUUUUGC UAAGA                                                                                        15

( 2 ) INFORMATION FOR SEQ ID NO:1310:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1310:

UUUUGCUAAG AACCA                                                                                        15

( 2 ) INFORMATION FOR SEQ ID NO:1311:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1311:

CAAGAAUUCA ACUAU                                                                                        15

( 2 ) INFORMATION FOR SEQ ID NO:1312:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1312:

AAGAAUUCAA CUAUC                                                                                        15

( 2 ) INFORMATION FOR SEQ ID NO:1313:

( i ) SEQUENCE CHARACTERISTICS:
            ( A ) LENGTH: 15 base pairs
            ( B ) TYPE: nucleic acid (C) STRANDEDNESS: single
                (D) TOPOLOGY: linear (xi) SEQUENCE DESCRIPTION: SEQ ID NO:1313:

UUCAACUAUC GAGUA                                                                                                15

(2) INFORMATION FOR SEQ ID NO:1314:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (xi) SEQUENCE DESCRIPTION: SEQ ID NO:1314:

CAACUAUCGA GUAUG                                                                                                15

(2) INFORMATION FOR SEQ ID NO:1315:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (xi) SEQUENCE DESCRIPTION: SEQ ID NO:1315:

AUCGAGUAUG AUGGU                                                                                                15

(2) INFORMATION FOR SEQ ID NO:1316:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (xi) SEQUENCE DESCRIPTION: SEQ ID NO:1316:

UGAUGGUAUU AUGCA                                                                                                15

(2) INFORMATION FOR SEQ ID NO:1317:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (xi) SEQUENCE DESCRIPTION: SEQ ID NO:1317:

AUGGUAUUAU GCAGA                                                                                                15

(2) INFORMATION FOR SEQ ID NO:1318:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (xi) SEQUENCE DESCRIPTION: SEQ ID NO:1318:

UGGUAUUAUG CAGAA                                                                                                15

(2) INFORMATION FOR SEQ ID NO:1319:

(i) SEQUENCE CHARACTERISTICS:
                (A) LENGTH: 15 base pairs
                (B) TYPE: nucleic acid
                (C) STRANDEDNESS: single
                (D) TOPOLOGY: linear ( x i ) SEQUENCE DESCRIPTION: SEQ ID NO:1319:

CAGAAAUCUC AAGAU          15

( 2 ) INFORMATION FOR SEQ ID NO:1320:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1320:

GAAAUCUCAA GAUAA          15

( 2 ) INFORMATION FOR SEQ ID NO:1321:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1321:

UCAAGAUAAU GUCAC          15

( 2 ) INFORMATION FOR SEQ ID NO:1322:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1322:

AUAAUGUCAC AGAAC          15

( 2 ) INFORMATION FOR SEQ ID NO:1323:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1323:

GAACUGUACG ACGUU          15

( 2 ) INFORMATION FOR SEQ ID NO:1324:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1324:

ACGACGUUUC CAUCA          15

( 2 ) INFORMATION FOR SEQ ID NO:1325:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1325:

CGACGUUUCC AUCAG    15

(2) INFORMATION FOR SEQ ID NO:1326:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:1326:

GACGUUUCCA UCAGC    15

(2) INFORMATION FOR SEQ ID NO:1327:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:1327:

UUUCCAUCAG CUUGU    15

(2) INFORMATION FOR SEQ ID NO:1328:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:1328:

AUCAGCUUGU CUGUU    15

(2) INFORMATION FOR SEQ ID NO:1329:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:1329:

AGCUUGUCUG UUUCA    15

(2) INFORMATION FOR SEQ ID NO:1330:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:1330:

UGUCUGUUUC AUUCC    15

(2) INFORMATION FOR SEQ ID NO:1331:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:1331:

GUCUGUUUCA UUCCC    15

( 2 ) INFORMATION FOR SEQ ID NO:1332:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1332:

UCUGUUUCAU UCCCU 15

( 2 ) INFORMATION FOR SEQ ID NO:1333:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1333:

GUUUCAUUCC CUGAU 15

( 2 ) INFORMATION FOR SEQ ID NO:1334:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1334:

UUUCAUUCCC UGAUG 15

( 2 ) INFORMATION FOR SEQ ID NO:1335:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1335:

CUGAUGUUAC GAGCA 15

( 2 ) INFORMATION FOR SEQ ID NO:1336:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1336:

UGAUGUUACG AGCAA 15

( 2 ) INFORMATION FOR SEQ ID NO:1337:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1337:

GAGCAAUAUG ACCAU 15

( 2 ) INFORMATION FOR SEQ ID NO:1338:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1338:

UGACCAUCUU CUGUA 15

( 2 ) INFORMATION FOR SEQ ID NO:1339:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1339:

ACCAUCUUCU GUAUU 15

( 2 ) INFORMATION FOR SEQ ID NO:1340:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1340:

CCAUCUUCUG UAUUC 15

( 2 ) INFORMATION FOR SEQ ID NO:1341:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1341:

CUUCUGUAUU CUGGA 15

( 2 ) INFORMATION FOR SEQ ID NO:1342:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1342:

UCUGUAUUCU GGAAA 15

( 2 ) INFORMATION FOR SEQ ID NO:1343:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1343:

CUGUAUUCUG GAAAC 15

( 2 ) INFORMATION FOR SEQ ID NO:1344:

( i ) SEQUENCE CHARACTERISTICS:
   ( A ) LENGTH: 15 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:1344:

CGCGGCUUUU AUCUU                                                                                        15

( 2 ) INFORMATION FOR SEQ ID NO:1345:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1345:

GCGGCUUUUA UCUUC                                                                                        15

( 2 ) INFORMATION FOR SEQ ID NO:1346:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1346:

CGGCUUUUAU CUUCA                                                                                        15

( 2 ) INFORMATION FOR SEQ ID NO:1347:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1347:

GGCUUUUAUC UUCAC                                                                                        15

( 2 ) INFORMATION FOR SEQ ID NO:1348:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1348:

CUUUUAUCUU CACCU                                                                                        15

( 2 ) INFORMATION FOR SEQ ID NO:1349:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1349:

UUUAUCUUCA CCUUU                                                                                        15

( 2 ) INFORMATION FOR SEQ ID NO:1350:

( i ) SEQUENCE CHARACTERISTICS:
      ( A ) LENGTH: 15 base pairs ( B ) TYPE: nucleic acid
( C ) STRANDEDNESS: single
( D ) TOPOLOGY: linear ( x i ) SEQUENCE DESCRIPTION: SEQ ID NO:1350:

UUAUCUUCAC CUUUC 15

( 2 ) INFORMATION FOR SEQ ID NO:1351:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:1351:

UUCACCUUUC UCUAU 15

( 2 ) INFORMATION FOR SEQ ID NO:1352:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:1352:

UCACCUUUCU CUAUA 15

( 2 ) INFORMATION FOR SEQ ID NO:1353:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:1353:

CACCUUUCUC UAUAG 15

( 2 ) INFORMATION FOR SEQ ID NO:1354:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:1354:

CCUUUCUCUA UAGAG 15

( 2 ) INFORMATION FOR SEQ ID NO:1355:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:1355:

UUUCUCUAUA GAGCU 15

( 2 ) INFORMATION FOR SEQ ID NO:1356:

( i ) SEQUENCE CHARACTERISTICS:
( A ) LENGTH: 15 base pairs
( B ) TYPE: nucleic acid
( C ) STRANDEDNESS: single (D) TOPOLOGY: linear (xi) SEQUENCE DESCRIPTION: SEQ ID NO:1356:

UCUCUAUAGA GCUUG                                                                                            15

(2) INFORMATION FOR SEQ ID NO:1357:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:1357:

UAGAGCUUGA GGACC                                                                                            15

(2) INFORMATION FOR SEQ ID NO:1358:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:1358:

GGACCCUCAG CCUCC                                                                                            15

(2) INFORMATION FOR SEQ ID NO:1359:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:1359:

UCAGCCUCCC CCAGA                                                                                            15

(2) INFORMATION FOR SEQ ID NO:1360:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:1360:

ACCACAUUCC UUGGA                                                                                            15

(2) INFORMATION FOR SEQ ID NO:1361:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:1361:

CCACAUUCCU UGGAU                                                                                            15

(2) INFORMATION FOR SEQ ID NO:1362:

(i) SEQUENCE CHARACTERISTICS:
        (A) LENGTH: 15 base pairs
        (B) TYPE: nucleic acid
        (C) STRANDEDNESS: single
        (D) TOPOLOGY: linear ( x i ) SEQUENCE DESCRIPTION: SEQ ID NO:1362:

CAUUCCUUGG AUUAC 15

( 2 ) INFORMATION FOR SEQ ID NO:1363:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1363:

CUUGGAUUAC AGCUG 15

( 2 ) INFORMATION FOR SEQ ID NO:1364:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1364:

UUGGAUUACA GCUGU 15

( 2 ) INFORMATION FOR SEQ ID NO:1365:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1365:

CAGCUGUACU UCCAA 15

( 2 ) INFORMATION FOR SEQ ID NO:1366:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1366:

CUGUACUUCC AACAG 15

( 2 ) INFORMATION FOR SEQ ID NO:1367:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1367:

UGUACUUCCA ACAGU 15

( 2 ) INFORMATION FOR SEQ ID NO:1368:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1368:

CAACAGUUAU UAUAU                                                          15

(2) INFORMATION FOR SEQ ID NO:1369:

(i) SEQUENCE CHARACTERISTICS:
       (A) LENGTH: 15 base pairs
       (B) TYPE: nucleic acid
       (C) STRANDEDNESS: single
       (D) TOPOLOGY: linear (xi) SEQUENCE DESCRIPTION: SEQ ID NO:1369:

AACAGUUAUU AUAUG                                                          15

(2) INFORMATION FOR SEQ ID NO:1370:

(i) SEQUENCE CHARACTERISTICS:
       (A) LENGTH: 15 base pairs
       (B) TYPE: nucleic acid
       (C) STRANDEDNESS: single
       (D) TOPOLOGY: linear (xi) SEQUENCE DESCRIPTION: SEQ ID NO:1370:

CAGUUAUUAU AUGUG                                                          15

(2) INFORMATION FOR SEQ ID NO:1371:

(i) SEQUENCE CHARACTERISTICS:
       (A) LENGTH: 15 base pairs
       (B) TYPE: nucleic acid
       (C) STRANDEDNESS: single
       (D) TOPOLOGY: linear (xi) SEQUENCE DESCRIPTION: SEQ ID NO:1371:

AGUUAUUAUA UGUGU                                                          15

(2) INFORMATION FOR SEQ ID NO:1372:

(i) SEQUENCE CHARACTERISTICS:
       (A) LENGTH: 15 base pairs
       (B) TYPE: nucleic acid
       (C) STRANDEDNESS: single
       (D) TOPOLOGY: linear (xi) SEQUENCE DESCRIPTION: SEQ ID NO:1372:

UUAUUAUAUG UGUGA                                                          15

(2) INFORMATION FOR SEQ ID NO:1373:

(i) SEQUENCE CHARACTERISTICS:
       (A) LENGTH: 15 base pairs
       (B) TYPE: nucleic acid
       (C) STRANDEDNESS: single
       (D) TOPOLOGY: linear (xi) SEQUENCE DESCRIPTION: SEQ ID NO:1373:

UGAUGGUUUU CUGUC                                                          15

(2) INFORMATION FOR SEQ ID NO:1374:

(i) SEQUENCE CHARACTERISTICS:
       (A) LENGTH: 15 base pairs
       (B) TYPE: nucleic acid
       (C) STRANDEDNESS: single
       (D) TOPOLOGY: linear (xi) SEQUENCE DESCRIPTION: SEQ ID NO:1374:

GAUGGUUUUC UGUCU                                                          15

(2) INFORMATION FOR SEQ ID NO:1375:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:1375:

AUGGUUUUCU GUCUA 15

(2) INFORMATION FOR SEQ ID NO:1376:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:1376:

UGGUUUUCUG UCUAA 15

(2) INFORMATION FOR SEQ ID NO:1377:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:1377:

UUUCUGUCUA AUUCU 15

(2) INFORMATION FOR SEQ ID NO:1378:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:1378:

UCUGUCUAAU UCUAU 15

(2) INFORMATION FOR SEQ ID NO:1379:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:1379:

GUCUAAUUCU AUGGA 15

(2) INFORMATION FOR SEQ ID NO:1380:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:1380:

UCUAAUUCUA UGGAA 15

(2) INFORMATION FOR SEQ ID NO:1381:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1381:

UAAUUCUAUG GAAAU 15

( 2 ) INFORMATION FOR SEQ ID NO:1382:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1382:

GCGGCCUCGC AACUC 15

( 2 ) INFORMATION FOR SEQ ID NO:1383:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1383:

CGCAACUCUU AUAAA 15

( 2 ) INFORMATION FOR SEQ ID NO:1384:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1384:

CAACUCUUAU AAAUG 15

( 2 ) INFORMATION FOR SEQ ID NO:1385:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1385:

AACUCUUAUA AAUGU 15

( 2 ) INFORMATION FOR SEQ ID NO:1386:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1386:

CUCUUAUAAA UGUGG 15

( 2 ) INFORMATION FOR SEQ ID NO:1387:

( i ) SEQUENCE CHARACTERISTICS:

(A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO:1387:

AAAAAAUCCA UAUAC 15

(2) INFORMATION FOR SEQ ID NO:1388:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO:1388:

AAUCCAUAUA CCUGA 15

(2) INFORMATION FOR SEQ ID NO:1389:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO:1389:

UCCAUAUACC UGAAA 15

(2) INFORMATION FOR SEQ ID NO:1390:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO:1390:

GAAAGAUCUG AUGAA 15

(2) INFORMATION FOR SEQ ID NO:1391:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO:1391:

AGCGUGUUUU UAAAA 15

(2) INFORMATION FOR SEQ ID NO:1392:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO:1392:

GCGUGUUUUU AAAAG 15

(2) INFORMATION FOR SEQ ID NO:1393:

(i) SEQUENCE CHARACTERISTICS:
            (A) LENGTH: 15 base pairs
            (B) TYPE: nucleic acid (C) STRANDEDNESS: single
(D) TOPOLOGY: linear (xi) SEQUENCE DESCRIPTION: SEQ ID NO:1393:

CGUGUUUUUA AAAGU                                            15

(2) INFORMATION FOR SEQ ID NO:1394:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (xi) SEQUENCE DESCRIPTION: SEQ ID NO:1394:

GUGUUUUUAA AAGUU                                            15

(2) INFORMATION FOR SEQ ID NO:1395:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (xi) SEQUENCE DESCRIPTION: SEQ ID NO:1395:

UGUUUUUAAA AGUUC                                            15

(2) INFORMATION FOR SEQ ID NO:1396:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (xi) SEQUENCE DESCRIPTION: SEQ ID NO:1396:

UAAAAGUUCG AAGAC                                            15

(2) INFORMATION FOR SEQ ID NO:1397:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (xi) SEQUENCE DESCRIPTION: SEQ ID NO:1397:

AAAAGUUCGA AGACA                                            15

(2) INFORMATION FOR SEQ ID NO:1398:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (xi) SEQUENCE DESCRIPTION: SEQ ID NO:1398:

AAGACAUCUU CAUGC                                            15

(2) INFORMATION FOR SEQ ID NO:1399:

(i) SEQUENCE CHARACTERISTICS:
    (A) LENGTH: 15 base pairs
    (B) TYPE: nucleic acid
    (C) STRANDEDNESS: single
    (D) TOPOLOGY: linear ( x i ) SEQUENCE DESCRIPTION: SEQ ID NO:1399:

GACAUCUUCA UGCGA 15

( 2 ) INFORMATION FOR SEQ ID NO:1400:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1400:

ACAUCUUCAU GCGAC 15

( 2 ) INFORMATION FOR SEQ ID NO:1401:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1401:

AAGUGAUACA UGUUU 15

( 2 ) INFORMATION FOR SEQ ID NO:1402:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1402:

UACAUGUUUU UAAUU 15

( 2 ) INFORMATION FOR SEQ ID NO:1403:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1403:

ACAUGUUUUU AAUUA 15

( 2 ) INFORMATION FOR SEQ ID NO:1404:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1404:

CAUGUUUUUA AUUAA 15

( 2 ) INFORMATION FOR SEQ ID NO:1405:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1405:

AUGUUUUUAA UUAAA                                                                                  15

(2) INFORMATION FOR SEQ ID NO:1406:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:1406:

UGUUUUUAAU UAAAG                                                                                  15

(2) INFORMATION FOR SEQ ID NO:1407:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:1407:

UUUUAAUUAA AGAGU                                                                                  15

(2) INFORMATION FOR SEQ ID NO:1408:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:1408:

UUUAAUUAAA GAGUA                                                                                  15

(2) INFORMATION FOR SEQ ID NO:1409:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1409:

AGAAGCACUG AUGAGGCCGA AAGGCCGAAA GCUUUC                                                            36

(2) INFORMATION FOR SEQ ID NO:1410:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1410:

GAGAAGCCUG AUGAGGCCGA AAGGCCGAAA AGCUUU                                                            36

(2) INFORMATION FOR SEQ ID NO:1411:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1411:

AGCAGAGCUG AUGAGGCCGA AAGGCCGAAA GCAAAG                                                            36

( 2 ) INFORMATION FOR SEQ ID NO:1412:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1412:

CAGCAGACUG AUGAGGCCGA AAGGCCGAAA AGCAAA    36

( 2 ) INFORMATION FOR SEQ ID NO:1413:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1413:

AGCAGCACUG AUGAGGCCGA AAGGCCGAAA GAAGCA    36

( 2 ) INFORMATION FOR SEQ ID NO:1414:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1414:

UCCCUGUCUG AUGAGGCCGA AAGGCCGAAA CAGCAG    36

( 2 ) INFORMATION FOR SEQ ID NO:1415:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1415:

UCUGUGCCUG AUGAGGCCGA AAGGCCGAAA GUCCCU    36

( 2 ) INFORMATION FOR SEQ ID NO:1416:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1416:

UGGAAAUCUG AUGAGGCCGA AAGGCCGAAA CCCCAC    36

( 2 ) INFORMATION FOR SEQ ID NO:1417:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1417:

AUCUGGACUG AUGAGGCCGA AAGGCCGAAA UGACCC    36

( 2 ) INFORMATION FOR SEQ ID NO:1418:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1418:

UAUCUGGCUG AUGAGGCCGA AAGGCCGAAA AUGACC    36

( 2 ) INFORMATION FOR SEQ ID NO:1419:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1419:

AUAUCUGCUG AUGAGGCCGA AAGGCCGAAA AAUGAC    36

( 2 ) INFORMATION FOR SEQ ID NO:1420:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1420:

GACCUAACUG AUGAGGCCGA AAGGCCGAAA UCUGGA    36

( 2 ) INFORMATION FOR SEQ ID NO:1421:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1421:

GUGACCUCUG AUGAGGCCGA AAGGCCGAAA UAUCUG    36

( 2 ) INFORMATION FOR SEQ ID NO:1422:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1422:

UGUGACCCUG AUGAGGCCGA AAGGCCGAAA AUAUCU    36

( 2 ) INFORMATION FOR SEQ ID NO:1423:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1423:

CUGCUGUCUG AUGAGGCCGA AAGGCCGAAA CCUAAU    36

( 2 ) INFORMATION FOR SEQ ID NO:1424:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1424:

CACUGGGCUG AUGAGGCCGA AAGGCCGAAA UCCAUU 36

( 2 ) INFORMATION FOR SEQ ID NO:1425:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1425:

AGUCCCACUG AUGAGGCCGA AAGGCCGAAA GUGCAC 36

( 2 ) INFORMATION FOR SEQ ID NO:1426:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1426:

AGAAUGUCUG AUGAGGCCGA AAGGCCGAAA CUCAGU 36

( 2 ) INFORMATION FOR SEQ ID NO:1427:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1427:

CAAAGAGCUG AUGAGGCCGA AAGGCCGAAA UGUUAC 36

( 2 ) INFORMATION FOR SEQ ID NO:1428:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1428:

ACAAAGACUG AUGAGGCCGA AAGGCCGAAA AUGUUA 36

( 2 ) INFORMATION FOR SEQ ID NO:1429:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1429:

UCACAAACUG AUGAGGCCGA AAGGCCGAAA GAAUGU 36

( 2 ) INFORMATION FOR SEQ ID NO:1430:

( i ) SEQUENCE CHARACTERISTICS:
        ( A ) LENGTH: 36 base pairs ( B ) TYPE: nucleic acid
        ( C ) STRANDEDNESS: single
        ( D ) TOPOLOGY: linear ( x i ) SEQUENCE DESCRIPTION: SEQ ID NO:1430:

CAUCACACUG AUGAGGCCGA AAGGCCGAAA GAGAAU 36

( 2 ) INFORMATION FOR SEQ ID NO:1431:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1431:

CCAUCACCUG AUGAGGCCGA AAGGCCGAAA AGAGAA 36

( 2 ) INFORMATION FOR SEQ ID NO:1432:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1432:

GAGCAGGCUG AUGAGGCCGA AAGGCCGAAA GGCCAU 36

( 2 ) INFORMATION FOR SEQ ID NO:1433:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1433:

AGAGCAGCUG AUGAGGCCGA AAGGCCGAAA AGGCCA 36

( 2 ) INFORMATION FOR SEQ ID NO:1434:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1434:

CACCAGACUG AUGAGGCCGA AAGGCCGAAA GCAGGA 36

( 2 ) INFORMATION FOR SEQ ID NO:1435:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1435:

AGCACCACUG AUGAGGCCGA AAGGCCGAAA GAGCAG 36

( 2 ) INFORMATION FOR SEQ ID NO:1436:

( i ) SEQUENCE CHARACTERISTICS:
        ( A ) LENGTH: 36 base pairs
        ( B ) TYPE: nucleic acid
        ( C ) STRANDEDNESS: single (D) TOPOLOGY: linear (xi) SEQUENCE DESCRIPTION: SEQ ID NO:1436:

UUCAGAGCUG AUGAGGCCGA AAGGCCGAAA GCAGCA 36

(2) INFORMATION FOR SEQ ID NO:1437:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1437:

AUCUUCACUG AUGAGGCCGA AAGGCCGAAA GGAGCA 36

(2) INFORMATION FOR SEQ ID NO:1438:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1438:

AAGCUUGCUG AUGAGGCCGA AAGGCCGAAA UCUUCA 36

(2) INFORMATION FOR SEQ ID NO:1439:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1439:

UAAGCUUCUG AUGAGGCCGA AAGGCCGAAA AUCUUC 36

(2) INFORMATION FOR SEQ ID NO:1440:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1440:

UUGAAAUCUG AUGAGGCCGA AAGGCCGAAA GCUUGA 36

(2) INFORMATION FOR SEQ ID NO:1441:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1441:

AUUGAAACUG AUGAGGCCGA AAGGCCGAAA AGCUUG 36

(2) INFORMATION FOR SEQ ID NO:1442:

(i) SEQUENCE CHARACTERISTICS:
        (A) LENGTH: 36 base pairs
        (B) TYPE: nucleic acid
        (C) STRANDEDNESS: single
        (D) TOPOLOGY: linear ( x i ) SEQUENCE DESCRIPTION: SEQ ID NO:1442:

UCAUUGACUG AUGAGGCCGA AAGGCCGAAA UAAGCU  36

( 2 ) INFORMATION FOR SEQ ID NO:1443:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1443:

CUCAUUGCUG AUGAGGCCGA AAGGCCGAAA AUAAGC  36

( 2 ) INFORMATION FOR SEQ ID NO:1444:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1444:

UCUCAUUCUG AUGAGGCCGA AAGGCCGAAA AAUAAG  36

( 2 ) INFORMATION FOR SEQ ID NO:1445:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1445:

GUUUGCACUG AUGAGGCCGA AAGGCCGAAA UUGGCA  36

( 2 ) INFORMATION FOR SEQ ID NO:1446:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1446:

AGUUUGCCUG AUGAGGCCGA AAGGCCGAAA AUUGGC  36

( 2 ) INFORMATION FOR SEQ ID NO:1447:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1447:

GUUUUGACUG AUGAGGCCGA AAGGCCGAAA GUUUGC  36

( 2 ) INFORMATION FOR SEQ ID NO:1448:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1448:

UGGUUUUCUG AUGAGGCCGA AAGGCCGAAA GAGUUU                      36

( 2 ) INFORMATION FOR SEQ ID NO:1449:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1449:

AUACUACCUG AUGAGGCCGA AAGGCCGAAA GCUCAC                      36

( 2 ) INFORMATION FOR SEQ ID NO:1450:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1450:

AAAAUACCUG AUGAGGCCGA AAGGCCGAAA CUAGCU                      36

( 2 ) INFORMATION FOR SEQ ID NO:1451:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1451:

GCCAAAACUG AUGAGGCCGA AAGGCCGAAA CUACUA                      36

( 2 ) INFORMATION FOR SEQ ID NO:1452:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1452:

CUGCCAACUG AUGAGGCCGA AAGGCCGAAA UACUAC                      36

( 2 ) INFORMATION FOR SEQ ID NO:1453:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1453:

CCUGCCACUG AUGAGGCCGA AAGGCCGAAA AUACUA                      36

( 2 ) INFORMATION FOR SEQ ID NO:1454:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1454:

UCCUGCCCUG AUGAGGCCGA AAGGCCGAAA AAUACU                      36

( 2 ) INFORMATION FOR SEQ ID NO:1455:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1455:

CAGAACCCUG AUGAGGCCGA AAGGCCGAAA GUUUUC    36

( 2 ) INFORMATION FOR SEQ ID NO:1456:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1456:

CAUUCAGCUG AUGAGGCCGA AAGGCCGAAA CCAAGU    36

( 2 ) INFORMATION FOR SEQ ID NO:1457:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1457:

UCAUUCACUG AUGAGGCCGA AAGGCCGAAA ACCAAG    36

( 2 ) INFORMATION FOR SEQ ID NO:1458:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1458:

CUAAGUACUG AUGAGGCCGA AAGGCCGAAA CCUCAU    36

( 2 ) INFORMATION FOR SEQ ID NO:1459:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1459:

GCCUAAGCUG AUGAGGCCGA AAGGCCGAAA UACCUC    36

( 2 ) INFORMATION FOR SEQ ID NO:1460:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1460:

UUUGCCUCUG AUGAGGCCGA AAGGCCGAAA GUAUAC    36

( 2 ) INFORMATION FOR SEQ ID NO:1461:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1461:

CUUUGCCCUG AUGAGGCCGA AAGGCCGAAA AGUAUA 36

( 2 ) INFORMATION FOR SEQ ID NO:1462:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1462:

ACUGUCACUG AUGAGGCCGA AAGGCCGAAA UUUCUC 36

( 2 ) INFORMATION FOR SEQ ID NO:1463:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1463:

CACUGUCCUG AUGAGGCCGA AAGGCCGAAA AUUUCU 36

( 2 ) INFORMATION FOR SEQ ID NO:1464:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1464:

UGGAAUGCUG AUGAGGCCGA AAGGCCGAAA CACUGU 36

( 2 ) INFORMATION FOR SEQ ID NO:1465:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1465:

UUGGAAUCUG AUGAGGCCGA AAGGCCGAAA ACACUG 36

( 2 ) INFORMATION FOR SEQ ID NO:1466:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1466:

UACUUGGCUG AUGAGGCCGA AAGGCCGAAA UGAACA 36

( 2 ) INFORMATION FOR SEQ ID NO:1467:

( i ) SEQUENCE CHARACTERISTICS:

(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:1467:

AUACUUGCUG AUGAGGCCGA AAGGCCGAAA AUGAAC    36

(2) INFORMATION FOR SEQ ID NO:1468:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:1468:

GCCCAUACUG AUGAGGCCGA AAGGCCGAAA CUUGGA    36

(2) INFORMATION FOR SEQ ID NO:1469:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:1469:

CGGCCCACUG AUGAGGCCGA AAGGCCGAAA UACUUG    36

(2) INFORMATION FOR SEQ ID NO:1470:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:1470:

GAAUCAACUG AUGAGGCCGA AAGGCCGAAA CUUGUG    36

(2) INFORMATION FOR SEQ ID NO:1471:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:1471:

CGAAUCACUG AUGAGGCCGA AAGGCCGAAA ACUUGU    36

(2) INFORMATION FOR SEQ ID NO:1472:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:1472:

CCGAAUCCUG AUGAGGCCGA AAGGCCGAAA AACUUG    36

(2) INFORMATION FOR SEQ ID NO:1473:

(i) SEQUENCE CHARACTERISTICS:
(A) LENGTH: 36 base pairs
(B) TYPE: nucleic acid ( C ) STRANDEDNESS: single
( D ) TOPOLOGY: linear ( x i ) SEQUENCE DESCRIPTION: SEQ ID NO:1473:

CUGUCCGCUG AUGAGGCCGA AAGGCCGAAA UCAAAA 36

( 2 ) INFORMATION FOR SEQ ID NO:1474:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1474:

ACUGUCCCUG AUGAGGCCGA AAGGCCGAAA AUCAAA 36

( 2 ) INFORMATION FOR SEQ ID NO:1475:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1475:

AGGGUCCCUG AUGAGGCCGA AAGGCCGAAA CUGUCC 36

( 2 ) INFORMATION FOR SEQ ID NO:1476:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1476:

GAUUGUGCUG AUGAGGCCGA AAGGCCGAAA GUCUCA 36

( 2 ) INFORMATION FOR SEQ ID NO:1477:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1477:

AGAUUGUCUG AUGAGGCCGA AAGGCCGAAA AGUCUC 36

( 2 ) INFORMATION FOR SEQ ID NO:1478:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1478:

AUCUGAACUG AUGAGGCCGA AAGGCCGAAA UUGUGA 36

( 2 ) INFORMATION FOR SEQ ID NO:1479:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1479:

UGAUCUGCUG AUGAGGCCGA AAGGCCGAAA GAUUGU                     36

( 2 ) INFORMATION FOR SEQ ID NO:1480:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1480:

UUGAUCUCUG AUGAGGCCGA AAGGCCGAAA AGAUUG                     36

( 2 ) INFORMATION FOR SEQ ID NO:1481:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1481:

UGUCCUUCUG AUGAGGCCGA AAGGCCGAAA UCUGAA                     36

( 2 ) INFORMATION FOR SEQ ID NO:1482:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1482:

UUGAUACCUG AUGAGGCCGA AAGGCCGAAA GCCCUU                     36

( 2 ) INFORMATION FOR SEQ ID NO:1483:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1483:

ACAUUGACUG AUGAGGCCGA AAGGCCGAAA CAAGCC                     36

( 2 ) INFORMATION FOR SEQ ID NO:1484:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1484:

AUACAUUCUG AUGAGGCCGA AAGGCCGAAA UACAAG                     36

( 2 ) INFORMATION FOR SEQ ID NO:1485:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1485:

UGGAUGACUG AUGAGGCCGA AAGGCCGAAA CAUUGA 36

(2) INFORMATION FOR SEQ ID NO:1486:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1486:

GAUGGAUCUG AUGAGGCCGA AAGGCCGAAA UACAUU 36

(2) INFORMATION FOR SEQ ID NO:1487:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1487:

UGUGAUGCUG AUGAGGCCGA AAGGCCGAAA UGAUAC 36

(2) INFORMATION FOR SEQ ID NO:1488:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1488:

UUUUUGUCUG AUGAGGCCGA AAGGCCGAAA UGGAUG 36

(2) INFORMATION FOR SEQ ID NO:1489:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1489:

GGAUGCGCUG AUGAGGCCGA AAGGCCGAAA UCAUUC 36

(2) INFORMATION FOR SEQ ID NO:1490:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1490:

UGGAUGCCUG AUGAGGCCGA AAGGCCGAAA AUCAUU 36

(2) INFORMATION FOR SEQ ID NO:1491:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1491:

UCUGGUGCUG AUGAGGCCGA AAGGCCGAAA UGCGAA 36

( 2 ) INFORMATION FOR SEQ ID NO:1492:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1492:

AGUUCAGCUG AUGAGGCCGA AAGGCCGAAA UUCAUC　　　　　　　　　　　36

( 2 ) INFORMATION FOR SEQ ID NO:1493:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1493:

CAGUUCACUG AUGAGGCCGA AAGGCCGAAA AUUCAU　　　　　　　　　　　36

( 2 ) INFORMATION FOR SEQ ID NO:1494:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1494:

AAGCACUCUG AUGAGGCCGA AAGGCCGAAA CAGUUC　　　　　　　　　　　36

( 2 ) INFORMATION FOR SEQ ID NO:1495:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1495:

AGUUAGCCUG AUGAGGCCGA AAGGCCGAAA GCACUG　　　　　　　　　　　36

( 2 ) INFORMATION FOR SEQ ID NO:1496:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1496:

CUGAAGUCUG AUGAGGCCGA AAGGCCGAAA GCAAGC　　　　　　　　　　　36

( 2 ) INFORMATION FOR SEQ ID NO:1497:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1497:

UUGACUGCUG AUGAGGCCGA AAGGCCGAAA GUUAGC　　　　　　　　　　　36

( 2 ) INFORMATION FOR SEQ ID NO:1498:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1498:

GUUGACUCUG AUGAGGCCGA AAGGCCGAAA AGUUAG    36

( 2 ) INFORMATION FOR SEQ ID NO:1499:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1499:

UCAGGUUCUG AUGAGGCCGA AAGGCCGAAA CUGAAG    36

( 2 ) INFORMATION FOR SEQ ID NO:1500:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1500:

UUGGUACCUG AUGAGGCCGA AAGGCCGAAA UUUCAG    36

( 2 ) INFORMATION FOR SEQ ID NO:1501:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1501:

AAAUUGGCUG AUGAGGCCGA AAGGCCGAAA CUAUUU    36

( 2 ) INFORMATION FOR SEQ ID NO:1502:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1502:

UAUUAGACUG AUGAGGCCGA AAGGCCGAAA UUGGUA    36

( 2 ) INFORMATION FOR SEQ ID NO:1503:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1503:

AUAUUAGCUG AUGAGGCCGA AAGGCCGAAA AUUGGU    36

( 2 ) INFORMATION FOR SEQ ID NO:1504:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1504:

UAUAUUACUG AUGAGGCCGA AAGGCCGAAA AAUUGG    36

( 2 ) INFORMATION FOR SEQ ID NO:1505:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1505:

GUUAUAUCUG AUGAGGCCGA AAGGCCGAAA GAAAUU    36

( 2 ) INFORMATION FOR SEQ ID NO:1506:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1506:

UCUGUUACUG AUGAGGCCGA AAGGCCGAAA UUAGAA    36

( 2 ) INFORMATION FOR SEQ ID NO:1507:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1507:

UUUCUGUCUG AUGAGGCCGA AAGGCCGAAA UAUUAG    36

( 2 ) INFORMATION FOR SEQ ID NO:1508:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1508:

AUUUAUGCUG AUGAGGCCGA AAGGCCGAAA CACAUU    36

( 2 ) INFORMATION FOR SEQ ID NO:1509:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1509:

UCAAAUUCUG AUGAGGCCGA AAGGCCGAAA UGUACA    36

( 2 ) INFORMATION FOR SEQ ID NO:1510:

( i ) SEQUENCE CHARACTERISTICS:
    ( A ) LENGTH: 36 base pairs (B) TYPE: nucleic acid
(C) STRANDEDNESS: single
(D) TOPOLOGY: linear (xi) SEQUENCE DESCRIPTION: SEQ ID NO:1510:

CAGGUCACUG AUGAGGCCGA AAGGCCGAAA UUUAUG 36

(2) INFORMATION FOR SEQ ID NO:1511:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:1511:

GCAGGUCCUG AUGAGGCCGA AAGGCCGAAA AUUUAU 36

(2) INFORMATION FOR SEQ ID NO:1512:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:1512:

UAUAGAUCUG AUGAGGCCGA AAGGCCGAAA GCAGGU 36

(2) INFORMATION FOR SEQ ID NO:1513:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:1513:

GUGUAUACUG AUGAGGCCGA AAGGCCGAAA UGAGCA 36

(2) INFORMATION FOR SEQ ID NO:1514:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:1514:

CCGUGUACUG AUGAGGCCGA AAGGCCGAAA GAUGAG 36

(2) INFORMATION FOR SEQ ID NO:1515:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:1515:

AACCGUGCUG AUGAGGCCGA AAGGCCGAAA UAGAUG 36

(2) INFORMATION FOR SEQ ID NO:1516:

(i) SEQUENCE CHARACTERISTICS:
(A) LENGTH: 36 base pairs
(B) TYPE: nucleic acid
(C) STRANDEDNESS: single ( D ) TOPOLOGY: linear ( x i ) SEQUENCE DESCRIPTION: SEQ ID NO:1516:

UCUGGGUCUG AUGAGGCCGA AAGGCCGAAA CCGUGU  36

( 2 ) INFORMATION FOR SEQ ID NO:1517:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1517:

UUCUGGGCUG AUGAGGCCGA AAGGCCGAAA ACCGUG  36

( 2 ) INFORMATION FOR SEQ ID NO:1518:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1518:

AUCUUCUCUG AUGAGGCCGA AAGGCCGAAA GGUUCU  36

( 2 ) INFORMATION FOR SEQ ID NO:1519:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1519:

UUAGCAACUG AUGAGGCCGA AAGGCCGAAA CACUCA  36

( 2 ) INFORMATION FOR SEQ ID NO:1520:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1520:

CUUAGCACUG AUGAGGCCGA AAGGCCGAAA ACACUC  36

( 2 ) INFORMATION FOR SEQ ID NO:1521:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1521:

UCUUAGCCUG AUGAGGCCGA AAGGCCGAAA AACACU  36

( 2 ) INFORMATION FOR SEQ ID NO:1522:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1522:

UGGUUCUCUG AUGAGGCCGA AAGGCCGAAA GCAAAA  36

( 2 ) INFORMATION FOR SEQ ID NO:1523:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1523:

AUAGUUGCUG AUGAGGCCGA AAGGCCGAAA UUCUUG  36

( 2 ) INFORMATION FOR SEQ ID NO:1524:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1524:

GAUAGUUCUG AUGAGGCCGA AAGGCCGAAA AUUCUU  36

( 2 ) INFORMATION FOR SEQ ID NO:1525:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1525:

UACUCGACUG AUGAGGCCGA AAGGCCGAAA GUUGAA  36

( 2 ) INFORMATION FOR SEQ ID NO:1526:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1526:

CAUACUCCUG AUGAGGCCGA AAGGCCGAAA UAGUUG  36

( 2 ) INFORMATION FOR SEQ ID NO:1527:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1527:

ACCAUCACUG AUGAGGCCGA AAGGCCGAAA CUCGAU  36

( 2 ) INFORMATION FOR SEQ ID NO:1528:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1528:

UGCAUAACUG AUGAGGCCGA AAGGCCGAAA CCAUCA 36

( 2 ) INFORMATION FOR SEQ ID NO:1529:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1529:

UCUGCAUCUG AUGAGGCCGA AAGGCCGAAA UACCAU 36

( 2 ) INFORMATION FOR SEQ ID NO:1530:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1530:

UUCUGCACUG AUGAGGCCGA AAGGCCGAAA AUACCA 36

( 2 ) INFORMATION FOR SEQ ID NO:1531:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1531:

AUCUUGACUG AUGAGGCCGA AAGGCCGAAA UUUCUG 36

( 2 ) INFORMATION FOR SEQ ID NO:1532:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1532:

UUAUCUUCUG AUGAGGCCGA AAGGCCGAAA GAUUUC 36

( 2 ) INFORMATION FOR SEQ ID NO:1533:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1533:

GUGACAUCUG AUGAGGCCGA AAGGCCGAAA UCUUGA 36

( 2 ) INFORMATION FOR SEQ ID NO:1534:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1534:

GUUCUGUCUG AUGAGGCCGA AAGGCCGAAA CAUUAU 36

( 2 ) INFORMATION FOR SEQ ID NO:1535:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1535:

AACGUCGCUG AUGAGGCCGA AAGGCCGAAA CAGUUC    36

( 2 ) INFORMATION FOR SEQ ID NO:1536:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1536:

UGAUGGACUG AUGAGGCCGA AAGGCCGAAA CGUCGU    36

( 2 ) INFORMATION FOR SEQ ID NO:1537:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1537:

CUGAUGGCUG AUGAGGCCGA AAGGCCGAAA ACGUCG    36

( 2 ) INFORMATION FOR SEQ ID NO:1538:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1538:

GCUGAUGCUG AUGAGGCCGA AAGGCCGAAA AACGUC    36

( 2 ) INFORMATION FOR SEQ ID NO:1539:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1539:

ACAAGCUCUG AUGAGGCCGA AAGGCCGAAA UGGAAA    36

( 2 ) INFORMATION FOR SEQ ID NO:1540:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1540:

AACAGACCUG AUGAGGCCGA AAGGCCGAAA GCUGAU    36

( 2 ) INFORMATION FOR SEQ ID NO:1541:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1541:

UGAAACACUG AUGAGGCCGA AAGGCCGAAA CAAGCU 36

( 2 ) INFORMATION FOR SEQ ID NO:1542:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1542:

GGAAUGACUG AUGAGGCCGA AAGGCCGAAA CAGACA 36

( 2 ) INFORMATION FOR SEQ ID NO:1543:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1543:

GGGAAUGCUG AUGAGGCCGA AAGGCCGAAA ACAGAC 36

( 2 ) INFORMATION FOR SEQ ID NO:1544:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1544:

AGGGAAUCUG AUGAGGCCGA AAGGCCGAAA AACAGA 36

( 2 ) INFORMATION FOR SEQ ID NO:1545:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1545:

AUCAGGGCUG AUGAGGCCGA AAGGCCGAAA UGAAAC 36

( 2 ) INFORMATION FOR SEQ ID NO:1546:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1546:

CAUCAGGCUG AUGAGGCCGA AAGGCCGAAA AUGAAA 36

( 2 ) INFORMATION FOR SEQ ID NO:1547:

( i ) SEQUENCE CHARACTERISTICS:

(A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1547:

UGCUCGUCUG AUGAGGCCGA AAGGCCGAAA CAUCAG 36

(2) INFORMATION FOR SEQ ID NO:1548:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1548:

UUGCUCGCUG AUGAGGCCGA AAGGCCGAAA ACAUCA 36

(2) INFORMATION FOR SEQ ID NO:1549:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1549:

AUGGUCACUG AUGAGGCCGA AAGGCCGAAA UUGCUC 36

(2) INFORMATION FOR SEQ ID NO:1550:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1550:

UACAGAACUG AUGAGGCCGA AAGGCCGAAA UGGUCA 36

(2) INFORMATION FOR SEQ ID NO:1551:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1551:

AAUACAGCUG AUGAGGCCGA AAGGCCGAAA GAUGGU 36

(2) INFORMATION FOR SEQ ID NO:1552:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1552:

GAAUACACUG AUGAGGCCGA AAGGCCGAAA AGAUGG 36

(2) INFORMATION FOR SEQ ID NO:1553:

(i) SEQUENCE CHARACTERISTICS:
        (A) LENGTH: 36 base pairs
        (B) TYPE: nucleic acid (C) STRANDEDNESS: single
(D) TOPOLOGY: linear (xi) SEQUENCE DESCRIPTION: SEQ ID NO:1553:

UCCAGAACUG AUGAGGCCGA AAGGCCGAAA CAGAAG 36

(2) INFORMATION FOR SEQ ID NO:1554:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:1554:

UUUCCAGCUG AUGAGGCCGA AAGGCCGAAA UACAGA 36

(2) INFORMATION FOR SEQ ID NO:1555:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:1555:

GUUUCCACUG AUGAGGCCGA AAGGCCGAAA AUACAG 36

(2) INFORMATION FOR SEQ ID NO:1556:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:1556:

AAGAUAACUG AUGAGGCCGA AAGGCCGAAA GCCGCG 36

(2) INFORMATION FOR SEQ ID NO:1557:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:1557:

GAAGAUACUG AUGAGGCCGA AAGGCCGAAA AGCCGC 36

(2) INFORMATION FOR SEQ ID NO:1558:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:1558:

UGAAGAUCUG AUGAGGCCGA AAGGCCGAAA AAGCCG 36

(2) INFORMATION FOR SEQ ID NO:1559:

(i) SEQUENCE CHARACTERISTICS:
(A) LENGTH: 36 base pairs
(B) TYPE: nucleic acid
(C) STRANDEDNESS: single
(D) TOPOLOGY: linear ( x i ) SEQUENCE DESCRIPTION: SEQ ID NO:1559:

GUGAAGACUG AUGAGGCCGA AAGGCCGAAA AAAGCC    36

( 2 ) INFORMATION FOR SEQ ID NO:1560:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1560:

AGGUGAACUG AUGAGGCCGA AAGGCCGAAA UAAAAG    36

( 2 ) INFORMATION FOR SEQ ID NO:1561:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1561:

AAAGGUGCUG AUGAGGCCGA AAGGCCGAAA GAUAAA    36

( 2 ) INFORMATION FOR SEQ ID NO:1562:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1562:

GAAAGGUCUG AUGAGGCCGA AAGGCCGAAA AGAUAA    36

( 2 ) INFORMATION FOR SEQ ID NO:1563:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1563:

AUAGAGACUG AUGAGGCCGA AAGGCCGAAA GGUGAA    36

( 2 ) INFORMATION FOR SEQ ID NO:1564:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1564:

UAUAGAGCUG AUGAGGCCGA AAGGCCGAAA AGGUGA    36

( 2 ) INFORMATION FOR SEQ ID NO:1565:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1565:

CUAUAGACUG AUGAGGCCGA AAGGCCGAAA AAGGUG 36

( 2 ) INFORMATION FOR SEQ ID NO:1566:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1566:

CUCUAUACUG AUGAGGCCGA AAGGCCGAAA GAAAGG 36

( 2 ) INFORMATION FOR SEQ ID NO:1567:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1567:

AGCUCUACUG AUGAGGCCGA AAGGCCGAAA GAGAAA 36

( 2 ) INFORMATION FOR SEQ ID NO:1568:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1568:

CAAGCUCCUG AUGAGGCCGA AAGGCCGAAA UAGAGA 36

( 2 ) INFORMATION FOR SEQ ID NO:1569:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1569:

GGUCCUCCUG AUGAGGCCGA AAGGCCGAAA GCUCUA 36

( 2 ) INFORMATION FOR SEQ ID NO:1570:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1570:

GGAGGCUCUG AUGAGGCCGA AAGGCCGAAA GGGUCC 36

( 2 ) INFORMATION FOR SEQ ID NO:1571:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1571:

UCUGGGGCUG AUGAGGCCGA AAGGCCGAAA GGCUGA 36

( 2 ) INFORMATION FOR SEQ ID NO:1572:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1572:

UCCAAGCUG AUGAGGCCGA AAGGCCGAAA UGUGGU     36

( 2 ) INFORMATION FOR SEQ ID NO:1573:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1573:

AUCCAAGCUG AUGAGGCCGA AAGGCCGAAA AUGUGG     36

( 2 ) INFORMATION FOR SEQ ID NO:1574:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1574:

GUAAUCCCUG AUGAGGCCGA AAGGCCGAAA GGAAUG     36

( 2 ) INFORMATION FOR SEQ ID NO:1575:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1575:

CAGCUGUCUG AUGAGGCCGA AAGGCCGAAA UCCAAG     36

( 2 ) INFORMATION FOR SEQ ID NO:1576:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1576:

ACAGCUGCUG AUGAGGCCGA AAGGCCGAAA AUCCAA     36

( 2 ) INFORMATION FOR SEQ ID NO:1577:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1577:

UUGGAAGCUG AUGAGGCCGA AAGGCCGAAA CAGCUG     36

( 2 ) INFORMATION FOR SEQ ID NO:1578:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1578:

CUGUUGGCUG AUGAGGCCGA AAGGCCGAAA GUACAG      36

( 2 ) INFORMATION FOR SEQ ID NO:1579:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1579:

ACUGUUGCUG AUGAGGCCGA AAGGCCGAAA AGUACA      36

( 2 ) INFORMATION FOR SEQ ID NO:1580:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1580:

AUAUAAUCUG AUGAGGCCGA AAGGCCGAAA CUGUUG      36

( 2 ) INFORMATION FOR SEQ ID NO:1581:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1581:

CAUAUAACUG AUGAGGCCGA AAGGCCGAAA ACUGUU      36

( 2 ) INFORMATION FOR SEQ ID NO:1582:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1582:

CACAUAUCUG AUGAGGCCGA AAGGCCGAAA UAACUG      36

( 2 ) INFORMATION FOR SEQ ID NO:1583:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1583:

ACACAUACUG AUGAGGCCGA AAGGCCGAAA AUAACU      36

( 2 ) INFORMATION FOR SEQ ID NO:1584:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1584:

UCACACACUG AUGAGGCCGA AAGGCCGAAA UAAUAA      36

( 2 ) INFORMATION FOR SEQ ID NO:1585:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1585:

GACAGAACUG AUGAGGCCGA AAGGCCGAAA CCAUCA      36

( 2 ) INFORMATION FOR SEQ ID NO:1586:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1586:

AGACAGACUG AUGAGGCCGA AAGGCCGAAA ACCAUC      36

( 2 ) INFORMATION FOR SEQ ID NO:1587:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1587:

UAGACAGCUG AUGAGGCCGA AAGGCCGAAA AACCAU      36

( 2 ) INFORMATION FOR SEQ ID NO:1588:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1588:

UUAGACACUG AUGAGGCCGA AAGGCCGAAA AAACCA      36

( 2 ) INFORMATION FOR SEQ ID NO:1589:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1589:

AGAAUUACUG AUGAGGCCGA AAGGCCGAAA CAGAAA      36

( 2 ) INFORMATION FOR SEQ ID NO:1590:

( i ) SEQUENCE CHARACTERISTICS:
        ( A ) LENGTH: 36 base pairs (B) TYPE: nucleic acid
(C) STRANDEDNESS: single
(D) TOPOLOGY: linear (xi) SEQUENCE DESCRIPTION: SEQ ID NO:1590:

AUAGAAUCUG AUGAGGCCGA AAGGCCGAAA GACAGA 36

(2) INFORMATION FOR SEQ ID NO:1591:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:1591:

UCCAUAGCUG AUGAGGCCGA AAGGCCGAAA UUAGAC 36

(2) INFORMATION FOR SEQ ID NO:1592:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:1592:

UUCCAUACUG AUGAGGCCGA AAGGCCGAAA AUUAGA 36

(2) INFORMATION FOR SEQ ID NO:1593:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:1593:

AUUCCACUG AUGAGGCCGA AAGGCCGAAA GAAUUA 36

(2) INFORMATION FOR SEQ ID NO:1594:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:1594:

GAGUUGCCUG AUGAGGCCGA AAGGCCGAAA GGCCGC 36

(2) INFORMATION FOR SEQ ID NO:1595:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:1595:

UUUAUAACUG AUGAGGCCGA AAGGCCGAAA GUUGCG 36

(2) INFORMATION FOR SEQ ID NO:1596:

(i) SEQUENCE CHARACTERISTICS:
(A) LENGTH: 36 base pairs
(B) TYPE: nucleic acid
(C) STRANDEDNESS: single (D) TOPOLOGY: linear (xi) SEQUENCE DESCRIPTION: SEQ ID NO:1596:

CAUUUAUCUG AUGAGGCCGA AAGGCCGAAA GAGUUG 36

(2) INFORMATION FOR SEQ ID NO:1597:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1597:

ACAUUUACUG AUGAGGCCGA AAGGCCGAAA AGAGUU 36

(2) INFORMATION FOR SEQ ID NO:1598:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1598:

CCACAUUCUG AUGAGGCCGA AAGGCCGAAA UAAGAG 36

(2) INFORMATION FOR SEQ ID NO:1599:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1599:

GUAUAUGCUG AUGAGGCCGA AAGGCCGAAA UUUUUU 36

(2) INFORMATION FOR SEQ ID NO:1600:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1600:

UCAGGUACUG AUGAGGCCGA AAGGCCGAAA UGGAUU 36

(2) INFORMATION FOR SEQ ID NO:1601:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1601:

UUUCAGGCUG AUGAGGCCGA AAGGCCGAAA UAUGGA 36

(2) INFORMATION FOR SEQ ID NO:1602:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:1602:

UUCAUCACUG AUGAGGCCGA AAGGCCGAAA UCUUUC 36

(2) INFORMATION FOR SEQ ID NO:1603:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:1603:

UUUUAAACUG AUGAGGCCGA AAGGCCGAAA CACGCU 36

(2) INFORMATION FOR SEQ ID NO:1604:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:1604:

CUUUUAACUG AUGAGGCCGA AAGGCCGAAA ACACGC 36

(2) INFORMATION FOR SEQ ID NO:1605:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:1605:

ACUUUUACUG AUGAGGCCGA AAGGCCGAAA AACACG 36

(2) INFORMATION FOR SEQ ID NO:1606:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:1606:

AACUUUUCUG AUGAGGCCGA AAGGCCGAAA AAACAC 36

(2) INFORMATION FOR SEQ ID NO:1607:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:1607:

GAACUUUCUG AUGAGGCCGA AAGGCCGAAA AAAACA 36

(2) INFORMATION FOR SEQ ID NO:1608:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:1608:

GUCUUCGCUG AUGAGGCCGA AAGGCCGAAA CUUUUA 36

(2) INFORMATION FOR SEQ ID NO:1609:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1609:

UGUCUUCCUG AUGAGGCCGA AAGGCCGAAA ACUUUU 36

(2) INFORMATION FOR SEQ ID NO:1610:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1610:

GCAUGAACUG AUGAGGCCGA AAGGCCGAAA UGUCUU 36

(2) INFORMATION FOR SEQ ID NO:1611:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1611:

UCGCAUGCUG AUGAGGCCGA AAGGCCGAAA GAUGUC 36

(2) INFORMATION FOR SEQ ID NO:1612:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1612:

GUCGCAUCUG AUGAGGCCGA AAGGCCGAAA AGAUGU 36

(2) INFORMATION FOR SEQ ID NO:1613:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1613:

AAACAUGCUG AUGAGGCCGA AAGGCCGAAA UCACUU 36

(2) INFORMATION FOR SEQ ID NO:1614:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1614:

AAUUAAACUG AUGAGGCCGA AAGGCCGAAA CAUGUA 36

( 2 ) INFORMATION FOR SEQ ID NO:1615:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1615:

UAAUUAACUG AUGAGGCCGA AAGGCCGAAA ACAUGU        36

( 2 ) INFORMATION FOR SEQ ID NO:1616:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1616:

UUAAUUACUG AUGAGGCCGA AAGGCCGAAA AACAUG        36

( 2 ) INFORMATION FOR SEQ ID NO:1617:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1617:

UUUAAUUCUG AUGAGGCCGA AAGGCCGAAA AAACAU        36

( 2 ) INFORMATION FOR SEQ ID NO:1618:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1618:

CUUUAAUCUG AUGAGGCCGA AAGGCCGAAA AAAACA        36

( 2 ) INFORMATION FOR SEQ ID NO:1619:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1619:

ACUCUUUCUG AUGAGGCCGA AAGGCCGAAA UUAAAA        36

( 2 ) INFORMATION FOR SEQ ID NO:1620:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1620:

UACUCUUCUG AUGAGGCCGA AAGGCCGAAA AUUAAA        36

( 2 ) INFORMATION FOR SEQ ID NO:1621:

( i ) SEQUENCE CHARACTERISTICS:
 ( A ) LENGTH: 15 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:1621:

ACGGACUUGA ACAAC   15

( 2 ) INFORMATION FOR SEQ ID NO:1622:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1622:

ACGGACUUGA ACAAC   15

( 2 ) INFORMATION FOR SEQ ID NO:1623:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1623:

CUCCUGUAGA CGUGU   15

( 2 ) INFORMATION FOR SEQ ID NO:1624:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1624:

CUCCUGUAGA CGUGU   15

( 2 ) INFORMATION FOR SEQ ID NO:1625:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1625:

GACGUGUUCC AGAAC   15

( 2 ) INFORMATION FOR SEQ ID NO:1626:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1626:

CAGAACUUAC GGAAG   15

( 2 ) INFORMATION FOR SEQ ID NO:1627:

( i ) SEQUENCE CHARACTERISTICS:

( A ) LENGTH: 15 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:1627:

C A A U C C U U A U  C U U U G                                                                              1 5

( 2 ) INFORMATION FOR SEQ ID NO:1628:

( i ) SEQUENCE CHARACTERISTICS:
                ( A ) LENGTH: 15 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:1628:

C A A U C C U U A U  C U U U G                                                                              1 5

( 2 ) INFORMATION FOR SEQ ID NO:1629:

( i ) SEQUENCE CHARACTERISTICS:
                ( A ) LENGTH: 15 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:1629:

C A A U C C U U A U  C U U U G                                                                              1 5

( 2 ) INFORMATION FOR SEQ ID NO:1630:

( i ) SEQUENCE CHARACTERISTICS:
                ( A ) LENGTH: 15 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:1630:

C A A U C C U U A U  C U U U G                                                                              1 5

( 2 ) INFORMATION FOR SEQ ID NO:1631:

( i ) SEQUENCE CHARACTERISTICS:
                ( A ) LENGTH: 15 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:1631:

C A A U C C U U A U  C U U U G                                                                              1 5

( 2 ) INFORMATION FOR SEQ ID NO:1632:

( i ) SEQUENCE CHARACTERISTICS:
                ( A ) LENGTH: 15 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:1632:

A A U C C U U A U C  U U U G U                                                                              1 5

( 2 ) INFORMATION FOR SEQ ID NO:1633:

( i ) SEQUENCE CHARACTERISTICS:
                ( A ) LENGTH: 15 base pairs
                ( B ) TYPE: nucleic acid ( C ) STRANDEDNESS: single
            ( D ) TOPOLOGY: linear ( x i ) SEQUENCE DESCRIPTION: SEQ ID NO:1633:

AAUCCUUAUC UUUGU                                                                                     15

( 2 ) INFORMATION FOR SEQ ID NO:1634:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1634:

AAUCCUUAUC UUUGU                                                                                     15

( 2 ) INFORMATION FOR SEQ ID NO:1635:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1635:

AAUCCUUAUC UUUGU                                                                                     15

( 2 ) INFORMATION FOR SEQ ID NO:1636:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1636:

UCCUUAUCUU UGUGA                                                                                     15

( 2 ) INFORMATION FOR SEQ ID NO:1637:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1637:

UCCUUAUCUU UGUGA                                                                                     15

( 2 ) INFORMATION FOR SEQ ID NO:1638:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1638:

UCCUUAUCUU UGUGA                                                                                     15

( 2 ) INFORMATION FOR SEQ ID NO:1639:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1639:

CUUAUCUUUG UGACA 15

( 2 ) INFORMATION FOR SEQ ID NO:1640:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1640:

UUAUCUUUGU GACAG 15

( 2 ) INFORMATION FOR SEQ ID NO:1641:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1641:

UUAUCUUUGU GACAG 15

( 2 ) INFORMATION FOR SEQ ID NO:1642:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1642:

UGACAGUCUU GCUGA 15

( 2 ) INFORMATION FOR SEQ ID NO:1643:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1643:

ACAGUCUUGC UGAUC 15

( 2 ) INFORMATION FOR SEQ ID NO:1644:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1644:

ACAGUCUUGC UGAUC 15

( 2 ) INFORMATION FOR SEQ ID NO:1645:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1645:

UGCUGAUCUC AGAUG                                                                                    15

( 2 ) INFORMATION FOR SEQ ID NO:1646:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1646:

UGCUGAUCUC AGAUG                                                                                    15

( 2 ) INFORMATION FOR SEQ ID NO:1647:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1647:

UGCUGAUCUC AGAUG                                                                                    15

( 2 ) INFORMATION FOR SEQ ID NO:1648:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1648:

UGCUGAUCUC AGAUG                                                                                    15

( 2 ) INFORMATION FOR SEQ ID NO:1649:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1649:

CUGAUCUCAG AUGCU                                                                                    15

( 2 ) INFORMATION FOR SEQ ID NO:1650:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1650:

CUGAUCUCAG AUGCU                                                                                    15

( 2 ) INFORMATION FOR SEQ ID NO:1651:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1651:

AUGCUGUUUC CGUGG                                                                                    15

( 2 ) INFORMATION FOR SEQ ID NO:1652:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1652:

UGCUGUUUCC GUGGA 15

( 2 ) INFORMATION FOR SEQ ID NO:1653:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1653:

GCUGUUUCCG UGGAG 15

( 2 ) INFORMATION FOR SEQ ID NO:1654:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1654:

GCAAGCUUAU UUCAA 15

( 2 ) INFORMATION FOR SEQ ID NO:1655:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1655:

GCAAGCUUAU UUCAA 15

( 2 ) INFORMATION FOR SEQ ID NO:1656:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1656:

GCAAGCUUAU UUCAA 15

( 2 ) INFORMATION FOR SEQ ID NO:1657:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1657:

CAAGCUUAUU UCAAU 15

( 2 ) INFORMATION FOR SEQ ID NO:1658:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1658:

CAAGCUUAUU UCAAU         15

( 2 ) INFORMATION FOR SEQ ID NO:1659:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1659:

AGCUUAUUUC AAUGG         15

( 2 ) INFORMATION FOR SEQ ID NO:1660:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1660:

AGCUUAUUUC AAUGG         15

( 2 ) INFORMATION FOR SEQ ID NO:1661:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1661:

GCUUAUUUCA AUGGG         15

( 2 ) INFORMATION FOR SEQ ID NO:1662:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1662:

GCUUAUUUCA AUGGG         15

( 2 ) INFORMATION FOR SEQ ID NO:1663:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1663:

CUUAUUUCAA UGGGA         15

( 2 ) INFORMATION FOR SEQ ID NO:1664:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1664:

CUUAUUUCAA UGGGA 15

( 2 ) INFORMATION FOR SEQ ID NO:1665:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1665:

ACUGCAUAUC UGCCG 15

( 2 ) INFORMATION FOR SEQ ID NO:1666:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1666:

UGCAUAUCUG CCGUG 15

( 2 ) INFORMATION FOR SEQ ID NO:1667:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1667:

UGCCCAUUUA CAAAG 15

( 2 ) INFORMATION FOR SEQ ID NO:1668:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1668:

UGCCCAUUUA CAAAG 15

( 2 ) INFORMATION FOR SEQ ID NO:1669:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1669:

GCCCAUUUAC AAAGG 15

( 2 ) INFORMATION FOR SEQ ID NO:1670:

( i ) SEQUENCE CHARACTERISTICS:
  ( A ) LENGTH: 15 base pairs (B) TYPE: nucleic acid
(C) STRANDEDNESS: single
(D) TOPOLOGY: linear (xi) SEQUENCE DESCRIPTION: SEQ ID NO:1670:

CCCAUUUACA AAGGC 15

(2) INFORMATION FOR SEQ ID NO:1671:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:1671:

CCCAUUUACA AAGGC 15

(2) INFORMATION FOR SEQ ID NO:1672:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:1672:

AAAACAUAAG CCUGA 15

(2) INFORMATION FOR SEQ ID NO:1673:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:1673:

AGCUGGUAGU AUUUU 15

(2) INFORMATION FOR SEQ ID NO:1674:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:1674:

AGCUGGUAGU AUUUU 15

(2) INFORMATION FOR SEQ ID NO:1675:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:1675:

UGGUAGUAUU UUGGC 15

(2) INFORMATION FOR SEQ ID NO:1676:

(i) SEQUENCE CHARACTERISTICS:
(A) LENGTH: 15 base pairs
(B) TYPE: nucleic acid
(C) STRANDEDNESS: single (D) TOPOLOGY: linear (x i) SEQUENCE DESCRIPTION: SEQ ID NO:1676:

UGGUAGUAUU UUGGC 15

(2) INFORMATION FOR SEQ ID NO:1677:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO:1677:

GUAGUAUUUU GGCAG 15

(2) INFORMATION FOR SEQ ID NO:1678:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO:1678:

GUAGUAUUUU GGCAG 15

(2) INFORMATION FOR SEQ ID NO:1679:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO:1679:

UAGUAUUUUG GCAGG 15

(2) INFORMATION FOR SEQ ID NO:1680:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO:1680:

UAGUAUUUUG GCAGG 15

(2) INFORMATION FOR SEQ ID NO:1681:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO:1681:

UAGUAUUUUG GCAGG 15

(2) INFORMATION FOR SEQ ID NO:1682:

(i) SEQUENCE CHARACTERISTICS:
        (A) LENGTH: 15 base pairs
        (B) TYPE: nucleic acid
        (C) STRANDEDNESS: single
        (D) TOPOLOGY: linear ( x i ) SEQUENCE DESCRIPTION: SEQ ID NO:1682:

A G U A U U U U G G   C A G G A                                                                    15

( 2 ) INFORMATION FOR SEQ ID NO:1683:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1683:

A G U A U U U U G G   C A G G A                                                                    15

( 2 ) INFORMATION FOR SEQ ID NO:1684:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1684:

C A A A A G U U G G   U U C U G                                                                    15

( 2 ) INFORMATION FOR SEQ ID NO:1685:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1685:

C A A A A G U U G G   U U C U G                                                                    15

( 2 ) INFORMATION FOR SEQ ID NO:1686:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1686:

A G U U G G U U C U   G U A C G                                                                    15

( 2 ) INFORMATION FOR SEQ ID NO:1687:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1687:

G U U G G U U C U G   U A C G A                                                                    15

( 2 ) INFORMATION FOR SEQ ID NO:1688:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1688:

GUUCUGUACG AGCAC                                                                15

( 2 ) INFORMATION FOR SEQ ID NO:1689:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1689:

GAGCACUAUU UGGGC                                                                15

( 2 ) INFORMATION FOR SEQ ID NO:1690:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1690:

CACUAUUUGG GCACA                                                                15

( 2 ) INFORMATION FOR SEQ ID NO:1691:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1691:

AGAAACUUGA UAGUG                                                                15

( 2 ) INFORMATION FOR SEQ ID NO:1692:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1692:

GCCAAGUACC UGGGC                                                                15

( 2 ) INFORMATION FOR SEQ ID NO:1693:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1693:

GCCAAGUACC UGGGC                                                                15

( 2 ) INFORMATION FOR SEQ ID NO:1694:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1694:

ACGAGCUUUG ACAGG                                                                15

( 2 ) INFORMATION FOR SEQ ID NO:1695:

( i ) SEQUENCE CHARACTERISTICS:
         ( A ) LENGTH: 15 base pairs
         ( B ) TYPE: nucleic acid
         ( C ) STRANDEDNESS: single
         ( D ) TOPOLOGY: linear ( x i ) SEQUENCE DESCRIPTION: SEQ ID NO:1695:

CUGGACUCUA CGACU 15

( 2 ) INFORMATION FOR SEQ ID NO:1696:

( i ) SEQUENCE CHARACTERISTICS:
         ( A ) LENGTH: 15 base pairs
         ( B ) TYPE: nucleic acid
         ( C ) STRANDEDNESS: single
         ( D ) TOPOLOGY: linear ( x i ) SEQUENCE DESCRIPTION: SEQ ID NO:1696:

GGACUCUACG ACUUC 15

( 2 ) INFORMATION FOR SEQ ID NO:1697:

( i ) SEQUENCE CHARACTERISTICS:
         ( A ) LENGTH: 15 base pairs
         ( B ) TYPE: nucleic acid
         ( C ) STRANDEDNESS: single
         ( D ) TOPOLOGY: linear ( x i ) SEQUENCE DESCRIPTION: SEQ ID NO:1697:

GGACUCUACG ACUUC 15

( 2 ) INFORMATION FOR SEQ ID NO:1698:

( i ) SEQUENCE CHARACTERISTICS:
         ( A ) LENGTH: 15 base pairs
         ( B ) TYPE: nucleic acid
         ( C ) STRANDEDNESS: single
         ( D ) TOPOLOGY: linear ( x i ) SEQUENCE DESCRIPTION: SEQ ID NO:1698:

UACGACUUCA CAAUG 15

( 2 ) INFORMATION FOR SEQ ID NO:1699:

( i ) SEQUENCE CHARACTERISTICS:
         ( A ) LENGTH: 15 base pairs
         ( B ) TYPE: nucleic acid
         ( C ) STRANDEDNESS: single
         ( D ) TOPOLOGY: linear ( x i ) SEQUENCE DESCRIPTION: SEQ ID NO:1699:

UACGACUUCA CAAUG 15

( 2 ) INFORMATION FOR SEQ ID NO:1700:

( i ) SEQUENCE CHARACTERISTICS:
         ( A ) LENGTH: 15 base pairs
         ( B ) TYPE: nucleic acid
         ( C ) STRANDEDNESS: single
         ( D ) TOPOLOGY: linear ( x i ) SEQUENCE DESCRIPTION: SEQ ID NO:1700:

ACGACUUCAC AAUGU 15

( 2 ) INFORMATION FOR SEQ ID NO:1701:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1701:

ACGACUUCAC AAUGU      15

( 2 ) INFORMATION FOR SEQ ID NO:1702:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1702:

ACAAUGUUCA GAUCA      15

( 2 ) INFORMATION FOR SEQ ID NO:1703:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1703:

ACAAUGUUCA GAUCA      15

( 2 ) INFORMATION FOR SEQ ID NO:1704:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1704:

ACAAUGUUCA GAUCA      15

( 2 ) INFORMATION FOR SEQ ID NO:1705:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1705:

CAAUGUUCAG AUCAA      15

( 2 ) INFORMATION FOR SEQ ID NO:1706:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1706:

CAAUGUUCAG AUCAA      15

( 2 ) INFORMATION FOR SEQ ID NO:1707:

( i ) SEQUENCE CHARACTERISTICS:

(A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO:1707:

CAAUGUUCAG AUCAA                                                                                           15

(2) INFORMATION FOR SEQ ID NO:1708:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO:1708:

CAAUGUUCAG AUCAA                                                                                           15

(2) INFORMATION FOR SEQ ID NO:1709:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO:1709:

CAAUGUUCAG AUCAA                                                                                           15

(2) INFORMATION FOR SEQ ID NO:1710:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO:1710:

CAAUGUUCAG AUCAA                                                                                           15

(2) INFORMATION FOR SEQ ID NO:1711:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO:1711:

CAAUGUUCAG AUCAA                                                                                           15

(2) INFORMATION FOR SEQ ID NO:1712:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO:1712:

UUCAGAUCAA GGACA                                                                                           15

(2) INFORMATION FOR SEQ ID NO:1713:

(i) SEQUENCE CHARACTERISTICS:
            (A) LENGTH: 15 base pairs
            (B) TYPE: nucleic acid ( C ) STRANDEDNESS: single
        ( D ) TOPOLOGY: linear ( x i ) SEQUENCE DESCRIPTION: SEQ ID NO:1713:

UUCAGAUCAA GGACA                                                                                    15

( 2 ) INFORMATION FOR SEQ ID NO:1714:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1714:

AUGGGCUCGU AUGAU                                                                                    15

( 2 ) INFORMATION FOR SEQ ID NO:1715:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1715:

AUGGGCUCGU AUGAU                                                                                    15

( 2 ) INFORMATION FOR SEQ ID NO:1716:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1716:

AUGGGCUCGU AUGAU                                                                                    15

( 2 ) INFORMATION FOR SEQ ID NO:1717:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1717:

GGCUCGUAUG AUUGU                                                                                    15

( 2 ) INFORMATION FOR SEQ ID NO:1718:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1718:

GGCUCGUAUG AUUGU                                                                                    15

( 2 ) INFORMATION FOR SEQ ID NO:1719:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1719:

UGAUUGUUUU AUACA 15

( 2 ) INFORMATION FOR SEQ ID NO:1720:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1720:

UGAUUGUUUU AUACA 15

( 2 ) INFORMATION FOR SEQ ID NO:1721:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1721:

AUUGUUUUAU ACAAA 15

( 2 ) INFORMATION FOR SEQ ID NO:1722:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1722:

AUUGUUUUAU ACAAA 15

( 2 ) INFORMATION FOR SEQ ID NO:1723:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1723:

UUGUUUUAUA CAAAA 15

( 2 ) INFORMATION FOR SEQ ID NO:1724:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1724:

UUGUUUUAUA CAAAA 15

( 2 ) INFORMATION FOR SEQ ID NO:1725:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1725:

UUGUUUUAUA CAAAA 15

(2) INFORMATION FOR SEQ ID NO:1726:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:1726:

GAUCAAUUAU CCUCC 15

(2) INFORMATION FOR SEQ ID NO:1727:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:1727:

AUCAAUUAUC CUCCA 15

(2) INFORMATION FOR SEQ ID NO:1728:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:1728:

CAAUUAUCCU CCAAC 15

(2) INFORMATION FOR SEQ ID NO:1729:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:1729:

UUAUCCUCCA ACAGA 15

(2) INFORMATION FOR SEQ ID NO:1730:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:1730:

UUAUCCUCCA ACAGA 15

(2) INFORMATION FOR SEQ ID NO:1731:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:1731:

UUAUCCUCCA ACAGA 15

( 2 ) INFORMATION FOR SEQ ID NO:1732:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1732:

UUAUCCUCCA ACAGA     15

( 2 ) INFORMATION FOR SEQ ID NO:1733:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1733:

GAACUGUCAG UGAUC     15

( 2 ) INFORMATION FOR SEQ ID NO:1734:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1734:

CAGUGAUCGC CAACU     15

( 2 ) INFORMATION FOR SEQ ID NO:1735:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1735:

GCCAACUUCA GUGAA     15

( 2 ) INFORMATION FOR SEQ ID NO:1736:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1736:

CCAACUUCAG UGAAC     15

( 2 ) INFORMATION FOR SEQ ID NO:1737:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1737:

CCAACUUCAG UGAAC     15

( 2 ) INFORMATION FOR SEQ ID NO:1738:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1738:

CUGAAAUAAA ACUGG        15

( 2 ) INFORMATION FOR SEQ ID NO:1739:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1739:

ACUGGCUCAG AAUGU        15

( 2 ) INFORMATION FOR SEQ ID NO:1740:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1740:

AGAAUGUAAC AGGAA        15

( 2 ) INFORMATION FOR SEQ ID NO:1741:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1741:

GGAAAUUCUG GCAUA        15

( 2 ) INFORMATION FOR SEQ ID NO:1742:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1742:

GGAAAUUCUG GCAUA        15

( 2 ) INFORMATION FOR SEQ ID NO:1743:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1743:

CUGGCAUAAA UUUGA        15

( 2 ) INFORMATION FOR SEQ ID NO:1744:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1744:

CAUAAAUUUG ACCUG 15

( 2 ) INFORMATION FOR SEQ ID NO:1745:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1745:

AUAAAUUUGA CCUGC 15

( 2 ) INFORMATION FOR SEQ ID NO:1746:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1746:

CACGUCUAAG CAAGG 15

( 2 ) INFORMATION FOR SEQ ID NO:1747:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1747:

GCAAGGUCAC CCGAA 15

( 2 ) INFORMATION FOR SEQ ID NO:1748:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1748:

GAAACCUAAG AAGAU 15

( 2 ) INFORMATION FOR SEQ ID NO:1749:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1749:

AAGAUGUAUU UUCUG 15

( 2 ) INFORMATION FOR SEQ ID NO:1750:

( i ) SEQUENCE CHARACTERISTICS:
        ( A ) LENGTH: 15 base pairs (B) TYPE: nucleic acid
                (C) STRANDEDNESS: single
                (D) TOPOLOGY: linear (xi) SEQUENCE DESCRIPTION: SEQ ID NO:1750:

UGUAUUUUCU GAUAA                                                                                   15

(2) INFORMATION FOR SEQ ID NO:1751:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (xi) SEQUENCE DESCRIPTION: SEQ ID NO:1751:

ACUAAUUCAA CUAAU                                                                                   15

(2) INFORMATION FOR SEQ ID NO:1752:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (xi) SEQUENCE DESCRIPTION: SEQ ID NO:1752:

UUCAACUAAU GAGUA                                                                                   15

(2) INFORMATION FOR SEQ ID NO:1753:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (xi) SEQUENCE DESCRIPTION: SEQ ID NO:1753:

UUCAACUAAU GAGUA                                                                                   15

(2) INFORMATION FOR SEQ ID NO:1754:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (xi) SEQUENCE DESCRIPTION: SEQ ID NO:1754:

AAUGAGUAUG GUGAU                                                                                   15

(2) INFORMATION FOR SEQ ID NO:1755:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (xi) SEQUENCE DESCRIPTION: SEQ ID NO:1755:

UGCAGAUAUC ACAAG                                                                                   15

(2) INFORMATION FOR SEQ ID NO:1756:

(i) SEQUENCE CHARACTERISTICS:
                (A) LENGTH: 15 base pairs
                (B) TYPE: nucleic acid
                (C) STRANDEDNESS: single -continued (D) TOPOLOGY: linear (xi) SEQUENCE DESCRIPTION: SEQ ID NO:1756:

CAGAUAUCAC AAGAU                                                                                          15

(2) INFORMATION FOR SEQ ID NO:1757:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO:1757:

CAGAUAUCAC AAGAU                                                                                          15

(2) INFORMATION FOR SEQ ID NO:1758:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO:1758:

CAGAUAUCAC AAGAU                                                                                          15

(2) INFORMATION FOR SEQ ID NO:1759:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO:1759:

CAGAUAUCAC AAGAU                                                                                          15

(2) INFORMATION FOR SEQ ID NO:1760:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO:1760:

ACAAGAUAAU GUCAC                                                                                          15

(2) INFORMATION FOR SEQ ID NO:1761:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO:1761:

ACAAGAUAAU GUCAC                                                                                          15

(2) INFORMATION FOR SEQ ID NO:1762:

(i) SEQUENCE CHARACTERISTICS:
            (A) LENGTH: 15 base pairs
            (B) TYPE: nucleic acid
            (C) STRANDEDNESS: single
            (D) TOPOLOGY: linear ( x i ) SEQUENCE DESCRIPTION: SEQ ID NO:1762:

AUAAUGUCAC AGAAC 15

( 2 ) INFORMATION FOR SEQ ID NO:1763:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1763:

AUAAUGUCAC AGAAC 15

( 2 ) INFORMATION FOR SEQ ID NO:1764:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1764:

AUAAUGUCAC AGAAC 15

( 2 ) INFORMATION FOR SEQ ID NO:1765:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1765:

GAACUGUUCA GUAUC 15

( 2 ) INFORMATION FOR SEQ ID NO:1766:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1766:

AACUGUUCAG UAUCU 15

( 2 ) INFORMATION FOR SEQ ID NO:1767:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1767:

AACUGUUCAG UAUCU 15

( 2 ) INFORMATION FOR SEQ ID NO:1768:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1768:

AGUAUCUCCA ACAGC 15

(2) INFORMATION FOR SEQ ID NO:1769:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:1769:

AGUAUCUCCA ACAGC 15

(2) INFORMATION FOR SEQ ID NO:1770:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:1770:

AGUAUCUCCA ACAGC 15

(2) INFORMATION FOR SEQ ID NO:1771:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:1771:

ACAGCCUCUC UCUUU 15

(2) INFORMATION FOR SEQ ID NO:1772:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:1772:

ACAGCCUCUC UCUUU 15

(2) INFORMATION FOR SEQ ID NO:1773:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:1773:

AGCCUCUCUC UUUCA 15

(2) INFORMATION FOR SEQ ID NO:1774:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:1774:

AGCCUCUCUC UUUCA 15

( 2 ) INFORMATION FOR SEQ ID NO:1775:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1775:

UCUCUCUUUC AUUCC           15

( 2 ) INFORMATION FOR SEQ ID NO:1776:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1776:

UCUCUCUUUC AUUCC           15

( 2 ) INFORMATION FOR SEQ ID NO:1777:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1777:

CUCUCUUUCA UUCCC           15

( 2 ) INFORMATION FOR SEQ ID NO:1778:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1778:

UCUCUUUCAU UCCCG           15

( 2 ) INFORMATION FOR SEQ ID NO:1779:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1779:

UCUCUUUCAU UCCCG           15

( 2 ) INFORMATION FOR SEQ ID NO:1780:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1780:

UCUCUUUCAU UCCCG           15

( 2 ) INFORMATION FOR SEQ ID NO:1781:

( i ) SEQUENCE CHARACTERISTICS:
 ( A ) LENGTH: 15 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:1781:

CUUUCAUUCC CGGAU 15

( 2 ) INFORMATION FOR SEQ ID NO:1782:

( i ) SEQUENCE CHARACTERISTICS:
 ( A ) LENGTH: 15 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:1782:

CUUUCAUUCC CGGAU 15

( 2 ) INFORMATION FOR SEQ ID NO:1783:

( i ) SEQUENCE CHARACTERISTICS:
 ( A ) LENGTH: 15 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:1783:

CUUUCAUUCC CGGAU 15

( 2 ) INFORMATION FOR SEQ ID NO:1784:

( i ) SEQUENCE CHARACTERISTICS:
 ( A ) LENGTH: 15 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:1784:

CUUUCAUUCC CGGAU 15

( 2 ) INFORMATION FOR SEQ ID NO:1785:

( i ) SEQUENCE CHARACTERISTICS:
 ( A ) LENGTH: 15 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:1785:

CUUUCAUUCC CGGAU 15

( 2 ) INFORMATION FOR SEQ ID NO:1786:

( i ) SEQUENCE CHARACTERISTICS:
 ( A ) LENGTH: 15 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:1786:

UUUCAUUCCC GGAUG 15

( 2 ) INFORMATION FOR SEQ ID NO:1787:

( i ) SEQUENCE CHARACTERISTICS:

(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:1787:

UUUCAUUCCC GGAUG 15

(2) INFORMATION FOR SEQ ID NO:1788:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:1788:

GUGGCAUAUG ACCGU 15

(2) INFORMATION FOR SEQ ID NO:1789:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:1789:

GUGGCAUAUG ACCGU 15

(2) INFORMATION FOR SEQ ID NO:1790:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:1790:

UGACCGUUGU GUGUG 15

(2) INFORMATION FOR SEQ ID NO:1791:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:1791:

UGUGUGUUCU GGAAA 15

(2) INFORMATION FOR SEQ ID NO:1792:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:1792:

UGUGUGUUCU GGAAA 15

(2) INFORMATION FOR SEQ ID NO:1793:

(i) SEQUENCE CHARACTERISTICS:
(A) LENGTH: 15 base pairs
(B) TYPE: nucleic acid ( C ) STRANDEDNESS: single
        ( D ) TOPOLOGY: linear ( x i ) SEQUENCE DESCRIPTION: SEQ ID NO:1793:

GUGUGUUCUG GAAAC                                                                                            15

( 2 ) INFORMATION FOR SEQ ID NO:1794:

( i ) SEQUENCE CHARACTERISTICS:
                ( A ) LENGTH: 15 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:1794:

GUGUGUUCUG GAAAC                                                                                            15

( 2 ) INFORMATION FOR SEQ ID NO:1795:

( i ) SEQUENCE CHARACTERISTICS:
                ( A ) LENGTH: 15 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:1795:

UGAAGAUUUC CUCCA                                                                                            15

( 2 ) INFORMATION FOR SEQ ID NO:1796:

( i ) SEQUENCE CHARACTERISTICS:
                ( A ) LENGTH: 15 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:1796:

AUUCCUCCA AACCU                                                                                             15

( 2 ) INFORMATION FOR SEQ ID NO:1797:

( i ) SEQUENCE CHARACTERISTICS:
                ( A ) LENGTH: 15 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:1797:

AACCUCUCAA UUUCA                                                                                            15

( 2 ) INFORMATION FOR SEQ ID NO:1798:

( i ) SEQUENCE CHARACTERISTICS:
                ( A ) LENGTH: 15 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:1798:

UUUCACUCAA GAGUU                                                                                            15

( 2 ) INFORMATION FOR SEQ ID NO:1799:

( i ) SEQUENCE CHARACTERISTICS:
                ( A ) LENGTH: 15 base pairs
                ( B ) TYPE: nucleic acid
                ( C ) STRANDEDNESS: single
                ( D ) TOPOLOGY: linear (x i) SEQUENCE DESCRIPTION: SEQ ID NO:1799:

CAAGAGUUUC CAUCU 15

(2) INFORMATION FOR SEQ ID NO:1800:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO:1800:

CAAGAGUUUC CAUCU 15

(2) INFORMATION FOR SEQ ID NO:1801:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO:1801:

AAGAGUUUCC AUCUC 15

(2) INFORMATION FOR SEQ ID NO:1802:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO:1802:

UUUCCAUCUC CUCAA 15

(2) INFORMATION FOR SEQ ID NO:1803:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO:1803:

UUUCCAUCUC CUCAA 15

(2) INFORMATION FOR SEQ ID NO:1804:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO:1804:

UCCAUCUCCU CAAAC 15

(2) INFORMATION FOR SEQ ID NO:1805:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO:1805:

AGGAGAUUAC AGCUU  15

( 2 ) INFORMATION FOR SEQ ID NO:1806:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1806:

AGGAGAUUAC AGCUU  15

( 2 ) INFORMATION FOR SEQ ID NO:1807:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1807:

GGAGAUUACA GCUUC  15

( 2 ) INFORMATION FOR SEQ ID NO:1808:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1808:

CUUCAGUUAC UGUGG  15

( 2 ) INFORMATION FOR SEQ ID NO:1809:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1809:

UGGCCCUCCU CCUUG  15

( 2 ) INFORMATION FOR SEQ ID NO:1810:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1810:

UGGCCCUCCU CCUUG  15

( 2 ) INFORMATION FOR SEQ ID NO:1811:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1811:

UGCUGCUCAU CAUUG  15

( 2 ) INFORMATION FOR SEQ ID NO:1812:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1812:

GCGGGAUAGU AACGC 15

( 2 ) INFORMATION FOR SEQ ID NO:1813:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1813:

AGACUAUCAA CCUGA 15

( 2 ) INFORMATION FOR SEQ ID NO:1814:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1814:

AGGAACUUGA ACCCC 15

( 2 ) INFORMATION FOR SEQ ID NO:1815:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1815:

AUUGCUUCAG CAAAA 15

( 2 ) INFORMATION FOR SEQ ID NO:1816:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1816:

AAAGAGUUAA AAAUU 15

( 2 ) INFORMATION FOR SEQ ID NO:1817:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1817:

AAGAGUUAAA AAUUG 15

( 2 ) INFORMATION FOR SEQ ID NO:1818:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1818:

UAAAAAUUGC UUUGC 15

( 2 ) INFORMATION FOR SEQ ID NO:1819:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1819:

CAGAGUUUCU CAGAA 15

( 2 ) INFORMATION FOR SEQ ID NO:1820:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1820:

AGUUUCUCAG AAUUC 15

( 2 ) INFORMATION FOR SEQ ID NO:1821:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1821:

UCAGAAUUCA AAAAU 15

( 2 ) INFORMATION FOR SEQ ID NO:1822:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1822:

UCAGAAUUCA AAAAU 15

( 2 ) INFORMATION FOR SEQ ID NO:1823:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1823:

UCAGAAUUCA AAAAU 15

( 2 ) INFORMATION FOR SEQ ID NO:1824:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1824:

AAAAUGUUCU CAGCU        15

( 2 ) INFORMATION FOR SEQ ID NO:1825:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1825:

AAAUGUUCUC AGCUG        15

( 2 ) INFORMATION FOR SEQ ID NO:1826:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1826:

UUGGAAUUCU ACAGU        15

( 2 ) INFORMATION FOR SEQ ID NO:1827:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1827:

UUGGAAUUCU ACAGU        15

( 2 ) INFORMATION FOR SEQ ID NO:1828:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1828:

GAAUUCUACA GUUGA        15

( 2 ) INFORMATION FOR SEQ ID NO:1829:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1829:

GAAUUCUACA GUUGA        15

( 2 ) INFORMATION FOR SEQ ID NO:1830:

( i ) SEQUENCE CHARACTERISTICS:
    ( A ) LENGTH: 15 base pairs ( B ) TYPE: nucleic acid
            ( C ) STRANDEDNESS: single
            ( D ) TOPOLOGY: linear ( x i ) SEQUENCE DESCRIPTION: SEQ ID NO:1830:

GUUGAAUAAU UAAAG 15

( 2 ) INFORMATION FOR SEQ ID NO:1831:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1831:

GAAUAAUUAA AGAAC 15

( 2 ) INFORMATION FOR SEQ ID NO:1832:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1832:

AAUAAUUAAA GAACA 15

( 2 ) INFORMATION FOR SEQ ID NO:1833:

( i ) SEQUENCE CHARACTERISTICS:
            ( A ) LENGTH: 36 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1833:

GUUGUUCCUG AUGAGGCCGA AAGGCCGAAA GUCCGU 36

( 2 ) INFORMATION FOR SEQ ID NO:1834:

( i ) SEQUENCE CHARACTERISTICS:
            ( A ) LENGTH: 36 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1834:

GUUGUUCCUG AUGAGGCCGA AAGGCCGAAA GUCCGU 36

( 2 ) INFORMATION FOR SEQ ID NO:1835:

( i ) SEQUENCE CHARACTERISTICS:
            ( A ) LENGTH: 36 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1835:

ACACGUCCUG AUGAGGCCGA AAGGCCGAAA CAGGAG 36

( 2 ) INFORMATION FOR SEQ ID NO:1836:

( i ) SEQUENCE CHARACTERISTICS:
            ( A ) LENGTH: 36 base pairs
            ( B ) TYPE: nucleic acid
            ( C ) STRANDEDNESS: single -continued (D) TOPOLOGY: linear (xi) SEQUENCE DESCRIPTION: SEQ ID NO:1836:

ACACGUCCUG AUGAGGCCGA AAGGCCGAAA CAGGAG      36

(2) INFORMATION FOR SEQ ID NO:1837:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (xi) SEQUENCE DESCRIPTION: SEQ ID NO:1837:

GUUCUGGCUG AUGAGGCCGA AAGGCCGAAA CACGUC      36

(2) INFORMATION FOR SEQ ID NO:1838:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (xi) SEQUENCE DESCRIPTION: SEQ ID NO:1838:

CUUCCGUCUG AUGAGGCCGA AAGGCCGAAA GUUCUG      36

(2) INFORMATION FOR SEQ ID NO:1839:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (xi) SEQUENCE DESCRIPTION: SEQ ID NO:1839:

CAAAGAUCUG AUGAGGCCGA AAGGCCGAAA GGAUUG      36

(2) INFORMATION FOR SEQ ID NO:1840:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (xi) SEQUENCE DESCRIPTION: SEQ ID NO:1840:

CAAAGAUCUG AUGAGGCCGA AAGGCCGAAA GGAUUG      36

(2) INFORMATION FOR SEQ ID NO:1841:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (xi) SEQUENCE DESCRIPTION: SEQ ID NO:1841:

CAAAGAUCUG AUGAGGCCGA AAGGCCGAAA GGAUUG      36

(2) INFORMATION FOR SEQ ID NO:1842:

(i) SEQUENCE CHARACTERISTICS:
    (A) LENGTH: 36 base pairs
    (B) TYPE: nucleic acid
    (C) STRANDEDNESS: single
    (D) TOPOLOGY: linear ( x i ) SEQUENCE DESCRIPTION: SEQ ID NO:1842:

CAAAGAUCUG AUGAGGCCGA AAGGCCGAAA GGAUUG　　　　　　　　　　　　　　　36

( 2 ) INFORMATION FOR SEQ ID NO:1843:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1843:

CAAAGAUCUG AUGAGGCCGA AAGGCCGAAA GGAUUG　　　　　　　　　　　　　　　36

( 2 ) INFORMATION FOR SEQ ID NO:1844:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1844:

ACAAAGACUG AUGAGGCCGA AAGGCCGAAA AGGAUU　　　　　　　　　　　　　　　36

( 2 ) INFORMATION FOR SEQ ID NO:1845:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1845:

ACAAAGACUG AUGAGGCCGA AAGGCCGAAA AGGAUU　　　　　　　　　　　　　　　36

( 2 ) INFORMATION FOR SEQ ID NO:1846:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1846:

ACAAAGACUG AUGAGGCCGA AAGGCCGAAA AGGAUU　　　　　　　　　　　　　　　36

( 2 ) INFORMATION FOR SEQ ID NO:1847:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1847:

ACAAAGACUG AUGAGGCCGA AAGGCCGAAA AGGAUU　　　　　　　　　　　　　　　36

( 2 ) INFORMATION FOR SEQ ID NO:1848:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1848:

UCACAAACUG AUGAGGCCGA AAGGCCGAAA UAAGGA 36

( 2 ) INFORMATION FOR SEQ ID NO:1849:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1849:

UCACAAACUG AUGAGGCCGA AAGGCCGAAA UAAGGA 36

( 2 ) INFORMATION FOR SEQ ID NO:1850:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1850:

UCACAAACUG AUGAGGCCGA AAGGCCGAAA UAAGGA 36

( 2 ) INFORMATION FOR SEQ ID NO:1851:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1851:

UGUCACACUG AUGAGGCCGA AAGGCCGAAA GAUAAG 36

( 2 ) INFORMATION FOR SEQ ID NO:1852:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1852:

CUGUCACCUG AUGAGGCCGA AAGGCCGAAA AGAUAA 36

( 2 ) INFORMATION FOR SEQ ID NO:1853:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1853:

CUGUCACCUG AUGAGGCCGA AAGGCCGAAA AGAUAA 36

( 2 ) INFORMATION FOR SEQ ID NO:1854:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1854:

UCAGCAACUG AUGAGGCCGA AAGGCCGAAA CUGUCA 36

( 2 ) INFORMATION FOR SEQ ID NO:1855:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1855:

GAUCAGCCUG AUGAGGCCGA AAGGCCGAAA GACUGU    36

( 2 ) INFORMATION FOR SEQ ID NO:1856:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1856:

GAUCAGCCUG AUGAGGCCGA AAGGCCGAAA GACUGU    36

( 2 ) INFORMATION FOR SEQ ID NO:1857:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1857:

CAUCUGACUG AUGAGGCCGA AAGGCCGAAA UCAGCA    36

( 2 ) INFORMATION FOR SEQ ID NO:1858:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1858:

CAUCUGACUG AUGAGGCCGA AAGGCCGAAA UCAGCA    36

( 2 ) INFORMATION FOR SEQ ID NO:1859:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1859:

CAUCUGACUG AUGAGGCCGA AAGGCCGAAA UCAGCA    36

( 2 ) INFORMATION FOR SEQ ID NO:1860:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1860:

CAUCUGACUG AUGAGGCCGA AAGGCCGAAA UCAGCA    36

( 2 ) INFORMATION FOR SEQ ID NO:1861:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1861:

AGCAUCUCUG AUGAGGCCGA AAGGCCGAAA GAUCAG    36

( 2 ) INFORMATION FOR SEQ ID NO:1862:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1862:

AGCAUCUCUG AUGAGGCCGA AAGGCCGAAA GAUCAG    36

( 2 ) INFORMATION FOR SEQ ID NO:1863:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1863:

CCACGGACUG AUGAGGCCGA AAGGCCGAAA CAGCAU    36

( 2 ) INFORMATION FOR SEQ ID NO:1864:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1864:

UCCACGGCUG AUGAGGCCGA AAGGCCGAAA ACAGCA    36

( 2 ) INFORMATION FOR SEQ ID NO:1865:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1865:

CUCCACGCUG AUGAGGCCGA AAGGCCGAAA AACAGC    36

( 2 ) INFORMATION FOR SEQ ID NO:1866:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1866:

UUGAAAUCUG AUGAGGCCGA AAGGCCGAAA GCUUGC    36

( 2 ) INFORMATION FOR SEQ ID NO:1867:

( i ) SEQUENCE CHARACTERISTICS:

(A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO:1867:

UUGAAAUCUG AUGAGGCCGA AAGGCCGAAA GCUUGC                        36

(2) INFORMATION FOR SEQ ID NO:1868:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO:1868:

UUGAAAUCUG AUGAGGCCGA AAGGCCGAAA GCUUGC                        36

(2) INFORMATION FOR SEQ ID NO:1869:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO:1869:

AUUGAAACUG AUGAGGCCGA AAGGCCGAAA AGCUUG                        36

(2) INFORMATION FOR SEQ ID NO:1870:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO:1870:

AUUGAAACUG AUGAGGCCGA AAGGCCGAAA AGCUUG                        36

(2) INFORMATION FOR SEQ ID NO:1871:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO:1871:

CCAUUGACUG AUGAGGCCGA AAGGCCGAAA UAAGCU                        36

(2) INFORMATION FOR SEQ ID NO:1872:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO:1872:

CCAUUGACUG AUGAGGCCGA AAGGCCGAAA UAAGCU                        36

(2) INFORMATION FOR SEQ ID NO:1873:

(i) SEQUENCE CHARACTERISTICS:
            (A) LENGTH: 36 base pairs
            (B) TYPE: nucleic acid ( C ) STRANDEDNESS: single
                    ( D ) TOPOLOGY: linear ( x i ) SEQUENCE DESCRIPTION: SEQ ID NO:1873:

CCCAUUGCUG  AUGAGGCCGA  AAGGCCGAAA  AUAAGC                                      36

( 2 ) INFORMATION FOR SEQ ID NO:1874:

( i ) SEQUENCE CHARACTERISTICS:
                    ( A ) LENGTH: 36 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:1874:

CCCAUUGCUG  AUGAGGCCGA  AAGGCCGAAA  AUAAGC                                      36

( 2 ) INFORMATION FOR SEQ ID NO:1875:

( i ) SEQUENCE CHARACTERISTICS:
                    ( A ) LENGTH: 36 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:1875:

UCCCAUUCUG  AUGAGGCCGA  AAGGCCGAAA  AAUAAG                                      36

( 2 ) INFORMATION FOR SEQ ID NO:1876:

( i ) SEQUENCE CHARACTERISTICS:
                    ( A ) LENGTH: 36 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:1876:

UCCCAUUCUG  AUGAGGCCGA  AAGGCCGAAA  AAUAAG                                      36

( 2 ) INFORMATION FOR SEQ ID NO:1877:

( i ) SEQUENCE CHARACTERISTICS:
                    ( A ) LENGTH: 36 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:1877:

CGGCAGACUG  AUGAGGCCGA  AAGGCCGAAA  UGCAGU                                      36

( 2 ) INFORMATION FOR SEQ ID NO:1878:

( i ) SEQUENCE CHARACTERISTICS:
                    ( A ) LENGTH: 36 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:1878:

CACGGCACUG  AUGAGGCCGA  AAGGCCGAAA  UAUGCA                                      36

( 2 ) INFORMATION FOR SEQ ID NO:1879:

( i ) SEQUENCE CHARACTERISTICS:
                    ( A ) LENGTH: 36 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:1879:

CUUUGUACUG AUGAGGCCGA AAGGCCGAAA UGGGCA    36

( 2 ) INFORMATION FOR SEQ ID NO:1880:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1880:

CUUUGUACUG AUGAGGCCGA AAGGCCGAAA UGGGCA    36

( 2 ) INFORMATION FOR SEQ ID NO:1881:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1881:

CCUUUGUCUG AUGAGGCCGA AAGGCCGAAA AUGGGC    36

( 2 ) INFORMATION FOR SEQ ID NO:1882:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1882:

GCCUUUGCUG AUGAGGCCGA AAGGCCGAAA AAUGGG    36

( 2 ) INFORMATION FOR SEQ ID NO:1883:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1883:

GCCUUUGCUG AUGAGGCCGA AAGGCCGAAA AAUGGG    36

( 2 ) INFORMATION FOR SEQ ID NO:1884:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1884:

UCAGGCUCUG AUGAGGCCGA AAGGCCGAAA UGUUUU    36

( 2 ) INFORMATION FOR SEQ ID NO:1885:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1885:

AAAAUACCUG AUGAGGCCGA AAGGCCGAAA CCAGCU 36

( 2 ) INFORMATION FOR SEQ ID NO:1886:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1886:

AAAAUACCUG AUGAGGCCGA AAGGCCGAAA CCAGCU 36

( 2 ) INFORMATION FOR SEQ ID NO:1887:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1887:

GCCAAAACUG AUGAGGCCGA AAGGCCGAAA CUACCA 36

( 2 ) INFORMATION FOR SEQ ID NO:1888:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1888:

GCCAAAACUG AUGAGGCCGA AAGGCCGAAA CUACCA 36

( 2 ) INFORMATION FOR SEQ ID NO:1889:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1889:

CUGCCAACUG AUGAGGCCGA AAGGCCGAAA UACUAC 36

( 2 ) INFORMATION FOR SEQ ID NO:1890:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1890:

CUGCCAACUG AUGAGGCCGA AAGGCCGAAA UACUAC 36

( 2 ) INFORMATION FOR SEQ ID NO:1891:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1891:

CCUGCCACUG AUGAGGCCGA AAGGCCGAAA AUACUA 36

( 2 ) INFORMATION FOR SEQ ID NO:1892:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1892:

CCUGCCACUG AUGAGGCCGA AAGGCCGAAA AUACUA     36

( 2 ) INFORMATION FOR SEQ ID NO:1893:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1893:

CCUGCCACUG AUGAGGCCGA AAGGCCGAAA AUACUA     36

( 2 ) INFORMATION FOR SEQ ID NO:1894:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1894:

UCCUGCCCUG AUGAGGCCGA AAGGCCGAAA AAUACU     36

( 2 ) INFORMATION FOR SEQ ID NO:1895:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1895:

UCCUGCCCUG AUGAGGCCGA AAGGCCGAAA AAUACU     36

( 2 ) INFORMATION FOR SEQ ID NO:1896:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1896:

CAGAACCCUG AUGAGGCCGA AAGGCCGAAA CUUUUG     36

( 2 ) INFORMATION FOR SEQ ID NO:1897:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1897:

CAGAACCCUG AUGAGGCCGA AAGGCCGAAA CUUUUG     36

( 2 ) INFORMATION FOR SEQ ID NO:1898:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1898:

CGUACAGCUG AUGAGGCCGA AAGGCCGAAA CCAACU 36

( 2 ) INFORMATION FOR SEQ ID NO:1899:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1899:

UCGUACACUG AUGAGGCCGA AAGGCCGAAA ACCAAC 36

( 2 ) INFORMATION FOR SEQ ID NO:1900:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1900:

GUGCUCGCUG AUGAGGCCGA AAGGCCGAAA CAGAAC 36

( 2 ) INFORMATION FOR SEQ ID NO:1901:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1901:

GCCCAAACUG AUGAGGCCGA AAGGCCGAAA GUGCUC 36

( 2 ) INFORMATION FOR SEQ ID NO:1902:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1902:

UGUGCCCUG AUGAGGCCGA AAGGCCGAAA AUAGUG 36

( 2 ) INFORMATION FOR SEQ ID NO:1903:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1903:

CACUAUCCUG AUGAGGCCGA AAGGCCGAAA GUUUCU 36

( 2 ) INFORMATION FOR SEQ ID NO:1904:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1904:

GCCCAGGCUG AUGAGGCCGA AAGGCCGAAA CUUGGC      36

( 2 ) INFORMATION FOR SEQ ID NO:1905:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1905:

GCCCAGGCUG AUGAGGCCGA AAGGCCGAAA CUUGGC      36

( 2 ) INFORMATION FOR SEQ ID NO:1906:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1906:

CCUGUCACUG AUGAGGCCGA AAGGCCGAAA GCUCGU      36

( 2 ) INFORMATION FOR SEQ ID NO:1907:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1907:

AGUCGUACUG AUGAGGCCGA AAGGCCGAAA GUCCAG      36

( 2 ) INFORMATION FOR SEQ ID NO:1908:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1908:

GAAGUCGCUG AUGAGGCCGA AAGGCCGAAA GAGUCC      36

( 2 ) INFORMATION FOR SEQ ID NO:1909:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1909:

GAAGUCGCUG AUGAGGCCGA AAGGCCGAAA GAGUCC      36

( 2 ) INFORMATION FOR SEQ ID NO:1910:

( i ) SEQUENCE CHARACTERISTICS:
    ( A ) LENGTH: 36 base pairs (B) TYPE: nucleic acid
(C) STRANDEDNESS: single
(D) TOPOLOGY: linear (xi) SEQUENCE DESCRIPTION: SEQ ID NO:1910:

CAUUGUGCUG AUGAGGCCGA AAGGCCGAAA GUCGUA 36

(2) INFORMATION FOR SEQ ID NO:1911:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:1911:

CAUUGUGCUG AUGAGGCCGA AAGGCCGAAA GUCGUA 36

(2) INFORMATION FOR SEQ ID NO:1912:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:1912:

ACAUUGUCUG AUGAGGCCGA AAGGCCGAAA AGUCGU 36

(2) INFORMATION FOR SEQ ID NO:1913:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:1913:

ACAUUGUCUG AUGAGGCCGA AAGGCCGAAA AGUCGU 36

(2) INFORMATION FOR SEQ ID NO:1914:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:1914:

UGAUCUGCUG AUGAGGCCGA AAGGCCGAAA CAUUGU 36

(2) INFORMATION FOR SEQ ID NO:1915:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:1915:

UGAUCUGCUG AUGAGGCCGA AAGGCCGAAA CAUUGU 36

(2) INFORMATION FOR SEQ ID NO:1916:

(i) SEQUENCE CHARACTERISTICS:
(A) LENGTH: 36 base pairs
(B) TYPE: nucleic acid
(C) STRANDEDNESS: single (D) TOPOLOGY: linear (xi) SEQUENCE DESCRIPTION: SEQ ID NO:1916:

UGAUCUGCUG AUGAGGCCGA AAGGCCGAAA CAUUGU 36

(2) INFORMATION FOR SEQ ID NO:1917:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1917:

UUGAUCUCUG AUGAGGCCGA AAGGCCGAAA ACAUUG 36

(2) INFORMATION FOR SEQ ID NO:1918:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1918:

UUGAUCUCUG AUGAGGCCGA AAGGCCGAAA ACAUUG 36

(2) INFORMATION FOR SEQ ID NO:1919:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1919:

UUGAUCUCUG AUGAGGCCGA AAGGCCGAAA ACAUUG 36

(2) INFORMATION FOR SEQ ID NO:1920:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1920:

UUGAUCUCUG AUGAGGCCGA AAGGCCGAAA ACAUUG 36

(2) INFORMATION FOR SEQ ID NO:1921:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1921:

UUGAUCUCUG AUGAGGCCGA AAGGCCGAAA ACAUUG 36

(2) INFORMATION FOR SEQ ID NO:1922:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:1922:

UUGAUCUCUG AUGAGGCCGA AAGGCCGAAA ACAUUG 36

(2) INFORMATION FOR SEQ ID NO:1923:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:1923:

UUGAUCUCUG AUGAGGCCGA AAGGCCGAAA ACAUUG 36

(2) INFORMATION FOR SEQ ID NO:1924:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:1924:

UGUCCUUCUG AUGAGGCCGA AAGGCCGAAA UCUGAA 36

(2) INFORMATION FOR SEQ ID NO:1925:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:1925:

UGUCCUUCUG AUGAGGCCGA AAGGCCGAAA UCUGAA 36

(2) INFORMATION FOR SEQ ID NO:1926:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:1926:

AUCAUACCUG AUGAGGCCGA AAGGCCGAAA GCCCAU 36

(2) INFORMATION FOR SEQ ID NO:1927:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:1927:

AUCAUACCUG AUGAGGCCGA AAGGCCGAAA GCCCAU 36

(2) INFORMATION FOR SEQ ID NO:1928:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:1928:

| | |
|---|---|
| AUCAUACCUG AUGAGGCCGA AAGGCCGAAA GCCCAU | 36 |

(2) INFORMATION FOR SEQ ID NO:1929:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1929:

| | |
|---|---|
| ACAAUCACUG AUGAGGCCGA AAGGCCGAAA CGAGCC | 36 |

(2) INFORMATION FOR SEQ ID NO:1930:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1930:

| | |
|---|---|
| ACAAUCACUG AUGAGGCCGA AAGGCCGAAA CGAGCC | 36 |

(2) INFORMATION FOR SEQ ID NO:1931:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1931:

| | |
|---|---|
| UGUAUAACUG AUGAGGCCGA AAGGCCGAAA CAAUCA | 36 |

(2) INFORMATION FOR SEQ ID NO:1932:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1932:

| | |
|---|---|
| UGUAUAACUG AUGAGGCCGA AAGGCCGAAA CAAUCA | 36 |

(2) INFORMATION FOR SEQ ID NO:1933:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1933:

| | |
|---|---|
| UUUGUAUCUG AUGAGGCCGA AAGGCCGAAA AACAAU | 36 |

(2) INFORMATION FOR SEQ ID NO:1934:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:1934:

| | |
|---|---|
| UUUGUAUCUG AUGAGGCCGA AAGGCCGAAA AACAAU | 36 |

( 2 ) INFORMATION FOR SEQ ID NO:1935:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1935:

UUUUGUACUG AUGAGGCCGA AAGGCCGAAA AAACAA   36

( 2 ) INFORMATION FOR SEQ ID NO:1936:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1936:

UUUUGUACUG AUGAGGCCGA AAGGCCGAAA AAACAA   36

( 2 ) INFORMATION FOR SEQ ID NO:1937:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1937:

UUUUGUACUG AUGAGGCCGA AAGGCCGAAA AAACAA   36

( 2 ) INFORMATION FOR SEQ ID NO:1938:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1938:

GGAGGAUCUG AUGAGGCCGA AAGGCCGAAA UUGAUC   36

( 2 ) INFORMATION FOR SEQ ID NO:1939:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1939:

UGGAGGACUG AUGAGGCCGA AAGGCCGAAA AUUGAU   36

( 2 ) INFORMATION FOR SEQ ID NO:1940:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1940:

GUUGGAGCUG AUGAGGCCGA AAGGCCGAAA UAAUUG   36

( 2 ) INFORMATION FOR SEQ ID NO:1941:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1941:

UCUGUUGCUG AUGAGGCCGA AAGGCCGAAA GGAUAA      36

( 2 ) INFORMATION FOR SEQ ID NO:1942:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1942:

UCUGUUGCUG AUGAGGCCGA AAGGCCGAAA GGAUAA      36

( 2 ) INFORMATION FOR SEQ ID NO:1943:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1943:

UCUGUUGCUG AUGAGGCCGA AAGGCCGAAA GGAUAA      36

( 2 ) INFORMATION FOR SEQ ID NO:1944:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1944:

UCUGUUGCUG AUGAGGCCGA AAGGCCGAAA GGAUAA      36

( 2 ) INFORMATION FOR SEQ ID NO:1945:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1945:

GAUCACUCUG AUGAGGCCGA AAGGCCGAAA CAGUUC      36

( 2 ) INFORMATION FOR SEQ ID NO:1946:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1946:

AGUUGGCCUG AUGAGGCCGA AAGGCCGAAA UCACUG      36

( 2 ) INFORMATION FOR SEQ ID NO:1947:

( i ) SEQUENCE CHARACTERISTICS:

(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:1947:

UUCACUGCUG AUGAGGCCGA AAGGCCGAAA GUUGGC 36

(2) INFORMATION FOR SEQ ID NO:1948:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:1948:

GUUCACUCUG AUGAGGCCGA AAGGCCGAAA AGUUGG 36

(2) INFORMATION FOR SEQ ID NO:1949:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:1949:

GUUCACUCUG AUGAGGCCGA AAGGCCGAAA AGUUGG 36

(2) INFORMATION FOR SEQ ID NO:1950:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:1950:

CCAGUUUCUG AUGAGGCCGA AAGGCCGAAA UUUCAG 36

(2) INFORMATION FOR SEQ ID NO:1951:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:1951:

ACAUUCUCUG AUGAGGCCGA AAGGCCGAAA GCCAGU 36

(2) INFORMATION FOR SEQ ID NO:1952:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:1952:

UUCCUGUCUG AUGAGGCCGA AAGGCCGAAA CAUUCU 36

(2) INFORMATION FOR SEQ ID NO:1953:

(i) SEQUENCE CHARACTERISTICS:
(A) LENGTH: 36 base pairs
(B) TYPE: nucleic acid (C) STRANDEDNESS: single
(D) TOPOLOGY: linear (xi) SEQUENCE DESCRIPTION: SEQ ID NO:1953:

UAUGCCACUG AUGAGGCCGA AAGGCCGAAA AUUUCC 36

(2) INFORMATION FOR SEQ ID NO:1954:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:1954:

UAUGCCACUG AUGAGGCCGA AAGGCCGAAA AUUUCC 36

(2) INFORMATION FOR SEQ ID NO:1955:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:1955:

UCAAAUUCUG AUGAGGCCGA AAGGCCGAAA UGCCAG 36

(2) INFORMATION FOR SEQ ID NO:1956:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:1956:

CAGGUCACUG AUGAGGCCGA AAGGCCGAAA UUUAUG 36

(2) INFORMATION FOR SEQ ID NO:1957:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:1957:

GCAGGUCCUG AUGAGGCCGA AAGGCCGAAA AUUUAU 36

(2) INFORMATION FOR SEQ ID NO:1958:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:1958:

CCUUGCUCUG AUGAGGCCGA AAGGCCGAAA GACGUG 36

(2) INFORMATION FOR SEQ ID NO:1959:

(i) SEQUENCE CHARACTERISTICS:
(A) LENGTH: 36 base pairs
(B) TYPE: nucleic acid
(C) STRANDEDNESS: single
(D) TOPOLOGY: linear ( x i ) SEQUENCE DESCRIPTION: SEQ ID NO:1959:

UUCGGGUCUG AUGAGGCCGA AAGGCCGAAA CCUUGC　　　　36

( 2 ) INFORMATION FOR SEQ ID NO:1960:

( i ) SEQUENCE CHARACTERISTICS:
　　　　( A ) LENGTH: 36 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:1960:

AUCUUCUCUG AUGAGGCCGA AAGGCCGAAA GGUUUC　　　　36

( 2 ) INFORMATION FOR SEQ ID NO:1961:

( i ) SEQUENCE CHARACTERISTICS:
　　　　( A ) LENGTH: 36 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:1961:

CAGAAAACUG AUGAGGCCGA AAGGCCGAAA CAUCUU　　　　36

( 2 ) INFORMATION FOR SEQ ID NO:1962:

( i ) SEQUENCE CHARACTERISTICS:
　　　　( A ) LENGTH: 36 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:1962:

UUAUCAGCUG AUGAGGCCGA AAGGCCGAAA AAUACA　　　　36

( 2 ) INFORMATION FOR SEQ ID NO:1963:

( i ) SEQUENCE CHARACTERISTICS:
　　　　( A ) LENGTH: 36 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:1963:

AUUAGUUCUG AUGAGGCCGA AAGGCCGAAA AUUAGU　　　　36

( 2 ) INFORMATION FOR SEQ ID NO:1964:

( i ) SEQUENCE CHARACTERISTICS:
　　　　( A ) LENGTH: 36 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:1964:

UACUCAUCUG AUGAGGCCGA AAGGCCGAAA GUUGAA　　　　36

( 2 ) INFORMATION FOR SEQ ID NO:1965:

( i ) SEQUENCE CHARACTERISTICS:
　　　　( A ) LENGTH: 36 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:1965:

UACUCAUCUG AUGAGGCCGA AAGGCCGAAA GUUGAA                    36

( 2 ) INFORMATION FOR SEQ ID NO:1966:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1966:

AUCACCACUG AUGAGGCCGA AAGGCCGAAA CUCAUU                    36

( 2 ) INFORMATION FOR SEQ ID NO:1967:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1967:

CUUGUGACUG AUGAGGCCGA AAGGCCGAAA UCUGCA                    36

( 2 ) INFORMATION FOR SEQ ID NO:1968:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1968:

AUCUUGUCUG AUGAGGCCGA AAGGCCGAAA UAUCUG                    36

( 2 ) INFORMATION FOR SEQ ID NO:1969:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1969:

AUCUUGUCUG AUGAGGCCGA AAGGCCGAAA UAUCUG                    36

( 2 ) INFORMATION FOR SEQ ID NO:1970:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1970:

AUCUUGUCUG AUGAGGCCGA AAGGCCGAAA UAUCUG                    36

( 2 ) INFORMATION FOR SEQ ID NO:1971:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1971:

AUCUUGUCUG AUGAGGCCGA AAGGCCGAAA UAUCUG                    36

( 2 ) INFORMATION FOR SEQ ID NO:1972:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1972:

GUGACAUCUG AUGAGGCCGA AAGGCCGAAA UCUUGU     36

( 2 ) INFORMATION FOR SEQ ID NO:1973:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1973:

GUGACAUCUG AUGAGGCCGA AAGGCCGAAA UCUUGU     36

( 2 ) INFORMATION FOR SEQ ID NO:1974:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1974:

GUUCUGUCUG AUGAGGCCGA AAGGCCGAAA CAUUAU     36

( 2 ) INFORMATION FOR SEQ ID NO:1975:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1975:

GUUCUGUCUG AUGAGGCCGA AAGGCCGAAA CAUUAU     36

( 2 ) INFORMATION FOR SEQ ID NO:1976:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1976:

GUUCUGUCUG AUGAGGCCGA AAGGCCGAAA CAUUAU     36

( 2 ) INFORMATION FOR SEQ ID NO:1977:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1977:

GAUACUGCUG AUGAGGCCGA AAGGCCGAAA CAGUUC     36

( 2 ) INFORMATION FOR SEQ ID NO:1978:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1978:

AGAUACUCUG AUGAGGCCGA AAGGCCGAAA ACAGUU      36

( 2 ) INFORMATION FOR SEQ ID NO:1979:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1979:

AGAUACUCUG AUGAGGCCGA AAGGCCGAAA ACAGUU      36

( 2 ) INFORMATION FOR SEQ ID NO:1980:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1980:

GCUGUUGCUG AUGAGGCCGA AAGGCCGAAA GAUACU      36

( 2 ) INFORMATION FOR SEQ ID NO:1981:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1981:

GCUGUUGCUG AUGAGGCCGA AAGGCCGAAA GAUACU      36

( 2 ) INFORMATION FOR SEQ ID NO:1982:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1982:

GCUGUUGCUG AUGAGGCCGA AAGGCCGAAA GAUACU      36

( 2 ) INFORMATION FOR SEQ ID NO:1983:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1983:

AAAGAGACUG AUGAGGCCGA AAGGCCGAAA GGCUGU      36

( 2 ) INFORMATION FOR SEQ ID NO:1984:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1984:

AAAGAGACUG AUGAGGCCGA AAGGCCGAAA GGCUGU 36

( 2 ) INFORMATION FOR SEQ ID NO:1985:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1985:

UGAAAGACUG AUGAGGCCGA AAGGCCGAAA GAGGCU 36

( 2 ) INFORMATION FOR SEQ ID NO:1986:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1986:

UGAAAGACUG AUGAGGCCGA AAGGCCGAAA GAGGCU 36

( 2 ) INFORMATION FOR SEQ ID NO:1987:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1987:

GGAAUGACUG AUGAGGCCGA AAGGCCGAAA GAGAGA 36

( 2 ) INFORMATION FOR SEQ ID NO:1988:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1988:

GGAAUGACUG AUGAGGCCGA AAGGCCGAAA GAGAGA 36

( 2 ) INFORMATION FOR SEQ ID NO:1989:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1989:

GGGAAUGCUG AUGAGGCCGA AAGGCCGAAA AGAGAG 36

( 2 ) INFORMATION FOR SEQ ID NO:1990:

( i ) SEQUENCE CHARACTERISTICS:
  ( A ) LENGTH: 36 base pairs (B) TYPE: nucleic acid
(C) STRANDEDNESS: single
(D) TOPOLOGY: linear (xi) SEQUENCE DESCRIPTION: SEQ ID NO:1990:

CGGGAAUCUG AUGAGGCCGA AAGGCCGAAA AAGAGA                36

(2) INFORMATION FOR SEQ ID NO:1991:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:1991:

CGGGAAUCUG AUGAGGCCGA AAGGCCGAAA AAGAGA                36

(2) INFORMATION FOR SEQ ID NO:1992:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:1992:

CGGGAAUCUG AUGAGGCCGA AAGGCCGAAA AAGAGA                36

(2) INFORMATION FOR SEQ ID NO:1993:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:1993:

AUCCGGGCUG AUGAGGCCGA AAGGCCGAAA UGAAAG                36

(2) INFORMATION FOR SEQ ID NO:1994:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:1994:

AUCCGGGCUG AUGAGGCCGA AAGGCCGAAA UGAAAG                36

(2) INFORMATION FOR SEQ ID NO:1995:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:1995:

AUCCGGGCUG AUGAGGCCGA AAGGCCGAAA UGAAAG                36

(2) INFORMATION FOR SEQ ID NO:1996:

(i) SEQUENCE CHARACTERISTICS:
(A) LENGTH: 36 base pairs
(B) TYPE: nucleic acid
(C) STRANDEDNESS: single ( D ) TOPOLOGY: linear ( x i ) SEQUENCE DESCRIPTION: SEQ ID NO:1996:

AUCCGGGCUG AUGAGGCCGA AAGGCCGAAA UGAAAG     36

( 2 ) INFORMATION FOR SEQ ID NO:1997:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1997:

AUCCGGGCUG AUGAGGCCGA AAGGCCGAAA UGAAAG     36

( 2 ) INFORMATION FOR SEQ ID NO:1998:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1998:

CAUCCGGCUG AUGAGGCCGA AAGGCCGAAA AUGAAA     36

( 2 ) INFORMATION FOR SEQ ID NO:1999:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1999:

CAUCCGGCUG AUGAGGCCGA AAGGCCGAAA AUGAAA     36

( 2 ) INFORMATION FOR SEQ ID NO:2000:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2000:

ACGGUCACUG AUGAGGCCGA AAGGCCGAAA UGCCAC     36

( 2 ) INFORMATION FOR SEQ ID NO:2001:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2001:

ACGGUCACUG AUGAGGCCGA AAGGCCGAAA UGCCAC     36

( 2 ) INFORMATION FOR SEQ ID NO:2002:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2002:

CACACACCUG AUGAGGCCGA AAGGCCGAAA CGGUCA   36

( 2 ) INFORMATION FOR SEQ ID NO:2003:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2003:

UUUCCAGCUG AUGAGGCCGA AAGGCCGAAA CACACA   36

( 2 ) INFORMATION FOR SEQ ID NO:2004:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2004:

UUUCCAGCUG AUGAGGCCGA AAGGCCGAAA CACACA   36

( 2 ) INFORMATION FOR SEQ ID NO:2005:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2005:

GUUUCCACUG AUGAGGCCGA AAGGCCGAAA ACACAC   36

( 2 ) INFORMATION FOR SEQ ID NO:2006:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2006:

GUUUCCACUG AUGAGGCCGA AAGGCCGAAA ACACAC   36

( 2 ) INFORMATION FOR SEQ ID NO:2007:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2007:

UGGAGGACUG AUGAGGCCGA AAGGCCGAAA UCUUCA   36

( 2 ) INFORMATION FOR SEQ ID NO:2008:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2008:

```
AGGUUUGCUG  AUGAGGCCGA  AAGGCCGAAA  GGAAAU                              36
```

( 2 ) INFORMATION FOR SEQ ID NO:2009:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2009:

```
UGAAAUUCUG  AUGAGGCCGA  AAGGCCGAAA  GAGGUU                              36
```

( 2 ) INFORMATION FOR SEQ ID NO:2010:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2010:

```
AACUCUUCUG  AUGAGGCCGA  AAGGCCGAAA  GUGAAA                              36
```

( 2 ) INFORMATION FOR SEQ ID NO:2011:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2011:

```
AGAUGGACUG  AUGAGGCCGA  AAGGCCGAAA  CUCUUG                              36
```

( 2 ) INFORMATION FOR SEQ ID NO:2012:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2012:

```
AGAUGGACUG  AUGAGGCCGA  AAGGCCGAAA  CUCUUG                              36
```

( 2 ) INFORMATION FOR SEQ ID NO:2013:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2013:

```
GAGAUGGCUG  AUGAGGCCGA  AAGGCCGAAA  ACUCUU                              36
```

( 2 ) INFORMATION FOR SEQ ID NO:2014:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2014:

```
UUGAGGACUG  AUGAGGCCGA  AAGGCCGAAA  UGGAAA                              36
```

( 2 ) INFORMATION FOR SEQ ID NO:2015:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2015:

UUGAGGACUG AUGAGGCCGA AAGGCCGAAA UGGAAA    36

( 2 ) INFORMATION FOR SEQ ID NO:2016:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2016:

GUUUGAGCUG AUGAGGCCGA AAGGCCGAAA GAUGGA    36

( 2 ) INFORMATION FOR SEQ ID NO:2017:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2017:

AAGCUGUCUG AUGAGGCCGA AAGGCCGAAA UCUCCU    36

( 2 ) INFORMATION FOR SEQ ID NO:2018:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2018:

AAGCUGUCUG AUGAGGCCGA AAGGCCGAAA UCUCCU    36

( 2 ) INFORMATION FOR SEQ ID NO:2019:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2019:

GAAGCUGCUG AUGAGGCCGA AAGGCCGAAA AUCUCC    36

( 2 ) INFORMATION FOR SEQ ID NO:2020:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2020:

CCACAGUCUG AUGAGGCCGA AAGGCCGAAA CUGAAG    36

( 2 ) INFORMATION FOR SEQ ID NO:2021:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2021:

CAAGGAGCUG AUGAGGCCGA AAGGCCGAAA GGGCCA    36

( 2 ) INFORMATION FOR SEQ ID NO:2022:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2022:

CAAGGAGCUG AUGAGGCCGA AAGGCCGAAA GGGCCA    36

( 2 ) INFORMATION FOR SEQ ID NO:2023:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2023:

CAAUGAUCUG AUGAGGCCGA AAGGCCGAAA GCAGCA    36

( 2 ) INFORMATION FOR SEQ ID NO:2024:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2024:

GCGUUACCUG AUGAGGCCGA AAGGCCGAAA UCCCGC    36

( 2 ) INFORMATION FOR SEQ ID NO:2025:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2025:

UCAGGUUCUG AUGAGGCCGA AAGGCCGAAA UAGUCU    36

( 2 ) INFORMATION FOR SEQ ID NO:2026:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2026:

GGGGUUCCUG AUGAGGCCGA AAGGCCGAAA GUUCCU    36

( 2 ) INFORMATION FOR SEQ ID NO:2027:

( i ) SEQUENCE CHARACTERISTICS:

( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2027:

UUUUGCUCUG AUGAGGCCGA AAGGCCGAAA AGCAAU    36

( 2 ) INFORMATION FOR SEQ ID NO:2028:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2028:

AAUUUUCUG AUGAGGCCGA AAGGCCGAAA CUCUUU    36

( 2 ) INFORMATION FOR SEQ ID NO:2029:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2029:

CAAUUUCUG AUGAGGCCGA AAGGCCGAAA ACUCUU    36

( 2 ) INFORMATION FOR SEQ ID NO:2030:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2030:

GCAAAGCCUG AUGAGGCCGA AAGGCCGAAA UUUUUA    36

( 2 ) INFORMATION FOR SEQ ID NO:2031:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2031:

UUCUGAGCUG AUGAGGCCGA AAGGCCGAAA ACUCUG    36

( 2 ) INFORMATION FOR SEQ ID NO:2032:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2032:

GAAUUCUCUG AUGAGGCCGA AAGGCCGAAA GAAACU    36

( 2 ) INFORMATION FOR SEQ ID NO:2033:

( i ) SEQUENCE CHARACTERISTICS:
        ( A ) LENGTH: 36 base pairs
        ( B ) TYPE: nucleic acid ( C ) STRANDEDNESS: single
                ( D ) TOPOLOGY: linear ( x i ) SEQUENCE DESCRIPTION: SEQ ID NO:2033:

AUUUUUGCUG  AUGAGGCCGA  AAGGCCGAAA  UUCUGA                                              36

( 2 ) INFORMATION FOR SEQ ID NO:2034:

( i ) SEQUENCE CHARACTERISTICS:
                ( A ) LENGTH: 36 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:2034:

AUUUUUGCUG  AUGAGGCCGA  AAGGCCGAAA  UUCUGA                                              36

( 2 ) INFORMATION FOR SEQ ID NO:2035:

( i ) SEQUENCE CHARACTERISTICS:
                ( A ) LENGTH: 36 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:2035:

AUUUUUGCUG  AUGAGGCCGA  AAGGCCGAAA  UUCUGA                                              36

( 2 ) INFORMATION FOR SEQ ID NO:2036:

( i ) SEQUENCE CHARACTERISTICS:
                ( A ) LENGTH: 36 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:2036:

AGCUGAGCUG  AUGAGGCCGA  AAGGCCGAAA  CAUUUU                                              36

( 2 ) INFORMATION FOR SEQ ID NO:2037:

( i ) SEQUENCE CHARACTERISTICS:
                ( A ) LENGTH: 36 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:2037:

CAGCUGACUG  AUGAGGCCGA  AAGGCCGAAA  ACAUUU                                              36

( 2 ) INFORMATION FOR SEQ ID NO:2038:

( i ) SEQUENCE CHARACTERISTICS:
                ( A ) LENGTH: 36 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:2038:

ACUGUAGCUG  AUGAGGCCGA  AAGGCCGAAA  UUCCAA                                              36

( 2 ) INFORMATION FOR SEQ ID NO:2039:

( i ) SEQUENCE CHARACTERISTICS:
                ( A ) LENGTH: 36 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:2039:

ACUGUAGCUG AUGAGGCCGA AAGGCCGAAA UUCCAA 36

( 2 ) INFORMATION FOR SEQ ID NO:2040:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2040:

UCAACUGCUG AUGAGGCCGA AAGGCCGAAA GAAUUC 36

( 2 ) INFORMATION FOR SEQ ID NO:2041:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2041:

UCAACUGCUG AUGAGGCCGA AAGGCCGAAA GAAUUC 36

( 2 ) INFORMATION FOR SEQ ID NO:2042:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2042:

CUUUAAUCUG AUGAGGCCGA AAGGCCGAAA UUCAAC 36

( 2 ) INFORMATION FOR SEQ ID NO:2043:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2043:

GUUCUUUCUG AUGAGGCCGA AAGGCCGAAA UUAUUC 36

( 2 ) INFORMATION FOR SEQ ID NO:2044:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2044:

UGUUCUUCUG AUGAGGCCGA AAGGCCGAAA AUUAUU 36

( 2 ) INFORMATION FOR SEQ ID NO:2045:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2045:

```
CCUCGCUCGG GCGCC                                                    15
```

( 2 ) INFORMATION FOR SEQ ID NO:2046:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2046:

```
CAGUGGUCCU GCCGC                                                    15
```

( 2 ) INFORMATION FOR SEQ ID NO:2047:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2047:

```
GCCUGGUCUC ACCUC                                                    15
```

( 2 ) INFORMATION FOR SEQ ID NO:2048:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2048:

```
CUGGUCUCAC CUCGC                                                    15
```

( 2 ) INFORMATION FOR SEQ ID NO:2049:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2049:

```
CUCACCUCGC CAUGG                                                    15
```

( 2 ) INFORMATION FOR SEQ ID NO:2050:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2050:

```
CCAUGGUUCG UCUGC                                                    15
```

( 2 ) INFORMATION FOR SEQ ID NO:2051:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2051:

```
CAUGGUUCGU CUGCC                                                    15
```

( 2 ) INFORMATION FOR SEQ ID NO:2052:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2052:

GGUUCGUCUG CCUCU 15

( 2 ) INFORMATION FOR SEQ ID NO:2053:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2053:

UCUGCCUCUG CAGUG 15

( 2 ) INFORMATION FOR SEQ ID NO:2054:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2054:

AGUGCGUCCU CUGGG 15

( 2 ) INFORMATION FOR SEQ ID NO:2055:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2055:

GCGUCCUCUG GGGCU 15

( 2 ) INFORMATION FOR SEQ ID NO:2056:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2056:

GGCUGCUUGC UGACC 15

( 2 ) INFORMATION FOR SEQ ID NO:2057:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2057:

CCGCUGUCCA UCCAG 15

( 2 ) INFORMATION FOR SEQ ID NO:2058:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2058:

UGUCCAUCCA GAACC　　　　　　　　　　　　　　　　　　　　　　15

( 2 ) INFORMATION FOR SEQ ID NO:2059:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2059:

AAACAGUACC UAAUA　　　　　　　　　　　　　　　　　　　　　　15

( 2 ) INFORMATION FOR SEQ ID NO:2060:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2060:

AGUACCUAAU AAACA　　　　　　　　　　　　　　　　　　　　　　15

( 2 ) INFORMATION FOR SEQ ID NO:2061:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2061:

ACCUAAUAAA CAGUC　　　　　　　　　　　　　　　　　　　　　　15

( 2 ) INFORMATION FOR SEQ ID NO:2062:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2062:

AAACAGUCAG UGCUG　　　　　　　　　　　　　　　　　　　　　　15

( 2 ) INFORMATION FOR SEQ ID NO:2063:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2063:

GUGCUGUUCU UUGUG　　　　　　　　　　　　　　　　　　　　　　15

( 2 ) INFORMATION FOR SEQ ID NO:2064:

( i ) SEQUENCE CHARACTERISTICS:
   ( A ) LENGTH: 15 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:2064:

UGCUGUUCUU UGUGC 15

( 2 ) INFORMATION FOR SEQ ID NO:2065:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:2065:

CUGUUCUUUG UGCCA 15

( 2 ) INFORMATION FOR SEQ ID NO:2066:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:2066:

UGUUCUUUGU GCCAG 15

( 2 ) INFORMATION FOR SEQ ID NO:2067:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:2067:

ACAGAGUUCA CUGAA 15

( 2 ) INFORMATION FOR SEQ ID NO:2068:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:2068:

CAGAGUUCAC UGAAA 15

( 2 ) INFORMATION FOR SEQ ID NO:2069:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:2069:

AAUGCCUUCC UUGCG 15

( 2 ) INFORMATION FOR SEQ ID NO:2070:

( i ) SEQUENCE CHARACTERISTICS:
      ( A ) LENGTH: 15 base pairs (B) TYPE: nucleic acid
            (C) STRANDEDNESS: single
            (D) TOPOLOGY: linear (xi) SEQUENCE DESCRIPTION: SEQ ID NO:2070:

AUGCCUUCCU UGCGG                                                                                    15

(2) INFORMATION FOR SEQ ID NO:2071:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO:2071:

CCUUCCUUGC GGUGA                                                                                    15

(2) INFORMATION FOR SEQ ID NO:2072:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO:2072:

AGCGAAUUCC UAGAC                                                                                    15

(2) INFORMATION FOR SEQ ID NO:2073:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO:2073:

GCGAAUUCCU AGACA                                                                                    15

(2) INFORMATION FOR SEQ ID NO:2074:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO:2074:

AAUUCCUAGA CACCU                                                                                    15

(2) INFORMATION FOR SEQ ID NO:2075:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO:2075:

CACAAAUACU GCGAC                                                                                    15

(2) INFORMATION FOR SEQ ID NO:2076:

(i) SEQUENCE CHARACTERISTICS:
            (A) LENGTH: 15 base pairs
            (B) TYPE: nucleic acid
            (C) STRANDEDNESS: single (D) TOPOLOGY: linear (xi) SEQUENCE DESCRIPTION: SEQ ID NO:2076:

CCAACCUAGG GCUUC 15

(2) INFORMATION FOR SEQ ID NO:2077:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:2077:

UAGGGCUUCG GGUCC 15

(2) INFORMATION FOR SEQ ID NO:2078:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:2078:

AGGGCUUCGG GUCCA 15

(2) INFORMATION FOR SEQ ID NO:2079:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:2079:

UUCGGGUCCA GCAGA 15

(2) INFORMATION FOR SEQ ID NO:2080:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:2080:

GGCACCUCAG AAACA 15

(2) INFORMATION FOR SEQ ID NO:2081:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:2081:

ACACCAUCUG CACCU 15

(2) INFORMATION FOR SEQ ID NO:2082:

(i) SEQUENCE CHARACTERISTICS:
(A) LENGTH: 15 base pairs
(B) TYPE: nucleic acid
(C) STRANDEDNESS: single
(D) TOPOLOGY: linear ( x i ) SEQUENCE DESCRIPTION: SEQ ID NO:2082:

GCACUGUACG AGUGA 15

( 2 ) INFORMATION FOR SEQ ID NO:2083:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2083:

GCUGUGUCCU GCACC 15

( 2 ) INFORMATION FOR SEQ ID NO:2084:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2084:

CACCGCUCAU GCUCG 15

( 2 ) INFORMATION FOR SEQ ID NO:2085:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2085:

UCAUGCUCGC CCGGC 15

( 2 ) INFORMATION FOR SEQ ID NO:2086:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2086:

CCCGGCUUUG GGGUC 15

( 2 ) INFORMATION FOR SEQ ID NO:2087:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2087:

CCGGCUUUGG GGUCA 15

( 2 ) INFORMATION FOR SEQ ID NO:2088:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2088:

UUGGGGUCAA GCAGA 15

(2) INFORMATION FOR SEQ ID NO:2089:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:2089:

AGCAGAUUGC UACAG 15

(2) INFORMATION FOR SEQ ID NO:2090:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:2090:

GAUUGCUACA GGGGU 15

(2) INFORMATION FOR SEQ ID NO:2091:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:2091:

CAGGGGUUUC UGAUA 15

(2) INFORMATION FOR SEQ ID NO:2092:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:2092:

AGGGGUUUCU GAUAC 15

(2) INFORMATION FOR SEQ ID NO:2093:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:2093:

GGGGUUUCUG AUACC 15

(2) INFORMATION FOR SEQ ID NO:2094:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:2094:

UUCUGAUACC AUCUG 15

( 2 ) INFORMATION FOR SEQ ID NO:2095:

( i ) SEQUENCE CHARACTERISTICS:
　　　　　　　( A ) LENGTH: 15 base pairs
　　　　　　　( B ) TYPE: nucleic acid
　　　　　　　( C ) STRANDEDNESS: single
　　　　　　　( D ) TOPOLOGY: linear ( x i ) SEQUENCE DESCRIPTION: SEQ ID NO:2095:

AUACCAUCUG CGAGC                                                                                                                                   1 5

( 2 ) INFORMATION FOR SEQ ID NO:2096:

( i ) SEQUENCE CHARACTERISTICS:
　　　　　　　( A ) LENGTH: 15 base pairs
　　　　　　　( B ) TYPE: nucleic acid
　　　　　　　( C ) STRANDEDNESS: single
　　　　　　　( D ) TOPOLOGY: linear ( x i ) SEQUENCE DESCRIPTION: SEQ ID NO:2096:

GCCCAGUCGG CUUCU                                                                                                                                   1 5

( 2 ) INFORMATION FOR SEQ ID NO:2097:

( i ) SEQUENCE CHARACTERISTICS:
　　　　　　　( A ) LENGTH: 15 base pairs
　　　　　　　( B ) TYPE: nucleic acid
　　　　　　　( C ) STRANDEDNESS: single
　　　　　　　( D ) TOPOLOGY: linear ( x i ) SEQUENCE DESCRIPTION: SEQ ID NO:2097:

GUCGGCUUCU UCUCC                                                                                                                                   1 5

( 2 ) INFORMATION FOR SEQ ID NO:2098:

( i ) SEQUENCE CHARACTERISTICS:
　　　　　　　( A ) LENGTH: 15 base pairs
　　　　　　　( B ) TYPE: nucleic acid
　　　　　　　( C ) STRANDEDNESS: single
　　　　　　　( D ) TOPOLOGY: linear ( x i ) SEQUENCE DESCRIPTION: SEQ ID NO:2098:

UCGGCUUCUU CUCCA                                                                                                                                   1 5

( 2 ) INFORMATION FOR SEQ ID NO:2099:

( i ) SEQUENCE CHARACTERISTICS:
　　　　　　　( A ) LENGTH: 15 base pairs
　　　　　　　( B ) TYPE: nucleic acid
　　　　　　　( C ) STRANDEDNESS: single
　　　　　　　( D ) TOPOLOGY: linear ( x i ) SEQUENCE DESCRIPTION: SEQ ID NO:2099:

GGCUUCUUCU CCAAU                                                                                                                                   1 5

( 2 ) INFORMATION FOR SEQ ID NO:2100:

( i ) SEQUENCE CHARACTERISTICS:
　　　　　　　( A ) LENGTH: 15 base pairs
　　　　　　　( B ) TYPE: nucleic acid
　　　　　　　( C ) STRANDEDNESS: single
　　　　　　　( D ) TOPOLOGY: linear ( x i ) SEQUENCE DESCRIPTION: SEQ ID NO:2100:

GCUUCUUCUC CAAUG                                                                                                                                   1 5

( 2 ) INFORMATION FOR SEQ ID NO:2101:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2101:

UUCUUCUCCA AUGUG 15

( 2 ) INFORMATION FOR SEQ ID NO:2102:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2102:

AAUGUGUCAU CUGCU 15

( 2 ) INFORMATION FOR SEQ ID NO:2103:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2103:

GUGUCAUCUG CUUUC 15

( 2 ) INFORMATION FOR SEQ ID NO:2104:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2104:

AUCUGCUUUC GAAAA 15

( 2 ) INFORMATION FOR SEQ ID NO:2105:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2105:

UCUGCUUUCG AAAAA 15

( 2 ) INFORMATION FOR SEQ ID NO:2106:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2106:

CUGCUUUCGA AAAAU 15

( 2 ) INFORMATION FOR SEQ ID NO:2107:

( i ) SEQUENCE CHARACTERISTICS:

( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2107:

AAAAUGUCAC CCUUG 15

( 2 ) INFORMATION FOR SEQ ID NO:2108:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2108:

UCACCCUUGG ACAAG 15

( 2 ) INFORMATION FOR SEQ ID NO:2109:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2109:

ACCUGGUUGU GCAAC 15

( 2 ) INFORMATION FOR SEQ ID NO:2110:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2110:

CUGAUGUUGU CUGUG 15

( 2 ) INFORMATION FOR SEQ ID NO:2111:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2111:

AUGUUGUCUG UGGUC 15

( 2 ) INFORMATION FOR SEQ ID NO:2112:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2112:

CUGUGGUCCC CAGGA 15

( 2 ) INFORMATION FOR SEQ ID NO:2113:

( i ) SEQUENCE CHARACTERISTICS:
        ( A ) LENGTH: 15 base pairs
        ( B ) TYPE: nucleic acid ( C ) STRANDEDNESS: single
( D ) TOPOLOGY: linear ( x i ) SEQUENCE DESCRIPTION: SEQ ID NO:2113:

CCAGGAUCGG CUGAG  15

( 2 ) INFORMATION FOR SEQ ID NO:2114:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:2114:

UGGUGAUCCC CAUCA  15

( 2 ) INFORMATION FOR SEQ ID NO:2115:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:2115:

UCCCCAUCAU CUUCG  15

( 2 ) INFORMATION FOR SEQ ID NO:2116:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:2116:

CCAUCAUCUU CGGGA  15

( 2 ) INFORMATION FOR SEQ ID NO:2117:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:2117:

AUCAUCUUCG GGAUC  15

( 2 ) INFORMATION FOR SEQ ID NO:2118:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:2118:

UCAUCUUCGG GAUCC  15

( 2 ) INFORMATION FOR SEQ ID NO:2119:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:2119:

UCGGGAUCCU GUUUG 15

( 2 ) INFORMATION FOR SEQ ID NO:2120:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2120:

AUCCUGUUUG CCAUC 15

( 2 ) INFORMATION FOR SEQ ID NO:2121:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2121:

UCCUGUUUGC CAUCC 15

( 2 ) INFORMATION FOR SEQ ID NO:2122:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2122:

UUGCCAUCCU CUUGG 15

( 2 ) INFORMATION FOR SEQ ID NO:2123:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2123:

CCAUCCUCUU GGUGC 15

( 2 ) INFORMATION FOR SEQ ID NO:2124:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2124:

AUCCUCUUGG UGCUG 15

( 2 ) INFORMATION FOR SEQ ID NO:2125:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2125:

UGCUGGUCUU UAUCA 15

(2) INFORMATION FOR SEQ ID NO:2126:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:2126:

CUGGUCUUUA UCAAA 15

(2) INFORMATION FOR SEQ ID NO:2127:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:2127:

UGGUCUUUAU CAAAA 15

(2) INFORMATION FOR SEQ ID NO:2128:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:2128:

GGUCUUUAUC AAAAA 15

(2) INFORMATION FOR SEQ ID NO:2129:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:2129:

UCUUUAUCAA AAAGG 15

(2) INFORMATION FOR SEQ ID NO:2130:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:2130:

AACCAUAAG GCCCC 15

(2) INFORMATION FOR SEQ ID NO:2131:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:2131:

AGGAGAUCAA UUUUC 15

( 2 ) INFORMATION FOR SEQ ID NO:2132:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2132:

GAUCAAUUUU CCCGA 15

( 2 ) INFORMATION FOR SEQ ID NO:2133:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2133:

AUCAAUUUUC CCGAC 15

( 2 ) INFORMATION FOR SEQ ID NO:2134:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2134:

UCAAUUUCC CGACG 15

( 2 ) INFORMATION FOR SEQ ID NO:2135:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2135:

CAAUUUCCC GACGA 15

( 2 ) INFORMATION FOR SEQ ID NO:2136:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2136:

CGACGAUCUU CCUGG 15

( 2 ) INFORMATION FOR SEQ ID NO:2137:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2137:

ACGAUCUUCC UGGCU 15

( 2 ) INFORMATION FOR SEQ ID NO:2138:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2138:

CGAUCUUCCU GGCUC　　　　　　　　　　　　　　　　　　　15

( 2 ) INFORMATION FOR SEQ ID NO:2139:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2139:

CCUGGCUCCA ACACU　　　　　　　　　　　　　　　　　　　15

( 2 ) INFORMATION FOR SEQ ID NO:2140:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2140:

UGCUGCUCCA GUGCA　　　　　　　　　　　　　　　　　　　15

( 2 ) INFORMATION FOR SEQ ID NO:2141:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2141:

GGAGACUUUA CAUGG　　　　　　　　　　　　　　　　　　　15

( 2 ) INFORMATION FOR SEQ ID NO:2142:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2142:

GAGACUUUAC AUGGA　　　　　　　　　　　　　　　　　　　15

( 2 ) INFORMATION FOR SEQ ID NO:2143:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2143:

AGACUUUACA UGGAU　　　　　　　　　　　　　　　　　　　15

( 2 ) INFORMATION FOR SEQ ID NO:2144:

( i ) SEQUENCE CHARACTERISTICS:
 ( A ) LENGTH: 15 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:2144:

AACCGGUCAC CCAGG 15

( 2 ) INFORMATION FOR SEQ ID NO:2145:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:2145:

AGAGAGUCGC AUCUC 15

( 2 ) INFORMATION FOR SEQ ID NO:2146:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:2146:

GUCGCAUCUC AGUGC 15

( 2 ) INFORMATION FOR SEQ ID NO:2147:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:2147:

CGCAUCUCAG UGCAG 15

( 2 ) INFORMATION FOR SEQ ID NO:2148:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:2148:

AGGCAGUUGG CCAGA 15

( 2 ) INFORMATION FOR SEQ ID NO:2149:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:2149:

GGGAGCUAUG CCCAG 15

( 2 ) INFORMATION FOR SEQ ID NO:2150:

( i ) SEQUENCE CHARACTERISTICS:
  ( A ) LENGTH: 15 base pairs (B) TYPE: nucleic acid
(C) STRANDEDNESS: single
(D) TOPOLOGY: linear (xi) SEQUENCE DESCRIPTION: SEQ ID NO:2150:

GCCCAGUCAG UGCCA                                                                15

(2) INFORMATION FOR SEQ ID NO:2151:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:2151:

GGCGCCCUG AUGAGGCCGA AAGGCCGAAA GCGAGG                                           36

(2) INFORMATION FOR SEQ ID NO:2152:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:2152:

GCGGCAGCUG AUGAGGCCGA AAGGCCGAAA CCACUG                                          36

(2) INFORMATION FOR SEQ ID NO:2153:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:2153:

GAGGUGACUG AUGAGGCCGA AAGGCCGAAA CCAGGC                                          36

(2) INFORMATION FOR SEQ ID NO:2154:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:2154:

GCGAGGUCUG AUGAGGCCGA AAGGCCGAAA GACCAG                                          36

(2) INFORMATION FOR SEQ ID NO:2155:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:2155:

CCAUGGCCUG AUGAGGCCGA AAGGCCGAAA GGUGAG                                          36

(2) INFORMATION FOR SEQ ID NO:2156:

(i) SEQUENCE CHARACTERISTICS:
(A) LENGTH: 36 base pairs
(B) TYPE: nucleic acid
(C) STRANDEDNESS: single -continued (D) TOPOLOGY: linear (xi) SEQUENCE DESCRIPTION: SEQ ID NO:2156:

GCAGACGCUG AUGAGGCCGA AAGGCCGAAA CCAUGG 36

(2) INFORMATION FOR SEQ ID NO:2157:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:2157:

GGCAGACCUG AUGAGGCCGA AAGGCCGAAA ACCAUG 36

(2) INFORMATION FOR SEQ ID NO:2158:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:2158:

AGAGGCACUG AUGAGGCCGA AAGGCCGAAA CGAACC 36

(2) INFORMATION FOR SEQ ID NO:2159:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:2159:

CACUGCACUG AUGAGGCCGA AAGGCCGAAA GGCAGA 36

(2) INFORMATION FOR SEQ ID NO:2160:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:2160:

CCCAGAGCUG AUGAGGCCGA AAGGCCGAAA CGCACU 36

(2) INFORMATION FOR SEQ ID NO:2161:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:2161:

AGCCCCACUG AUGAGGCCGA AAGGCCGAAA GGACGC 36

(2) INFORMATION FOR SEQ ID NO:2162:

(i) SEQUENCE CHARACTERISTICS:
        (A) LENGTH: 36 base pairs
        (B) TYPE: nucleic acid
        (C) STRANDEDNESS: single
        (D) TOPOLOGY: linear ( x i ) SEQUENCE DESCRIPTION: SEQ ID NO:2162:

GGUCAGCCUG AUGAGGCCGA AAGGCCGAAA GCAGCC 36

( 2 ) INFORMATION FOR SEQ ID NO:2163:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2163:

CUGGAUGCUG AUGAGGCCGA AAGGCCGAAA CAGCGG 36

( 2 ) INFORMATION FOR SEQ ID NO:2164:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2164:

GGUUCUGCUG AUGAGGCCGA AAGGCCGAAA UGGACA 36

( 2 ) INFORMATION FOR SEQ ID NO:2165:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2165:

UAUUAGGCUG AUGAGGCCGA AAGGCCGAAA CUGUUU 36

( 2 ) INFORMATION FOR SEQ ID NO:2166:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2166:

UGUUUAUCUG AUGAGGCCGA AAGGCCGAAA GGUACU 36

( 2 ) INFORMATION FOR SEQ ID NO:2167:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2167:

GACUGUUCUG AUGAGGCCGA AAGGCCGAAA UUAGGU 36

( 2 ) INFORMATION FOR SEQ ID NO:2168:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2168:

CAGCACUCUG AUGAGGCCGA AAGGCCGAAA CUGUUU 36

(2) INFORMATION FOR SEQ ID NO:2169:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:2169:

CACAAAGCUG AUGAGGCCGA AAGGCCGAAA CAGCAC 36

(2) INFORMATION FOR SEQ ID NO:2170:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:2170:

GCACAAACUG AUGAGGCCGA AAGGCCGAAA ACAGCA 36

(2) INFORMATION FOR SEQ ID NO:2171:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:2171:

UGGCACACUG AUGAGGCCGA AAGGCCGAAA GAACAG 36

(2) INFORMATION FOR SEQ ID NO:2172:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:2172:

CUGGCACCUG AUGAGGCCGA AAGGCCGAAA AGAACA 36

(2) INFORMATION FOR SEQ ID NO:2173:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:2173:

UUCAGUGCUG AUGAGGCCGA AAGGCCGAAA CUCUGU 36

(2) INFORMATION FOR SEQ ID NO:2174:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:2174:

UUUCAGUCUG AUGAGGCCGA AAGGCCGAAA ACUCUG 36

( 2 ) INFORMATION FOR SEQ ID NO:2175:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2175:

CGCAAGGCUG AUGAGGCCGA AAGGCCGAAA GGCAUU      36

( 2 ) INFORMATION FOR SEQ ID NO:2176:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2176:

CCGCAAGCUG AUGAGGCCGA AAGGCCGAAA AGGCAU      36

( 2 ) INFORMATION FOR SEQ ID NO:2177:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2177:

UCACCGCCUG AUGAGGCCGA AAGGCCGAAA GGAAGG      36

( 2 ) INFORMATION FOR SEQ ID NO:2178:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2178:

GUCUAGGCUG AUGAGGCCGA AAGGCCGAAA UUCGCU      36

( 2 ) INFORMATION FOR SEQ ID NO:2179:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2179:

UGUCUAGCUG AUGAGGCCGA AAGGCCGAAA AUUCGC      36

( 2 ) INFORMATION FOR SEQ ID NO:2180:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2180:

AGGUGUCCUG AUGAGGCCGA AAGGCCGAAA GGAAUU      36

( 2 ) INFORMATION FOR SEQ ID NO:2181:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2181:

GUCGCAGCUG AUGAGGCCGA AAGGCCGAAA UUUGUG 36

( 2 ) INFORMATION FOR SEQ ID NO:2182:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2182:

GAAGCCCUG AUGAGGCCGA AAGGCCGAAA GGUUGG 36

( 2 ) INFORMATION FOR SEQ ID NO:2183:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2183:

GGACCCGCUG AUGAGGCCGA AAGGCCGAAA GCCCUA 36

( 2 ) INFORMATION FOR SEQ ID NO:2184:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2184:

UGGACCCCUG AUGAGGCCGA AAGGCCGAAA AGCCCU 36

( 2 ) INFORMATION FOR SEQ ID NO:2185:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2185:

UCUGCUGCUG AUGAGGCCGA AAGGCCGAAA CCCGAA 36

( 2 ) INFORMATION FOR SEQ ID NO:2186:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2186:

UGUUUCUCUG AUGAGGCCGA AAGGCCGAAA GGUGCC 36

( 2 ) INFORMATION FOR SEQ ID NO:2187:

( i ) SEQUENCE CHARACTERISTICS:

( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:2187:

AGGUGCACUG AUGAGGCCGA AAGGCCGAAA UGGUGU    36

( 2 ) INFORMATION FOR SEQ ID NO:2188:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:2188:

UCACUCGCUG AUGAGGCCGA AAGGCCGAAA CAGUGC    36

( 2 ) INFORMATION FOR SEQ ID NO:2189:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:2189:

GGUGCAGCUG AUGAGGCCGA AAGGCCGAAA CACAGC    36

( 2 ) INFORMATION FOR SEQ ID NO:2190:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:2190:

CGAGCAUCUG AUGAGGCCGA AAGGCCGAAA GCGGUG    36

( 2 ) INFORMATION FOR SEQ ID NO:2191:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:2191:

GCCGGGCCUG AUGAGGCCGA AAGGCCGAAA GCAUGA    36

( 2 ) INFORMATION FOR SEQ ID NO:2192:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:2192:

GACCCCACUG AUGAGGCCGA AAGGCCGAAA GCCGGG    36

( 2 ) INFORMATION FOR SEQ ID NO:2193:

( i ) SEQUENCE CHARACTERISTICS:
( A ) LENGTH: 36 base pairs
( B ) TYPE: nucleic acid (C) STRANDEDNESS: single
(D) TOPOLOGY: linear (x i) SEQUENCE DESCRIPTION: SEQ ID NO:2193:

UGACCCCUG AUGAGGCCGA AAGGCCGAAA AGCCGG    36

(2) INFORMATION FOR SEQ ID NO:2194:

(i) SEQUENCE CHARACTERISTICS:
(A) LENGTH: 36 base pairs
(B) TYPE: nucleic acid
(C) STRANDEDNESS: single
(D) TOPOLOGY: linear (x i) SEQUENCE DESCRIPTION: SEQ ID NO:2194:

UCUGCUUCUG AUGAGGCCGA AAGGCCGAAA CCCCAA    36

(2) INFORMATION FOR SEQ ID NO:2195:

(i) SEQUENCE CHARACTERISTICS:
(A) LENGTH: 36 base pairs
(B) TYPE: nucleic acid
(C) STRANDEDNESS: single
(D) TOPOLOGY: linear (x i) SEQUENCE DESCRIPTION: SEQ ID NO:2195:

CUGUAGCCUG AUGAGGCCGA AAGGCCGAAA UCUGCU    36

(2) INFORMATION FOR SEQ ID NO:2196:

(i) SEQUENCE CHARACTERISTICS:
(A) LENGTH: 36 base pairs
(B) TYPE: nucleic acid
(C) STRANDEDNESS: single
(D) TOPOLOGY: linear (x i) SEQUENCE DESCRIPTION: SEQ ID NO:2196:

ACCCCUGCUG AUGAGGCCGA AAGGCCGAAA GCAAUC    36

(2) INFORMATION FOR SEQ ID NO:2197:

(i) SEQUENCE CHARACTERISTICS:
(A) LENGTH: 36 base pairs
(B) TYPE: nucleic acid
(C) STRANDEDNESS: single
(D) TOPOLOGY: linear (x i) SEQUENCE DESCRIPTION: SEQ ID NO:2197:

UAUCAGACUG AUGAGGCCGA AAGGCCGAAA CCCCUG    36

(2) INFORMATION FOR SEQ ID NO:2198:

(i) SEQUENCE CHARACTERISTICS:
(A) LENGTH: 36 base pairs
(B) TYPE: nucleic acid
(C) STRANDEDNESS: single
(D) TOPOLOGY: linear (x i) SEQUENCE DESCRIPTION: SEQ ID NO:2198:

GUAUCAGCUG AUGAGGCCGA AAGGCCGAAA ACCCCU    36

(2) INFORMATION FOR SEQ ID NO:2199:

(i) SEQUENCE CHARACTERISTICS:
(A) LENGTH: 36 base pairs
(B) TYPE: nucleic acid
(C) STRANDEDNESS: single
(D) TOPOLOGY: linear ( x i ) SEQUENCE DESCRIPTION: SEQ ID NO:2199:

GGUAUCACUG AUGAGGCCGA AAGGCCGAAA AACCCC 36

( 2 ) INFORMATION FOR SEQ ID NO:2200:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2200:

CAGAUGGCUG AUGAGGCCGA AAGGCCGAAA UCAGAA 36

( 2 ) INFORMATION FOR SEQ ID NO:2201:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2201:

GCUCGCACUG AUGAGGCCGA AAGGCCGAAA UGGUAU 36

( 2 ) INFORMATION FOR SEQ ID NO:2202:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2202:

AGAAGCCCUG AUGAGGCCGA AAGGCCGAAA CUGGGC 36

( 2 ) INFORMATION FOR SEQ ID NO:2203:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2203:

GGAGAAGCUG AUGAGGCCGA AAGGCCGAAA GCCGAC 36

( 2 ) INFORMATION FOR SEQ ID NO:2204:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2204:

UGGAGAACUG AUGAGGCCGA AAGGCCGAAA AGCCGA 36

( 2 ) INFORMATION FOR SEQ ID NO:2205:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2205:

AUUGGAGCUG AUGAGGCCGA AAGGCCGAAA GAAGCC 36

(2) INFORMATION FOR SEQ ID NO:2206:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:2206:

CAUUGGACUG AUGAGGCCGA AAGGCCGAAA AGAAGC 36

(2) INFORMATION FOR SEQ ID NO:2207:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:2207:

CACAUUGCUG AUGAGGCCGA AAGGCCGAAA GAAGAA 36

(2) INFORMATION FOR SEQ ID NO:2208:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:2208:

AGCAGAUCUG AUGAGGCCGA AAGGCCGAAA CACAUU 36

(2) INFORMATION FOR SEQ ID NO:2209:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:2209:

GAAAGCACUG AUGAGGCCGA AAGGCCGAAA UGACAC 36

(2) INFORMATION FOR SEQ ID NO:2210:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:2210:

UUUUCGACUG AUGAGGCCGA AAGGCCGAAA GCAGAU 36

(2) INFORMATION FOR SEQ ID NO:2211:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:2211:

UUUUUCGCUG AUGAGGCCGA AAGGCCGAAA AGCAGA 36

( 2 ) INFORMATION FOR SEQ ID NO:2212:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2212:

AUUUUCCUG AUGAGGCCGA AAGGCCGAAA AAGCAG    36

( 2 ) INFORMATION FOR SEQ ID NO:2213:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2213:

CAAGGGUCUG AUGAGGCCGA AAGGCCGAAA CAUUUU    36

( 2 ) INFORMATION FOR SEQ ID NO:2214:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2214:

CUUGUCCCUG AUGAGGCCGA AAGGCCGAAA GGGUGA    36

( 2 ) INFORMATION FOR SEQ ID NO:2215:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2215:

GUUGCACCUG AUGAGGCCGA AAGGCCGAAA CCAGGU    36

( 2 ) INFORMATION FOR SEQ ID NO:2216:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2216:

CACAGACCUG AUGAGGCCGA AAGGCCGAAA CAUCAG    36

( 2 ) INFORMATION FOR SEQ ID NO:2217:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2217:

GACCACACUG AUGAGGCCGA AAGGCCGAAA CAACAU    36

( 2 ) INFORMATION FOR SEQ ID NO:2218:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2218:

UCCUGGGCUG AUGAGGCCGA AAGGCCGAAA CCACAG      36

( 2 ) INFORMATION FOR SEQ ID NO:2219:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2219:

CUCAGCCCUG AUGAGGCCGA AAGGCCGAAA UCCUGG      36

( 2 ) INFORMATION FOR SEQ ID NO:2220:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2220:

UGAUGGGCUG AUGAGGCCGA AAGGCCGAAA UCACCA      36

( 2 ) INFORMATION FOR SEQ ID NO:2221:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2221:

CGAAGAUCUG AUGAGGCCGA AAGGCCGAAA UGGGGA      36

( 2 ) INFORMATION FOR SEQ ID NO:2222:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2222:

UCCCGAACUG AUGAGGCCGA AAGGCCGAAA UGAUGG      36

( 2 ) INFORMATION FOR SEQ ID NO:2223:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2223:

GAUCCCGCUG AUGAGGCCGA AAGGCCGAAA GAUGAU      36

( 2 ) INFORMATION FOR SEQ ID NO:2224:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2224:

GGAUCCCUG AUGAGGCCGA AAGGCCGAAA AGAUGA      36

( 2 ) INFORMATION FOR SEQ ID NO:2225:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2225:

CAAACAGCUG AUGAGGCCGA AAGGCCGAAA UCCCGA      36

( 2 ) INFORMATION FOR SEQ ID NO:2226:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2226:

GAUGGCACUG AUGAGGCCGA AAGGCCGAAA CAGGAU      36

( 2 ) INFORMATION FOR SEQ ID NO:2227:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2227:

GGAUGGCCUG AUGAGGCCGA AAGGCCGAAA ACAGGA      36

( 2 ) INFORMATION FOR SEQ ID NO:2228:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2228:

CCAAGAGCUG AUGAGGCCGA AAGGCCGAAA UGGCAA      36

( 2 ) INFORMATION FOR SEQ ID NO:2229:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2229:

GCACCAACUG AUGAGGCCGA AAGGCCGAAA GGAUGG      36

( 2 ) INFORMATION FOR SEQ ID NO:2230:

( i ) SEQUENCE CHARACTERISTICS:
    ( A ) LENGTH: 36 base pairs ( B ) TYPE: nucleic acid
            ( C ) STRANDEDNESS: single
            ( D ) TOPOLOGY: linear ( x i ) SEQUENCE DESCRIPTION: SEQ ID NO:2230:

CAGCACCCUG AUGAGGCCGA AAGGCCGAAA GAGGAU                        36

( 2 ) INFORMATION FOR SEQ ID NO:2231:

( i ) SEQUENCE CHARACTERISTICS:
            ( A ) LENGTH: 36 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:2231:

UGAUAAACUG AUGAGGCCGA AAGGCCGAAA CCAGCA                        36

( 2 ) INFORMATION FOR SEQ ID NO:2232:

( i ) SEQUENCE CHARACTERISTICS:
            ( A ) LENGTH: 36 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:2232:

UUUGAUACUG AUGAGGCCGA AAGGCCGAAA GACCAG                        36

( 2 ) INFORMATION FOR SEQ ID NO:2233:

( i ) SEQUENCE CHARACTERISTICS:
            ( A ) LENGTH: 36 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:2233:

UUUUGAUCUG AUGAGGCCGA AAGGCCGAAA AGACCA                        36

( 2 ) INFORMATION FOR SEQ ID NO:2234:

( i ) SEQUENCE CHARACTERISTICS:
            ( A ) LENGTH: 36 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:2234:

UUUUUGACUG AUGAGGCCGA AAGGCCGAAA AAGACC                        36

( 2 ) INFORMATION FOR SEQ ID NO:2235:

( i ) SEQUENCE CHARACTERISTICS:
            ( A ) LENGTH: 36 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:2235:

CCUUUUUCUG AUGAGGCCGA AAGGCCGAAA UAAAGA                        36

( 2 ) INFORMATION FOR SEQ ID NO:2236:

( i ) SEQUENCE CHARACTERISTICS:
            ( A ) LENGTH: 36 base pairs
            ( B ) TYPE: nucleic acid
            ( C ) STRANDEDNESS: single (D) TOPOLOGY: linear (xi) SEQUENCE DESCRIPTION: SEQ ID NO:2236:

GGGGCCUCUG AUGAGGCCGA AAGGCCGAAA UUGGUU 36

(2) INFORMATION FOR SEQ ID NO:2237:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:2237:

GAAAAUUCUG AUGAGGCCGA AAGGCCGAAA UCUCCU 36

(2) INFORMATION FOR SEQ ID NO:2238:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:2238:

UCGGGAACUG AUGAGGCCGA AAGGCCGAAA UUGAUC 36

(2) INFORMATION FOR SEQ ID NO:2239:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:2239:

GUCGGGACUG AUGAGGCCGA AAGGCCGAAA AUUGAU 36

(2) INFORMATION FOR SEQ ID NO:2240:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:2240:

CGUCGGGCUG AUGAGGCCGA AAGGCCGAAA AAUUGA 36

(2) INFORMATION FOR SEQ ID NO:2241:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:2241:

UCGUCGGCUG AUGAGGCCGA AAGGCCGAAA AAAUUG 36

(2) INFORMATION FOR SEQ ID NO:2242:

(i) SEQUENCE CHARACTERISTICS:
        (A) LENGTH: 36 base pairs
        (B) TYPE: nucleic acid
        (C) STRANDEDNESS: single
        (D) TOPOLOGY: linear ( x i ) SEQUENCE DESCRIPTION: SEQ ID NO:2242:

CCAGGAACUG AUGAGGCCGA AAGGCCGAAA UCGUCG　　　　　　　　　　　　36

( 2 ) INFORMATION FOR SEQ ID NO:2243:

( i ) SEQUENCE CHARACTERISTICS:
　　　　( A ) LENGTH: 36 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:2243:

AGCCAGGCUG AUGAGGCCGA AAGGCCGAAA GAUCGU　　　　　　　　　　　　36

( 2 ) INFORMATION FOR SEQ ID NO:2244:

( i ) SEQUENCE CHARACTERISTICS:
　　　　( A ) LENGTH: 36 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:2244:

GAGCCAGCUG AUGAGGCCGA AAGGCCGAAA AGAUCG　　　　　　　　　　　　36

( 2 ) INFORMATION FOR SEQ ID NO:2245:

( i ) SEQUENCE CHARACTERISTICS:
　　　　( A ) LENGTH: 36 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:2245:

AGUGUUGCUG AUGAGGCCGA AAGGCCGAAA GCCAGG　　　　　　　　　　　　36

( 2 ) INFORMATION FOR SEQ ID NO:2246:

( i ) SEQUENCE CHARACTERISTICS:
　　　　( A ) LENGTH: 36 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:2246:

UGCACUGCUG AUGAGGCCGA AAGGCCGAAA GCAGCA　　　　　　　　　　　　36

( 2 ) INFORMATION FOR SEQ ID NO:2247:

( i ) SEQUENCE CHARACTERISTICS:
　　　　( A ) LENGTH: 36 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:2247:

CCAUGUACUG AUGAGGCCGA AAGGCCGAAA GUCUCC　　　　　　　　　　　　36

( 2 ) INFORMATION FOR SEQ ID NO:2248:

( i ) SEQUENCE CHARACTERISTICS:
　　　　( A ) LENGTH: 36 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:2248:

UCCAUGUCUG AUGAGGCCGA AAGGCCGAAA AGUCUC    36

( 2 ) INFORMATION FOR SEQ ID NO:2249:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2249:

AUCCAUGCUG AUGAGGCCGA AAGGCCGAAA AAGUCU    36

( 2 ) INFORMATION FOR SEQ ID NO:2250:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2250:

CCUGGGUCUG AUGAGGCCGA AAGGCCGAAA CCGGUU    36

( 2 ) INFORMATION FOR SEQ ID NO:2251:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2251:

GAGAUGCCUG AUGAGGCCGA AAGGCCGAAA CUCUCU    36

( 2 ) INFORMATION FOR SEQ ID NO:2252:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2252:

GCACUGACUG AUGAGGCCGA AAGGCCGAAA UGCGAC    36

( 2 ) INFORMATION FOR SEQ ID NO:2253:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2253:

CUGCACUCUG AUGAGGCCGA AAGGCCGAAA GAUGCG    36

( 2 ) INFORMATION FOR SEQ ID NO:2254:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2254:

UCUGGCCCUG AUGAGGCCGA AAGGCCGAAA CUGCCU    36

(2) INFORMATION FOR SEQ ID NO:2255:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:2255:

CUGGGCACUG AUGAGGCCGA AAGGCCGAAA GCUCCC    36

(2) INFORMATION FOR SEQ ID NO:2256:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:2256:

UGGCACUCUG AUGAGGCCGA AAGGCCGAAA CUGGGC    36

(2) INFORMATION FOR SEQ ID NO:2257:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:2257:

GGUGUCUUUG CCUCG    15

(2) INFORMATION FOR SEQ ID NO:2258:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:2258:

GGUGUCUUUG CCUCG    15

(2) INFORMATION FOR SEQ ID NO:2259:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:2259:

UUUGCCUCGG CUGUG    15

(2) INFORMATION FOR SEQ ID NO:2260:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:2260:

GCGCGCUAUG GGGCU    15

(2) INFORMATION FOR SEQ ID NO:2261:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2261:

CAGCGGUCCA UCUAG                    15

( 2 ) INFORMATION FOR SEQ ID NO:2262:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2262:

CAGCGGUCCA UCUAG                    15

( 2 ) INFORMATION FOR SEQ ID NO:2263:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2263:

GGUCCAUCUA GGGCA                    15

( 2 ) INFORMATION FOR SEQ ID NO:2264:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2264:

AGUGUGUUAC GUGCA                    15

( 2 ) INFORMATION FOR SEQ ID NO:2265:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2265:

AGUGUGUUAC GUGCA                    15

( 2 ) INFORMATION FOR SEQ ID NO:2266:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2266:

GUGUGUUACG UGCAG                    15

( 2 ) INFORMATION FOR SEQ ID NO:2267:

( i ) SEQUENCE CHARACTERISTICS:

(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:2267:

AAACAGUACC UCCAC 15

(2) INFORMATION FOR SEQ ID NO:2268:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:2268:

CUGUGAUUUG UGCCA 15

(2) INFORMATION FOR SEQ ID NO:2269:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:2269:

UGUGAUUUGU GCCAG 15

(2) INFORMATION FOR SEQ ID NO:2270:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:2270:

CAGCUCUUGA GAAGA 15

(2) INFORMATION FOR SEQ ID NO:2271:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:2271:

GGCGAAUUCU CAGCC 15

(2) INFORMATION FOR SEQ ID NO:2272:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:2272:

GCGAAUUCUC AGCCC 15

(2) INFORMATION FOR SEQ ID NO:2273:

(i) SEQUENCE CHARACTERISTICS:
(A) LENGTH: 15 base pairs
(B) TYPE: nucleic acid ( C ) STRANDEDNESS: single
( D ) TOPOLOGY: linear ( x i ) SEQUENCE DESCRIPTION: SEQ ID NO:2273:

GGGAGAUUCG CUGUC 15

( 2 ) INFORMATION FOR SEQ ID NO:2274:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:2274:

ACCCAAUCAA GGGCU 15

( 2 ) INFORMATION FOR SEQ ID NO:2275:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:2275:

ACCCAAUCAA GGGCU 15

( 2 ) INFORMATION FOR SEQ ID NO:2276:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:2276:

AAGGGCUUCG GGUUA 15

( 2 ) INFORMATION FOR SEQ ID NO:2277:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:2277:

AAGGGCUUCG GGUUA 15

( 2 ) INFORMATION FOR SEQ ID NO:2278:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:2278:

AGGGCUUCGG GUUAA 15

( 2 ) INFORMATION FOR SEQ ID NO:2279:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:2279:

UUCGGGUUAA GAAGG                                                            15

( 2 ) INFORMATION FOR SEQ ID NO:2280:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2280:

UUCGGGUUAA GAAGG                                                            15

( 2 ) INFORMATION FOR SEQ ID NO:2281:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2281:

ACACUGUCUG UACCU                                                            15

( 2 ) INFORMATION FOR SEQ ID NO:2282:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2282:

CAAGGAUUGC GAGGC                                                            15

( 2 ) INFORMATION FOR SEQ ID NO:2283:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2283:

CCUGUACCC UGGCU                                                             15

( 2 ) INFORMATION FOR SEQ ID NO:2284:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2284:

CCUGGCUUUG GAGUU                                                            15

( 2 ) INFORMATION FOR SEQ ID NO:2285:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2285:

CCUGGCUUUG GAGUU 15

(2) INFORMATION FOR SEQ ID NO:2286:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:2286:

CUGGCUUUGG AGUUA 15

(2) INFORMATION FOR SEQ ID NO:2287:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:2287:

CACUGAUACC GUCUG 15

(2) INFORMATION FOR SEQ ID NO:2288:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:2288:

AUACCGUCUG UCAUC 15

(2) INFORMATION FOR SEQ ID NO:2289:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:2289:

AUACCGUCUG UCAUC 15

(2) INFORMATION FOR SEQ ID NO:2290:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:2290:

CUGUCAUCCC UGCCC 15

(2) INFORMATION FOR SEQ ID NO:2291:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:2291:

GCCCAGUCGG CUUCU 15

( 2 ) INFORMATION FOR SEQ ID NO:2292:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2292:

GCCCAGUCGG CUUCU     15

( 2 ) INFORMATION FOR SEQ ID NO:2293:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2293:

GUCGGCUUCU UCUCC     15

( 2 ) INFORMATION FOR SEQ ID NO:2294:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2294:

UCGGCUUCUU CUCCA     15

( 2 ) INFORMATION FOR SEQ ID NO:2295:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2295:

GGCUUCUUCU CCAAU     15

( 2 ) INFORMATION FOR SEQ ID NO:2296:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2296:

GCUUCUUCUC CAAUC     15

( 2 ) INFORMATION FOR SEQ ID NO:2297:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2297:

UUCUUCUCCA AUCAG     15

( 2 ) INFORMATION FOR SEQ ID NO:2298:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2298:

AAUCAGUCAU CACUU                     15

( 2 ) INFORMATION FOR SEQ ID NO:2299:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2299:

AAUCAGUCAU CACUU                     15

( 2 ) INFORMATION FOR SEQ ID NO:2300:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2300:

CAUCACUUUU CGAAA                     15

( 2 ) INFORMATION FOR SEQ ID NO:2301:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2301:

AUCACUUUUC GAAAA                     15

( 2 ) INFORMATION FOR SEQ ID NO:2302:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2302:

UCACUUUUCG AAAAG                     15

( 2 ) INFORMATION FOR SEQ ID NO:2303:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2303:

UCACUUUUCG AAAAG                     15

( 2 ) INFORMATION FOR SEQ ID NO:2304:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2304:

AAAGUGUUAU CCCUG 15

( 2 ) INFORMATION FOR SEQ ID NO:2305:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2305:

CUAAUGUCAU CUGUG 15

( 2 ) INFORMATION FOR SEQ ID NO:2306:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2306:

AUGUCAUCUG UGGUU 15

( 2 ) INFORMATION FOR SEQ ID NO:2307:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2307:

GUGGUUUAAA GUCCC 15

( 2 ) INFORMATION FOR SEQ ID NO:2308:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2308:

GUGGUUUAAA GUCCC 15

( 2 ) INFORMATION FOR SEQ ID NO:2309:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2309:

UUAAAGUCCC GGAUG 15

( 2 ) INFORMATION FOR SEQ ID NO:2310:

( i ) SEQUENCE CHARACTERISTICS:
    ( A ) LENGTH: 15 base pairs

```
            ( B ) TYPE: nucleic acid
            ( C ) STRANDEDNESS: single
            ( D ) TOPOLOGY: linear ( x i ) SEQUENCE DESCRIPTION: SEQ ID NO:2310:

UGGGCAUCCU CAUCA                                                                        15

( 2 ) INFORMATION FOR SEQ ID NO:2311:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:2311:

UCCUCAUCAC CAUUU                                                                        15

( 2 ) INFORMATION FOR SEQ ID NO:2312:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:2312:

UCACCAUUUU CGGGG                                                                        15

( 2 ) INFORMATION FOR SEQ ID NO:2313:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:2313:

UCACCAUUUU CGGGG                                                                        15

( 2 ) INFORMATION FOR SEQ ID NO:2314:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:2314:

ACCAUUUUCG GGGUG                                                                        15

( 2 ) INFORMATION FOR SEQ ID NO:2315:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:2315:

CCAUUUUCGG GGUGU                                                                        15

( 2 ) INFORMATION FOR SEQ ID NO:2316:

( i ) SEQUENCE CHARACTERISTICS:
            ( A ) LENGTH: 15 base pairs
            ( B ) TYPE: nucleic acid
            ( C ) STRANDEDNESS: single
```

( D ) TOPOLOGY: linear ( x i ) SEQUENCE DESCRIPTION: SEQ ID NO:2316:

CCAUUUUCGG GGUGU                                                                                            15

( 2 ) INFORMATION FOR SEQ ID NO:2317:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:2317:

CCAUUUUCGG GGUGU                                                                                            15

( 2 ) INFORMATION FOR SEQ ID NO:2318:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:2318:

UGUUUCUCUA UAUCA                                                                                            15

( 2 ) INFORMATION FOR SEQ ID NO:2319:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:2319:

UUUCUCUAUA UCAAA                                                                                            15

( 2 ) INFORMATION FOR SEQ ID NO:2320:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:2320:

UCUCUAUAUC AAAAA                                                                                            15

( 2 ) INFORMATION FOR SEQ ID NO:2321:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:2321:

UCUAUAUCAA AAAGG                                                                                            15

( 2 ) INFORMATION FOR SEQ ID NO:2322:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:2322:

GGAAGAUUAU CCCGG                                                                                                   15

( 2 ) INFORMATION FOR SEQ ID NO:2323:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2323:

CGCUGCUCCA GUGCA                                                                                                   15

( 2 ) INFORMATION FOR SEQ ID NO:2324:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2324:

AGCCUGUCAC ACAGG                                                                                                   15

( 2 ) INFORMATION FOR SEQ ID NO:2325:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2325:

AGCCUGUCAC ACAGG                                                                                                   15

( 2 ) INFORMATION FOR SEQ ID NO:2326:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2326:

AGAGAGUCGC AUCUC                                                                                                   15

( 2 ) INFORMATION FOR SEQ ID NO:2327:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2327:

GUCGCAUCUC AGUGC                                                                                                   15

( 2 ) INFORMATION FOR SEQ ID NO:2328:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2328:

CGCAUCUCAG UGCAG 15

( 2 ) INFORMATION FOR SEQ ID NO:2329:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2329:

CCCUGGUCUG AACCC 15

( 2 ) INFORMATION FOR SEQ ID NO:2330:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2330:

GGCUGCUUGC UGACC 15

( 2 ) INFORMATION FOR SEQ ID NO:2331:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2331:

CUCAACUUGC UUUUU 15

( 2 ) INFORMATION FOR SEQ ID NO:2332:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2332:

UUGCUUUUUA AGGAU 15

( 2 ) INFORMATION FOR SEQ ID NO:2333:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2333:

UUGCUUUUUA AGGAU 15

( 2 ) INFORMATION FOR SEQ ID NO:2334:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2334:

GAAAGCUCGG GCAUC 15

( 2 ) INFORMATION FOR SEQ ID NO:2335:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2335:

CAGUGAUAUC UACCA 15

( 2 ) INFORMATION FOR SEQ ID NO:2336:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2336:

GAUAUCUACC AAGUG 15

( 2 ) INFORMATION FOR SEQ ID NO:2337:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2337:

CCAGAGUUGU CUUGC 15

( 2 ) INFORMATION FOR SEQ ID NO:2338:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2338:

GAGUUGUCUU GCUGC 15

( 2 ) INFORMATION FOR SEQ ID NO:2339:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2339:

GUUGCUUGC UGCGG 15

( 2 ) INFORMATION FOR SEQ ID NO:2340:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2340:

GCGGCGUUCA CUGUA 15

( 2 ) INFORMATION FOR SEQ ID NO:2341:

```
        ( i ) SEQUENCE CHARACTERISTICS:
                ( A ) LENGTH: 15 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:2341:

CGGCGUUCAC UGUAA                                                                            15

( 2 ) INFORMATION FOR SEQ ID NO:2342:

( i ) SEQUENCE CHARACTERISTICS:
                ( A ) LENGTH: 15 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:2342:

CGUGGCUACA GGAGU                                                                            15

( 2 ) INFORMATION FOR SEQ ID NO:2343:

( i ) SEQUENCE CHARACTERISTICS:
                ( A ) LENGTH: 15 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:2343:

CGUGGCUACA GGAGU                                                                            15

( 2 ) INFORMATION FOR SEQ ID NO:2344:

( i ) SEQUENCE CHARACTERISTICS:
                ( A ) LENGTH: 15 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:2344:

CGCAGCUUGU GCUCG                                                                            15

( 2 ) INFORMATION FOR SEQ ID NO:2345:

( i ) SEQUENCE CHARACTERISTICS:
                ( A ) LENGTH: 15 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:2345:

ACCUGGUUGC CAUCA                                                                            15

( 2 ) INFORMATION FOR SEQ ID NO:2346:

( i ) SEQUENCE CHARACTERISTICS:
                ( A ) LENGTH: 15 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:2346:

UGUAAUUAUU UAUAC                                                                            15

( 2 ) INFORMATION FOR SEQ ID NO:2347:

( i ) SEQUENCE CHARACTERISTICS:
```

( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:2347:

GGCAUCUCAG AAACU                    15

( 2 ) INFORMATION FOR SEQ ID NO:2348:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:2348:

GGCAUCUCAG AAACU                    15

( 2 ) INFORMATION FOR SEQ ID NO:2349:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:2349:

AGAAACUCUA GCAGG                    15

( 2 ) INFORMATION FOR SEQ ID NO:2350:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:2350:

AACAGGUAGU GGAAU                    15

( 2 ) INFORMATION FOR SEQ ID NO:2351:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:2351:

AGGAGCUUGC UGCCC                    15

( 2 ) INFORMATION FOR SEQ ID NO:2352:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:2352:

UUUUGAUCCC UGGGA                    15

( 2 ) INFORMATION FOR SEQ ID NO:2353:

( i ) SEQUENCE CHARACTERISTICS:
( A ) LENGTH: 15 base pairs
( B ) TYPE: nucleic acid ( C ) STRANDEDNESS: single
        ( D ) TOPOLOGY: linear ( x i ) SEQUENCE DESCRIPTION: SEQ ID NO:2353:

GGGACUUCAU GGUAA                                                                                        15

( 2 ) INFORMATION FOR SEQ ID NO:2354:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2354:

GGGACUUCAU GGUAA                                                                                        15

( 2 ) INFORMATION FOR SEQ ID NO:2355:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2355:

UUGUCAUUUG ACCUC                                                                                        15

( 2 ) INFORMATION FOR SEQ ID NO:2356:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2356:

GUAAUGUACC CCGUG                                                                                        15

( 2 ) INFORMATION FOR SEQ ID NO:2357:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2357:

CACAUAUCCU AAAAU                                                                                        15

( 2 ) INFORMATION FOR SEQ ID NO:2358:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2358:

GUGGUGUAUU GUAGA                                                                                        15

( 2 ) INFORMATION FOR SEQ ID NO:2359:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2359:

GUAUUGUAGA AAUUA                                                    15

( 2 ) INFORMATION FOR SEQ ID NO:2360:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2360:

AUUAUUUAAU CCGCC                                                    15

( 2 ) INFORMATION FOR SEQ ID NO:2361:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2361:

AUUAUUUAAU CCGCC                                                    15

( 2 ) INFORMATION FOR SEQ ID NO:2362:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2362:

CUGGGUUUCU ACCUG                                                    15

( 2 ) INFORMATION FOR SEQ ID NO:2363:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2363:

CGAGGCACUG AUGAGGCCGA AAGGCCGAAA GACACC                             36

( 2 ) INFORMATION FOR SEQ ID NO:2364:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2364:

CGAGGCACUG AUGAGGCCGA AAGGCCGAAA GACACC                             36

( 2 ) INFORMATION FOR SEQ ID NO:2365:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2365:

CACAGCCCUG AUGAGGCCGA AAGGCCGAAA GGCAAA    36

( 2 ) INFORMATION FOR SEQ ID NO:2366:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2366:

AGCCCCACUG AUGAGGCCGA AAGGCCGAAA GCGCGC    36

( 2 ) INFORMATION FOR SEQ ID NO:2367:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2367:

CUAGAUGCUG AUGAGGCCGA AAGGCCGAAA CCGCUG    36

( 2 ) INFORMATION FOR SEQ ID NO:2368:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2368:

CUAGAUGCUG AUGAGGCCGA AAGGCCGAAA CCGCUG    36

( 2 ) INFORMATION FOR SEQ ID NO:2369:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2369:

UGCCCUACUG AUGAGGCCGA AAGGCCGAAA UGGACC    36

( 2 ) INFORMATION FOR SEQ ID NO:2370:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2370:

UGCACGUCUG AUGAGGCCGA AAGGCCGAAA CACACU    36

( 2 ) INFORMATION FOR SEQ ID NO:2371:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2371:

UGCACGUCUG AUGAGGCCGA AAGGCCGAAA CACACU    36

( 2 ) INFORMATION FOR SEQ ID NO:2372:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2372:

CUGCACGCUG AUGAGGCCGA AAGGCCGAAA ACACAC        36

( 2 ) INFORMATION FOR SEQ ID NO:2373:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2373:

GUGGAGGCUG AUGAGGCCGA AAGGCCGAAA CUGUUU        36

( 2 ) INFORMATION FOR SEQ ID NO:2374:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2374:

UGGCACACUG AUGAGGCCGA AAGGCCGAAA UCACAG        36

( 2 ) INFORMATION FOR SEQ ID NO:2375:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2375:

CUGGCACCUG AUGAGGCCGA AAGGCCGAAA AUCACA        36

( 2 ) INFORMATION FOR SEQ ID NO:2376:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2376:

UCUUCUCCUG AUGAGGCCGA AAGGCCGAAA GAGCUG        36

( 2 ) INFORMATION FOR SEQ ID NO:2377:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2377:

GGCUGAGCUG AUGAGGCCGA AAGGCCGAAA UUCGCC        36

( 2 ) INFORMATION FOR SEQ ID NO:2378:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2378:

GGGCUGACUG AUGAGGCCGA AAGGCCGAAA AUUCGC    36

( 2 ) INFORMATION FOR SEQ ID NO:2379:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2379:

GACAGCGCUG AUGAGGCCGA AAGGCCGAAA UCUCCC    36

( 2 ) INFORMATION FOR SEQ ID NO:2380:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2380:

AGCCCUUCUG AUGAGGCCGA AAGGCCGAAA UUGGGU    36

( 2 ) INFORMATION FOR SEQ ID NO:2381:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2381:

AGCCCUUCUG AUGAGGCCGA AAGGCCGAAA UUGGGU    36

( 2 ) INFORMATION FOR SEQ ID NO:2382:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2382:

UAACCCGCUG AUGAGGCCGA AAGGCCGAAA GCCCUU    36

( 2 ) INFORMATION FOR SEQ ID NO:2383:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2383:

UAACCCGCUG AUGAGGCCGA AAGGCCGAAA GCCCUU    36

( 2 ) INFORMATION FOR SEQ ID NO:2384:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2384:

UUAACCCUG AUGAGGCCGA AAGGCCGAAA AGCCCU      36

( 2 ) INFORMATION FOR SEQ ID NO:2385:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2385:

CCUUCUUCUG AUGAGGCCGA AAGGCCGAAA CCCGAA      36

( 2 ) INFORMATION FOR SEQ ID NO:2386:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2386:

CCUUCUUCUG AUGAGGCCGA AAGGCCGAAA CCCGAA      36

( 2 ) INFORMATION FOR SEQ ID NO:2387:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2387:

AGGUACACUG AUGAGGCCGA AAGGCCGAAA CAGUGU      36

( 2 ) INFORMATION FOR SEQ ID NO:2388:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2388:

GCCUCGCCUG AUGAGGCCGA AAGGCCGAAA UCCUUG      36

( 2 ) INFORMATION FOR SEQ ID NO:2389:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2389:

AGCCAGGCUG AUGAGGCCGA AAGGCCGAAA UACAGG      36

( 2 ) INFORMATION FOR SEQ ID NO:2390:

( i ) SEQUENCE CHARACTERISTICS:
        ( A ) LENGTH: 36 base pairs (B) TYPE: nucleic acid
(C) STRANDEDNESS: single
(D) TOPOLOGY: linear (xi) SEQUENCE DESCRIPTION: SEQ ID NO:2390:

AACUCCACUG AUGAGGCCGA AAGGCCGAAA GCCAGG 36

(2) INFORMATION FOR SEQ ID NO:2391:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:2391:

AACUCCACUG AUGAGGCCGA AAGGCCGAAA GCCAGG 36

(2) INFORMATION FOR SEQ ID NO:2392:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:2392:

UAACUCCCUG AUGAGGCCGA AAGGCCGAAA AGCCAG 36

(2) INFORMATION FOR SEQ ID NO:2393:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:2393:

CAGACGGCUG AUGAGGCCGA AAGGCCGAAA UCAGUG 36

(2) INFORMATION FOR SEQ ID NO:2394:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:2394:

GAUGACACUG AUGAGGCCGA AAGGCCGAAA CGGUAU 36

(2) INFORMATION FOR SEQ ID NO:2395:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:2395:

GAUGACACUG AUGAGGCCGA AAGGCCGAAA CGGUAU 36

(2) INFORMATION FOR SEQ ID NO:2396:

(i) SEQUENCE CHARACTERISTICS:
(A) LENGTH: 36 base pairs
(B) TYPE: nucleic acid
(C) STRANDEDNESS: single -continued ( D ) TOPOLOGY: linear ( x i ) SEQUENCE DESCRIPTION: SEQ ID NO:2396:

GGGCAGGCUG AUGAGGCCGA AAGGCCGAAA UGACAG 36

( 2 ) INFORMATION FOR SEQ ID NO:2397:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2397:

AGAAGCCCUG AUGAGGCCGA AAGGCCGAAA CUGGGC 36

( 2 ) INFORMATION FOR SEQ ID NO:2398:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2398:

AGAAGCCCUG AUGAGGCCGA AAGGCCGAAA CUGGGC 36

( 2 ) INFORMATION FOR SEQ ID NO:2399:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2399:

GGAGAAGCUG AUGAGGCCGA AAGGCCGAAA GCCGAC 36

( 2 ) INFORMATION FOR SEQ ID NO:2400:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2400:

UGGAGAACUG AUGAGGCCGA AAGGCCGAAA AGCCGA 36

( 2 ) INFORMATION FOR SEQ ID NO:2401:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2401:

AUUGGAGCUG AUGAGGCCGA AAGGCCGAAA GAAGCC 36

( 2 ) INFORMATION FOR SEQ ID NO:2402:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2402:

GAUUGGACUG AUGAGGCCGA AAGGCCGAAA AGAAGC 36

( 2 ) INFORMATION FOR SEQ ID NO:2403:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2403:

CUGAUUGCUG AUGAGGCCGA AAGGCCGAAA GAAGAA 36

( 2 ) INFORMATION FOR SEQ ID NO:2404:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2404:

AAGUGAUCUG AUGAGGCCGA AAGGCCGAAA CUGAUU 36

( 2 ) INFORMATION FOR SEQ ID NO:2405:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2405:

AAGUGAUCUG AUGAGGCCGA AAGGCCGAAA CUGAUU 36

( 2 ) INFORMATION FOR SEQ ID NO:2406:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2406:

UUUCGAACUG AUGAGGCCGA AAGGCCGAAA GUGAUG 36

( 2 ) INFORMATION FOR SEQ ID NO:2407:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2407:

UUUUCGACUG AUGAGGCCGA AAGGCCGAAA AGUGAU 36

( 2 ) INFORMATION FOR SEQ ID NO:2408:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2408:

CUUUUCGCUG AUGAGGCCGA AAGGCCGAAA AAGUGA 36

( 2 ) INFORMATION FOR SEQ ID NO:2409:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2409:

CUUUUCGCUG AUGAGGCCGA AAGGCCGAAA AAGUGA 36

( 2 ) INFORMATION FOR SEQ ID NO:2410:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2410:

CAGGGAUCUG AUGAGGCCGA AAGGCCGAAA CACUUU 36

( 2 ) INFORMATION FOR SEQ ID NO:2411:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2411:

CACAGAUCUG AUGAGGCCGA AAGGCCGAAA CAUUAG 36

( 2 ) INFORMATION FOR SEQ ID NO:2412:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2412:

AACCACACUG AUGAGGCCGA AAGGCCGAAA UGACAU 36

( 2 ) INFORMATION FOR SEQ ID NO:2413:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2413:

GGGACUUCUG AUGAGGCCGA AAGGCCGAAA AACCAC 36

( 2 ) INFORMATION FOR SEQ ID NO:2414:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2414:

GGGACUUCUG AUGAGGCCGA AAGGCCGAAA AACCAC 36

( 2 ) INFORMATION FOR SEQ ID NO:2415:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2415:

CAUCCGGCUG AUGAGGCCGA AAGGCCGAAA CUUUAA    36

( 2 ) INFORMATION FOR SEQ ID NO:2416:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2416:

UGAUGAGCUG AUGAGGCCGA AAGGCCGAAA UGCCCA    36

( 2 ) INFORMATION FOR SEQ ID NO:2417:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2417:

AAAUGGUCUG AUGAGGCCGA AAGGCCGAAA UGAGGA    36

( 2 ) INFORMATION FOR SEQ ID NO:2418:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2418:

CCCCGAACUG AUGAGGCCGA AAGGCCGAAA UGGUGA    36

( 2 ) INFORMATION FOR SEQ ID NO:2419:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2419:

CCCCGAACUG AUGAGGCCGA AAGGCCGAAA UGGUGA    36

( 2 ) INFORMATION FOR SEQ ID NO:2420:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2420:

CACCCCGCUG AUGAGGCCGA AAGGCCGAAA AAUGGU    36

( 2 ) INFORMATION FOR SEQ ID NO:2421:

( i ) SEQUENCE CHARACTERISTICS:
   ( A ) LENGTH: 36 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:2421:

ACACCCCUG AUGAGGCCGA AAGGCCGAAA AAAUGG 36

( 2 ) INFORMATION FOR SEQ ID NO:2422:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:2422:

ACACCCCUG AUGAGGCCGA AAGGCCGAAA AAAUGG 36

( 2 ) INFORMATION FOR SEQ ID NO:2423:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:2423:

ACACCCCUG AUGAGGCCGA AAGGCCGAAA AAAUGG 36

( 2 ) INFORMATION FOR SEQ ID NO:2424:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:2424:

UGAUAUACUG AUGAGGCCGA AAGGCCGAAA GAAACA 36

( 2 ) INFORMATION FOR SEQ ID NO:2425:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:2425:

UUUGAUACUG AUGAGGCCGA AAGGCCGAAA GAGAAA 36

( 2 ) INFORMATION FOR SEQ ID NO:2426:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:2426:

UUUUUGACUG AUGAGGCCGA AAGGCCGAAA UAGAGA 36

( 2 ) INFORMATION FOR SEQ ID NO:2427:

( i ) SEQUENCE CHARACTERISTICS:

(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:2427:

CCUUUUUCUG AUGAGGCCGA AAGGCCGAAA UAUAGA 36

(2) INFORMATION FOR SEQ ID NO:2428:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:2428:

CCGGGAUCUG AUGAGGCCGA AAGGCCGAAA UCUUCC 36

(2) INFORMATION FOR SEQ ID NO:2429:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:2429:

UGCACUGCUG AUGAGGCCGA AAGGCCGAAA GCAGCG 36

(2) INFORMATION FOR SEQ ID NO:2430:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:2430:

CCUGUGUCUG AUGAGGCCGA AAGGCCGAAA CAGGCU 36

(2) INFORMATION FOR SEQ ID NO:2431:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:2431:

CCUGUGUCUG AUGAGGCCGA AAGGCCGAAA CAGGCU 36

(2) INFORMATION FOR SEQ ID NO:2432:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:2432:

GAGAUGCCUG AUGAGGCCGA AAGGCCGAAA CUCUCU 36

(2) INFORMATION FOR SEQ ID NO:2433:

(i) SEQUENCE CHARACTERISTICS:
(A) LENGTH: 36 base pairs
(B) TYPE: nucleic acid ( C ) STRANDEDNESS: single
( D ) TOPOLOGY: linear ( x i ) SEQUENCE DESCRIPTION: SEQ ID NO:2433:

GCACUGACUG AUGAGGCCGA AAGGCCGAAA UGCGAC        36

( 2 ) INFORMATION FOR SEQ ID NO:2434:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2434:

CUGCACUCUG AUGAGGCCGA AAGGCCGAAA GAUGCG        36

( 2 ) INFORMATION FOR SEQ ID NO:2435:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2435:

GGGUUCACUG AUGAGGCCGA AAGGCCGAAA CCAGGG        36

( 2 ) INFORMATION FOR SEQ ID NO:2436:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2436:

GGUCAGCCUG AUGAGGCCGA AAGGCCGAAA GCAGCC        36

( 2 ) INFORMATION FOR SEQ ID NO:2437:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2437:

AAAAAGCCUG AUGAGGCCGA AAGGCCGAAA GUUGAG        36

( 2 ) INFORMATION FOR SEQ ID NO:2438:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2438:

AUCCUUACUG AUGAGGCCGA AAGGCCGAAA AAGCAA        36

( 2 ) INFORMATION FOR SEQ ID NO:2439:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear (x i) SEQUENCE DESCRIPTION: SEQ ID NO:2439:

AUCCUUACUG AUGAGGCCGA AAGGCCGAAA AAGCAA 36

(2) INFORMATION FOR SEQ ID NO:2440:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:2440:

GAUGCCCUG AUGAGGCCGA AAGGCCGAAA GCUUUC 36

(2) INFORMATION FOR SEQ ID NO:2441:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:2441:

UGGUAGACUG AUGAGGCCGA AAGGCCGAAA UCACUG 36

(2) INFORMATION FOR SEQ ID NO:2442:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:2442:

CACUUGGCUG AUGAGGCCGA AAGGCCGAAA GAUAUC 36

(2) INFORMATION FOR SEQ ID NO:2443:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:2443:

GCAAGACCUG AUGAGGCCGA AAGGCCGAAA CUCUGG 36

(2) INFORMATION FOR SEQ ID NO:2444:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:2444:

GCAGCAACUG AUGAGGCCGA AAGGCCGAAA CAACUC 36

(2) INFORMATION FOR SEQ ID NO:2445:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:2445:

CCGCAGCCUG AUGAGGCCGA AAGGCCGAAA GACAAC                                36

( 2 ) INFORMATION FOR SEQ ID NO:2446:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2446:

UACAGUGCUG AUGAGGCCGA AAGGCCGAAA CGCCGC                                36

( 2 ) INFORMATION FOR SEQ ID NO:2447:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2447:

UUACAGUCUG AUGAGGCCGA AAGGCCGAAA ACGCCG                                36

( 2 ) INFORMATION FOR SEQ ID NO:2448:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2448:

ACUCCUGCUG AUGAGGCCGA AAGGCCGAAA GCCACG                                36

( 2 ) INFORMATION FOR SEQ ID NO:2449:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2449:

ACUCCUGCUG AUGAGGCCGA AAGGCCGAAA GCCACG                                36

( 2 ) INFORMATION FOR SEQ ID NO:2450:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2450:

CGAGCACCUG AUGAGGCCGA AAGGCCGAAA GCUGCG                                36

( 2 ) INFORMATION FOR SEQ ID NO:2451:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2451:

UGAUGGCCUG AUGAGGCCGA AAGGCCGAAA CCAGGU                                36

( 2 ) INFORMATION FOR SEQ ID NO:2452:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2452:

GUAUAAACUG AUGAGGCCGA AAGGCCGAAA AUUACA    36

( 2 ) INFORMATION FOR SEQ ID NO:2453:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2453:

AGUUUCUCUG AUGAGGCCGA AAGGCCGAAA GAUGCC    36

( 2 ) INFORMATION FOR SEQ ID NO:2454:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2454:

AGUUUCUCUG AUGAGGCCGA AAGGCCGAAA GAUGCC    36

( 2 ) INFORMATION FOR SEQ ID NO:2455:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2455:

CCUGCUACUG AUGAGGCCGA AAGGCCGAAA GUUUCU    36

( 2 ) INFORMATION FOR SEQ ID NO:2456:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2456:

AUUCCACCUG AUGAGGCCGA AAGGCCGAAA CCUGUU    36

( 2 ) INFORMATION FOR SEQ ID NO:2457:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2457:

GGGCAGCCUG AUGAGGCCGA AAGGCCGAAA GCUCCU    36

( 2 ) INFORMATION FOR SEQ ID NO:2458:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2458:

UCCCAGGCUG AUGAGGCCGA AAGGCCGAAA UCAAAA     36

( 2 ) INFORMATION FOR SEQ ID NO:2459:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2459:

UUACCAUCUG AUGAGGCCGA AAGGCCGAAA AGUCCC     36

( 2 ) INFORMATION FOR SEQ ID NO:2460:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2460:

UUACCAUCUG AUGAGGCCGA AAGGCCGAAA AGUCCC     36

( 2 ) INFORMATION FOR SEQ ID NO:2461:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2461:

GAGGUCACUG AUGAGGCCGA AAGGCCGAAA UGACAA     36

( 2 ) INFORMATION FOR SEQ ID NO:2462:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2462:

CACGGGGCUG AUGAGGCCGA AAGGCCGAAA CAUUAC     36

( 2 ) INFORMATION FOR SEQ ID NO:2463:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2463:

AUUUUAGCUG AUGAGGCCGA AAGGCCGAAA UAUGUG     36

( 2 ) INFORMATION FOR SEQ ID NO:2464:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2464:

UCUACAACUG AUGAGGCCGA AAGGCCGAAA CACCAC      36

( 2 ) INFORMATION FOR SEQ ID NO:2465:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2465:

UAAUUCCUG AUGAGGCCGA AAGGCCGAAA CAAUAC      36

( 2 ) INFORMATION FOR SEQ ID NO:2466:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2466:

GGCGGAUCUG AUGAGGCCGA AAGGCCGAAA AAUAAU      36

( 2 ) INFORMATION FOR SEQ ID NO:2467:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2467:

GGCGGAUCUG AUGAGGCCGA AAGGCCGAAA AAUAAU      36

( 2 ) INFORMATION FOR SEQ ID NO:2468:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2468:

CAGGUAGCUG AUGAGGCCGA AAGGCCGAAA ACCCAG      36

( 2 ) INFORMATION FOR SEQ ID NO:2469:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2469:

ACAGGCAGAG AAGAUGACAC CAGAGAAACA CACGUUGUGG UACAUUACCU GGUA      54

( 2 ) INFORMATION FOR SEQ ID NO:2470:

( i ) SEQUENCE CHARACTERISTICS:
        ( A ) LENGTH: 54 base pairs ( B ) TYPE: nucleic acid
( C ) STRANDEDNESS: single
( D ) TOPOLOGY: linear ( x i ) SEQUENCE DESCRIPTION: SEQ ID NO:2470:

GCAAACAAG AAGGGCUGAC CAGAGAAACA CACGUUGUGG UACAUUACCU GGUA  54

( 2 ) INFORMATION FOR SEQ ID NO:2471:

( i ) SEQUENCE CHARACTERISTICS:
( A ) LENGTH: 54 base pairs
( B ) TYPE: nucleic acid
( C ) STRANDEDNESS: single
( D ) TOPOLOGY: linear ( x i ) SEQUENCE DESCRIPTION: SEQ ID NO:2471:

AGGUGCAAAG AAGGCAGGAC CAGAGAAACA CACGUUGUGG UACAUUACCU GGUA  54

( 2 ) INFORMATION FOR SEQ ID NO:2472:

( i ) SEQUENCE CHARACTERISTICS:
( A ) LENGTH: 54 base pairs
( B ) TYPE: nucleic acid
( C ) STRANDEDNESS: single
( D ) TOPOLOGY: linear ( x i ) SEQUENCE DESCRIPTION: SEQ ID NO:2472:

GCACCAAGAG AAGAAAGAAC CAGAGAAACA CACGUUGUGG UACAUUACCU GGUA  54

( 2 ) INFORMATION FOR SEQ ID NO:2473:

( i ) SEQUENCE CHARACTERISTICS:
( A ) LENGTH: 54 base pairs
( B ) TYPE: nucleic acid
( C ) STRANDEDNESS: single
( D ) TOPOLOGY: linear ( x i ) SEQUENCE DESCRIPTION: SEQ ID NO:2473:

AACACCUGAG AAGAAGUGAC CAGAGAAACA CACGUUGUGG UACAUUACCU GGUA  54

( 2 ) INFORMATION FOR SEQ ID NO:2474:

( i ) SEQUENCE CHARACTERISTICS:
( A ) LENGTH: 54 base pairs
( B ) TYPE: nucleic acid
( C ) STRANDEDNESS: single
( D ) TOPOLOGY: linear ( x i ) SEQUENCE DESCRIPTION: SEQ ID NO:2474:

GACCACAGAG AAGCGUUGAC CAGAGAAACA CACGUUGUGG UACAUUACCU GGUA  54

( 2 ) INFORMATION FOR SEQ ID NO:2475:

( i ) SEQUENCE CHARACTERISTICS:
( A ) LENGTH: 54 base pairs
( B ) TYPE: nucleic acid
( C ) STRANDEDNESS: single
( D ) TOPOLOGY: linear ( x i ) SEQUENCE DESCRIPTION: SEQ ID NO:2475:

AGCUCUUCAG AAGAAACAAC CAGAGAAACA CACGUUGUGG UACAUUACCU GGUA  54

( 2 ) INFORMATION FOR SEQ ID NO:2476:

( i ) SEQUENCE CHARACTERISTICS:
( A ) LENGTH: 54 base pairs
( B ) TYPE: nucleic acid
( C ) STRANDEDNESS: single -continued (D) TOPOLOGY: linear (xi) SEQUENCE DESCRIPTION: SEQ ID NO:2476:

ACAUCAUAAG AAGCACCAAC CAGAGAAACA CACGUUGUGG UACAUUACCU GGUA 54

(2) INFORMATION FOR SEQ ID NO:2477:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:2477:

CAAAGAUGAG AAGGUUCUAC CAGAGAAACA CACGUUGUGG UACAUUACCU GGUA 54

(2) INFORMATION FOR SEQ ID NO:2478:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:2478:

GUGCCCUCAG AAGAUGGGAC CAGAGAAACA CACGUUGUGG UACAUUACCU GGUA 54

(2) INFORMATION FOR SEQ ID NO:2479:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:2479:

GUAGGGAAAG AAGCUUUGAC CAGAGAAACA CACGUUGUGG UACAUUACCU GGUA 54

(2) INFORMATION FOR SEQ ID NO:2480:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:2480:

AUUUCAAAAG AAGAUAUAAC CAGAGAAACA CACGUUGUGG UACAUUACCU GGUA 54

(2) INFORMATION FOR SEQ ID NO:2481:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:2481:

UCUUGGGAAG AAGUUGUGAC CAGAGAAACA CACGUUGUGG UACAUUACCU GGUA 54

(2) INFORMATION FOR SEQ ID NO:2482:

(i) SEQUENCE CHARACTERISTICS:
        (A) LENGTH: 54 base pairs
        (B) TYPE: nucleic acid
        (C) STRANDEDNESS: single
        (D) TOPOLOGY: linear ( x i ) SEQUENCE DESCRIPTION: SEQ ID NO:2482:

ACACAUGAAG AAGUGGUUAC CAGAGAAACA CACGUUGUGG UACAUUACCU GGUA     54

( 2 ) INFORMATION FOR SEQ ID NO:2483:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2483:

AGUUGAAGAG AAGAUUCAAC CAGAGAAACA CACGUUGUGG UACAUUACCU GGUA     54

( 2 ) INFORMATION FOR SEQ ID NO:2484:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2484:

AGGAUGGGAG AAGGUUAUAC CAGAGAAACA CACGUUGUGG UACAUUACCU GGUA     54

( 2 ) INFORMATION FOR SEQ ID NO:2485:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2485:

GUAGGUCAAG AAGCAUAUAC CAGAGAAACA CACGUUGUGG UACAUUACCU GGUA     54

( 2 ) INFORMATION FOR SEQ ID NO:2486:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2486:

AGCAGUAGAG AAGGCAGCAC CAGAGAAACA CACGUUGUGG UACAUUACCU GGUA     54

( 2 ) INFORMATION FOR SEQ ID NO:2487:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2487:

UGGGGCAAAG AAGUAGGUAC CAGAGAAACA CACGUUGUGG UACAUUACCU GGUA     54

( 2 ) INFORMATION FOR SEQ ID NO:2488:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2488:

GUGGGUAAAG AAGCUUAAAC CAGAGAAACA CACGUUGUGG UACAUUACCU GGUA    54

( 2 ) INFORMATION FOR SEQ ID NO:2489:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2489:

UCAGCUUAAG AAGAAAGAAC CAGAGAAACA CACGUUGUGG UACAUUACCU GGUA    54

( 2 ) INFORMATION FOR SEQ ID NO:2490:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2490:

GUCAUCAGCC CUGCCUGU    18

( 2 ) INFORMATION FOR SEQ ID NO:2491:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2491:

CAGCCCUGCC UGUUUUGC    18

( 2 ) INFORMATION FOR SEQ ID NO:2492:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2492:

CCUGCCUGUU UUGCACCU    18

( 2 ) INFORMATION FOR SEQ ID NO:2493:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2493:

UCUUUCAGCU CUUGGUGC    18

( 2 ) INFORMATION FOR SEQ ID NO:2494:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2494:

CACUUCUGUU CAGGUGUU    18

( 2 ) INFORMATION FOR SEQ ID NO:2495:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2495:

CAACGCUGUC CUGUGGUC     18

( 2 ) INFORMATION FOR SEQ ID NO:2496:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2496:

UGUUUCUGUU GAAGAGCU     18

( 2 ) INFORMATION FOR SEQ ID NO:2497:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2497:

UGGUGCUGAC UAUGAUGU     18

( 2 ) INFORMATION FOR SEQ ID NO:2498:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2498:

AGAACCGGAC CAUCUUUG     18

( 2 ) INFORMATION FOR SEQ ID NO:2499:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2499:

CCCAUCUGAC GAGGGCAC     18

( 2 ) INFORMATION FOR SEQ ID NO:2500:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2500:

CAAAGCUGAC UUCCCUAC     18

( 2 ) INFORMATION FOR SEQ ID NO:2501:

( i ) SEQUENCE CHARACTERISTICS:
  ( A ) LENGTH: 18 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:2501:

UAUAUCUGAC UUUGAAAU 18

( 2 ) INFORMATION FOR SEQ ID NO:2502:

( i ) SEQUENCE CHARACTERISTICS:
  ( A ) LENGTH: 18 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:2502:

CACAACAGUU UCCCAAGA 18

( 2 ) INFORMATION FOR SEQ ID NO:2503:

( i ) SEQUENCE CHARACTERISTICS:
  ( A ) LENGTH: 18 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:2503:

AACCACAGCU UCAUGUGU 18

( 2 ) INFORMATION FOR SEQ ID NO:2504:

( i ) SEQUENCE CHARACTERISTICS:
  ( A ) LENGTH: 18 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:2504:

UGAAUCAGAC CUUCAACU 18

( 2 ) INFORMATION FOR SEQ ID NO:2505:

( i ) SEQUENCE CHARACTERISTICS:
  ( A ) LENGTH: 18 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:2505:

AUAACCUGCU CCCAUCCU 18

( 2 ) INFORMATION FOR SEQ ID NO:2506:

( i ) SEQUENCE CHARACTERISTICS:
  ( A ) LENGTH: 18 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:2506:

AUAUGCUGCC UGACCUAC 18

( 2 ) INFORMATION FOR SEQ ID NO:2507:

( i ) SEQUENCE CHARACTERISTICS:

(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:2507:

GCUGCCUGAC CUACUGCU 18

(2) INFORMATION FOR SEQ ID NO:2508:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:2508:

ACCUACUGCU UUGCCCCA 18

(2) INFORMATION FOR SEQ ID NO:2509:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:2509:

UUAAGCUGUU UUACCCAC 18

(2) INFORMATION FOR SEQ ID NO:2510:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:2510:

UCUUUCAGAU UAAGCUGA 18

(2) INFORMATION FOR SEQ ID NO:2511:

(i) SEQUENCE CHARACTERISTICS:
(A) LENGTH: 54 base pairs
(B) TYPE: nucleic acid
(C) STRANDEDNESS: single
(D) TOPOLOGY: linear (xi) SEQUENCE DESCRIPTION: SEQ ID NO:2511:

AGAAAUGGAG AAGAGUGUAC CAGAGAAACA CACGUUGUGG UACAUUACCU GGUA 54

(2) INFORMATION FOR SEQ ID NO:2512:

(i) SEQUENCE CHARACTERISTICS:
(A) LENGTH: 54 base pairs
(B) TYPE: nucleic acid
(C) STRANDEDNESS: single
(D) TOPOLOGY: linear (xi) SEQUENCE DESCRIPTION: SEQ ID NO:2512:

AUCCACCCAG AAGAUGCUAC CAGAGAAACA CACGUUGUGG UACAUUACCU GGUA 54

(2) INFORMATION FOR SEQ ID NO:2513:

(i) SEQUENCE CHARACTERISTICS:
(A) LENGTH: 54 base pairs
(B) TYPE: nucleic acid ( C ) STRANDEDNESS: single
                    ( D ) TOPOLOGY: linear ( x i ) SEQUENCE DESCRIPTION: SEQ ID NO:2513:

AAUCGAGAAG AAGAGAUGAC CAGAGAAACA CACGUUGUGG UACAUUACCU GGUA          54

( 2 ) INFORMATION FOR SEQ ID NO:2514:

( i ) SEQUENCE CHARACTERISTICS:
                    ( A ) LENGTH: 54 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:2514:

CCUGCAUCAG AAGACAAUAC CAGAGAAACA CACGUUGUGG UACAUUACCU GGUA          54

( 2 ) INFORMATION FOR SEQ ID NO:2515:

( i ) SEQUENCE CHARACTERISTICS:
                    ( A ) LENGTH: 54 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:2515:

GACGAAUCAG AAGCACAAAC CAGAGAAACA CACGUUGUGG UACAUUACCU GGUA          54

( 2 ) INFORMATION FOR SEQ ID NO:2516:

( i ) SEQUENCE CHARACTERISTICS:
                    ( A ) LENGTH: 54 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:2516:

AAAGACGAAG AAGCAGCAAC CAGAGAAACA CACGUUGUGG UACAUUACCU GGUA          54

( 2 ) INFORMATION FOR SEQ ID NO:2517:

( i ) SEQUENCE CHARACTERISTICS:
                    ( A ) LENGTH: 54 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:2517:

UCAUCAACAG AAGAAGACAC CAGAGAAACA CACGUUGUGG UACAUUACCU GGUA          54

( 2 ) INFORMATION FOR SEQ ID NO:2518:

( i ) SEQUENCE CHARACTERISTICS:
                    ( A ) LENGTH: 54 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:2518:

CUGACUUGAG AAGUUGUUAC CAGAGAAACA CACGUUGUGG UACAUUACCU GGUA          54

( 2 ) INFORMATION FOR SEQ ID NO:2519:

( i ) SEQUENCE CHARACTERISTICS:
                    ( A ) LENGTH: 54 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:2519:

AACGGCAAAG AAGCAAUAAC CAGAGAAACA CACGUUGUGG UACAUUACCU GGUA    54

( 2 ) INFORMATION FOR SEQ ID NO:2520:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2520:

CAAUGACAAG AAGCACCAAC CAGAGAAACA CACGUUGUGG UACAUUACCU GGUA    54

( 2 ) INFORMATION FOR SEQ ID NO:2521:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2521:

CAUAUAAAAG AAGGUUCUAC CAGAGAAACA CACGUUGUGG UACAUUACCU GGUA    54

( 2 ) INFORMATION FOR SEQ ID NO:2522:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2522:

GUGCCCCGAG AAGAAAGGAC CAGAGAAACA CACGUUGUGG UACAUUACCU GGUA    54

( 2 ) INFORMATION FOR SEQ ID NO:2523:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2523:

AACGACACAG AAGUAUGUAC CAGAGAAACA CACGUUGUGG UACAUUACCU GGUA    54

( 2 ) INFORMATION FOR SEQ ID NO:2524:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2524:

GUAGAGAAAG AAGCUUUGAC CAGAGAAACA CACGUUGUGG UACAUUACCU GGUA    54

( 2 ) INFORMATION FOR SEQ ID NO:2525:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2525:

GGAAGCAAAG AAGGUAAUAC CAGAGAAACA CACGUUGUGG UACAUUACCU GGUA    54

( 2 ) INFORMATION FOR SEQ ID NO:2526:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2526:

AUGACGACAG AAGUUAUUAC CAGAGAAACA CACGUUGUGG UACAUUACCU GGUA    54

( 2 ) INFORMATION FOR SEQ ID NO:2527:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2527:

UCUUCGAAG AAGCUUCUAC CAGAGAAACA CACGUUGUGG UACAUUACCU GGUA    54

( 2 ) INFORMATION FOR SEQ ID NO:2528:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2528:

GAAGGUAAAG AAGUUGUUAC CAGAGAAACA CACGUUGUGG UACAUUACCU GGUA    54

( 2 ) INFORMATION FOR SEQ ID NO:2529:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2529:

GGAAGACGAG AAGUUCAGAC CAGAGAAACA CACGUUGUGG UACAUUACCU GGUA    54

( 2 ) INFORMATION FOR SEQ ID NO:2530:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2530:

UAAAGGAAAG AAGUCUGUAC CAGAGAAACA CACGUUGUGG UACAUUACCU GGUA    54

( 2 ) INFORMATION FOR SEQ ID NO:2531:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2531:

CCCACAUGAG AAGAGAAGAC CAGAGAAACA CACGUUGUGG UACAUUACCU GGUA    54

( 2 ) INFORMATION FOR SEQ ID NO:2532:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2532:

UCCGAAAGAG AAGCUAGCAC CAGAGAAACA CACGUUGUGG UACAUUACCU GGUA    54

( 2 ) INFORMATION FOR SEQ ID NO:2533:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2533:

CAGAAAAGAG AAGGCCUCAC CAGAGAAACA CACGUUGUGG UACAUUACCU GGUA    54

( 2 ) INFORMATION FOR SEQ ID NO:2534:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2534:

ACACUCUGUU CCAUUUCU    18

( 2 ) INFORMATION FOR SEQ ID NO:2535:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2535:

AGCAUCUGCC GGGUGGAU    18

( 2 ) INFORMATION FOR SEQ ID NO:2536:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2536:

CAUCUCUGUU UCUCGAUU    18

( 2 ) INFORMATION FOR SEQ ID NO:2537:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2537:

AUUGUCAGUU GAUGCAGG    18

-continued ( 2 ) INFORMATION FOR SEQ ID NO:2538:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2538:

UUGUGCUGCU GAUUCGUC                                             18

( 2 ) INFORMATION FOR SEQ ID NO:2539:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2539:

UGCUGCUGAU UCGUCUUU                                             18

( 2 ) INFORMATION FOR SEQ ID NO:2540:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2540:

GUCUUCAGAU GUUGAUGA                                             18

( 2 ) INFORMATION FOR SEQ ID NO:2541:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2541:

AACAACUGUC CAAGUCAG                                             18

( 2 ) INFORMATION FOR SEQ ID NO:2542:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2542:

UAUUGCUGCC UUGCCGUU                                             18

( 2 ) INFORMATION FOR SEQ ID NO:2543:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2543:

UGGUGCUGUC UGUCAUUG                                             18

( 2 ) INFORMATION FOR SEQ ID NO:2544:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2544:

AGAACCGGAC UUUAUAUG    18

( 2 ) INFORMATION FOR SEQ ID NO:2545:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2545:

CCUUUCAGAC CGGGGCAC    18

( 2 ) INFORMATION FOR SEQ ID NO:2546:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2546:

ACAUACAGCU GUGUCGUU    18

( 2 ) INFORMATION FOR SEQ ID NO:2547:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2547:

CAAAGCUGAC UUCUCUAC    18

( 2 ) INFORMATION FOR SEQ ID NO:2548:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2548:

AUUACCUGCU UUGCUUCC    18

( 2 ) INFORMATION FOR SEQ ID NO:2549:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2549:

AAUAACAGUC GUCGUCAU    18

( 2 ) INFORMATION FOR SEQ ID NO:2550:

( i ) SEQUENCE CHARACTERISTICS:
        ( A ) LENGTH: 18 base pairs ( B ) TYPE: nucleic acid
        ( C ) STRANDEDNESS: single
        ( D ) TOPOLOGY: linear ( x i ) SEQUENCE DESCRIPTION: SEQ ID NO:2550:

AGAAGCUGUU UCAGAAGA                                                                                  18

( 2 ) INFORMATION FOR SEQ ID NO:2551:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2551:

AACAACAGCC UUACCUUC                                                                                  18

( 2 ) INFORMATION FOR SEQ ID NO:2552:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2552:

CUGAACAGAC CGUCUUCC                                                                                  18

( 2 ) INFORMATION FOR SEQ ID NO:2553:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2553:

ACAGACCGUC UUCCUUUA                                                                                  18

( 2 ) INFORMATION FOR SEQ ID NO:2554:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2554:

CUUCUCUGUC CAUGUGGG                                                                                  18

( 2 ) INFORMATION FOR SEQ ID NO:2555:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2555:

GCUAGCUGAU CUUUCGGA                                                                                  18

( 2 ) INFORMATION FOR SEQ ID NO:2556:

( i ) SEQUENCE CHARACTERISTICS:
        ( A ) LENGTH: 18 base pairs
        ( B ) TYPE: nucleic acid
        ( C ) STRANDEDNESS: single -continued (D) TOPOLOGY: linear (xi) SEQUENCE DESCRIPTION: SEQ ID NO:2556:

GAGGCCUGCC CUUUUCUG                                                                                      18

(2) INFORMATION FOR SEQ ID NO:2557:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:2557:

GUUACAGCAG AAGAGAAGAC CAGAGAAACA CACGUUGUGG UACAUUACCU GGUA              54

(2) INFORMATION FOR SEQ ID NO:2558:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:2558:

CCUGUUACAG AAGCAGAGAC CAGAGAAACA CACGUUGUGG UACAUUACCU GGUA              54

(2) INFORMATION FOR SEQ ID NO:2559:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:2559:

CCCCACUCAG AAGUGUGUAC CAGAGAAACA CACGUUGUGG UACAUUACCU GGUA              54

(2) INFORMATION FOR SEQ ID NO:2560:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:2560:

CACCAGAGAG AAGGAAGGAC CAGAGAAACA CACGUUGUGG UACAUUACCU GGUA              54

(2) INFORMATION FOR SEQ ID NO:2561:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:2561:

UUCAGAGGAG AAGCACCAAC CAGAGAAACA CACGUUGUGG UACAUUACCU GGUA              54

(2) INFORMATION FOR SEQ ID NO:2562:

(i) SEQUENCE CHARACTERISTICS:
        (A) LENGTH: 54 base pairs
        (B) TYPE: nucleic acid
        (C) STRANDEDNESS: single
        (D) TOPOLOGY: linear ( x i ) SEQUENCE DESCRIPTION: SEQ ID NO:2562:

CAUGGCAGAG AAGCAGUCAC CAGAGAAACA CACGUUGUGG UACAUUACCU GGUA    54

( 2 ) INFORMATION FOR SEQ ID NO:2563:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2563:

CAGGGUCCAG AAGUCCGAAC CAGAGAAACA CACGUUGUGG UACAUUACCU GGUA    54

( 2 ) INFORMATION FOR SEQ ID NO:2564:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2564:

UGUCCUUGAG AAGAAGAUAC CAGAGAAACA CACGUUGUGG UACAUUACCU GGUA    54

( 2 ) INFORMATION FOR SEQ ID NO:2565:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2565:

CAGAAUUCAG AAGGUGGAAC CAGAGAAACA CACGUUGUGG UACAUUACCU GGUA    54

( 2 ) INFORMATION FOR SEQ ID NO:2566:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2566:

UAUAGAUGAG AAGGUCAAAC CAGAGAAACA CACGUUGUGG UACAUUACCU GGUA    54

( 2 ) INFORMATION FOR SEQ ID NO:2567:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2567:

AACAGACAAG AAGAUGGAAC CAGAGAAACA CACGUUGUGG UACAUUACCU GGUA    54

( 2 ) INFORMATION FOR SEQ ID NO:2568:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2568:

GGGAAUGAAG AAGACAAGAC CAGAGAAACA CACGUUGUGG UACAUUACCU GGUA 54

( 2 ) INFORMATION FOR SEQ ID NO:2569:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2569:

CUCGUAACAG AAGGGAAUAC CAGAGAAACA CACGUUGUGG UACAUUACCU GGUA 54

( 2 ) INFORMATION FOR SEQ ID NO:2570:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2570:

AAGAUAAAAG AAGCGUCUAC CAGAGAAACA CACGUUGUGG UACAUUACCU GGUA 54

( 2 ) INFORMATION FOR SEQ ID NO:2571:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2571:

CUGGGGGAAG AAGAGGGUAC CAGAGAAACA CACGUUGUGG UACAUUACCU GGUA 54

( 2 ) INFORMATION FOR SEQ ID NO:2572:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2572:

GGAAUGUGAG AAGGGGAAC CAGAGAAACA CACGUUGUGG UACAUUACCU GGUA 54

( 2 ) INFORMATION FOR SEQ ID NO:2573:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2573:

GGAAGUACAG AAGUAAUCAC CAGAGAAACA CACGUUGUGG UACAUUACCU GGUA 54

( 2 ) INFORMATION FOR SEQ ID NO:2574:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2574:

UAGAAUUAAG AAGAAAACAC CAGAGAAACA CACGUUGUGG UACAUUACCU GGUA 54

( 2 ) INFORMATION FOR SEQ ID NO:2575:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2575:

AGUUGCGAAG AAGCUUCUAC CAGAGAAACA CACGUUGUGG UACAUUACCU GGUA    54

( 2 ) INFORMATION FOR SEQ ID NO:2576:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2576:

UUUUCUUGAG AAGUUCACAC CAGAGAAACA CACGUUGUGG UACAUUACCU GGUA    54

( 2 ) INFORMATION FOR SEQ ID NO:2577:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2577:

UGGGCUUCAG AAGAUCUUAC CAGAGAAACA CACGUUGUGG UACAUUACCU GGUA    54

( 2 ) INFORMATION FOR SEQ ID NO:2578:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2578:

CUUCUCUGCU GCUGUAAC    18

( 2 ) INFORMATION FOR SEQ ID NO:2579:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2579:

CUCUGCUGCU GUAACAGG    18

( 2 ) INFORMATION FOR SEQ ID NO:2580:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2580:

ACACACGGAU GAGUGGGG    18

( 2 ) INFORMATION FOR SEQ ID NO:2581:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2581:

CCUUCCUGCU CUCUGGUG    18

( 2 ) INFORMATION FOR SEQ ID NO:2582:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2582:

UGGUGCUGCU CCUCUGAA    18

( 2 ) INFORMATION FOR SEQ ID NO:2583:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2583:

GACUGCAGAC CUGCCAUG    18

( 2 ) INFORMATION FOR SEQ ID NO:2584:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2584:

UCGGACAGUU GGACCCUG    18

( 2 ) INFORMATION FOR SEQ ID NO:2585:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2585:

AUCUUCAGAU CAAGGACA    18

( 2 ) INFORMATION FOR SEQ ID NO:2586:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2586:

UCCACCAGAU GAAUUCUG    18

( 2 ) INFORMATION FOR SEQ ID NO:2587:

( i ) SEQUENCE CHARACTERISTICS:

( A ) LENGTH: 18 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:2587:

UUGACCUGCU CAUCUAUA                                                                                      18

( 2 ) INFORMATION FOR SEQ ID NO:2588:

( i ) SEQUENCE CHARACTERISTICS:
            ( A ) LENGTH: 18 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:2588:

UCCAUCAGCU UGUCUGUU                                                                                      18

( 2 ) INFORMATION FOR SEQ ID NO:2589:

( i ) SEQUENCE CHARACTERISTICS:
            ( A ) LENGTH: 18 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:2589:

CUUGUCUGUU UCAUUCCC                                                                                      18

( 2 ) INFORMATION FOR SEQ ID NO:2590:

( i ) SEQUENCE CHARACTERISTICS:
            ( A ) LENGTH: 18 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:2590:

AUUCCCUGAU GUUACGAG                                                                                      18

( 2 ) INFORMATION FOR SEQ ID NO:2591:

( i ) SEQUENCE CHARACTERISTICS:
            ( A ) LENGTH: 18 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:2591:

AGACGCGGCU UUUAUCUU                                                                                      18

( 2 ) INFORMATION FOR SEQ ID NO:2592:

( i ) SEQUENCE CHARACTERISTICS:
            ( A ) LENGTH: 18 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:2592:

ACCCUCAGCC UCCCCCAG                                                                                      18

( 2 ) INFORMATION FOR SEQ ID NO:2593:

( i ) SEQUENCE CHARACTERISTICS:
            ( A ) LENGTH: 18 base pairs
            ( B ) TYPE: nucleic acid (C) STRANDEDNESS: single
(D) TOPOLOGY: linear (xi) SEQUENCE DESCRIPTION: SEQ ID NO:2593:

UCCCCCAGAC CACAUUCC 18

(2) INFORMATION FOR SEQ ID NO:2594:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:2594:

GAUUACAGCU GUACUUCC 18

(2) INFORMATION FOR SEQ ID NO:2595:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:2595:

GUUUCUGUC UAAUUCUA 18

(2) INFORMATION FOR SEQ ID NO:2596:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:2596:

AGAAGCGGCC UCGCAACU 18

(2) INFORMATION FOR SEQ ID NO:2597:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:2597:

GUGAACAGAC CAAGAAAA 18

(2) INFORMATION FOR SEQ ID NO:2598:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:2598:

AAGAUCUGAU GAAGCCCA 18

(2) INFORMATION FOR SEQ ID NO:2599:

(i) SEQUENCE CHARACTERISTICS:
(A) LENGTH: 54 base pairs
(B) TYPE: nucleic acid
(C) STRANDEDNESS: single
(D) TOPOLOGY: linear ( x i ) SEQUENCE DESCRIPTION: SEQ ID NO:2599:

UCUUACGCAG AAGCUUGCAC CAGAGAAACA CACGUUGUGG UACAUUACCU GGUA          54

( 2 ) INFORMATION FOR SEQ ID NO:2600:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2600:

UUGUUCAAAG AAGUGCUGAC CAGAGAAACA CACGUUGUGG UACAUUACCU GGUA          54

( 2 ) INFORMATION FOR SEQ ID NO:2601:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2601:

CUACAGGAAG AAGGUUGUAC CAGAGAAACA CACGUUGUGG UACAUUACCU GGUA          54

( 2 ) INFORMATION FOR SEQ ID NO:2602:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2602:

CAUGGUGCAG AAGGGGUCAC CAGAGAAACA CACGUUGUGG UACAUUACCU GGUA          54

( 2 ) INFORMATION FOR SEQ ID NO:2603:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2603:

AUCAGCAAAG AAGUCACAAC CAGAGAAACA CACGUUGUGG UACAUUACCU GGUA          54

( 2 ) INFORMATION FOR SEQ ID NO:2604:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2604:

CAUCUGAGAG AAGCAAGAAC CAGAGAAACA CACGUUGUGG UACAUUACCU GGUA          54

( 2 ) INFORMATION FOR SEQ ID NO:2605:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2605:

GAAACAGCAG AAGAGAUCAC CAGAGAAACA CACGUUGUGG UACAUUACCU GGUA 54

(2) INFORMATION FOR SEQ ID NO:2606:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:2606:

UCCACGGAAG AAGCAUCUAC CAGAGAAACA CACGUUGUGG UACAUUACCU GGUA 54

(2) INFORMATION FOR SEQ ID NO:2607:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:2607:

AUGGGCACAG AAGAUAUGAC CAGAGAAACA CACGUUGUGG UACAUUACCU GGUA 54

(2) INFORMATION FOR SEQ ID NO:2608:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:2608:

UGUCCUUGAG AAGAACAUAC CAGAGAAACA CACGUUGUGG UACAUUACCU GGUA 54

(2) INFORMATION FOR SEQ ID NO:2609:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:2609:

AGAUACUGAG AAGUUCUGAC CAGAGAAACA CACGUUGUGG UACAUUACCU GGUA 54

(2) INFORMATION FOR SEQ ID NO:2610:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:2610:

AAGAGAGAAG AAGUUGGAAC CAGAGAAACA CACGUUGUGG UACAUUACCU GGUA 54

(2) INFORMATION FOR SEQ ID NO:2611:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:2611:

CACACACCAG AAGGGAAUAC CAGAGAAACA CACGUUGUGG UACAUUACCU GGUA 54

( 2 ) INFORMATION FOR SEQ ID NO:2612:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2612:

ACACACACAG AAGUCAUAAC CAGAGAAACA CACGUUGUGG UACAUUACCU GGUA    54

( 2 ) INFORMATION FOR SEQ ID NO:2613:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2613:

GUAACUGAAG AAGUAAUCAC CAGAGAAACA CACGUUGUGG UACAUUACCU GGUA    54

( 2 ) INFORMATION FOR SEQ ID NO:2614:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2614:

CAAUGAUGAG AAGCAUCAAC CAGAGAAACA CACGUUGUGG UACAUUACCU GGUA    54

( 2 ) INFORMATION FOR SEQ ID NO:2615:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2615:

GCCUGCUAAG AAGAUUCGAC CAGAGAAACA CACGUUGUGG UACAUUACCU GGUA    54

( 2 ) INFORMATION FOR SEQ ID NO:2616:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2616:

AACUUAGAAG AAGUGUUGAC CAGAGAAACA CACGUUGUGG UACAUUACCU GGUA    54

( 2 ) INFORMATION FOR SEQ ID NO:2617:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2617:

UUCCAAUCAG AAGAGAACAC CAGAGAAACA CACGUUGUGG UACAUUACCU GGUA    54

( 2 ) INFORMATION FOR SEQ ID NO:2618:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2618:

GAAUUCCAAG AAGCUGAGAC CAGAGAAACA CACGUUGUGG UACAUUACCU GGUA    54

( 2 ) INFORMATION FOR SEQ ID NO:2619:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2619:

AAUUAUUCAG AAGUAGAAAC CAGAGAAACA CACGUUGUGG UACAUUACCU GGUA    54

( 2 ) INFORMATION FOR SEQ ID NO:2620:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2620:

GCAAGCAGAC GCGUAAGA    18

( 2 ) INFORMATION FOR SEQ ID NO:2621:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2621:

CAGCACGGAC UUGAACAA    18

( 2 ) INFORMATION FOR SEQ ID NO:2622:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2622:

ACAACCAGAC UCCUGUAG    18

( 2 ) INFORMATION FOR SEQ ID NO:2623:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2623:

GACCCCAGAU GCACCAUG    18

( 2 ) INFORMATION FOR SEQ ID NO:2624:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2624:

UGUGACAGUC UUGCUGAU 18

( 2 ) INFORMATION FOR SEQ ID NO:2625:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2625:

UCUUGCUGAU CUCAGAUG 18

( 2 ) INFORMATION FOR SEQ ID NO:2626:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2626:

GAUCUCAGAU GCUGUUUC 18

( 2 ) INFORMATION FOR SEQ ID NO:2627:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2627:

AGAUGCUGUU UCCGUGGA 18

( 2 ) INFORMATION FOR SEQ ID NO:2628:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2628:

CAUAUCUGCC GUGCCCAU 18

( 2 ) INFORMATION FOR SEQ ID NO:2629:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2629:

AUGUUCAGAU CAAGGACA 18

( 2 ) INFORMATION FOR SEQ ID NO:2630:

( i ) SEQUENCE CHARACTERISTICS:
    ( A ) LENGTH: 18 base pairs (B) TYPE: nucleic acid
(C) STRANDEDNESS: single
(D) TOPOLOGY: linear (xi) SEQUENCE DESCRIPTION: SEQ ID NO:2630:

CAGAACUGUU CAGUAUCU 18

(2) INFORMATION FOR SEQ ID NO:2631:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:2631:

UCCAACAGCC UCUCUCUU 18

(2) INFORMATION FOR SEQ ID NO:2632:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:2632:

AUUCCCGGAU GGUGUGUG 18

(2) INFORMATION FOR SEQ ID NO:2633:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:2633:

UAUGACCGUU GUGUGUGU 18

(2) INFORMATION FOR SEQ ID NO:2634:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:2634:

GAUUACAGCU UCAGUUAC 18

(2) INFORMATION FOR SEQ ID NO:2635:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:2635:

UGAUGCUGCU CAUCAUUG 18

(2) INFORMATION FOR SEQ ID NO:2636:

(i) SEQUENCE CHARACTERISTICS:
(A) LENGTH: 18 base pairs
(B) TYPE: nucleic acid
(C) STRANDEDNESS: single (D) TOPOLOGY: linear (xi) SEQUENCE DESCRIPTION: SEQ ID NO:2636:

CGAAUCAGCC UAGCAGGC 18

(2) INFORMATION FOR SEQ ID NO:2637:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:2637:

CAACACAGCC UCUAAGUU 18

(2) INFORMATION FOR SEQ ID NO:2638:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:2638:

GUUCUCAGCU GAUUGGAA 18

(2) INFORMATION FOR SEQ ID NO:2639:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:2639:

CUCAGCUGAU UGGAAUUC 18

(2) INFORMATION FOR SEQ ID NO:2640:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:2640:

UUCUACAGUU GAAUAAUU 18

(2) INFORMATION FOR SEQ ID NO:2641:

(i) SEQUENCE CHARACTERISTICS:
(A) LENGTH: 54 base pairs
(B) TYPE: nucleic acid
(C) STRANDEDNESS: single
(D) TOPOLOGY: linear (xi) SEQUENCE DESCRIPTION: SEQ ID NO:2641:

GACCAGGCAG AAGGACCAAC CAGAGAAACA CACGUUGUGG UACAUUACCU GGUA 54

(2) INFORMATION FOR SEQ ID NO:2642:

(i) SEQUENCE CHARACTERISTICS:
(A) LENGTH: 54 base pairs
(B) TYPE: nucleic acid
(C) STRANDEDNESS: single
(D) TOPOLOGY: linear ( x i ) SEQUENCE DESCRIPTION: SEQ ID NO:2642:

UGAGACCAAG AAGCAGGAAC CAGAGAAACA CACGUUGUGG UACAUUACCU GGUA 54

( 2 ) INFORMATION FOR SEQ ID NO:2643:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2643:

ACUGCAGAAG AAGACGAAAC CAGAGAAACA CACGUUGUGG UACAUUACCU GGUA 54

( 2 ) INFORMATION FOR SEQ ID NO:2644:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2644:

GGUCAGCAAG AAGCCCCAAC CAGAGAAACA CACGUUGUGG UACAUUACCU GGUA 54

( 2 ) INFORMATION FOR SEQ ID NO:2645:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2645:

GGACAGCGAG AAGCAAGCAC CAGAGAAACA CACGUUGUGG UACAUUACCU GGUA 54

( 2 ) INFORMATION FOR SEQ ID NO:2646:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2646:

GGAUGGACAG AAGUCAGCAC CAGAGAAACA CACGUUGUGG UACAUUACCU GGUA 54

( 2 ) INFORMATION FOR SEQ ID NO:2647:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2647:

UCUGGAUGAG AAGCGGUCAC CAGAGAAACA CACGUUGUGG UACAUUACCU GGUA 54

( 2 ) INFORMATION FOR SEQ ID NO:2648:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2648:

GCACAAAGAG AAGCACUGAC CAGAGAAACA CACGUUGUGG UACAUUACCU GGUA    54

(2) INFORMATION FOR SEQ ID NO:2649:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:2649:

CGAGCAUGAG AAGUGCAGAC CAGAGAAACA CACGUUGUGG UACAUUACCU GGUA    54

(2) INFORMATION FOR SEQ ID NO:2650:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:2650:

GACCCCAAAG AAGGGCGAAC CAGAGAAACA CACGUUGUGG UACAUUACCU GGUA    54

(2) INFORMATION FOR SEQ ID NO:2651:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:2651:

CUGUAGCAAG AAGCUUGAAC CAGAGAAACA CACGUUGUGG UACAUUACCU GGUA    54

(2) INFORMATION FOR SEQ ID NO:2652:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:2652:

GCCGACUGAG AAGGGCUCAC CAGAGAAACA CACGUUGUGG UACAUUACCU GGUA    54

(2) INFORMATION FOR SEQ ID NO:2653:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:2653:

AAGAAGCCAG AAGGGCAGAC CAGAGAAACA CACGUUGUGG UACAUUACCU GGUA    54

(2) INFORMATION FOR SEQ ID NO:2654:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:2654:

GGAGAAGAAG AAGACUGGAC CAGAGAAACA CACGUUGUGG UACAUUACCU GGUA    54

( 2 ) INFORMATION FOR SEQ ID NO:2655:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2655:

UUUUCGAAAG AAGAUGACAC CAGAGAAACA CACGUUGUGG UACAUUACCU GGUA     54

( 2 ) INFORMATION FOR SEQ ID NO:2656:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2656:

CAGACAACAG AAGUCUUGAC CAGAGAAACA CACGUUGUGG UACAUUACCU GGUA     54

( 2 ) INFORMATION FOR SEQ ID NO:2657:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2657:

GGGCUCUCAG AAGAUCCUAC CAGAGAAACA CACGUUGUGG UACAUUACCU GGUA     54

( 2 ) INFORMATION FOR SEQ ID NO:2658:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2658:

GGAUGGCAAG AAGGAUCCAC CAGAGAAACA CACGUUGUGG UACAUUACCU GGUA     54

( 2 ) INFORMATION FOR SEQ ID NO:2659:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2659:

GGAAGAUCAG AAGGAAAAAC CAGAGAAACA CACGUUGUGG UACAUUACCU GGUA     54

( 2 ) INFORMATION FOR SEQ ID NO:2660:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2660:

ACUGGAGCAG AAGUGUUGAC CAGAGAAACA CACGUUGUGG UACAUUACCU GGUA     54

( 2 ) INFORMATION FOR SEQ ID NO:2661:

-continued ( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2661:

UGCACUGGAG AAGCAGUGAC CAGAGAAACA CACGUUGUGG UACAUUACCU GGUA    54

( 2 ) INFORMATION FOR SEQ ID NO:2662:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2662:

CUCUGGCCAG AAGCCUGUAC CAGAGAAACA CACGUUGUGG UACAUUACCU GGUA    54

( 2 ) INFORMATION FOR SEQ ID NO:2663:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2663:

CCUGCAGCAG AAGCACCAAC CAGAGAAACA CACGUUGUGG UACAUUACCU GGUA    54

( 2 ) INFORMATION FOR SEQ ID NO:2664:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2664:

ACCCCUGCAG AAGCAGCAAC CAGAGAAACA CACGUUGUGG UACAUUACCU GGUA    54

( 2 ) INFORMATION FOR SEQ ID NO:2665:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2665:

UGGUCCUGCC GCCUGGUC    18

( 2 ) INFORMATION FOR SEQ ID NO:2666:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2666:

UCCUGCCGCC UGGUCUCA    18

( 2 ) INFORMATION FOR SEQ ID NO:2667:

( i ) SEQUENCE CHARACTERISTICS:

(A) LENGTH: 18 base pairs
                    (B) TYPE: nucleic acid
                    (C) STRANDEDNESS: single
                    (D) TOPOLOGY: linear (xi) SEQUENCE DESCRIPTION: SEQ ID NO:2667:

UUCGUCUGCC UCUGCAGU                                                                         18

(2) INFORMATION FOR SEQ ID NO:2668:

(i) SEQUENCE CHARACTERISTICS:
                    (A) LENGTH: 18 base pairs
                    (B) TYPE: nucleic acid
                    (C) STRANDEDNESS: single
                    (D) TOPOLOGY: linear (xi) SEQUENCE DESCRIPTION: SEQ ID NO:2668:

UGGGGCUGCU UGCUGACC                                                                         18

(2) INFORMATION FOR SEQ ID NO:2669:

(i) SEQUENCE CHARACTERISTICS:
                    (A) LENGTH: 18 base pairs
                    (B) TYPE: nucleic acid
                    (C) STRANDEDNESS: single
                    (D) TOPOLOGY: linear (xi) SEQUENCE DESCRIPTION: SEQ ID NO:2669:

GCUUGCUGAC CGCUGUCC                                                                         18

(2) INFORMATION FOR SEQ ID NO:2670:

(i) SEQUENCE CHARACTERISTICS:
                    (A) LENGTH: 18 base pairs
                    (B) TYPE: nucleic acid
                    (C) STRANDEDNESS: single
                    (D) TOPOLOGY: linear (xi) SEQUENCE DESCRIPTION: SEQ ID NO:2670:

GCUGACCGCU GUCCAUCC                                                                         18

(2) INFORMATION FOR SEQ ID NO:2671:

(i) SEQUENCE CHARACTERISTICS:
                    (A) LENGTH: 18 base pairs
                    (B) TYPE: nucleic acid
                    (C) STRANDEDNESS: single
                    (D) TOPOLOGY: linear (xi) SEQUENCE DESCRIPTION: SEQ ID NO:2671:

GACCGCUGUC CAUCCAGA                                                                         18

(2) INFORMATION FOR SEQ ID NO:2672:

(i) SEQUENCE CHARACTERISTICS:
                    (A) LENGTH: 18 base pairs
                    (B) TYPE: nucleic acid
                    (C) STRANDEDNESS: single
                    (D) TOPOLOGY: linear (xi) SEQUENCE DESCRIPTION: SEQ ID NO:2672:

CAGUGCUGUU CUUUGUGC                                                                         18

(2) INFORMATION FOR SEQ ID NO:2673:

(i) SEQUENCE CHARACTERISTICS:
                    (A) LENGTH: 18 base pairs
                    (B) TYPE: nucleic acid (C) STRANDEDNESS: single
              (D) TOPOLOGY: linear (xi) SEQUENCE DESCRIPTION: SEQ ID NO:2673:

CUGCACCGCU CAUGCUCG                                                                          18

(2) INFORMATION FOR SEQ ID NO:2674:

(i) SEQUENCE CHARACTERISTICS:
              (A) LENGTH: 18 base pairs
              (B) TYPE: nucleic acid
              (C) STRANDEDNESS: single
              (D) TOPOLOGY: linear (xi) SEQUENCE DESCRIPTION: SEQ ID NO:2674:

UCGCCCGGCU UUGGGGUC                                                                          18

(2) INFORMATION FOR SEQ ID NO:2675:

(i) SEQUENCE CHARACTERISTICS:
              (A) LENGTH: 18 base pairs
              (B) TYPE: nucleic acid
              (C) STRANDEDNESS: single
              (D) TOPOLOGY: linear (xi) SEQUENCE DESCRIPTION: SEQ ID NO:2675:

UCAAGCAGAU UGCUACAG                                                                          18

(2) INFORMATION FOR SEQ ID NO:2676:

(i) SEQUENCE CHARACTERISTICS:
              (A) LENGTH: 18 base pairs
              (B) TYPE: nucleic acid
              (C) STRANDEDNESS: single
              (D) TOPOLOGY: linear (xi) SEQUENCE DESCRIPTION: SEQ ID NO:2676:

GAGCCCUGCC CAGUCGGC                                                                          18

(2) INFORMATION FOR SEQ ID NO:2677:

(i) SEQUENCE CHARACTERISTICS:
              (A) LENGTH: 18 base pairs
              (B) TYPE: nucleic acid
              (C) STRANDEDNESS: single
              (D) TOPOLOGY: linear (xi) SEQUENCE DESCRIPTION: SEQ ID NO:2677:

CUGCCCAGUC GGCUUCUU                                                                          18

(2) INFORMATION FOR SEQ ID NO:2678:

(i) SEQUENCE CHARACTERISTICS:
              (A) LENGTH: 18 base pairs
              (B) TYPE: nucleic acid
              (C) STRANDEDNESS: single
              (D) TOPOLOGY: linear (xi) SEQUENCE DESCRIPTION: SEQ ID NO:2678:

CCAGUCGGCU UCUUCUCC                                                                          18

(2) INFORMATION FOR SEQ ID NO:2679:

(i) SEQUENCE CHARACTERISTICS:
              (A) LENGTH: 18 base pairs
              (B) TYPE: nucleic acid
              (C) STRANDEDNESS: single
              (D) TOPOLOGY: linear ( x i ) SEQUENCE DESCRIPTION: SEQ ID NO:2679:

GUCAUCUGCU UUCGAAAA 18

( 2 ) INFORMATION FOR SEQ ID NO:2680:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( x i ) SEQUENCE DESCRIPTION: SEQ ID NO:2680:

CAAGACUGAU GUUGUCUG 18

( 2 ) INFORMATION FOR SEQ ID NO:2681:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( x i ) SEQUENCE DESCRIPTION: SEQ ID NO:2681:

AGGAUCGGCU GAGAGCCC 18

( 2 ) INFORMATION FOR SEQ ID NO:2682:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( x i ) SEQUENCE DESCRIPTION: SEQ ID NO:2682:

GGAUCCUGUU UGCCAUCC 18

( 2 ) INFORMATION FOR SEQ ID NO:2683:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( x i ) SEQUENCE DESCRIPTION: SEQ ID NO:2683:

UUUUCCCGAC GAUCUUCC 18

( 2 ) INFORMATION FOR SEQ ID NO:2684:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( x i ) SEQUENCE DESCRIPTION: SEQ ID NO:2684:

CAACACUGCU GCUCCAGU 18

( 2 ) INFORMATION FOR SEQ ID NO:2685:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( x i ) SEQUENCE DESCRIPTION: SEQ ID NO:2685:

```
CACUGCUGCU CCAGUGCA                                                                          18
```

(2) INFORMATION FOR SEQ ID NO:2686:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:2686:

```
ACAGGCAGUU GGCCAGAG                                                                          18
```

(2) INFORMATION FOR SEQ ID NO:2687:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:2687:

```
UGGUGCUGCU GCUGCAGG                                                                          18
```

(2) INFORMATION FOR SEQ ID NO:2688:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:2688:

```
UGCUGCUGCU GCAGGGGU                                                                          18
```

(2) INFORMATION FOR SEQ ID NO:2689:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:2689:

```
GCGCGCACAG AAGAGGCAAC CAGAGAAACA CACGUUGUGG UACAUUACCU GGUA         54
```

(2) INFORMATION FOR SEQ ID NO:2690:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:2690:

```
UGUCAACAAG AAGCCCCAAC CAGAGAAACA CACGUUGUGG UACAUUACCU GGUA         54
```

(2) INFORMATION FOR SEQ ID NO:2691:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:2691:

```
CCUAGAUGAG AAGCUGUCAC CAGAGAAACA CACGUUGUGG UACAUUACCU GGUA         54
```

( 2 ) INFORMATION FOR SEQ ID NO:2692:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2692:

GCUUGCAAG AAGCUUCCAC CAGAGAAACA CACGUUGUGG UACAUUACCU GGUA    54

( 2 ) INFORMATION FOR SEQ ID NO:2693:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2693:

UUCUCAAGAG AAGUGCAGAC CAGAGAAACA CACGUUGUGG UACAUUACCU GGUA    54

( 2 ) INFORMATION FOR SEQ ID NO:2694:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2694:

UUCCACUGAG AAGAGAAUAC CAGAGAAACA CACGUUGUGG UACAUUACCU GGUA    54

( 2 ) INFORMATION FOR SEQ ID NO:2695:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2695:

CAGGUACAAG AAGUGUCUAC CAGAGAAACA CACGUUGUGG UACAUUACCU GGUA    54

( 2 ) INFORMATION FOR SEQ ID NO:2696:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2696:

GGAUGACAAG AAGUAUCAAC CAGAGAAACA CACGUUGUGG UACAUUACCU GGUA    54

( 2 ) INFORMATION FOR SEQ ID NO:2697:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2697:

GCCGACUGAG AAGGGAUGAC CAGAGAAACA CACGUUGUGG UACAUUACCU GGUA    54

( 2 ) INFORMATION FOR SEQ ID NO:2698:

( i ) SEQUENCE CHARACTERISTICS:
       ( A ) LENGTH: 54 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:2698:

AAGAAGCCAG AAGGGCAGAC CAGAGAAACA CACGUUGUGG UACAUUACCU GGUA                    54

( 2 ) INFORMATION FOR SEQ ID NO:2699:

( i ) SEQUENCE CHARACTERISTICS:
       ( A ) LENGTH: 54 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:2699:

GGAGAAGAAG AAGACUGGAC CAGAGAAACA CACGUUGUGG UACAUUACCU GGUA                    54

( 2 ) INFORMATION FOR SEQ ID NO:2700:

( i ) SEQUENCE CHARACTERISTICS:
       ( A ) LENGTH: 54 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:2700:

UGACAUUAAG AAGACUCGAC CAGAGAAACA CACGUUGUGG UACAUUACCU GGUA                    54

( 2 ) INFORMATION FOR SEQ ID NO:2701:

( i ) SEQUENCE CHARACTERISTICS:
       ( A ) LENGTH: 54 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:2701:

GGGCUCGCAG AAGGGACUAC CAGAGAAACA CACGUUGUGG UACAUUACCU GGUA                    54

( 2 ) INFORMATION FOR SEQ ID NO:2702:

( i ) SEQUENCE CHARACTERISTICS:
       ( A ) LENGTH: 54 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:2702:

GAAUGACCAG AAGGGCUCAC CAGAGAAACA CACGUUGUGG UACAUUACCU GGUA                    54

( 2 ) INFORMATION FOR SEQ ID NO:2703:

( i ) SEQUENCE CHARACTERISTICS:
       ( A ) LENGTH: 54 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:2703:

CCCAUCACAG AAGGAAUGAC CAGAGAAACA CACGUUGUGG UACAUUACCU GGUA                    54

( 2 ) INFORMATION FOR SEQ ID NO:2704:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2704:

UGCCGUCGAG AAGCAGGGAC CAGAGAAACA CACGUUGUGG UACAUUACCU GGUA    54

( 2 ) INFORMATION FOR SEQ ID NO:2705:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2705:

ACUGGAGCAG AAGUGUUAAC CAGAGAAACA CACGUUGUGG UACAUUACCU GGUA    54

( 2 ) INFORMATION FOR SEQ ID NO:2706:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2706:

UGCACUGGAG AAGCGGUGAC CAGAGAAACA CACGUUGUGG UACAUUACCU GGUA    54

( 2 ) INFORMATION FOR SEQ ID NO:2707:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2707:

GUGUGACAAG AAGACACCAC CAGAGAAACA CACGUUGUGG UACAUUACCU GGUA    54

( 2 ) INFORMATION FOR SEQ ID NO:2708:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2708:

CCUCCAAAAG AAGUUCCAAC CAGAGAAACA CACGUUGUGG UACAUUACCU GGUA    54

( 2 ) INFORMATION FOR SEQ ID NO:2709:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2709:

GGUCAGCAAG AAGCCAUCAC CAGAGAAACA CACGUUGUGG UACAUUACCU GGUA    54

( 2 ) INFORMATION FOR SEQ ID NO:2710:

( i ) SEQUENCE CHARACTERISTICS:
        ( A ) LENGTH: 54 base pairs ( B ) TYPE: nucleic acid
        ( C ) STRANDEDNESS: single
        ( D ) TOPOLOGY: linear ( x i ) SEQUENCE DESCRIPTION: SEQ ID NO:2710:

UUCAAAAGAG AAGCAAGCAC CAGAGAAACA CACGUUGUGG UACAUUACCU GGUA 54

( 2 ) INFORMATION FOR SEQ ID NO:2711:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2711:

UGACAGGGAG AAGGCAUGAC CAGAGAAACA CACGUUGUGG UACAUUACCU GGUA 54

( 2 ) INFORMATION FOR SEQ ID NO:2712:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2712:

CGAGCACAAG AAGCGGGCAC CAGAGAAACA CACGUUGUGG UACAUUACCU GGUA 54

( 2 ) INFORMATION FOR SEQ ID NO:2713:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2713:

GUUUUAAAAG AAGUUCUAC CAGAGAAACA CACGUUGUGG UACAUUACCU GGUA 54

( 2 ) INFORMATION FOR SEQ ID NO:2714:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2714:

CGGGUUUGAG AAGCAAGCAC CAGAGAAACA CACGUUGUGG UACAUUACCU GGUA 54

( 2 ) INFORMATION FOR SEQ ID NO:2715:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2715:

GGAUCAAAAG AAGGUAACAC CAGAGAAACA CACGUUGUGG UACAUUACCU GGUA 54

( 2 ) INFORMATION FOR SEQ ID NO:2716:

( i ) SEQUENCE CHARACTERISTICS:
        ( A ) LENGTH: 54 base pairs
        ( B ) TYPE: nucleic acid
        ( C ) STRANDEDNESS: single (D) TOPOLOGY: linear (xi) SEQUENCE DESCRIPTION: SEQ ID NO:2716:

AAACCCAGAG AAGAUUAAAC CAGAGAAACA CACGUUGUGG UACAUUACCU GGUA 54

(2) INFORMATION FOR SEQ ID NO:2717:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:2717:

UGCCUCGGCU GUGCGCGC 18

(2) INFORMATION FOR SEQ ID NO:2718:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:2718:

UGGGGCUGCU UGUUGACA 18

(2) INFORMATION FOR SEQ ID NO:2719:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:2719:

GACAGCGGUC CAUCUAGG 18

(2) INFORMATION FOR SEQ ID NO:2720:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:2720:

GGAAGCCGAC UGACAAGC 18

(2) INFORMATION FOR SEQ ID NO:2721:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:2721:

CUGCACAGCU CUUGAGAA 18

(2) INFORMATION FOR SEQ ID NO:2722:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (x i) SEQUENCE DESCRIPTION: SEQ ID NO:2722:

AUUCUCAGCC CAGUGGAA                                                                                          18

(2) INFORMATION FOR SEQ ID NO:2723:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (x i) SEQUENCE DESCRIPTION: SEQ ID NO:2723:

AGACACUGUC UGUACCUG                                                                                          18

(2) INFORMATION FOR SEQ ID NO:2724:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (x i) SEQUENCE DESCRIPTION: SEQ ID NO:2724:

UGAUACCGUC UGUCAUCC                                                                                          18

(2) INFORMATION FOR SEQ ID NO:2725:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (x i) SEQUENCE DESCRIPTION: SEQ ID NO:2725:

CAUCCCUGCC CAGUCGGC                                                                                          18

(2) INFORMATION FOR SEQ ID NO:2726:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (x i) SEQUENCE DESCRIPTION: SEQ ID NO:2726:

CUGCCCAGUC GGCUUCUU                                                                                          18

(2) INFORMATION FOR SEQ ID NO:2727:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (x i) SEQUENCE DESCRIPTION: SEQ ID NO:2727:

CCAGUCGGCU UCUUCUCC                                                                                          18

(2) INFORMATION FOR SEQ ID NO:2728:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (x i) SEQUENCE DESCRIPTION: SEQ ID NO:2728:

CGAGUCAGAC UAAUGUCA                                                                                                                    18

(2) INFORMATION FOR SEQ ID NO:2729:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:2729:

AGUCCCGGAU GCGAGCCC                                                                                                                    18

(2) INFORMATION FOR SEQ ID NO:2730:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:2730:

GAGCCCUGCU GGUCAUUC                                                                                                                    18

(2) INFORMATION FOR SEQ ID NO:2731:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:2731:

CAUUCCUGUC GUGAUGGG                                                                                                                    18

(2) INFORMATION FOR SEQ ID NO:2732:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:2732:

CCCUGCGGCU CGACGGCA                                                                                                                    18

(2) INFORMATION FOR SEQ ID NO:2733:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:2733:

UAACACCGCU GCUCCAGU                                                                                                                    18

(2) INFORMATION FOR SEQ ID NO:2734:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:2734:

CACCGCUGCU CCAGUGCA                                                                                                                    18

( 2 ) INFORMATION FOR SEQ ID NO:2735:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2735:

GGUGUCAGCC UGUCACAC　　　　　　　　　　　　　　　　　　　　　　　　　　18

( 2 ) INFORMATION FOR SEQ ID NO:2736:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2736:

UGGAACUGCU UUUGGAGG　　　　　　　　　　　　　　　　　　　　　　　　　　18

( 2 ) INFORMATION FOR SEQ ID NO:2737:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2737:

GAUGGCUGCU UGCUGACC　　　　　　　　　　　　　　　　　　　　　　　　　　18

( 2 ) INFORMATION FOR SEQ ID NO:2738:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2738:

GCUUGCUGAC CUUUUGAA　　　　　　　　　　　　　　　　　　　　　　　　　　18

( 2 ) INFORMATION FOR SEQ ID NO:2739:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2739:

CAUGCCUGCC CCCUGUCA　　　　　　　　　　　　　　　　　　　　　　　　　　18

( 2 ) INFORMATION FOR SEQ ID NO:2740:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2740:

GCCCGCAGCU UGUGCUCG　　　　　　　　　　　　　　　　　　　　　　　　　　18

( 2 ) INFORMATION FOR SEQ ID NO:2741:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2741:

AGAAACAGCU UUUAAAAC     18

( 2 ) INFORMATION FOR SEQ ID NO:2742:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2742:

GCUUGCUGCC CAAACCCG     18

( 2 ) INFORMATION FOR SEQ ID NO:2743:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2743:

GUUACCUGAU UUUGAUCC     18

( 2 ) INFORMATION FOR SEQ ID NO:2744:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2744:

UUAAUCCGCC CUGGGUUU     18

( 2 ) INFORMATION FOR SEQ ID NO:2745:

( i ) SEQUENCE CHARACTERISTICS:
    ( A ) LENGTH: 11 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N"stands for any
      base. The letter "H"stands
      for A, U, or C.

( x i ) SEQUENCE DESCRIPTION: SEQ ID NO:2745:

NNNNUHNNNN N     11

( 2 ) INFORMATION FOR SEQ ID NO:2746:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N"stands for any
      base.

(x i) SEQUENCE DESCRIPTION: SEQ ID NO:2746:

NNNNCUGAN GAGNNNNNC GAAANNNN                28

(2) INFORMATION FOR SEQ ID NO:2747:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (i x) FEATURE:
        (D) OTHER INFORMATION: The letter "N"stands for any base. The leter "Y"stands for U or C. The letter "H"stands for A, U, or C.

(x i) SEQUENCE DESCRIPTION: SEQ ID NO:2747:

NNNNNNNYNG HYNNN                15

(2) INFORMATION FOR SEQ ID NO:2748:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (i x) FEATURE:
        (D) OTHER INFORMATION: The letter "N"stands for any base.

(x i) SEQUENCE DESCRIPTION: SEQ ID NO:2748:

NNNNGAAGNN NNNNNNNNA AAHANNNNN NACAUUACNN NNNNNNN                47

(2) INFORMATION FOR SEQ ID NO:2749:

(i) SEQUENCE CHARACTERISTICS:
        (A) LENGTH: 85 base pairs
        (B) TYPE: nucleic acid
        (C) STRANDEDNESS: single
        (D) TOPOLOGY: linear (x i) SEQUENCE DESCRIPTION: SEQ ID NO:2749:

UGGCCGGCAU GGUCCCAGCC UCCUCGCUGG CGCCGGCUGG GCAACAUUCC GAGGGGACCG                60

UCCCCUCGGU AAUGGCGAAU GGGAC                85

(2) INFORMATION FOR SEQ ID NO:2750:

(i) SEQUENCE CHARACTERISTICS:
        (A) LENGTH: 176 base pairs
        (B) TYPE: nucleic acid
        (C) STRANDEDNESS: single
        (D) TOPOLOGY: linear (x i) SEQUENCE DESCRIPTION: SEQ ID NO:2750:

GGGAAAGCUU GCGAAGGGCG UCGUCGCCCC GAGCGGUAGU AAGCAGGGAA CUCACCUCCA                60

AUUUCAGUAC UGAAAUUGUC GUAGCAGUUG ACUACUGUUA UGUGAUUGGU AGAGGCUAAG                120

UGACGGUAUU GGCGUAAGUC AGUAUUGCAG CACAGCACAA GCCCGCUUGC GAGAAU                176

(2) INFORMATION FOR SEQ ID NO:2751:

(i) SEQUENCE CHARACTERISTICS:
        (A) LENGTH: 12 base pairs
        (B) TYPE: nucleic acid
        (C) STRANDEDNESS: single -continued (D) TOPOLOGY: linear (x i) SEQUENCE DESCRIPTION: SEQ ID NO:2751:

GGCCGAAAGG CC 12

1

B7-1 TARGETED RIBOZYMES

RELATED APPLICATIONS

This application claims the benefit of U.S. provisional application No. 60/000,951, filed Jul. 7, 1995 entitled Method and Reagent for the Induction of Graft Tolerance and Reversal of Immune Responses, which is hereby incorporated by reference herein in totality (including drawings and tables).

BACKGROUND OF THE INVENTION

This invention relates to methods for the induction of graft tolerance, treatment of autoimmune diseases, inflammatory disorders and allergies in particular, by inhibition of B7-1, B7-2, B7-3 and CD40.

The following is a discussion of relevant art, none of which is admitted to be prior art to the present invention.

An adaptive immune response requires activation, clonal expansion, and differentiation of a class of cells termed T lymphocytes (T cells). T cell activation is a multi-step process requiring several signalling events between the T cell and an antigen presenting cell. The ensuing discussion details signals that are exchanged between T cells and antigen presenting B cells. Similar pathways are thought to occur between T cells and other antigen presenting cells such as monocytes or follicular dendritic cells.

T cell activation is initiated when the T-cell receptor (TCR) binds to a specific antigen that is associated with the MHC proteins on the surface of an antigen presenting cell. This primary stimulus activates the T cell and induces expression of CD40 ligand (CD40L) on the surface of the T cell. CD40L then interacts with its cognate receptor, CD40, which is constitutively expressed on the surface of B cells; CD40 transduces the signal leading to B cell activation. B cell activations result in the expression of B7-1, B7-2 and/or B7-3, which in turn interacts with constitutively expressed CD28 on the surface of T cells. The interaction generates a secondary co-stimulatory signal that is required to fully activate the T cell. Complete T cell activation via the T cell receptor and CD28 leads to cytokine secretion, clonal expansion, and differentiation. If the T cell receptor is engaged, absence of this secondary co-stimulus mediated by CD28, then the T cell is inactivated, either by clonal anergy (non-responsiveness or reduced reactivity of the immune system to specific antigen(s)) or clonal deletion (Jenkins et al., 1987 Proc. Natl. Acad. Sci. USA 84, 5409). Thus, engagement of the TCR without a concomitant costimulatory signal results in a state of tolerance toward the specific antigen recognized by the T cell. This co-stimulatory signal can be mediated by the binding of B7-1 or B7-2 or B7-3, present on activated antigen-presenting cells, to CD28, a receptor that is constitutively expressed on the surface of the T cell (Marshall et al., 1993 J Clin Immun 13, 165–174; Linsley, et al., 1991 J Exp Med 173, 721; Koulova et al., 1991 J Exp Med 173, 759; Harding et al., 1992 Nature 356, 607).

Several homologs of B7 (now known as B7-1; Cohen, 1993 Science 262, 844) are expressed in activated B cells (Freeman et al., 1993 Science 262, 907; Lenschow et al., 1993 Proc Natl Acad Sci USA 90, 11054; Azuma et al., 1993 Nature 366, 76; Hathcock et al., 1993 Science 262, 905; Freeman et al., 1993 Science 262, 909). B7-1 and B7-3 are only expressed on the surface of a subset of B cells after 48 hours of contact with T cells. In contrast, B7-2 mRNA is constitutively expressed by unstimulated B cells and increases 4-fold within 4 hours of activation (Freeman et al., 1993 Science 262, 909; Boussiotis et al., 1993 Proc Natl Acad Sci USA 90, 11059). Since T cells commit to either the anergy or the activation pathway within 12–24 hours of the initial TCR signal, it is thought that B7-2 is the molecule responsible for the primary costimulatory signal. B7-1 and B7-3 may provide a subsequent signal necessary for clonal expansion. Antibodies to B7-2 completely block T cell proliferation in a mixed lymphocyte reaction (Azuma et al., 1993 supra), supporting the central role of B7-2 in T cell activation. These experiments indicate that inhibition of B7-2 expression (for example with a ribozyme) would likely induce anergy. Similarly, inhibition of CD40 expression by a ribozyme would prevent B7-2 upregulation and could induce tolerance to specific antigens.

B7 (B7-1) is a 60 KD modified trans-membrane glycoprotein usually present on the surface of antigen presenting cells (APC). B7 has two ligands-CD28 and CTLA4. Interaction of B7-1 with CD28 and/or CTLA4 causes activation of T cell responses (Janeway and Bottomly, 1994 Cell 76, 275).

B7-2 is a 70 KD (34 KD unmodified) trans-membrane glycoprotein found on the surface of APCs. B7-2 encodes a 323 amino-acid protein which is 26% identical to human B7-1 protein. Like B7-1, CD28 and CTLA4 are selectively bound by B7-2. B7-2, unlike B7-1, is expressed on the surface of unstimulated B cells (Freeman et al., 1993 supra).

CD40 is a 45–50 KD surface glycoprotein found on the surface of late pre-B cells in bone marrow, mature B cells, bone marrow-derived dendritic cells and follicular dendritic cells (Clark and Ledbetter, 1994 Nature 367, 425).

Successful organ transplantation currently requires suppression of the recipient's immune system in order to prevent graft rejection and maintain good graft function. The available therapies, including cyclosporin A, FK506 and various monoclonal antibodies, all have serious side effects (Caine, 1992 Transplantation Proceedings 24, 1260; Fuleihan et al., 1994 J. Clin. Invest. 93, 1315; Van Gool et al., 1994 Blood 83, 176). In addition, existing therapies result in general immune suppression, leaving the patient susceptible to a variety of opportunistic infections. The ability to induce a state of long-term, antigen-specific tolerance to the donor tissue would revolutionize the field of organ and tissue transplantation. Since organ graft rejection is mediated by T cell effector function, the goal is to block specifically the activation of the subset of T cells that recognize donor antigens. A limitation in the field of transplantation is the supply of donor organs (Nowak 1994 Science 266, 1148). The ability to induce donor-specific tolerance would substantially increase the chances of successful allographs, xenographs, thereby greatly increasing the donor pool.

Such transplantation includes grafting of tissues and/or organ ie., implantation or transplantation of tissue and/or organs, from the body of an individual to a different place within the same or different individual. Transplantation also involve grafting of tissues and/or organs from one area of the body to another. Transplantation of tissues and/or organs between genetically dissimilar animals of the same species is termed as allogeneic transplantation. Transplantation of animal organs into humans is termed xenotransplants (for a review see Nowak, 1994 Science 266, 1148).

One therapy currently being developed that has similar potential to induce antigen-specific tolerance is treatment with a CTLA4-lg fusion protein. "CTLA4" is a homologue of CD28 that binds B7-1 and B7-2 with high affinity. The engineered, soluble fusion protein, CTLA4-lg, binds B7-1, thereby blocking its interaction with CD28. The results of CTLA4-lg treatment in animal studies are mixed. CTLA4-lg treatment significantly enhanced survival rates and ameliorated the symptoms of graft-versus host disease in a murine bone marrow tranplant model (Blazer et al., 1994 *Blood* 83, 3815). CTLA4-lg induced long-term (>110 days) donor-specific tolerance in pancreatic islet xenographs (Lenschow et al., 1992 *Science* 257, 789). Conversely, in another study CTLA4-lg treatment delayed but did not ultimately prevent cardiac allograft rejection (Turka, et al., 1992 *Proc Natl Acad Sci USA* 89, 11102). Mice immunized with sheep erythrocytes in the presence of CTLA4-lg failed to mount a primary immune response (Linsley, et al., 1992 *Science* 257, 792). A secondary immunization did elicit some response, however, indicating incomplete tolerance. Interestingly, identical results were obtained when CTLA4-lg was administered 2 days after primary immunization, leading the authors to conclude that CTLA4-lg blocked amplification rather than initiation of the immune response. Since CTLA4-lg has been shown to dissociate more rapidly from B7-2 compared with B7-1, this may explain the failure to induce long term tolerance in this model (Linsley et al., 1994 *Immunity* 1, 793).

CTLA4:lg has recently been shown to ameliorate symptoms of spontaneous autoimmune disease in lupus-prone mice (Finck et al., 1994 *Science* 265, 1225).

Linsley et al., WO 92/00092 describe B7 antigen as a ligand for CD28 receptor on T cells. The application states that "The B7 antigen, or its fragments or derivatives are reacted with CD28 positive T cells to regulate T cell interactions with other cells . . . B7 antigen or CD28 receptor may be used to inhibit interaction of cells associated with these molecules, thereby regulating T cell responses."

De Boer and Conroy, WO 94/01547 describe the use of anti-B7 and anti-CD40 antibodies to treat allograft transplant rejection, graft versus host disease and rhematoid arthritis. The application states that " . . . anti-B7 and anti-CD40 antibodies . . . can be used to prevent or treat an antibody-mediated or immune system disease in a patient."

Since signalling via CD40 precedes induction of B-7, blocking the CD40-CD40L interaction would also have the potential to produce tolerance. According to one report, simultaneous treatment of mice with antibodies to CD40L and sheep red blood cells produced antigen-specific tolerance for up to 3 weeks following cessation of treatment (Foy et al., 1993 *J Exp Med* 178, 1567). Anti-CD40L also produces antigen specific tolerance in a pancreatic islet transplant model (R. Noelle, personal communication). Targeted inhibition of CD40 expression in B cells in addition to B7 would therefore afford double protection against activation of T cells.

Therapeutic agents used to prevent rejection of a transplanted organ are all cytotoxic compounds or antibodies designed to suppress the cell-mediated immune system. The side effects of these agents are those of immunosuppression and infections. The primary approved agents are azathioprine, corticosteroids, cyclosporine; the antibodies are antilymphocyte or antithymocyte globulins. All of these are given to individuals who have been as closely matched as possible to their donors by both major and minor histocompatibility typing. Since the principal problem in transplantation is an antigenic mismatch and the resulting need for cytotoxic therapy, any therapeutic improvement which decreases the local immune response without general immunosuppression should capture the transplant market.

Cyclosporine

At the end of the 1970's and early 1980's the introduction of cyclosporine revolutionized the transplantation field. It is a potent immunosuppressant which can inhibit immunocompetent lymphocytes specifically and reversibly. Its primary mechanism of action appears to be inhibition of the production and release of interleukin-2 by T helper cells. In addition it also interferes with the release of interleukin-1 by macrophages, as well as proliferation of B lymphocytes. It was approved by the FDA in 1983 and by 1989 was almost universally given to transplant recipients. At first it was believed that the toxicity and side effects from cyclosporine were minimal and it was hailed as a "wonder drug." Numerous side effects have been progressively cited, including the appearance of lymphomas, especially in the gastrointestinal tract; acute and chronic nephrotoxicity; hypertension; hepatotoxicity; hirsutism; anemia; neurotoxicity; endocrine and neurological complications; and gastrointestinal distress. It is now widely acknowledged that the non-specific side effects of the drug demand caution and close monitoring of its use. One-year survival rates for cadaver kidney transplants treated with cyclosporine is 80%, much better than the 50–60% rates without the drug. The one-year survival is almost 90% for transplants with related donors and the use of cyclosporine.

Azathioprine

In addition to cyclosporine, azathioprine is used for transplant patients. Azathioprine is one of the mercaptopurine class of drugs and inhibits nucleic acid synthesis. Patients are maintained indefinitely on daily doses of 1 mg/kg or less, with a dosage adjusted in accordance with the white cell count. The drug may cause depression of bone marrow elements and may cause jaundice.

Corticosteroids

Prednisone, used in almost all transplant recipients, is usually given in association with azathioprine and cyclosporine. The dosage must be regulated carefully so as so prevent complications such as infection, development of cushingoid features, and hypertension. Usually the initial maintenance prednisone dosage is 0.5 mg/kg/d. This dosage is usually further decreased in the outpatient clinic until maintenance levels of about 10 mg/d for adults are obtained. The exact site of action of corticosteroids on the immune response is not known.

Antithymoblast or antilymphocyte globulin (ALG) and antithymocyte globulin (ATG)

These are important adjunctive immunosuppressants. They are effective, particularly in induction of immunosuppressive therapy and in the treatment of corticosteroid-resistant rejection. Both ALG and ATG can be made by immunizing horses, rabbits, or sheep; the main source is horses. Lymphocytes from human peripheral blood, spleen, lymph nodes, or thymus serve as the immunogen.

Tacrolimus

On Apr. 13, 1994 the Food and Drug Administration approved another drug to help prevent the rejection of organ transplants. The drug, tacrolimus, was approved only for use in liver transplant patients. An alternative to cyclosporine, the macrolide immunosuppressant tacrolimus is a powerful and selective anti-T-lymphocyte agent that was discovered in 1984. Tacrolimus, isolated from the fungus *Streptomyces tsukubaensis*, possesses immunodepressant properties similar to but more potent than cyclosporine. It inhibits both cell-mediated and humoral immune responses. Like cyclosporine, tacrolimus demonstrates considerable interindividual variation in its pharmacokinetic profile. Most clinical studies with tacrolimus have neither been published in their entirety nor subjected to extensive peer review; there is also a paucity of published randomized investigations of tacrolimus vs. cyclosporine, particularly in renal transplantation. Despite these drawbacks, tacrolimus has shown notable efficacy as a rescue or primary immunosuppressant therapy when combined with corticosteroids. The potential for reductional withdrawal of corticosteroid therapy with tacrolimus appears to be a distinct advantage compared with the cyclosporine. This benefit may be enhanced by reduced incidence of infectious complications, hypertension and hypercholesterolemia reported by some investigators. In other respects, the tolerability profile of tacrolimus appears to be broadly similar to that of cyclosporine.

In addition to induction of graft tolerance, T cell anergy can be used to reverse autoimmune diseases. Autoimmune diseases represent a broad category of conditions. A few examples include insulin-dependent diabetes mellitus (IDDM), multiple schlerosis (MS), systemic lupus erythematosus (SLE), rheumatoid arthritis (RA), myasthenia gravis (MG), and psoriasis. These seemingly disparate diseases all share the common feature of inappropriate immune response to specific self-antigens. Finck et al. supra have reported that CTLA4 lg treatment of mice blocked auto-antibody production in a mice model of SLE. In fact, this effect was observed even when the CTLA4 lg treatment was initiated during the advanced stages of the disease, suggesting that the autoimmune response was a reversible process.

Chappel., WO 94/11011 describes method to treat autoimmune diseases by inducing tolerance to cells, tissues and organs. The application states that "Cells genetically engineered with DNA encoding a plurality of antigens of a cell, tissue, or organ to which tolerance is to be induced. The cells are free of co-stimulatory antigens, such as B7 antigen. Such cells induce T-cell anergy against the proteins encoded by the DNA, and may be administered to a patient in order to prevent the onset of or to treat an autoimmune disease, or to induce tolerance to a tissue or organ prior to transplantation."

Allergic reactions represent an immediate hypersensitivity response to environmental antigens, typically mediated by IgE antibodies. The ability to induce antigen-specific tolerance provides a powerful avenue to alleviate allergies by exposure to the antigen in conjunction with down-regulation of B7-1, B7-2, B7-3 or CD40.

The specific roles of B7-1, B7-2 and B7-3 in T cell activation remains to be determined. Some studies suggest that their functions are essentially redundant (Hathcock et al 1994 *J Exp. Med.* 180, 631), or that the differences observed in the kinetics of expression might simply indicate that B7-2 is important in the initiation of the co-stimulatory signal, while B7-1 plays a role in the amplification of that signal. Other studies point to more specific functions. For example, Kuchroo et al., 1995 *Cell* 80, 707, have reported that blocking B7-1 expression may favor a Th2 response, while blocking B7-2 expression favors a Th1 response. These two helper T cell subpopulations play distinct roles in the immune response and inflammatory disease. Th1 cells are strongly correlated with auto-immune disease. Allergic responses are typically triggered by Th2 response. Therefore, the decision to target B7-1, B7-2, CD40 or a combination of the above will depend to the particular disease application.

SUMMARY OF THE INVENTION

The invention features novel nucleic acid-based techniques [e.g., enzymatic nucleic acid molecules (ribozymes), antisense nucleic acids, 2-5A antisense chimeras, triplex DNA, antisense nucleic acids containing RNA cleaving chemical groups (Cook et al., U.S. Pat. No. 5,359,051)] and methods for their use to induce graft tolerance, to treat autoimmune diseases such as lupus, rheumatoid arthritis, multiple sclerosis and to treatment of allergies.

In a preferred embodiment, the invention features use of one or more of the nucleic acid-based techniques to induce graft tolerance by inhibiting the synthesis of B7-1, B7-2, B7-3 and CD40 proteins.

Those in the art will recognize the other potential targets, for e.g., ICAM-1, VCAM-1, β1 integrin (VLA4) are also suitable for treatment with the nucleic acid-based techniques described in the present invention.

By "inhibit" is meant that the activity of B7-1, B7-2, B7-3 and/or CD40 or level of mRNAs encoded by B7-1, B7-2, B7-3 and/or CD40 is reduced below that observed in the absence of the nucleic acid. In one embodiment, inhibition with ribozymes preferably is below that level observed in the presence of an enzymatically inactive RNA molecule able to bind to the same site on the mRNA, but unable to cleave that RNA.

By "enzymatic RNA molecule" it is meant an RNA molecule which has complementarity in a substrate binding region to a specified gene target, and also has an enzymatic activity which is active to specifically cleave RNA in that target. That is, the enzymatic RNA molecule is able to intermolecularly cleave RNA and thereby inactivate a target RNA molecule. This complementarity functions to allow sufficient hybridization of the enzymatic RNA molecule to the target RNA to allow the cleavage to occur. One hundred percent complementarity is preferred, but complementarity as low as 50–75% may also be useful in this invention. By "equivalent" RNA to B7-1, B7-2, B7-3 and/or CD40 is meant to include those naturally occurring RNA molecules associated with graft rejection in various animals, including human, mice, rats, rabbits, primates and pigs.

By "antisense nucleic acid" is meant a non-enzymatic nucleic acid molecule that binds to another RNA (target RNA) by means of RNA-RNA or RNA-DNA or RNA-PNA (protein nucleic acid; Egholm et al., 1993 *Nature* 365, 566) interactions and alters the activity of the target RNA (for a review see Stein and Cheng, 1993 *Science* 261, 1004).

By "2-5A antisense chimera" is meant, an antisense oligonucleotide containing a 5' phosphorylated 2'-5'-linked adenylate residues. These chimeras bind to target RNA in a sequence-specific manner and activate a cellular 2-5A-dependent ribonuclease which in turn cleaves the target RNA (Torrence et al., 1993 *Proc. Natl. Acad. Sci. U.S.A.* 90, 1300).

By "triplex DNA" is meant an oligonucleotide that can bind to a double-stranded DNA in a sequence-specific manner to form a triple-strand helix. Triple-helix formation has been shown to inhibit transcription of the targeted gene (Duval-Valentin et al., 1992 *Proc. Natl. Acad. Sci. USA* 89, 504).

By "gene" is meant a nucleic acid that encodes an RNA.

By "complementarity" is meant a nucleic acid that can form hydrogen bond(s) with other RNA sequence by either traditional Watson-Crick or other non-traditional types (for example, Hoogsteen type) of base-paired interactions.

Six basic varieties of naturally-occurring enzymatic RNAs are known presently. Each can catalyze the hydrolysis of RNA phosphodiester bonds in trans (and thus can cleave other RNA molecules) under physiological conditions. Table I summarizes some of the characteristics of these ribozymes. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nature of a ribozyme is advantageous over other technologies, since the concentration of ribozyme necessary to affect a therapeutic treatment is lower. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base-pairing mechanism of binding to the target RNA, but also on the mechanism of target RNA cleavage. Single mismatches, or base-substitutions, near the site of cleavage can completely eliminate catalytic activity of a ribozyme.

Ribozymes that cleave the specified sites in B7-1, B7-2, B7-3 and/or CD40 mRNAs represent a novel therapeutic approach to induce graft tolerance and treat autoimmune diseases, allergies and other inflammatory conditions. Applicant indicates that ribozymes are able to inhibit the activity of B7-1, B7-2, B7-3 and/or CD40 and that the catalytic activity of the ribozymes is required for their inhibitory effect. Those of ordinary skill in the art, will find that it is clear from the examples described that other ribozymes that cleave these sites in B7-1, B7-2, B7-3 and/or CD40 mRNAs may be readily designed and are within the invention.

In preferred embodiments of this invention, the enzymatic nucleic acid molecule is formed in a hammerhead or hairpin motif, but may also be formed in the motif of a hepatitis delta virus, group I intron or RNaseP RNA (in association with an RNA guide sequence) or Neurospora VS RNA. Examples of such hammerhead motifs are described by Rossi et al., 1992, *Aids Research and Human Retroviruses* 8, 183, of hairpin motifs by Hampel et al., EP0360257, Hampel and Tritz, 1989 *Biochemistry* 28, 4929, and Hampel et al., 1990 *Nucleic Acids Res.* 18, 299, and an example of the hepatitis delta virus motif is described by Perrotta and Been, 1992 *Biochemistry* 31, 16; of the RNaseP motif by Guerrier-Takada et al., 1983 *Cell* 35, 849, Neurospora VS RNA ribozyme motif is described by Collins (Saville and Collins, 1990 *Cell* 61, 685–696; Saville and Collins, 1991 *Proc. Natl. Acad. Sci. USA* 88, 8826–8830; Collins and Olive, 1993 *Biochemistry* 32, 2795–2799) and of the Group I intron by Cech et al., U.S. Pat. No. 4,987,071. These specific motifs are not limiting in the invention and those skilled in the art will recognize that all that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule.

In a preferred embodiment the invention provides a method for producing a class of enzymatic cleaving agents which exhibit a high degree of specificity for the RNA of a desired target. The enzymatic nucleic acid molecule is preferably targeted to a highly conserved sequence region of a target mRNAs encoding B7-1, B7-2, B7-3 and/or CD40 proteins such that specific treatment of a disease or condition can be provided with either one or several enzymatic nucleic acids. Such enzymatic nucleic acid molecules can be delivered exogenously to specific cells as required. Alternatively, the ribozymes can be expressed from DNA/RNA vectors that are delivered to specific cells.

Synthesis of nucleic acids greater than 100 nucleotides in length is difficult using automated methods, and the therapeutic cost of such molecules is prohibitive. In this invention, small enzymatic nucleic acid motifs (e.g., of the hammerhead or the hairpin structure) are used for exogenous delivery. The simple structure of these molecules increases the ability of the enzymatic nucleic acid to invade targeted regions of the mRNA structure. However, these catalytic RNA molecules can also be expressed within cells from eukaryotic promoters (e.g., Scanlon et al., 1991, *Proc. Natl. Acad. Sci. USA,* 88, 10591–5; Kashani-Sabet et al., 1992 *Antisense Res. Dev.,* 2, 3–15; Dropulic et al., 1992 *J. Virol,* 66, 1432–41; Weerasinghe et al., 1991 *J. Virol,* 65, 5531–4; Ojwang et al., 1992 *Proc. Natl. Acad. Sci. USA* 89, 10802–6; Chen et al., 1992 *Nucleic Acids Res.,* 20, 4581–9; Sarver et al., 1990 *Science* 247, 1222–1225). Those skilled in the art realize that any ribozyme can be expressed in eukaryotic cells from the appropriate DNA/RNA vector. The activity of such ribozymes can be augmented by their release from the primary transcript by a second ribozyme (Draper et al., PCT WO93/23569, and Sullivan et al., PCT WO94/02595, both hereby incorporated in their totality by reference herein; Ohkawa et al., 1992 *Nucleic Acids Symp. Ser.,* 27, 15–6; Taira et al., 1991, *Nucleic Acids Res.,* 19, 5125–30; Ventura et al., 1993 *Nucleic Acids Res.* 21, 3249–55; Chowrira et al., 1994 *J. Biol. Chem.* 269, 25856).

Such ribozymes are useful for the prevention of the diseases and conditions discussed above, and any other diseases or conditions that are related to the levels of B7-1, B7-2, B7-3 and/or CD40 activity in a cell or tissue. By "related" is meant that the inhibition of B7-1, B7-2, B7-3 and/or CD40 mRNAs and thus reduction in the level respective protein activity will relieve to some extent the symptoms of the disease or condition.

Ribozymes are added directly, or can be complexed with cationic lipids, packaged within liposomes, or otherwise delivered to target cells. The nucleic acid or nucleic acid complexes can be locally administered to relevant tissues ex vivo, or in vivo through injection, infusion pump or stent, with or without their incorporation in biopolymers. In preferred embodiments, the ribozymes have binding arms which are complementary to the sequences in Tables II, IV, VI, VIII, X, XII, XIV, XV, XVI, XVII, XVIII and XIX. Examples of such ribozymes are shown in Tables III, V, VI, VII, IX, XI, XIII, XIV, XV, XVI, XVII, XVIII and XIX. Examples of such ribozymes consist essentially of sequences defined in these Tables. By "consists essentially of" is meant that the active ribozyme contains an enzymatic center equivalent to those in the examples, and binding arms able to bind mRNA such that cleavage at the target site occurs. Other sequences may be present which do not interfere with such cleavage.

In another aspect of the invention, ribozymes that cleave target molecules and inhibit B7-1, B7-2, B7-3 and/or CD40 activity are expressed from transcription units inserted into DNA or RNA vectors. The recombinant vectors are preferably DNA plasmids or viral vectors. Ribozyme expressing viral vectors could be constructed based on, but not limited to, adeno-associated virus, retrovirus, adenovirus, or alphavirus. Preferably, the recombinant vectors capable of expressing the ribozymes are delivered as described above, and persist in target cells. Alternatively, viral vectors may be used that provide for transient expression of ribozymes. Such vectors might be repeatedly administered as necessary. Once expressed, the ribozymes cleave the target mRNA. Delivery of ribozyme expressing vectors could be systemic, such as by intravenous or intramuscular administration, by administration to target cells ex-planted from the patient followed by reintroduction into the patient, or by any other means that would allow for introduction into the desired target cell.

By "vectors" is meant any nucleic acid- and/or viral-based technique used to deliver a desired nucleic acid.

Other features and advantages of the invention will be apparent from the following description of the preferred embodiments thereof, and from the claims.

DESCRIPTION OF THE PREFERRED EMBODIMENTS

The drawings will first briefly be described.
Drawings

FIG. 2a is a diagrammatic representation of the hammerhead ribozyme domain known in the art;

FIG. 2b is a diagrammatic representation of the hammerhead ribozyme as divided by Uhlenbeck (1987, Nature, 327, 596–600) into a substrate and enzyme portion;

FIG. 2c is a similar diagram showing the hammerhead divided by Haseloff and Gerlach (1988, Nature, 334, 585–591) into two portions; and FIG. 2d is a similar diagram showing the hammerhead divided by Jeffries and Symons (1989, Nucl. Acids. Res., 17, 1371–1371) into two portions.

Figure 1:
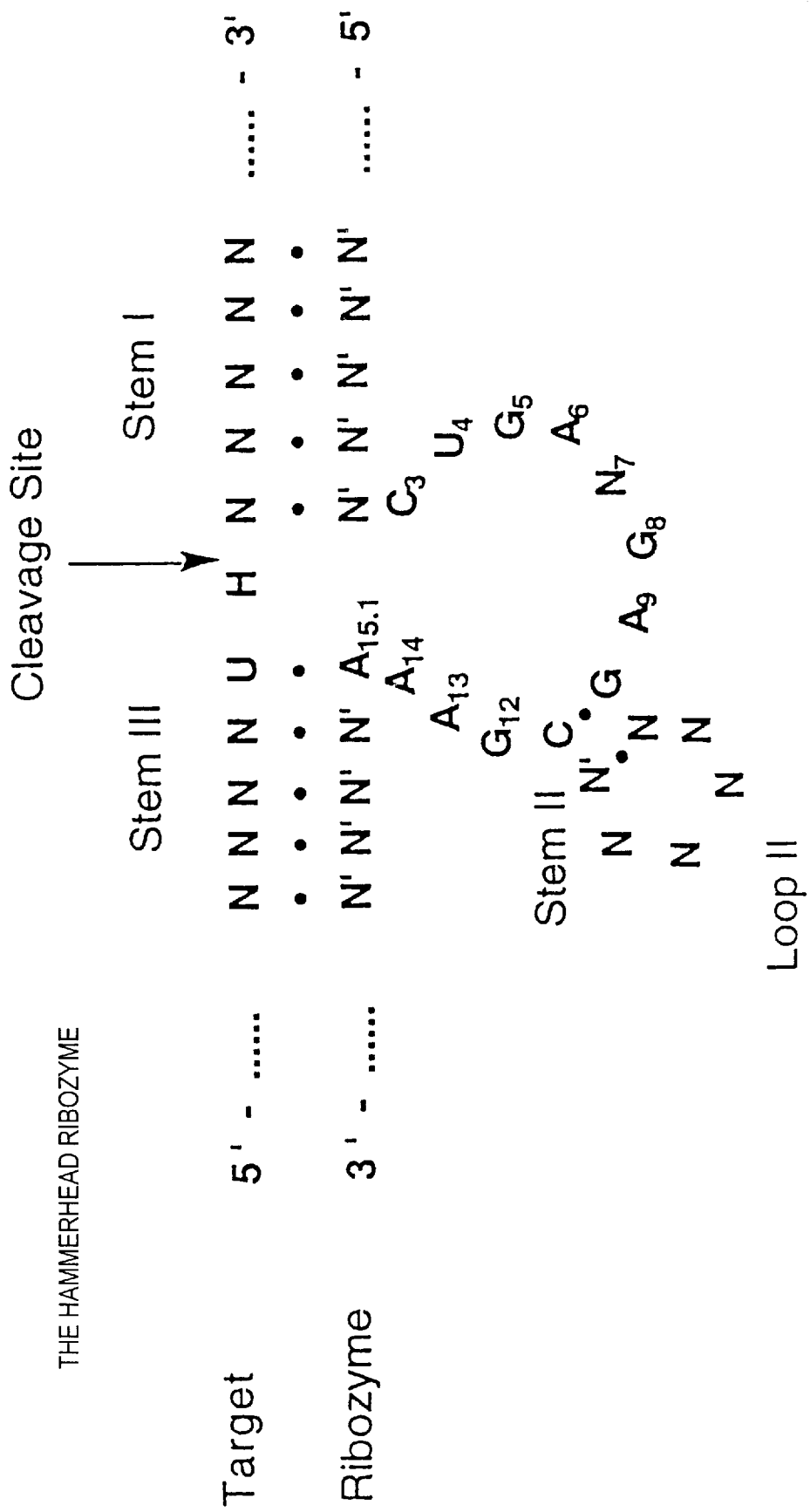
FIG. 1 is a diagrammatic representation of the hammerhead ribozyme domain known in the art. Stem II can be $\geq 2$ base-pair long.
Figure 3:
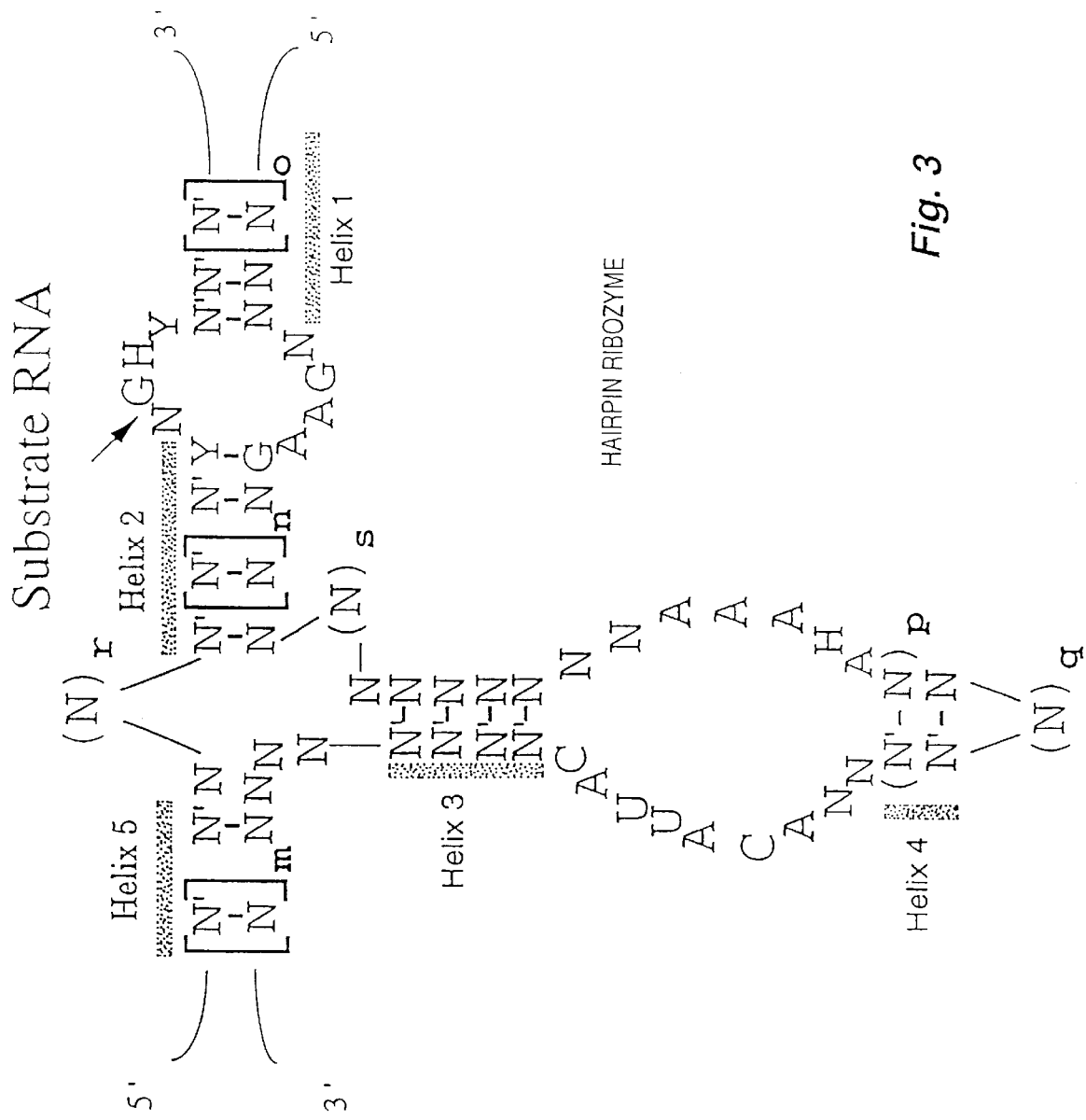

FIG. 3 is a diagramatic representation of the general structure of a hairpin ribozyme. Helix 2 (H2) is provided with a least 4 base pairs (i.e., n is 1, 2, 3 or 4) and helix 5 can be optionally provided of length 2 or more bases (preferably 3–20 bases, i.e., m is from 1–20 or more). Helix 2 and helix 5 may be covalently linked by one or more bases (i.e., r is $\geq 1$ base). Helix 1, 4 or 5 may also be extended by 2 or more base pairs (e.g., 4–20 base pairs) to stabilize the ribozyme structure, and preferably is a protein binding site. In each instance, each N and N' independently is any normal or modified base and each dash represents a potential base-pairing interaction. These nucleotides may be modified at the sugar, base or phosphate. Complete base-pairing is not required in the helices, but is preferred. Helix 1 and 4 can be of any size (i.e., o and p is each independently from 0 to any number, e.g., 20) as long as some base-pairing is maintained. Essential bases are shown as specific bases in the structure, but those in the art will recognize that one or more may be modified chemically (abasic, base, sugar and/or phosphate modifications) or replaced with another base without significant effect. Helix 4 can be formed from two separate molecules, i.e., without a connecting loop. The connecting loop when present may be a ribonucleotide with or without modifications to its base, sugar or phosphate. "q" is $\geq 2$ bases. The connecting loop can also be replaced with a non-nucleotide linker molecule. H, refers to bases A, U or C. Y refers to pyrimidine bases.

Figure 4:
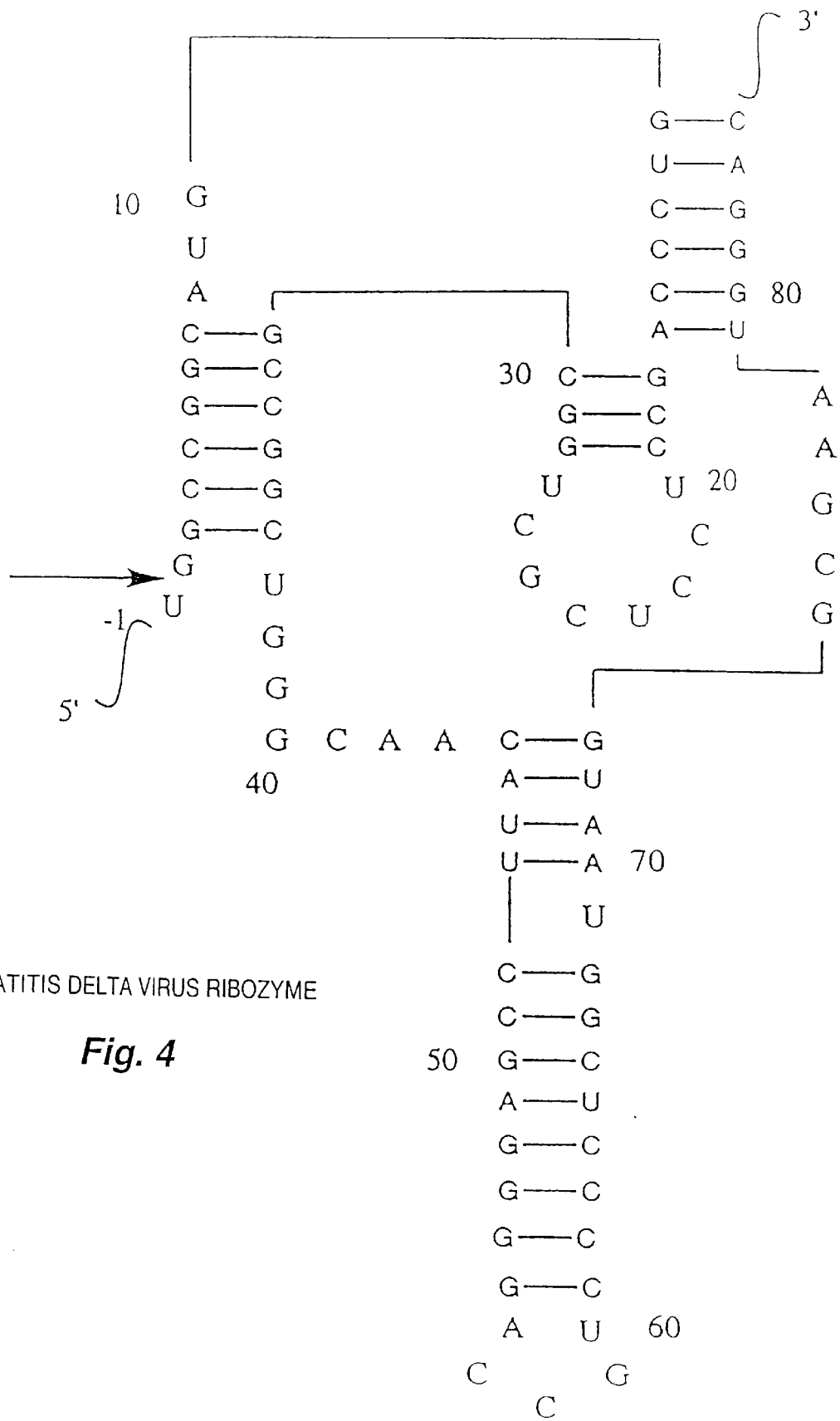

FIG. 4 is a representation of the general structure of the hepatitis delta virus ribozyme domain known in the art.

Figure 5:
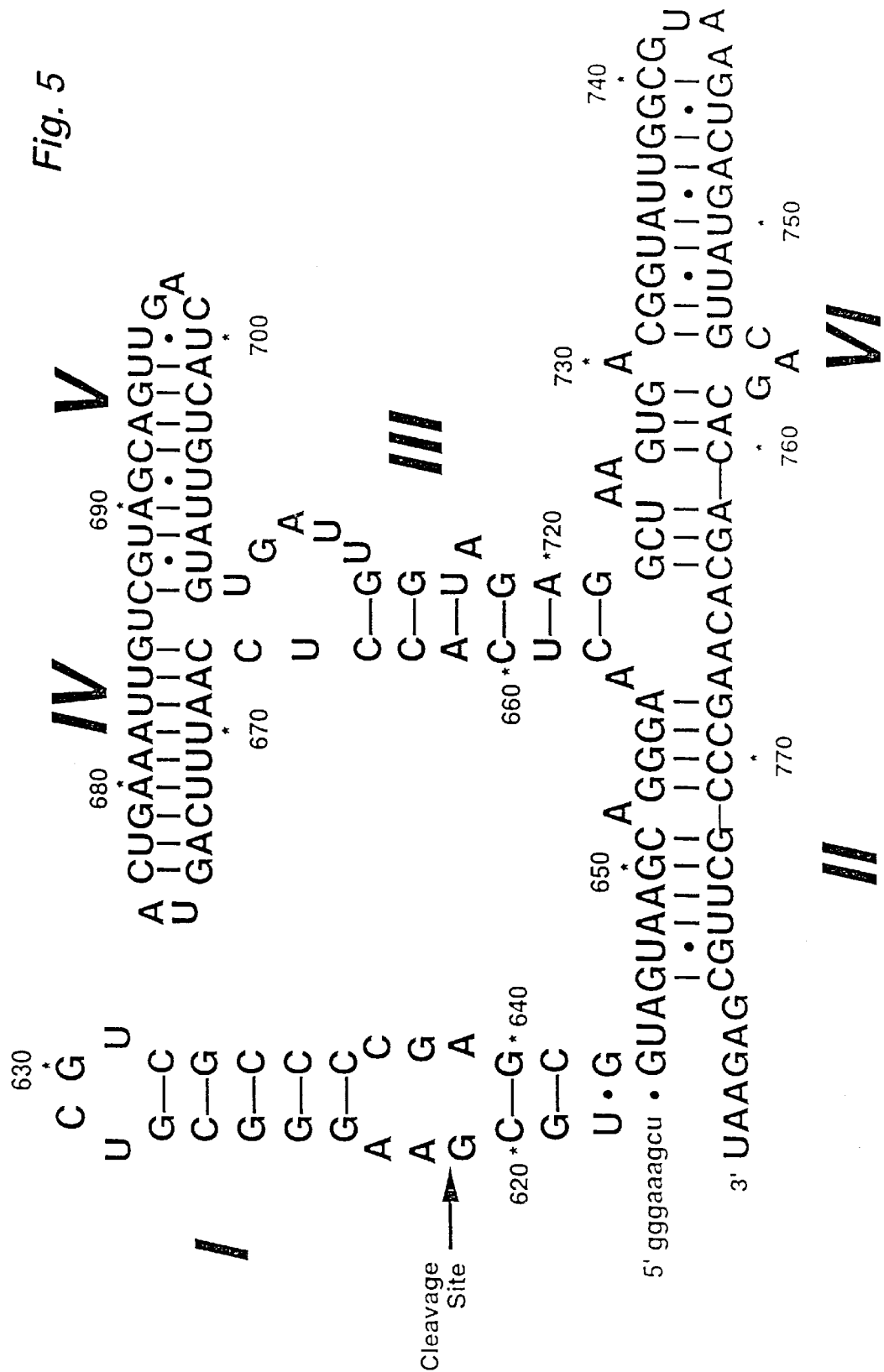

FIG. 5 is a representation of the general structure of the self-cleaving VS RNA ribozyme domain.

Figure 6B:
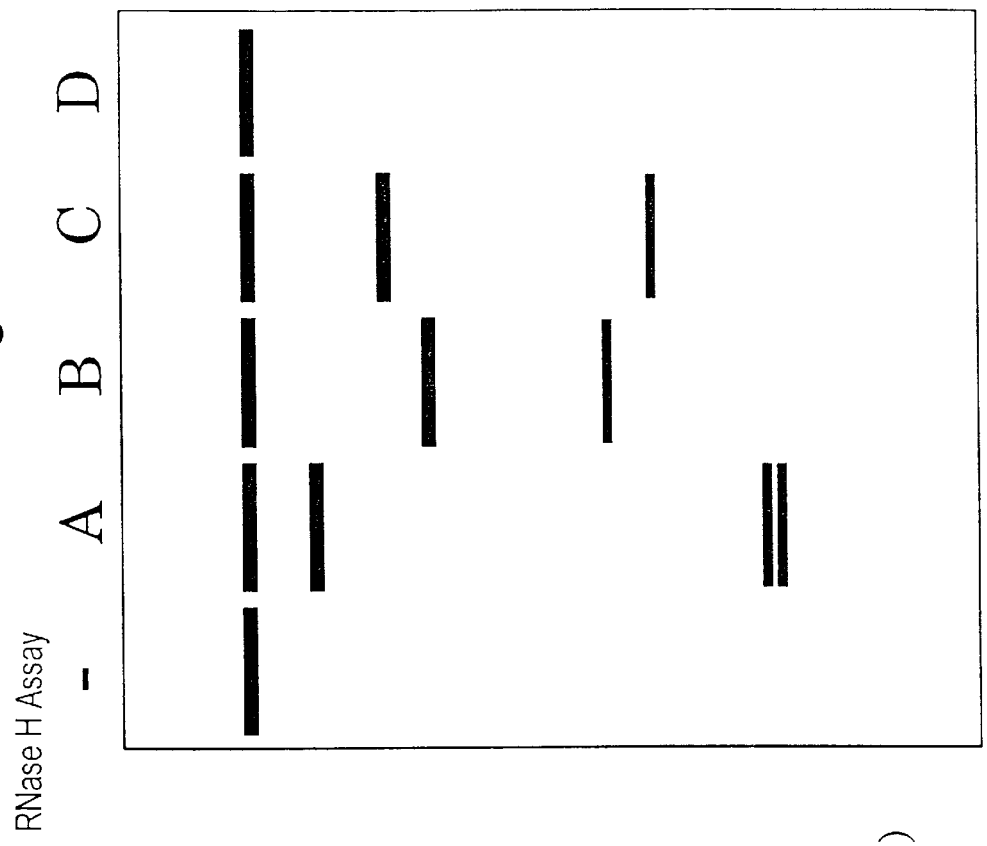
Figure 6A:
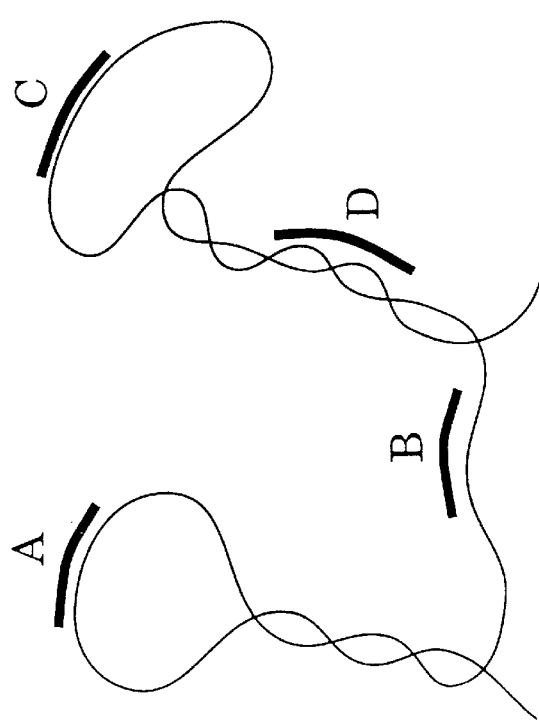

FIG. 6 is a schematic representation of an RNAseH accessibility assay. Specifically, the left side of FIG. 6 is a diagram of complementary DNA oligonucleotides bound to accessible sites on the target RNA. Complementary DNA oligonucleotides are represented by broad lines labeled A, B, and C. Target RNA is represented by the thin, twisted line. The right side of FIG. 6 is a schematic of a gel separation of uncut target RNA from a cleaved target RNA. Detection of target RNA is by autoradiography of body-labeled, T7 transcript. The bands common to each lane represent uncleaved target RNA; the bands unique to each lane represent the cleaved products.

RIBOZYMES

Ribozymes of this invention block to some extent B7-1, B7-2, B7-3 and/or CD40 production and can be used to treat disease or diagnose such disease. Ribozymes will be delivered to cells in culture, to cells or tissues in animal models of transplantation, autoimmune diseases and/or allergies and to human cells or tissues ex vivo or in vivo. Ribozyme cleavage of B7-1, B7-2 and/or CD40 encoded mRNAs in these systems may alleviate disease symptoms.

Target sites

Targets for useful ribozymes can be determined as disclosed in Draper et al., "Method and reagent for treatment of arthritic conditions" U.S. Ser. No. 08/152,487, filed Nov. 12, 1993, and hereby incorporated by reference herein in totality. Rather than repeat the guidance provided in those documents here, below are provided specific examples of such methods, not limiting to those in the art. Ribozymes to such targets are designed as described in those applications and synthesized to be tested in vitro and in vivo, as also described.

The sequence of human and mouse B7-1, B7-2, B7-3 and/or CD40 mRNAs were screened for optimal ribozyme target sites using a computer folding algorithm. Hammerhead or hairpin ribozyme cleavage sites were identified. These sites are shown in Tables II, IV, VI, VIII, X, XII, XIV, XV, XVI, XVII, XVIII and XIX (All sequences are 5' to 3' in the tables) The nucleotide base position is noted in the Tables as that site to be cleaved by the designated type of ribozyme. While mouse and human sequences can be screened and ribozymes thereafter designed, the human targeted sequences are of most utility. However, as discussed in Stinchcomb et al., "Method and Composition for Treatment of Restenosis and Cancer Using Ribozymes," filed May 18, 1994, U.S. Ser. No. 08/245,466, mouse targeted ribozymes may be useful to test efficacy of action of the ribozyme prior to testing in humans. The nucleotide base position is noted in the Tables as that site to be cleaved by the designated type of ribozyme.

Hammerhead or hairpin ribozymes were designed that could bind and were individually analyzed by computer folding (Jaeger et al., 1989 Proc. Natl. Acad. Sci. USA, 86, 7706) to assess whether the ribozyme sequences fold into the appropriate secondary structure. Those ribozymes with unfavorable intramolecular interactions between the binding arms and the catalytic core were eliminated from consideration. Varying binding arm lengths can be chosen to optimize activity. Generally, at least 5 bases on each arm are able to bind to, or otherwise interact with, the target RNA.

Referring to FIG. 6, mRNA is screened for accessible cleavage sites by the method described generally in McSwiggen, U.S. patent application 07/883,849 filed on May 1, 1992, entitled "Assay for ribozyme target site", hereby incorporated by reference herein. Briefly, DNA oligonucleotides representing potential hammerhead or hairpin ribozyme cleavage sites were synthesized. A polymerase chain reaction is used to generate substrates for T7 RNA polymerase transcription from human and mouse B7-1, B7-2 and CD40 cDNA clones. Labeled RNA transcripts are synthesized in vitro from the templates. The oligonucleotides and the labeled transcripts were annealed, RNAseH was added and the mixtures were incubated for the designated times at 37° C. Reactions are stopped and RNA separated on sequencing polyacrylamide gels. The percentage of the substrate cleaved is determined by autoradiographic quantitation using PhosphorImaging system. From these data, hammerhead or hairpin ribozyme sites are chosen as the most accessible.

Ribozymes of the hammerhead or hairpin motif are designed to anneal to various sites in the mRNA message. The binding arms are complementary to the target site sequences described above. The ribozymes are chemically synthesized. The method of synthesis used follows the procedure for normal RNA synthesis as described in Usman et al., 1987 *J. Am. Chem. Soc.,* 109, 7845 and in Scaringe et al., 1990 *Nucleic Acids Res.,* 18, 5433 and makes use of common nucleic acid protecting and coupling groups, such as dimethoxytrityl at the 5'-end, and phosphoramidites at the 3'-end. The average stepwise coupling yields were >98%. Inactive ribozymes were synthesized by substituting a U for $G_5$ and a U for $A_{14}$ (numbering from Hertel et al., 1992 *Nucleic Acids Res.,* 20, 3252). Hairpin ribozymes were synthesized in two parts and annealed to reconstruct the active ribozyme (Chowrira and Burke, 1992 *Nucleic Acids Res.,* 20, 2835–2840). Ribozymes were also synthesized from DNA templates using bacteriophage T7 RNA polymerase (Milligan and Uhlenbeck, 1989, *Methods Enzymol.* 180, 51). All ribozymes are modified extensively to enhance stability by modification with nuclease resistant groups, for example, 2'-amino, 2'-C-allyl, 2'-flouro, 2'-O-methyl, 2'-H (for a review see Usman and Cedergren, 1992 *TIBS* 17, 34). Ribozymes are purified by gel electrophoresis using general methods or are purified by high pressure liquid chromatography (HPLC; See Usman et al., Synthesis, deprotection, analysis and purification of RNA and ribozymes, filed May, 18, 1994, U.S. Ser. No. 08/245,736 the totality of which is hereby incorporated herein by reference) and are resuspended in water.

The sequences of the ribozymes that are chemically synthesized, useful in this study, are shown in Tables III, V, VI, VII, IX, XI, XIII, XIV, XV, XVI, XVII, XVIII and XIX. Those in the art will recognize that these sequences are representative only of many more such sequences where the enzymatic portion of the ribozyme (all but the binding arms) is altered to affect activity. For example, stem-loop II sequence of hammerhead ribozymes listed in Tables III and V (5'-GGCCGAAAGGCC-3') can be altered (substitution, deletion, and/or insertion) to contain any sequences provided a minimum of two base-paired stem structure can form. Similarly, stem-loop IV sequence of hairpin ribozymes listed in Tables VI and VII (5'-CACGUUGUG-3') can be altered (substitution, deletion, and/or insertion) to contain any sequence, provided a minimum of two base-paired stem structure can form. The sequences listed in Tables III, V, VI, VII, IX, XI, XIII, XIV, XV, XVI, XVII, XVIII and XIX may be formed of ribonucleotides or other nucleotides or non-nucleotides. Such ribozymes are equivalent to the ribozymes described specifically in the Tables.

Optimizing Ribozyme Activity

Ribozyme activity can be optimized as described by Stinchcomb et al., supra. The details will not be repeated here, but include altering the length of the ribozyme binding arms (stems I and III, see FIG. 2c), or chemically synthesizing ribozymes with modifications that prevent their degradation by serum ribonucleases (see e.g., Eckstein et al., International Publication No. WO 92/07065; Perrault et al., 1990 *Nature* 344, 565; Pieken et al., 1991 *Science* 253, 314; Usman and Cedergren, 1992 *Trends in Biochem. Sci.* 17, 334; Usman et al., International Publication No. WO 93/15187; and Rossi et al., International Publication No. WO 91/03162, as well as Usman, N. et al. U.S. patent application 07/829,729, and Sproat, European Patent Application 92110298.4 which describe various chemical modifications that can be made to the sugar moieties of enzymatic RNA molecules). Modifications which enhance their efficacy in cells, and removal of stem II bases to shorten RNA synthesis times and reduce chemical requirements are desired. (All these publications are hereby incorporated by reference herein.).

Sullivan, et al., supra, describes the general methods for delivery of enzymatic RNA molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, ribozymes may be directly delivered ex vivo to cells or tissues with or without the aforementioned vehicles. Alternatively, the RNA/vehicle combination is locally delivered by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of ribozyme delivery and administration are provided in Sullivan et al., supra and Draper et al., supra which have been incorporated by reference herein.

In another preferred embodiment, the ribozyme is administered to the site of B7-1, B7-2, B7-3 and/or CD40 expression (APC) in an appropriate liposomal vesicle. APCs isolated from donor (for example) are treated with the ribozyme preparation (or other nucleic acid therapeutics) ex vivo and the treated cells are infused into recipient. Alternatively, cells, tissues or organs are directly treated with nucleic acids of the present invention prior to transplantation into a recipient.

Another means of accumulating high concentrations of a ribozyme(s) within cells is to incorporate the ribozyme-encoding sequences into a DNA or RNA expression vector. Transcription of the ribozyme sequences are driven from a promoter for eukaryotic RNA polymerase I (pol I), RNA polymerase II (pol II), or RNA polymerase III (pol III). Transcripts from pol II or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters are also used, providing that the prokaryotic RNA polymerase enzyme is expressed in the appropriate cells (Elroy-Stein and Moss, 1990 *Proc. Natl. Acad. Sci. USA,* 87, 6743–7; Gao and Huang 1993 *Nucleic Acids Res.,* 21, 2867–72; Lieber et al., 1993 Methods Enzymol., 217, 47–66; Zhou et al., 1990 *Mol. Cell. Biol,* 10, 4529–37). Several investigators have demonstrated that ribozymes expressed from such promoters can function in mammalian cells (e.g. Kashani-Sabet et al., 1992 *Antisense Res. Dev.,* 2, 3–15; Ojwang et al., 1992 *Proc. Natl. Acad. Sci. USA,* 89, 10802–6; Chen et al., 1992 *Nucleic Acids Res.,* 20, 4581–9; Yu et al., 1993

*Proc. Natl. Acad. Sci. USA*, 90, 6340–4; L'Huillier et al., 1992 *EMBO J*. 11, 4411–8; Liszewicz et al., 1993 *Proc. Natl. Acad. Sci. U.S.A.*, 90, 8000–4). The above ribozyme transcription units can be incorporated into a variety of vectors for introduction into mammalian cells, including but not restricted to, plasmid DNA vectors, viral DNA vectors (such as adenovirus or adeno-associated virus vectors), or viral RNA vectors (such as retroviral or alphavirus vectors).

In a preferred embodiment of the invention, a transcription unit expressing a ribozyme that cleaves mRNAs encoded by B7-1, B7-2, B7-3 and/or CD40 are inserted into a plasmid DNA vector or an adenovirus or adeno-associated virus DNA viral vector or a retroviral RNA vector. Viral vectors have been used to transfer genes and lead to either transient or long term gene expression (Zabner et al., 1993 *Cell* 75, 207; Carter, 1992 *Curr. Opi. Biotech*. 3, 533). The adenovirus vector is delivered as recombinant adenoviral particles. The DNA may be delivered alone or complexed with vehicles (as described for RNA above). The recombinant adenovirus or AAV particles are locally administered to the site of treatment, e.g., through incubation or inhalation in vivo or by direct application to cells or tissues ex vivo.

B7-1, B7-2, B7-3 and CD40 are attractive ribozyme targets by several criteria. The molecular mechanism of T cell activation is well-established. Efficacy can be tested in well-defined and predictive animal models. The clinical end-point of graft rejection is clear. Since delivery would be ex vivo, treatment of the correct cell population would be assured. Finally, the disease condition is serious and current therapies are inadequate. Whereas protein-based based therapies would induce anergy against all antigens encountered during the several week treatment period, ex vivo ribozyme therapy provides a direct and elegant approach to truly donor-specific anergy.

Similarly, autoimmune diseases and allergies can be prevented or treated by reversing the devastating course of immune response to self-antigens. Specifically, nucleic acids of this inventions can dampen the response to naturally occuring antigens.

Example 1

B7-1. B7-2. B7-3 and/or CD40 Hammerhead ribozymes

By engineering ribozyme motifs we have designed several ribozymes directed against B7-1, B7-2, B7-3 and/or CD40 encoded mRNA sequences. These ribozymes were synthesized with modifications that improve their nuclease resistance. The ability of ribozymes to cleave target sequences in vitro was evaluated.

Several common human cell lines are available that can be induced to express endogenous B7-1, B7-2, B7-3 and/or CD40. Alternatively, murine splenic cells can be isolated and induced, to express B7-1 or B7-2, with IL-4 or recombinant CD40 ligand. B7-1 and B7-2 can be detected easily with monoclonal antibodies. Use of appropriate flourescent reagents and flourescence-activated cell-sorting (FACS) will permit direct quantitation of surface B7-1 and B7-2 on a cell-by-cell basis. Active ribozymes are expected to directly reduce B7-1 or B7-2 expression. Ribozymes targeted to CD40 would prevent induction of B7-2 by CD40 ligand.

Several animal models of transplantation are available -Mouse, rat, Porcine model (Fodor et al., 1994, *Proc. Natl. Acad. Sci. USA* 91, 11153); or Baboon (reviewed by Nowak, 1994 *Science* 266, 1148). B7-1, B7-2, B7-3 and/or CD40 protein levels can be measured clinically or experimentally by FACS analysis. B7-1, B7-2, B7-3 and/or CD40 encoded mRNA levels will be assessed by Northern analysis, RNase-protection, primer extension analysis and/or quantitative RT-PCR. Ribozymes that block the induction of B7-1, B7-2, B7-3 and/or CD40 activity and/or B7-1, B7-2, B7-3 and/or CD40 protein encoding mRNAs by more than 20% in vitro will be identified.

Several animals models of autoimmune disorders are available—allergic encephalomyelitis (EAE) in Lewis rats (Carlson et al., 1993 Ann. N.Y. Acad. Sci. 685, 86); animal models of multiple sclerosis (Wekerle et al., 1994 Ann. Neurol. 36, s47) and rheumatoid arthritis (van Laar et al., 1994 Chem. Immunol. 58, 206).

Several animal models of allergy are available and are reviewed by Kemeny and Diaz-Sanchez, 1990, Clin. Exp. Immunol. 82, 423 and Pretolani et al., 1994 Ann. N.Y. Acad. Sci. 725, 247).

RNA ribozymes and/or genes encoding them will be delivered by either free delivery, liposome delivery, cationic lipid delivery, adeno-associated virus vector delivery, adenovirus vector delivery, retrovirus vector delivery or plasmid vector delivery in these animal model experiments (see above). One dose of a ribozyme vector that constitutively expresses the ribozyme or one or more doses of a stable anti-B7-1, B7-2, B7-3 and/or CD40 ribozymes or a transiently expressing ribozyme vector to donor APC, followed by infusion into the recipient may reduce the incidence of graft rejection. Alternatively, graft tissues may be treated as described above prior to transplantation.

Diagnostic uses

Ribozymes of this invention may be used as diagnostic tools to examine genetic drift and mutations within diseased cells or to detect the presence of B7-1, B7-2, B7-3 and/or CD40 RNA in a cell. The close relationship between ribozyme activity and the structure of the target RNA allows the detection of mutations in any region of the molecule which alters the base-pairing and three-dimensional structure of the target RNA. By using multiple ribozymes described in this invention, one may map nucleotide changes which are important to RNA structure and function in vitro, as well as in cells and tissues. Cleavage of target RNAs with ribozymes may be used to inhibit gene expression and define the role (essentially) of specified gene products in the progression of disease. In this manner, other genetic targets may be defined as important mediators of the disease. These experiments will lead to better treatment of the disease progression by affording the possibility of combinational therapies (e.g., multiple ribozymes targeted to different genes, ribozymes coupled with known small molecule inhibitors, or intermittent treatment with combinations of ribozymes and/or other chemical or biological molecules). Other in vitro uses of ribozymes of this invention are well known in the art, and include detection of the presence of mRNAs associated with B7-1, B7-2, B7-3 and/or CD40 related condition. Such RNA is detected by determining the presence of a cleavage product after treatment with a ribozyme using standard methodology.

In a specific example, ribozymes which can cleave only wild-type or mutant forms of the target RNA are used for the assay. The first ribozyme is used to identify wild-type RNA present in the sample and the second ribozyme will be used to identify mutant RNA in the sample. As reaction controls, synthetic substrates of both wild-type and mutant RNA will be cleaved by both ribozymes to demonstrate the relative ribozyme efficiencies in the reactions and the absence of cleavage of the "non-targeted" RNA species. The cleavage products from the synthetic substrates will also serve to generate size markers for the analysis of wild-type and mutant RNAs in the sample population. Thus each analysis will require two ribozymes, two substrates and one unknown sample which will be combined into six reactions. The presence of cleavage products will be determined using an RNAse protection assay so that full-length and cleavage fragments of each RNA can be analyzed in one lane of a polyacrylamide gel. It is not absolutely required to quantify the results to gain insight into the expression of mutant RNAs and putative risk of the desired phenotypic changes in target cells. The expression of mRNA whose protein product is implicated in the development of the phenotype (i.e., B7-1, B7-2, B7-3 and/or CD40) is adequate to establish risk. If probes of comparable specific activity are used for both transcripts, then a qualitative comparison of RNA levels will be adequate and will decrease the cost of the initial diagnosis. Higher mutant form to wild-type ratios will be correlated with higher risk whether RNA levels are compared qualitatively or quantitatively.

Other embodiments are within the following claims.

TABLE I

Characteristics of Ribozymes

Group I Introns

Size: ~200 to >1000 nucleotides.
Requires a U in the target sequence immediately 5' of the cleavage site.
Binds 4–6 nucleotides at 5' side of cleavage site.
Over 75 known members of this class. Found in *Tetrahymena thermophila* rRNA, fungal mitochondria, chloroplasts, phage T4, blue-green algae, and others.

RNAseP RNA (M1 RNA)

Size: ~290 to 400 nucleotides.
RNA portion of a ribonucleoprotein enzyme. Cleaves tRNA precursors to form mature tRNA.
Roughly 10 known members of this group all are bacterial in origin.

Hammerhead Ribozyme

Size: ~13 to 40 nucleotides.
Requires the target sequence UH immediately 5' of the cleavage site.
Binds a variable number nucleotides on both sides of the cleavage site.
14 known members of this class. Found in a number of plant pathogens (virusoids) that use RNA as the infectious agent (FIG. 1)

Hairpin Ribozyme

Size: ~50 nucleotides.
Requires the target sequence GUC immediately 3' of the cleavage site.
Binds 4–6 nucleotides at 5' side of the cleavage site and a variable number to the 3' side of the cleavage site.
Only 3 known member of this class. Found in three plant pathogen (satellite RNAs of the tobacco ringspot virus, arabis mosaic virus and chicory yellow mottle virus) which uses RNA as the infectious agent (FIG. 3).

Hepatitis Delta Virus (HDV) Ribozyme

Size: 50–60 nucleotides (at present).
Cleavage of target RNAs recently demonstrated.
Sequence requirements not fully determined.
Binding sites and structural requirements not fully determined, although no sequences 5' of cleavage site are required.
Only 1 known member of this class. Found in human HDV (FIG. 4).

Neurospara VS RNA Ribozyme

Size: ~144 nucleotides (at present)
Cleavage of target RNAs recently demonstrated.
Sequence requirements not fully determined.
Binding sites and structural requirements not fully determined. Only 1 known member of this class. Found in Neurospora VS RNA (FIG. 5).

TABLE II

Human B7-1 Hammerhead Ribozyme Sequences

| nt. Position | HH Target Sequence | | | Seq. ID No. |
|---|---|---|---|---|
| 8 | AAACCCU | C | UGUAAAG | 1 |
| 12 | CCUCUGU | A | AAGUAAC | 2 |
| 17 | GUAAAGU | A | ACAGAAG | 3 |
| 26 | CAGAAGU | U | AGAAGGG | 4 |
| 27 | AGAAGUU | A | GAAGGGG | 5 |
| 41 | GAAAUGU | C | GCCUCUC | 6 |
| 46 | GUCGCCU | C | UCUGAAG | 7 |
| 48 | CGCCUCU | C | UGAAGAU | 8 |
| 56 | UGAAGAU | U | ACCCAAA | 9 |
| 57 | GAAGAUU | A | CCCAAAG | 10 |
| 75 | AAGUGAU | U | UGUCAUU | 11 |
| 76 | AGUGAUU | U | GUCAUUG | 12 |
| 79 | GAUUUGU | C | AUUGCUU | 13 |
| 82 | UUGUCAU | U | GCUUUAU | 14 |
| 86 | CAUUGCU | U | UAUAGAC | 15 |
| 87 | AUUGCUU | U | AUAGACU | 16 |
| 88 | UUGCUUU | A | UAGACUG | 17 |
| 90 | GCUUUAU | A | GACUGUA | 18 |
| 97 | AGACUGU | A | AGAAGAG | 19 |
| 110 | AGAACAU | C | UCAGAAG | 20 |
| 112 | AACAUCU | C | AGAAGUG | 21 |
| 124 | GUGGAGU | C | UUACCCU | 22 |
| 126 | GGAGUCU | U | ACCCUGA | 23 |
| 127 | GAGUCUU | A | CCCUGAA | 24 |
| 137 | CUGAAAU | C | AAAGGAU | 25 |
| 145 | AAAGGAU | U | UAAAGAA | 26 |
| 146 | AAGGAUU | U | AAAGAAA | 27 |
| 147 | AGGAUUU | A | AAGAAAA | 28 |
| 163 | GUGGAAU | U | UUUCUUC | 29 |
| 164 | UGGAAUU | U | UUCUUCA | 30 |
| 165 | GGAAUUU | U | UCUUCAG | 31 |
| 166 | GAAUUUU | U | CUUCAGC | 32 |
| 167 | AAUUUUU | C | UUCAGCA | 33 |
| 169 | UUUUUCU | U | CAGCAAG | 34 |
| 170 | UUUUCUU | C | AGCAAGC | 35 |
| 187 | UGAAACU | A | AAUCCAC | 36 |
| 191 | ACUAAAU | C | CACAACC | 37 |
| 200 | ACAACCU | U | UGGAGAC | 38 |
| 201 | CAACCUU | U | GGAGACC | 39 |
| 221 | ACACCCU | C | CAAUCUC | 40 |
| 226 | CUCCAAU | C | UCUGUGU | 41 |
| 228 | CCAAUCU | C | UGUGUGU | 42 |
| 236 | UGUGUGU | U | UUGUAAA | 43 |
| 237 | GUGUGUU | U | UGUAAAC | 44 |
| 238 | UGUGUUU | U | GUAAACA | 45 |
| 241 | GUUUUGU | A | AACAUCA | 46 |
| 247 | UAAACAU | C | ACUGGAG | 47 |
| 258 | GGAGGGU | C | UUCUACG | 48 |
| 260 | AGGGUCU | U | CUACGUG | 49 |
| 261 | GGGUCUU | C | UACGUGA | 50 |
| 263 | GUCUUCU | A | CGUGAGC | 51 |
| 274 | GAGCAAU | U | GGAUUGU | 52 |
| 279 | AUUGGAU | U | GUCAUCA | 53 |
| 282 | GGAUUGU | C | AUCAGCC | 54 |
| 285 | UUGUCAU | C | AGCCCUG | 55 |
| 298 | UGCCUGU | U | UUGCACC | 56 |
| 299 | GCCUGUU | U | UGCACCU | 57 |
| 300 | CCUGUUU | U | GCACCUG | 58 |
| 322 | CCCUGGU | C | UUACUUG | 59 |
| 324 | CUGGUCU | U | ACUUGGG | 60 |
| 325 | UGGUCUU | A | CUUGGGU | 61 |
| 328 | UCUUACU | U | GGGUCCA | 62 |
| 333 | CUUGGGU | C | CAAAUUG | 63 |
| 339 | UCCAAAU | U | GUUGGCU | 64 |
| 342 | AAAUUGU | U | GGCUUUC | 65 |
| 347 | GUUGGCU | U | UCACUUU | 66 |
| 348 | UUGGCUU | U | CACUUUU | 67 |
| 349 | UGGCUUU | C | ACUUUUG | 68 |
| 353 | UUUCACU | U | UUGACCC | 69 |
| 354 | UUCACUU | U | UGACCCU | 70 |
| 355 | UCACUUU | U | GACCCUA | 71 |
| 362 | UGACCCU | A | AGCAUCU | 72 |
| 368 | UAAGCAU | C | UGAAGCC | 73 |
| 404 | GGAACAU | C | ACCAUCC | 74 |
| 410 | UCACCAU | C | CAAGUGU | 75 |

TABLE II-continued

Human B7-1 Hammerhead Ribozyme Sequences

| nt. Position | HH Target Sequence | | Seq. ID No. |
|---|---|---|---|
| 418 | CAAGUGU | C CAUACCU | 76 |
| 422 | UGUCCAU | A CCUCAAU | 77 |
| 426 | CAUACCU | C AAUUUCU | 78 |
| 430 | CCUCAAU | U UCUUUCA | 79 |
| 431 | CUCAAUU | U CUUUCAG | 80 |
| 432 | UCAAUUU | C UUUCAGC | 81 |
| 434 | AAUUUCU | U UCAGCUC | 82 |
| 435 | AUUUCUU | U CAGCUCU | 83 |
| 436 | UUUCUUU | C AGCUCUU | 84 |
| 441 | UUCAGCU | C UUGGUGC | 85 |
| 443 | CAGCUCU | U GGUGCUG | 86 |
| 457 | GGCUGGU | C UUUCUCA | 87 |
| 459 | CUGGUCU | U UCUCACU | 88 |
| 460 | UGGUCUU | U CUCACUU | 89 |
| 461 | GGUCUUU | C UCACUUC | 90 |
| 463 | UCUUUCU | C ACUUCUG | 91 |
| 467 | UCUCACU | U CUGUUCA | 92 |
| 468 | CUCACUU | C UGUUCAG | 93 |
| 472 | CUUCUGU | C CAGGUGU | 94 |
| 473 | UUCUGUU | C AGGUGUU | 95 |
| 480 | CAGGUGU | U AUCCACG | 96 |
| 481 | AGGUGUU | A UCCACGU | 97 |
| 483 | GUGUUAU | C CACGUGA | 98 |
| 521 | ACGCUGU | C CUGUGGU | 99 |
| 529 | CUGUGGU | C ACAAUGU | 100 |
| 537 | ACAAUGU | U UCUGUUG | 101 |
| 538 | CAAUGUU | U CUGUUGA | 102 |
| 539 | AAUGUUU | C UGUUGAA | 103 |
| 543 | UUUCUGU | U GAAGAGC | 104 |
| 562 | ACAAACU | C GCAUCUA | 105 |
| 567 | CUCGCAU | C UACUGGC | 106 |
| 569 | CGCAUCU | A CUGGCAA | 107 |
| 601 | GCUGACU | A UGAUGUC | 108 |
| 608 | AUGAUGU | C UGGGGAC | 109 |
| 622 | CAUGAAU | A UAUGGCC | 110 |
| 624 | UGAAUAU | A UGGCCCG | 111 |
| 635 | CCCGAGU | A CAAGAAC | 112 |
| 651 | GGACCAU | C UUUGAUA | 113 |
| 653 | ACCAUCU | U UGAUAUC | 114 |
| 654 | CCAUCUU | U GAUAUCA | 115 |
| 658 | CUUUGAU | A UCACUAA | 116 |
| 660 | UUGAUAU | C ACUAAUA | 117 |
| 664 | UAUCACU | A AUAACCU | 118 |
| 667 | CACUAAU | A ACCUCUC | 119 |
| 672 | AUAACCU | C UCCAUUG | 120 |
| 674 | AACCUCU | C CAUUGUG | 121 |
| 678 | UCUCCAU | U GUGAUCC | 122 |
| 684 | UUGUGAU | C CUGGCUC | 123 |
| 691 | CCUGGCU | C UGCGCCC | 124 |
| 701 | CGCCCAU | C UGACGAG | 125 |
| 716 | GGCACAU | A CGAGUGU | 126 |
| 726 | AGUGUGU | U GUUCUGA | 127 |
| 729 | GUGUUGU | U CUGAAGU | 128 |
| 730 | UGUUGUU | C UGAAGUA | 129 |
| 737 | CUGAAGU | A UGAAAAA | 130 |
| 751 | AGACGCU | U UCAAGCG | 131 |
| 752 | GACGCUU | U CAAGCGG | 132 |
| 753 | ACGCUUU | C AAGCGGG | 133 |
| 782 | GUGACGU | U AUCAGUC | 134 |
| 783 | UGACGUU | A UCAGUCA | 135 |
| 785 | ACGUUAU | C AGUCAGA | 136 |
| 789 | UAUCAGU | C AAAGCUG | 137 |
| 800 | GCUGACU | U CCCUACA | 138 |
| 801 | CUGACUU | C CCUACAC | 139 |
| 805 | CUUCCCU | A CACCUAG | 140 |
| 811 | UACACCU | A GUAUAUC | 141 |
| 814 | ACCUAGU | A UAUCUGA | 142 |
| 816 | CUAGUAU | A UCUGACU | 143 |
| 818 | AGUAUAU | C UGACUGU | 144 |
| 824 | UCUGACU | U GAAAUUU | 145 |
| 825 | CUGACUU | U GAAAUUC | 146 |
| 831 | UUGAAAU | U CCAACUU | 147 |
| 832 | UGAAAUU | C CAACUUC | 148 |
| 838 | UCCAACU | U CUAUAUU | 149 |
| 839 | CCAACUU | C UAUAUAU | 150 |
| 841 | AACUUCU | A AUAUUAG | 151 |
| 844 | UUCUAAU | A UUAGAAG | 152 |
| 846 | CUAAUAU | U AGAAGGA | 153 |
| 847 | UAAUAUU | A GAAGGAU | 154 |
| 855 | GAAGGAU | A AUUUGCU | 155 |
| 858 | GGAUAAU | U UGCUCAA | 156 |
| 859 | GAUAAUU | U GCUCAAC | 157 |
| 863 | AUUUGCU | C AACCUCU | 158 |
| 869 | UCAACCU | C UGGAGGU | 159 |
| 877 | UGGAGGU | U UUCCAGA | 160 |
| 878 | GGAGGUU | U UCCAGAG | 161 |
| 879 | GAGGUUU | U CCAGAGC | 162 |
| 880 | AGGUUUU | C CAGAGCC | 163 |
| 889 | AGAGCCU | C ACCUCUC | 164 |
| 894 | CUCACCU | C UCCUGGU | 165 |
| 896 | CACCUCU | C CUGGUUG | 166 |
| 902 | UCCUGGU | U GGAAAAU | 167 |
| 920 | GAAGAAU | U AAAUGCC | 168 |
| 921 | AAGAAUU | A AAUGCCA | 169 |
| 930 | AUGCCAU | U AACACAA | 170 |
| 942 | CAACAGU | U UCCCAAG | 171 |
| 943 | AACAGUU | U CCCAAGA | 172 |
| 944 | ACAGUUU | C CCAAGAU | 173 |
| 952 | CCAAGAU | C CUGAAAC | 174 |
| 966 | CUGAGCU | C UAUGCUG | 175 |
| 968 | GAGCUCU | A UGCUGUU | 176 |
| 975 | AUGCUGU | U AGCAGCA | 177 |
| 976 | UGCUGUU | A GCAGCAA | 178 |
| 991 | ACUGGAU | U UCAAUAU | 179 |
| 992 | CUGGAUU | U CAAUAUG | 180 |
| 993 | UGGAUUU | C AAUAUGA | 181 |
| 997 | UUUCAAU | A UGACAAC | 182 |
| 1016 | CACAGCU | U CAUGUGU | 183 |
| 1017 | ACAGCUU | C AUGUGUC | 184 |
| 1024 | CAUGUGU | C UCAUCAA | 185 |
| 1026 | UGUGUCU | C AUCAAGU | 186 |
| 1029 | GUCUCAU | C AAGUAUG | 187 |
| 1034 | AUCAAGU | A UGGACAU | 188 |
| 1042 | UGGACAU | U UAAGAGU | 189 |
| 1043 | GGACAUU | U AAGAGUG | 190 |
| 1044 | GACAUUU | A AGAGUGA | 191 |
| 1054 | AGUGAAU | C AGACCUU | 192 |
| 1061 | CAGACCU | U CAACUGG | 193 |
| 1062 | AGACCUU | C AACUGGA | 194 |
| 1072 | CUGGAAU | A CAACCAA | 195 |
| 1090 | AGAGCAU | U UCCUGA | 196 |
| 1091 | GAGCAUU | U CCUGAU | 197 |
| 1092 | AGCAUUU | U CCUGAUA | 198 |
| 1093 | GCAUUUU | C CUGAUAA | 199 |
| 1099 | UCCUGAU | A ACCUGCU | 200 |
| 1107 | ACCUGCU | C CCAUCCU | 201 |
| 1112 | CUCCCAU | C CUGGGCC | 202 |
| 1122 | GGGCCAU | U ACCUUAA | 203 |
| 1123 | GGCCAUU | A CCUUAAU | 204 |
| 1127 | AUUACCU | U AAUCUCA | 205 |
| 1128 | UUACCUU | A AUCUCAG | 206 |
| 1131 | CCUUAAU | C UCAGUAA | 207 |
| 1133 | UUAAUCU | C AGUAAAU | 208 |
| 1137 | UCUCAGU | A AAUGGAA | 209 |
| 1146 | AUGGAAU | U UUUGUGA | 210 |
| 1147 | UGGAAUU | U UUGUGAU | 211 |
| 1148 | GGAAUUU | U UGUGAUA | 212 |
| 1149 | GAAUUUU | U GUGAUAU | 213 |
| 1155 | UUGUGAU | A UGCUGCC | 214 |
| 1169 | CUGACCU | A CUGCUUU | 215 |
| 1175 | UACUGCU | U UGCCCCA | 216 |
| 1176 | ACUGCUU | U GCCCAA | 217 |
| 1214 | GAGAGAU | U GAGAAGG | 218 |
| 1230 | AAAGUGU | A CGCCCUG | 219 |
| 1239 | GCCCUGU | U UAACAGU | 220 |
| 1241 | CCUGUAU | A ACAGUGU | 221 |
| 1249 | ACAGUGU | C CGCAGAA | 222 |
| 1275 | AAAAGAU | C UGAAGGU | 223 |
| 1283 | UGAAGGU | A GCCUCCG | 224 |
| 1288 | GUAGCCU | C CGUCAUC | 225 |

TABLE II-continued

Human B7-1 Hammerhead Ribozyme Sequences

| nt. Position | HH Target Sequence | | | Seq. ID No. |
|---|---|---|---|---|
| 1292 | CCUCCGU | C | AUCUCUU | 226 |
| 1295 | CCGUCAU | C | UCUUCUG | 227 |
| 1297 | GUCAUCU | C | UUCUGGG | 228 |
| 1299 | CAUCUCU | U | CUGGGAU | 229 |
| 1300 | AUCUCUU | C | UGGGAUA | 230 |
| 1307 | CUGGGAU | A | CAUGGAU | 231 |
| 1315 | CAUGGAU | C | GUGGGGA | 232 |
| 1324 | UGGGGAU | C | AUGAGGC | 233 |
| 1334 | GAGGCAU | U | CUUCCCU | 234 |
| 1335 | AGGCAUU | C | UUCCCUU | 235 |
| 1337 | GCAUUCU | U | CCCUUAA | 236 |
| 1338 | CAUUCUU | C | CCUUAAC | 237 |
| 1342 | CUUCCCU | U | AACAAAU | 238 |
| 1343 | UUCCCUU | A | ACAAAUU | 239 |
| 1350 | AACAAAU | U | UAAGCUG | 240 |
| 1351 | ACAAAUU | U | AAGCUGU | 241 |
| 1352 | CAAAUUU | A | AGCUGUU | 242 |
| 1359 | AAGCUGU | U | UUACCCA | 243 |
| 1360 | AGCUGUU | U | UACCCAC | 244 |
| 1361 | GCUGUUU | U | ACCCACU | 245 |
| 1362 | CUGUUUU | A | CCCACUA | 246 |
| 1369 | ACCCACU | A | CCUCACC | 247 |
| 1373 | ACUACCU | C | ACCUUCU | 248 |
| 1378 | CUCACCU | U | CUUAAAA | 249 |
| 1379 | UCACCUU | C | UUAAAAA | 250 |
| 1381 | ACCUUCU | U | AAAAACC | 251 |
| 1382 | CCUUCUU | A | AAAACCU | 252 |
| 1390 | AAAACCU | C | UUUCAGA | 253 |
| 1392 | AACCUCU | U | UCAGAUU | 254 |
| 1393 | ACCUCUU | U | CAGAUUA | 255 |
| 1394 | CCUCUUU | C | AGAUUAA | 256 |
| 1399 | UUCAGAU | U | AAGCUGA | 257 |
| 1400 | UCAGAUU | A | AGCUGAA | 258 |
| 1412 | GAACAGU | U | ACAAGAU | 259 |
| 1413 | AACAGUU | A | CAAGAUG | 260 |
| 1429 | CUGGCAU | C | CCUCUCC | 261 |
| 1433 | CAUCCCU | C | UCCUUUC | 262 |
| 1435 | UCCCUCU | C | CUUUCUC | 263 |
| 1438 | CUCUCCU | U | UCUCCCC | 264 |
| 1439 | UCUCCUU | C | CUCCCCA | 265 |
| 1440 | CUCCUUU | C | UCCCCAU | 266 |
| 1442 | CCUUUCU | C | CCCAUAU | 267 |
| 1448 | UCCCCAU | A | UGCAAUU | 268 |
| 1455 | AUGCAAU | U | UGCUUAA | 269 |
| 1456 | UGCAAUU | U | GCUUAAU | 270 |
| 1460 | AUUUGCU | U | AAUGUAA | 271 |
| 1461 | UUUGCUU | A | AUGUAAC | 272 |
| 1466 | UUAAUGU | A | ACCUCUU | 273 |
| 1471 | GUAACCU | C | UUCUUUU | 274 |
| 1473 | AACCUCU | U | CUUUUGC | 275 |
| 1474 | ACCUCUU | C | UUUUGCC | 276 |
| 1476 | CUCUUCU | U | UUGCCAU | 277 |
| 1477 | UCUUCUU | U | UGCCAUG | 278 |
| 1478 | CUUCUUU | U | GCCAUGU | 279 |
| 1486 | GCCAUGU | U | UCCAUUC | 280 |
| 1487 | CCAUGUU | U | CCAUUCU | 281 |
| 1488 | CAUGUUU | C | CAUUCUG | 282 |
| 1492 | UUUCCAU | U | CUGCCAU | 283 |
| 1493 | UUCCAUU | C | UGCCAUC | 284 |
| 1500 | CUGCCAU | C | UUGAAUU | 285 |
| 1502 | GCCAUCU | U | GAAUUGU | 286 |
| 1507 | CUUGAAU | U | GUCUUGU | 287 |
| 1510 | GAAUUGU | C | UUGUCAG | 288 |
| 1512 | AUUGUCU | U | GUCAGCC | 289 |
| 1515 | GUCUUGU | C | AGCCAAU | 290 |
| 1523 | AGCCAAU | U | CAUUAUC | 291 |
| 1524 | GCCAAUU | C | AUUAUCU | 292 |
| 1527 | AAUUCAU | U | AUCUAUU | 293 |
| 1528 | AUUCAUU | A | UCUAUUA | 294 |
| 1530 | UCAUUAU | C | UAUUAAA | 295 |
| 1532 | AUUAUCU | A | UUAAACA | 296 |
| 1534 | UAUCUAU | U | AAACACU | 297 |
| 1535 | AUCUAUU | A | AACACUA | 298 |
| 1542 | AAACACU | A | AUUUGAG | 299 |

TABLE III

Human B7-1 Hammerhead Ribozyme Sequences

| nt. Position | HH Ribozyme Sequence | | | Seq. ID No. |
|---|---|---|---|---|
| 8 | CUUUACA | CUGAUGAGGCCGAAAGGCCGAA | AGGGUUU | 300 |
| 12 | GUUACUU | CUGAUGAGGCCGAAAGGCCGAA | ACAGAGG | 301 |
| 17 | CUUCUGU | CUGAUGAGGCCGAAAGGCCGAA | ACUUUAC | 302 |
| 26 | CCCUUCU | CUGAUGAGGCCGAAAGGCCGAA | ACUUCUG | 303 |
| 27 | CCCCUUC | CUGAUGAGGCCGAAAGGCCGAA | AACUUCU | 304 |
| 41 | GAGAGGC | CUGAUGAGGCCGAAAGGCCGAA | ACAUUUC | 305 |
| 46 | CUUCAGA | CUGAUGAGGCCGAAAGGCCGAA | AGGCGAC | 306 |
| 48 | AUCUUCA | CUGAUGAGGCCGAAAGGCCGAA | AGAGGCG | 307 |
| 56 | UUUGGGU | CUGAUGAGGCCGAAAGGCCGAA | AUCUUCA | 308 |
| 57 | CUUUGGG | CUGAUGAGGCCGAAAGGCCGAA | AAUCUUC | 309 |
| 75 | AAUGACA | CUGAUGAGGCCGAAAGGCCGAA | AUCACUU | 310 |
| 76 | CAAUGAC | CUGAUGAGGCCGAAAGGCCGAA | AAUCACU | 311 |
| 79 | AAGCAAU | CUGAUGAGGCCGAAAGGCCGAA | ACAAAUC | 312 |
| 82 | AUAAAGC | CUGAUGAGGCCGAAAGGCCGAA | AUGACAA | 313 |
| 86 | GUCUAUA | CUGAUGAGGCCGAAAGGCCGAA | AGCAAUG | 314 |
| 87 | AGUCUAU | CUGAUGAGGCCGAAAGGCCGAA | AAGCAAU | 315 |
| 88 | CAGUCUA | CUGAUGAGGCCGAAAGGCCGAA | AAAGCAA | 316 |
| 90 | UACAGUC | CUGAUGAGGCCGAAAGGCCGAA | AUAAAGC | 317 |
| 97 | CUCUUCU | CUGAUGAGGCCGAAAGGCCGAA | ACAGUCU | 318 |
| 110 | CUUCUGA | CUGAUGAGGCCGAAAGGCCGAA | AUGUUCU | 319 |
| 112 | CACUUCU | CUGAUGAGGCCGAAAGGCCGAA | AGAUGUU | 320 |
| 124 | AGGGUAA | CUGAUGAGGCCGAAAGGCCGAA | ACUCCAC | 321 |
| 126 | UCAGGGU | CUGAUGAGGCCGAAAGGCCGAA | AGACUCC | 322 |
| 127 | UUCAGGG | CUGAUGAGGCCGAAAGGCCGAA | AAGACUC | 323 |
| 137 | AUCCUUU | CUGAUGAGGCCGAAAGGCCGAA | AUUUCAG | 324 |
| 145 | UUCUUUA | CUGAUGAGGCCGAAAGGCCGAA | AUCCUUU | 325 |
| 146 | UUUCUUU | CUGAUGAGGCCGAAAGGCCGAA | AAUCCUU | 326 |

TABLE III-continued

Human B7-1 Hammerhead Ribozyme Sequences

| nt. Position | HH Ribozyme Sequence | | | Seq. ID No. |
|---|---|---|---|---|
| 147 | UUUUCUU | CUGAUGAGGCCGAAAGGCCGAA | AAAUCCU | 327 |
| 163 | GAAGAAA | CUGAUGAGGCCGAAAGGCCGAA | AUUCCAC | 328 |
| 164 | UGAAGAA | CUGAUGAGGCCGAAAGGCCGAA | AAUUCCA | 329 |
| 165 | CUGAAGA | CUGAUGAGGCCGAAAGGCCGAA | AAAUUCC | 330 |
| 166 | GCUGAAG | CUGAUGAGGCCGAAAGGCCGAA | AAAAUUC | 331 |
| 167 | UGCUGAA | CUGAUGAGGCCGAAAGGCCGAA | AAAAAUU | 332 |
| 169 | CUUGCUG | CUGAUGAGGCCGAAAGGCCGAA | AGAAAAA | 333 |
| 170 | GCUUGCU | CUGAUGAGGCCGAAAGGCCGAA | AAGAAAA | 334 |
| 187 | GUGGAUU | CUGAUGAGGCCGAAAGGCCGAA | AGUUUCA | 335 |
| 191 | GGUUGUG | CUGAUGAGGCCGAAAGGCCGAA | AUUUAGU | 336 |
| 200 | GUCUCCA | CUGAUGAGGCCGAAAGGCCGAA | AGGUUGU | 337 |
| 201 | GGUCUCC | CUGAUGAGGCCGAAAGGCCGAA | AAGGUUG | 338 |
| 221 | GAGAUUG | CUGAUGAGGCCGAAAGGCCGAA | AGGGUGU | 339 |
| 226 | ACACAGA | CUGAUGAGGCCGAAAGGCCGAA | AUUGGAG | 340 |
| 228 | ACACACA | CUGAUGAGGCCGAAAGGCCGAA | AGAUUGG | 341 |
| 236 | UUUACAA | CUGAUGAGGCCGAAAGGCCGAA | ACACACA | 342 |
| 237 | GUUUACA | CUGAUGAGGCCGAAAGGCCGAA | AACACAC | 343 |
| 238 | UGUUUAC | CUGAUGAGGCCGAAAGGCCGAA | AAACACA | 344 |
| 241 | UGAUGUU | CUGAUGAGGCCGAAAGGCCGAA | ACAAAAC | 345 |
| 247 | CUCCAGU | CUGAUGAGGCCGAAAGGCCGAA | AUGUUUA | 346 |
| 258 | CGUAGAA | CUGAUGAGGCCGAAAGGCCGAA | ACCCUCC | 347 |
| 260 | CACGUAG | CUGAUGAGGCCGAAAGGCCGAA | AGACCCU | 348 |
| 261 | UCACGUA | CUGAUGAGGCCGAAAGGCCGAA | AAGACCC | 349 |
| 263 | GCUCACG | CUGAUGAGGCCGAAAGGCCGAA | AGAAGAC | 350 |
| 274 | ACAAUCC | CUGAUGAGGCCGAAAGGCCGAA | AUUGCUC | 351 |
| 279 | UGAUGAC | CUGAUGAGGCCGAAAGGCCGAA | AUCCAAU | 352 |
| 282 | GGCUGAU | CUGAUGAGGCCGAAAGGCCGAA | ACAAUCC | 353 |
| 285 | CAGGGCU | CUGAUGAGGCCGAAAGGCCGAA | AUGACAA | 354 |
| 298 | GGUGCAA | CUGAUGAGGCCGAAAGGCCGAA | ACAGGCA | 355 |
| 299 | AGGUGCA | CUGAUGAGGCCGAAAGGCCGAA | AACAGGC | 356 |
| 300 | CAGGUGC | CUGAUGAGGCCGAAAGGCCGAA | AAACAGG | 357 |
| 322 | CAAGUAA | CUGAUGAGGCCGAAAGGCCGAA | ACCAGGG | 358 |
| 324 | CCCAAGU | CUGAUGAGGCCGAAAGGCCGAA | AGACCAG | 359 |
| 325 | ACCCAAG | CUGAUGAGGCCGAAAGGCCGAA | AAGACCA | 360 |
| 328 | UGGACCC | CUGAUGAGGCCGAAAGGCCGAA | AGUAAGA | 361 |
| 333 | CAAUUUG | CUGAUGAGGCCGAAAGGCCGAA | ACCCAAG | 362 |
| 339 | AGCCAAC | CUGAUGAGGCCGAAAGGCCGAA | AUUUGGA | 363 |
| 342 | GAAAGCC | CUGAUGAGGCCGAAAGGCCGAA | ACAAUUU | 364 |
| 347 | AAAGUGA | CUGAUGAGGCCGAAAGGCCGAA | AGCCAAC | 365 |
| 348 | AAAAGUG | CUGAUGAGGCCGAAAGGCCGAA | AAGCCAA | 366 |
| 349 | CAAAAGU | CUGAUGAGGCCGAAAGGCCGAA | AAAGCCA | 367 |
| 353 | GGGUCAA | CUGAUGAGGCCGAAAGGCCGAA | AGUGAAA | 368 |
| 354 | AGGGUCA | CUGAUGAGGCCGAAAGGCCGAA | AAGUGAA | 369 |
| 355 | UAGGGUC | CUGAUGAGGCCGAAAGGCCGAA | AAAGUGA | 370 |
| 362 | AGAUGCU | CUGAUGAGGCCGAAAGGCCGAA | AGGGUCA | 371 |
| 368 | GGCUUCA | CUGAUGAGGCCGAAAGGCCGAA | AUGCUUA | 372 |
| 404 | GGAUGGU | CUGAUGAGGCCGAAAGGCCGAA | AUGUUCC | 373 |
| 410 | ACACUUG | CUGAUGAGGCCGAAAGGCCGAA | AUGGUGA | 374 |
| 418 | AGGUAUG | CUGAUGAGGCCGAAAGGCCGAA | ACACUUG | 375 |
| 422 | AUUGAGG | CUGAUGAGGCCGAAAGGCCGAA | AUGGACA | 376 |
| 426 | AGAAAUU | CUGAUGAGGCCGAAAGGCCGAA | AGGUAUG | 377 |
| 430 | UGAAAGA | CUGAUGAGGCCGAAAGGCCGAA | AUUGAGG | 378 |
| 431 | CUGAAAG | CUGAUGAGGCCGAAAGGCCGAA | AAUUGAG | 379 |
| 432 | GCUGAAA | CUGAUGAGGCCGAAAGGCCGAA | AAAUUGA | 380 |
| 434 | GAGCUGA | CUGAUGAGGCCGAAAGGCCGAA | AGAAAUU | 381 |
| 435 | AGAGCUG | CUGAUGAGGCCGAAAGGCCGAA | AAGAAAU | 382 |
| 436 | AAGAGCU | CUGAUGAGGCCGAAAGGCCGAA | AAAGAAA | 383 |
| 441 | GCACCAA | CUGAUGAGGCCGAAAGGCCGAA | AGCUGAA | 384 |
| 443 | CAGCACC | CUGAUGAGGCCGAAAGGCCGAA | AGAGCUG | 385 |
| 457 | UGAGAAA | CUGAUGAGGCCGAAAGGCCGAA | ACCAGCC | 386 |
| 459 | AGUGAGA | CUGAUGAGGCCGAAAGGCCGAA | AGACCAG | 387 |
| 460 | AAGUGAG | CUGAUGAGGCCGAAAGGCCGAA | AAGACCA | 388 |
| 461 | GAAGUGA | CUGAUGAGGCCGAAAGGCCGAA | AAAGACC | 389 |
| 463 | CAGAAGU | CUGAUGAGGCCGAAAGGCCGAA | AGAAAGA | 390 |
| 467 | UGAACAG | CUGAUGAGGCCGAAAGGCCGAA | AGUGAGA | 391 |
| 468 | CUGAACA | CUGAUGAGGCCGAAAGGCCGAA | AAGUGAG | 392 |
| 472 | ACACCUG | CUGAUGAGGCCGAAAGGCCGAA | ACAGAAG | 393 |
| 473 | AACACCU | CUGAUGAGGCCGAAAGGCCGAA | AACAGAA | 394 |
| 480 | CGUGGAU | CUGAUGAGGCCGAAAGGCCGAA | ACACCUG | 395 |
| 481 | ACGUGGA | CUGAUGAGGCCGAAAGGCCGAA | AACACCU | 396 |
| 483 | UCACGUG | CUGAUGAGGCCGAAAGGCCGAA | AUAACAC | 397 |
| 521 | ACCACAG | CUGAUGAGGCCGAAAGGCCGAA | ACAGCGU | 398 |
| 529 | ACAUUGU | CUGAUGAGGCCGAAAGGCCGAA | ACCACAG | 399 |
| 537 | CAACAGA | CUGAUGAGGCCGAAAGGCCGAA | ACAUUGU | 400 |
| 538 | UCAACAG | CUGAUGAGGCCGAAAGGCCGAA | AACAUUG | 401 |

TABLE III-continued

Human B7-1 Hammerhead Ribozyme Sequences

| nt. Position | HH Ribozyme Sequence | | | Seq. ID No. |
|---|---|---|---|---|
| 539 | UUCAACA | CUGAUGAGGCCGAAAGGCCGAA | AAACAUU | 402 |
| 543 | GCUCUUC | CUGAUGAGGCCGAAAGGCCGAA | ACAGAAA | 403 |
| 562 | UAGAUGC | CUGAUGAGGCCGAAAGGCCGAA | AGUUUGU | 404 |
| 567 | GCCAGUA | CUGAUGAGGCCGAAAGGCCGAA | AUGCGAG | 405 |
| 569 | UUGCCAG | CUGAUGAGGCCGAAAGGCCGAA | AGAUGCG | 406 |
| 601 | GACAUCA | CUGAUGAGGCCGAAAGGCCGAA | AGUCAGC | 407 |
| 608 | GUCCCCA | CUGAUGAGGCCGAAAGGCCGAA | ACAUCAU | 408 |
| 622 | GGCCAUA | CUGAUGAGGCCGAAAGGCCGAA | AUUCAUG | 409 |
| 624 | CGGGCCA | CUGAUGAGGCCGAAAGGCCGAA | AUAUUCA | 410 |
| 635 | GUUCUUG | CUGAUGAGGCCGAAAGGCCGAA | ACUCGGG | 411 |
| 651 | UAUCAAA | CUGAUGAGGCCGAAAGGCCGAA | AUGGUCC | 412 |
| 653 | GAUAUCA | CUGAUGAGGCCGAAAGGCCGAA | AGAUGGU | 413 |
| 654 | UGAUAUC | CUGAUGAGGCCGAAAGGCCGAA | AAGAUGG | 414 |
| 658 | UUAGUGA | CUGAUGAGGCCGAAAGGCCGAA | AUCAAAG | 415 |
| 660 | UAUUAGU | CUGAUGAGGCCGAAAGGCCGAA | AUAUCAA | 416 |
| 664 | AGGUUAU | CUGAUGAGGCCGAAAGGCCGAA | AGUGAUA | 417 |
| 667 | GAGAGGU | CUGAUGAGGCCGAAAGGCCGAA | AUUAGUG | 418 |
| 672 | CAAUGGA | CUGAUGAGGCCGAAAGGCCGAA | AGGUUAU | 419 |
| 674 | CACAAUG | CUGAUGAGGCCGAAAGGCCGAA | AGAGGUU | 420 |
| 678 | GGAUCAC | CUGAUGAGGCCGAAAGGCCGAA | AUGGAGA | 421 |
| 684 | GAGCCAG | CUGAUGAGGCCGAAAGGCCGAA | AUCACAA | 422 |
| 691 | GGGCGCA | CUGAUGAGGCCGAAAGGCCGAA | AGCCAGG | 423 |
| 701 | CUCGUCA | CUGAUGAGGCCGAAAGGCCGAA | AUGGGCG | 424 |
| 716 | ACACUCG | CUGAUGAGGCCGAAAGGCCGAA | AUGUGCC | 425 |
| 726 | UCAGAAC | CUGAUGAGGCCGAAAGGCCGAA | ACACACU | 426 |
| 729 | ACUUCAG | CUGAUGAGGCCGAAAGGCCGAA | ACAACAC | 427 |
| 730 | UACUUCA | CUGAUGAGGCCGAAAGGCCGAA | AACAACA | 428 |
| 737 | UUUUUCA | CUGAUGAGGCCGAAAGGCCGAA | ACUUCAG | 429 |
| 751 | CGCUUGA | CUGAUGAGGCCGAAAGGCCGAA | AGCGUCU | 430 |
| 752 | CCGCUUG | CUGAUGAGGCCGAAAGGCCGAA | AAGCGUC | 431 |
| 753 | CCCGCUU | CUGAUGAGGCCGAAAGGCCGAA | AAAGCGU | 432 |
| 782 | GACUGAU | CUGAUGAGGCCGAAAGGCCGAA | ACGUCAC | 433 |
| 783 | UGACUGA | CUGAUGAGGCCGAAAGGCCGAA | AACGUCA | 434 |
| 785 | UUUGACU | CUGAUGAGGCCGAAAGGCCGAA | AUAACGU | 435 |
| 789 | CAGCUUU | CUGAUGAGGCCGAAAGGCCGAA | ACUGAUA | 436 |
| 800 | UGUAGGG | CUGAUGAGGCCGAAAGGCCGAA | AGUCAGC | 437 |
| 801 | GUGUAGG | CUGAUGAGGCCGAAAGGCCGAA | AAGUCAG | 438 |
| 805 | CUAGGUG | CUGAUGAGGCCGAAAGGCCGAA | AGGGAAG | 439 |
| 811 | GAUAUAC | CUGAUGAGGCCGAAAGGCCGAA | AGGUGUA | 440 |
| 814 | UCAGAUA | CUGAUGAGGCCGAAAGGCCGAA | ACUAGGU | 441 |
| 816 | AGUCAGA | CUGAUGAGGCCGAAAGGCCGAA | AUACUAG | 442 |
| 818 | AAAGUCA | CUGAUGAGGCCGAAAGGCCGAA | AUAUACU | 443 |
| 824 | AAUUUCA | CUGAUGAGGCCGAAAGGCCGAA | AGUCAGA | 444 |
| 825 | GAAUUUC | CUGAUGAGGCCGAAAGGCCGAA | AAGUCAG | 445 |
| 831 | AAGUUGG | CUGAUGAGGCCGAAAGGCCGAA | AUUUCAA | 446 |
| 832 | GAAGUUG | CUGAUGAGGCCGAAAGGCCGAA | AAUUUCA | 447 |
| 838 | AUAUUAG | CUGAUGAGGCCGAAAGGCCGAA | AGUUGGA | 448 |
| 839 | AAUAUUA | CUGAUGAGGCCGAAAGGCCGAA | AAGUUGG | 449 |
| 841 | CUAAUAU | CUGAUGAGGCCGAAAGGCCGAA | AGAAGUU | 450 |
| 844 | CUUCUAA | CUGAUGAGGCCGAAAGGCCGAA | AUUAGAA | 451 |
| 846 | UCCUUCU | CUGAUGAGGCCGAAAGGCCGAA | AUAUUAG | 452 |
| 847 | AUCCUUC | CUGAUGAGGCCGAAAGGCCGAA | AAUAUUA | 453 |
| 855 | AGCAAAU | CUGAUGAGGCCGAAAGGCCGAA | AUCCUUC | 454 |
| 858 | UUGAGCA | CUGAUGAGGCCGAAAGGCCGAA | AUUAUCC | 455 |
| 859 | GUUGAGC | CUGAUGAGGCCGAAAGGCCGAA | AAUUAUC | 456 |
| 863 | AGAGGUU | CUGAUGAGGCCGAAAGGCCGAA | AGCAAAU | 457 |
| 869 | ACCUCCA | CUGAUGAGGCCGAAAGGCCGAA | AGGUUGA | 458 |
| 877 | UCUGGAA | CUGAUGAGGCCGAAAGGCCGAA | ACCUCCA | 459 |
| 878 | CUCUGGA | CUGAUGAGGCCGAAAGGCCGAA | AACCUCC | 460 |
| 879 | GCUCUGG | CUGAUGAGGCCGAAAGGCCGAA | AAACCUC | 461 |
| 880 | GGCUCUG | CUGAUGAGGCCGAAAGGCCGAA | AAAACCU | 462 |
| 889 | GAGAGGU | CUGAUGAGGCCGAAAGGCCGAA | AGGCUCU | 463 |
| 894 | ACCAGGA | CUGAUGAGGCCGAAAGGCCGAA | AGGUGAG | 464 |
| 896 | CAACCAG | CUGAUGAGGCCGAAAGGCCGAA | AGAGGUG | 465 |
| 902 | AUUUUCC | CUGAUGAGGCCGAAAGGCCGAA | ACCAGGA | 466 |
| 920 | GGCAUUU | CUGAUGAGGCCGAAAGGCCGAA | AUUCUUC | 467 |
| 921 | UGGCAUU | CUGAUGAGGCCGAAAGGCCGAA | AAUUCUU | 468 |
| 930 | UUGUGUU | CUGAUGAGGCCGAAAGGCCGAA | AUGGCAU | 469 |
| 942 | CUUGGGA | CUGAUGAGGCCGAAAGGCCGAA | ACUGUUG | 470 |
| 943 | UCUUGGG | CUGAUGAGGCCGAAAGGCCGAA | AACUGUU | 471 |
| 944 | AUCUUGG | CUGAUGAGGCCGAAAGGCCGAA | AAACUGU | 472 |
| 952 | GUUUCAG | CUGAUGAGGCCGAAAGGCCGAA | AUCUUGG | 473 |
| 966 | CAGCAUA | CUGAUGAGGCCGAAAGGCCGAA | AGCUCAG | 474 |
| 968 | AACAGCA | CUGAUGAGGCCGAAAGGCCGAA | AGAGCUC | 475 |
| 975 | UGCUGCU | CUGAUGAGGCCGAAAGGCCGAA | ACAGCAU | 476 |

TABLE III-continued

Human B7-1 Hammerhead Ribozyme Sequences

| nt. Position | HH Ribozyme Sequence | | | Seq. ID No. |
|---|---|---|---|---|
| 976 | UUGCUGC | CUGAUGAGGCCGAAAGGCCGAA | AACAGCA | 477 |
| 991 | AUAUUGA | CUGAUGAGGCCGAAAGGCCGAA | AUCCAGU | 478 |
| 992 | CAUAUUG | CUGAUGAGGCCGAAAGGCCGAA | AAUCCAG | 479 |
| 993 | UCAUAUU | CUGAUGAGGCCGAAAGGCCGAA | AAAUCCA | 480 |
| 997 | GUUGUCA | CUGAUGAGGCCGAAAGGCCGAA | AUUGAAA | 481 |
| 1016 | ACACAUG | CUGAUGAGGCCGAAAGGCCGAA | AGCUGUG | 482 |
| 1017 | GACACAU | CUGAUGAGGCCGAAAGGCCGAA | AAGCUGU | 483 |
| 1024 | UUGAUGA | CUGAUGAGGCCGAAAGGCCGAA | ACACAUG | 484 |
| 1026 | ACUUGAU | CUGAUGAGGCCGAAAGGCCGAA | AGACACA | 485 |
| 1029 | CAUACUU | CUGAUGAGGCCGAAAGGCCGAA | AUGAGAC | 486 |
| 1034 | AUGUCCA | CUGAUGAGGCCGAAAGGCCGAA | ACUUGAU | 487 |
| 1042 | ACUCUUA | CUGAUGAGGCCGAAAGGCCGAA | AUGUCCA | 488 |
| 1043 | CACUCUU | CUGAUGAGGCCGAAAGGCCGAA | AAUGUCC | 489 |
| 1044 | UCACUCU | CUGAUGAGGCCGAAAGGCCGAA | AAAUGUC | 490 |
| 1054 | AAGGUCU | CUGAUGAGGCCGAAAGGCCGAA | AUUCACU | 491 |
| 1061 | CCAGUUG | CUGAUGAGGCCGAAAGGCCGAA | AGGUCUG | 492 |
| 1062 | UCCAGUU | CUGAUGAGGCCGAAAGGCCGAA | AAGGUCU | 493 |
| 1072 | UUGGUUG | CUGAUGAGGCCGAAAGGCCGAA | AUUCCAG | 494 |
| 1090 | UCAGGAA | CUGAUGAGGCCGAAAGGCCGAA | AUGCUCU | 495 |
| 1091 | AUCAGGA | CUGAUGAGGCCGAAAGGCCGAA | AAUGCUC | 496 |
| 1092 | UAUCAGG | CUGAUGAGGCCGAAAGGCCGAA | AAAUGCU | 497 |
| 1093 | UUAUCAG | CUGAUGAGGCCGAAAGGCCGAA | AAAAUGC | 498 |
| 1099 | AGCAGGU | CUGAUGAGGCCGAAAGGCCGAA | AUCAGGA | 499 |
| 1107 | AGGAUGG | CUGAUGAGGCCGAAAGGCCGAA | AGCAGGU | 500 |
| 1112 | GGCCCAG | CUGAUGAGGCCGAAAGGCCGAA | AUGGGAG | 501 |
| 1122 | UUAAGGU | CUGAUGAGGCCGAAAGGCCGAA | AUGGCCC | 502 |
| 1123 | AUUAAGG | CUGAUGAGGCCGAAAGGCCGAA | AAUGGCC | 503 |
| 1127 | UGAGAUU | CUGAUGAGGCCGAAAGGCCGAA | AGGUAAU | 504 |
| 1128 | CUGAGAU | CUGAUGAGGCCGAAAGGCCGAA | AAGGUAA | 505 |
| 1131 | UUACUGA | CUGAUGAGGCCGAAAGGCCGAA | AUUAAGG | 506 |
| 1133 | AUUUACU | CUGAUGAGGCCGAAAGGCCGAA | AGAUUAA | 507 |
| 1137 | UUCCAUU | CUGAUGAGGCCGAAAGGCCGAA | ACUGAGA | 508 |
| 1146 | UCACAAA | CUGAUGAGGCCGAAAGGCCGAA | AUUCCAU | 509 |
| 1147 | AUCACAA | CUGAUGAGGCCGAAAGGCCGAA | AAUUCCA | 510 |
| 1148 | UAUCACA | CUGAUGAGGCCGAAAGGCCGAA | AAAUUCC | 511 |
| 1149 | AUAUCAC | CUGAUGAGGCCGAAAGGCCGAA | AAAAUUC | 512 |
| 1155 | GGCAGCA | CUGAUGAGGCCGAAAGGCCGAA | AUCACAA | 513 |
| 1169 | AAAGCAG | CUGAUGAGGCCGAAAGGCCGAA | AGGUCAG | 514 |
| 1175 | UGGGGCA | CUGAUGAGGCCGAAAGGCCGAA | AGCAGUA | 515 |
| 1176 | UUGGGGC | CUGAUGAGGCCGAAAGGCCGAA | AAGCAGU | 516 |
| 1214 | CCUUCUC | CUGAUGAGGCCGAAAGGCCGAA | AUCUCUC | 517 |
| 1230 | CAGGGCG | CUGAUGAGGCCGAAAGGCCGAA | ACACUUU | 518 |
| 1239 | ACUGUUA | CUGAUGAGGCCGAAAGGCCGAA | ACAGGGC | 519 |
| 1241 | ACACUGU | CUGAUGAGGCCGAAAGGCCGAA | AUACAGG | 520 |
| 1249 | UUCUGCG | CUGAUGAGGCCGAAAGGCCGAA | ACACUGU | 521 |
| 1275 | ACCUUCA | CUGAUGAGGCCGAAAGGCCGAA | AUCUUUU | 522 |
| 1283 | CGGAGGC | CUGAUGAGGCCGAAAGGCCGAA | ACCUUCA | 523 |
| 1288 | GAUGACG | CUGAUGAGGCCGAAAGGCCGAA | AGGCUAC | 524 |
| 1292 | AAGAGAU | CUGAUGAGGCCGAAAGGCCGAA | ACGGAGG | 525 |
| 1295 | CAGAAGA | CUGAUGAGGCCGAAAGGCCGAA | AUGACGG | 526 |
| 1297 | CCCAGAA | CUGAUGAGGCCGAAAGGCCGAA | AGAUGAC | 527 |
| 1299 | AUCCCAG | CUGAUGAGGCCGAAAGGCCGAA | AGAGAUG | 528 |
| 1300 | UAUCCCA | CUGAUGAGGCCGAAAGGCCGAA | AAGAGAU | 529 |
| 1307 | AUCCAUG | CUGAUGAGGCCGAAAGGCCGAA | AUCCCAG | 530 |
| 1315 | UCCCCAC | CUGAUGAGGCCGAAAGGCCGAA | AUCCAUG | 531 |
| 1324 | GCCUCAU | CUGAUGAGGCCGAAAGGCCGAA | AUCCCCA | 532 |
| 1334 | AGGGAAG | CUGAUGAGGCCGAAAGGCCGAA | AUGCCUC | 533 |
| 1335 | AAGGGAA | CUGAUGAGGCCGAAAGGCCGAA | AAUGCCU | 534 |
| 1337 | UUAAGGG | CUGAUGAGGCCGAAAGGCCGAA | AGAAUGC | 535 |
| 1338 | GUUAAGG | CUGAUGAGGCCGAAAGGCCGAA | AAGAAUG | 536 |
| 1342 | AUUUGUU | CUGAUGAGGCCGAAAGGCCGAA | AGGGAAG | 537 |
| 1343 | AAUUUGU | CUGAUGAGGCCGAAAGGCCGAA | AAGGGAA | 538 |
| 1350 | CAGCUUA | CUGAUGAGGCCGAAAGGCCGAA | AUUUGUU | 539 |
| 1351 | ACAGCUU | CUGAUGAGGCCGAAAGGCCGAA | AAUUUGU | 540 |
| 1352 | AACAGCU | CUGAUGAGGCCGAAAGGCCGAA | AAAUUUG | 541 |
| 1359 | UGGGUAA | CUGAUGAGGCCGAAAGGCCGAA | ACAGCUU | 542 |
| 1360 | GUGGGUA | CUGAUGAGGCCGAAAGGCCGAA | AACAGCU | 543 |
| 1361 | AGUGGGU | CUGAUGAGGCCGAAAGGCCGAA | AAACAGC | 544 |
| 1362 | UAGUGGG | CUGAUGAGGCCGAAAGGCCGAA | AAAACAG | 545 |
| 1369 | GGUGAGG | CUGAUGAGGCCGAAAGGCCGAA | AGUGGGU | 546 |
| 1373 | AGAAGGU | CUGAUGAGGCCGAAAGGCCGAA | AGGUAGU | 547 |
| 1378 | UUUUAAG | CUGAUGAGGCCGAAAGGCCGAA | AGGUGAG | 548 |
| 1379 | UUUUUAA | CUGAUGAGGCCGAAAGGCCGAA | AAGGUGA | 549 |
| 1381 | GGUUUUU | CUGAUGAGGCCGAAAGGCCGAA | AGAAGGU | 550 |
| 1382 | AGGUUUU | CUGAUGAGGCCGAAAGGCCGAA | AAGAAGG | 551 |

TABLE III-continued

Human B7-1 Hammerhead Ribozyme Sequences

| nt. Position | HH Ribozyme Sequence | | | Seq. ID No. |
|---|---|---|---|---|
| 1390 | UCUGAAA | CUGAUGAGGCCGAAAGGCCGAA | AGGUUUU | 552 |
| 1392 | AAUCUGA | CUGAUGAGGCCGAAAGGCCGAA | AGAGGUU | 553 |
| 1393 | UAAUCUG | CUGAUGAGGCCGAAAGGCCGAA | AAAGAGG | 554 |
| 1394 | UUAAUCU | CUGAUGAGGCCGAAAGGCCGAA | AAAAGAGG | 555 |
| 1399 | UCAGCUU | CUGAUGAGGCCGAAAGGCCGAA | AUCUGAA | 556 |
| 1400 | UUCAGCU | CUGAUGAGGCCGAAAGGCCGAA | AAUCUGA | 557 |
| 1412 | AUCUUGU | CUGAUGAGGCCGAAAGGCCGAA | ACUGUUC | 558 |
| 1413 | CAUCUUG | CUGAUGAGGCCGAAAGGCCGAA | AACUGUU | 559 |
| 1429 | GGAGAGG | CUGAUGAGGCCGAAAGGCCGAA | AUGCCAG | 560 |
| 1433 | GAAAGGA | CUGAUGAGGCCGAAAGGCCGAA | AGGGAUG | 561 |
| 1435 | GAGAAAG | CUGAUGAGGCCGAAAGGCCGAA | AGAGGGA | 562 |
| 1438 | GGGGAGA | CUGAUGAGGCCGAAAGGCCGAA | AGGAGAG | 563 |
| 1439 | UGGGGAG | CUGAUGAGGCCGAAAGGCCGAA | AAGGAGA | 564 |
| 1440 | AUGGGGA | CUGAUGAGGCCGAAAGGCCGAA | AAAGGAG | 565 |
| 1442 | AUAUGGG | CUGAUGAGGCCGAAAGGCCGAA | AGAAAGG | 566 |
| 1448 | AAUUGCA | CUGAUGAGGCCGAAAGGCCGAA | AUGGGGA | 567 |
| 1455 | UUAAGCA | CUGAUGAGGCCGAAAGGCCGAA | AUUGCAU | 568 |
| 1456 | AUUAAGC | CUGAUGAGGCCGAAAGGCCGAA | AAUUGCA | 569 |
| 1460 | UUACAUU | CUGAUGAGGCCGAAAGGCCGAA | AGCAAAU | 570 |
| 1461 | GUUACAU | CUGAUGAGGCCGAAAGGCCGAA | AAGCAAA | 571 |
| 1466 | AAGAGGU | CUGAUGAGGCCGAAAGGCCGAA | ACAUUAA | 572 |
| 1471 | AAAAGAA | CUGAUGAGGCCGAAAGGCCGAA | AGGUUAC | 573 |
| 1473 | GCAAAAG | CUGAUGAGGCCGAAAGGCCGAA | AGAGGUU | 574 |
| 1474 | GGCAAAA | CUGAUGAGGCCGAAAGGCCGAA | AAGAGGU | 575 |
| 1476 | AUGGCAA | CUGAUGAGGCCGAAAGGCCGAA | AGAAGCA | 576 |
| 1477 | CAUGGCA | CUGAUGAGGCCGAAAGGCCGAA | AAGAAGA | 577 |
| 1478 | ACAUGGC | CUGAUGAGGCCGAAAGGCCGAA | AAAGAAG | 578 |
| 1486 | GAAUGGA | CUGAUGAGGCCGAAAGGCCGAA | ACAUGGC | 579 |
| 1487 | AGAAUGG | CUGAUGAGGCCGAAAGGCCGAA | AACAUGG | 580 |
| 1488 | CAGAAUG | CUGAUGAGGCCGAAAGGCCGAA | AAACAUG | 581 |
| 1492 | AUGGCAG | CUGAUGAGGCCGAAAGGCCGAA | AUGGAAA | 582 |
| 1493 | GAUGGCA | CUGAUGAGGCCGAAAGGCCGAA | AAUGGAA | 583 |
| 1500 | AAUUCAA | CUGAUGAGGCCGAAAGGCCGAA | AUGGCAG | 584 |
| 1502 | ACAAUUC | CUGAUGAGGCCGAAAGGCCGAA | AGAUGGC | 585 |
| 1507 | ACAAGAC | CUGAUGAGGCCGAAAGGCCGAA | AUUCAAG | 586 |
| 1510 | CUGACAA | CUGAUGAGGCCGAAAGGCCGAA | ACAAUUC | 587 |
| 1512 | GGCUGAC | CUGAUGAGGCCGAAAGGCCGAA | AGACAAU | 588 |
| 1515 | AUUGGCU | CUGAUGAGGCCGAAAGGCCGAA | ACAAGAC | 589 |
| 1523 | GAUAAUG | CUGAUGAGGCCGAAAGGCCGAA | AUUGGCU | 590 |
| 1524 | AGAUAAU | CUGAUGAGGCCGAAAGGCCGAA | AAUUGGC | 591 |
| 1527 | AAUAGAU | CUGAUGAGGCCGAAAGGCCGAA | AUGAAUU | 592 |
| 1528 | UAAUAGA | CUGAUGAGGCCGAAAGGCCGAA | AAUGAAU | 593 |
| 1530 | UUUAAUA | CUGAUGAGGCCGAAAGGCCGAA | AUAAUGA | 594 |
| 1532 | UGUUUAA | CUGAUGAGGCCGAAAGGCCGAA | AGAUAAU | 595 |
| 1534 | AGUGUUU | CUGAUGAGGCCGAAAGGCCGAA | AUAGAUA | 596 |
| 1535 | UAGUGUU | CUGAUGAGGCCGAAAGGCCGAA | AAUAGAU | 597 |
| 1542 | CUCAAAU | CUGAUGAGGCCGAAAGGCCGAA | AGUGUUU | 598 |

TABLE IV

Mouse B7-1 Hammerhead Ribozyme Target Sequences

| nt. Position | HH Target Sequence | | | Seq. ID No. |
|---|---|---|---|---|
| 8 | GaGUuUU | a | UACcUcA | 599 |
| 10 | guUuuAU | A | CCUCAAU | 600 |
| 10 | GUuUUaU | a | ccuCAAU | 601 |
| 14 | UAUacCU | c | aAUAGAC | 602 |
| 18 | CcucAAU | A | gaCUCUu | 603 |
| 18 | CCUcaaU | a | gaCUCUU | 604 |
| 18 | CcUcAAU | a | GaCUcuU | 605 |
| 23 | AuaGaCU | c | uUACuaG | 606 |
| 25 | AGACuCU | U | aCuAGuu | 607 |
| 26 | GACuCUU | a | CuAGuuu | 608 |
| 29 | UCUUACU | a | GuuUCuc | 609 |
| 29 | UcUuACU | a | gUuuCuC | 610 |
| 29 | UCUUaCU | a | guUUCUc | 611 |
| 29 | UCuuaCU | a | gUUUCUC | 612 |
| 34 | CUaGUuU | c | UCUuuuU | 613 |
| 34 | CUAGUuU | c | UCUuuuU | 614 |
| 34 | cUAgUuU | c | uCuUuUU | 615 |

TABLE IV-continued

Mouse B7-1 Hammerhead Ribozyme Target Sequences

| nt. Position | HH Target Sequence | | | Seq. ID No. |
|---|---|---|---|---|
| 40 | ucuCUuU | U | UCAGgUU | 616 |
| 41 | cUCUuUU | u | caGGuUg | 617 |
| 41 | cuCUuUU | U | CAGgUUg | 618 |
| 42 | uCUuUUU | C | AGgUUgu | 619 |
| 56 | UGAAACU | c | AAcCuuC | 620 |
| 56 | UGAAAcU | C | aAcCUUC | 621 |
| 62 | uCAACCU | U | caaAGAC | 622 |
| 62 | UCaAcCU | U | CaAAgAc | 623 |
| 62 | UCAACCU | u | caaAGac | 624 |
| 63 | CAACCUU | c | aaAGACa | 625 |
| 73 | aGAcAcU | c | UGuUCcA | 626 |
| 77 | acUCUgU | u | cCAuUUC | 627 |
| 78 | CucUGUU | c | CauUUCU | 628 |
| 83 | UucCAuU | U | CUGUggA | 629 |
| 93 | GUggAcU | A | AuAGgAu | 630 |
| 93 | gUgdacU | a | AUAGgaU | 631 |
| 93 | gUGgAcU | a | AuAGGAU | 632 |

TABLE IV-continued

Mouse B7-1 Hammerhead Ribozyme Target Sequences

| nt. Position | HH Target Sequence | | | Seq. ID No. |
|---|---|---|---|---|
| 96  | GAcuAAU  | a | GGAUcaU | 633 |
| 96  | gacuAAU  | a | gGAuCaU | 634 |
| 101 | AUaGGAU  | a | aUCuUuA | 635 |
| 104 | GGAuCAU  | C | uuuAgCa | 636 |
| 104 | GGAuCAU  | C | UUUagcA | 637 |
| 106 | AuCAUCU  | U | UagcAUC | 638 |
| 107 | UcAuCuU  | a | AGCAUCU | 639 |
| 107 | uCaUCUU  | u | AgcAuCU | 640 |
| 108 | CaUcUUU  | a | GCAuCUG | 641 |
| 108 | CAUcUUU  | a | gcaUCUG | 642 |
| 131 | aUGCCAU  | C | caGgcUU | 643 |
| 142 | gCUuCUU  | U | uUCuaCA | 644 |
| 142 | gCuUCUU  | u | UUCuaCa | 645 |
| 143 | CUuCUUU  | u | UCuaCAU | 646 |
| 143 | CuUcUuU  | u | uCuAcAU | 647 |
| 143 | CUUCUUU  | U | uCUAcaU | 648 |
| 143 | cUUCuUU  | u | UCUAcau | 649 |
| 144 | UuCuUuU  | U | cUaCAuC | 650 |
| 144 | UuCuuuU  | u | cUAcAUC | 651 |
| 144 | UUCuuUU  | u | cuaCAUC | 652 |
| 147 | uUUUuCU  | a | cAuCUCU | 653 |
| 153 | UAcAuCU  | C | ugUUUCU | 654 |
| 165 | uCUCgAU  | U | UuUgUgA | 655 |
| 165 | uCUcgAU  | u | UuuGUgA | 656 |
| 165 | ucucgAU  | U | UUUGUGA | 657 |
| 166 | CUCgAUU  | U | uUgUgAG | 658 |
| 167 | uCgAUuU  | u | UGUGaGc | 659 |
| 167 | ucGauUU  | U | UGUgAgC | 660 |
| 167 | UCgAUUU  | u | UgUgAGC | 661 |
| 168 | cGAUUuU  | u | gUgAGCC | 662 |
| 168 | cgAUUUU  | U | GUGAgcc | 663 |
| 197 | GCUccAU  | U | GgCUcUA | 664 |
| 202 | aUUGGCU  | c | UagaUUc | 665 |
| 208 | UCUAgAU  | U | ccUGGCU | 666 |
| 216 | CCUGGCU  | u | UcCcCau | 667 |
| 217 | cUGGCUU  | U | CcCcaUc | 668 |
| 217 | cUgGCuU  | u | CccCAUC | 669 |
| 217 | CUGGCuU  | u | CCcCauC | 670 |
| 218 | UGGcuUU  | c | ccCaUCA | 671 |
| 218 | UGGCUUU  | c | cCcaUca | 672 |
| 218 | UGgCuUU  | c | cCcaUCA | 673 |
| 218 | ugGcUUU  | c | CCCAucA | 674 |
| 224 | UCcCCAU  | c | aUGuUCu | 675 |
| 224 | UccCCAU  | c | aUGuucU | 676 |
| 230 | UCAugUU  | C | UccAAAg | 677 |
| 232 | AuGUUcU  | C | CAaAGCa | 678 |
| 232 | AUGuUcU  | c | caaAGCA | 679 |
| 232 | AugUUCU  | c | cAAAgCa | 680 |
| 241 | AAAGcAU  | C | UgAAGcu | 681 |
| 241 | aAAGCAU  | C | UGAAGCu | 682 |
| 241 | AAAgcAU  | C | UGAAGcU | 683 |
| 249 | UGAAgcU  | A | UGGCuuG | 684 |
| 264 | CAAuUgU  | c | AGuUGaU | 685 |
| 287 | CAcCaCU  | c | CUcaagU | 686 |
| 295 | CUCaAgU  | u | UCcaUGU | 687 |
| 295 | cuCAaGU  | U | UCCAUgu | 688 |
| 296 | uCAAgUU  | u | ccAUgUc | 689 |
| 297 | CAAGUuU  | C | CAUguCc | 690 |
| 297 | CAaGuuU  | c | cAUGuCC | 691 |
| 314 | GGCUcaU  | u | cUUCUCu | 692 |
| 314 | GgcUCAU  | U | CUUCuCU | 693 |
| 315 | GcuCAUU  | c | UuCUcuU | 694 |
| 315 | gcuCAUU  | C | UUCuCUU | 695 |
| 317 | uCAUUCU  | U | CuCUUug | 696 |
| 318 | CAUUCUU  | c | uCUUugu | 697 |
| 318 | CAUcCuU  | C | UCuUUgu | 698 |
| 320 | uUCUUCU  | c | uuUgUgC | 699 |
| 320 | UUCuuCU  | C | UUuGUGC | 700 |
| 322 | CuuCUCU  | U | uGUGCUG | 701 |
| 322 | CUucuCU  | U | UgUGCUG | 702 |
| 323 | UUcuCUU  | u | gUGcugC | 703 |
| 336 | gcUGAUU  | c | GUCuUUc | 704 |
| 341 | uUCGuCU  | u | UCacAAG | 705 |
| 341 | UUCgucU  | u | UcAcAAG | 706 |
| 342 | UcGUCUU  | U | CaCAagU | 707 |
| 343 | cgucUuU  | C | AcAAGUG | 708 |
| 343 | cGuCuUU  | c | AcaAGUG | 709 |
| 352 | caAGUGU  | C | uuCAGAu | 710 |
| 355 | gUgUcUU  | C | AGaUGUU | 711 |
| 382 | UCcaAGU  | c | AgUGaAA | 712 |
| 408 | gCUGCcU  | U | GCCguuA | 713 |
| 414 | UUGccgU  | U | aCAACUc | 714 |
| 414 | UUgCCgU  | u | ACAAcUc | 715 |
| 421 | UaCAAcU  | c | uCcUcAU | 716 |
| 426 | CUCuCCU  | c | aUgAAgA | 717 |
| 439 | GaUGAgU  | C | UGAaGaC | 718 |
| 452 | acCGaAU  | C | UACUGGC | 719 |
| 454 | CGaAUCU  | A | CUGGCAA | 720 |
| 484 | GuGCUgU  | c | UGucaUU | 721 |
| 484 | GugCUGU  | C | UguCAuU | 722 |
| 488 | ugUcUGU  | C | AUUGCUg | 723 |
| 503 | gGAAacU  | A | aAAGuGu | 724 |
| 503 | ggAAACU  | a | AAAgUGU | 725 |
| 520 | CCCGAGU  | C | uAAGAAC | 726 |
| 535 | cGGAcUU  | U | aUaUGAc | 727 |
| 536 | GGAcUUU  | a | UaUGAcA | 728 |
| 538 | AcUuUAU  | a | UGACaac | 729 |
| 553 | acuACCU  | a | cUCUcUU | 730 |
| 553 | AcUaCcU  | a | cUCUcUU | 731 |
| 556 | ACCuACU  | c | uCUuAuC | 732 |
| 556 | AcCuAcU  | c | ucUUAUC | 733 |
| 560 | AcUcUCU  | U | aUCAuCC | 734 |
| 561 | cUCuCUU  | a | UcAuCCU | 735 |
| 561 | cuCUcuU  | a | uCAUCCU | 736 |
| 561 | CUCUCuU  | a | UCauCCu | 737 |
| 566 | UUaUcAU  | C | CUGGgcC | 738 |
| 566 | uUauCAU  | C | CUGGGCC | 739 |
| 581 | UGGuCcU  | U | UcAGAcc | 740 |
| 583 | gucCUUU  | C | AgaCcGG | 741 |
| 583 | GuCcUUU  | c | AGAccGg | 742 |
| 598 | GGCACAU  | A | CagcUGU | 743 |
| 608 | gcUGUGU  | c | GUUCaaA | 744 |
| 611 | GUGUcgU  | u | CAaaaGA | 745 |
| 611 | GUGUcGU  | U | CaaAAGa | 746 |
| 612 | UGUcGUU  | C | aaAAGaA | 747 |
| 641 | aUGaAGU  | u | aaACaCU | 748 |
| 649 | AAAcacU  | U | GGCUUUa | 749 |
| 649 | AaaCAcU  | U | gGCUUuA | 750 |
| 655 | UUggcuU  | u | GUAAAg  | 751 |
| 656 | UGgcUUU  | a | GUAAAgu | 752 |
| 659 | CuUuaGU  | A | AAGUugu | 753 |
| 664 | GUaAaGU  | U | gUCcaUC | 754 |
| 667 | AaGUUgU  | C | caUCAAA | 755 |
| 671 | UgUCcaU  | C | AAAGCUG | 756 |
| 682 | gCUgAcU  | u | CuCuACC | 757 |
| 682 | GCUGACU  | U | CuCUACc | 758 |
| 682 | GCUGacU  | U | cuCuAcc | 759 |
| 683 | CUGACUU  | C | uCUACcc | 760 |
| 683 | CUGACUU  | c | ucuAccC | 761 |
| 685 | gACUuCU  | c | UaCCCCc | 762 |
| 685 | gaCUucU  | c | UACCCcC | 763 |
| 687 | CUUCuCU  | C | CcCCcAa | 764 |
| 698 | ccAACAU  | a | ACUGagu | 765 |
| 698 | CCaacAU  | A | ACuGaGU | 766 |
| 718 | AAcCCAU  | C | UGcAgAc | 767 |
| 718 | aaCCCAU  | c | UGCAgac | 768 |
| 729 | AGACacU  | A | AaAgGAu | 769 |
| 729 | agAcAcU  | A | aAAGGAU | 770 |
| 729 | agACAcU  | a | AaAgGAU | 771 |
| 737 | aAAGGAU  | u | AccUGCU | 772 |
| 737 | aAAGgAU  | U | AccUGCu | 773 |
| 737 | aaagGAU  | u | ACCUGCU | 774 |
| 745 | aCCUGcU  | U | UGCuuCc | 775 |
| 745 | accUGcU  | u | UGCUuCC | 776 |
| 759 | cGggGgU  | U | uCCCAAA | 777 |
| 759 | cGgGGGU  | u | UcCcAaa | 778 |
| 759 | cGGGGGU  | U | UcCCAaA | 779 |
| 760 | GggGgUU  | u | CCCAAAG | 780 |
| 760 | gGggGUU  | u | cCCAaag | 781 |
| 760 | GGgGGUU  | U | cCCAaAG | 782 |

TABLE IV-continued

Mouse B7-1 Hammerhead Ribozyme Target Sequences

| nt. Position | HH Target Sequence | | | Seq. ID No. |
|---|---|---|---|---|
| 761 | GgGGUUU | c | CCAaAGC | 783 |
| 771 | aAAgccU | C | GCuUCUC | 784 |
| 771 | AaAGCCU | c | gCuUCUC | 785 |
| 776 | CUCgCUU | C | UcUUggu | 786 |
| 776 | CUCgCuU | C | UCuUGGU | 787 |
| 778 | CgCuUCU | C | uUGGUUG | 788 |
| 784 | UCuUGGU | U | GGAAAAU | 789 |
| 803 | GAGaaUU | A | CCugGcA | 790 |
| 803 | gAGAAUU | A | ccUGgCA | 791 |
| 803 | gagAaUU | a | CCUGgcA | 792 |
| 812 | cUGgCAU | C | AAuACgA | 793 |
| 812 | CUGGcAU | c | aAuaCgA | 794 |
| 816 | caUCAAU | A | cGACAaU | 795 |
| 816 | cAUCaAU | a | cgACAaU | 796 |
| 824 | CgACAaU | U | UCCCAgG | 797 |
| 825 | gACAaUU | U | CCCAgGA | 798 |
| 826 | ACAaUUU | C | CCAgGAU | 799 |
| 834 | CCAgGAU | C | CUGAAuC | 800 |
| 841 | CcUGaaU | C | ugAAUUG | 801 |
| 841 | cCUGAaU | c | UGAAuUg | 802 |
| 850 | gAAuUGU | A | CaCCaUu | 803 |
| 869 | gccAaCU | a | gAUuUCA | 804 |
| 869 | GCCAaCU | a | GAuUUca | 805 |
| 869 | GCCAAcU | a | gaUuUCa | 806 |
| 873 | acUaGAU | u | UCAaUAc | 807 |
| 873 | ACUaGAU | U | UCAAUAc | 808 |
| 874 | CUaGAUU | U | CAAUAcG | 809 |
| 875 | UaGAUUU | C | AAUAcGA | 810 |
| 885 | UAcgACU | c | gcAACCa | 811 |
| 899 | ACACCaU | u | aAgUgUC | 812 |
| 899 | ACAcCaU | u | AaGUGUC | 813 |
| 906 | UaaGUGU | C | UcaUuAA | 814 |
| 906 | UAaGUGU | C | UCAUuAA | 815 |
| 908 | aGUGUCU | C | AUuAAaU | 816 |
| 911 | GUCUCAU | u | AAaUAUG | 817 |
| 916 | AUuAaaU | a | UGGaGAu | 818 |
| 916 | AUuAAaU | A | UGGAgAU | 819 |
| 943 | gAGgaCU | U | CAcCUGG | 820 |
| 944 | AGgaCUU | C | AcCUGGg | 821 |
| 1001 | UGCUcUU | u | GggGCAg | 822 |
| 1034 | CAGucGU | c | gUCauCG | 823 |
| 1037 | UcGUCgU | C | AuCguUG | 824 |
| 1043 | uCAUCgU | U | GucAUCA | 825 |
| 1046 | ucgUUGU | c | AuCAUCA | 826 |
| 1049 | uUguCaU | c | AuCAAAU | 827 |
| 1060 | aAAUGcU | U | CUGUaag | 828 |
| 1060 | AAaUgCU | u | cUgUaAG | 829 |
| 1060 | aAAUgcU | u | cUGUaAG | 830 |
| 1060 | AAAugCU | u | cUgUaAG | 831 |
| 1061 | AAUGcUU | C | UGUaagc | 832 |
| 1080 | AagcugU | u | UCAGAAG | 833 |
| 1080 | AAGCUGU | U | UcAgaag | 834 |
| 1081 | AgCUGUU | U | CAgaAga | 835 |
| 1121 | acAGcCU | U | ACCuUcg | 836 |
| 1121 | AcAgCCU | u | aCCuUcG | 837 |
| 1121 | ACagCCU | u | ACCUUCg | 838 |
| 1122 | CaGcCuU | a | cCUUCgG | 839 |
| 1126 | CUuACCU | u | CgGgccU | 840 |
| 1127 | UUaCcUU | c | ggGcCUG | 841 |
| 1127 | UuACcUU | c | GggCCUg | 842 |
| 1144 | GaagCAU | U | AgCUgAA | 843 |
| 1144 | gaAGcaU | u | AGCUGAA | 844 |
| 1145 | aAgcAUU | a | GCUgAAC | 845 |
| 1160 | AGAcCgU | c | UUCCUuu | 846 |
| 1162 | AcCgUCU | u | CcUUuaG | 847 |
| 1163 | ccGUCUU | c | CUUuaGU | 848 |
| 1167 | cUUCcUU | u | AGuUCUU | 849 |
| 1177 | uUCUUCU | c | UguCCAU | 850 |
| 1181 | UCuCugU | C | CAuGUGg | 851 |
| 1181 | ucUCUGU | c | CAuGUGg | 852 |
| 1192 | gUGGGAU | A | CAUGGua | 853 |
| 1199 | aCaUGGU | a | UUAugUG | 854 |
| 1201 | AuGgUaU | u | aUGUGGc | 855 |
| 1210 | ugUGGcU | C | aUGaGGu | 856 |
| 1210 | UGuGGCU | C | AUGAGGu | 857 |
| 1223 | GUacAAU | c | UUUCUUu | 858 |
| 1225 | ACAAUcU | U | UCUuUca | 859 |
| 1225 | ACAAuCU | u | uCuUucA | 860 |
| 1226 | caAuCUU | u | cUuUCAG | 861 |
| 1227 | aAucUUU | c | uUUCAGC | 862 |
| 1227 | AAucuuU | C | UUUCAGc | 863 |
| 1227 | AAuCUuU | c | uUUcaGC | 864 |
| 1229 | ucUUUCU | U | UCAGCaC | 865 |
| 1230 | cUUUCUU | U | CAGCaCc | 866 |
| 1252 | cUgAUCU | u | UcggACA | 867 |
| 1274 | acaAGAU | a | gAGuUaA | 868 |
| 1310 | UGAgGaU | u | uCuUuCc | 869 |
| 1312 | aGgAUUU | c | UuUcCAu | 870 |
| 1314 | gAUUUcU | u | UcCAuCA | 871 |
| 1316 | UUUcUuU | c | CAuCAgG | 872 |
| 1320 | UUUcCaU | C | AGgAAGC | 873 |
| 1320 | UUUCcaU | c | aggaAGC | 874 |
| 1339 | GgCAagU | u | UgCUGGG | 875 |
| 1355 | cUuUgAU | U | GCUUgAU | 876 |
| 1437 | gUGguaU | A | aGAAAAA | 877 |
| 1437 | gUggUAU | a | AGAAaaA | 878 |
| 1475 | gCCUAGU | c | UuaCUGc | 879 |
| 1477 | CUaGUCU | U | ACUgcaa | 880 |
| 1487 | ugCAaCU | U | gAUaUGU | 881 |
| 1491 | AcuUGAU | a | UGUCAUg | 882 |
| 1491 | aCUUgaU | a | UguCAUG | 883 |
| 1505 | gUUUGgU | U | ggUGUcu | 884 |
| 1530 | UGCCcUU | u | uCUgAAg | 885 |
| 1531 | GcccUUU | u | CUGAagA | 886 |
| 1532 | CcCuUuU | C | UGAAGAg | 887 |
| 1644 | CcCuuuU | C | UGAaGAG | 888 |
| 1652 | CUaUGGU | u | gggAUGU | 889 |
| 1652 | ggGAuGU | a | AaAAcGG | 890 |
| 1670 | GgGAugU | a | aAaAcGG | 891 |
| 1674 | aUaAUAU | a | AaUAuUA | 892 |
| 1676 | UAuAAAU | a | UuUAaaUa | 893 |
| 1677 | UaAaUAU | u | aAaUAAA | 894 |
| 1677 | AAauAUU | a | AAuaAAA | 895 |
| 1694 | AaaUAUU | A | AAuAaaA | 896 |

TABLE V

Mouse B7-1 Hammerhead Ribozyme Sequences

| nt. Position | HH Ribozyme Sequence | | | Seq. ID No. |
|---|---|---|---|---|
| 8 | UGAGGUA | CUGAUGAGGCCGAAAGGCCGAA | AAAACUC | 898 |
| 10 | AUUGAGG | CUGAUGAGGCCGAAAGGCCGAA | AUAAAAC | 899 |
| 10 | AUUGAGG | CUGAUGAGGCCGAAAGGCCGAA | AUAAAAC | 900 |
| 14 | GUCUAUU | CUGAUGAGGCCGAAAGGCCGAA | AGGUAUA | 901 |
| 18 | AAGAGUC | CUGAUGAGGCCGAAAGGCCGAA | AUUGAGG | 902 |
| 18 | AAGAGUC | CUGAUGAGGCCGAAAGGCCGAA | AUUGAGG | 903 |
| 18 | AAGAGUC | CUGAUGAGGCCGAAAGGCCGAA | AUUGAGG | 904 |
| 23 | CUAGUAA | CUGAUGAGGCCGAAAGGCCGAA | AGUCUAU | 905 |
| 25 | AACUAGU | CUGAUGAGGCCGAAAGGCCGAA | AGAGUCU | 906 |
| 26 | AAACUAG | CUGAUGAGGCCGAAAGGCCGAA | AAGAGUC | 907 |
| 29 | GAGAAAC | CUGAUGAGGCCGAAAGGCCGAA | AGUAAGA | 908 |
| 29 | GAGAAAC | CUGAUGAGGCCGAAAGGCCGAA | AGUAAGA | 909 |
| 29 | GAGAAAC | CUGAUGAGGCCGAAAGGCCGAA | AGUAAGA | 910 |
| 29 | GAGAAAC | CUGAUGAGGCCGAAAGGCCGAA | AGUAAGA | 911 |
| 34 | AAAAAGA | CUGAUGAGGCCGAAAGGCCGAA | AAACUAG | 912 |
| 34 | AAAAAGA | CUGAUGAGGCCGAAAGGCCGAA | AAACUAG | 913 |
| 34 | AAAAAGA | CUGAUGAGGCCGAAAGGCCGAA | AAACUAG | 914 |
| 40 | AACCUGA | CUGAUGAGGCCGAAAGGCCGAA | AAAGAGA | 915 |
| 41 | CAACCUG | CUGAUGAGGCCGAAAGGCCGAA | AAAAGAG | 916 |
| 41 | CAACCUG | CUGAUGAGGCCGAAAGGCCGAA | AAAAGAG | 917 |
| 42 | ACAACCU | CUGAUGAGGCCGAAAGGCCGAA | AAAAAGA | 918 |
| 56 | GAAGGUU | CUGAUGAGGCCGAAAGGCCGAA | AGUUUCA | 919 |
| 56 | GAAGGUU | CUGAUGAGGCCGAAAGGCCGAA | AGUUUCA | 920 |
| 62 | GUCUUUG | CUGAUGAGGCCGAAAGGCCGAA | AGGUUGA | 921 |
| 62 | GUCUUUG | CUGAUGAGGCCGAAAGGCCGAA | AGGUUGA | 922 |
| 62 | GUCUUUG | CUGAUGAGGCCGAAAGGCCGAA | AGGUUGA | 923 |
| 63 | UGUCUUU | CUGAUGAGGCCGAAAGGCCGAA | AAGGUUG | 924 |
| 73 | UGGAACA | CUGAUGAGGCCGAAAGGCCGAA | AGUGUCU | 925 |
| 77 | GAAAUGG | CUGAUGAGGCCGAAAGGCCGAA | ACAGAGU | 926 |
| 78 | AGAAAUG | CUGAUGAGGCCGAAAGGCCGAA | AACAGAG | 927 |
| 83 | UCCACAG | CUGAUGAGGCCGAAAGGCCGAA | AAUGGAA | 928 |
| 93 | AUCCUAU | CUGAUGAGGCCGAAAGGCCGAA | AGUCCAC | 929 |
| 93 | AUCCUAU | CUGAUGAGGCCGAAAGGCCGAA | AGUCCAC | 930 |
| 93 | AUCCUAU | CUGAUGAGGCCGAAAGGCCGAA | AGUCCAC | 931 |
| 96 | AUGAUCC | CUGAUGAGGCCGAAAGGCCGAA | AUUAGUC | 932 |
| 96 | AUGAUCC | CUGAUGAGGCCGAAAGGCCGAA | AUUAGUC | 933 |
| 101 | UAAAGAU | CUGAUGAGGCCGAAAGGCCGAA | AUCCUAU | 934 |
| 104 | UGCUAAA | CUGAUGAGGCCGAAAGGCCGAA | AUGAUCC | 935 |
| 104 | UGCUAAA | CUGAUGAGGCCGAAAGGCCGAA | AUGAUCC | 936 |
| 106 | GAUGCUA | CUGAUGAGGCCGAAAGGCCGAA | AGAUGAU | 937 |
| 107 | AGAUGCU | CUGAUGAGGCCGAAAGGCCGAA | AAGAUGA | 938 |
| 107 | AGAUGCU | CUGAUGAGGCCGAAAGGCCGAA | AAGAUGA | 939 |
| 108 | CAGAUGC | CUGAUGAGGCCGAAAGGCCGAA | AAAGAUG | 940 |
| 108 | CAGAUGC | CUGAUGAGGCCGAAAGGCCGAA | AAAGAUG | 941 |
| 131 | AAGCCUG | CUGAUGAGGCCGAAAGGCCGAA | AUGGCAU | 942 |
| 142 | UGUAGAA | CUGAUGAGGCCGAAAGGCCGAA | AAGAAGC | 943 |
| 142 | UGUAGAA | CUGAUGAGGCCGAAAGGCCGAA | AAGAAGC | 944 |
| 143 | AUGUAGA | CUGAUGAGGCCGAAAGGCCGAA | AAAGAAG | 945 |
| 143 | AUGUAGA | CUGAUGAGGCCGAAAGGCCGAA | AAAGAAG | 946 |
| 143 | AUGUAGA | CUGAUGAGGCCGAAAGGCCGAA | AAAGAAG | 947 |
| 143 | AUGUAGA | CUGAUGAGGCCGAAAGGCCGAA | AAAGAAG | 948 |
| 144 | GAUGUAG | CUGAUGAGGCCGAAAGGCCGAA | AAAAGAA | 949 |
| 144 | GAUGUAG | CUGAUGAGGCCGAAAGGCCGAA | AAAAGAA | 950 |
| 144 | GAUGUAG | CUGAUGAGGCCGAAAGGCCGAA | AAAAGAA | 951 |
| 147 | AGAGAUG | CUGAUGAGGCCGAAAGGCCGAA | AGAAAAA | 952 |
| 153 | AGAAACA | CUGAUGAGGCCGAAAGGCCGAA | AGAUGUA | 953 |
| 165 | UCACAAA | CUGAUGAGGCCGAAAGGCCGAA | AUCGAGA | 954 |
| 165 | UCACAAA | CUGAUGAGGCCGAAAGGCCGAA | AUCGAGA | 955 |
| 165 | UCACAAA | CUGAUGAGGCCGAAAGGCCGAA | AUCGAGA | 956 |
| 166 | CUCACAA | CUGAUGAGGCCGAAAGGCCGAA | AAUCGAG | 957 |
| 167 | GCUCACA | CUGAUGAGGCCGAAAGGCCGAA | AAAUCGA | 958 |
| 167 | GCUCACA | CUGAUGAGGCCGAAAGGCCGAA | AAAUCGA | 959 |
| 167 | GCUCACA | CUGAUGAGGCCGAAAGGCCGAA | AAAUCGA | 960 |
| 168 | GGCUCAC | CUGAUGAGGCCGAAAGGCCGAA | AAAAUCG | 961 |
| 168 | GGCUCAC | CUGAUGAGGCCGAAAGGCCGAA | AAAAUCG | 962 |
| 197 | UAGAGCC | CUGAUGAGGCCGAAAGGCCGAA | AUGGAGC | 963 |
| 202 | GAAUCUA | CUGAUGAGGCCGAAAGGCCGAA | AGCCAAU | 964 |
| 208 | AGCCAGG | CUGAUGAGGCCGAAAGGCCGAA | AUCUAGA | 965 |
| 216 | AUGGGGA | CUGAUGAGGCCGAAAGGCCGAA | AGCCAGG | 966 |
| 217 | GAUGGGG | CUGAUGAGGCCGAAAGGCCGAA | AAGCCAG | 967 |
| 217 | GAUGGGG | CUGAUGAGGCCGAAAGGCCGAA | AAGCCAG | 968 |
| 217 | GAUGGGG | CUGAUGAGGCCGAAAGGCCGAA | AAGCCAG | 969 |
| 218 | UGAUGGG | CUGAUGAGGCCGAAAGGCCGAA | AAAGCCA | 970 |
| 218 | UGAUGGG | CUGAUGAGGCCGAAAGGCCGAA | AAAGCCA | 971 |
| 218 | UGAUGGG | CUGAUGAGGCCGAAAGGCCGAA | AAAGCCA | 972 |

TABLE V-continued

Mouse B7-1 Hammerhead Ribozyme Sequences

| nt. Position | | HH Ribozyme Sequence | | Seq. ID No. |
|---|---|---|---|---|
| 218 | UGAUGGG | CUGAUGAGGCCGAAAGGCCGAA | AAAGCCA | 973 |
| 224 | AGAACAU | CUGAUGAGGCCGAAAGGCCGAA | AUGGGGA | 974 |
| 224 | AGAACAU | CUGAUGAGGCCGAAAGGCCGAA | AUGGGGA | 975 |
| 230 | CUUUGGA | CUGAUGAGGCCGAAAGGCCGAA | AACAUGA | 976 |
| 232 | UGCUUUG | CUGAUGAGGCCGAAAGGCCGAA | AGAACAU | 977 |
| 232 | UGCUUUG | CUGAUGAGGCCGAAAGGCCGAA | AGAACAU | 978 |
| 232 | UGCUUUG | CUGAUGAGGCCGAAAGGCCGAA | AGAACAU | 979 |
| 241 | AGCUUCA | CUGAUGAGGCCGAAAGGCCGAA | AUGCUUU | 980 |
| 241 | AGCUUCA | CUGAUGAGGCCGAAAGGCCGAA | AUGCUUU | 981 |
| 241 | AGCUUCA | CUGAUGAGGCCGAAAGGCCGAA | AUGCUUU | 982 |
| 249 | CAAGCCA | CUGAUGAGGCCGAAAGGCCGAA | AGCUUCA | 983 |
| 264 | AUCAACU | CUGAUGAGGCCGAAAGGCCGAA | ACAAUUG | 984 |
| 287 | ACUUGAG | CUGAUGAGGCCGAAAGGCCGAA | AGUGGUG | 985 |
| 295 | ACAUGGA | CUGAUGAGGCCGAAAGGCCGAA | ACUUGAG | 986 |
| 295 | ACAUGGA | CUGAUGAGGCCGAAAGGCCGAA | ACUUGAG | 987 |
| 296 | GACAUGG | CUGAUGAGGCCGAAAGGCCGAA | AACUUGA | 988 |
| 297 | GGACAUG | CUGAUGAGGCCGAAAGGCCGAA | AAACUUG | 989 |
| 297 | GGACAUG | CUGAUGAGGCCGAAAGGCCGAA | AAACUUG | 990 |
| 314 | AGAGAAG | CUGAUGAGGCCGAAAGGCCGAA | AUGAGCC | 991 |
| 314 | AGAGAAG | CUGAUGAGGCCGAAAGGCCGAA | AUGAGCC | 992 |
| 315 | AAGAGAA | CUGAUGAGGCCGAAAGGCCGAA | AAUGAGC | 993 |
| 315 | AAGAGAA | CUGAUGAGGCCGAAAGGCCGAA | AAUGAGC | 994 |
| 317 | CAAAGAG | CUGAUGAGGCCGAAAGGCCGAA | AGAAUGA | 995 |
| 318 | ACAAAGA | CUGAUGAGGCCGAAAGGCCGAA | AAGAAUG | 996 |
| 318 | ACAAAGA | CUGAUGAGGCCGAAAGGCCGAA | AAGAAUG | 997 |
| 320 | GCACAAA | CUGAUGAGGCCGAAAGGCCGAA | AGAAGAA | 998 |
| 320 | GCACAAA | CUGAUGAGGCCGAAAGGCCGAA | AGAAGAA | 999 |
| 322 | CAGCACA | CUGAUGAGGCCGAAAGGCCGAA | AGAGAAG | 1000 |
| 322 | CAGCACA | CUGAUGAGGCCGAAAGGCCGAA | AGAGAAG | 1001 |
| 323 | GCAGCAC | CUGAUGAGGCCGAAAGGCCGAA | AAGAGAA | 1002 |
| 336 | GAAAGAC | CUGAUGAGGCCGAAAGGCCGAA | AAUCAGC | 1003 |
| 341 | CUUGUGA | CUGAUGAGGCCGAAAGGCCGAA | AGACGAA | 1004 |
| 341 | CUUGUGA | CUGAUGAGGCCGAAAGGCCGAA | AGACGAA | 1005 |
| 342 | ACUUGUG | CUGAUGAGGCCGAAAGGCCGAA | AAGACGA | 1006 |
| 343 | CACUUGU | CUGAUGAGGCCGAAAGGCCGAA | AAAGACG | 1007 |
| 343 | CACUUGU | CUGAUGAGGCCGAAAGGCCGAA | AAAGACG | 1008 |
| 352 | AUCUGAA | CUGAUGAGGCCGAAAGGCCGAA | ACACUUG | 1009 |
| 355 | AACAUCU | CUGAUGAGGCCGAAAGGCCGAA | AAGACAC | 1010 |
| 382 | UUUCACU | CUGAUGAGGCCGAAAGGCCGAA | ACUUGGA | 1011 |
| 408 | UAACGGC | CUGAUGAGGCCGAAAGGCCGAA | AGGCAGC | 1012 |
| 414 | GAGUUGU | CUGAUGAGGCCGAAAGGCCGAA | ACGGCAA | 1013 |
| 414 | GAGUUGU | CUGAUGAGGCCGAAAGGCCGAA | ACGGCAA | 1014 |
| 421 | AUGAGGA | CUGAUGAGGCCGAAAGGCCGAA | AGUUGUA | 1015 |
| 426 | UCUUCAU | CUGAUGAGGCCGAAAGGCCGAA | AGGAGAG | 1016 |
| 439 | GUCUUCA | CUGAUGAGGCCGAAAGGCCGAA | ACUCAUC | 1017 |
| 452 | GCCAGUA | CUGAUGAGGCCGAAAGGCCGAA | AUUCGGU | 1018 |
| 454 | UUGCCAG | CUGAUGAGGCCGAAAGGCCGAA | AGAUUCG | 1019 |
| 484 | AAUGACA | CUGAUGAGGCCGAAAGGCCGAA | ACAGCAC | 1020 |
| 484 | AAUGACA | CUGAUGAGGCCGAAAGGCCGAA | ACAGCAC | 1021 |
| 488 | CAGCAAU | CUGAUGAGGCCGAAAGGCCGAA | ACAGACA | 1022 |
| 503 | ACACUUU | CUGAUGAGGCCGAAAGGCCGAA | AGUUUCC | 1023 |
| 503 | ACACUUU | CUGAUGAGGCCGAAAGGCCGAA | AGUUUCC | 1024 |
| 520 | GUUCUUA | CUGAUGAGGCCGAAAGGCCGAA | ACUCGGG | 1025 |
| 535 | GUCAUAU | CUGAUGAGGCCGAAAGGCCGAA | AAGUCCG | 1026 |
| 536 | UGUCAUA | CUGAUGAGGCCGAAAGGCCGAA | AAAGUCC | 1027 |
| 538 | GUUGUCA | CUGAUGAGGCCGAAAGGCCGAA | AUAAAGU | 1028 |
| 553 | AAGAGAG | CUGAUGAGGCCGAAAGGCCGAA | AGGUAGU | 1029 |
| 553 | AAGAGAG | CUGAUGAGGCCGAAAGGCCGAA | AGGUAGU | 1030 |
| 556 | GAUAAGA | CUGAUGAGGCCGAAAGGCCGAA | AGUAGGU | 1031 |
| 556 | GAUAAGA | CUGAUGAGGCCGAAAGGCCGAA | AGUAGGU | 1032 |
| 560 | GGAUGAU | CUGAUGAGGCCGAAAGGCCGAA | AGAGAUG | 1033 |
| 561 | AGGAUGA | CUGAUGAGGCCGAAAGGCCGAA | AAGAGAG | 1034 |
| 561 | AGGAUGA | CUGAUGAGGCCGAAAGGCCGAA | AAGAGAG | 1035 |
| 561 | AGGAUGA | CUGAUGAGGCCGAAAGGCCGAA | AAGAGAG | 1036 |
| 566 | GGCCCAG | CUGAUGAGGCCGAAAGGCCGAA | AUGAUAA | 1037 |
| 566 | GGCCCAG | CUGAUGAGGCCGAAAGGCCGAA | AUGAUAA | 1038 |
| 581 | GGUCUGA | CUGAUGAGGCCGAAAGGCCGAA | AGGACCA | 1039 |
| 583 | CCGGUCU | CUGAUGAGGCCGAAAGGCCGAA | AAAGGAC | 1040 |
| 583 | CCGGUCU | CUGAUGAGGCCGAAAGGCCGAA | AAAGGAC | 1041 |
| 598 | ACAGCUG | CUGAUGAGGCCGAAAGGCCGAA | AUGUGCC | 1042 |
| 608 | UUUGAAC | CUGAUGAGGCCGAAAGGCCGAA | ACACAGC | 1043 |
| 611 | UCUUUUG | CUGAUGAGGCCGAAAGGCCGAA | ACGACAC | 1044 |
| 611 | UCUUUUG | CUGAUGAGGCCGAAAGGCCGAA | ACGACAC | 1045 |
| 612 | UUCUUUU | CUGAUGAGGCCGAAAGGCCGAA | AACGACA | 1046 |
| 641 | AGUGUUU | CUGAUGAGGCCGAAAGGCCGAA | ACUUCAU | 1047 |

TABLE V-continued

Mouse B7-1 Hammerhead Ribozyme Sequences

| nt. Position | HH Ribozyme Sequence | | | Seq. ID No. |
|---|---|---|---|---|
| 649 | UAAAGCC | CUGAUGAGGCCGAAAGGCCGAA | AGUGUUU | 1048 |
| 649 | UAAAGCC | CUGAUGAGGCCGAAAGGCCGAA | AGUGUUU | 1049 |
| 655 | CUUUACU | CUGAUGAGGCCGAAAGGCCGAA | AAGCCAA | 1050 |
| 656 | ACUUUAC | CUGAUGAGGCCGAAAGGCCGAA | AAAGCCA | 1051 |
| 659 | ACAACUU | CUGAUGAGGCCGAAAGGCCGAA | ACUAAAG | 1052 |
| 664 | GAUGGAC | CUGAUGAGGCCGAAAGGCCGAA | ACUUUAC | 1053 |
| 667 | UUUGAUG | CUGAUGAGGCCGAAAGGCCGAA | ACAACUU | 1054 |
| 671 | CAGCUUU | CUGAUGAGGCCGAAAGGCCGAA | AUGGACA | 1055 |
| 682 | GGUAGAG | CUGAUGAGGCCGAAAGGCCGAA | AGUCAGC | 1056 |
| 682 | GGUAGAG | CUGAUGAGGCCGAAAGGCCGAA | AGUCAGC | 1057 |
| 682 | GGUAGAG | CUGAUGAGGCCGAAAGGCCGAA | AGUCAGC | 1058 |
| 683 | GGGUAGA | CUGAUGAGGCCGAAAGGCCGAA | AAGUCAG | 1059 |
| 683 | GGGUAGA | CUGAUGAGGCCGAAAGGCCGAA | AAGUCAG | 1060 |
| 685 | GGGGGUA | CUGAUGAGGCCGAAAGGCCGAA | AGAAGUC | 1061 |
| 685 | GGGGGUA | CUGAUGAGGCCGAAAGGCCGAA | AGAAGUC | 1062 |
| 687 | UUGGGGG | CUGAUGAGGCCGAAAGGCCGAA | AGAGAAG | 1063 |
| 698 | ACUCAGU | CUGAUGAGGCCGAAAGGCCGAA | AUGUUGG | 1064 |
| 698 | ACUCAGU | CUGAUGAGGCCGAAAGGCCGAA | AUGUUGG | 1065 |
| 718 | GUCUGCA | CUGAUGAGGCCGAAAGGCCGAA | AUGGGUU | 1066 |
| 718 | GUCUGCA | CUGAUGAGGCCGAAAGGCCGAA | AUGGGUU | 1067 |
| 729 | AUCCUUU | CUGAUGAGGCCGAAAGGCCGAA | AGUGUCU | 1068 |
| 729 | AUCCUUU | CUGAUGAGGCCGAAAGGCCGAA | AGUGUCU | 1069 |
| 729 | AUCCUUU | CUGAUGAGGCCGAAAGGCCGAA | AGUGUCU | 1070 |
| 737 | AGCAGGU | CUGAUGAGGCCGAAAGGCCGAA | AUCCUUU | 1071 |
| 737 | AGCAGGU | CUGAUGAGGCCGAAAGGCCGAA | AUCCUUU | 1072 |
| 737 | AGCAGGU | CUGAUGAGGCCGAAAGGCCGAA | AUCCUUU | 1073 |
| 745 | GGAAGCA | CUGAUGAGGCCGAAAGGCCGAA | AGCAGGU | 1074 |
| 745 | GGAAGCA | CUGAUGAGGCCGAAAGGCCGAA | AGCAGGU | 1075 |
| 759 | UUUGGGA | CUGAUGAGGCCGAAAGGCCGAA | ACCCCCG | 1076 |
| 759 | UUUGGGA | CUGAUGAGGCCGAAAGGCCGAA | ACCCCCG | 1077 |
| 759 | UUUGGGA | CUGAUGAGGCCGAAAGGCCGAA | ACCCCCG | 1078 |
| 760 | CUUUGGG | CUGAUGAGGCCGAAAGGCCGAA | AACCCCC | 1079 |
| 760 | CUUUGGG | CUGAUGAGGCCGAAAGGCCGAA | AACCCCC | 1080 |
| 760 | CUUUGGG | CUGAUGAGGCCGAAAGGCCGAA | AACCCCC | 1081 |
| 761 | GCUUUGG | CUGAUGAGGCCGAAAGGCCGAA | AAACCCC | 1082 |
| 771 | GAGAAGC | CUGAUGAGGCCGAAAGGCCGAA | AGGCUUU | 1083 |
| 771 | GAGAAGC | CUGAUGAGGCCGAAAGGCCGAA | AGGCUUU | 1084 |
| 776 | ACCAAGA | CUGAUGAGGCCGAAAGGCCGAA | AAGCGAG | 1085 |
| 776 | ACCAAGA | CUGAUGAGGCCGAAAGGCCGAA | AAGCGAG | 1086 |
| 778 | CAACCAA | CUGAUGAGGCCGAAAGGCCGAA | AGAAGCG | 1087 |
| 784 | AUUUCC | CUGAUGAGGCCGAAAGGCCGAA | ACCAAGA | 1088 |
| 803 | UGCCAGG | CUGAUGAGGCCGAAAGGCCGAA | AAUUCUC | 1089 |
| 803 | UGCCAGG | CUGAUGAGGCCGAAAGGCCGAA | AAUUCUC | 1090 |
| 803 | UGCCAGG | CUGAUGAGGCCGAAAGGCCGAA | AAUUCUC | 1091 |
| 812 | UCGUAUU | CUGAUGAGGCCGAAAGGCCGAA | AUGCCAG | 1092 |
| 812 | UCGUAUU | CUGAUGAGGCCGAAAGGCCGAA | AUGCCAG | 1093 |
| 816 | AUUGUCG | CUGAUGAGGCCGAAAGGCCGAA | AUUGAUG | 1094 |
| 816 | AUUGUCG | CUGAUGAGGCCGAAAGGCCGAA | AUUGAUG | 1095 |
| 824 | CCUGGGA | CUGAUGAGGCCGAAAGGCCGAA | AUUGUCG | 1096 |
| 825 | UCCUGGG | CUGAUGAGGCCGAAAGGCCGAA | AAUUGUC | 1097 |
| 826 | AUCCUGG | CUGAUGAGGCCGAAAGGCCGAA | AAAUUGU | 1098 |
| 834 | GAUUCAG | CUGAUGAGGCCGAAAGGCCGAA | AUCCUGG | 1099 |
| 841 | CAAUUCA | CUGAUGAGGCCGAAAGGCCGAA | AUUCAGG | 1100 |
| 841 | CAAUUCA | CUGAUGAGGCCGAAAGGCCGAA | AUUCAGG | 1101 |
| 850 | AAUGGUG | CUGAUGAGGCCGAAAGGCCGAA | ACAAUUC | 1102 |
| 869 | UGAAAUC | CUGAUGAGGCCGAAAGGCCGAA | AGUUGGC | 1103 |
| 869 | UGAAAUC | CUGAUGAGGCCGAAAGGCCGAA | AGUUGGC | 1104 |
| 869 | UGAAAUC | CUGAUGAGGCCGAAAGGCCGAA | AGUUGGC | 1105 |
| 873 | GUAUUGA | CUGAUGAGGCCGAAAGGCCGAA | AUCUAGU | 1106 |
| 873 | GUAUUGA | CUGAUGAGGCCGAAAGGCCGAA | AUCUAGU | 1107 |
| 874 | CGUAUUG | CUGAUGAGGCCGAAAGGCCGAA | AAUCUAG | 1108 |
| 875 | UCGUAUU | CUGAUGAGGCCGAAAGGCCGAA | AAAUCUA | 1109 |
| 885 | UGGUUGC | CUGAUGAGGCCGAAAGGCCGAA | AGUCGUA | 1110 |
| 899 | GACACUU | CUGAUGAGGCCGAAAGGCCGAA | AUGGUGU | 1111 |
| 899 | GACACUU | CUGAUGAGGCCGAAAGGCCGAA | AUGGUGU | 1112 |
| 906 | UUAAUGA | CUGAUGAGGCCGAAAGGCCGAA | ACACUUA | 1113 |
| 906 | UUAAUGA | CUGAUGAGGCCGAAAGGCCGAA | ACACUUA | 1114 |
| 908 | AUUUAAU | CUGAUGAGGCCGAAAGGCCGAA | AGACACU | 1115 |
| 911 | CAUAUUU | CUGAUGAGGCCGAAAGGCCGAA | AUGAGAC | 1116 |
| 916 | AUCUCCA | CUGAUGAGGCCGAAAGGCCGAA | AUUUAAU | 1117 |
| 916 | AUCUCCA | CUGAUGAGGCCGAAAGGCCGAA | AUUUAAU | 1118 |
| 943 | CCAGGUG | CUGAUGAGGCCGAAAGGCCGAA | AGUCCUC | 1119 |
| 944 | CCCAGGU | CUGAUGAGGCCGAAAGGCCGAA | AAGUCCU | 1120 |
| 1001 | CUGCCCC | CUGAUGAGGCCGAAAGGCCGAA | AAGAGCA | 1121 |
| 1034 | CGAUGAC | CUGAUGAGGCCGAAAGGCCGAA | ACGACUG | 1122 |

TABLE V-continued

Mouse B7-1 Hammerhead Ribozyme Sequences

| nt. Position | HH Ribozyme Sequence | | Seq. ID No. |
|---|---|---|---|
| 1037 | CAACGAU | CUGAUGAGGCCGAAAGGCCGAA ACGACGA | 1123 |
| 1043 | UGAUGAC | CUGAUGAGGCCGAAAGGCCGAA ACGAUGA | 1124 |
| 1046 | UGAUGAU | CUGAUGAGGCCGAAAGGCCGAA ACAACGA | 1125 |
| 1049 | AUUUGAU | CUGAUGAGGCCGAAAGGCCGAA AUGACAA | 1126 |
| 1060 | CUUACAG | CUGAUGAGGCCGAAAGGCCGAA AGCAUUU | 1127 |
| 1060 | CUUACAG | CUGAUGAGGCCGAAAGGCCGAA AGCAUUU | 1128 |
| 1060 | CUUACAG | CUGAUGAGGCCGAAAGGCCGAA AGCAUUU | 1129 |
| 1060 | CUUACAG | CUGAUGAGGCCGAAAGGCCGAA AGCAUUU | 1130 |
| 1061 | GCUUACA | CUGAUGAGGCCGAAAGGCCGAA AAGCAUU | 1131 |
| 1080 | CUUCUGA | CUGAUGAGGCCGAAAGGCCGAA ACAGCUU | 1132 |
| 1080 | CUUCUGA | CUGAUGAGGCCGAAAGGCCGAA ACAGCUU | 1133 |
| 1081 | UCUUCUG | CUGAUGAGGCCGAAAGGCCGAA AACAGCU | 1134 |
| 1121 | CGAAGGU | CUGAUGAGGCCGAAAGGCCGAA AGGCUGU | 1135 |
| 1121 | CGAAGGU | CUGAUGAGGCCGAAAGGCCGAA AGGCUGU | 1136 |
| 1121 | CGAAGGU | CUGAUGAGGCCGAAAGGCCGAA AGGCUGU | 1137 |
| 1122 | CCGAAGG | CUGAUGAGGCCGAAAGGCCGAA AAGGCUG | 1138 |
| 1126 | AGGCCCG | CUGAUGAGGCCGAAAGGCCGAA AGGUAAG | 1139 |
| 1127 | CAGGCCC | CUGAUGAGGCCGAAAGGCCGAA AAGGUAA | 1140 |
| 1127 | CAGGCCC | CUGAUGAGGCCGAAAGGCCGAA AAGGUAA | 1141 |
| 1144 | UUCAGCU | CUGAUGAGGCCGAAAGGCCGAA AUGCUUC | 1142 |
| 1144 | UUCAGCU | CUGAUGAGGCCGAAAGGCCGAA AUGCUUC | 1143 |
| 1145 | GUUCAGC | CUGAUGAGGCCGAAAGGCCGAA AAUGCUU | 1144 |
| 1160 | AAAGGAA | CUGAUGAGGCCGAAAGGCCGAA ACGGUCU | 1145 |
| 1162 | CUAAAGG | CUGAUGAGGCCGAAAGGCCGAA AGACGGU | 1146 |
| 1163 | ACUAAAG | CUGAUGAGGCCGAAAGGCCGAA AAGACGG | 1147 |
| 1167 | AAGAACU | CUGAUGAGGCCGAAAGGCCGAA AAGGAAG | 1148 |
| 1177 | AUGGACA | CUGAUGAGGCCGAAAGGCCGAA AGAAGAA | 1149 |
| 1181 | CCACAUG | CUGAUGAGGCCGAAAGGCCGAA ACAGAGA | 1150 |
| 1181 | CCACAUG | CUGAUGAGGCCGAAAGGCCGAA ACAGAGA | 1151 |
| 1192 | UACCAUG | CUGAUGAGGCCGAAAGGCCGAA AUCCCAC | 1152 |
| 1199 | CACAUAA | CUGAUGAGGCCGAAAGGCCGAA ACCAUGU | 1153 |
| 1201 | GCCACAU | CUGAUGAGGCCGAAAGGCCGAA AUACCAU | 1154 |
| 1210 | ACCUCAU | CUGAUGAGGCCGAAAGGCCGAA AGCCACA | 1155 |
| 1210 | ACCUCAU | CUGAUGAGGCCGAAAGGCCGAA AGCCACA | 1156 |
| 1223 | AAAGAAA | CUGAUGAGGCCGAAAGGCCGAA AUUGUAC | 1157 |
| 1225 | UGAAAGA | CUGAUGAGGCCGAAAGGCCGAA AGAUUGU | 1158 |
| 1225 | UGAAAGA | CUGAUGAGGCCGAAAGGCCGAA AGAUUGU | 1159 |
| 1226 | CUGAAAG | CUGAUGAGGCCGAAAGGCCGAA AAGAUUG | 1160 |
| 1227 | GCUGAAA | CUGAUGAGGCCGAAAGGCCGAA AAAGAUU | 1161 |
| 1227 | GCUGAAA | CUGAUGAGGCCGAAAGGCCGAA AAAGAUU | 1162 |
| 1227 | GCUGAAA | CUGAUGAGGCCGAAAGGCCGAA AAAGAUU | 1163 |
| 1229 | GUGCUGA | CUGAUGAGGCCGAAAGGCCGAA AGAAAGA | 1164 |
| 1230 | GGUGCUG | CUGAUGAGGCCGAAAGGCCGAA AAGAAAG | 1165 |
| 1252 | UGUCCGA | CUGAUGAGGCCGAAAGGCCGAA AGAUCAG | 1166 |
| 1274 | UUAACUC | CUGAUGAGGCCGAAAGGCCGAA AUCUUGU | 1167 |
| 1310 | GGAAAGA | CUGAUGAGGCCGAAAGGCCGAA AUCCUCA | 1168 |
| 1312 | AUGGAAA | CUGAUGAGGCCGAAAGGCCGAA AAAUCCU | 1169 |
| 1314 | UGAUGGA | CUGAUGAGGCCGAAAGGCCGAA AGAAAUC | 1170 |
| 1316 | CCUGAUG | CUGAUGAGGCCGAAAGGCCGAA AAAGAAA | 1171 |
| 1320 | GCUUCCU | CUGAUGAGGCCGAAAGGCCGAA AUGGAAA | 1172 |
| 1320 | GCUUCCU | CUGAUGAGGCCGAAAGGCCGAA AUGGAAA | 1173 |
| 1339 | CCCAGCA | CUGAUGAGGCCGAAAGGCCGAA ACUUGCC | 1174 |
| 1355 | AUCAAGC | CUGAUGAGGCCGAAAGGCCGAA AUCAAGC | 1175 |
| 1437 | UUUUUCU | CUGAUGAGGCCGAAAGGCCGAA AUACCAC | 1176 |
| 1437 | UUUUUCU | CUGAUGAGGCCGAAAGGCCGAA AUACCAC | 1177 |
| 1475 | GCAGUAA | CUGAUGAGGCCGAAAGGCCGAA ACUAGGC | 1178 |
| 1477 | UUGCAGU | CUGAUGAGGCCGAAAGGCCGAA AGACUAG | 1179 |
| 1487 | ACAUAUC | CUGAUGAGGCCGAAAGGCCGAA AGUUGCA | 1180 |
| 1491 | CAUGACA | CUGAUGAGGCCGAAAGGCCGAA AUCAAGU | 1181 |
| 1491 | CAUGACA | CUGAUGAGGCCGAAAGGCCGAA AUCAAGU | 1182 |
| 1505 | AGACACC | CUGAUGAGGCCGAAAGGCCGAA ACCAAAC | 1183 |
| 1530 | CUUCAGA | CUGAUGAGGCCGAAAGGCCGAA AAGGGCA | 1184 |
| 1531 | UCUUCAG | CUGAUGAGGCCGAAAGGCCGAA AAAGGGC | 1185 |
| 1532 | CUCUUCA | CUGAUGAGGCCGAAAGGCCGAA AAAAGGG | 1186 |
| 1532 | CUCUUCA | CUGAUGAGGCCGAAAGGCCGAA AAAAGGG | 1187 |
| 1644 | ACAUCCC | CUGAUGAGGCCGAAAGGCCGAA ACCAUAG | 1188 |
| 1652 | CCGUUUU | CUGAUGAGGCCGAAAGGCCGAA ACAUCCC | 1189 |
| 1652 | CCGUUUU | CUGAUGAGGCCGAAAGGCCGAA ACAUCCC | 1190 |
| 1670 | UAAUAUU | CUGAUGAGGCCGAAAGGCCGAA AUAUUAU | 1191 |
| 1674 | UAUUUUA | CUGAUGAGGCCGAAAGGCCGAA AUUUAUA | 1192 |
| 1676 | UUUAUUU | CUGAUGAGGCCGAAAGGCCGAA AUAUUUA | 1193 |
| 1677 | UUUUAUU | CUGAUGAGGCCGAAAGGCCGAA AAUAUUU | 1194 |
| 1677 | UUUUAUU | CUGAUGAGGCCGAAAGGCCGAA AAUAUUU | 1195 |
| 1694 | UUUGCUC | CUGAUGAGGCCGAAAGGCCGAA AUACUCU | 1196 |

TABLE VI

Human B7-2 Hammerhead Ribozyme Sequences

| nt. Position | HH Target Sequence | | | Seq. ID No. |
|---|---|---|---|---|
| 16 | GAAAGCU | U | UGCUUCU | 1197 |
| 17 | AAAGCUU | U | GCUUCUC | 1198 |
| 21 | CUUUGCU | U | CUCUGCU | 1199 |
| 22 | UUUGCUU | C | UCUGCUG | 1200 |
| 24 | UGCUUCU | C | UGCUGCU | 1201 |
| 34 | CUGCUGU | A | ACAGGGA | 1202 |
| 44 | AGGGACU | A | GCACAGA | 1203 |
| 70 | GUGGGGU | C | AUUUCCA | 1204 |
| 73 | GGGUCAU | U | UCCAGAU | 1205 |
| 74 | GGUCAUU | U | CCAGAUA | 1206 |
| 75 | GUCAUUU | C | CAGAUAU | 1207 |
| 81 | UCCAGAU | A | UUAGGUC | 1208 |
| 83 | CAGAUAU | U | AGGUCAC | 1209 |
| 84 | AGAUAUU | A | GGUCACA | 1210 |
| 88 | AUUAGGU | C | ACAGCAG | 1211 |
| 113 | AAUGGAU | C | CCCAGUG | 1212 |
| 125 | GUGCACU | A | UGGGACU | 1213 |
| 137 | ACUGAGU | A | ACAUUCU | 1214 |
| 142 | GUAACAU | U | CUCUUUG | 1215 |
| 143 | UAACAUU | C | UCUUUGU | 1216 |
| 145 | ACAUUCU | C | UUUGUGA | 1217 |
| 147 | AUUCUCU | U | UGUGAUG | 1218 |
| 148 | UUCUCUU | U | GUGAUGG | 1219 |
| 159 | AUGGCCU | C | CUGCUCU | 1220 |
| 160 | UGGCCUU | C | CUGCUCU | 1221 |
| 166 | UCCUGCU | C | UCUGGUG | 1222 |
| 168 | CUGCUCU | C | UGGUGCU | 1223 |
| 179 | UGCUGCU | C | CUCUGAA | 1224 |
| 182 | UGCUCCU | C | UGAAGAU | 1225 |
| 190 | UGAAGAU | U | CAAGCUU | 1226 |
| 191 | GAAGAUU | C | AAGCUUA | 1227 |
| 197 | UCAAGCU | U | AUUUCAA | 1228 |
| 198 | CAAGCUU | A | UUUCAAU | 1229 |
| 200 | AGCUUAU | U | UCAAUGA | 1230 |
| 201 | GCUUAUU | U | CAAUGAG | 1231 |
| 202 | CUUAUUU | C | AAUGAGA | 1232 |
| 231 | UGCCAAU | U | UGCAAAC | 1233 |
| 232 | GCCAAUU | U | GCAAACU | 1234 |
| 240 | GCAAACU | C | UCAAAAC | 1235 |
| 242 | AAACUCU | C | AAAACCA | 1236 |
| 265 | GUGAGCU | A | GUAGUAU | 1237 |
| 268 | AGCUAGU | A | GUAUUUU | 1238 |
| 271 | UAGUAGU | A | UUUUGGC | 1239 |
| 273 | GUAGUAU | U | UUGGCAG | 1240 |
| 274 | UAGUAUU | U | UGGCAGG | 1241 |
| 275 | AGUAUUU | U | GGCAGGA | 1242 |
| 294 | GAAAACU | U | GGUUCUG | 1243 |
| 298 | ACUUGGU | U | CUGAAUG | 1244 |
| 299 | CUUGGUU | C | UGAAUGA | 1245 |
| 310 | AUGAGGU | A | UACUUAG | 1246 |
| 312 | GAGGUAU | A | CUUAGGC | 1247 |
| 315 | GUAUACU | U | AGGCAAA | 1248 |
| 316 | UAUACUU | A | GGCAAAG | 1249 |
| 330 | GAGAAAU | U | UGACAGU | 1250 |
| 331 | AGAAAUU | U | GACAGUG | 1251 |
| 340 | ACAGUGU | U | CAUUCCA | 1252 |
| 341 | CAGUGUU | C | AUUCCAA | 1253 |
| 344 | UGUUCAU | U | CCAAGUA | 1254 |
| 345 | GUUCAUU | C | CAAGUAU | 1255 |
| 351 | UCCAAGU | A | UAUGGGC | 1256 |
| 353 | CAAGUAU | A | UGGGCCG | 1257 |
| 368 | CACAAGU | U | UUGAUUC | 1258 |
| 369 | ACAAGUU | U | UGAUUCG | 1259 |
| 370 | CAAGUUU | U | GAUUCGG | 1260 |
| 374 | UUUUGAU | U | CGGACAG | 1261 |
| 375 | UUUGAUU | C | GGACAGU | 1262 |
| 383 | GGACAGU | U | GGACCCU | 1263 |
| 397 | UGAGACU | U | CACAAUC | 1264 |
| 398 | GAGACUU | C | ACAAUCU | 1265 |
| 404 | UCACAAU | C | UUCAGAU | 1266 |
| 406 | ACAAUCU | U | CAGAUCA | 1267 |
| 407 | CAAUCUU | C | AGAUCAA | 1268 |
| 412 | UUCAGAU | C | AAGGACA | 1269 |
| 426 | AAGGGCU | U | GUAUCAA | 1270 |
| 429 | GGCUUGU | A | UCAAUGU | 1271 |
| 431 | CUUGUAU | C | AAUGUAU | 1272 |
| 437 | UCAAUGU | A | UCAUCCA | 1273 |
| 439 | AAUGUAU | C | AUCCAUC | 1274 |
| 442 | GUAUCAU | C | CAUCACA | 1275 |
| 446 | CAUCCAU | C | ACAAAAA | 1276 |
| 469 | GAAUGAU | U | CGCAUCC | 1277 |
| 470 | AAUGAUU | C | GCAUCCA | 1278 |
| 475 | UUCGCAU | C | CACCAGA | 1279 |
| 488 | GAUGAAU | U | CUGAACU | 1280 |
| 489 | AUGAAUU | C | UGAACUG | 1281 |
| 498 | GAACUGU | C | AGUGCUU | 1282 |
| 505 | CAGUGCU | U | GCUAACU | 1283 |
| 509 | GCUUGCU | A | ACUUCAG | 1284 |
| 513 | GCUAACU | U | CAGUCAA | 1285 |
| 514 | CUAACUU | C | AGUCAAC | 1286 |
| 518 | CUUCAGU | C | AACCUGA | 1287 |
| 529 | CUGAAAU | A | GUACCAA | 1288 |
| 532 | AAAUAGU | A | CCAAUUU | 1289 |
| 538 | UACCAAU | U | UCUAAUA | 1290 |
| 539 | ACCAAUU | U | CUAAUAU | 1291 |
| 540 | CCAAUUU | C | UAAUAUA | 1292 |
| 542 | AAUUUCU | A | AUAUAAC | 1293 |
| 545 | UUCUAAU | A | UAACAGA | 1294 |
| 547 | CUAAUAU | A | ACAGAAA | 1295 |
| 561 | AAUGUGU | A | CAUAAAU | 1296 |
| 565 | UGUACAU | A | AAUUUGA | 1297 |
| 569 | CAUAAAU | U | UGACCUG | 1298 |
| 570 | AUAAAUU | U | GACCUGC | 1299 |
| 579 | ACCUGCU | C | AUCUAUA | 1300 |
| 582 | UGCUCAU | C | UAUACAC | 1301 |
| 584 | CUCAUCU | A | UACACGG | 1302 |
| 586 | CAUCUAU | A | CACGGUU | 1303 |
| 593 | ACACGGU | U | ACCCAGA | 1304 |
| 594 | CACGGUU | A | CCCAGAA | 1305 |
| 605 | AGAACCU | A | AGAAGAU | 1306 |
| 619 | UGAGUGU | U | UUGCUAA | 1307 |
| 620 | GAGUGUU | U | UGCUAAG | 1308 |
| 621 | AGUGUUU | U | GCUAAGA | 1309 |
| 625 | UUUUGCU | A | AGAACCA | 1310 |
| 638 | CAAGAAU | U | CAACUAU | 1311 |
| 639 | AAGAAUU | C | AACUAUC | 1312 |
| 644 | UUCAACU | A | UCGAGUA | 1313 |
| 646 | CAACUAU | C | GAGUAUG | 1314 |
| 651 | AUCGAGU | A | UGAUGGU | 1315 |
| 659 | UGAUGGU | A | UUAUGCA | 1316 |
| 661 | AUGGUAU | U | AUGCAGA | 1317 |
| 662 | UGGUAUU | A | UGCAGAA | 1318 |
| 672 | CAGAAAU | C | UCAAGAU | 1319 |
| 674 | GAAAUCU | C | AAGAUAA | 1320 |
| 680 | UCAAGAU | A | AUGUCAC | 1321 |
| 685 | AUAAUGU | C | ACAGAAC | 1322 |
| 696 | GAACUGU | A | CGACGUU | 1323 |
| 703 | ACGACGU | U | UCCAUCA | 1324 |
| 704 | CGACGUU | U | CCAUCAG | 1325 |
| 705 | GACGUUU | C | CAUCAGC | 1326 |
| 709 | UUUCCAU | C | AGCUUGU | 1327 |
| 714 | AUCAGCU | U | GUCUGUU | 1328 |
| 717 | AGCUUGU | C | UGUUUCA | 1329 |
| 721 | UGUCUGU | U | UCAUUCC | 1330 |
| 722 | GUCUGUU | U | CAUUCCC | 1331 |
| 723 | UCUGUUU | C | AUUCCCU | 1332 |
| 726 | GUUUCAU | U | CCCUGAU | 1333 |
| 727 | UUUCAUU | C | CCUGAUG | 1334 |
| 736 | CUGAUGU | U | ACGAGCA | 1335 |
| 737 | UGAUGUU | A | CGAGCAA | 1336 |
| 746 | GAGCAAU | A | UGACCAU | 1337 |
| 754 | UGACCAU | C | UUCUGUA | 1338 |
| 756 | ACCAUCU | U | CUGUAUU | 1339 |
| 757 | CCAUCUU | C | UGUAUUC | 1340 |
| 761 | CUUCUGU | A | UUCUGGA | 1341 |
| 763 | UCUGUAU | U | CUGGAAA | 1342 |
| 764 | CUGUAUU | C | UGGAAAC | 1343 |
| 787 | CGCGGCU | U | UUAUCUU | 1344 |
| 788 | GCGGCUU | U | UAUCUUC | 1345 |
| 789 | CGGCUUU | U | AUCUUCA | 1346 |

TABLE VI-continued

Human B7-2 Hammerhead Ribozyme Sequences

| nt. Position | HH Target Sequence | | | Seq. ID No. |
|---|---|---|---|---|
| 790 | GGCUUUU | A | UCUUCAC | 1347 |
| 792 | CUUUUAU | C | UUCACCU | 1348 |
| 794 | UUUAUCU | U | CACCUUU | 1349 |
| 795 | UUAUCUU | C | ACCUUUC | 1350 |
| 800 | UUCACCU | U | UCUCUAU | 1351 |
| 801 | UCACCUU | U | CUCUAUA | 1352 |
| 802 | CACCUUU | C | UCUAUAG | 1353 |
| 804 | CCUUUCU | C | UAUAGAG | 1354 |
| 806 | UUUCUCU | A | UAGAGCU | 1355 |
| 808 | UCUCUAU | A | GAGCUUG | 1356 |
| 814 | UAGAGCU | U | GAGGACC | 1357 |
| 824 | GGACCCU | C | AGCCUCC | 1358 |
| 830 | UCAGCCU | C | CCCCAGA | 1359 |
| 844 | ACCACAU | U | CCUUGGA | 1360 |
| 845 | CCACAUU | C | CUUGGAU | 1361 |
| 848 | CAUUCCU | U | GGAUUAC | 1362 |
| 853 | CUUGGAU | U | ACAGCUG | 1363 |
| 854 | UUGGAUU | A | CAGCUGU | 1364 |
| 862 | CAGCUGU | A | CUUCCAA | 1365 |
| 865 | CUGUACU | U | CCAACAG | 1366 |
| 866 | UGUACUU | C | CAACAGU | 1367 |
| 874 | CAACAGU | U | AUUAUAU | 1368 |
| 875 | AACAGUU | A | UUAUAUG | 1369 |
| 877 | CAGUUAU | U | AUAUGUG | 1370 |
| 878 | AGUUAUU | A | UAUGUGU | 1371 |
| 880 | UUAUUAU | A | UGUGUGA | 1372 |
| 892 | UGAUGGU | U | UUCUGUC | 1373 |
| 893 | GAUGGUU | U | UCUGUCU | 1374 |
| 894 | AUGGUUU | U | CUGUCUA | 1375 |
| 895 | UGGUUUU | C | UGUCUAA | 1376 |
| 899 | UUUCUGU | C | UAAUUCU | 1377 |
| 901 | UCUGUCU | A | AUUCUAU | 1378 |
| 904 | GUCUAAU | U | CUAUGGA | 1379 |
| 905 | UCUAAUU | C | UAUGGAA | 1380 |
| 907 | UAAUUCU | A | UGGAAAU | 1381 |
| 935 | GCGGCCU | C | GCAACUC | 1382 |
| 942 | CGCAACU | C | UUAUAAA | 1383 |
| 944 | CAACUCU | U | AUAAAUG | 1384 |
| 945 | AACUCUU | A | UAAAUGU | 1385 |
| 947 | CUCUUAU | A | AAUGUGG | 1386 |
| 1009 | AAAAAAU | C | CAUAUAC | 1387 |
| 1013 | AAUCCAU | A | UACCUGA | 1388 |
| 1015 | UCCAUAU | A | CCUGAAA | 1389 |
| 1026 | GAAAGAU | U | GAUGAA | 1390 |
| 1045 | AGCGUGU | U | UUUAAAA | 1391 |
| 1046 | GCGUGUU | U | UUAAAAG | 1392 |
| 1047 | CGUGUUU | U | UAAAAGU | 1393 |
| 1048 | GUGUUUU | U | AAAAGUU | 1394 |
| 1049 | UGUUUUU | A | AAAGUUC | 1395 |
| 1055 | UAAAAGU | U | CGAAGAC | 1396 |
| 1056 | AAAAGUU | C | GAAGACA | 1397 |
| 1065 | AAGACAU | C | UUCAUGC | 1398 |
| 1067 | GACAUCU | U | CAUGCGA | 1399 |
| 1068 | ACAUCUU | C | AUGCGAC | 1400 |
| 1085 | AAGUGAU | A | CAUGUUU | 1401 |
| 1091 | UACAUGU | U | UUUAAUU | 1402 |
| 1092 | ACAUGUU | U | UUAAUUA | 1403 |
| 1093 | CAUGUUU | U | UAAUUAA | 1404 |
| 1094 | AUGUUUU | U | AAUUAAA | 1405 |
| 1095 | UGUUUUU | A | AUUAAAG | 1406 |
| 1098 | UUUUAAU | U | AAAGAGU | 1407 |
| 1099 | UUUAAUU | A | AAGAGUA | 1408 |

TABLE VII

Human B7-2 Hammerhead Ribozyme Sequences

| nt. Position | HH Ribozyme Sequences | | | Seq. Id No. |
|---|---|---|---|---|
| 16 | AGAAGCA | CUGAUGAGGCCGAAAGGCCGAA | AGCUUUC | 1409 |
| 17 | GAGAAGC | CUGAUGAGGCCGAAAGGCCGAA | AAGCUUU | 1410 |
| 21 | AGCAGAG | CUGAUGAGGCCGAAAGGCCGAA | AGCAAAG | 1411 |
| 22 | CAGCAGA | CUGAUGAGGCCGAAAGGCCGAA | AAGCAAA | 1412 |
| 24 | AGCAGCA | CUGAUGAGGCCGAAAGGCCGAA | AGAAGCA | 1413 |
| 34 | UCCCUGU | CUGAUGAGGCCGAAAGGCCGAA | ACAGCAG | 1414 |
| 44 | UCUGUGC | CUGAUGAGGCCGAAAGGCCGAA | AGUCCCU | 1415 |
| 70 | UGGAAAU | CUGAUGAGGCCGAAAGGCCGAA | ACCCCAC | 1416 |
| 73 | AUCUGGA | CUGAUGAGGCCGAAAGGCCGAA | AUGACCC | 1417 |
| 74 | UAUCUGG | CUGAUGAGGCCGAAAGGCCGAA | AAUGACC | 1418 |
| 75 | AUAUCUG | CUGAUGAGGCCGAAAGGCCGAA | AAAUGAC | 1419 |
| 81 | GACCUAA | CUGAUGAGGCCGAAAGGCCGAA | AUCUGGA | 1420 |
| 83 | GUGACCU | CUGAUGAGGCCGAAAGGCCGAA | AUAUCUG | 1421 |
| 84 | UGUGACC | CUGAUGAGGCCGAAAGGCCGAA | AAUAUCU | 1422 |
| 88 | CUGCUGU | CUGAUGAGGCCGAAAGGCCGAA | ACCUAAU | 1423 |
| 113 | CACUGGG | CUGAUGAGGCCGAAAGGCCGAA | AUCCAUU | 1424 |
| 125 | AGUCCCA | CUGAUGAGGCCGAAAGGCCGAA | AGUGCAC | 1425 |
| 137 | AGAAUGU | CUGAUGAGGCCGAAAGGCCGAA | ACUCAGU | 1426 |
| 142 | CAAAGAG | CUGAUGAGGCCGAAAGGCCGAA | AUGUUAC | 1427 |
| 143 | ACAAAGA | CUGAUGAGGCCGAAAGGCCGAA | AAUGUUA | 1428 |
| 145 | UCACAAA | CUGAUGAGGCCGAAAGGCCGAA | AGAAUGU | 1429 |
| 147 | CAUCACA | CUGAUGAGGCCGAAAGGCCGAA | AGAGAAU | 1430 |
| 148 | CCAUCAC | CUGAUGAGGCCGAAAGGCCGAA | AAGAGAA | 1431 |
| 159 | GAGCAGG | CUGAUGAGGCCGAAAGGCCGAA | AGGCCAU | 1432 |
| 160 | AGAGCAG | CUGAUGAGGCCGAAAGGCCGAA | AAGGCCA | 1433 |
| 166 | CACCAGA | CUGAUGAGGCCGAAAGGCCGAA | AGCAGGA | 1434 |
| 168 | AGCACCA | CUGAUGAGGCCGAAAGGCCGAA | AGAGCAG | 1435 |

TABLE VII-continued

Human B7-2 Hammerhead Ribozyme Sequences

| nt. Position | | HH Ribozyme Sequences | | Seq. Id No. |
|---|---|---|---|---|
| 179 | UUCAGAG | CUGAUGAGGCCGAAAGGCCGAA | AGCAGCA | 1436 |
| 182 | AUCUUCA | CUGAUGAGGCCGAAAGGCCGAA | AGGAGCA | 1437 |
| 190 | AAGCUUG | CUGAUGAGGCCGAAAGGCCGAA | AUCUUCA | 1438 |
| 191 | UAAGCUU | CUGAUGAGGCCGAAAGGCCGAA | AAUCUUC | 1439 |
| 197 | UUGAAAU | CUGAUGAGGCCGAAAGGCCGAA | AGCUUGA | 1440 |
| 198 | AUUGAAA | CUGAUGAGGCCGAAAGGCCGAA | AAGCUUG | 1441 |
| 200 | UCAUUGA | CUGAUGAGGCCGAAAGGCCGAA | AUAAGCU | 1442 |
| 201 | CUCAUUG | CUGAUGAGGCCGAAAGGCCGAA | AAUAAGC | 1443 |
| 202 | UCUCAUU | CUGAUGAGGCCGAAAGGCCGAA | AAAUAAG | 1444 |
| 231 | GUUUGCA | CUGAUGAGGCCGAAAGGCCGAA | AUUGGCA | 1445 |
| 232 | AGUUUGC | CUGAUGAGGCCGAAAGGCCGAA | AAUUGGC | 1446 |
| 240 | GUUUUGA | CUGAUGAGGCCGAAAGGCCGAA | AGUUUGC | 1447 |
| 242 | UGGUUUU | CUGAUGAGGCCGAAAGGCCGAA | AGAGUUU | 1448 |
| 265 | AUACUAC | CUGAUGAGGCCGAAAGGCCGAA | AGCUCAC | 1449 |
| 268 | AAAAUAC | CUGAUGAGGCCGAAAGGCCGAA | ACUAGCU | 1450 |
| 271 | GCCAAAA | CUGAUGAGGCCGAAAGGCCGAA | ACUACUA | 1451 |
| 273 | CUGCCAA | CUGAUGAGGCCGAAAGGCCGAA | AUACUAC | 1452 |
| 274 | CCUGCCA | CUGAUGAGGCCGAAAGGCCGAA | AAUACUA | 1453 |
| 275 | UCCUGCC | CUGAUGAGGCCGAAAGGCCGAA | AAAUACU | 1454 |
| 294 | CAGAACC | CUGAUGAGGCCGAAAGGCCGAA | AGUUUUC | 1455 |
| 298 | CAUUCAG | CUGAUGAGGCCGAAAGGCCGAA | ACCAAGU | 1456 |
| 299 | UCAUUCA | CUGAUGAGGCCGAAAGGCCGAA | AACCAAG | 1457 |
| 310 | CUAAGUA | CUGAUGAGGCCGAAAGGCCGAA | ACCUCAU | 1458 |
| 312 | GCCUAAG | CUGAUGAGGCCGAAAGGCCGAA | AUACCUC | 1459 |
| 315 | UUUGCCU | CUGAUGAGGCCGAAAGGCCGAA | AGUAUAC | 1460 |
| 316 | CUUUGCC | CUGAUGAGGCCGAAAGGCCGAA | AAGUAUA | 1461 |
| 330 | ACUGUCA | CUGAUGAGGCCGAAAGGCCGAA | AUUUCUC | 1462 |
| 331 | CACUGUC | CUGAUGAGGCCGAAAGGCCGAA | AAUUUCU | 1463 |
| 340 | UGGAAUG | CUGAUGAGGCCGAAAGGCCGAA | ACACUGU | 1464 |
| 341 | UUGGAAU | CUGAUGAGGCCGAAAGGCCGAA | AACACUG | 1465 |
| 344 | UACUUGG | CUGAUGAGGCCGAAAGGCCGAA | AUGAACA | 1466 |
| 345 | AUACUUG | CUGAUGAGGCCGAAAGGCCGAA | AAUGAAC | 1467 |
| 351 | GCCCAUA | CUGAUGAGGCCGAAAGGCCGAA | ACUUGGA | 1468 |
| 353 | CGGCCCA | CUGAUGAGGCCGAAAGGCCGAA | AUACUUG | 1469 |
| 368 | GAAUCAA | CUGAUGAGGCCGAAAGGCCGAA | ACUUGUG | 1470 |
| 369 | CGAAUCA | CUGAUGAGGCCGAAAGGCCGAA | AACUUGU | 1471 |
| 370 | CCGAAUC | CUGAUGAGGCCGAAAGGCCGAA | AAACUUG | 1472 |
| 374 | CUGUCCG | CUGAUGAGGCCGAAAGGCCGAA | AUCAAAA | 1473 |
| 375 | ACUGUCC | CUGAUGAGGCCGAAAGGCCGAA | AAUCAAA | 1474 |
| 383 | AGGGUCC | CUGAUGAGGCCGAAAGGCCGAA | ACUGUCC | 1475 |
| 397 | GAUUGUG | CUGAUGAGGCCGAAAGGCCGAA | AGUCUCA | 1476 |
| 398 | AGAUUGU | CUGAUGAGGCCGAAAGGCCGAA | AAGUCUC | 1477 |
| 404 | AUCUGAA | CUGAUGAGGCCGAAAGGCCGAA | AUUGUGA | 1478 |
| 406 | UGAUCUG | CUGAUGAGGCCGAAAGGCCGAA | AGAUUGU | 1479 |
| 407 | UUGAUCU | CUGAUGAGGCCGAAAGGCCGAA | AAGAUUG | 1480 |
| 412 | UGUCCUU | CUGAUGAGGCCGAAAGGCCGAA | AUCUGAA | 1481 |
| 426 | UUGAUAC | CUGAUGAGGCCGAAAGGCCGAA | AGCCCUU | 1482 |
| 429 | ACAUUGA | CUGAUGAGGCCGAAAGGCCGAA | ACAAGCC | 1483 |
| 431 | AUACAUU | CUGAUGAGGCCGAAAGGCCGAA | AUACAAG | 1484 |
| 437 | UGGAUGA | CUGAUGAGGCCGAAAGGCCGAA | ACAUUGA | 1485 |
| 439 | GAUGGAU | CUGAUGAGGCCGAAAGGCCGAA | AUACAUU | 1486 |
| 442 | UGUGAUG | CUGAUGAGGCCGAAAGGCCGAA | AUGAUAC | 1487 |
| 446 | UUUUUGU | CUGAUGAGGCCGAAAGGCCGAA | AUGGAUG | 1488 |
| 469 | GGAUGCG | CUGAUGAGGCCGAAAGGCCGAA | AUCAUUC | 1489 |
| 470 | UGGAUGC | CUGAUGAGGCCGAAAGGCCGAA | AAUCAUU | 1490 |
| 475 | UCUGGUG | CUGAUGAGGCCGAAAGGCCGAA | AUGCGAA | 1491 |
| 488 | AGUUCAG | CUGAUGAGGCCGAAAGGCCGAA | AUUCAUC | 1492 |
| 489 | CAGUUCA | CUGAUGAGGCCGAAAGGCCGAA | AAUUCAU | 1493 |
| 498 | AAGCACU | CUGAUGAGGCCGAAAGGCCGAA | ACAGUUC | 1494 |
| 505 | AGUUAGC | CUGAUGAGGCCGAAAGGCCGAA | AGCACUG | 1495 |
| 509 | CUGAAGU | CUGAUGAGGCCGAAAGGCCGAA | AGCAAGC | 1496 |
| 513 | UUGACUG | CUGAUGAGGCCGAAAGGCCGAA | AGUUAGC | 1497 |
| 514 | GUUGACU | CUGAUGAGGCCGAAAGGCCGAA | AAGUUAG | 1498 |
| 518 | UCAGGUU | CUGAUGAGGCCGAAAGGCCGAA | ACUGAAG | 1499 |
| 529 | UUGGUAC | CUGAUGAGGCCGAAAGGCCGAA | AUUUCAG | 1500 |
| 532 | AAAUUGG | CUGAUGAGGCCGAAAGGCCGAA | ACUAUUU | 1501 |
| 538 | UAUUAGA | CUGAUGAGGCCGAAAGGCCGAA | AUUGGUA | 1502 |
| 539 | AUAUUAG | CUGAUGAGGCCGAAAGGCCGAA | AAUUGGU | 1503 |
| 540 | UAUAUUA | CUGAUGAGGCCGAAAGGCCGAA | AAAUUGG | 1504 |
| 542 | GUUAUAU | CUGAUGAGGCCGAAAGGCCGAA | AGAAAUU | 1505 |
| 545 | UCUGUUA | CUGAUGAGGCCGAAAGGCCGAA | AUUAGAA | 1506 |
| 547 | UUUCUGU | CUGAUGAGGCCGAAAGGCCGAA | AUAUUAG | 1507 |
| 561 | AUUUAUG | CUGAUGAGGCCGAAAGGCCGAA | ACACAUU | 1508 |
| 565 | UCAAAUU | CUGAUGAGGCCGAAAGGCCGAA | AUGUACA | 1509 |
| 569 | CAGGUCA | CUGAUGAGGCCGAAAGGCCGAA | AUUUAUG | 1510 |

TABLE VII-continued

Human B7-2 Hammerhead Ribozyme Sequences

| nt. Position | HH Ribozyme Sequences | | | Seq. Id No. |
|---|---|---|---|---|
| 570 | GCAGGUC | CUGAUGAGGCCGAAAGGCCGAA | AAUUUAU | 1511 |
| 579 | UAUAGAU | CUGAUGAGGCCGAAAGGCCGAA | AGCAGGU | 1512 |
| 582 | GUGUAUA | CUGAUGAGGCCGAAAGGCCGAA | AUGAGCA | 1513 |
| 584 | CCGUGUA | CUGAUGAGGCCGAAAGGCCGAA | AGAUGAG | 1514 |
| 586 | AACCGUG | CUGAUGAGGCCGAAAGGCCGAA | AUAGAUG | 1515 |
| 593 | UCUGGGU | CUGAUGAGGCCGAAAGGCCGAA | ACCGUGU | 1516 |
| 594 | UUCUGGG | CUGAUGAGGCCGAAAGGCCGAA | AACCGUG | 1517 |
| 605 | AUCUUCU | CUGAUGAGGCCGAAAGGCCGAA | AGGUUCU | 1518 |
| 619 | UUAGCAA | CUGAUGAGGCCGAAAGGCCGAA | ACACUCA | 1519 |
| 620 | CUUAGCA | CUGAUGAGGCCGAAAGGCCGAA | AACACUC | 1520 |
| 621 | UCUUAGC | CUGAUGAGGCCGAAAGGCCGAA | AAACACU | 1521 |
| 625 | UGGUUCU | CUGAUGAGGCCGAAAGGCCGAA | AGCAAAA | 1522 |
| 638 | AUAGUUG | CUGAUGAGGCCGAAAGGCCGAA | AUUCUUG | 1523 |
| 639 | GAUAGUU | CUGAUGAGGCCGAAAGGCCGAA | AAUUCUU | 1524 |
| 644 | UACUCGA | CUGAUGAGGCCGAAAGGCCGAA | AGUUGAA | 1525 |
| 646 | CAUACUC | CUGAUGAGGCCGAAAGGCCGAA | AUAGUUG | 1526 |
| 651 | ACCAUCA | CUGAUGAGGCCGAAAGGCCGAA | ACUCGAU | 1527 |
| 659 | UGCAUAA | CUGAUGAGGCCGAAAGGCCGAA | ACCAUCA | 1528 |
| 661 | UCUGCAU | CUGAUGAGGCCGAAAGGCCGAA | AUACCAU | 1529 |
| 662 | UUCUGCA | CUGAUGAGGCCGAAAGGCCGAA | AAUACCA | 1530 |
| 672 | AUCUUGA | CUGAUGAGGCCGAAAGGCCGAA | AUUUCUG | 1531 |
| 674 | UUAUCUU | CUGAUGAGGCCGAAAGGCCGAA | AGAUUUC | 1532 |
| 680 | GUGACAU | CUGAUGAGGCCGAAAGGCCGAA | AUCUUGA | 1533 |
| 685 | GUUCGGU | CUGAUGAGGCCGAAAGGCCGAA | ACAUUAU | 1534 |
| 696 | AACGUCG | CUGAUGAGGCCGAAAGGCCGAA | ACAGUUC | 1535 |
| 703 | UGAUGGA | CUGAUGAGGCCGAAAGGCCGAA | ACGUCGU | 1536 |
| 704 | CUGAUGG | CUGAUGAGGCCGAAAGGCCGAA | AACGUCG | 1537 |
| 705 | GCUGAUG | CUGAUGAGGCCGAAAGGCCGAA | AAACGUC | 1538 |
| 709 | ACAAGCU | CUGAUGAGGCCGAAAGGCCGAA | AUGGAAA | 1539 |
| 714 | AACAGAC | CUGAUGAGGCCGAAAGGCCGAA | AGCUGAU | 1540 |
| 717 | UGAAACA | CUGAUGAGGCCGAAAGGCCGAA | ACAAGCU | 1541 |
| 721 | GGAAUGA | CUGAUGAGGCCGAAAGGCCGAA | ACAGACA | 1542 |
| 722 | GGGAAUG | CUGAUGAGGCCGAAAGGCCGAA | AACAGAC | 1543 |
| 723 | AGGGAAU | CUGAUGAGGCCGAAAGGCCGAA | AAACAGA | 1544 |
| 726 | AUCAGGG | CUGAUGAGGCCGAAAGGCCGAA | AUGAAAC | 1545 |
| 727 | CAUCAGG | CUGAUGAGGCCGAAAGGCCGAA | AAUGAAA | 1546 |
| 736 | UGCUCGU | CUGAUGAGGCCGAAAGGCCGAA | ACAUCAG | 1547 |
| 737 | UUGCUCG | CUGAUGAGGCCGAAAGGCCGAA | AACAUCA | 1548 |
| 746 | AUGGUCA | CUGAUGAGGCCGAAAGGCCGAA | AUUGCUC | 1549 |
| 754 | UACAGAA | CUGAUGAGGCCGAAAGGCCGAA | AUGGUCA | 1550 |
| 756 | AAUACAG | CUGAUGAGGCCGAAAGGCCGAA | AGAUGGU | 1551 |
| 757 | GAAUACA | CUGAUGAGGCCGAAAGGCCGAA | AAGAUGG | 1552 |
| 761 | UCCAGAA | CUGAUGAGGCCGAAAGGCCGAA | ACAGAAG | 1553 |
| 763 | UUUCCAG | CUGAUGAGGCCGAAAGGCCGAA | AUACAGA | 1554 |
| 764 | GUUUCCA | CUGAUGAGGCCGAAAGGCCGAA | AAUACAG | 1555 |
| 787 | AAGAUAA | CUGAUGAGGCCGAAAGGCCGAA | AGCCGCG | 1556 |
| 788 | GAAGAUA | CUGAUGAGGCCGAAAGGCCGAA | AAGCCGC | 1557 |
| 789 | UGAAGAU | CUGAUGAGGCCGAAAGGCCGAA | AAAGCCG | 1558 |
| 790 | GUGAAGA | CUGAUGAGGCCGAAAGGCCGAA | AAAAGCC | 1559 |
| 792 | AGGUGAA | CUGAUGAGGCCGAAAGGCCGAA | AUAAAAG | 1560 |
| 794 | AAAGGUG | CUGAUGAGGCCGAAAGGCCGAA | AGAUAAA | 1561 |
| 795 | GAAAGGU | CUGAUGAGGCCGAAAGGCCGAA | AAGAUAA | 1562 |
| 800 | AUAGAGA | CUGAUGAGGCCGAAAGGCCGAA | AGGUGAA | 1563 |
| 801 | UAUAGAG | CUGAUGAGGCCGAAAGGCCGAA | AAGGUGA | 1564 |
| 802 | CUAUAGA | CUGAUGAGGCCGAAAGGCCGAA | AAAGGUG | 1565 |
| 804 | CUCUAUA | CUGAUGAGGCCGAAAGGCCGAA | AGAAAGG | 1566 |
| 806 | AGCUCUA | CUGAUGAGGCCGAAAGGCCGAA | AGAGACA | 1567 |
| 808 | CAAGCUC | CUGAUGAGGCCGAAAGGCCGAA | AUAGAGA | 1568 |
| 814 | GGUCCUC | CUGAUGAGGCCGAAAGGCCGAA | AGCUCUA | 1569 |
| 824 | GGAGGCU | CUGAUGAGGCCGAAAGGCCGAA | AGGGUCC | 1570 |
| 830 | UCUGGGG | CUGAUGAGGCCGAAAGGCCGAA | AGGCUGA | 1571 |
| 844 | UCCAAGG | CUGAUGAGGCCGAAAGGCCGAA | AUGUGGU | 1572 |
| 845 | AUCCAAG | CUGAUGAGGCCGAAAGGCCGAA | AAUGUGG | 1573 |
| 848 | GUAAUCC | CUGAUGAGGCCGAAAGGCCGAA | AGGAAUG | 1574 |
| 853 | CAGCUGU | CUGAUGAGGCCGAAAGGCCGAA | AUCCAAG | 1575 |
| 854 | ACAGCUG | CUGAUGAGGCCGAAAGGCCGAA | AAUCCAA | 1576 |
| 862 | UUGGAAG | CUGAUGAGGCCGAAAGGCCGAA | ACAGCUG | 1577 |
| 865 | CUGUUGG | CUGAUGAGGCCGAAAGGCCGAA | AGUACAG | 1578 |
| 866 | ACUGUUG | CUGAUGAGGCCGAAAGGCCGAA | AAGUACA | 1579 |
| 874 | AUAUAAU | CUGAUGAGGCCGAAAGGCCGAA | ACUGUUG | 1580 |
| 875 | CAUAUAA | CUGAUGAGGCCGAAAGGCCGAA | AACUGUU | 1581 |
| 877 | CACAUAU | CUGAUGAGGCCGAAAGGCCGAA | AUAACUG | 1582 |
| 878 | ACACAUA | CUGAUGAGGCCGAAAGGCCGAA | AAUAACU | 1583 |
| 880 | UCACACA | CUGAUGAGGCCGAAAGGCCGAA | AUAAUAA | 1584 |
| 892 | GACAGAA | CUGAUGAGGCCGAAAGGCCGAA | ACCAUCA | 1585 |

TABLE VII-continued

Human B7-2 Hammerhead Ribozyme Sequences

| nt. Position | HH Ribozyme Sequences | | Seq. Id No. |
|---|---|---|---|
| 893 | AGACAGA CUGAUGAGGCCGAAAGGCCGAA | AACCAUC | 1586 |
| 894 | UAGACAG CUGAUGAGGCCGAAAGGCCGAA | AAACCAU | 1587 |
| 895 | UUAGACA CUGAUGAGGCCGAAAGGCCGAA | AAAACCA | 1588 |
| 899 | AGAAUUA CUGAUGAGGCCGAAAGGCCGAA | ACAGAAA | 1589 |
| 901 | AUAGAAU CUGAUGAGGCCGAAAGGCCGAA | AGACAGA | 1590 |
| 904 | UCCAUAG CUGAUGAGGCCGAAAGGCCGAA | AUUAGAC | 1591 |
| 905 | UUCCAUA CUGAUGAGGCCGAAAGGCCGAA | AAUUAGA | 1592 |
| 907 | AUUUCCA CUGAUGAGGCCGAAAGGCCGAA | AGAAUUA | 1593 |
| 935 | GAGUUGC CUGAUGAGGCCGAAAGGCCGAA | AGGCCGC | 1594 |
| 942 | UUUAUAA CUGAUGAGGCCGAAAGGCCGAA | AGUUGCG | 1595 |
| 944 | CAUUUAU CUGAUGAGGCCGAAAGGCCGAA | AGAGUUG | 1596 |
| 945 | ACAUUUA CUGAUGAGGCCGAAAGGCCGAA | AAGAGUU | 1597 |
| 947 | CCACAUU CUGAUGAGGCCGAAAGGCCGAA | AUAAGAG | 1598 |
| 1009 | GUAUAUG CUGAUGAGGCCGAAAGGCCGAA | AUUUUUU | 1599 |
| 1013 | UCAGGUA CUGAUGAGGCCGAAAGGCCGAA | AUGGAUU | 1600 |
| 1015 | UUUCAGG CUGAUGAGGCCGAAAGGCCGAA | AUAUGGA | 1601 |
| 1026 | UUCAUCA CUGAUGAGGCCGAAAGGCCGAA | AUCUUUC | 1602 |
| 1045 | UUUUAAA CUGAUGAGGCCGAAAGGCCGAA | ACACGCU | 1603 |
| 1046 | CUUUUAA CUGAUGAGGCCGAAAGGCCGAA | AACACGC | 1604 |
| 1047 | ACUUUUA CUGAUGAGGCCGAAAGGCCGAA | AAACACG | 1605 |
| 1048 | AACUUUU CUGAUGAGGCCGAAAGGCCGAA | AAAACAC | 1606 |
| 1049 | GAACUUU CUGAUGAGGCCGAAAGGCCGAA | AAAAACA | 1607 |
| 1055 | GUCUUCG CUGAUGAGGCCGAAAGGCCGAA | ACUUUUA | 1608 |
| 1056 | UGUCUUC CUGAUGAGGCCGAAAGGCCGAA | AACUUUU | 1609 |
| 1065 | GCAUGAA CUGAUGAGGCCGAAAGGCCGAA | AUGUCUU | 1610 |
| 1067 | UCGCAUG CUGAUGAGGCCGAAAGGCCGAA | AGAUGUC | 1611 |
| 1068 | GUCGCAU CUGAUGAGGCCGAAAGGCCGAA | AAGAUGU | 1612 |
| 1085 | AAACAUG CUGAUGAGGCCGAAAGGCCGAA | AUCACUU | 1613 |
| 1091 | AAUUAAA CUGAUGAGGCCGAAAGGCCGAA | ACAUGUA | 1614 |
| 1092 | UAAUUAA CUGAUGAGGCCGAAAGGCCGAA | AACAUGU | 1615 |
| 1093 | UUAAUUA CUGAUGAGGCCGAAAGGCCGAA | AAACAUG | 1616 |
| 1094 | UUUAAUU CUGAUGAGGCCGAAAGGCCGAA | AAAACAU | 1617 |
| 1095 | CUUUAAU CUGAUGAGGCCGAAAGGCCGAA | AAAAACA | 1618 |
| 1098 | ACUCUUU CUGAUGAGGCCGAAAGGCCGAA | AUUAAAA | 1619 |
| 1099 | UACUCUU CUGAUGAGGCCGAAAGGCCGAA | AAUUAAA | 1620 |

TABLE VIII

Mouse B7-2 Hammerhead Ribozyme Target Sequences

| nt. Position | HH Target Sequence | | | Seq. ID No. |
|---|---|---|---|---|
| 47 | AcGGACU | u | GaACAac | 1621 |
| 47 | aCggACU | u | gaAcAAC | 1622 |
| 66 | CUccUgU | a | gAcGUgU | 1623 |
| 66 | CUCcUgU | A | gAcGUGu | 1624 |
| 74 | gAcGUGU | u | CcagAAc | 1625 |
| 83 | CaGaACU | U | aCggaAG | 1626 |
| 134 | caAuCcU | U | aUCUUUG | 1627 |
| 134 | CaauccU | U | AUCUUug | 1628 |
| 134 | caAUCcU | U | AuCUUUg | 1629 |
| 134 | CAaUccU | U | AUcUuUG | 1630 |
| 134 | CAAucCU | U | AUcuuUG | 1631 |
| 135 | aAuCcUU | a | UCUUUGU | 1632 |
| 135 | aAuCcUU | U | UCUuUgu | 1633 |
| 135 | AaUccUU | A | UcUuUGU | 1634 |
| 135 | aAUccUU | a | UCUuUgU | 1635 |
| 137 | uCcUUaU | C | UUUGUGA | 1636 |
| 137 | UccUUAU | c | UuUGUGA | 1637 |
| 137 | UCCuUAU | c | uuUGugA | 1638 |
| 139 | cUUaUCU | U | UGUGAca | 1639 |
| 140 | UUaUCUU | U | GUGAcaG | 1640 |
| 140 | UUaUcuU | U | guGACAG | 1641 |
| 149 | UGAcaGU | c | UUGCUgA | 1642 |
| 151 | AcAGucU | U | GCUgaUC | 1643 |
| 151 | AcaGucU | U | gCUgaUC | 1644 |
| 158 | UgCuGAU | c | UcAgaUg | 1645 |
| 158 | UgCUGaU | C | UCaGaUG | 1646 |
| 158 | UgCUgAU | c | uCAgaUg | 1647 |
| 158 | UgCugAU | c | UCagAUg | 1648 |
| 160 | CUGaUCU | C | aGaUGCU | 1649 |
| 160 | cUGaUcU | c | AgAuGcU | 1650 |
| 170 | AUGcuGU | u | UcCgUgG | 1651 |
| 171 | UGCUGuU | u | CcgUGgA | 1652 |
| 172 | gCUgUuU | C | cgUgGAG | 1653 |
| 189 | GcaaGcU | u | AUUUCaA | 1654 |
| 189 | gCAAGCU | U | AUUUCAA | 1655 |
| 189 | GCaaGCU | u | AuUUCAa | 1656 |
| 190 | CAAGCUU | A | UUUCAAU | 1657 |
| 190 | CaAgcUU | a | uUUcaAU | 1658 |
| 192 | AGCUUAU | U | UCAAUGg | 1659 |
| 192 | aGCUUaU | u | UCAAUGg | 1660 |
| 193 | GCUUAUU | U | CAAUGgG | 1661 |
| 193 | GcuUAuU | U | CaAUGGg | 1662 |
| 194 | CUUAUUU | C | AAUGgGA | 1663 |
| 194 | cuUAuUU | C | aAUGGgA | 1664 |
| 208 | acUGCaU | a | UCUGCcG | 1665 |
| 210 | UGCaUaU | C | UGCcGug | 1666 |
| 223 | UGCCcAU | U | UaCAAAg | 1667 |
| 223 | UGCcCAU | u | UAcAaAg | 1668 |
| 224 | GCCcAUU | U | aCAAAgg | 1669 |
| 225 | ccCAUUU | a | CAaAggc | 1670 |
| 225 | CccaUUU | a | cAAAgGc | 1671 |
| 242 | AAaACAU | a | agCcUGa | 1672 |
| 260 | AGCUgGU | A | GUAUUUU | 1673 |
| 260 | aGCuGgU | a | gUAUuUU | 1674 |
| 263 | UgGUAGU | A | UUUUGGC | 1675 |
| 263 | UGgUaGU | a | UUuUGgC | 1676 |
| 265 | GUAGUAU | U | UUGGCAG | 1677 |
| 265 | guAGUAU | u | UuGGCaG | 1678 |

TABLE VIII-continued

Mouse B7-2 Hammerhead Ribozyme Target Sequences

| nt. Position | HH Target Sequence | Seq. ID No. |
|---|---|---|
| 266 | UAGUAUU U UGGCAGG | 1679 |
| 266 | uAGUaUU U UGgcAgG | 1680 |
| 266 | UAgUauU U UGGcAgg | 1681 |
| 267 | AGUAUUU U GGCAGGA | 1682 |
| 267 | AGUaUUU U GgcAgGA | 1683 |
| 286 | cAAAAgU U GGUUCUG | 1684 |
| 286 | CAAaagU U GgUUCuG | 1685 |
| 290 | AgUUGGU U CUGuAcG | 1686 |
| 291 | gUUGGUU C UGuAcGA | 1687 |
| 295 | GUUCugU a CgAGcAc | 1688 |
| 304 | GAGcacU A uUUgGGC | 1689 |
| 307 | cacUAUU u GGgCACA | 1690 |
| 323 | AGAAAcU U GAuAGUG | 1691 |
| 343 | gCCAAGU A ccUGGGC | 1692 |
| 343 | gCCAagU a CCUgGGc | 1693 |
| 361 | ACgAGcU U UGAcagG | 1694 |
| 381 | cUGgACU c UacGACU | 1695 |
| 383 | GgACUcU A CGACuUc | 1696 |
| 383 | GGACuCU a cGaCUuC | 1697 |
| 389 | UAcGacU u CaCAaUG | 1698 |
| 389 | UacGACU U CACAAUg | 1699 |
| 390 | acGACUU C ACAAUgU | 1700 |
| 390 | ACgAcUU c acAAUgU | 1701 |
| 398 | ACAaUGU U CAgauCA | 1702 |
| 398 | ACAAUgU U CAGAUCA | 1703 |
| 398 | ACaAuGU U cagAUCA | 1704 |
| 399 | CAaUGUU C AgauCAA | 1705 |
| 399 | CAAUgUU C AGAUCAA | 1706 |
| 399 | CaAuGUU c agAUcAa | 1707 |
| 399 | caAUGUU c aGAuCAA | 1708 |
| 399 | CAaUguU c aGAUCAa | 1709 |
| 399 | cAAUgUU C aGAUcAA | 1710 |
| 399 | CAaugUU c agAUcAA | 1711 |
| 404 | UUCAGAU C AAGGACA | 1712 |
| 404 | UucAGaU c aAGGACa | 1713 |
| 418 | aUGgGCU U GUAugAU | 1714 |
| 418 | AuGGGCU c GUAUgAu | 1715 |
| 418 | AUggGCU c GUaUGaU | 1716 |
| 421 | gGCUCgU a UGAuugU | 1717 |
| 421 | ggCUCgU A UgAuUGU | 1718 |
| 429 | UgAuUGU u UuAUaCA | 1719 |
| 429 | UGAUuGU u UUAUaCA | 1720 |
| 431 | AuUgUuU u AUAcAAa | 1721 |
| 431 | AUuGUuU U AUaCAaA | 1722 |
| 432 | UuGUuUU A UaCAaAA | 1723 |
| 432 | UuGUUUU a UacaaAA | 1724 |
| 432 | uUGUUUU a uAcaAAA | 1725 |
| 461 | gAUcaAU u AUCCucC | 1726 |
| 462 | AucaAUU a uCcUCCA | 1727 |
| 464 | CAauUaU c CUcCaAc | 1728 |
| 467 | uUAUCcU C CAaCAgA | 1729 |
| 467 | UUauCcU C CAaCAGA | 1730 |
| 467 | UUaUccU c cAACAGA | 1731 |
| 467 | UuAuCCU C CaaCAGA | 1732 |
| 490 | GAACUGU C AGUGaUc | 1733 |
| 497 | CAGUGaU c GCcAACU | 1734 |
| 505 | GCcAACU U CAGUgAA | 1735 |
| 506 | CcAACUU C AGUgAAC | 1736 |
| 506 | CCAacUU C aGUgaaC | 1737 |
| 521 | CUGAAAU A aaACugg | 1738 |
| 531 | ACUGgcU c AgAaUgU | 1739 |
| 539 | agaaUGU A ACAGGaA | 1740 |
| 550 | GgAaAuU c uGGCAuA | 1741 |
| 550 | ggAAaUU C UggcAUA | 1742 |
| 557 | cuggCAU A AAUUUGA | 1743 |
| 561 | CAUAAAU U UGACCUG | 1744 |
| 562 | AUAAAUU U GACCUGC | 1745 |
| 576 | CaCgUCU A agCAaGG | 1746 |
| 585 | gCAaGGU c ACCCgaA | 1747 |
| 597 | gaAACCU A AGAAGAU | 1748 |
| 607 | AaGaUgU a uUuUCUg | 1749 |
| 611 | UGUaUUU u cUgAuAa | 1750 |
| 625 | AcuAAUU C AACUAau | 1751 |
| 630 | UUCAACU A auGAGUA | 1752 |
| 630 | UUcAAcU A AuGAGUA | 1753 |
| 637 | AauGAGU A UGgUGaU | 1754 |
| 656 | uGCAgaU a UcAcAAg | 1755 |
| 658 | CAGAUAU c AcaagAu | 1756 |
| 658 | CAgauAU C ACAAgAu | 1757 |
| 658 | CAGAuAU C aCAAGAU | 1758 |
| 658 | CaGAUaU c ACaAGau | 1759 |
| 666 | aCAAGAU A AUGUCAC | 1760 |
| 666 | ACAagaU a AUGucAC | 1761 |
| 671 | AUaAuGU C ACAGaAc | 1762 |
| 671 | aUAAUgU c ACAGAAc | 1763 |
| 671 | AUAAUGU C ACAGAAC | 1764 |
| 682 | gAACUgU u cAGUAUc | 1765 |
| 683 | aAcUGuU c aGuAUCu | 1766 |
| 683 | AAcUGuU c agUaUcU | 1767 |
| 691 | aguaUcU C CAaCAGC | 1768 |
| 691 | agUAUCU c CAaCagc | 1769 |
| 691 | aGUAucU C CAACAGc | 1770 |
| 701 | aCaGCcU c UcUCUUu | 1771 |
| 701 | acagCCU c UCUCUuU | 1772 |
| 703 | AGCcUcU U UcUUUCA | 1773 |
| 703 | aGCcUcU c UCUUuca | 1774 |
| 707 | UcUCUcU U UCAUUCC | 1775 |
| 707 | UcUCUcU u UcAUUCc | 1776 |
| 708 | cUCUcUU C CAUUCCC | 1777 |
| 709 | UCUcUUU C AUUCCCg | 1778 |
| 709 | UCUCUuU c auuCccG | 1779 |
| 709 | UCUcUuU c AUUCccg | 1780 |
| 712 | CUUUcaU U CcCgGaU | 1781 |
| 712 | cuuUCAU U cCCgGAU | 1782 |
| 712 | CuUucAU u CcCGGaU | 1783 |
| 712 | cUUUCAU U CCCgGAU | 1784 |
| 712 | CUUUcAU u ccCggaU | 1785 |
| 713 | uuUCAUU c CCgGAUg | 1786 |
| 713 | UUUCAUU C CCgGAUG | 1787 |
| 732 | GuGgcAU a UGACcGU | 1788 |
| 732 | GuGgcAU A UGACCgU | 1789 |
| 740 | UGACCgU u gUgUGUg | 1790 |
| 749 | UgUGUgU U CUGGAAA | 1791 |
| 749 | uGuGUGU U cUggAAA | 1792 |
| 750 | gUGUgUU C UGGAAAC | 1793 |
| 750 | GuGUGUU c UggAAAc | 1794 |
| 773 | ugAAGaU U UcCUcCa | 1795 |
| 778 | aUUUcCU c caAACCu | 1796 |
| 788 | AAcCUCU C AAuuuCA | 1797 |
| 798 | UUUUCaCU U aAGAGuU | 1798 |
| 805 | CAagAGU U UccAUcu | 1799 |
| 805 | CAAgAGU U uccAUcU | 1800 |
| 806 | AAgAGUU u ccAUcUc | 1801 |
| 811 | UUUCCAU C ucCUcaa | 1802 |
| 811 | uUUCcaU c UcCUcaA | 1803 |
| 813 | uCCAUCU c CUcaAac | 1804 |
| 836 | aGgAGAU U acAGCUU | 1805 |
| 836 | aggaGAU U ACAGCUu | 1806 |
| 837 | GgAGAUU a cAGCUUc | 1807 |
| 848 | CUUCAGU u AcugUGg | 1808 |
| 860 | UGGCCcU C CUcCUug | 1809 |
| 860 | UggCCcU c CUCcuUg | 1810 |
| 878 | ugCUGCU C AUCauUg | 1811 |
| 951 | GCGGgaU a GuAACgC | 1812 |
| 974 | AgaCuAU c aACCUGA | 1813 |
| 989 | aGgaAcU U GaACCCc | 1814 |
| 1006 | auUgCUU c aGCAAAa | 1815 |
| 1055 | AAAgAGU u aaAAaUU | 1816 |
| 1056 | AaGAgUU a aaAAuUG | 1817 |
| 1062 | uAAAAAU u gcUuUgC | 1818 |
| 1092 | CAgaGUU u CuCAGAA | 1819 |
| 1095 | aGUUUcU c AgAaUUC | 1820 |
| 1101 | UCAgAAU u caaAaAU | 1821 |
| 1101 | ucAGAAU U CAAaaAU | 1822 |
| 1101 | UcAgAaU U CaAAaAu | 1823 |
| 1111 | aAaAUGU U cUcAgcU | 1824 |
| 1112 | AaAUGUU c UcAgcUg | 1825 |
| 1128 | UUgGAaU u cuACAGU | 1826 |
| 1128 | UUGGAaU u CuaCaGU | 1827 |
| 1131 | GAAuUCU a cAGuUgA | 1828 |

TABLE VIII-continued

Mouse B7-2 Hammerhead Ribozyme Target Sequences

| nt. Position | HH Target Sequence | | | Seq. ID No. |
|---|---|---|---|---|
| 1131 | GAauUCU | a | CAguuGA | 1829 |
| 1141 | GuUGAAU | a | aUuAAag | 1830 |
| 1144 | gaaUAAU | U | AAAGAac | 1831 |
| 1145 | AAuAaUU | a | aAgaACA | 1832 |

TABLE IX

Mouse B7-2 Hammerhead Ribozyme Sequences

| nt. Position | HH Ribozyme Sequences | | | Seq. ID No. |
|---|---|---|---|---|
| 47 | GUUGUUC | CUGAUGAGGCCGAAAGGCCGAA | AGUCCGU | 1833 |
| 47 | GUUGUUC | CUGAUGAGGCCGAAAGGCCGAA | AGUCCGU | 1834 |
| 66 | ACACGUC | CUGAUGAGGCCGAAAGGCCGAA | ACAGGAG | 1835 |
| 66 | ACACGUC | CUGAUGAGGCCGAAAGGCCGAA | ACAGGAG | 1836 |
| 74 | GUUCUGG | CUGAUGAGGCCGAAAGGCCGAA | ACACGUC | 1837 |
| 83 | CUUCCGU | CUGAUGAGGCCGAAAGGCCGAA | AGUUCUG | 1838 |
| 134 | CAAAGAU | CUGAUGAGGCCGAAAGGCCGAA | AGGAUUG | 1839 |
| 134 | CAAAGAU | CUGAUGAGGCCGAAAGGCCGAA | AGGAUUG | 1840 |
| 134 | CAAAGAU | CUGAUGAGGCCGAAAGGCCGAA | AGGAUUG | 1841 |
| 134 | CAAAGAU | CUGAUGAGGCCGAAAGGCCGAA | AGGAUUG | 1842 |
| 134 | CAAAGAU | CUGAUGAGGCCGAAAGGCCGAA | AGGAUUG | 1843 |
| 135 | ACAAAGA | CUGAUGAGGCCGAAAGGCCGAA | AAGGAUU | 1844 |
| 135 | ACAAAGA | CUGAUGAGGCCGAAAGGCCGAA | AAGGAUU | 1845 |
| 135 | ACAAAGA | CUGAUGAGGCCGAAAGGCCGAA | AAGGAUU | 1846 |
| 135 | ACAAAGA | CUGAUGAGGCCGAAAGGCCGAA | AAGGAUU | 1847 |
| 137 | UCACAAA | CUGAUGAGGCCGAAAGGCCGAA | AUAAGGA | 1848 |
| 137 | UCACAAA | CUGAUGAGGCCGAAAGGCCGAA | AUAAGGA | 1849 |
| 137 | UCACAAA | CUGAUGAGGCCGAAAGGCCGAA | AUAAGGA | 1850 |
| 139 | UGUCACA | CUGAUGAGGCCGAAAGGCCGAA | AGAUAAG | 1851 |
| 140 | CUGUCAC | CUGAUGAGGCCGAAAGGCCGAA | AAGAUAA | 1852 |
| 140 | CUGUCAC | CUGAUGAGGCCGAAAGGCCGAA | AAGAUAA | 1853 |
| 149 | UCAGCAA | CUGAUGAGGCCGAAAGGCCGAA | ACUGUCA | 1854 |
| 151 | GAUCAGC | CUGAUGAGGCCGAAAGGCCGAA | AGACUGU | 1855 |
| 151 | GAUCAGC | CUGAUGAGGCCGAAAGGCCGAA | AGACUGU | 1856 |
| 158 | CAUCUGA | CUGAUGAGGCCGAAAGGCCGAA | AUCAGCA | 1857 |
| 158 | CAUCUGA | CUGAUGAGGCCGAAAGGCCGAA | AUCAGCA | 1858 |
| 158 | CAUCUGA | CUGAUGAGGCCGAAAGGCCGAA | AUCAGCA | 1859 |
| 158 | CAUCUGA | CUGAUGAGGCCGAAAGGCCGAA | AUCAGCA | 1860 |
| 160 | AGCAUCU | CUGAUGAGGCCGAAAGGCCGAA | AGAUCAG | 1861 |
| 160 | AGCAUCU | CUGAUGAGGCCGAAAGGCCGAA | AGAUCAG | 1862 |
| 170 | CCACGGA | CUGAUGAGGCCGAAAGGCCGAA | ACAGCAU | 1863 |
| 171 | UCCACGG | CUGAUGAGGCCGAAAGGCCGAA | AACAGCA | 1864 |
| 172 | CUCCACG | CUGAUGAGGCCGAAAGGCCGAA | AAACAGC | 1865 |
| 189 | UUGAAAU | CUGAUGAGGCCGAAAGGCCGAA | AGCUUGC | 1866 |
| 189 | UUGAAAU | CUGAUGAGGCCGAAAGGCCGAA | AGCUUGC | 1867 |
| 189 | UUGAAAU | CUGAUGAGGCCGAAAGGCCGAA | AGCUUGC | 1868 |
| 190 | AUUGAAA | CUGAUGAGGCCGAAAGGCCGAA | AAGCUUG | 1869 |
| 190 | AUUGAAA | CUGAUGAGGCCGAAAGGCCGAA | AAGCUUG | 1870 |
| 192 | CCAUUGA | CUGAUGAGGCCGAAAGGCCGAA | AUAAGCU | 1871 |
| 192 | CCAUUGA | CUGAUGAGGCCGAAAGGCCGAA | AUAAGCU | 1872 |
| 193 | CCCAUUG | CUGAUGAGGCCGAAAGGCCGAA | AAUAAGC | 1873 |
| 193 | CCCAUUG | CUGAUGAGGCCGAAAGGCCGAA | AAUAAGC | 1874 |
| 194 | UCCCAUU | CUGAUGAGGCCGAAAGGCCGAA | AAAUAAG | 1875 |
| 194 | UCCCAUU | CUGAUGAGGCCGAAAGGCCGAA | AAAUAAG | 1876 |
| 208 | CGGCAGA | CUGAUGAGGCCGAAAGGCCGAA | AUGCAGU | 1877 |
| 210 | CACGGCA | CUGAUGAGGCCGAAAGGCCGAA | AUAUGCA | 1878 |
| 223 | CUUUGUA | CUGAUGAGGCCGAAAGGCCGAA | AUGGGCA | 1879 |
| 223 | CUUUGUA | CUGAUGAGGCCGAAAGGCCGAA | AUGGGCA | 1880 |
| 224 | CCUUUGU | CUGAUGAGGCCGAAAGGCCGAA | AAUGGGC | 1881 |
| 225 | GCCUUUG | CUGAUGAGGCCGAAAGGCCGAA | AAAUGGG | 1882 |
| 225 | GCCUUUG | CUGAUGAGGCCGAAAGGCCGAA | AAAUGGG | 1883 |
| 242 | UCAGGCU | CUGAUGAGGCCGAAAGGCCGAA | AUGUUUU | 1884 |
| 260 | AAAAUAC | CUGAUGAGGCCGAAAGGCCGAA | ACCAGCU | 1885 |
| 260 | AAAAUAC | CUGAUGAGGCCGAAAGGCCGAA | ACCAGCU | 1886 |
| 263 | GCCAAAA | CUGAUGAGGCCGAAAGGCCGAA | ACUACCA | 1887 |
| 263 | GCCAAAA | CUGAUGAGGCCGAAAGGCCGAA | ACUACCA | 1888 |
| 265 | CUGCCAA | CUGAUGAGGCCGAAAGGCCGAA | AUACUAC | 1889 |

TABLE IX-continued

Mouse B7-2 Hammerhead Ribozyme Sequences

| nt. Position | HH Ribozyme Sequences | | | Seq. ID No. |
|---|---|---|---|---|
| 265 | CUGCCAA | CUGAUGAGGCCGAAAGGCCGAA | AUACUAC | 1890 |
| 266 | CCUGCCA | CUGAUGAGGCCGAAAGGCCGAA | AAUACUA | 1891 |
| 266 | CCUGCCA | CUGAUGAGGCCGAAAGGCCGAA | AAUACUA | 1892 |
| 266 | CCUGCCA | CUGAUGAGGCCGAAAGGCCGAA | AAUACUA | 1893 |
| 267 | UCCUGCC | CUGAUGAGGCCGAAAGGCCGAA | AAAUACU | 1894 |
| 267 | UCCUGCC | CUGAUGAGGCCGAAAGGCCGAA | AAAUACU | 1895 |
| 286 | CAGAACC | CUGAUGAGGCCGAAAGGCCGAA | ACUUUUG | 1896 |
| 286 | CAGAACC | CUGAUGAGGCCGAAAGGCCGAA | ACUUUUG | 1897 |
| 290 | CGUACAG | CUGAUGAGGCCGAAAGGCCGAA | ACCAACU | 1898 |
| 291 | UCGUACA | CUGAUGAGGCCGAAAGGCCGAA | AACCAAC | 1899 |
| 295 | GUGCUCG | CUGAUGAGGCCGAAAGGCCGAA | ACAGAAC | 1900 |
| 304 | GCCCAAA | CUGAUGAGGCCGAAAGGCCGAA | AGUGCUC | 1901 |
| 307 | UGUGCCC | CUGAUGAGGCCGAAAGGCCGAA | AAUAGUG | 1902 |
| 323 | CACUAUC | CUGAUGAGGCCGAAAGGCCGAA | AGUUUCU | 1903 |
| 343 | GCCCAGG | CUGAUGAGGCCGAAAGGCCGAA | ACUUGGC | 1904 |
| 343 | GCCCAGG | CUGAUGAGGCCGAAAGGCCGAA | ACUUGGC | 1905 |
| 361 | CCUGUCA | CUGAUGAGGCCGAAAGGCCGAA | AGCUCGU | 1906 |
| 381 | AGUCGUA | CUGAUGAGGCCGAAAGGCCGAA | AGUCCAG | 1907 |
| 383 | GAAGUCG | CUGAUGAGGCCGAAAGGCCGAA | AGAGUCC | 1908 |
| 383 | GAAGUCG | CUGAUGAGGCCGAAAGGCCGAA | AGAGUCC | 1909 |
| 389 | CAUUGUG | CUGAUGAGGCCGAAAGGCCGAA | AGUCGUA | 1910 |
| 389 | CAUUGUG | CUGAUGAGGCCGAAAGGCCGAA | AGUCGUA | 1911 |
| 390 | ACAUUGU | CUGAUGAGGCCGAAAGGCCGAA | AAGUCGU | 1912 |
| 390 | ACAUUGU | CUGAUGAGGCCGAAAGGCCGAA | AAGUCGU | 1913 |
| 398 | UGAUCUG | CUGAUGAGGCCGAAAGGCCGAA | ACAUUGU | 1914 |
| 398 | UGAUCUG | CUGAUGAGGCCGAAAGGCCGAA | ACAUUGU | 1915 |
| 398 | UGAUCUG | CUGAUGAGGCCGAAAGGCCGAA | ACAUUGU | 1916 |
| 399 | UUGAUCU | CUGAUGAGGCCGAAAGGCCGAA | AACAUUG | 1917 |
| 399 | UUGAUCU | CUGAUGAGGCCGAAAGGCCGAA | AACAUUG | 1918 |
| 399 | UUGAUCU | CUGAUGAGGCCGAAAGGCCGAA | AACAUUG | 1919 |
| 399 | UUGAUCU | CUGAUGAGGCCGAAAGGCCGAA | AACAUUG | 1920 |
| 399 | UUGAUCU | CUGAUGAGGCCGAAAGGCCGAA | AACAUUG | 1921 |
| 399 | UUGAUCU | CUGAUGAGGCCGAAAGGCCGAA | AACAUUG | 1922 |
| 399 | UUGAUCU | CUGAUGAGGCCGAAAGGCCGAA | AACAUUG | 1923 |
| 404 | UGUCCUU | CUGAUGAGGCCGAAAGGCCGAA | AUCUGAA | 1924 |
| 404 | UGUCCUU | CUGAUGAGGCCGAAAGGCCGAA | AUCUGAA | 1925 |
| 418 | AUCAUAC | CUGAUGAGGCCGAAAGGCCGAA | AGCCCAU | 1926 |
| 418 | AUCAUAC | CUGAUGAGGCCGAAAGGCCGAA | AGCCCAU | 1927 |
| 418 | AUCAUAC | CUGAUGAGGCCGAAAGGCCGAA | AGCCCAU | 1928 |
| 421 | ACAAUCA | CUGAUGAGGCCGAAAGGCCGAA | ACGAGCC | 1929 |
| 421 | ACAAUCA | CUGAUGAGGCCGAAAGGCCGAA | ACGAGCC | 1930 |
| 429 | UGUAUAA | CUGAUGAGGCCGAAAGGCCGAA | ACAAUCA | 1931 |
| 429 | UGUAUAA | CUGAUGAGGCCGAAAGGCCGAA | ACAAUCA | 1932 |
| 431 | UUUGUAU | CUGAUGAGGCCGAAAGGCCGAA | AAACAAU | 1933 |
| 431 | UUUGUAU | CUGAUGAGGCCGAAAGGCCGAA | AAACAAU | 1934 |
| 432 | UUUUGUA | CUGAUGAGGCCGAAAGGCCGAA | AAAACAA | 1935 |
| 432 | UUUUGUA | CUGAUGAGGCCGAAAGGCCGAA | AAAACAA | 1936 |
| 432 | UUUUGUA | CUGAUGAGGCCGAAAGGCCGAA | AAAACAA | 1937 |
| 461 | GGAGGAU | CUGAUGAGGCCGAAAGGCCGAA | AUUGAUC | 1938 |
| 462 | UGGAGGA | CUGAUGAGGCCGAAAGGCCGAA | AAUUGAU | 1939 |
| 464 | GUUGGAG | CUGAUGAGGCCGAAAGGCCGAA | AUAAUUG | 1940 |
| 467 | UCUGUUG | CUGAUGAGGCCGAAAGGCCGAA | AGGAUAA | 1941 |
| 467 | UCUGUUG | CUGAUGAGGCCGAAAGGCCGAA | AGGAUAA | 1942 |
| 467 | UCUGUUG | CUGAUGAGGCCGAAAGGCCGAA | AGGAUAA | 1943 |
| 467 | UCUGUUG | CUGAUGAGGCCGAAAGGCCGAA | AGGAUAA | 1944 |
| 490 | GAUCACU | CUGAUGAGGCCGAAAGGCCGAA | ACAGUUC | 1945 |
| 497 | AGUUGGC | CUGAUGAGGCCGAAAGGCCGAA | AUCACUG | 1946 |
| 505 | UUCACUG | CUGAUGAGGCCGAAAGGCCGAA | AGUUGGC | 1947 |
| 506 | GUUCACU | CUGAUGAGGCCGAAAGGCCGAA | AAGUUGG | 1948 |
| 506 | GUUCACU | CUGAUGAGGCCGAAAGGCCGAA | AAGUUGG | 1949 |
| 521 | CCAGUUU | CUGAUGAGGCCGAAAGGCCGAA | AUUUCAG | 1950 |
| 531 | ACAUUCU | CUGAUGAGGCCGAAAGGCCGAA | AGCCAGU | 1951 |
| 539 | UUCCUGU | CUGAUGAGGCCGAAAGGCCGAA | ACAUUCU | 1952 |
| 550 | UAUGCCA | CUGAUGAGGCCGAAAGGCCGAA | AAUUUCC | 1953 |
| 550 | UAUGCCA | CUGAUGAGGCCGAAAGGCCGAA | AAUUUCC | 1954 |
| 557 | UCAAAUU | CUGAUGAGGCCGAAAGGCCGAA | AUGCCAG | 1955 |
| 561 | CAGGUCA | CUGAUGAGGCCGAAAGGCCGAA | AUUUAUG | 1956 |
| 562 | GCAGGUC | CUGAUGAGGCCGAAAGGCCGAA | AAUUUAU | 1957 |
| 576 | CCUUGCU | CUGAUGAGGCCGAAAGGCCGAA | AGACGUG | 1958 |
| 585 | UUCGGGU | CUGAUGAGGCCGAAAGGCCGAA | ACCUUGC | 1959 |
| 597 | AUCUUCU | CUGAUGAGGCCGAAAGGCCGAA | AGGUUUC | 1960 |
| 607 | CAGAAAA | CUGAUGAGGCCGAAAGGCCGAA | ACAUCUU | 1961 |
| 611 | UUAUCAG | CUGAUGAGGCCGAAAGGCCGAA | AAAUACA | 1962 |
| 625 | AUUAGUU | CUGAUGAGGCCGAAAGGCCGAA | AAUUAGU | 1963 |
| 630 | UACUCAU | CUGAUGAGGCCGAAAGGCCGAA | AGUUGAA | 1964 |

TABLE IX-continued

Mouse B7-2 Hammerhead Ribozyme Sequences

| nt. Position | HH Ribozyme Sequences | | | Seq. ID No. |
|---|---|---|---|---|
| 630 | UACUCAU | CUGAUGAGGCCGAAAGGCCGAA | AGUUGAA | 1965 |
| 637 | AUCACCA | CUGAUGAGGCCGAAAGGCCGAA | ACUCAUU | 1966 |
| 656 | CUUGUGA | CUGAUGAGGCCGAAAGGCCGAA | AUCUGCA | 1967 |
| 658 | AUCUUGU | CUGAUGAGGCCGAAAGGCCGAA | AUAUCUG | 1968 |
| 658 | AUCUUGU | CUGAUGAGGCCGAAAGGCCGAA | AUAUCUG | 1969 |
| 658 | AUCUUGU | CUGAUGAGGCCGAAAGGCCGAA | AUAUCUG | 1970 |
| 658 | AUCUUGU | CUGAUGAGGCCGAAAGGCCGAA | AUAUCUG | 1971 |
| 666 | GUGACAU | CUGAUGAGGCCGAAAGGCCGAA | AUCUUGU | 1972 |
| 666 | GUGACAU | CUGAUGAGGCCGAAAGGCCGAA | AUCUUGU | 1973 |
| 671 | GUUCUGU | CUGAUGAGGCCGAAAGGCCGAA | ACAUUAU | 1974 |
| 671 | GUUCUGU | CUGAUGAGGCCGAAAGGCCGAA | ACAUUAU | 1975 |
| 671 | GUUCUGU | CUGAUGAGGCCGAAAGGCCGAA | ACAUUAU | 1976 |
| 682 | GAUACUG | CUGAUGAGGCCGAAAGGCCGAA | ACAGUUC | 1977 |
| 683 | AGAUACU | CUGAUGAGGCCGAAAGGCCGAA | AACAGUU | 1978 |
| 683 | AGAUACU | CUGAUGAGGCCGAAAGGCCGAA | AACAGUU | 1979 |
| 691 | GCUGUUG | CUGAUGAGGCCGAAAGGCCGAA | AGAUACU | 1980 |
| 691 | GCUGUUG | CUGAUGAGGCCGAAAGGCCGAA | AGAUACU | 1981 |
| 691 | GCUGUUG | CUGAUGAGGCCGAAAGGCCGAA | AGAUACU | 1982 |
| 701 | AAAGAGA | CUGAUGAGGCCGAAAGGCCGAA | AGGCUGU | 1983 |
| 701 | AAAGAGA | CUGAUGAGGCCGAAAGGCCGAA | AGGCUGU | 1984 |
| 703 | UGAAAGA | CUGAUGAGGCCGAAAGGCCGAA | AGAGGCU | 1985 |
| 703 | UGAAAGA | CUGAUGAGGCCGAAAGGCCGAA | AGAGGCU | 1986 |
| 707 | GGAAUGA | CUGAUGAGGCCGAAAGGCCGAA | AGAGAGA | 1987 |
| 707 | GGAAUGA | CUGAUGAGGCCGAAAGGCCGAA | AGAGAGA | 1988 |
| 708 | GGGAAUG | CUGAUGAGGCCGAAAGGCCGAA | AAGAGAG | 1989 |
| 709 | CGGGAAU | CUGAUGAGGCCGAAAGGCCGAA | AAAGAGA | 1990 |
| 709 | CGGGAAU | CUGAUGAGGCCGAAAGGCCGAA | AAAGAGA | 1991 |
| 709 | CGGGAAU | CUGAUGAGGCCGAAAGGCCGAA | AAAGAGA | 1992 |
| 712 | AUCCGGG | CUGAUGAGGCCGAAAGGCCGAA | AUGAAAG | 1993 |
| 712 | AUCCGGG | CUGAUGAGGCCGAAAGGCCGAA | AUGAAAG | 1994 |
| 712 | AUCCGGG | CUGAUGAGGCCGAAAGGCCGAA | AUGAAAG | 1995 |
| 712 | AUCCGGG | CUGAUGAGGCCGAAAGGCCGAA | AUGAAAG | 1996 |
| 712 | AUCCGGG | CUGAUGAGGCCGAAAGGCCGAA | AUGAAAG | 1997 |
| 713 | CAUCCGG | CUGAUGAGGCCGAAAGGCCGAA | AAUGAAA | 1998 |
| 713 | CAUCCGG | CUGAUGAGGCCGAAAGGCCGAA | AAUGAAA | 1999 |
| 732 | ACGGUCA | CUGAUGAGGCCGAAAGGCCGAA | AUGCCAC | 2000 |
| 732 | ACGGUCA | CUGAUGAGGCCGAAAGGCCGAA | AUGCCAC | 2001 |
| 740 | CACACAC | CUGAUGAGGCCGAAAGGCCGAA | ACGGUCA | 2002 |
| 749 | UUUCCAG | CUGAUGAGGCCGAAAGGCCGAA | ACACACA | 2003 |
| 749 | UUUCCAG | CUGAUGAGGCCGAAAGGCCGAA | ACACACA | 2004 |
| 750 | GUUUCCA | CUGAUGAGGCCGAAAGGCCGAA | AACACAC | 2005 |
| 750 | GUUUCCA | CUGAUGAGGCCGAAAGGCCGAA | AACACAC | 2006 |
| 773 | UGGAGGA | CUGAUGAGGCCGAAAGGCCGAA | AUCUUCA | 2007 |
| 778 | AGGUUUG | CUGAUGAGGCCGAAAGGCCGAA | AGGAAAU | 2008 |
| 788 | UGAAAUU | CUGAUGAGGCCGAAAGGCCGAA | AGAGGUU | 2009 |
| 798 | AACUCUU | CUGAUGAGGCCGAAAGGCCGAA | AGUGAAA | 2010 |
| 805 | AGAUGGA | CUGAUGAGGCCGAAAGGCCGAA | ACUCUUG | 2011 |
| 805 | AGAUGGA | CUGAUGAGGCCGAAAGGCCGAA | ACUCUUG | 2012 |
| 806 | GAGAUGG | CUGAUGAGGCCGAAAGGCCGAA | AACUCUU | 2013 |
| 811 | UUGAGGA | CUGAUGAGGCCGAAAGGCCGAA | AUGGAAA | 2014 |
| 811 | UUGAGGA | CUGAUGAGGCCGAAAGGCCGAA | AUGGAAA | 2015 |
| 813 | GUUUGAG | CUGAUGAGGCCGAAAGGCCGAA | AGAUGGA | 2016 |
| 836 | AAGCUGU | CUGAUGAGGCCGAAAGGCCGAA | AUCUCCU | 2017 |
| 836 | AAGCUGU | CUGAUGAGGCCGAAAGGCCGAA | AUCUCCU | 2018 |
| 837 | GAAGCUG | CUGAUGAGGCCGAAAGGCCGAA | AAUCUCC | 2019 |
| 848 | CCACAGU | CUGAUGAGGCCGAAAGGCCGAA | ACUGAAG | 2020 |
| 860 | CAAGGAG | CUGAUGAGGCCGAAAGGCCGAA | AGGGCCA | 2021 |
| 860 | CAAGGAG | CUGAUGAGGCCGAAAGGCCGAA | AGGGCCA | 2022 |
| 878 | CAAUGAU | CUGAUGAGGCCGAAAGGCCGAA | AGCAGCA | 2023 |
| 951 | GCGUUAC | CUGAUGAGGCCGAAAGGCCGAA | AUCCCGC | 2024 |
| 974 | UCAGGUU | CUGAUGAGGCCGAAAGGCCGAA | AUAGUCU | 2025 |
| 989 | GGGGUUC | CUGAUGAGGCCGAAAGGCCGAA | AGUUCCU | 2026 |
| 1006 | UUUUGCU | CUGAUGAGGCCGAAAGGCCGAA | AAGCAAU | 2027 |
| 1055 | AAUUUUU | CUGAUGAGGCCGAAAGGCCGAA | ACUCUUU | 2028 |
| 1056 | CAAUUUU | CUGAUGAGGCCGAAAGGCCGAA | AACUCUU | 2029 |
| 1062 | GCAAAGC | CUGAUGAGGCCGAAAGGCCGAA | AUUUUUA | 2030 |
| 1092 | UUCUGAG | CUGAUGAGGCCGAAAGGCCGAA | AACUCUG | 2031 |
| 1095 | GAAUUCU | CUGAUGAGGCCGAAAGGCCGAA | AGAAACU | 2032 |
| 1101 | AUUUUUG | CUGAUGAGGCCGAAAGGCCGAA | AUUCGGA | 2033 |
| 1101 | AUUUUUG | CUGAUGAGGCCGAAAGGCCGAA | AUUCUGA | 2034 |
| 1101 | AUUUUUG | CUGAUGAGGCCGAAAGGCCGAA | AUUCUGA | 2035 |
| 1111 | AGCUGAG | CUGAUGAGGCCGAAAGGCCGAA | ACAUUUU | 2036 |
| 1112 | CAGCUGA | CUGAUGAGGCCGAAAGGCCGAA | AACAUUU | 2037 |
| 1128 | ACUGUAG | CUGAUGAGGCCGAAAGGCCGAA | AUUCCAA | 2038 |
| 1128 | ACUGUAG | CUGAUGAGGCCGAAAGGCCGAA | AUUCCAA | 2039 |

TABLE IX-continued

Mouse B7-2 Hammerhead Ribozyme Sequences

| nt. Position | HH Ribozyme Sequences | | | Seq. ID No. |
|---|---|---|---|---|
| 1131 | UCAACUG | CUGAUGAGGCCGAAAGGCCGAA | AGAAUUC | 2040 |
| 1131 | UCAACUG | CUGAUGAGGCCGAAAGGCCGAA | AGAAUUC | 2041 |
| 1141 | CUUUAAU | CUGAUGAGGCCGAAAGGCCGAA | AUUCAAC | 2042 |
| 1144 | GUUCUUU | CUGAUGAGGCCGAAAGGCCGAA | AUUAUUC | 2043 |
| 1145 | UGUUCUU | CUGAUGAGGCCGAAAGGCCGAA | AAUUAUU | 2044 |

TABLE X

Human CD40 Hammerhead Ribozyme Target Sequences

| nt. Position | HH Target Sequence | | | Seq. ID No. |
|---|---|---|---|---|
| 9 | CCUCGCU | C | GGGCGCC | 2045 |
| 24 | CAGUGGU | C | CUGCCGC | 2046 |
| 37 | GCCUGGU | C | UCACCUC | 2047 |
| 39 | CUGGUCU | C | ACCUCGC | 2048 |
| 44 | CUCACCU | C | GCCAUGG | 2049 |
| 53 | CCAUGGU | U | CGUCUGC | 2050 |
| 54 | CAUGGUU | C | GUCUGCC | 2051 |
| 57 | GGUUCGU | C | UGCCUCU | 2052 |
| 63 | UCUGCCU | C | UGCAGUG | 2053 |
| 74 | AGUGCGU | C | CUCUGGG | 2054 |
| 77 | GCGUCCU | C | UGGGGCU | 2055 |
| 88 | GGCUGCU | U | GCUGACC | 2056 |
| 101 | CCGCUGU | C | CAUCCAG | 2057 |
| 105 | UGUCCAU | C | CAGAACC | 2058 |
| 139 | AAACAGU | A | CCUAAUA | 2059 |
| 143 | AGUACCU | A | AUAAACA | 2060 |
| 146 | ACCUAAU | A | AACAGUC | 2061 |
| 153 | AAACAGU | C | AGUGCUG | 2062 |
| 162 | GUGCUGU | U | CUUUGUG | 2063 |
| 163 | UGCUGUU | C | UUUGUGC | 2064 |
| 165 | CUGUUCU | U | UGUGCCA | 2065 |
| 166 | UGUUCUU | U | GUGCCAG | 2066 |
| 208 | ACAGAGU | U | CACUGAA | 2067 |
| 209 | CAGAGUU | C | ACUGAAA | 2068 |
| 227 | AAUGCCU | U | CCUUGCG | 2069 |
| 228 | AUGCCUU | C | CUUGCGG | 2070 |
| 231 | CCUUCCU | U | GCGGUGA | 2071 |
| 247 | AGCGAAU | U | CCUAGAC | 2072 |
| 248 | GCGAAUU | C | CUAGACA | 2073 |
| 251 | AAUUCCU | A | GACACCU | 2074 |
| 292 | CACAAAU | A | CUGCGAC | 2075 |
| 308 | CCAACCU | A | GGGCUUC | 2076 |
| 314 | UAGGGCU | U | CGGGUCC | 2077 |
| 315 | AGGGCUU | C | GGGUCCA | 2078 |
| 320 | UUCGGGU | C | CAGCAGA | 2079 |
| 337 | GGCACCU | C | AGAAACA | 2080 |
| 353 | ACACCAU | C | UGCACCU | 2081 |
| 381 | GCACUGU | A | CGAGUGA | 2082 |
| 407 | GCUGUGU | C | CUGCACC | 2083 |
| 418 | CACCGCU | C | AUGCUCG | 2084 |
| 424 | UCAUGCU | C | GCCCGGC | 2085 |
| 433 | CCCGGCU | U | UGGGGUC | 2086 |
| 434 | CCGGCUU | U | GGGGUCA | 2087 |
| 440 | UUGGGGU | C | AAGCAGA | 2088 |
| 449 | AGCAGAU | U | GCUACAG | 2089 |
| 453 | GAUUGCU | A | CAGGGGU | 2090 |
| 461 | CAGGGGU | U | UCUGAUA | 2091 |
| 462 | AGGGGUU | C | UGAUACC | 2092 |
| 463 | GGGGUUU | C | UGAUACC | 2093 |
| 468 | UUCUGAU | A | CCAUCUG | 2094 |
| 473 | AUACCAU | C | UGCGAGC | 2095 |
| 491 | GCCCAGU | C | GGCUUCU | 2096 |
| 496 | GUCCGCU | U | CUUCUCC | 2097 |
| 497 | UCGGCUU | C | UUCUCCA | 2098 |
| 499 | GGCUUCU | U | CUCCAAU | 2099 |
| 500 | GCUUCUU | C | UCCAAUG | 2100 |
| 502 | UUCUUCU | C | CAAUGUG | 2101 |
| 511 | AAUGUGU | C | AUCUGCU | 2102 |
| 514 | GUGUCAU | C | UGCUUUC | 2103 |
| 519 | AUCUGCU | U | UCGAAAA | 2104 |
| 520 | UCUGCUU | U | CGAAAAA | 2105 |
| 521 | CUGCUUU | C | GAAAAAU | 2106 |
| 531 | AAAAUGU | C | ACCCUUG | 2107 |
| 537 | UCACCCU | U | GGACAAG | 2108 |
| 566 | ACCUGGU | U | GUGCAAC | 2109 |
| 599 | CUGAUGU | U | GUCUGUG | 2110 |
| 602 | AUGUUGU | C | UGUGGUC | 2111 |
| 609 | CUGUGGU | C | CCCAGGA | 2112 |
| 618 | CCAGGAU | C | GGCUGAG | 2113 |
| 641 | UGGUGAU | C | CCCAUCA | 2114 |
| 647 | UCCCCAU | C | AUCUUCG | 2115 |
| 650 | CCAUCAU | C | UUCGGGA | 2116 |
| 652 | AUCAUCU | U | CGGGAUC | 2117 |
| 653 | UCAUCUU | C | GGGAUCC | 2118 |
| 659 | UCGGGAU | C | CUGUUUG | 2119 |
| 664 | AUCCUGU | U | UGCCAUC | 2120 |
| 665 | UCCUGUU | U | GCCAUCC | 2121 |
| 671 | UUGCCAU | C | CUCUUGG | 2122 |
| 674 | CCAUCCU | C | UUGGUGC | 2123 |
| 676 | AUCCUCU | U | GGUGCUG | 2124 |
| 686 | UGCUGGU | C | UUUAUCA | 2125 |
| 688 | CUGGUCU | U | UAUCAAA | 2126 |
| 689 | UGGUCUU | U | AUCAAAA | 2127 |
| 690 | GGUCUUU | A | UCAAAAA | 2128 |
| 692 | UCUUUAU | C | AAAAAGG | 2129 |
| 720 | AACCAAU | A | AGGCCCC | 2130 |
| 755 | AGGAGAU | U | AAUUUUC | 2131 |
| 759 | GAUCAAU | U | UUCCCGA | 2132 |
| 760 | AUCAAUU | U | UCCCGAC | 2133 |
| 761 | UCAAUUU | U | CCCGACG | 2134 |
| 762 | CAAUUUU | C | CCGACGA | 2135 |
| 771 | CGACGAU | C | UUCCUGG | 2136 |
| 773 | ACGAUCU | U | CCUGGCU | 2137 |
| 774 | CGAUCUU | C | CUGGCUC | 2138 |
| 781 | CCUGGCU | C | CAACACU | 2139 |
| 795 | UGCUGCU | C | CAGUGCA | 2140 |
| 810 | GGAGACU | U | UACAUGG | 2141 |
| 811 | GAGACUU | U | ACAUGGA | 2142 |
| 812 | AGACUUU | A | CAUGGAU | 2143 |
| 830 | AACCGGU | C | ACCCAGG | 2144 |
| 855 | AGAGAGU | C | GCAUCUC | 2145 |
| 860 | GUCGCAU | C | UCAGUGC | 2146 |
| 862 | CGCAUCU | C | AGUGCAG | 2147 |
| 927 | AGGCAGU | U | GGCCAGA | 2148 |
| 981 | GGGAGCU | A | UGCCCAG | 2149 |
| 990 | GCCCAGU | C | AGUGCCA | 2150 |

TABLE XI

Human CD40 Hammerhead Ribozyme Sequences

| nt. Position | HH Ribozyme Sequences | | | Seq. ID No. |
|---|---|---|---|---|
| 9 | GGCGCCC | CUGAUGAGGCCGAAAGGCCGAA | AGCGAGG | 2151 |
| 24 | GCGGCAG | CUGAUGAGGCCGAAAGGCCGAA | ACCACUG | 2152 |
| 37 | GAGGUGA | CUGAUGAGGCCGAAAGGCCGAA | ACCAGGC | 2153 |
| 39 | GCGAGGU | CUGAUGAGGCCGAAAGGCCGAA | AGACCAG | 2154 |
| 44 | CCAUGGC | CUGAUGAGGCCGAAAGGCCGAA | AGGUGAG | 2155 |
| 53 | GCAGACG | CUGAUGAGGCCGAAAGGCCGAA | ACCAUGG | 2156 |
| 54 | GGCAGAC | CUGAUGAGGCCGAAAGGCCGAA | AACCAUG | 2157 |
| 57 | AGAGGCA | CUGAUGAGGCCGAAAGGCCGAA | ACGAACC | 2158 |
| 63 | CACUGCA | CUGAUGAGGCCGAAAGGCCGAA | AGGCAGA | 2159 |
| 74 | CCCAGAG | CUGAUGAGGCCGAAAGGCCGAA | ACGCACU | 2160 |
| 77 | AGCCCCA | CUGAUGAGGCCGAAAGGCCGAA | AGGACGC | 2161 |
| 88 | GGUCAGC | CUGAUGAGGCCGAAAGGCCGAA | AGCAGCC | 2162 |
| 101 | CUGGAUG | CUGAUGAGGCCGAAAGGCCGAA | ACAGCGG | 2163 |
| 105 | GGUUCUG | CUGAUGAGGCCGAAAGGCCGAA | AUGGACA | 2164 |
| 139 | UAUUAGG | CUGAUGAGGCCGAAAGGCCGAA | ACUGUUU | 2165 |
| 143 | UGUUUAU | CUGAUGAGGCCGAAAGGCCGAA | AGGUACU | 2166 |
| 146 | GACUGUU | CUGAUGAGGCCGAAAGGCCGAA | AUUAGGU | 2167 |
| 153 | CAGCACU | CUGAUGAGGCCGAAAGGCCGAA | ACUGUUU | 2168 |
| 162 | CACAAAG | CUGAUGAGGCCGAAAGGCCGAA | ACAGCAC | 2169 |
| 163 | GCACAAA | CUGAUGAGGCCGAAAGGCCGAA | AACAGCA | 2170 |
| 165 | UGGCACA | CUGAUGAGGCCGAAAGGCCGAA | AGAACAG | 2171 |
| 166 | CUGGCAC | CUGAUGAGGCCGAAAGGCCGAA | AAGAACA | 2172 |
| 208 | UUCAGUG | CUGAUGAGGCCGAAAGGCCGAA | ACUCUGU | 2173 |
| 209 | UUUCAGU | CUGAUGAGGCCGAAAGGCCGAA | AACUCUG | 2174 |
| 227 | CGCAAGG | CUGAUGAGGCCGAAAGGCCGAA | AGGCAUU | 2175 |
| 228 | CCGCAAG | CUGAUGAGGCCGAAAGGCCGAA | AAGGCAU | 2176 |
| 231 | UCACCGC | CUGAUGAGGCCGAAAGGCCGAA | AGGAAGG | 2177 |
| 247 | GUCUAGG | CUGAUGAGGCCGAAAGGCCGAA | AUUCGCU | 2178 |
| 248 | UGUCUAG | CUGAUGAGGCCGAAAGGCCGAA | AAUUCGC | 2179 |
| 251 | AGGUGUC | CUGAUGAGGCCGAAAGGCCGAA | AGGAAUU | 2180 |
| 292 | GUCGCAG | CUGAUGAGGCCGAAAGGCCGAA | AUUUGUG | 2181 |
| 308 | GAAGCCC | CUGAUGAGGCCGAAAGGCCGAA | AGGUUGG | 2182 |
| 314 | GGACCCG | CUGAUGAGGCCGAAAGGCCGAA | AGCCCUA | 2183 |
| 315 | UGGACCC | CUGAUGAGGCCGAAAGGCCGAA | AAGCCCU | 2184 |
| 320 | UCUGCUG | CUGAUGAGGCCGAAAGGCCGAA | ACCCGAA | 2185 |
| 337 | UGUUUCU | CUGAUGAGGCCGAAAGGCCGAA | AGGUUCC | 2186 |
| 353 | AGGUGCA | CUGAUGAGGCCGAAAGGCCGAA | AUGGUGU | 2187 |
| 381 | UCACUCG | CUGAUGAGGCCGAAAGGCCGAA | ACAGUGC | 2188 |
| 407 | GGUGCAG | CUGAUGAGGCCGAAAGGCCGAA | ACACAGC | 2189 |
| 418 | CGAGCAU | CUGAUGAGGCCGAAAGGCCGAA | AGCGGUG | 2190 |
| 424 | GCCGGGC | CUGAUGAGGCCGAAAGGCCGAA | AGCAUGA | 2191 |
| 433 | GACCCCA | CUGAUGAGGCCGAAAGGCCGAA | AGCCGGG | 2192 |
| 434 | UGACCCC | CUGAUGAGGCCGAAAGGCCGAA | AAGCCGG | 2193 |
| 440 | UCUGCUU | CUGAUGAGGCCGAAAGGCCGAA | ACCCCAA | 2194 |
| 449 | CUGUAGC | CUGAUGAGGCCGAAAGGCCGAA | AUCUGCU | 2195 |
| 453 | ACCCCUG | CUGAUGAGGCCGAAAGGCCGAA | AGCAAUC | 2196 |
| 461 | UAUCAGA | CUGAUGAGGCCGAAAGGCCGAA | ACCCCUG | 2197 |
| 462 | GUAUCAG | CUGAUGAGGCCGAAAGGCCGAA | AACCCCU | 2198 |
| 463 | GGUAUCA | CUGAUGAGGCCGAAAGGCCGAA | AAACCCC | 2199 |
| 468 | CAGAUGG | CUGAUGAGGCCGAAAGGCCGAA | AUCAGAA | 2200 |
| 473 | GCUCGCA | CUGAUGAGGCCGAAAGGCCGAA | AUGGUAU | 2201 |
| 491 | AGAAGCC | CUGAUGAGGCCGAAAGGCCGAA | ACUGGGC | 2202 |
| 496 | GGAGAAG | CUGAUGAGGCCGAAAGGCCGAA | AGCCGAC | 2203 |
| 497 | UGGAGAA | CUGAUGAGGCCGAAAGGCCGAA | AAGCCGA | 2204 |
| 499 | AUUGGAG | CUGAUGAGGCCGAAAGGCCGAA | AGAAGCC | 2205 |
| 500 | CAUUGGA | CUGAUGAGGCCGAAAGGCCGAA | AAGAAGC | 2206 |
| 502 | CACAUUG | CUGAUGAGGCCGAAAGGCCGAA | AGAAGAA | 2207 |
| 511 | AGCAGAU | CUGAUGAGGCCGAAAGGCCGAA | ACACAUU | 2208 |
| 514 | GAAAGCA | CUGAUGAGGCCGAAAGGCCGAA | AUGACAC | 2209 |
| 519 | UUUUCGA | CUGAUGAGGCCGAAAGGCCGAA | AGCAGAU | 2210 |
| 520 | UUUUUCG | CUGAUGAGGCCGAAAGGCCGAA | AAGCAGA | 2211 |
| 521 | AUUUUUC | CUGAUGAGGCCGAAAGGCCGAA | AAAGCAG | 2212 |
| 531 | CAAGGGU | CUGAUGAGGCCGAAAGGCCGAA | ACAUUUU | 2213 |
| 537 | CUUGUCC | CUGAUGAGGCCGAAAGGCCGAA | AGGGUGA | 2214 |
| 566 | GUUGCAC | CUGAUGAGGCCGAAAGGCCGAA | ACCAGGU | 2215 |
| 599 | CACAGAC | CUGAUGAGGCCGAAAGGCCGAA | ACAUCAG | 2216 |
| 602 | GACCACA | CUGAUGAGGCCGAAAGGCCGAA | ACAACAU | 2217 |
| 609 | UCCUGGG | CUGAUGAGGCCGAAAGGCCGAA | ACCACAG | 2218 |
| 618 | CUCAGCC | CUGAUGAGGCCGAAAGGCCGAA | AUCCUGG | 2219 |
| 641 | UGAUGGG | CUGAUGAGGCCGAAAGGCCGAA | AUCACCA | 2220 |
| 647 | CGAAGAU | CUGAUGAGGCCGAAAGGCCGAA | AUGGGGA | 2221 |
| 650 | UCCCGAA | CUGAUGAGGCCGAAAGGCCGAA | AUGAUGG | 2222 |
| 652 | GAUCCCG | CUGAUGAGGCCGAAAGGCCGAA | AGAUGAU | 2223 |
| 653 | GGAUCCC | CUGAUGAGGCCGAAAGGCCGAA | AAGAUGA | 2224 |
| 659 | CAAACAG | CUGAUGAGGCCGAAAGGCCGAA | AUCCCGA | 2225 |

TABLE XI-continued

Human CD40 Hammerhead Ribozyme Sequences

| nt. Position | HH Ribozyme Sequences | | | Seq. ID No. |
|---|---|---|---|---|
| 664 | GAUGGCA | CUGAUGAGGCCGAAAGGCCGAA | ACAGGAU | 2226 |
| 665 | GGAUGGC | CUGAUGAGGCCGAAAGGCCGAA | AACAGGA | 2227 |
| 671 | CCAAGAG | CUGAUGAGGCCGAAAGGCCGAA | AUGGCAA | 2228 |
| 674 | GCACCAA | CUGAUGAGGCCGAAAGGCCGAA | AGGAUGG | 2229 |
| 676 | CAGCACC | CUGAUGAGGCCGAAAGGCCGAA | AGAGGAU | 2230 |
| 686 | UGAUAAA | CUGAUGAGGCCGAAAGGCCGAA | ACCAGCA | 2231 |
| 688 | UUUGAUA | CUGAUGAGGCCGAAAGGCCGAA | AGACCAG | 2232 |
| 689 | UUUUGAU | CUGAUGAGGCCGAAAGGCCGAA | AAGACCA | 2233 |
| 690 | UUUUUGA | CUGAUGAGGCCGAAAGGCCGAA | AAAGACC | 2234 |
| 692 | CCUUUUU | CUGAUGAGGCCGAAAGGCCGAA | AUAAAGA | 2235 |
| 720 | GGGGCCU | CUGAUGAGGCCGAAAGGCCGAA | AUUGGUU | 2236 |
| 755 | GAAAAUU | CUGAUGAGGCCGAAAGGCCGAA | AUCUCCU | 2237 |
| 759 | UCGGGAA | CUGAUGAGGCCGAAAGGCCGAA | AUUGAUC | 2238 |
| 760 | GUCGGGA | CUGAUGAGGCCGAAAGGCCGAA | AAUUGAU | 2239 |
| 761 | CGUCGGG | CUGAUGAGGCCGAAAGGCCGAA | AAAUUGA | 2240 |
| 762 | UCGUCGG | CUGAUGAGGCCGAAAGGCCGAA | AAAAUUG | 2241 |
| 771 | CCAGGAA | CUGAUGAGGCCGAAAGGCCGAA | AUCGUCG | 2242 |
| 773 | AGCCAGG | CUGAUGAGGCCGAAAGGCCGAA | AGAUCGU | 2243 |
| 774 | GAGCCAG | CUGAUGAGGCCGAAAGGCCGAA | AAGAUCG | 2244 |
| 781 | AGUGUUG | CUGAUGAGGCCGAAAGGCCGAA | AGCCAGG | 2245 |
| 795 | UGCACUG | CUGAUGAGGCCGAAAGGCCGAA | AGCAGCA | 2246 |
| 810 | CCAUGUA | CUGAUGAGGCCGAAAGGCCGAA | AGUCUCC | 2247 |
| 811 | UCCAUGU | CUGAUGAGGCCGAAAGGCCGAA | AAGUCUC | 2248 |
| 812 | AUCCAUG | CUGAUGAGGCCGAAAGGCCGAA | AAAGUCU | 2249 |
| 830 | CCUGGGU | CUGAUGAGGCCGAAAGGCCGAA | ACCGGUU | 2250 |
| 855 | GAGAUGC | CUGAUGAGGCCGAAAGGCCGAA | ACUCUCU | 2251 |
| 860 | GCACUGA | CUGAUGAGGCCGAAAGGCCGAA | AUGCGAC | 2252 |
| 862 | CUGCACU | CUGAUGAGGCCGAAAGGCCGAA | AGAUGCG | 2253 |
| 927 | UCUGGCC | CUGAUGAGGCCGAAAGGCCGAA | ACUGCCU | 2254 |
| 981 | CUGGGCA | CUGAUGAGGCCGAAAGGCCGAA | AGCUCCC | 2255 |
| 990 | UGGCACU | CUGAUGAGGCCGAAAGGCCGAA | ACUGGGC | 2256 |

TABLE XII

Mouse CD40 Hammerhead Ribozyme Target Sequences

| nt. Position | HH Target Sequence | | | Seq. ID No. |
|---|---|---|---|---|
| 18 | GGUgucU | u | UGCCUCg | 2257 |
| 18 | GGuguCU | u | UGCCUcG | 2258 |
| 24 | UuUGCCU | C | gGCuGUG | 2259 |
| 38 | GCGcgCU | a | UGGGGCU | 2260 |
| 62 | CagcGGU | c | CaUCUag | 2261 |
| 62 | CaGCgGU | C | CAUCuAG | 2262 |
| 66 | gGUCCAU | C | uAGggCa | 2263 |
| 80 | AGUGuGU | u | acgUGca | 2264 |
| 80 | AgUGUGU | u | AcgUGCa | 2265 |
| 81 | gUGugUU | a | CgUGCaG | 2266 |
| 100 | AAACAGU | A | CCUccac | 2267 |
| 126 | CUGUgaU | U | UGUGCCA | 2268 |
| 127 | UGUgaUU | U | GUGCCAG | 2269 |
| 170 | CAgcUcU | u | gaGAaGA | 2270 |
| 208 | gGCGAAU | U | CucAGcC | 2271 |
| 209 | GCGAAUU | C | ucAGcCc | 2272 |
| 233 | gGGAGAU | u | cgcUgUC | 2273 |
| 267 | ACCcAAU | c | AAggGcu | 2274 |
| 267 | AcCCAAU | c | AaGggCu | 2275 |
| 275 | aAGGGCU | U | CGGGUua | 2276 |
| 275 | AaGGGcU | U | CgGgUua | 2277 |
| 276 | AGGGCUU | C | GGGUuaA | 2278 |
| 281 | UUCGGGU | u | aAGaAGg | 2279 |
| 281 | UUcGGGU | u | AAGaAGg | 2280 |
| 314 | ACACugU | C | UGuACCU | 2281 |
| 354 | caAgGaU | a | GCgaGGC | 2282 |
| 386 | cCugUaU | c | CCUGGCU | 2283 |
| 394 | CCUgGCU | u | uGGaGuu | 2284 |
| 394 | CCuGGCU | U | UGGaGUu | 2285 |
| 395 | CuGGCUU | U | GGaGUuA | 2286 |
| 429 | caCUGAU | A | CCgUCUG | 2287 |
| 434 | AUACCgU | C | UGucAuC | 2288 |
| 434 | AUaCcGU | c | UGuCAUC | 2289 |
| 441 | CugUCaU | C | CcuGCcC | 2290 |
| 452 | GCCCAGU | C | GGCUUCU | 2291 |
| 452 | GCCCAGU | C | gGcuuCu | 2292 |
| 457 | GUCGGCU | U | CUUCUCC | 2293 |
| 458 | UCGGCUU | C | UUCUCCA | 2294 |
| 460 | GGCUUCU | U | CUCCAAU | 2295 |
| 461 | GCUUCUU | C | UCCAAUc | 2296 |
| 463 | UUCUUCU | C | CAAUcaG | 2297 |
| 472 | AAuCAGU | C | AucaCUu | 2298 |
| 472 | AAUcagU | c | auCACuU | 2299 |
| 479 | cAUCAcU | U | UUCgaaA | 2300 |
| 480 | AUCacuU | U | UCGAAAA | 2301 |
| 481 | UCacuUU | U | CGAAAAg | 2302 |
| 481 | UCACuuU | U | cGAaAAG | 2303 |
| 492 | AAAgUGU | u | AuCCcUG | 2304 |
| 560 | CUaAUGU | c | aUCUGUG | 2305 |
| 563 | AUGUcaU | C | UGUGGGu | 2306 |
| 572 | gUGGUuU | a | AagUCcC | 2307 |
| 572 | GuGGUUU | a | aagUcCC | 2308 |
| 577 | UuAAagU | c | CCgGAuG | 2309 |
| 620 | UGGgcAU | C | CuCAUCA | 2310 |
| 626 | UCCuCAU | C | AcCaUuu | 2311 |
| 632 | uCAcCAU | u | UUCGGGg | 2312 |
| 632 | UcaCCAU | u | uUCggGG | 2313 |
| 634 | AcCAUuU | U | CGGGgUg | 2314 |
| 635 | CCaUuuU | c | GgGGUGu | 2315 |
| 635 | cCAUuUU | U | GGGgUgu | 2316 |
| 635 | CCAUuuU | C | ggGGUGu | 2317 |
| 647 | UGuUucU | C | UaUAUCA | 2318 |
| 649 | uUucUCU | a | UAUCAAA | 2319 |
| 651 | ucUCUaU | A | UCAAAAA | 2320 |
| 653 | UCUaUAU | C | AAAAAGG | 2321 |
| 735 | gGAaGAU | u | aUCCcGG | 2322 |

TABLE XII-continued

Mouse CD40 Hammerhead Ribozyme Target Sequences

| nt. Position | HH Target Sequence | | | Seq. ID No. |
|---|---|---|---|---|
| 759 | cGCUGCU | C | CAGUGCA | 2323 |
| 794 | AgCCuGU | C | ACaCAGG | 2324 |
| 794 | AGcCuGU | c | acaCAGg | 2325 |
| 819 | AGAGAGU | C | GCAUCUC | 2326 |
| 824 | GUCGCAU | C | UCAGUGC | 2327 |
| 826 | CGCAUCU | C | AGUGCAG | 2328 |
| 876 | cCCUGGU | C | UgAaCcC | 2329 |
| 913 | GGCUGCU | U | GCUGACC | 2330 |
| 997 | CUCAaCU | u | GCuuUuu | 2331 |
| 1003 | uUGCUUU | u | UAAggAU | 2332 |
| 1003 | uugCUUU | u | UAaGGAU | 2333 |
| 1023 | gaAAgCU | c | GGGCaUC | 2334 |
| 1048 | CAGuGaU | a | UCUaccA | 2335 |
| 1052 | gAUauCU | a | CCaaGuG | 2336 |
| 1081 | CCAGagU | u | GuCUugc | 2337 |
| 1084 | gAGUuGU | C | uUGCuGC | 2338 |
| 1086 | gUugUCU | U | GcUGCgG | 2339 |
| 1097 | gCgGcGU | U | CACUGuA | 2340 |
| 1098 | CgGcGUU | C | ACUGuAA | 2341 |
| 1118 | cgUgGCU | A | CAGGaGU | 2342 |
| 1118 | CgUGGCU | a | CaggAgU | 2343 |
| 1141 | CgCaGCU | u | gUGCUCG | 2344 |
| 1164 | aCCUGgU | U | GCCAUCa | 2345 |
| 1202 | UGuaaUU | a | UUUaUaC | 2346 |
| 1220 | gGcAuCU | c | AgAAACu | 2347 |
| 1220 | GGCAuCU | C | AGAAACu | 2348 |
| 1228 | aGAaACU | c | UAgcaGG | 2349 |
| 1253 | AaCaGGU | a | GUGgAAu | 2350 |
| 1331 | AGgAGcU | U | GCUgCcc | 2351 |
| 1362 | uUuUGaU | C | CCugGGA | 2352 |
| 1373 | gGGaCUU | c | AUgguAA | 2353 |
| 1373 | GgGACUU | c | AugguaA | 2354 |
| 1413 | uUGUCAU | u | UGaccUC | 2355 |
| 1443 | GUaaUGU | a | CcccGUG | 2356 |
| 1470 | CACAuAU | c | CUaaaAu | 2357 |
| 1492 | GugGUGU | a | uUGuAga | 2358 |
| 1497 | GuAuUGU | A | gaAaUuA | 2359 |
| 1508 | auUauUU | a | aUCcGCC | 2360 |
| 1508 | AUuAuUU | a | auCCGcC | 2361 |
| 1523 | cuGGGuU | u | CUaccUG | 2362 |

TABLE XIII

Mouse CD40 Hammerhead Ribozyme Sequences

| nt. Position | HH Ribozyme Sequences | | | Seq. ID No. |
|---|---|---|---|---|
| 18 | CGAGGCA | CUGAUGAGGCCGAAAGGCCGAA | AGACACC | 2363 |
| 18 | CGAGGCA | CUGAUGAGGCCGAAAGGCCGAA | AGACACC | 2364 |
| 24 | CACAGCC | CUGAUGAGGCCGAAAGGCCGAA | AGGCAAA | 2365 |
| 38 | AGCCCCA | CUGAUGAGGCCGAAAGGCCGAA | AGCGCGC | 2366 |
| 62 | CUAGAUG | CUGAUGAGGCCGAAAGGCCGAA | ACCGCUG | 2367 |
| 62 | CUAGAUG | CUGAUGAGGCCGAAAGGCCGAA | ACCGCUG | 2368 |
| 66 | UGCCCUA | CUGAUGAGGCCGAAAGGCCGAA | AUGGACC | 2369 |
| 80 | UGCACGU | CUGAUGAGGCCGAAAGGCCGAA | ACACACU | 2370 |
| 80 | UGCACGU | CUGAUGAGGCCGAAAGGCCGAA | ACACACU | 2371 |
| 81 | CUGCACG | CUGAUGAGGCCGAAAGGCCGAA | AACACAC | 2372 |
| 100 | GUGGAGG | CUGAUGAGGCCGAAAGGCCGAA | ACUGUUU | 2373 |
| 126 | UGGCACA | CUGAUGAGGCCGAAAGGCCGAA | AUCACAG | 2374 |
| 127 | CUGGCAC | CUGAUGAGGCCGAAAGGCCGAA | AAUCACA | 2375 |
| 170 | UCUUCUC | CUGAUGAGGCCGAAAGGCCGAA | AGAGCUG | 2376 |
| 208 | GGCUGAG | CUGAUGAGGCCGAAAGGCCGAA | AUUCGCC | 2377 |
| 209 | GGGCUGA | CUGAUGAGGCCGAAAGGCCGAA | AAUUCGC | 2378 |
| 233 | GACAGCG | CUGAUGAGGCCGAAAGGCCGAA | AUCUCCC | 2379 |
| 267 | AGCCCUU | CUGAUGAGGCCGAAAGGCCGAA | AUUGGGU | 2380 |
| 267 | AGCCCUU | CUGAUGAGGCCGAAAGGCCGAA | AUUGGGU | 2381 |
| 275 | UAACCCG | CUGAUGAGGCCGAAAGGCCGAA | AGCCCUU | 2382 |
| 275 | UAACCCG | CUGAUGAGGCCGAAAGGCCGAA | AGCCCUU | 2383 |
| 276 | UUAACCC | CUGAUGAGGCCGAAAGGCCGAA | AAGCCCU | 2384 |
| 281 | CCUUCUU | CUGAUGAGGCCGAAAGGCCGAA | ACCCGAA | 2385 |
| 281 | CCUUCUU | CUGAUGAGGCCGAAAGGCCGAA | ACCCGAA | 2386 |
| 314 | AGGUACA | CUGAUGAGGCCGAAAGGCCGAA | ACAGUGU | 2387 |
| 354 | GCCUCGC | CUGAUGAGGCCGAAAGGCCGAA | AUCCUUG | 2388 |
| 386 | AGCCAGG | CUGAUGAGGCCGAAAGGCCGAA | AUACAGG | 2389 |
| 394 | AACUCCA | CUGAUGAGGCCGAAAGGCCGAA | AGCCAGG | 2390 |
| 394 | AACUCCA | CUGAUGAGGCCGAAAGGCCGAA | AGCCAGG | 2391 |
| 395 | UAACUCC | CUGAUGAGGCCGAAAGGCCGAA | AAGCCAG | 2392 |

TABLE XIII-continued

Mouse CD40 Hammerhead Ribozyme Sequences

| nt. Position | HH Ribozyme Sequences | | | Seq. ID No. |
|---|---|---|---|---|
| 429 | CAGACGG | CUGAUGAGGCCGAAAGGCCGAA | AUCAGUG | 2393 |
| 434 | GAUGACA | CUGAUGAGGCCGAAAGGCCGAA | ACGGUAU | 2394 |
| 434 | GAUGACA | CUGAUGAGGCCGAAAGGCCGAA | ACGGUAU | 2395 |
| 441 | GGGCAGG | CUGAUGAGGCCGAAAGGCCGAA | AUGACAG | 2396 |
| 452 | AGAAGCC | CUGAUGAGGCCGAAAGGCCGAA | ACUGGGC | 2397 |
| 452 | AGAAGCC | CUGAUGAGGCCGAAAGGCCGAA | ACUGGGC | 2398 |
| 457 | GGAGAAG | CUGAUGAGGCCGAAAGGCCGAA | AGCCGAC | 2399 |
| 458 | UGGAGAA | CUGAUGAGGCCGAAAGGCCGAA | AAGCCGA | 2400 |
| 460 | AUUGGAG | CUGAUGAGGCCGAAAGGCCGAA | AGAAGCC | 2401 |
| 461 | GAUUGGA | CUGAUGAGGCCGAAAGGCCGAA | AAGAAGC | 2402 |
| 463 | CUGAUUG | CUGAUGAGGCCGAAAGGCCGAA | AGAAGAA | 2403 |
| 472 | AAGUGAU | CUGAUGAGGCCGAAAGGCCGAA | ACUGAUU | 2404 |
| 472 | AAGUGAU | CUGAUGAGGCCGAAAGGCCGAA | ACUGAUU | 2405 |
| 479 | UUUCGAA | CUGAUGAGGCCGAAAGGCCGAA | AGUGAUG | 2406 |
| 480 | UUUCGA | CUGAUGAGGCCGAAAGGCCGAA | AAGUGAU | 2407 |
| 481 | CUUUUCG | CUGAUGAGGCCGAAAGGCCGAA | AAAGUGA | 2408 |
| 481 | CUUUUCG | CUGAUGAGGCCGAAAGGCCGAA | AAAGUGA | 2409 |
| 492 | CAGGGAU | CUGAUGAGGCCGAAAGGCCGAA | ACACUUU | 2410 |
| 560 | CACAGAU | CUGAUGAGGCCGAAAGGCCGAA | ACAUUAG | 2411 |
| 563 | AACCACA | CUGAUGAGGCCGAAAGGCCGAA | AUGACAU | 2412 |
| 572 | GGGACUU | CUGAUGAGGCCGAAAGGCCGAA | AAACCAC | 2413 |
| 572 | GGGACUU | CUGAUGAGGCCGAAAGGCCGAA | AAACCAC | 2414 |
| 577 | CAUCCGG | CUGAUGAGGCCGAAAGGCCGAA | ACUUUAA | 2415 |
| 620 | UGAUGAG | CUGAUGAGGCCGAAAGGCCGAA | AUGCCCA | 2416 |
| 626 | AAAUGGU | CUGAUGAGGCCGAAAGGCCGAA | AUGAGGA | 2417 |
| 632 | CCCCGAA | CUGAUGAGGCCGAAAGGCCGAA | AUGGUGA | 2418 |
| 632 | CCCCGAA | CUGAUGAGGCCGAAAGGCCGAA | AUGGUGA | 2419 |
| 634 | CACCCCG | CUGAUGAGGCCGAAAGGCCGAA | AAAUGGU | 2420 |
| 635 | ACACCCC | CUGAUGAGGCCGAAAGGCCGAA | AAAAUGG | 2421 |
| 635 | ACACCCC | CUGAUGAGGCCGAAAGGCCGAA | AAAAUGG | 2422 |
| 635 | ACACCCC | CUGAUGAGGCCGAAAGGCCGAA | AAAAUGG | 2423 |
| 647 | UGAUAUA | CUGAUGAGGCCGAAAGGCCGAA | AGAAACA | 2424 |
| 649 | UUUGAUA | CUGAUGAGGCCGAAAGGCCGAA | AGAGAAA | 2425 |
| 651 | UUUUUGA | CUGAUGAGGCCGAAAGGCCGAA | AUAGAGA | 2426 |
| 653 | CCUUUUU | CUGAUGAGGCCGAAAGGCCGAA | AUAUAGA | 2427 |
| 735 | CCGGGAU | CUGAUGAGGCCGAAAGGCCGAA | AUCUUCC | 2428 |
| 759 | UGCACUG | CUGAUGAGGCCGAAAGGCCGAA | AGCAGCG | 2429 |
| 794 | CCUGUGU | CUGAUGAGGCCGAAAGGCCGAA | ACAGGCU | 2430 |
| 794 | CCUGUGU | CUGAUGAGGCCGAAAGGCCGAA | ACAGGCU | 2431 |
| 819 | GAGAUGC | CUGAUGAGGCCGAAAGGCCGAA | ACUCUCU | 2432 |
| 824 | GCACUGA | CUGAUGAGGCCGAAAGGCCGAA | AUGCGAC | 2433 |
| 826 | CUGCACU | CUGAUGAGGCCGAAAGGCCGAA | AGAUGCG | 2434 |
| 876 | GGGUUCA | CUGAUGAGGCCGAAAGGCCGAA | ACCAGGG | 2435 |
| 913 | GGUCAGC | CUGAUGAGGCCGAAAGGCCGAA | AGCAGCC | 2436 |
| 997 | AAAAAGC | CUGAUGAGGCCGAAAGGCCGAA | AGUUGAG | 2437 |
| 1003 | AUCCUUA | CUGAUGAGGCCGAAAGGCCGAA | AAAGCAA | 2438 |
| 1003 | AUCCUUA | CUGAUGAGGCCGAAAGGCCGAA | AAAGCAA | 2439 |
| 1023 | GAUGCCC | CUGAUGAGGCCGAAAGGCCGAA | AGCUUUC | 2440 |
| 1048 | UGGUAGA | CUGAUGAGGCCGAAAGGCCGAA | AUCACUG | 2441 |
| 1052 | CACUUGG | CUGAUGAGGCCGAAAGGCCGAA | AGAUAUC | 2442 |
| 1081 | GCAAGAC | CUGAUGAGGCCGAAAGGCCGAA | ACUCUGG | 2443 |
| 1084 | GCAGCAA | CUGAUGAGGCCGAAAGGCCGAA | ACAACUC | 2444 |
| 1086 | CCGCAGC | CUGAUGAGGCCGAAAGGCCGAA | AGACAAC | 2445 |
| 1097 | UACAGUG | CUGAUGAGGCCGAAAGGCCGAA | ACGCCGC | 2446 |
| 1098 | UUACAGU | CUGAUGAGGCCGAAAGGCCGAA | AACGCCG | 2447 |
| 1118 | ACUCCUG | CUGAUGAGGCCGAAAGGCCGAA | AGCCACG | 2448 |
| 1118 | ACUCCUG | CUGAUGAGGCCGAAAGGCCGAA | AGCCACG | 2449 |
| 1141 | CGAGCAC | CUGAUGAGGCCGAAAGGCCGAA | AGCUGCG | 2450 |
| 1164 | UGAUGGC | CUGAUGAGGCCGAAAGGCCGAA | ACCAGGU | 2451 |
| 1202 | GUAUAAA | CUGAUGAGGCCGAAAGGCCGAA | AAUUACA | 2452 |
| 1220 | AGUUUCU | CUGAUGAGGCCGAAAGGCCGAA | AGAUGCC | 2453 |
| 1220 | AGUUUCU | CUGAUGAGGCCGAAAGGCCGAA | AGAUGCC | 2454 |
| 1228 | CCUGCUA | CUGAUGAGGCCGAAAGGCCGAA | AGUUUCU | 2455 |
| 1253 | AUUCCAC | CUGAUGAGGCCGAAAGGCCGAA | ACCUGUU | 2456 |
| 1331 | GGGCAGC | CUGAUGAGGCCGAAAGGCCGAA | AGCUCCU | 2457 |
| 1362 | UCCCAGG | CUGAUGAGGCCGAAAGGCCGAA | AUCAAAA | 2458 |
| 1373 | UUACCAU | CUGAUGAGGCCGAAAGGCCGAA | AAGUCCC | 2459 |
| 1373 | UUACCAU | CUGAUGAGGCCGAAAGGCCGAA | AAGUCCC | 2460 |
| 1413 | GAGGUCA | CUGAUGAGGCCGAAAGGCCGAA | AUGACAA | 2461 |
| 1443 | CACGGGG | CUGAUGAGGCCGAAAGGCCGAA | ACAUUAC | 2462 |
| 1470 | AUUUUAG | CUGAUGAGGCCGAAAGGCCGAA | AUAUGUG | 2463 |
| 1492 | UCUACAA | CUGAUGAGGCCGAAAGGCCGAA | ACACCAC | 2464 |
| 1497 | UAAUUUC | CUGAUGAGGCCGAAAGGCCGAA | ACAAUAC | 2465 |
| 1508 | GGCGGAU | CUGAUGAGGCCGAAAGGCCGAA | AAAUAAU | 2466 |

TABLE XIII-continued

Mouse CD40 Hammerhead Ribozyme Sequences

| nt. Position | HH Ribozyme Sequences | | | Seq. ID No. |
|---|---|---|---|---|
| 1508 | GGCGGAU | CUGAUGAGGCCGAAAGGCCGAA | AAAUAAU | 2467 |
| 1523 | CAGGUAG | CUGAUGAGGCCGAAAGGCCGAA | AACCCAG | 2468 |

TABLE XIV

Human B7 Hairpin Ribozyme and Target Sequence

| nt. Position | Hairpin Ribozyme Sequence | | | | Seq. ID No. |
|---|---|---|---|---|---|
| 286 | ACAGGCAG | AGAA | GAUGAC | ACCAGAGAAACACACGUUGUGGUACAUUACCUGGUA | 2469 |
| 291 | GCAAAACA | AGAA | GGGCUG | ACCAGAGAAACACACGUUGUGGUACAUUACCUGGUA | 2470 |
| 295 | AGGUGCAA | AGAA | GGCAGG | ACCAGAGAAACACACGUUGUGGUACAUUACCUGGUA | 2471 |
| 437 | GCACCAAG | AGAA | GAAAGA | ACCAGAGAAACACACGUUGUGGUACAUUACCUGGUA | 2472 |
| 469 | AACACCUG | AGAA | GAAGUG | ACCAGAGAAACACACGUUGUGGUACAUUACCUGGUA | 2473 |
| 518 | GACCACAG | AGAA | GCGUUG | ACCAGAGAAACACACGUUGUGGUACAUUACCUGGUA | 2474 |
| 540 | AGCUCUUC | AGAA | GAAACA | ACCAGAGAAACACACGUUGUGGUACAUUACCUGGUA | 2475 |
| 596 | ACAUCAUA | AGAA | GCACCA | ACCAGAGAAACACACGUUGUGGUACAUUACCUGGUA | 2476 |
| 644 | CAAAGAUG | AGAA | GGUUCU | ACCAGAGAAACACACGUUGUGGUACAUUACCUGGUA | 2477 |
| 702 | GUGCCCUC | AGAA | GAUGGG | ACCAGAGAAACACACGUUGUGGUACAUUACCUGGUA | 2478 |
| 795 | GUAGGGAA | AGAA | GCUUUG | ACCAGAGAAACACACGUUGUGGUACAUUACCUGGUA | 2479 |
| 819 | AUUUCAAA | AGAA | GAUAUA | ACCAGAGAAACACACGUUGUGGUACAUUACCUGGUA | 2480 |
| 939 | UCUUGGGA | AGAA | GUUGUG | ACCAGAGAAACACACGUUGUGGUACAUUACCUGGUA | 2481 |
| 1012 | ACACAUGA | AGAA | GUGGUU | ACCAGAGAAACACACGUUGUGGUACAUUACCUGGUA | 2482 |
| 1055 | AGUUGAAG | AGAA | GAUUCA | ACCAGAGAAACACACGUUGUGGUACAUUACCUGGUA | 2483 |
| 1103 | AGGAUGGG | AGAA | GGUUAU | ACCAGAGAAACACACGUUGUGGUACAUUACCUGGUA | 2484 |
| 1159 | GUAGGUCA | AGAA | GCAUAU | ACCAGAGAAACACACGUUGUGGUACAUUACCUGGUA | 2485 |
| 1163 | AGCAGUAG | AGAA | GGCAGC | ACCAGAGAAACACACGUUGUGGUACAUUACCUGGUA | 2486 |
| 1171 | UGGGGCAA | AGAA | GUAGGU | ACCAGAGAAACACACGUUGUGGUACAUUACCUGGUA | 2487 |
| 1356 | GUGGGUAA | AGAA | GCUUAA | ACCAGAGAAACACACGUUGUGGUACAUUACCUGGUA | 2488 |
| 1395 | UCAGCUUA | AGAA | GAAAGA | ACCAGAGAAACACACGUUGUGGUACAUUACCUGGUA | 2489 |

| nt. Position | Substrate | | | Seq. ID No. |
|---|---|---|---|---|
| 286 | GUCAUCA | GCC | CUGCCUGU | 2490 |
| 291 | CAGCCCU | GCC | UGUUUUGC | 2491 |
| 295 | CCUGCCU | GUU | UUGCACCU | 2492 |
| 437 | UCUUUCA | GCU | CUUGGUGC | 2493 |
| 469 | CACUUCU | GUU | CAGGUGUU | 2494 |
| 518 | CAACGCU | GUC | CUGUGGUC | 2495 |
| 540 | UGUUUCU | GUU | GAAGAGCU | 2496 |
| 596 | UGGUGCU | GAC | UAUGAUGU | 2497 |
| 644 | AGAACCG | GAC | CAUCUUUG | 2498 |
| 702 | CCCAUCU | GAC | GAGGGCAC | 2499 |
| 795 | CAAAGCU | GAC | UUCCCUAC | 2500 |
| 819 | UAUAUCU | GAC | UUUGAAAU | 2501 |
| 939 | CACAACA | GUU | UCCCAAGA | 2502 |
| 1012 | AACCACA | GCU | UCAUGUGU | 2503 |
| 1055 | UGAAUCA | GAC | CUUCAACU | 2504 |
| 1103 | AUAACCU | GCU | CCCAUCCU | 2505 |
| 1159 | AUAUGCU | GCC | UGACCUAC | 2506 |
| 1163 | GCUGCCU | GAC | CUACUGCU | 2507 |
| 1171 | ACCUACU | GCU | UUGCCCCA | 2508 |
| 1356 | UUAAGCU | GUU | UUACCCAC | 2509 |
| 1395 | UCUUUCA | GAU | UAAGCUGA | 2510 |

TABLE XV

Mouse B7 Hairpin Ribozyme and Target Sequence

| nt. Position | Hairpin Ribozyme Sequence | | | | Seq. ID No. |
|---|---|---|---|---|---|
| 74 | AGAAAUGG | AGAA | GAGUGU | ACCAGAGAAACACACGUUGUGGUACAUUACCUGGUA | 2511 |
| 114 | AUCCACCC | AGAA | GAUGCU | ACCAGAGAAACACACGUUGUGGUACAUUACCUGGUA | 2512 |
| 154 | AAUCGAGA | AGAA | GAGAUG | ACCAGAGAAACACACGUUGUGGUACAUUACCUGGUA | 2513 |
| 265 | CCUGCAUC | AGAA | GACAAU | ACCAGAGAAACACACGUUGUGGUACAUUACCUGGUA | 2514 |
| 328 | GACGAAUC | AGAA | GCACAA | ACCAGAGAAACACACGUUGUGGUACAUUACCUGGUA | 2515 |
| 331 | AAAGACGA | AGAA | GCAGCA | ACCAGAGAAACACACGUUGUGGUACAUUACCUGGUA | 2516 |
| 356 | UCAUCAAC | AGAA | GAAGAC | ACCAGAGAAACACACGUUGUGGUACAUUACCUGGUA | 2517 |
| 373 | CUGACUUG | AGAA | GUUGUU | ACCAGAGAAACACACGUUGUGGUACAUUACCUGGUA | 2518 |
| 403 | AACGGCAA | AGAA | GCAAUA | ACCAGAGAAACACACGUUGUGGUACAUUACCUGGUA | 2519 |

TABLE XV-continued

| | | | | | |
|---|---|---|---|---|---|
| 481 | CAAUGACA | AGAA | GCACCA | ACCAGAGAAACACACGUUGUGGUACAUUACCUGGUA | 2520 |
| 529 | CAUAUAAA | AGAA | GGUUCU | ACCAGAGAAACACACGUUGUGGUACAUUACCUGGUA | 2521 |
| 584 | GUGCCCCG | AGAA | GAAAGG | ACCAGAGAAACACACGUUGUGGUACAUUACCUGGUA | 2522 |
| 600 | AACGACAC | AGAA | GUAUGU | ACCAGAGAAACACACGUUGUGGUACAUUACCUGGUA | 2523 |
| 677 | GUAGAGAA | AGAA | GCUUUG | ACCAGAGAAACACACGUUGUGGUACAUUACCUGGUA | 2524 |
| 741 | GGAAGCAA | AGAA | GGUAAU | ACCAGAGAAACACACGUUGUGGUACAUUACCUGGUA | 2525 |
| 1028 | AUGACGAC | AGAA | GUUAUU | ACCAGAGAAACACACGUUGUGGUACAUUACCUGGUA | 2526 |
| 1077 | UCUUCUGA | AGAA | GCUUCU | ACCAGAGAAACACACGUUGUGGUACAUUACCUGGUA | 2527 |
| 1116 | GAAGGUAA | AGAA | GUUGUU | ACCAGAGAAACACACGUUGUGGUACAUUACCUGGUA | 2528 |
| 1153 | GGAAGACG | AGAA | GUUCAG | ACCAGAGAAACACACGUUGUGGUACAUUACCUGGUA | 2529 |
| 1157 | UAAAGGAA | AGAA | GUCUGU | ACCAGAGAAACACACGUUGUGGUACAUUACCUGGUA | 2530 |
| 1178 | CCCACAUG | AGAA | GAGAAG | ACCAGAGAAACACACGUUGUGGUACAUUACCUGGUA | 2531 |
| 1246 | UCCGAAAG | AGAA | GCUAGC | ACCAGAGAAACACACGUUGUGGUACAUUACCUGGUA | 2532 |
| 1523 | CAGAAAAG | AGAA | GGCCUC | ACCAGAGAAACACACGUUGUGGUACAUUACCUGGUA | 2533 |

| nt. Position | Substrate | | | Seq. ID No. |
|---|---|---|---|---|
| 74 | ACACUCU | GUU | CCAUUUCU | 2534 |
| 114 | AGCAUCU | GCC | GGGUGGAU | 2535 |
| 154 | CAUCUCU | GUU | UCUCGAUU | 2536 |
| 265 | AUUGUCA | GUU | GAUGCAGG | 2537 |
| 328 | UUGUGCU | GCU | GAUUCGUC | 2538 |
| 331 | UGCUGCU | GAU | UCGUCUUU | 2539 |
| 356 | GUCUUCA | GAU | GUUGAUGA | 2540 |
| 373 | AACAACU | GUC | CAAGUCAG | 2541 |
| 403 | UAUUGCU | GCC | UUGCCGUU | 2542 |
| 481 | UGGUGCU | GUC | UGUCAUUG | 2543 |
| 529 | AGAACCG | GAC | UUUAUAUG | 2544 |
| 584 | CCUUUCA | GAC | CGGGGCAC | 2545 |
| 600 | ACAUACA | GCU | GUGUCGUU | 2546 |
| 677 | CAAAGCU | GAC | UUCUCUAC | 2547 |
| 741 | AUUACCU | GCU | UUGCUUCC | 2548 |
| 1028 | AAUAACA | GUC | GUCGUCAU | 2549 |
| 1077 | AGAAGCU | GUU | UCAGAAGA | 2550 |
| 1116 | AACAACA | GCC | UUACCUUC | 2551 |
| 1153 | CUGAACA | GAC | CGUCUUCC | 2552 |
| 1157 | ACAGACC | GUC | UUCCUUUA | 2553 |
| 1178 | CUUCUCU | GUC | CAUGUGGG | 2554 |
| 1246 | GCUAGCU | GAU | CUUUCGGA | 2555 |
| 1523 | GAGGCCU | GCC | CUUUUCUG | 2556 |

TABLE XVI

Human B7-2 Hairpin Ribozyme and Target Sequences

| nt. Position | HP Ribozyme Sequences | | | | Seq. ID No. |
|---|---|---|---|---|---|
| 25 | GUUACAGC | AGAA | GAGAAG | ACCAGAGAAACACACGUUGUGGUACAUUACCUGGUA | 2557 |
| 28 | CCUGUUAC | AGAA | GCAGAG | ACCAGAGAAACACACGUUGUGGUACAUUACCUGGUA | 2558 |
| 57 | CCCCACUC | AGAA | GUGUGU | ACCAGAGAAACACACGUUGUGGUACAUUACCUGGUA | 2559 |
| 162 | CACCAGAG | AGAA | GGAAGG | ACCAGAGAAACACACGUUGUGGUACAUUACCUGGUA | 2560 |
| 175 | UUCAGAGG | AGAA | GCACCA | ACCAGAGAAACACACGUUGUGGUACAUUACCUGGUA | 2561 |
| 214 | CAUGGCAG | AGAA | GCAGUC | ACCAGAGAAACACACGUUGUGGUACAUUACCUGGUA | 2562 |
| 380 | CAGGGUCC | AGAA | GUCCGA | ACCAGAGAAACACACGUUGUGGUACAUUACCUGGUA | 2563 |
| 408 | UGUCCUUG | AGAA | GAAGAU | ACCAGAGAAACACACGUUGUGGUACAUUACCUGGUA | 2564 |
| 480 | CAGAAUUC | AGAA | GGUGGA | ACCAGAGAAACACACGUUGUGGUACAUUACCUGGUA | 2565 |
| 575 | UAUAGAUG | AGAA | GGUCAA | ACCAGAGAAACACACGUUGUGGUACAUUACCUGGUA | 2566 |
| 710 | AACAGACA | AGAA | GAUGGA | ACCAGAGAAACACACGUUGUGGUACAUUACCUGGUA | 2567 |
| 718 | GGGAAUGA | AGAA | GACAAG | ACCAGAGAAACACACGUUGUGGUACAUUACCUGGUA | 2568 |
| 730 | CUCGUAAC | AGAA | GGGAAU | ACCAGAGAAACACACGUUGUGGUACAUUACCUGGUA | 2569 |
| 783 | AAGAUAAA | AGAA | GCGUCU | ACCAGAGAAACACACGUUGUGGUACAUUACCUGGUA | 2570 |
| 825 | CUGGGGGA | AGAA | GAGGGU | ACCAGAGAAACACACGUUGUGGUACAUUACCUGGUA | 2571 |
| 835 | GGAAUGUG | AGAA | GGGGGA | ACCAGAGAAACACACGUUGUGGUACAUUACCUGGUA | 2572 |
| 856 | GGAAGUAC | AGAA | GUAAUC | ACCAGAGAAACACACGUUGUGGUACAUUACCUGGUA | 2573 |
| 896 | UAGAAUUA | AGAA | GAAAAC | ACCAGAGAAACACACGUUGUGGUACAUUACCUGGUA | 2574 |
| 930 | AGUUGCGA | AGAA | GCUUCU | ACCAGAGAAACACACGUUGUGGUACAUUACCUGGUA | 2575 |
| 987 | UUUUCUUG | AGAA | GUUCAC | ACCAGAGAAACACACGUUGUGGUACAUUACCUGGUA | 2576 |
| 1027 | UGGGCUUC | AGAA | GAUCUU | ACCAGAGAAACACACGUUGUGGUACAUUACCUGGUA | 2577 |

| nt. Position | Substrate | | | Seq. ID No. |
|---|---|---|---|---|
| 25 | CUUCUCU | GCU | GCUGUAAC | 2578 |
| 28 | CUCUGCU | GCU | GUAACAGG | 2579 |
| 57 | ACACACG | GAU | GAGUGGGG | 2580 |
| 162 | CCUUCCU | GCU | CUCUGGUG | 2581 |
| 175 | UGGUGCU | GCU | CCUCUGAA | 2582 |

TABLE XVI-continued

| | | | | |
|---|---|---|---|---|
| 214 | GACUGCA | GAC | CUGCCAUG | 2583 |
| 380 | UCGGACA | GUU | GGACCCUG | 2584 |
| 408 | AUCUUCA | GAU | CAAGGACA | 2585 |
| 480 | UCCACCA | GAU | GAAUUCUG | 2586 |
| 575 | UUGACCU | GCU | CAUCUAUA | 2587 |
| 710 | UCCAUCA | GCU | UGUCUGUU | 2588 |
| 718 | CUUGUCU | GUU | UCAUUCCC | 2589 |
| 730 | AUUCCCU | GAU | GUUACGAG | 2590 |
| 783 | AGACGCG | GCU | UUUAUCUU | 2591 |
| 825 | ACCCUCA | GCC | UCCCCCAG | 2592 |
| 835 | UCCCCCA | GAC | CACAUUCC | 2593 |
| 856 | GAUUACA | GCU | GUACUUCC | 2594 |
| 896 | GUUUUCU | GUC | UAAUUCUA | 2595 |
| 930 | AGAAGCG | GCC | UCGCAACU | 2596 |
| 987 | GUGAACA | GAC | CAAGAAAA | 2597 |
| 1027 | AAGAUCU | GAU | GAAGCCCA | 2598 |

TABLE XVII

Mouse B7-2 Hairpin Ribozyme and Target Sequences

| nt. Position | HP Ribozyme Sequences | | | | Seq. ID No. |
|---|---|---|---|---|---|
| 10 | UCUUACGC | AGAA | GCUUGC | ACCAGAGAAACACACGUUGUGGUACAUUACCUGGUA | 2599 |
| 42 | UUGUUCAA | AGAA | GUGCUG | ACCAGAGAAACACACGUUGUGGUACAUUACCUGGUA | 2600 |
| 56 | CUACAGGA | AGAA | GGUUGU | ACCAGAGAAACACACGUUGUGGUACAUUACCUGGUA | 2601 |
| 108 | CAUGGUGC | AGAA | GGGGUC | ACCAGAGAAACACACGUUGUGGUACAUUACCUGGUA | 2602 |
| 146 | AUCAGCAA | AGAA | GUCACA | ACCAGAGAAACACACGUUGUGGUACAUUACCUGGUA | 2603 |
| 154 | CAUCUGAG | AGAA | GCAAGA | ACCAGAGAAACACACGUUGUGGUACAUUACCUGGUA | 2604 |
| 161 | GAAACAGC | AGAA | GAGAUC | ACCAGAGAAACACACGUUGUGGUACAUUACCUGGUA | 2605 |
| 167 | UCCACGGA | AGAA | GCAUCU | ACCAGAGAAACACACGUUGUGGUACAUUACCUGGUA | 2606 |
| 211 | AUGGGCAC | AGAA | GAUAUG | ACCAGAGAAACACACGUUGUGGUACAUUACCUGGUA | 2607 |
| 400 | UGUCCUUG | AGAA | GAACAU | ACCAGAGAAACACACGUUGUGGUACAUUACCUGGUA | 2608 |
| 679 | AGAUACUG | AGAA | GUUCUG | ACCAGAGAAACACACGUUGUGGUACAUUACCUGGUA | 2609 |
| 696 | AAGAGAGA | AGAA | GUUGGA | ACCAGAGAAACACACGUUGUGGUACAUUACCUGGUA | 2610 |
| 716 | CACACACC | AGAA | GGGAAU | ACCAGAGAAACACACGUUGUGGUACAUUACCUGGUA | 2611 |
| 737 | ACACACAC | AGAA | GUCAUA | ACCAGAGAAACACACGUUGUGGUACAUUACCUGGUA | 2612 |
| 839 | GUAACUGA | AGAA | GUAAUC | ACCAGAGAAACACACGUUGUGGUACAUUACCUGGUA | 2613 |
| 874 | CAAUGAUG | AGAA | GCAUCA | ACCAGAGAAACACACGUUGUGGUACAUUACCUGGUA | 2614 |
| 907 | GCCUGCUA | AGAA | GAUUCG | ACCAGAGAAACACACGUUGUGGUACAUUACCUGGUA | 2615 |
| 929 | AACUUAGA | AGAA | GUGUUG | ACCAGAGAAACACACGUUGUGGUACAUUACCUGGUA | 2616 |
| 1115 | UUCCAAUC | AGAA | GAGAAC | ACCAGAGAAACACACGUUGUGGUACAUUACCUGGUA | 2617 |
| 1118 | GAAUUCCA | AGAA | GCUGAG | ACCAGAGAAACACACGUUGUGGUACAUUACCUGGUA | 2618 |
| 1133 | AAUUAUUC | AGAA | GUAGAA | ACCAGAGAAACACACGUUGUGGUACAUUACCUGGUA | 2619 |

| nt. Position | Substrate | | | Seq. ID No. |
|---|---|---|---|---|
| 10 | GCAAGCA | GAC | GCGUAAGA | 2620 |
| 42 | CAGCACG | GAC | UUGAACAA | 2621 |
| 56 | ACAACCA | GAC | UCCUGUAG | 2622 |
| 108 | GACCCCA | GAU | GCACCAUG | 2623 |
| 146 | UGUGACA | GUC | UUGCUGAU | 2624 |
| 154 | UCUUGCU | GAU | CUCAGAUG | 2625 |
| 161 | GAUCUCA | GAU | GCUGUUUC | 2626 |
| 167 | AGAUGCU | GUU | UCCGUGGA | 2627 |
| 211 | CAUAUCU | GCC | GUGCCCAU | 2628 |
| 400 | AUGUUCA | GAU | CAAGGACA | 2629 |
| 679 | CAGAACU | GUU | CAGUAUCU | 2630 |
| 696 | UCCAACA | GCC | UCUCUCUU | 2631 |
| 716 | AUUCCCG | GAU | GGUGUGUG | 2632 |
| 737 | UAUGACC | GUU | GUGUGUGU | 2633 |
| 839 | GAUUACA | GCU | UCAGUUAC | 2634 |
| 874 | UGAUGCU | GCU | CAUCAUUG | 2635 |
| 907 | CGAAUCA | GCC | UAGCAGGC | 2636 |
| 929 | CAACACA | GCC | UCUAAGUU | 2637 |
| 1115 | GUUCUCA | GCU | GAUUGGAA | 2638 |
| 1118 | CUCAGCU | GAU | UGGAAUUC | 2639 |
| 1133 | UUCUACA | GUU | GAAUAAUU | 2640 |

TABLE XVIII

Human CD40 Hairpin Ribozyme and Target Sequences

| nt. Position | Hairpin Ribozyme Sequences | | | Seq. ID No. |
|---|---|---|---|---|
| 26  | GACCAGGC | AGAA | GGACCA ACCAGAGAAACACACGUUGUGGUACAUUACCUGGUA | 2641 |
| 29  | UGAGACCA | AGAA | GCAGGA ACCAGAGAAACACACGUUGUGGUACAUUACCUGGUA | 2642 |
| 58  | ACUGCAGA | AGAA | GACGAA ACCAGAGAAACACACGUUGUGGUACAUUACCUGGUA | 2643 |
| 84  | GGUCAGCA | AGAA | GCCCCA ACCAGAGAAACACACGUUGUGGUACAUUACCUGGUA | 2644 |
| 91  | GGACAGCG | AGAA | GCAAGC ACCAGAGAAACACACGUUGUGGUACAUUACCUGGUA | 2645 |
| 95  | GGAUGGAC | AGAA | GUCAGC ACCAGAGAAACACACGUUGUGGUACAUUACCUGGUA | 2646 |
| 98  | UCUGGAUG | AGAA | GCGGUC ACCAGAGAAACACACGUUGUGGUACAUUACCUGGUA | 2647 |
| 159 | GCACAAAG | AGAA | GCACUG ACCAGAGAAACACACGUUGUGGUACAUUACCUGGUA | 2648 |
| 414 | CGAGCAUG | AGAA | GUGCAG ACCAGAGAAACACACGUUGUGGUACAUUACCUGGUA | 2649 |
| 429 | GACCCCAA | AGAA | GGGCGA ACCAGAGAAACACACGUUGUGGUACAUUACCUGGUA | 2650 |
| 445 | CUGUAGCA | AGAA | GCUUGA ACCAGAGAAACACACGUUGUGGUACAUUACCUGGUA | 2651 |
| 483 | GCCGACUG | AGAA | GGGCUC ACCAGAGAAACACACGUUGUGGUACAUUACCUGGUA | 2652 |
| 488 | AAGAAGCC | AGAA | GGGCAG ACCAGAGAAACACACGUUGUGGUACAUUACCUGGUA | 2653 |
| 492 | GGAGAAGA | AGAA | GACUGG ACCAGAGAAACACACGUUGUGGUACAUUACCUGGUA | 2654 |
| 515 | UUUUCGAA | AGAA | GAUGAC ACCAGAGAAACACACGUUGUGGUACAUUACCUGGUA | 2655 |
| 593 | CAGACAAC | AGAA | GUCUUG ACCAGAGAAACACACGUUGUGGUACAUUACCUGGUA | 2656 |
| 619 | GGGCUCUC | AGAA | GAUCCU ACCAGAGAAACACACGUUGUGGUACAUUACCUGGUA | 2657 |
| 661 | GGAUGGCA | AGAA | GGAUCC ACCAGAGAAACACACGUUGUGGUACAUUACCUGGUA | 2658 |
| 764 | GGAAGAUC | AGAA | GGAAAA ACCAGAGAAACACACGUUGUGGUACAUUACCUGGUA | 2659 |
| 788 | ACUGGAGC | AGAA | GUGUUG ACCAGAGAAACACACGUUGUGGUACAUUACCUGGUA | 2660 |
| 791 | UGCACUGG | AGAA | GCAGUG ACCAGAGAAACACACGUUGUGGUACAUUACCUGGUA | 2661 |
| 924 | CUCUGGCC | AGAA | GCCUGU ACCAGAGAAACACACGUUGUGGUACAUUACCUGGUA | 2662 |
| 946 | CCUGCAGC | AGAA | GCACCA ACCAGAGAAACACACGUUGUGGUACAUUACCUGGUA | 2663 |
| 949 | ACCCCUGC | AGAA | GCAGCA ACCAGAGAAACACACGUUGUGGUACAUUACCUGGUA | 2664 |

| nt. Position | Substrate | | | Seq. ID No. |
|---|---|---|---|---|
| 26  | UGGUCCU | GCC | GCCUGGUC | 2665 |
| 29  | UCCUGCC | GCC | UGGUCUCA | 2666 |
| 58  | UUCGUCU | GCC | UCUGCAGU | 2667 |
| 84  | UGGGGCU | GCU | UGCUGACC | 2668 |
| 91  | GCUUGCU | GAC | CGCUGUCC | 2669 |
| 95  | GCUGACC | GCU | GUCCAUCC | 2670 |
| 98  | GACCGCU | GUC | CAUCCAGA | 2671 |
| 159 | CAGUGCU | GUU | CUUUGUGC | 2672 |
| 414 | CUGCACC | GCU | CAUGCUCG | 2673 |
| 429 | UCGCCCG | GCU | UUGGGGUC | 2674 |
| 445 | UCAAGCA | GAU | UGCUACAG | 2675 |
| 483 | GAGCCCU | GCC | CAGUCGGC | 2676 |
| 488 | CUGCCCA | GUC | GGCUUCUU | 2677 |
| 492 | CCAGUCG | GCU | UCUUCUCC | 2678 |
| 515 | GUCAUCU | GCU | UUCGAAAA | 2679 |
| 593 | CAAGACU | GAU | GUUGUCUG | 2680 |
| 619 | AGGAUCG | GCU | GAGAGCCC | 2681 |
| 661 | GGAUCCU | GUU | UGCCAUCC | 2682 |
| 764 | UUUUCCC | GAC | GAUCUUCC | 2683 |
| 788 | CAACACU | GCU | GCUCCAGU | 2684 |
| 791 | CACUGCU | GCU | CCAGUGCA | 2685 |
| 924 | ACAGGCA | GUU | GGCCAGAG | 2686 |
| 946 | UGGUGCU | GCU | GCUGCAGG | 2687 |
| 949 | UGCUGCU | GCU | GCAGGGGU | 2688 |

TABLE XIX

Mouse CD40 Hairpin Ribozyme and Substrate Sequences

| nt. Position | HP Ribozyme Sequences | | | Seq. ID No. |
|---|---|---|---|---|
| 25  | GCGCGCAC | AGAA | GAGGCA ACCAGAGAAACACACGUUGUGGUACAUUACCUGGUA | 2689 |
| 45  | UGUCAACA | AGAA | GCCCCA ACCAGAGAAACACACGUUGUGGUACAUUACCUGGUA | 2690 |
| 59  | CCUAGAUG | AGAA | GCUGUC ACCAGAGAAACACACGUUGUGGUACAUUACCUGGUA | 2691 |
| 144 | GCUUGUCA | AGAA | GCUUCC ACCAGAGAAACACACGUUGUGGUACAUUACCUGGUA | 2692 |
| 164 | UUCUCAAG | AGAA | GUGCAG ACCAGAGAAACACACGUUGUGGUACAUUACCUGGUA | 2693 |
| 212 | UUCCACUG | AGAA | GAGAAU ACCAGAGAAACACACGUUGUGGUACAUUACCUGGUA | 2694 |
| 311 | CAGGUACA | AGAA | GUGUCU ACCAGAGAAACACACGUUGUGGUACAUUACCUGGUA | 2695 |
| 431 | GGAUGACA | AGAA | GUAUCA ACCAGAGAAACACACGUUGUGGUACAUUACCUGGUA | 2696 |
| 444 | GCCGACUG | AGAA | GGGAUG ACCAGAGAAACACACGUUGUGGUACAUUACCUGGUA | 2697 |
| 449 | AAGAAGCC | AGAA | GGGCAG ACCAGAGAAACACACGUUGUGGUACAUUACCUGGUA | 2698 |
| 453 | GGAGAAGA | AGAA | GACUGG ACCAGAGAAACACACGUUGUGGUACAUUACCUGGUA | 2699 |
| 550 | UGACAUUA | AGAA | GACUCG ACCAGAGAAACACACGUUGUGGUACAUUACCUGGUA | 2700 |
| 580 | GGGCUCGC | AGAA | GGGACU ACCAGAGAAACACACGUUGUGGUACAUUACCUGGUA | 2701 |
| 592 | GAAUGACC | AGAA | GGGCUC ACCAGAGAAACACACGUUGUGGUACAUUACCUGGUA | 2702 |

TABLE XIX-continued

| | | | | | |
|---|---|---|---|---|---|
| 605 | CCCAUCAC | AGAA | GGAAUG | ACCAGAGAAACACACGUUGUGGUACAUUACCUGGUA | 2703 |
| 701 | UGCCGUCG | AGAA | GCAGGG | ACCAGAGAAACACACGUUGUGGUACAUUACCUGGUA | 2704 |
| 752 | ACUGGAGC | AGAA | GUGUUA | ACCAGAGAAACACACGUUGUGGUACAUUACCUGGUA | 2705 |
| 755 | UGCACUGG | AGAA | GCGGUG | ACCAGAGAAACACACGUUGUGGUACAUUACCUGGUA | 2706 |
| 787 | GUGUGACA | AGAA | GACACC | ACCAGAGAAACACACGUUGUGGUACAUUACCUGGUA | 2707 |
| 890 | CCUCCAAA | AGAA | GUUCCA | ACCAGAGAAACACACGUUGUGGUACAUUACCUGGUA | 2708 |
| 909 | GGUCAGCA | AGAA | GCCAUC | ACCAGAGAAACACACGUUGUGGUACAUUACCUGGUA | 2709 |
| 916 | UUCAAAAG | AGAA | GCAAGC | ACCAGAGAAACACACGUUGUGGUACAUUACCUGGUA | 2710 |
| 975 | UGACAGGG | AGAA | GGCAUG | ACCAGAGAAACACACGUUGUGGUACAUUACCUGGUA | 2711 |
| 1137 | CGAGCACA | AGAA | GCGGGC | ACCAGAGAAACACACGUUGUGGUACAUUACCUGGUA | 2712 |
| 1276 | GUUUUAAA | AGAA | GUUUCU | ACCAGAGAAACACACGUUGUGGUACAUUACCUGGUA | 2713 |
| 1334 | CGGGUUUG | AGAA | GCAAGC | ACCAGAGAAACACACGUUGUGGUACAUUACCUGGUA | 2714 |
| 1352 | GGAUCAAA | AGAA | GGUAAC | ACCAGAGAAACACACGUUGUGGUACAUUACCUGGUA | 2715 |
| 1512 | AAACCCAG | AGAA | GAUUAA | ACCAGAGAAACACACGUUGUGGUACAUUACCUGGUA | 2716 |

| nt. Position | Substrate | | | Seq. ID No. |
|---|---|---|---|---|
| 25 | UGCCUCG | GCU | GUGCGCGC | 2717 |
| 45 | UGGGGCU | GCU | UGUUGACA | 2718 |
| 59 | GACAGCG | GUC | CAUCUAGG | 2719 |
| 144 | GGAAGCC | GAC | UGACAAGC | 2720 |
| 164 | CUGCACA | GCU | CUUGAGAA | 2721 |
| 212 | AUUCUCA | GCC | CAGUGGAA | 2722 |
| 311 | AGACACU | GUC | UGUACCUG | 2723 |
| 431 | UGAUACC | GUC | UGUCAUCC | 2724 |
| 444 | CAUCCCU | GCC | CAGUCGGC | 2725 |
| 449 | CUGCCCA | GUC | GGCUUCUU | 2726 |
| 453 | CCAGUCG | GCU | UCUUCUCC | 2727 |
| 550 | CGAGUCA | GAC | UAAUGUCA | 2728 |
| 580 | AGUCCCG | GAU | GCGAGCCC | 2729 |
| 592 | GAGCCCU | GCU | GGUCAUUC | 2730 |
| 605 | CAUUCCU | GUC | GUGAUGGG | 2731 |
| 701 | CCCUGCG | GCU | CGACGGCA | 2732 |
| 752 | UAACACC | GCU | GCUCCAGU | 2733 |
| 755 | CACCGCU | GCU | CCAGUGCA | 2734 |
| 787 | GGUGUCA | GCC | UGUCACAC | 2735 |
| 890 | UGGAACU | GCU | UUUGGAGG | 2736 |
| 909 | GAUGGCU | GCU | UGCUGACC | 2737 |
| 916 | GCUUGCU | GAC | CUUUUGAA | 2738 |
| 975 | CAUGCCU | GCC | CCCUGUCA | 2739 |
| 1137 | GCCCGCA | GCU | UGUGCUCG | 2740 |
| 1276 | AGAAACA | GCU | UUUAAAAC | 2741 |
| 1334 | GCUUGCU | GCC | CAAACCCG | 2742 |
| 1352 | GUUACCU | GAU | UUUGAUCC | 2743 |
| 1512 | UUAAUCC | GCC | CUGGGUUU | 2744 |

We claim:

1. An enzymatic nucleic acid molecule which specifically blocks synthesis and/or expression of an mRNA encoding B7-1.

2. The enzymatic nucleic acid molecule of claim 1, wherein, the binding arms of said enzymatic nucleic acid molecule comprise sequences complementary to any of sequences defined as Seq ID Nos 1–299 and 599–896.

3. The enzymatic nucleic acid molecule of claim 1, wherein said enzymatic nucleic acid molecule is in a hammerhead motif.

4. The enzymatic nucleic acid molecule of claim 1, wherein said enzymatic nucleic acid molecule is in a hairpin, hepatitis Delta virus, group I intron, VS nucleic acid or RNaseP nucleic acid motif.

5. The enzymatic nucleic acid molecule of any of claim 1, wherein said enzymatic nucleic acid molecule comprises between 12 and 100 bases complementary to the RNA of said region.

6. The enzymatic nucleic acid of claim 5, wherein said enzymatic nucleic acid molecule comprises between 14 and 24 bases complementary to the RNA of said region.

7. A mammalian cell including an enzymatic nucleic acid molecule of claim 1.

8. The mammalian cell of claim 7, wherein said mammalian cell is a human cell.

9. An expression vector comprising a nucleic acid sequence encoding the enzymatic nucleic acid molecule of claim 1, in a manner which allows expression and/or delivery of that enzymatic RNA molecule within a mammalian cell.

10. A mammalian cell including the expression vector of claim 9.

11. The mammalian cell of claim 10, wherein said mammalian cell is a human cell.

* * * * *